US011827880B2

(12) United States Patent
Huss et al.

(10) Patent No.: US 11,827,880 B2

(45) Date of Patent: Nov. 28, 2023

(54) THERAPEUTIC EDITING

(71) Applicant: Shape Therapeutics Inc., Seattle, WA (US)

(72) Inventors: David Huss, Seattle, WA (US); Prashant Mali, San Diego, CA (US); Anupama Lakshmanan, Sammamish, WA (US); Christopher Nye, Issaquah, WA (US); Yiannis Savva, Seattle, WA (US); Liana Stein, Kenmore, WA (US); Richard Sullivan, Seattle, WA (US); Rafael Ponce, Seattle, WA (US); Susan Byrne, Lexington, MA (US)

(73) Assignee: Shape Therapeutics Inc., Seattle, WA (US)

( * ) Notice: Subject to any disclaimer, the term of this patent is extended or adjusted under 35 U.S.C. 154(b) by 0 days.

(21) Appl. No.: 17/781,877

(22) PCT Filed: Dec. 1, 2020

(86) PCT No.: PCT/US2020/062756

§ 371 (c)(1), (2) Date: Jun. 2, 2022

(87) PCT Pub. No.: WO2021/113270

PCT Pub. Date: Jun. 10, 2021

(65) Prior Publication Data

US 2023/0044119 A1 Feb. 9, 2023

Related U.S. Application Data

(60) Provisional application No. 63/112,286, filed on Nov. 11, 2020, provisional application No. 63/030,165, filed on May 26, 2020, provisional application No. 63/022,727, filed on May 11, 2020, provisional application No. 62/942,683, filed on Dec. 2, 2019, provisional application No. 62/942,667, filed on Dec. 2, 2019, provisional application No. 62/942,693, filed on Dec. 2, 2019.

(51) Int. Cl.

| | |
|---|---|
| ***A61P 25/28*** | (2006.01) |
| ***C12N 15/11*** | (2006.01) |
| ***A61K 48/00*** | (2006.01) |
| ***C07K 14/47*** | (2006.01) |
| ***C12N 9/78*** | (2006.01) |
| ***C12N 15/86*** | (2006.01) |

(52) U.S. Cl.

CPC .......... *C12N 15/11* (2013.01); *A61K 48/0066* (2013.01); *A61P 25/28* (2018.01); *C07K 14/47* (2013.01); *C12N 9/78* (2013.01); *C12N 15/86* (2013.01); *C12Y 305/04004* (2013.01); *C12N 2310/122* (2013.01); *C12N 2310/333* (2013.01); *C12N 2310/334* (2013.01); *C12N 2310/336* (2013.01); *C12N 2310/531* (2013.01); *C12N 2310/533* (2013.01); *C12N 2750/14143* (2013.01); *C12N 2750/14171* (2013.01)

(58) Field of Classification Search

None

See application file for complete search history.

(56) References Cited

U.S. PATENT DOCUMENTS

| | | | | |
|---|---|---|---|---|
| 5,759,833 | A | 6/1998 | Shiba | |
| 6,309,830 | B1 | 10/2001 | Panchal | |
| 7,456,269 | B2 * | 11/2008 | Gurney | C07K 14/4711 435/254.11 |
| 7,709,616 | B2 | 5/2010 | Bentwich | |
| 7,790,154 | B2 | 9/2010 | Samulski | |
| 9,068,179 | B1 | 6/2015 | Liu et al. | |
| 9,238,814 | B2 | 1/2016 | Fukuda | |
| 9,650,627 | B1 | 5/2017 | Rosenthal | |
| 9,745,576 | B2 | 8/2017 | De Visser | |
| 9,840,699 | B2 | 12/2017 | Liu et al. | |
| 9,890,379 | B2 | 2/2018 | De Kimpe | |
| 9,994,856 | B2 | 6/2018 | De Boer | |
| 10,113,163 | B2 | 10/2018 | Liu et al. | |
| 10,421,963 | B2 | 9/2019 | Biasutto | |
| 10,450,568 | B2 | 10/2019 | Butler | |
| 10,465,176 | B2 | 11/2019 | Liu et al. | |
| 10,476,825 | B2 | 11/2019 | Hsu | |
| 10,479,995 | B2 | 11/2019 | Vargeese | |
| 10,563,198 | B2 | 2/2020 | Haisma | |
| 10,612,025 | B2 | 4/2020 | Van Diepen | |

(Continued)

FOREIGN PATENT DOCUMENTS

| | | | |
|---|---|---|---|
| DE | 102015012522 | B3 | 6/2016 |
| EP | 3234134 | B1 | 10/2017 |

(Continued)

OTHER PUBLICATIONS

György B, Lööv C, Zaborowski MP, et al. CRISPR/Cas9 Mediated Disruption of the Swedish APP Allele as a Therapeutic Approach for Early-Onset Alzheimer's Disease. Mol Ther Nucleic Acids. 2018;11:429-440. (Year: 2018).*

Raikwar SP, Kikkeri NS, Sakuru R, et al. Next Generation Precision Medicine: CRISPR-mediated Genome Editing for the Treatment of Neurodegenerative Disorders. J Neuroimmune Pharmacol. 2019;14(4):608-641. (Year: 2019).*

Lehmann, K. A., & Bass, B. L. (1999). The importance of internal loops within RNA substrates of ADAR1. Journal of molecular biology, 291(1), 1-13. (Year: 1999).*

Brutlag et al., Improved sensitivity of biological sequence database searches, Comp. App. Biosci. 6:237-245 (1990).

(Continued)

*Primary Examiner* — Nancy J Leith

*Assistant Examiner* — Khaleda B Hasan

(74) *Attorney, Agent, or Firm* — Greenberg Traurig, LLP

(57) ABSTRACT

Disclosed herein are compositions that comprise engineered polynucleotides, pharmaceutical compositions comprising the same, methods of making the same, and methods of treatment comprising the compositions that comprise the engineered polynucleotides.

34 Claims, 39 Drawing Sheets

Specification includes a Sequence Listing.

(56) References Cited

U.S. PATENT DOCUMENTS

| | | | | |
|---|---|---|---|---|
| 10,676,737 | B2 | 6/2020 | Klein | |
| 10,689,636 | B2 | 6/2020 | McFarland | |
| 10,689,646 | B2 | 6/2020 | De Kimpe | |
| 10,760,076 | B2 | 9/2020 | Adamson | |
| 10,900,041 | B2 | 1/2021 | De Vlaam | |
| 10,941,402 | B2 | 3/2021 | Turunen | |
| 10,988,763 | B2 | 4/2021 | Turunen | |
| 11,053,481 | B2 | 7/2021 | Liu et al. | |
| 11,479,775 | B2 | 10/2022 | Mali | |
| 2002/0156042 | A1 | 10/2002 | Panchal | |
| 2007/0050146 | A1 | 3/2007 | Bentwich | |
| 2016/0175462 | A1 | 6/2016 | Zhang | |
| 2016/0194630 | A1 | 7/2016 | Krainer | |
| 2017/0306335 | A1 | 10/2017 | Zhang | |
| 2018/0094266 | A1 | 4/2018 | Hastings | |
| 2018/0110877 | A1 | 4/2018 | Wilson | |
| 2018/0208924 | A1 | 7/2018 | Fukuda | |
| 2018/0245128 | A1 | 8/2018 | Chuan | |
| 2018/0327784 | A1 | 11/2018 | Jin | |
| 2018/0334685 | A1 | 11/2018 | Yeo | |
| 2019/0040383 | A1* | 2/2019 | Klein | C12N 15/907 |
| 2019/0093098 | A1 | 3/2019 | Stafforst | |
| 2019/0218552 | A1 | 7/2019 | Turunen | |
| 2019/0330622 | A1 | 10/2019 | Turunen | |
| 2019/0352641 | A1 | 11/2019 | Aalto | |
| 2020/0140857 | A1 | 5/2020 | De Kimpe | |
| 2020/0149043 | A1 | 5/2020 | De Visser | |
| 2020/0199586 | A1 | 6/2020 | Klein | |
| 2020/0283755 | A1 | 9/2020 | Zhang | |
| 2020/0291383 | A1 | 9/2020 | Mandel | |
| 2020/0385713 | A1 | 12/2020 | Fraley | |
| 2020/0392486 | A1 | 12/2020 | Fraley | |
| 2020/0392496 | A1 | 12/2020 | Fukuda | |
| 2020/0399303 | A1 | 12/2020 | Fraley | |
| 2020/0407704 | A1 | 12/2020 | Zheng | |
| 2021/0019305 | A1 | 1/2021 | Hornsby | |
| 2021/0079393 | A1 | 3/2021 | Boudet | |
| 2021/0115439 | A1 | 4/2021 | Yilmaz-Elis | |
| 2021/0198673 | A1 | 7/2021 | Mali | |
| 2021/0230590 | A1 | 7/2021 | Boudet | |
| 2021/0310026 | A1 | 10/2021 | Wei | |
| 2021/0340529 | A1 | 11/2021 | Turunen | |
| 2022/0010333 | A1 | 1/2022 | Mali | |

FOREIGN PATENT DOCUMENTS

| | | | |
|---|---|---|---|
| EP | 3323890 | A1 | 5/2018 |
| EP | 3353299 | B1 | 8/2018 |
| EP | 3642342 | A1 | 4/2020 |
| EP | 3712269 | A1 | 9/2020 |
| EP | 3722420 | A1 | 10/2020 |
| GB | 1521987.6 | | 12/2015 |
| JP | 2002508959 | A | 3/2002 |
| JP | 2016182140 | A | 10/2016 |
| WO | 2004094593 | A2 | 11/2004 |
| WO | 2005003294 | A2 | 1/2005 |
| WO | 2005094370 | A2 | 10/2005 |
| WO | 2013075035 | A1 | 5/2013 |
| WO | 2014011053 | A1 | 1/2014 |
| WO | 2015021432 | A1 | 2/2015 |
| WO | 2015120197 | A1 | 8/2015 |
| WO | 2015157555 | A2 | 10/2015 |
| WO | 2016025339 | A2 | 2/2016 |
| WO | 2016094845 | A2 | 6/2016 |
| WO | 2016097212 | A1 | 6/2016 |
| WO | 2017010556 | A1 | 1/2017 |
| WO | 2017050306 | A1 | 3/2017 |
| WO | 2017064308 | A1 | 4/2017 |
| WO | 2017106767 | A1 | 6/2017 |
| WO | 2017201091 | A1 | 11/2017 |
| WO | 2017219027 | A1 | 12/2017 |
| WO | 2017220751 | A1 | 12/2017 |
| WO | 2018017144 | A1 | 1/2018 |
| WO | 2018041973 | A1 | 3/2018 |
| WO | 2018129129 | A1 | 7/2018 |
| WO | 2018134301 | A1 | 7/2018 |
| WO | 2018161032 | A1 | 9/2018 |
| WO | 2018189376 | A1 | 10/2018 |
| WO | 2018213708 | A1 | 11/2018 |
| WO | 2019005884 | A1 | 1/2019 |
| WO | 2019014262 | A1 | 1/2019 |
| WO | 2019014267 | A1 | 1/2019 |
| WO | 2019023680 | A1 | 1/2019 |
| WO | 2019043027 | A1 | 3/2019 |
| WO | 2019071048 | A1 | 4/2019 |
| WO | 2019071274 | A1 | 4/2019 |
| WO | 2019084062 | A1 | 5/2019 |
| WO | 2019094486 | A1 | 5/2019 |
| WO | 2019104094 | A2 | 5/2019 |
| WO | 2019158475 | A1 | 8/2019 |
| WO | 2019162692 | A1 | 8/2019 |
| WO | 2019217944 | A1 | 11/2019 |
| WO | 2019219581 | A1 | 11/2019 |
| WO | 2020001793 | A1 | 1/2020 |
| WO | 2020018918 | A1 | 1/2020 |
| WO | 2020023655 | A1 | 1/2020 |
| WO | 2020051555 | A1 | 3/2020 |
| WO | 2020074001 | A1 | 4/2020 |
| WO | 2020113135 | A1 | 6/2020 |
| WO | 2020118246 | A1 | 6/2020 |
| WO | 2020124257 | A1 | 6/2020 |
| WO | 2020142479 | A1 | 7/2020 |
| WO | 2020154342 | A1 | 7/2020 |
| WO | 2020154343 | A1 | 7/2020 |
| WO | 2020154344 | A1 | 7/2020 |
| WO | 2020157008 | A1 | 8/2020 |
| WO | 2020157014 | A1 | 8/2020 |
| WO | 2020160336 | A1 | 8/2020 |
| WO | 2020165077 | A1 | 8/2020 |
| WO | 2020201144 | A1 | 10/2020 |
| WO | 2020201406 | A1 | 10/2020 |
| WO | 2020211780 | A1 | 10/2020 |
| WO | 2020212567 | A1 | 10/2020 |
| WO | 2020216637 | A1 | 10/2020 |
| WO | 2020246560 | A1 | 12/2020 |
| WO | 2020252376 | A1 | 12/2020 |
| WO | 2020254249 | A1 | 12/2020 |
| WO | 2021008447 | A1 | 1/2021 |
| WO | 2021018750 | A1 | 2/2021 |
| WO | 2021020550 | A1 | 2/2021 |
| WO | 2021060527 | A1 | 4/2021 |
| WO | 2021113270 | A1 | 6/2021 |
| WO | 2021117729 | A1 | 6/2021 |
| WO | 2021130313 | A1 | 7/2021 |
| WO | 2021136404 | A1 | 7/2021 |
| WO | 2021136408 | A1 | 7/2021 |
| WO | 2021136520 | A1 | 7/2021 |
| WO | 2021175904 | A1 | 9/2021 |
| WO | 2021209010 | A1 | 10/2021 |
| WO | 2021216853 | A1 | 10/2021 |
| WO | 2021242889 | A1 | 12/2021 |
| WO | 2021261957 | A1 | 12/2021 |
| WO | 2022119975 | A2 | 6/2022 |

OTHER PUBLICATIONS

Fukuda et al, Construction of a guide-RNA for site-directed RNA mutagenesis utilising intracellular A-to-I RNA editing, Scientific Reports, 2017, vol. 7, p. 1-13.

International Search Report and Written Opinion for PCT/US2020/062756, dated Mar. 26, 2021.

Merkle et al., "Precise RNA editing by recruiting endogenous ADARs with antisense oligonucleotides," Nature Biotechnology, 2019, vol. 37(2), p. 133-138.

Qu et al., Programmable RNA editing by recruiting endogenous ADAR using engineered RNAs, Nature Biotechnology, 2019, Gale Group Inc., NY, vol. 37, No. 9, p. 1059-1069.

Thinakaran et al., Amyloid precursor protein trafficking, processing, and function. J. Biol. Chem., 2008, vol. 283, p. 29615-29619.

Ho et al., "In vivo aminoacylation of human and Xenopus suppressor IRNAs constructed by site-specific mutagenesis", Proc Natl Acad Sci U S A, Apr. 1987, 84(8):2185-8.

(56) References Cited

OTHER PUBLICATIONS

Hodges et al., The splash mouse: a missense mutation in the ornithine transcarbamylase gene also causes aberrant mRNA splicing, Proc. Natl. Acad. Sci. USA, 1989, vol. 86, p. 4142-4146.
Hsu et al., Development and applications of CRISPR-Cas9 for genome engineering. Cell, 2014, vol. 157, p. 1262-1278.
Hudziak et al., "Establishment of Mammalian Cell Lines Containing Multiple Nonsense Mutations and Functional Suppressor tRNA Genes", Cell, Nov. 1982, vol. 31, 127-146.
Hui et al., AAV capsid CD8+ T-cell epitopes are highly conserved across AAV serotypes. Mol. Ther. Methods Clin. Dev., 2015, vol. 2, p. 1-11.
Jinek, M. et al. A Programmable Dual-RNA-Guided DNA Endonuclease in Adaptive Bacterial Immunity. Science, 2012, vol. 337, p. 816-821.
Jonsson et al., A mutation in APP protects against Alzheimer's disease and age- related cognitive decline. Nature, 2012, vol. 488, p. 96-99.
Kallman et al., ADAR2 A-→I editing: site selectivity and editing efficiency are separate events, Nucleic Acids Research, 2003, vol. 31, No. 16, p. 4874-4881.
Katrekar et al., In vivo RNA editing of point mutations via RNA-guided Adenosine Deaminases, Nat Methods, 2019, vol. 16, No. 3, p. 239-242, Supplementary Figures.
Katrekar et al., In vivo RNA editing point mutations via RNA-guided adenosine deaminases, Nature Methods, 2019, vol. 16, No. 3, p. 239-242.
Katrekar, D. et al., In Vivo RNA Targeting of Ponit Mutations Via Suppressor tRNAs and Adenosine Deaminases, BioRxiv., Oct. 27, 2017, p. 1-25.
Kim et al., Widespread RNA editing of embedded alu elements in the human transcriptome. Genome Res., 2004, vol. 14, p. 1719-25.
Kim, K. et al. Highly efficient RNA-guided base editing in mouse embryos. Nat. Biotechnol., 2017, vol. 9, p. 12-15.
Kimble et al., "Suppression of an amber mutation by microinjection of suppressor tRNA in C. elegans", Nature, Sep. 30, 1982, vol. 299, No. 5882, p. 456-458.
Kiselev, et al., Suppression of Nonsense Mutations in the Dystrophin Gene by a Suppressor tRNA Gene, Mol. Biol., 2002, vol. 36, No. 1, p. 43-47.
Koeris et al., Modulation of ADAR1 editing activity by Z-RNA in vitro. Nucleic Acids Res., 2005, vol. 33, p. 5362-70.
Komor et al., Programmable editing of a target base in genomic DNA without double-stranded DNA cleavage. Nature, 2016, vol. 533, p. 420-424.
Konermann et al., Transcriptome Engineering with RNA-Targeting Type VI-D CRISPR Effectors. Cell, 2018, vol. 173, p. 665-676.
Kotterman et al., Viral Vectors for Gene Therapy: Translational and Clinical Outlook. Annu. Rev. Biomed. Eng., 2015, vol. 17, p. 63-89.
Koukuntla et al., "U6 promoter-enhanced GlnUAG suppressor tRNA has higher suppression efficacy and can be stably expressed in 293 cells", J Gene Med, Feb. 2013, vol. 15(2), p. 93-101.
Kurosaki et al., Memory B cells. Nat. Rev. Immunol., 2015, vol. 15, p. 149-159.
Kuttan et al., Mechanistic insights into editing-site specificity of ADARs, Proc. Natl. Acad. Sci., 2012, vol. 109, E3295-E3304.
Laski et al., "An amber suppressor tRNA gene derived by site-specific mutagenesis: Cloning and function in mammalian cells", Proc. Natl. Acad. Sci. USA, Oct. 1982, vol. 79, pp. 5813-5817.
Lee et al., Adeno-associated virus (AAV) vectors: Rational design strategies for capsid engineering. Curr. Opin. Biomed. Eng., 2018, vol. 7, p. 58-63.
Leger et al., Adeno-Associated Viral Vector-Mediated Transgene Expression Is Independent of DNA Methylation in Primate Liver and Skeletal Muscle. PLoS One, 2011, vol. 6, Issue 6, e20881, p. 1-11.
Lennox et al., Chemical modification and design of anti-miRNA, oligonucleotides, Gene Ther., Dec. 2011; 18(12): 1111-20.
Lewis et al., RNA Editing as a Therapeutic Approach for Retinal Gene Therapy Requiring Long Coding Sequences, Int. J. Mol. Sci., 2020, vol. 21, No. 777, p. 1-20.
Li et al., Rapamycin: one drug, many effects. Cell Metab., 2014, vol. 19, p. 373-9.
Li, et al., Ochre Suppressor Transfer RNA Restored Dystrophin Expression in MDX Mice. Life Sci., 1997, vol. 61, PL205-PL209.
Lomeli et al., "Control of kinetic properties of AMPA receptor channels by nuclear RNA editing" Science, 1994, vol. 266(5191), p. 1709-1713.
Long et al., Prevention of muscular dystrophy in mice by CRISPR/Cas9-mediated editing of germline DNA, Science, 2014, vol. 345, p. 1184-1188.
Long, C. et al., Postnatal genome editing partially restores dystrophin expression in a mouse model of muscular dystrophy, Science, vol. 351, p. 400-403, 2016.
Lueck et al., "Engineered tRNA suppression of a CFTR nonsense mutation", BioRxiv, Nov. 19, 2016, p. 1-9.
Lueck et al., "Engineered tRNA suppression of premature termination condons", Nature Commun. Feb. 18, 2019; vol. 10(1), 822, p. 1-11.
Macbeth et al., Evidence for auto-inhibition by the N terminus of hADAR2 and activation by dsRNA binding, RNA, 2004, vol. 10, pp. 1563-1571.
Mah, J. Current and emerging treatment strategies for Duchenne muscular dystrophy. Neuropsychiatr. Dis. Treat. vol. 12, 1795-1807 (2016).
Makarova et al., Snapshot: Class 2 CRISPR-Cas Systems. Cell, 2017, vol. 168, 328-328.el.
Mali, P. et al. RNA-guided human genome engineering via Cas9. Science, 2013, vol. 339, 823-826.
Malik, V. et al. Gentamicin induced readthrough of stop codons in Duchenne muscular dystrophy. Ann. Neurol. 67, NANA (2010).
Mann et al., Antisense-induced exon skipping and synthesis of dystrophin in the mdx mouse. PNAS, 2001, vol. 98, No. 1, p. 42-47.
Mays et al., The Complex and Evolving Story of T cell Activation to AAV Vector-encoded Transgene Products. Mol. Ther., 2011, vol. 19, p. 16-27.
Melcher, T. et al. A mammalian RNA editing enzyme. Nature, 1996, vol. 379, p. 460-464.
Meliani et al., Antigen-selective modulation of AAV immunogenicity with tolerogenic rapamycin nanoparticles enables successful vector re-administration. Nat. Commun., 2018, vol. 9, p. 1-13.
Mingozzi et al., Adeno-Associated Viral Vectors at the Frontier between Tolerance and Immunity. Front. Immunol., 2015, vol. 6, Article 120, p. 1-3.
Mingozzi et al., Prevalence and pharmacological modulation of humoral immunity to AAV vectors in gene transfer to synovial tissue. Gene Ther, 2013, vol. 20, p. 417-424.
Modahl et al., Transcription of hepatitis delta antigen mRNA continues throughout hepatitis delta virus (HDV) replication: a new model of HDV RNA transcription and replication. Journal of virology, 1998, vol. 72, No. 7, p. 5449-5456.
Montiel-Gonzalez et al., An efficient system for selectively altering genetic information within mRNAs. Nucleic Acids Res., 2016, vol. 44, No. 21, e157, p. 1-12.
Montiel-Gonzalez et al., Correction of mutations within the cystic fibrosis transmembrane conductance regulator by site-directed RNA editing. Proc. Natl. Acad. Sci. USA, 2013, vol. 110, p. 18285-90.
Moreno et al., In Situ Gene Therapy via AAV-CRISPR-Cas9-Mediated Targeted Gene Regulation. Mol. Ther., 2018, vol. 26, No. 7, p. 1818-1827.
Mort et al., A meta-analysis of nonsense mutations causing human genetic disease. Hum. Mutation, 2008, vol. 29, p. 1037-1047.
Abudayyeh et al., C2c2 is a single-component programmable RNA-guided RNA—targeting CRISPR effector, Science, 2016, vol. 35, p. 1-9.
Abudayyeh et al., RNA targeting with CRISPR-Cas13, Nature, 2017, vol. 550, p. 280-284.
Adamala et al., Programmable RNA-binding protein composed of repeats of a single modular unit, Proc. Natl. Acad. Sci., 2016, vol. 113, E2579-E2588.

(56) References Cited

OTHER PUBLICATIONS

Alon et al., Systematic identification of edited microRNAs in the human brain, Genome Research, 2012, vol. 22, p. 1533-1540.
Andreatta et al., Accurate pan-specific prediction of peptide-MHC class II binding affinity with improved binding core identification. Immunogenetics, 2015, vol. 67, p. 641-650.
Andreatta et al., Gapped sequence alignment using artificial neural networks: application to the MHC class I system. Bioinformatics, 2015, vol. 32, p. 511-517.
Aquino-Jarquin, Novel Engineered Programmable Systems for ADAR-Mediated RNA Editing, Molecular Therapy Nucleic Acids, 2020, vol. 19, p. 1065-1072.
Aruscavage, A phylogenetic analysis reveals an unusual sequence conservation within introns involved in RNA editing, RNA, 2000, vol. 6, p. 257-269.
Azad et al., Site-directed RNA editing by adenosine deaminase acting on RNA for correction of the genetic code in gene therapy Gene Ther., 2017, vol. 24, p. 779-786.
Bartel et al., Enhancing the clinical potential of AAV vectors by capsid engineering to evade pre-existing immunity. Front. Microbiol., 2011, vol. 2, Article 204, p. 1-10.
Basner-Tschakarjan et al., Pre-clinical assessment of immune responses to adeno-associated virus (AAV) vectors. Front. Immunol., 2014, vol. 5, p. 1-5.
Bass, B. L. (2002). RNA editing by adenosine deaminases that act on RNA. Annual review of biochemistry, 2002, vol. 71, No. 1, p. 817-846.
Battaglia et al., Rapamycin promotes expansion of functional CD4+ CD25+FOXP3+ regulatory T cells of both healthy subjects and type 1 diabetic patients. J. Immunol., 2006, vol. 177, p. 8338-47.
Bengtsson, et al., Muscle-specific CRISPR/Cas9 dystrophin gene editing ameliorates pathophysiology in a mouse model for Duchenne muscular dystrophy, Nat. Commun., 2017, vol. 8, p. 1-10.
Biddle et al., Modification of Orthogonal tRNAs: Unexpected Consequences for Sense Codon Reassignment. Nucleic Acids Research, Oct. 23, 2016, vol. 44, No. 21, p. 10042-10050.
Bidou et al., Sense from nonsense: therapies for premature stop codon diseases. Trends Mol. Med., 2012, vol. 18, p. 679-688.
Booth Brian et al., Deep Screening of Guide RNAs Enables Therapeutic RNA Editing with Endogenous ADAR, ASGCT 2021 Annual Meeting, Retrieved from the Internet: ASGCT-2021 Poster Final.
Bordeira-Carrico et al., "Rescue of wild-type E-cadherin expression from nonsense-mutated cancer cells by a suppressor-tRNA", European Journal of Human Genetics, 2014, 22, 1085-1092.
Borel et al., Recombinant AAV as a platform for translating the therapeutic potential of RNA interference. Mol. Ther., 2014, vol. 22, p. 692-701.
Boutin et al., Prevalence of Serum IgG and Neutralizing Factors Against Adeno-Associated Virus (AAV) Types 1, 2, 5, 6, 8, and 9 in the Healthy Population: Implications for Gene Therapy Using AAV Vectors. Hum. Gene Ther., 2010, vol. 21, p. 704-712.
Brendel et al., Readthrough of nonsense mutations in Rett syndrome: evaluation of novel aminoglycosides and generation of a new mouse model, J. Mol. Med, 2011, vol. 89, p. 389-398.
Bulfield et al., X chromosome-linked muscular dystrophy (mdx) in the mouse, Proc. Natl. Acad. Sci. USA, 1984, vol. 81, 1189-92.
Burstein et al., New CRISPR-Cas systems from uncultivated microbes. Nature, 2017, vol. 542, p. 1-28.
Buvoli et al., "Suppression of Nonsense Mutations in Cell Culture and Mice by Multimerized Suppressor tRNA Benes", Mol Cell Biol., May 2000, 20(9): 3116-3124.
Calcedo et al., AAV Natural Infection Induces Broad Cross-Neutralizing Antibody Responses to Multiple AAV Serotypes in Chimpanzees. Hum. Gene Ther. Clin. Dev., 2016, vol. 27, p. 79-82.
Capecchi, Altering the genome by Homologous Recombination, Science, 1989, vol. 244, 1288-1292.
Capone, et al., Amber, ochre and opal suppressor tRNA genes derived from a human serine tRNA gene. EMBO J., 1985, vol. 4, p. 213-21.
Casey J. L., Control of ADAR1 editing of hepatitis delta virus RNAs. Curr Top Microbiol, 2012, vol. 353, p. 123-143.
Chang et al., "Suppression of the nonsense mutation in homozygous β0 thalassaemia", Nature, Oct. 18, 1979, vol. 281, No. 5732, p. 602-603.
Chang et al., Replication of the human hepatitis delta virus genome is initiated in mouse hepatocytes following Intravenous injection of naked DNA or RNA sequences. Journal of virology, 2001, vol. 75, No. 7, p. 3469-3473.
Chatterjee et al., Efficient viral delivery system for unnatural amino acid mutagenesis in mammalian cells. PNAS, 2013, vol. 110, p. 11803-11808.
Cong et al., Multiplex genome engineering using CRISPR/Cas systems. Science, 2013, vol. 339, p. 819-23.
Chen et al., Determination of specific CD4 and CD8 T cell epitopes after AAV2- and AAV8-hF.IX gene therapy. Mol Ther, 2006, vol. 13, p. 260-269.
Chen et al., Recoding RNA editing of AZIN1 predisposes to hepatocellular carcinoma. Nat. Med., 2013, vol. 19, p. 209-216.
Chew et al., A multifunctional AAV-CRISPR-Cas9 and its host response. Nature Methods, 2016, vol. 13, No. 10, p. 868-874.
Cho, S. W. et al., Analysis of off-target effects of CRISPR/Cas-derived RNA-guided endonucleases and nickases. Genome Res., 2014, vol. 24, p. 132-141.
Christian, M. et al. Targeting DNA Double-Strand Breaks with TAL Effector Nucleases. Genetics, 2010, vol. 186, p. 757-761.
Chung et al., Human ADAR1 Prevents Endogenous RNA from Triggering Translational Shutdown. Cell, 2018, vol. 172, p. 811-824.
Chylinski et al., E. V. Classification and evolution of type II CRISPR-Cas systems. Nucleic Acids Research, 2014, vol. 42, p. 6091-6105.
Cirak, S. et al. Exon skipping and dystrophin restoration in patients with Duchenne muscular dystrophy after systemic phosphorodiamidate morpholino oligomer treatment: an open label, phase 2, dose escalation study. Lancet 378, 595-605 (2011).
Clemente et al., In vivo assessment of specific cytotoxic T lymphocyte killing. Methods, 2013, vol. 61, p. 105-109.
Cox et al., RNA editing with CRISPR-Cas13, Science, 2017, vol. 358, p. 1019-1027.
Daniel et al. "Editing inducer elements increases A-to-I editing efficiency in the mammalian transciptome," Genome Biology, 2017, 18:195, pp. 1-16.
Daniel et al., "Alu elements shape the primate transcriptome by cis-regulation of RNA editing," Genome Biology, 15: R28, pp. 1-17, 2014.
Deaton et al., CpG islands and the regulation of transcription. Genes Dev., 2011, vol. 25, p. 1010-22.
Degroot et al., De-immunization of therapeutic proteins by T-cell epitope modification. Dev. Biol., 2005, vol. 122, p. 171-194 (2005).
Desterro et al, Dynamic association of RNA-editing enzymes with the nucleolus J Cell Sci., May 2003; 116(Pt 9): 1805-18.
Deverman et al., Cre-dependent selection yields AAV variants for widespread gene transfer to the adult brain. Nat. Biotechnol., 2016, vol. 34, p. 204-209.
East-Seletsky et al., A RNA Targeting by Functionally Orthogonal Type VI-A CRISPR-Cas Enzymes, Mol. Cell, 2017, vol. 66, 373-383, e3.
East-Seletsky et al., Two distinct RNase activities of CRISPR-C2c2 enable guide-RNA processing and RNA detection. Nature, 2016, vol. 538, p. 270-273.
Eggington et al., "Predicting sites of ADAR editing in double-stranded RNA," Nature Communications. Feb. 2011, vol. 2, No. 319, pp. 1-9.
Ellis et al., A survey of ex vivo/in vitro transduction efficiency of mammalian primary cells and cell lines with Nine natural adeno-associated virus (AAV 1-9) and one engineered adeno-associated virus serotype. Virol. J., 2013, vol. 10, p. 1-10.
Ernst, R. J. et al. Genetic code expansion in the mouse brain. Nat. Chem. Bio, 2016, p. 1-5.
Ertl et al., Impact of AAV Capsid-Specific T-Cell Responses on Design and Outcome of Clinical Gene Transfer Trials with Recom-

(56) References Cited

OTHER PUBLICATIONS binant Adeno-Associated Viral Vectors: An Evolving Controversy. Hum. Gene Ther., 2017, vol. 28, p. 328-337.
Faust et al., CpG-depleted adeno-associated virus vectors evade immune detection. J. Clin. Invest., 2013, vol. 123, p. 2994-3001.
Ferdosi et al., Multifunctional CRISPR/Cas9 with engineered immunosilenced human T cell epitopes. Nature Comm., 2019, vol. 10; p. 18-42.
Fu et al., Improving CRISPR-Cas nuclease specificity using truncated guide RNAs, Nat. Biotechnol., 2014, vol. 32, p. 279-84.
Gabriel et al., Bioengineering of AAV2 Capsid at Specific Serine, Threonine, or Lysine Residues Improves Its Transduction Efficiency in vitro and in vivo. Hum. Gene Ther. Methods, 2013, vol. 24, p. 80-93.
Gallo et al., ADARs: allies or enemies? The importance of A-to-I RNA editing in human disease: from cancer to HIV-1. Biological Reviews, 2012, 87(1), 95-110.
Gao et al., New Recombinant Serotypes of AAV Vectors. Curr. Gene Ther., 2005, vol. 5, p. 285-297.
Garncarz et al., "A high-throughput screen to identify enhancers of ADAR-mediated RNA-editing", RNA Biology, 2013, 10:2, 192-204.
Gatti, SMRT Compounds Correct Nonsense Mutations in Primary Immunodeficiency and Other Genetic Models, Annals of the New York Academy of Sciencers, Feb. 2012, vol. 1250, p. 1-13.
Gaudelli, N. M. et al., Programmable base editing of AT to G.C in genomic DNA without DNA cleavage, Nature, 2017, vol. 551, p. 464-471.
Gautier et al., Genetically Encoded Photocontrol of Protein Localization in Mammalian Cells, J. Am. Chem. Soc., 2010, vol. 132, p. 4086-4088.
Gernoux et al., Regulatory and Exhausted T Cell Responses to AAV Capsid, Hum. Gene Ther., 2017, vol. 28, p. 338-349.
Geslain et al., Functional analysis of human tRNA isodecoders, J. Mol. Biol, 2010, vol. 396, p. 1-20.
Gootenberg et al., Nucleic acid detection with CRISPR-Cas13a/C2c2, Science, 2017, vol. 356, p. 438-442.
Gorman et al., Stable alteraction of pre-mRNA splicing patterns by modified U7 small nuclear RNAs, PNAS, 1998, vol. 95, No. 9, p. 4929-4934.
Gou et al., A novel approach for the construction of multiple shRNA expression vectors, J. Gene Med, 2007, vol. 9, p. 751-763.
Greiss et al., Expanding the Genetic Code of an Animal, American Chemistry Society, 2011, vol. 2, p. 14196-14199.
Grieger et al., Production and characterization of adeno-associated viral vectors, Nat. Protoc., 2006, vol. 1, p. 1412-1428.
Grimm et al., In vitro and In vivo Gene Therapy Vector Evolution via Multispecies Interbreeding and Retargeting of Adeno-Associated Viruses. J. Virol., 2008, vol. 82, p. 5887-5911.
Han, S. et al. Expanding the genetic code of Mus musculus. Nat. Commun., 2017, vol. 8, p. 1-7.
Hanswillemenke et al., Site-Directed RNA Editing in vivo Can Be Triggered by the Light- Driven Assembly of an Artificial Riboprotein. JACS, 2015, vol. 137, p. 15875-15881.
Harbison et al., Examining the cross-reactivity and neutralization mechanisms of a panel of mabs against adeno-associated virus serotypes 1 and 5. J. Gen. Virol., 2012, vol. 93, p. 347-355.
Harding et al., The immunogenicity of humanized and fully human antibodies: Residual immunogenicity resides in the CDR regions. MAbs, 2010, vol. 2, p. 256-265.
Heep et al., Applying Human ADARlpl IO and ADARlpl50 for Site-Directed RNA Editing—G/C Substitution Stabilizes GuideRNAs against Editing. Genes, 2017, vol. 8, No. 34, p. 1-7.
Hendel, A. et al.. Chemically modified guide RN As enhance CRISPR-Cas genome editing in human primary cells. Nature Biotechnology, 33(9), pp. 985-989 (2015).
Herbert, Z-DNA and Z-RNA in human disease. Communications Biology, 2019, vol. 2, p. 1_10.
Higuchi et al, RNA editing of AMPA receptor subunit GluR-B: A base-paired intron-exon structure determines position and efficiency, Cell., 1993, vol. 75, p. 1361-1370.
Hinderer et al., Severe toxicity in nonhuman primates and piglets following high-dose intravenous administration of an AAV vector expressing human SMN. Hum Gene Ther, 2018, vol. 29, No. 3, p. 285-300.
Hirsch et al., Rationally Designed AAV Inverted Terminal Repeats Enhance Gene Targeting. Mol. Ther., 2016, vol. 24, S129.
Altschul et al., Basic Local Alignment Search Tool, J. Mol. Biol., 1990, vol. 215, p. 403-410.
Harper Scott: "Progress Update: DUX4 mRNA silencing using RNA editing", Friends of FSH Research, 2021, 2 pages.
International Search Report and Written Opinion for PCT/US2022/030503 dated Oct. 20, 2022.
Jouberet al: "Gene Editing Targeting the DUX4 Polyadenylation Signal: A Therapy for FSHD?", Journal of Personalized Medicine, 2020, vol. 11, No. 7, pp. 1-10.
Lim. et al: "Genetic Approaches for the Treatment of Facioscapulohumeral Muscular Dystrophy", Frontiers in Pharmacology, 2021, vol. 12, Article 643858, p. 1-14.
Lu-Nguyen et al: "Systemic antisense therapeutics inhibiting DUX4 expression ameliorates FSHD-like pathology in an.FSHD mouse model"+A53, Human Molecular Genetics, 2021, vol. 30, No. 15, pp. 1398-1412.
Marsollier et al: "Antisense targeting of 3' end elements involved in DUX4 mRNA processing is an efficient therapeutic strategy for facioscapulohumeral dystrophy: a new gene-silencing approach", Human Molecular Genetics, 2016, p. 1-11.
Montiel-Gonzalez et al: Current strategies for Site-Directed RNA Editing using ADARs, Current strategies for Site-Directed RNA Editing using ADARs, METHODS, 2019, vol. 56, p. 16-24.
Savva et al., The ADAR protein family; Genome Biology, 2012, vol. 13, No. 252, p. 1-10.
Sikrova D et al: "Adenine base editing of the DUX4 somatic polyadenylation signal in facioscapulohumeral muscular dystrophy", ASHG 2019 Annual Meeting, Abstract.
Nelson et al., In vivo genome editing improves muscle function in a mouse model of Duchenne muscular dystrophy, Science, 2016, vol. 351, p. 403-407.
Nishikura (2010), "Functions and Regulation of RNA Editing by ADAR Deaminases", Annu Rev Biochem., 79, pp. 321-349.
Nishikura K., Editor meets silencer: crosstalk between RNA editing and RNA interference. Nature Reviews Molecular and Cellular Biology, 2006, vol. 7, p. 919-931.
Nose et al, Short-Chain Guide RNA for Site-Directed A-to-I RNA Editing, Nucleic Acid Therapeutics, 2020, vol. 31, No. 1, p. 1-10.
O'Connell et al., Programmable RNA recognition and cleavage by CRISPR/Cas9. Nature, 2014, vol. 516, p. 263-266.
Panchal et al., Partial Functional Correction of Xeroderma Pigmentosum Group A Cells by Suppressor tRNA. Hum. Gene Ther., 1999, vol. 10, p. 2209-2219.
Peisley et al., Cooperative assembly and dynamic disassembly of MDA5 filaments for viral dsRNA recognition. PNAS, 2011, vol. 108, p. 21010-21015.
Pinello et al., Analyzing CRISPR genome-editing experiments with CRISPResso. Nat. Biotechnol., 2016, vol. 34, p. 695-697.
Qu et al., "Leveraging Endogenous ADAR for Programmable Editing on RNA", bioRxiv, Apr. 19, 2019, 46 pages.
Raikwar et al., Next Generation Precision Medicine: CRISPR-mediated Genome Editing for the Treatment of Neurodegenerative Disorders, Journal of Neuroimmue Pharmacology, 2019, vol. 14, No. 4, p. 608-641.
Ran et al., In vivo genome editing using *Staphylococcus aureus* Cas9. Nature, 2015, vol. 520, p. 186-190.
Reider et al, Tertiary structural elements determine the extent and specificity of messenger RNA editing, Nat. Commun., Feb. 2013, vol. 4, p. 1-11.
Riviere et al., Long-term expression and repeated administration of AAV type 1, 2 and 5 vectors in skeletal muscle of Immunocompetent adult mice. Gene Ther., 2006, vol. 13, p. 1300-1308.

(56) References Cited

OTHER PUBLICATIONS

Robinson-Hamm et al., Gene therapies that restore dystrophin expression for the treatment of Duchenne muscular dystrophy, Hum. Genet., 2016, vol. 135, p. 1029-1040.
Rogers et al., TLR9 and Dendritic Cells Are Required for CD8+ T Cell Responses to the AAV Capsid. Blood, 2014, vol. 124.
Rueter et al., Glutamate receptor RNA editing in vitro by enzymatic conversion of adenosine to inosine. Science, 1995, vol. 267, p. 1491-4.
Sako et al., "A novel therapeutic approach for genetic diseases by introduction of suppressor tRNA", Nucleic Acids Symposium Series , 2006, No. 50, 239-240.
Schade et al., "A 6 bp Z-DNA hairpin binds two Za domains from the human RNA editing enzyme ADAR1", FEBS Letters, Sep. 3, 1999, vol. 458, p. 27-31.
Schaefer, K. A. et al. Unexpected mutations after CRISPR—Cas9 editing in vivo Digenome-seq web tool for profiling CRISPR specificity. Nature, 2017, vol. 14, p. 547-548.
Schneider et al., "Optimal guide-RNAs for re-directing deaminase activity of hADAR1 and hADAR2 in trans", Nucleic Acids Research, Apr. 17, 2014, vol. 42, No. 10, e87, pp. 1-9.
Senis et al., "CRISPR/Cas9-mediated genome engineering: An adeno-associated viral (AAV) vector toolbox," Biotechnol. J., 2014, vol. 9, p. 1402-1412.
Shao et al., Double-stranded RNA innate immune response activation from long term adeno-associated virus vector transduction. JCI Insight, 2018, vol. 3, p. 1-15.
Shen et al., Engraftment of a Galactose Receptor Footprint onto Adeno-associated Viral Capsids Improves Transduction Efficiency. J. Biol. Chem., 2013, vol. 288, p. 28814-28823.
Sicinski et al., The molecular basis of muscular dystrophy in the mdx mouse: a point mutation. Science, 1989, vol. 244, p. 1578-80.
SignaGen, SignaGen, pp. 1-2, 2015.
Sinnamon et al., Site-directed RNA repair of endogenous Mecp2 RNA in neurons. PNAS, 2017, vol. 114, E9395-E9402.
Smalley, First AAV gene therapy poised for landmark approval. Nat. Biotechnol., 2017, No. 11, p. 998-999.
Smith et al., Creating an arsenal of Adeno-associated virus (AAV) gene delivery stealth vehicles. PLOS Pathog, 2018, p. 1-6.
Stafforst et al., An RNA-Deaminase Conjugate Selectively Repairs Point Mutations. Angew. Chemie Int. Ed., 2012, vol. 51, p. 11166-11169.
Stefl et al., A novel RNA pentaloop fold involved in targeting ADAR2, RNA, 2005, vol. 11(5), pp. 592-597.
Stribling, et al., "Aerosol Gene Delivery In Vivo," Proc. Natl. Acad. Sci. USA, 1992, vol. 89, p. 11277-11281.
Sun et al., CRISPR/Cas9 editing of APP C-terminus attenuates b-cleavage and promotes a-cleavage. Nat. Commun., 2019, vol. 10, p. 1-11.
Sun et al., The physical approximation of APP and BACE-I: A key event in alzheimer's disease pathogenesis. Dev. Neurobiol., 2018, vol. 78, p. 340-347.
Svoboda et al., (2006), "Hairpin RNA: a secondary structure of primary importance", Cell Mo/ Life Sci. (7-8), pp. 901-908.
Tabebordbar, M. et al., In vivo gene editing in dystrophic mouse muscle and muscle stem cells, Science, 2016, vol. 351, p. 407-411.
Takata, M. et al. Homologous recombination and non-homologous end-joining pathways of DNA double-strand break repair have overlapping roles in the maintenance of chromosomal integrity in vertebrate cells. EMBO J., 1988, vol. 17, p. 5497-508.
Tan et al.,. Dynamic landscape and regulation of RNA editing in mammals. Nature, 2017, vol. 550, p. 249-254.
Temple et al., "Construction of a functional human suppressor tRNA gene: an approach to gene therapy for β-thalassaemia", Nature, Apr. 1, 1982, vol. 296, p. 537-540.
Truong et al., Development of an intein-mediated split-Cas9 system for gene therapy. Nucleic Acids Res., 2015, vol. 13, p. 6450-6458.
Tuerk et al., CUUCGG hairpins: Extraordinarily stable RNA secondary structures associated with various biochemical processes (hairpin stability/sequence analysis/reverse transcriptase). Biochemistry, 1988, vol. 85, p. 1364-1368.
UniProt "Adenosine deaminase RNA specific BI from Western lowland gorilla", XP002805391, 2011, retrieved from EBI accession No. UNIPROT:G3RBQ6 Database accession No. G3RBQ6 sequence.
Urnov, F. D. et al. Highly efficient endogenous human gene correction using designed zinc-finger nucleases. Nature 435, 646-651 (2005).
Urnov, F. D., Rebar, E. J., Holmes, M. C., Zhang, H. S. & Gregory, P. D. Genome editing with engineered zinc finger nucleases. Nat. Rev. Genet. 11, 636-646 (2010).
Vallecillo-Viejo et al., Abundant off-target edits from site-directed RNA editing can be reduced by nuclear localization of the editing enzyme. RNA Biol., 2018, vol. 15, p. 104-114.
Varani et al., Structure of an Unusually Stable RNA Hairpint, Biochemistry, 1991, vol. 30, p. 3280-3289.
Veronese et al., The impact of PEGylation on biological therapies. BioDrugs, 2008, vol. 22, p. 315-329.
Vogel et al., "Improving Site-Directed RNA Editing In vitro and in Cell Culture by Chemical Modification of the GuideRNA", Angewandte Chemie, 2014, vol. 53(24), p. 6267-6271.
Vogel et al., Efficient and precise editing of endogenous transcripts with SNAP-tagged ADARs. Nat. Methods, 2018, vol. 15, p. 535-538.
Wong et al., (2001), "Substrate recognition by ADAR1 and ADAR2", RNA, 7(6), pp. 846-858.
International Preliminary Examination Report on Patentability & Written Opinion, PCT/US2018/020762, The International Bureau of WIPO, dated Sep. 12, 2019.
International Search Report & Written Opinion, PCT/US2018/020762 dated Aug. 1, 2018 (dated Jul. 17, 2018).
International Search Report and Written Opinion for PCT/US2021/028618, dated Oct. 11, 2021.
International Search Report and Written Opinion for PCT/US2021/034272, dated Sep. 13, 2021.
International Search Report and Written Opinion for PCT/US2021/034323, dated Dec. 6, 2021.
International Search Report and Written Opinion for PCT/US2021/049530, dated Apr. 14, 2022.
International Search Report and Written Opinion for PCT/US2021/058799, dated Feb. 22, 2022.
International Search Report for PCT/US2019/050095, dated Feb. 12, 2020.
Wagner et al., High prevalence of S. pyogenes Cas9-specific T cell sensitization within the adult human population—A balanced effector/regulatory T cell response. bioRxiv 2018.
Wagner, K. R. et al. Gentamicin treatment of Duchenne and Becker muscular dystrophy due to nonsense mutations. Ann. Neurol. 49, 706-11 (2001).
Walters et al., Structure of Adeno-Associated Virus Serotype 5. J. Virol., 2004, vol. 78, p. 3361-3371.
Wang et al., "A Phenotypic Screen for Functional Mutants of Human Adenosine Deaminase Acting on RNA 1", ACS Chemical Biology, 2015, vol. 10, No. 11, pp. 2512-2519.
Wang et al., Adenovirus Mediated Somatic Genome Editing of Pten by CRISPR/Cas9 in Mouse Liver in Spite of Cas9-Specific Immune Responses. Hum Gene Ther., 2015, vol. 26, No. 7, p. 432-442.
Wang et al., Expanding the Genetic Code of *Escherichia coli*. Science, 2001, vol. 292, p. 498-500.
Weinmann et al., Next-generation AAV vectors for clinical use: an ever-accelerating race. Virus Genes, 2017, vol. 53, p. 707-713.
Welch, E. M. et al. PTC 124 targets genetic disorders caused by nonsense mutations. Nature 447, 87-91 (2007).
Wettengel et al., Harnessing human ADAR2 for RNA repair—recoding a PINK.I mutation rescues mitophagy. Nucleic Acids Research, 2016, vol. 45, No. 5, p. 2797-2808.
Woolf et al., "Toward the therapeutic editing of mutated RNA sequences", Proc. Natl. Acad. Sci. USA, Aug. 1995, vol. 92, pp. 8298-8302.
Xie et al., Adeno-associated virus-mediated microRNA delivery and therapeutics. Semin. Liver Dis., 2015, vol. 35, p. 81-8.

(56) References Cited

OTHER PUBLICATIONS

Xie et al., The atomic structure of adeno-associated virus (AAV-2), a vector for human gene therapy. PNAS, 2002, vol. 99, p. 10405-10.
Yamashita et al., Rescue of amyotrophic lateral sclerosis phenotype in a mouse model by intravenous AAV9-ADAR2 delivery to motor neurons, EMBO Mol Med, 2013, vol. 5, p. 1710-1719.
Yang et al., A dual AA V system enables the Cas9-mediated correction of a metabolic liver disease in newborn mice, Nat. Biotechnol., 2016, vol. 34, p. 334-338.
Yang et al., Intracellular localization of differentially regulated RNA-specific adenosine deaminase isoforms in inflammation. J. Biol. Chem., 2003, vol. 278, p. 45833-42.
Zabel et al., Distinct T helper cell dependence of memory B-cell proliferation versus plasma cell differentiation. Immunology, 2017, vol. 150, p. 329-342.
Zhong et al., Next generation of adeno-associated virus 2 vectors: Point mutations in tyrosines lead to high-efficiency transduction at lower doses; PNAS, vol. 105, No. 22, pp. 7827-7832, 2008.
Zhu et al., The TLR9-MyD88 pathway is critical for adaptive immune responses to adeno-associated virus gene therapy vectors in mice. J. Clin. Invest., 2009, vol. 119, p. 2388-2398.
Zinn et al., In Silico Reconstruction of the Viral Evolutionary Lineage Yields a Potent Gene Therapy Vector. Cell Rep., 2017, vol. 12, p. 1056-1068.

* cited by examiner

A673T mutation is protective (reduced Aβ1-42, improved cognition with age), suggests reduced BACE1 cleavage

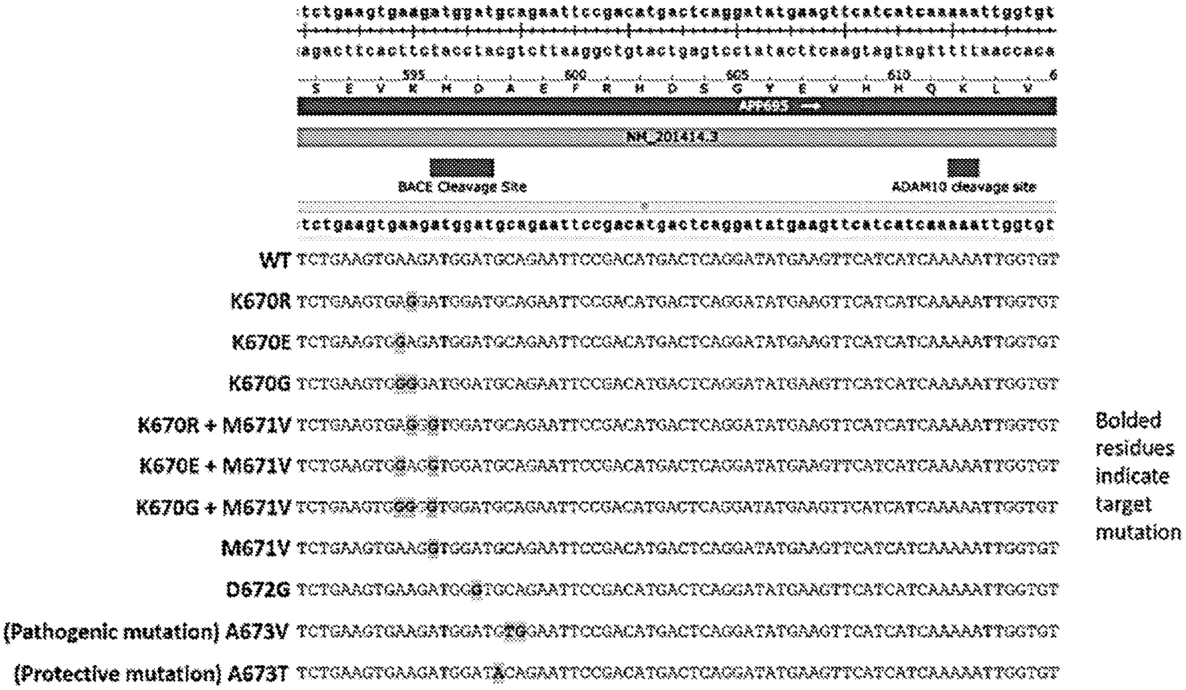

Fig. 7

```
                   tctgaagtgaagatggatgcagaattccgacatgactcaggatatgaagttcatcatcaaaaattggtgt
                   agacttcacttctacctacgtcttaaggctgtactgagtcctatacttcaagtagtagttttttaaccaca
                      595        600        605        610              6
                    S  E  V  K  M  D  A  E  F  R  H  D  S  G  Y  E  V  H  H  Q  K  L  V
                                              APP⇒
                                              NM_201414.3
                           BACE Cleavage Site                    ADAM10 cleavage site
                   tctgaagtgaagatggatgcagaattccgacatgactcaggatatgaagttcatcatcaaaaattggtgt
            WT     TCTGAAGTGAAGATGGATGCAGAATTCCGACATGACTCAGGATATGAAGTTCATCATCAAAAATTGGTGT
            K670R  TCTGAAGTGAGGATGGATGCAGAATTCCGACATGACTCAGGATATGAAGTTCATCATCAAAAATTGGTGT
            K670E  TCTGAAGTGGAGATGGATGCAGAATTCCGACATGACTCAGGATATGAAGTTCATCATCAAAAATTGGTGT
            K670G  TCTGAAGTGGGGATGGATGCAGAATTCCGACATGACTCAGGATATGAAGTTCATCATCAAAAATTGGTGT
    K670R + M671V  TCTGAAGTGAGGTGGATGCAGAATTCCGACATGACTCAGGATATGAAGTTCATCATCAAAAATTGGTGT   Bolded
    K670E + M671V  TCTGAAGTGGAGGTGGATGCAGAATTCCGACATGACTCAGGATATGAAGTTCATCATCAAAAATTGGTGT   residues
    K670G + M671V  TCTGAAGTGGGGGTGGATGCAGAATTCCGACATGACTCAGGATATGAAGTTCATCATCAAAAATTGGTGT   indicate
            M671V  TCTGAAGTGAAGGTGGATGCAGAATTCCGACATGACTCAGGATATGAAGTTCATCATCAAAAATTGGTGT   target
            D672G  TCTGAAGTGAAGATGGGTGCAGAATTCCGACATGACTCAGGATATGAAGTTCATCATCAAAAATTGGTGT   mutation
(Pathogenic mutation) A673V  TCTGAAGTGAAGATGGATGCGGAATTCCGACATGACTCAGGATATGAAGTTCATCATCAAAAATTGGTGT
(Protective mutation) A673T  TCTGAAGTGAAGATGGATACAGAATTCCGACATGACTCAGGATATGAAGTTCATCATCAAAAATTGGTGT
```

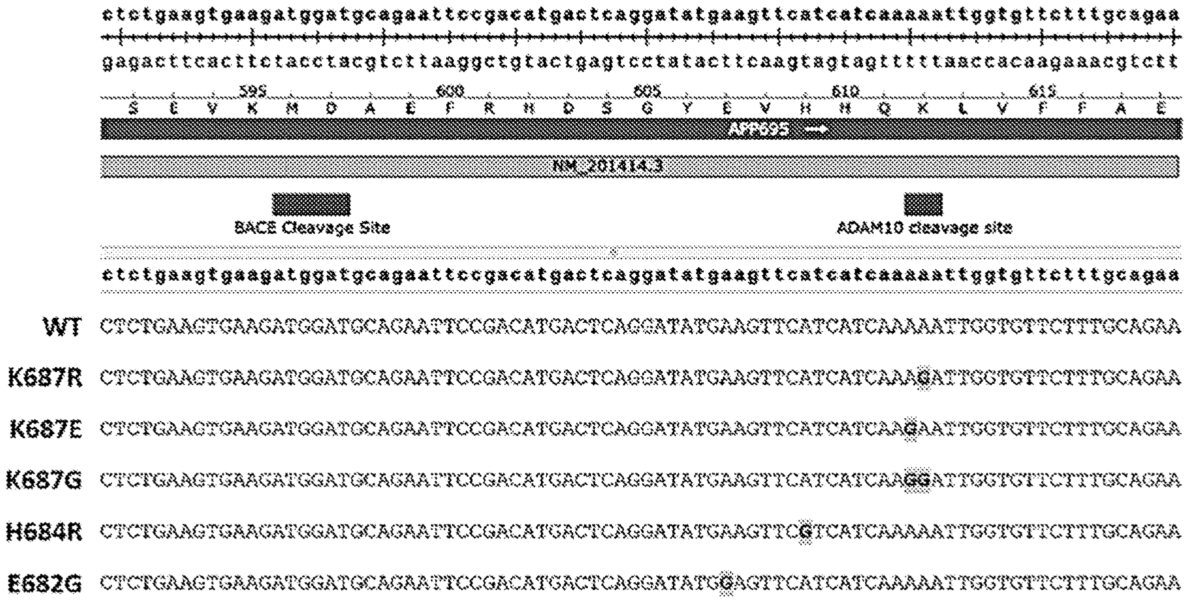

Fig. 8

```
      ctctgaagtgaagatggatgcagaattccgacatgactcaggatatgaagttcatcatcaaaaattggtgttctttgcagaa
      gagacttcacttctacctacgtcttaaggctgtactgagtcctatacttcaagtagtagttttttaaccacaagaaacgtctt
           595            600            605            610            615
       S  E  V  K  M  D  A  E  F  R  H  D  S  G  Y  E  V  H  H  Q  K  L  V  F  F  A  E
                                         APP695 →
                                         NM_201414.3
                BACE Cleavage Site                              ADAM10 cleavage site
      ctctgaagtgaagatggatgcagaattccgacatgactcaggatatgaagttcatcatcaaaaattggtgttctttgcagaa

WT    CTCTGAAGTGAAGATGGATGCAGAATTCCGACATGACTCAGGATATGAAGTTCATCATCAAAAATTGGTGTTCTTTGCAGAA
K687R CTCTGAAGTGAAGATGGATGCAGAATTCCGACATGACTCAGGATATGAAGTTCATCATCAAAGATTGGTGTTCTTTGCAGAA
K687E CTCTGAAGTGAAGATGGATGCAGAATTCCGACATGACTCAGGATATGAAGTTCATCATCAAGAATTGGTGTTCTTTGCAGAA
K687G CTCTGAAGTGAAGATGGATGCAGAATTCCGACATGACTCAGGATATGAAGTTCATCATCAAGGATTGGTGTTCTTTGCAGAA
H684R CTCTGAAGTGAAGATGGATGCAGAATTCCGACATGACTCAGGATATGAAGTTCGTCATCAAAAATTGGTGTTCTTTGCAGAA
E682G CTCTGAAGTGAAGATGGATGCAGAATTCCGACATGACTCAGGATATGGAGTTCATCATCAAAAATTGGTGTTCTTTGCAGAA
```

Mutated residue(s) shown in bold

ADAR2 domains

78-144 DRBM 1

231-298 DRBM 2

370-737 A to I editase

THERAPEUTIC EDITING

CROSS-REFERENCE

This application is a national phase application of PCT/US2020/062756, filed Dec. 1, 2020, which claims the benefit of U.S. Provisional Application Ser. No. 63/112,286, filed Nov. 11, 2020, U.S. Provisional Application Ser. No. 63/030,165, filed May 26, 2020, U.S. Provisional Application Ser. No. 63/022,727, filed May 11, 2020, U.S. Provisional Application Ser. No. 62/942,693, filed Dec. 2, 2019, U.S. Provisional Application Ser. No. 62/942,667, filed Dec. 2, 2019, and U.S. Provisional Application Ser. No. 62/942,683, filed Dec. 2, 2019, the disclosures of which are incorporated herein by reference in their entirety.

SEQUENCE LISTING

The instant application contains a Sequence Listing which has been submitted electronically in ASCII format and is hereby incorporated by reference in its entirety. Said ASCII copy, created on Dec. 1, 2020, is named 54761-712_601_SL.txt and is 353,400 bytes in size.

SUMMARY

Disclosed herein, in some embodiments, are engineered polynucleotides. In an aspect, an engineered polynucleotide comprises an engineered polynucleotide comprising a targeting sequence that is at least partially complementary to a region of a target RNA, wherein the region of the target RNA: (a) comprises a sequence that at least partially encodes for an amyloid precursor protein (APP) polypeptide; (b) comprises a sequence that is proximal to (a); or (c) comprises (a) and (b); and wherein the engineered polynucleotide is configured to facilitate an editing of a base of a nucleotide of the target RNA by an RNA editing entity.

In some embodiments, the editing of the base of the nucleotide of the target RNA by the RNA editing entity facilitates an increase or a decrease of: (a) a processing; (b) a cleavage; or (c) (a) and (b), of the APP polypeptide by a secretase enzyme, relative to an APP polypeptide encoded by the target RNA without the editing. In some embodiments, the secretase enzyme comprises: an alpha secretase; a beta secretase; a gamma secretase; or a combination thereof. In some embodiments, the secretase enzyme comprises the beta secretase, and wherein the beta secretase comprises beta-site amyloid precursor protein cleaving enzyme 1 (BACE1), cathepsin B, or Meprin beta.

In some embodiments, the engineered polynucleotide, when associated with the target RNA, further comprises a structural feature which at least in part recruits the RNA editing entity. In some embodiments, the structural feature comprises a bulge, an internal loop, a hairpin, a mismatch, a wobble base pair, or any combination thereof. In some embodiments, the structural feature comprises the bulge. In some embodiments, the bulge comprises an asymmetric bulge. In some embodiments, the bulge comprises a symmetric bulge. In some embodiments, the bulge comprises from about 1 to about 4 nucleotides of the engineered polynucleotide and from about 0 to about 4 nucleotides of the target RNA. In some embodiments, the bulge comprises from about 0 to about 4 nucleotides of the engineered polynucleotide and from about 1 to about 4 nucleotides of the target RNA. In some embodiments, the bulge comprises 3 nucleotides of the engineered polynucleotide and 3 nucleotides of the target RNA. In some embodiments, the structural feature comprises the internal loop. In some embodiments, the internal loop comprises an asymmetric internal loop. In some embodiments, the internal loop comprises a symmetric internal loop. In some embodiments, the internal loop is formed by from about 5 to about 10 nucleotides of either the engineered polynucleotide or the target RNA. In some embodiments, the structural feature comprises the hairpin. In some embodiments, the hairpin comprises a double stranded RNA molecule, and wherein the hairpin does not comprise the targeting sequence. In some embodiments, wherein a stem loop of the hairpin is from about 3 to about 15 nucleotides in length. In some embodiments, the structural feature comprises the mismatch. In some embodiments, the mismatch comprises a base in the targeting sequence of the engineered polynucleotide opposite to and unpaired with the base of the nucleotide of the target RNA. In some embodiments, the mismatch comprises a guanine-guanine mismatch. In some embodiments, the mismatch comprises an adenosine-cytosine mismatch, and wherein the adenosine is in the target RNA and the cytosine is in the targeting sequence of the engineered polynucleotide. In some embodiments, the adenosine in the adenosine-cytosine mismatch is the base of the nucleotide in the target RNA edited by the RNA editing entity. In some embodiments, the structural feature comprises the wobble base pair. In some embodiments, the wobble base pair comprises a guanine paired with a uracil. In some embodiments, the structural feature comprises a structural motif, and wherein the structural motif comprises two bulges and an adenosine-cytosine mismatch.

In some embodiments, the engineered polynucleotide further comprises an RNA editing entity recruiting domain that is capable of recruiting the RNA editing entity. In some embodiments, the RNA editing entity comprises an adenosine deaminase acting on RNA (ADAR) polypeptide or biologically active fragment thereof. In some embodiments, the ADAR polypeptide or the biologically active fragment thereof comprises ADAR1, ADAR2, or a biologically active fragment of any of these. In some embodiments, the ADAR polypeptide or biologically active fragment thereof is synthetically overexpressed in a neuronal cell that comprises the target RNA. In some embodiments, the engineered polynucleotide does not comprise an RNA editing entity recruiting domain. In some embodiments, the nucleotide is comprised in a codon which encodes an amino acid in proximity to a cleavage site of the APP polypeptide, and wherein the amino acid is at position 670, 671, 672, 673, 682, 684, 687, 712, or 714 of the APP polypeptide comprising the polypeptide sequence of SEQ ID NO: 2. In some embodiments, the cleavage site is selected from the group consisting of: an alpha-secretase cleavage site, a beta-secretase cleavage site, a beta'-secretase cleavage site, a gamma-secretase cleavage site, and any combination thereof. In some embodiments, the target RNA encodes for an unmodified APP polypeptide that comprises at least one amino acid residue difference as compared to the modified APP polypeptide generated from the editing of the base of the nucleotide of the target RNA. In some embodiments, the at least one amino acid residue difference comprises K670E, K670R, K670G, M671V, D672G, E682G, H684R, K687R, K687E, or K687G of the APP polypeptide comprising the polypeptide sequence of SEQ ID NO: 2. In some embodiments, the at least one amino acid residue difference comprises K670G or M671V of the APP polypeptide comprising the polypeptide sequence of SEQ ID NO: 2.

In some embodiments, the composition further comprises a second engineered polynucleotide comprising a second targeting sequence that is at least partially complementary to a region of a second target RNA. In some embodiments, the region of the second target RNA: (a) at least partially encodes for a tau polypeptide or an alpha-synuclein (SNCA) polypeptide; (b) comprises a sequence that is proximal to (a); or (c) comprises (a) and (b). In some embodiments, the region of the second target RNA at least partially encodes for the tau polypeptide, and wherein the region comprises: SEQ ID NO: 16-SEQ ID NO: 27. In some embodiments, the composition disclosed therein, wherein the region of the second target RNA at least partially encodes for the SNCA polypeptide, and wherein the region comprises: SEQ ID NO: 36-SEQ ID NO: 44.

In some embodiments, the editing further comprises editing of at least a second base of a second nucleotide of the target RNA by the RNA editing entity. In some embodiments, the editing of the base of the nucleotide of the target RNA or the second target RNA by the RNA editing entity is sufficient to reduce, prevent, or eliminate formation of: β-amyloid, SNCA polypeptide, tau polypeptide; or an RNA encoding the β-amyloid, the SNCA polypeptide, or the tau polypeptide, as determined by an in vitro assay comprising: (a) contacting the engineered polynucleotide or the second engineered polynucleotide with the target RNA or the second target RNA, and (b) determining a modulation of: a processing; a cleavage; or a processing and a cleavage; of a modified APP polypeptide encoded by an edited target RNA; a modified tau polypeptide encoded by an edited second target RNA; or a modified SNCA polypeptide encoded by the edited second target RNA; as compared to a modulation of a processing; a cleavage; or a processing and cleavage of an unmodified APP polypeptide encoded by an unedited target RNA; an unmodified tau polypeptide encoded by an unedited second target RNA; or an unmodified SNCA polypeptide encoded by the unedited second target RNA.

In some embodiments, the editing of the base of the nucleotide of the target RNA and the second target RNA by the RNA editing entity is sufficient to reduce, prevent, or eliminate formation of the β-amyloid, and wherein the β-amyloid comprises: an Abeta40 fragment, an Abeta42 fragment, or the Abeta40 fragment and the Abeta 42 fragment. In some embodiments, the editing of the base of the nucleotide of the target RNA and the second target RNA by the RNA editing entity is sufficient to reduce the formation by about 1-fold, 3-fold, 5-fold, 10-fold, or 50-fold, as compared to an otherwise comparable cell lacking the contact with the composition. In some embodiments, the editing is sufficient to eliminate the β-amyloid peptide formation. In some embodiments, the editing is sufficient to increase an amount of secreted ectodomain APP alpha (sAPPa).

Disclosed herein, in some embodiments, are compositions. In an aspect, a composition comprises: (a) an engineered polynucleotide comprising a targeting sequence that is at least partially complementary to a region of a target RNA, wherein the region of the target RNA at least partially encodes for an amyloid precursor protein (APP) polypeptide; and (b) a second engineered polynucleotide comprising a second targeting sequence that is at least partially complementary to a region of a second target RNA, wherein the region of the second target RNA at least partially encodes for: a tau polypeptide or an alpha-synuclein (SNCA) polypeptide, and wherein the engineered polynucleotide and the second engineered polynucleotide are independently configured to facilitate an editing of a base of a nucleotide of the target RNA or the second target RNA by an RNA editing entity.

In some embodiments, the region of the second target RNA at least partially encodes for the tau polypeptide, and wherein the region comprises: SEQ ID NO: 16-SEQ ID NO: 27. In some embodiments, the region of the second target RNA at least partially encodes for the SNCA polypeptide, and wherein the region comprises: SEQ ID NO: 36-SEQ ID NO: 44.

In some embodiments, the editing of the base of the nucleotide of the target RNA or the second target RNA by the RNA editing entity is sufficient to reduce or eliminate formation of: β-amyloid, SNCA polypeptide, tau polypeptide; or an RNA encoding the β-amyloid, the SNCA polypeptide, or the tau polypeptide, as determined by an in vitro assay comprising: (a) contacting the engineered polynucleotide with the target RNA or the second engineered polynucleotide with the second target RNA, and (b) determining a modulation of: a processing; a cleavage; or a processing and a cleavage of a modified APP polypeptide encoded by an edited target RNA; a modified tau polypeptide encoded by an edited second target RNA; or a modified SNCA polypeptide encoded by the edited second target RNA; as compared to a modulation of: a processing; a cleavage; or a processing and cleavage of an unmodified APP polypeptide encoded by an unedited target RNA; an unmodified tau polypeptide encoded by an unedited second target RNA; or an unmodified SNCA polypeptide encoded by the unedited second target RNA.

In some embodiments, the editing of the base of the nucleotide of the target RNA and the second target RNA by the RNA editing entity is sufficient to reduce the formation by about 1-fold, 3-fold, 5-fold, 10-fold, or 50-fold, as compared to an otherwise comparable cell lacking the contact with the composition. In some embodiments, the modulation is determined by measuring a level of: a) the modified APP polypeptide, the modified Tau polypeptide, the modified SNCA polypeptide, or a combination of any of these; b) a mRNA transcript encoding the modified APP polypeptide, a mRNA transcript encoding the modified Tau polypeptide, a mRNA transcript encoding the modified SNCA polypeptide, or a combination of any of these; c) phosphorylation of the modified APP polypeptide, phosphorylation of the modified Tau polypeptide, phosphorylation of the modified SNCA polypeptide, or a combination of any of these; d) aggregation of the modified APP polypeptide, aggregation of the modified Tau polypeptide, aggregation of the modified SNCA polypeptide, or a combination of any of these; or e) a combination of any of these.

Disclosed herein, in some embodiments, are vectors. In an aspect, a vector comprises: (a) a polynucleotide sequence that encodes the engineered polynucleotide described herein and thereof; (b) a second engineered polynucleotide; or (c) a combination of any of these. In some embodiments, the third engineered polynucleotide comprises an siRNA, an shRNA, a miRNA, a piRNA, an antisense oligonucleotide; or does not comprise at least one of these. In some embodiments, the AAV vector is of a serotype selected from the group comprising: AAV2, AAV5, AAV6, AAV8, AAV9, a portion thereof, a fusion product thereof, and any combination thereof. In some embodiments, the AAV vector comprises rep and inverted terminal repeats (ITR) sequences from AAV2 and a cap sequence from AAV5. In some embodiments, the AAV vector comprises an ITR sequence that is an ITR with a mutated terminal resolution site (TRS).

Disclosed herein, in some embodiments, are pharmaceutical composition in unit dose forms. In an aspect, a pharmaceutical composition in unit dose form comprises the engineered polynucleotide described herein and thereof or the vector described herein and thereof.

Disclosed herein, in some embodiments, are methods of treating or preventing a disease or condition in a subject in need thereof. In an aspect, a method of treating or preventing a disease or condition in a subject in need thereof comprises administering to the subject: (a) the vector described herein and thereof; (b) the pharmaceutical composition described herein and thereof; or (c) (a) and (b), wherein after the administering, the subject comprises: (a) at least a 1-fold reduced formation of 3-amyloid as compared to an otherwise comparable subject lacking the administering, as measured by: a brain scan, a blood test, or both; (b) or at least a 1-fold increase in secreted ectodomain APP alpha (sAPPa), as compared to an otherwise comparable subject lacking the administering, as determined by an in vitro assay comprising: contacting the engineered polynucleotide with the target RNA and determining a level of the sAPPa by Western Blot.

In some embodiments, the β-amyloid comprises at least one of: an Abeta 40 fragment, an Abeta42 fragment, or both.

Disclosed herein, in some embodiments, are methods of treating or preventing a disease or condition in a subject in need thereof. In an aspect, a method of treating or preventing a disease or condition in a subject in need thereof comprises: administering to the subject a composition that comprises an engineered polynucleotide or a vector that encodes the engineered polynucleotide, wherein the engineered polynucleotide comprises a targeting sequence that is at least partially complementary to a region of a target RNA, wherein the region of the target RNA: (a). comprises a sequence that at least partially encodes for an amyloid precursor protein (APP) polypeptide; (b) comprises a sequence that is proximal to (a); or (c). comprises (a) and (b), wherein the engineered polynucleotide is configured to facilitate an editing of a base of a nucleotide of the target RNA by an RNA editing entity, whereby the edited target RNA encodes for a modified APP polypeptide that has reduced susceptibility to cleavage by a beta secretase, as compared to an unmodified APP polypeptide encoded by an otherwise comparable unedited target RNA, wherein the reduced susceptibility to cleavage of the modified APP polypeptide results in reduced β-amyloid formation, as determined by: i. an in vitro assay comprising contacting the engineered polynucleotide with the target RNA and determining cleavage of the modified APP polypeptide encoded by the edited target RNA by the beta secretase as compared to cleavage of the unmodified APP polypeptide encoded by the unedited target RNA; ii. an in vivo diagnostic after the administering; iii. an in vitro assay comprising a blood test after the administering; iv. histology of a brain tissue of the subject after the administering; or v. any combination thereof.

In some embodiments, the beta secretase comprises: beta-site amyloid precursor protein cleaving enzyme 1 (BACE1), cathepsin B, or Meprin beta. In some embodiments, the engineered polynucleotide, when associated with the target RNA, further comprises a structural feature which at least in part recruits the RNA editing entity. In some embodiments, the engineered polynucleotide further comprises an RNA editing entity recruiting domain. In some embodiments, the disease or condition comprises a neurodegenerative disease or condition. In some embodiments, the neurodegenerative disease or condition comprises Alzheimer's disease, Parkinson's disease, a dementia, Lewy Body Dementia, a progressive supranuclear palsy, a frontotemporal lobar degeneration, a corticobasal degeneration, or any combination thereof.

In some embodiments, the method further comprises a second administering. In some embodiments, the administering, the second administering, or both, are independently repeated at least once a month. In some embodiments, the administering, the second administering, or both, are independently performed by a: parenteral route, oral route, respiratory route, intraduodenal route, rectal route, or a combination thereof. In some embodiments, the in vivo diagnostic comprises: a positron emission tomography scan, a computerized tomography scan, magnetic resonance imaging, spinal tap, or a combination thereof.

In some embodiments, the modified APP polypeptide has increased susceptibility to cleavage by an alpha secretase, as compared to an unmodified APP polypeptide encoded by an unedited target RNA polypeptide. In some embodiments, the cleavage of the modified APP polypeptide by the alpha secretase results in an increased amount of secreted ectodomain APP alpha (sAPPa) in the subject as compared to an otherwise comparable subject lacking the administering. In some embodiments, the reduced β-amyloid formation comprises at least about a 1-fold, 3-fold, 5-fold, 10-fold, or 50-fold reduction as compared to an otherwise comparable subject lacking the administering.

In some embodiments, the vector comprises an AAV vector of a serotype selected from the group comprising: AAV2, AAV5, AAV6, AAV8, AAV9, a portion thereof, a fusion product thereof, or any combination thereof. In some embodiments, the composition further comprises: (a) a second engineered polynucleotide; (b) a second vector encoding the second engineered polynucleotide; (c) the vector further encoding the second engineered polynucleotide; or (d) any combination thereof, wherein the second engineered polynucleotide comprises a second targeting sequence that is at least partially complementary to a region of a second target RNA. In some embodiments, the region of the second target RNA: (a) at least partially encodes for a tau polypeptide or an alpha-synuclein (SNCA) polypeptide; (b) comprises a sequence that is proximal to (a); or (c) comprises (a) and (b). In some embodiments, the editing of the base of the nucleotide of the target RNA or the second target RNA by the RNA editing entity is sufficient to reduce or eliminate formation of: β-amyloid, SNCA polypeptide, tau polypeptide; or an RNA encoding the β-amyloid, the SNCA polypeptide, or the tau polypeptide, as determined by an in vitro assay comprising: (a) contacting the engineered polynucleotide with the target RNA or the second engineered polynucleotide with the second target RNA, and (b) determining a modulation of: a processing; a cleavage; or a processing and a cleavage of a modified APP polypeptide encoded by an edited target RNA; a modified tau polypeptide encoded by an edited second target RNA; or a modified SNCA polypeptide encoded by the edited second target RNA; as compared to a modulation of: a processing; a cleavage; or a processing and cleavage of an unmodified APP polypeptide encoded by an unedited target RNA; an unmodified tau polypeptide encoded by an unedited second target RNA; or an unmodified SNCA polypeptide encoded by the unedited second target RNA.

In some embodiments, wherein when an ex vivo population of neuronal cells is contacted with the composition, at least 5% of the neuronal cells in the population are edited after the contacting, as measured by Sanger sequencing. In some embodiments, wherein at least 10%, 15%, 20%, 30%, 40%, or 50% of the neuronal cells in the population are edited. In some embodiments, the editing further comprises editing of at least a second base of a second nucleotide of the target RNA by the RNA editing entity. In some embodiments, the subject is diagnosed with the disease or condition. In some embodiments, the method further comprises a second administering of an additional therapeutic agent. In some embodiments, the administering and the second administering are consecutive. In some embodiments, the administering and the second administering are concurrent.

Disclosed herein, in some embodiments, are engineered polynucleotides. In an aspect, an engineered polynucleotide comprises a sequence that comprises at least 90%, 95%, 97%, or 99% sequence identity with at least a portion of a sequence selected from: SEQ ID NO: 52-SEQ ID NO: 52, SEQ ID NO: 71-SEQ ID NO: 148, and SEQ ID NO: 159-SEQ ID NO: 167.

Disclosed herein, in some embodiments, are engineered polynucleotides. In an aspect, an engineered polynucleotide comprises a targeting sequence capable of at least partially binding to a sequence that comprises at least 90%, 95%, 97%, or 99% sequence identity with a portion of a sequence selected from: SEQ ID NO: 150-SEQ ID NO: 158 as determined by BLAST.

Disclosed herein, in some embodiments, are engineered polynucleotides. In an aspect, an engineered polynucleotide comprises a targeting sequence that is at least partially complementary to a region of a target RNA, wherein the region of the target RNA: (a) at least partially encodes for: an amyloid precursor protein (APP) polypeptide, an alpha-synuclein (SNCA) polypeptide, or a Tau polypeptide; (b) comprises a sequence that is proximal to (a); or (c) comprises (a) and (b); wherein the engineered polynucleotide is configured to: facilitate an editing of a base of a nucleotide of a polynucleotide in the region of the target RNA by an RNA editing entity; facilitate a modulation of the expression of the APP polypeptide, the SNCA polypeptide, or the Tau polypeptide; or a combination thereof.

In some embodiments, the facilitating the editing of the base of the nucleotide of the polynucleotide in the region of the target RNA by the RNA editing entity, the engineered polynucleotide is configured to facilitate modulation of processing and/or cleavage of the target RNA by a secretase enzyme. In some embodiments, the target RNA is the APP polypeptide. In some embodiments, the region of the target RNA is cleaved by a secretase enzyme. In some embodiments, the secretase is: a beta secretase; a γ-secretase; or a beta secretase and a γ-secretase. In some embodiments, the beta secretase, and wherein the beta secretase comprises beta-site amyloid precursor protein cleaving enzyme 1, cathepsin B, or Meprin beta. In some embodiments, for the engineered polynucleotide comprising (b), the sequence that is proximal to the region of the target RNA at least partially encoding the APP polypeptide, the SNCA polypeptide, or the Tau polypeptide comprises at least a portion of a three prime untranslated region (3' UTR). In some embodiments, for the engineered polynucleotide comprising (b), the sequence that is proximal to the region of the target RNA at least partially encoding the APP polypeptide, the SNCA polypeptide, or the Tau polypeptide comprises at least a portion of a five prime untranslated region (5' UTR). In some embodiments, the editing of a base of the 5'UTR results in at least partially regulating gene translation of the APP polypeptide, the SNCA polypeptide, or the Tau polypeptide. In some embodiments, the editing of the base of the nucleotide of the polynucleotide of the region of the 5'UTR results in facilitating regulating mRNA translation of the APP. In some embodiments, for the engineered polynucleotide comprising (b), the sequence that is proximal to the region of the target RNA at least partially encoding the APP polypeptide, the SNCA polypeptide, or the Tau polypeptide comprises at least a portion of: a poly(A) tail, microRNA response element (MRE), AU-rich element (ARE), or any combination thereof. In some embodiments, the region of the target RNA at least partially encodes for the APP polypeptide. In some embodiments, the region of the target RNA at least partially encodes for the SNCA polypeptide. In some embodiments, the region of the target RNA at least partially encodes for the Tau polypeptide. In some embodiments, the engineered polynucleotide is configured to facilitate the cleavage of the target RNA by the beta-site amyloid precursor protein cleaving enzyme 1. In some embodiments, the engineered polynucleotide is configured to facilitate the editing of the base of the nucleotide of the polynucleotide of the region of the target RNA by the RNA editing entity. In some embodiments, the targeting sequence that is at least partially complementary to the region of the target RNA comprises at least one nucleotide that is not complementary to a nucleotide in the region of the target RNA. In some embodiments, the at least one nucleotide that is not complementary is an adenosine (A), and wherein the A is comprised in an A/C mismatch. In some embodiments, the target RNA is selected from the group comprising: a mRNA, a tRNA, a lncRNA, a lincRNA, a miRNA, a rRNA, a snRNA, a microRNA, a siRNA, a piRNA, a snoRNA, a snRNA, a exRNA, a scaRNA, a YRNA, and a hnRNA. In some embodiments, the target RNA is the mRNA. In some embodiments, the region of the target RNA comprises a mutation as compared to an otherwise comparable region encoding a wildtype APP polypeptide, a wildtype SNCA polypeptide, or a wildtype Tau polypeptide. In some embodiments, the mutation comprises a polymorphism. In some embodiments, the targeting sequence is about: 40, 60, 80, 100, or 120 nucleotides in length. In some embodiments, the targeting sequence is about 100 nucleotides in length.

In some embodiments, the engineered polynucleotide further comprises an RNA editing entity recruiting domain that is capable of recruiting the RNA editing entity. In some embodiments, the RNA editing entity recruiting domain is at least 1 to about 75 nucleotides in length. In some embodiments, the RNA editing entity recruiting domain is at least 30-50 nucleotides in length.

The engineered polynucleotide disclosed herein, wherein the RNA editing entity recruiting domain comprises a glutamate ionotropic receptor AMPA type subunit 2 (GluR2) sequence. In some embodiments, the GluR2 sequence comprises at least about 80%, 85%, 90%, 95%, or 99% sequence identity to SEQ ID NO: 1. In some embodiments, the GluR2 sequences comprises SEQ ID NO: 1. In some embodiments, the RNA editing entity comprises an adenosine deaminase acting on RNA (ADAR) polypeptide or biologically active fragment thereof or adenosine deaminase acting on tRNA (ADAT) polypeptide or biologically active fragment thereof. In some embodiments, the ADAR polypeptide or biologically active fragment thereof, which comprises ADAR1 or ADAR2. In some embodiments, the engineered polynucleotide lacks a recruiting domain.

In some embodiments, the engineered polynucleotide further comprises a structural feature which at least in part recruits an RNA editing entity. In some embodiments, the structural feature comprises: a bulge, a hairpin, an internal loop, a structured motif, and any combination thereof. In some embodiments, the structural feature comprises the bulge. In some embodiments, the bulge is an asymmetric bulge. In some embodiments, the bulge is a symmetric bulge. In some embodiments, the bulge is from 1-29 nucleotides in length. In some embodiments, the structural feature comprises the hairpin. In some embodiments, the structural feature comprises the internal loop. In some embodiments, the internal loop is an asymmetric loop. In some embodiments, the internal loop is a symmetric loop. In some embodiments, the structural feature comprises the structured motif. In some embodiments, the structured motif comprises at least two of: the bulge, the hairpin, and the internal loop. In some embodiments, the structured motif comprises the bulge and the hairpin. In some embodiments, the structured motif comprises the bulge and the internal loop.

In some embodiments, the engineered polynucleotide comprises a backbone that comprises a plurality of sugar and phosphate moieties covalently linked together, and wherein the backbone comprises a 5' reducing hydroxyl, a 3' reducing hydroxyl, or both. In some embodiments, each of the 5' reducing hydroxyl in the backbone is linked to each of the 3' reducing hydroxyl via a phosphodiester bond. In some embodiments, the engineered polynucleotide comprises a backbone that comprises a plurality of sugar and phosphate moieties covalently linked together, and wherein the backbone lacks a 5' reducing hydroxyl, a 3' reducing hydroxyl, or both. In some embodiments, the engineered polynucleotide associates with the region of the target RNA, the association comprises hybridized polynucleotide strands. In some embodiments, the hybridized polynucleotide strands at least in part form a duplex. In some embodiments, the engineered polynucleotide further comprises a chemical modification. In some embodiments, the engineered polynucleotide comprises RNA, DNA, or both. In some embodiments, the engineered polynucleotide comprises the RNA.

Disclosed herein, in some embodiments, are engineered polynucleotides. In an aspect, an engineered polynucleotide is configured to facilitate an editing of a base of a nucleotide of a polynucleotide of a region of a target RNA at least partially encoding an amyloid precursor protein (APP), wherein an RNA editing entity, in association with the engineered polynucleotide and the target RNA, edits the base of the nucleotide of the polynucleotide of the region of the target RNA, wherein the editing results in generation of an edited target RNA at least partially encoding a modified amyloid precursor protein (APP).

In some embodiments, the RNA editing entity comprises a secretase enzyme. In some embodiments, the secretase enzyme is beta secretase; a γ-secretase; or a beta secretase and a γ-secretase. In some embodiments, the secretase enzyme is the beta secretase, and wherein the beta secretase is selected from the group consisting of: beta-site amyloid precursor protein cleaving enzyme 1, cathepsin B, and Meprin beta.

Disclosed herein, in some embodiments, are engineered polynucleotides. In an aspect, an engineered polynucleotide is configured to facilitate, by an RNA editing entity, an editing of a base of a nucleotide of a polynucleotide of a region of a target RNA at least partially encoding an amyloid precursor protein (APP), wherein the editing results in generation of an edited target RNA that comprises at least one amino acid substitution compared to an otherwise comparable unedited target RNA, wherein the edited target RNA encodes an APP with an altered susceptibility to a beta secretase cleavage compared to the otherwise comparable APP encoded by the otherwise comparable unedited target RNA; and wherein a cell expressing an APP polypeptide generated from the edited target RNA has substantially no decrease in beta secretase activity on an endogenous substrate of beta secretase compared to a corresponding cell expressing an APP polypeptide generated from the unedited target RNA, as determined by an in vitro assay comprising a measurement of a metabolite indicative of cleavage of the endogenous substrate by beta-site amyloid precursor protein cleaving enzyme 1 (BACE1), and wherein the endogenous substrate comprises amyloid-like protein 1 (APLP1), amyloid-like protein 2 (APLP2), Contactin 2, Jagged 1, neural cell adhesion molecule L1 (CHL1), Neurexin 1α, Neurexin 3β, neuregulin 1 (NRG1), seizure related protein 6 (SEZ6), seizure related protein 6 precursor protein (SEZ6L), a β (β1-4) Auxiliary subunit of the voltage-gated sodium ion channel (VGSC) subtype Nav1, VGSC Accessory Subunits KCNE1 or KCNE2, a functional portion of any of these, or any combination of thereof.

In some embodiments, the beta secretase comprises BACE1, cathepsin B, or Meprin beta. In some embodiments, the endogenous substrate comprises the NRG1, the SEZ6, or the CHL1.

Disclosed herein, in some embodiments, are engineered polynucleotides. In an aspect, an engineered polynucleotide is configured to facilitate, by an RNA editing entity, an editing of a base of a nucleotide of a polynucleotide of a region of a target RNA at least partially encoding an amyloid precursor protein (APP), wherein the editing results in generation of a modified APP encoded by an edited target RNA that comprises at least one amino acid substitution compared to an otherwise comparable unmodified APP encoded by an comparable unedited target RNA, and wherein the modified APP polypeptide generated from the edited target RNA: (i) produces a lower amount of Abeta40, Abeta42, or both when expressed in a cell as compared to an APP polypeptide generated from the unedited target RNA as measured by an Abeta40 or Abeta42 enzyme linked immunosorbent assay (ELISA); (ii) produces an increased amount of secreted ectodomain APP alpha (sAPPa) when expressed in a cell as compared to the sAPPa generated from the unedited target RNA as measured by an sAPPa ELISA; or (iii) any combination of (i) and (ii).

Disclosed herein, in some embodiments, are vectors. In an aspect, a vector comprises: (a) the engineered polynucleotides herein and thereof (b) a polynucleotide encoding the engineered polynucleotides herein and thereof or (c) (a) and (b).

In some embodiments, the vector further comprises a second engineered polynucleotide or a second polynucleotide encoding the second engineered polynucleotide. In some embodiments, the engineered polynucleotide and the second engineered polynucleotide are the same. In some embodiments, the engineered polynucleotide and the second engineered polynucleotide are different. In some embodiments, the second engineered polynucleotide comprises a second targeting sequence that at least partially hybridizes to a region of a second target RNA. In some embodiments, the second engineered polynucleotide comprises an siRNA, an shRNA, an miRNA, a piRNA, an anti-sense oligonucleotide; or does not comprise at least one of these. In some embodiments, the engineered polynucleotide and the second engineered polynucleotide are contiguous with each other. In some embodiments, the polynucleotide of the vector independently encodes: the engineered polynucleotide and the second engineered polynucleotide, are operatively linked to a same promoter sequence. In some embodiments, the engineered polynucleotide and the second engineered polynucleotide not contiguous with each other.

In some embodiments, the engineered polynucleotide comprises a targeting sequence that is at least partially complementary to a region of the APP target RNA, and wherein the second engineered polynucleotide comprises a targeting sequence that is at least partially complementary to a region of the SNCA or the Tau target RNA. In some embodiments, the engineered polynucleotide comprises a targeting sequence that is at least partially complementary to a region of the APP target RNA, and wherein the second engineered polynucleotide comprises the siRNA, the shRNA, the miRNA, the piRNA, or the antisense oligonucleotide that targets the SNCA polypeptide or the Tau polypeptide.

In some embodiments, the vector is a viral vector. In some embodiments, the viral vector is an AAV vector, and wherein the AAV vector is of a serotype selected from the group comprising: AAV2, AAV5, AAV6, AAV8, AAV9, a portion thereof, a fusion product thereof, and any combination thereof. In some embodiments, the AAV vector comprises rep and ITR sequences from AAV2 and a cap sequence from AAV5. In some embodiments, the AAV vector comprises an ITR sequence that is a self-complementary ITR. In some embodiments, the AAV vector that encodes for the engineered polynucleotide is self-complementary.

Disclosed herein, in some embodiments, are pharmaceutical compositions in unit dose form. In an aspect, a pharmaceutical composition in unit dose dorm comprises the engineered polynucleotides and vectors herein and thereof. In some embodiments, the pharmaceutical composition in unit dose further comprises a pharmaceutically acceptable: excipient, carrier, or diluent.

Disclosed herein, in some embodiments, are methods of making compositions. In an aspect, a method of making a pharmaceutical composition comprising admixing the engineered polynucleotides herein and thereof with a pharmaceutically acceptable excipient, diluent, or carrier.

Disclosed herein, in some embodiments, are isolated cells. In an aspect, an isolated cell comprises the engineered polynucleotides herein or thereof, the vectors herein or thereof, or both.

Disclosed herein, in some embodiments, are kits. In an aspect, a kit comprises the engineered polynucleotides herein and thereof, the vectors herein and thereof, or both in a container. In some embodiments, the kit comprises inserting the engineered polynucleotide disclosed therein into a container.

Disclosed herein, in some embodiments, are methods of treating or preventing a disease or condition in a subject in need thereof. In an aspect, a method of treating or preventing a disease or condition in a subject in need thereof comprises administering to a subject in need thereof: (a) the vectors herein and thereof; (b) the pharmaceutical compositions herein and thereof; or (c) (a) and (b).

Disclosed herein, in some embodiments, are methods of treating or preventing a disease or condition. In an aspect, a method of treating or preventing a disease or condition comprises administering a therapeutic to a subject in need thereof, wherein the therapeutic facilitates, by an RNA editing entity, an editing of a base of a nucleotide of a polynucleotide of a region of a target RNA that at least partially encodes for an amyloid precursor protein (APP), thereby generating an edited RNA that at least partially encodes for a beta secretase-resistant APP as compared to an otherwise comparable APP encoded by an otherwise comparable RNA lacking the edit as determined by in vitro assay comprising contacting the beta secretase-resistant APP and the otherwise comparable APP with: a) a beta secretase; b) a γ-secretase; c) or a beta secretase and a γ-secretase.

In some embodiments, the beta secretase comprises beta-site amyloid precursor protein cleaving enzyme 1, cathepsin B, or Meprin beta. In some embodiments, the therapeutic comprises a vector comprising or encoding an engineered polynucleotide that comprises a targeting sequence that at least partially hybridizes to a region of the target RNA. In some embodiments, the engineered polynucleotide further comprises an RNA editing entity recruiting domain that is capable of recruiting the RNA editing entity. In some embodiments, the RNA editing entity recruiting domain is at least 1 to about 75 nucleotides in length. In some embodiments, the RNA editing entity recruiting domain comprises a glutamate ionotropic receptor AMPA type subunit 2 (GluR2) sequence. In some embodiments, the RNA editing entity comprises an adenosine deaminase acting on RNA (ADAR) polypeptide or biologically active fragment thereof or adenosine deaminase acting on tRNA (ADAT) polypeptide or biologically active fragment thereof. In some embodiments, the RNA editing entity comprises the ADAR polypeptide or biologically active fragment thereof, and wherein the ADAR comprises ADAR1 or ADAR2. In some embodiments, the engineered polynucleotide lacks a RNA editing entity recruiting sequence.

In some embodiments, the engineered polynucleotide further comprises a structural feature. In some embodiments, the structural feature comprises: a bulge, a hairpin, an internal loop, a structured motif, and any combination thereof. In some embodiments, the structural feature comprises the bulge. In some embodiments, the bulge is an asymmetric bulge. In some embodiments, the bulge is a symmetric bulge. In some embodiments, the bulge is from 1-29 nucleotides in length. In some embodiments, the structural feature comprises the hairpin. In some embodiments, the structural feature comprises the internal loop. In some embodiments, the internal loop is asymmetric. In some embodiments, the internal loop is asymmetric. In some embodiments, the structural feature comprises the structured motif. In some embodiments, the structured motif comprises at least two of: the bulge, the hairpin, and the internal loop. In some embodiments, the structured motif comprises the bulge and the hairpin. In some embodiments, the structured motif comprises the bulge and the internal loop.

In some embodiments, the engineered polynucleotide comprises a backbone that comprises a plurality of sugar and phosphate moieties covalently linked together, and wherein the backbone comprises a 5' reducing hydroxyl, a 3' reducing hydroxyl, or both. In some embodiments, each of the 5' reducing hydroxyl in the backbone is linked to each of the β' reducing hydroxyl via a phosphodiester bond. In some embodiments, the engineered polynucleotide comprises a backbone that comprises a plurality of sugar and phosphate moieties covalently linked together, and wherein the backbone lacks a 5' reducing hydroxyl, a 3' reducing hydroxyl, or both.

In some embodiments, the beta secretase-resistant APP has reduced susceptibility to cleavage at a position cleavable by a beta secretase as compared to the otherwise comparable APP produced from the otherwise comparable RNA lacking the edit. In some embodiments, the beta secretase comprises BACE1, cathepsin B, or Meprin beta. In some embodiments, the nucleotide is comprised in a codon which encodes an amino acid in proximity to a cleavage site of the APP. In some embodiments, the cleavage site at the APP is selected from the group consisting of: an α-secretase cleavage site, a β-secretase cleavage site, a β'-secretase cleavage site, a γ-secretase cleavage site, and any combination thereof. In some embodiments, the amino acid is at position 669, 670, 671, 672, 673, 682, 683, 684, 687, 688, 711, 712, 713, or 714 of the APP of SEQ ID NO: 2. In some embodiments, the BACE protease-resistant APP comprises at least one amino acid residue difference as compared to the otherwise comparable APP produced from the otherwise comparable RNA lacking the edit. In some embodiments, the one amino acid residue difference comprises an amino acid substitution that results in a change in charge, hydrophobicity, or polarity of the amino acid, or any combination thereof. In some embodiments, the difference in the amino acid comprises a conservative substitution. In some embodiments, the difference in the amino acid comprises a charge neutral substitution. In some embodiments, the amino acid residue comprises a K to E change, a K to R change, a K to G change, an M to V change, a D to G change, an E to G change, an H to R change, or any combination thereof. In some embodiments, the difference in the amino acid residue comprises K670E, K670R, K670G, M671V, D672G, E682G, H684R, K687R, K687E, or K687G of the amyloid precursor protein of SEQ ID NO: 2. In some embodiments, the change in the one amino acid comprises K670G or M671V of the amyloid precursor protein of SEQ ID NO: 2.

In some embodiments, the target RNA is selected from the group comprising: an mRNA, a tRNA, a lncRNA, a lincRNA, a miRNA, a rRNA, a snRNA, a siRNA, a piRNA, a snoRNA, a exRNA, a scaRNA, a YRNA, an eRNA, and a hnRNA. In some embodiments, the target RNA is the mRNA.

In some embodiments, the therapeutic directly facilitates the edit. In some embodiments, the therapeutic indirectly facilitates the edit. In some embodiments, the disease or condition comprises a neurodegenerative disease or condition. In some embodiments, the neurodegenerative condition comprises Alzheimer's disease, Parkinson's disease, dementia, Lewy Body Dementia, progressive supranuclear palsy, frontotemporal lobar degeneration, corticobasal degeneration, or any combination thereof. In some embodiments, the condition comprises traumatic brain injury, Down's syndrome, cancer, Fragile X Syndrome, autism, amyotrophic lateral sclerosis, multiple sclerosis, Lesch-Nyhan disease, metabolic disorder, or any combination thereof. In some embodiments, the edited RNA or the BACE protease-resistant APP is generated in at least 5%, 8%, 10%, 15%, 20%, 30%, 40%, or 50% of the subjects administered the therapeutic in a clinical trial. In some embodiments, the method further comprises a second administering of an additional therapeutic agent. In some embodiments, the administering and the second administering are consecutive. In some embodiments, the administering and the second administering are concurrent. In some embodiments, the administering or the second administering or both are independently repeated at least once a week. In some embodiments, the administering or the second administering or both are independently performed by parenteral route of administration. In some embodiments, the administering or the second administering or both are independently performed by parenchymal injection, intra-thecal injection, intra-ventricular injection, intra-cisternal injection, intravenous injection, or intranasal administration or any combination thereof.

BRIEF DESCRIPTION OF THE DRAWINGS

FIG. 2D shows that during the normal and nonamyloidogenic processing of APP, cleavages with alpha secretase followed by gamma secretase will generate soluble ectodomains alpha sAPP alpha, an intracellular C-terminal fragment AICD, and p3 fragments. FIG. 2E shows that during pathogenic and amyloidogenic processing of APP, cleavages involving BACE1 followed by gamma secretase will generate a soluble ectodomain sAPP beta AICD, and pathogenic Abeta fragments.

FIG. 7 shows a cartoon denoting the target nucleotide mutations in APP used to generate modified APP proteins. The BACE and ADAM10 cleavage sites are indicated. The boxed nucleotides indicate target mutations. Figure discloses SEQ ID NOS 207-208, 207, 207, and 209-218, respectively, in order of appearance.

FIG. 8 shows a cartoon denoting the target nucleotide mutations in APP used to generate modified APP proteins. The BACE and ADAM10 cleavage sites are indicated. The boxed nucleotides indicate target mutations. Figure discloses SEQ ID NOS 219-220, 219, 219, and 221-225, respectively, in order of appearance.

FIG. 13A shows the exon structure of human RAB7A and SNCA. Exons are shown as gray segments; the coding region is denoted as a black line above. Locations of the guide RNA targeting sites are shown in purple; PCR primers are shown in green. FIG. 13B shows ADAR editing at each target site (measured by Sanger sequencing). FIG. 13C shows cDNA from edited transcripts were PCR amplified using the above primers and analyzed on an agarose gel. PCR amplicons showed the predicted size for correctly spliced exons. FIG. 13D shows Sanger sequencing chromatograms show specific editing at the target adenosine of the indicated transcripts. Figure discloses SEQ ID NOS 202, 202, 202, 202, 202, 202, 202, 204, 204, 204-205, 204, 204, and 204, respectively, in order of appearance.

FIG. 14A shows an example Sanger sequencing chromatogram of the edited sites of the β' UTR, as well as, off-target editing that can occur. Figure discloses SEQ ID NO: 206. FIG. 14B shows the mouse or human U7 promoter with 3' SmOPT U7 hairpin constructs of the human SNCA 3'UTR target site, with or without ADAR2 overexpression, in a different cell type (K562-VPR-SNCA) under different transfection conditions (nucleofection, Lonza). FIG. 14C shows the percentage of off target editing occurring at the 5'G in the β' UTR using the same constructs as FIG. 14B.

FIG. 16A shows a cartoon schematic of the targeting strategy of different engineered polynucleotide. 0.100.50 (Exon-Exon) (SEQ ID NO: 97) is specific to the APP mRNA because it targets the continuous sequence across the exon with the target adenosine and its preceding exon. 0.100.50 (Exon-Intron) (SEQ ID NO: 98) is specific to the APP pre-mRNA because it targets the continuous sequence between the exon with the target adenosine and its preceding intron. 0.90.45 (Exon only) (SEQ ID NO: 99) can target both APP pre-mRNA and mRNA because it only targets the sequence of the target adenosine. White rectangles denote exons of the APP transcripts. Diagonal stripped rectangle denotes intron of the APP transcript. The targeting sequence of the engineered polynucleotide is shown as a black line above the APP transcript. FIG. 16B shows a bar graph of the RNA editing efficiency using the engineered polynucleotides in FIG. 16A and their negative controls (GFP plasmid and no transfection). Wild type HEK293 cells were transfected with plasmids encoding different polynucleotides or GFP. The RNA editing of APP mRNA was analyzed 48 hours after transfection. About 15-20% editing of the target adenosine in APP was achieved using the engineered polynucleotides in FIG. 16A, as compared to less than 3% editing in the negative controls.

FIG. 17A shows a cartoon schematic of a luciferase reporter as the unedited target (ATG) and edited control (GTG). The reporter contains two open reading frames, each with one kozak and ATG start codon. The first open reading frame contains a target RNA sequence, while the second one contains a secreted luciferase. Deamination of the adenosine within the target start codon promotes secondary translation of luciferase proportional to the rate of editing. By incorporating the target RNA sequence surrounding the first ATG, the RNA editing efficiencies of the guides with different features—such as the length of the guide, the location of the bulge in the guide, or the location of the GLUR2-recruiting domains in the guide can be tested. FIG. 17B-FIG. 17C describes the results of one such experiment; FIG. 17B shows a heatmap of the luciferase expression of a fPMP22 reporter in response to a multitude of varied ADAR guides. The fPMP22 reporter was generated by inserting the target transcript sequence in Charcot-Marie-Tooth Syndrome 1A into the first open reading frame. The reporter was transposed into HEK293 cells for stable expression. Guides of different lengths (20, 30, 40, 50, 75, 100, 150, and 200 nucleotides), mismatch placement ($10^{th}$ percentile (5' end), $90^{th}$ percentile (3' end), or $50^{th}$ percentile (middle)) of the guide as it's transcribed from 5' to 3' from the plasmid are listed in TABLE 16. The fold-change of the luciferase expression normalized to that of cells transfected with plasmids with non-specific guides and ADAR2 (ST0145). FIG. 17C shows a line graph of the relationship of the guide length (x-axis) and the fold-change of the reporter expression (y-axis) in two biological replicates for each guide. The result of 3 sets of experiments, in which the guide contained a GLUR2-recruiting domain in the β' end of the guide and the location of the bulge was varied, was shown.

FIG. 18A shows a carton schematic of the gene structure of ADAR1 and knockout strategy. Two gRNAs US gRNA and DS gRNA were designed to cover a 6 kb region of the ADAR1 locus, encompassing the deaminase domain ($789^{th}$ to $1221^{st}$ amino acid). The nicking of the DNA strands directed by the gRNAs, combining with a homology directed repair (HDR) oligo with 80 bp homology arms outside the 6 kb region, creates the 6 kb deletion in the ADAR1 locus, removing the deaminase domain. FIG. 18B shows a western blot of ADAR1 in different clones transfected with US and DS gRNA. GAPDH was used as a control. Clones #9 and #11 showed no detectable ADAR1 protein expression by the western blot.

FIG. 19A shows a carton schematic of the gene structure of ADAR2 and knockout strategy. Two gRNAs US gRNA and DS gRNA were designed to cover a 9.5 kb region of the ADAR1 locus, encompassing the deaminase domain ($70^{th}$ to $522^{nd}$ amino acid). The nicking of the DNA strands directed by the gRNAs, combining with a homology directed repair (HDR) oligo with 80 bp homology arms outside the 9.5 kb region, creates the 9.5 kb deletion in the ADAR2 locus, removing the deaminase domain. FIG. 19B shows a bar-graph of Q-PCR of ADARs in different clones transfected with US and DS gRNA.

FIG. 20A shows a carton schematic of the strategy to generate the ADAR1 knockout (KO) cell line that overexpresses ADAR2. An ADAR2 overexpression construct, maintained as a PiggyBac transposon with a puromycin-resistant marker, was transfected and integrated into an ADAR1 KO K562 cell line. The successfully integrated cell was selected by puromycin resistance. FIG. 20B shows a western blot of ADAR1 and ADAR2 protein expression in wildtype, ADAR1 KO, and ADAR1 KO+ADAR2 cell. GAPDH was used as a control. The wildtype or ADAR1 KO cell did not express ADAR2. Only the ADAR1 KO cell successfully integrated with ADAR2 OE construct expressed ADAR2.

FIG. 22A shows a carton schematic of using different DNA probe sets in the drop-off ddPCR assay to measure RNA editing efficiency. A forward and reverse primer are designed to flank the genomic locus or mRNA target of interest. A drop-off probe and reference TaqMan probe is designed to bind a target site and the region adjacent to the target site, respectively. Both probes can bind the wildtype sequence of the target site and the adjacent site to release signals; the drop-off probe cannot bind an edited or mutated sequence on the target site to release the signal. One of each target molecules, drop-off probes, and reference probes are allocated into one droplet. The percentage of the populations of the edited and wildtype target genomic loci or mRNAs, measured by the drop-off ddPCR, can be used to determine the frequency of editing. FIG. 22B depicts two dot-plots showing Rab7A RNA editing in human cells. Each Rab7A mRNA molecule was converted to a cDNA molecule by reverse transcription and PCR amplification, and allocated into individual droplet. Two TaqMan probes were designed for the target site and the reference site, bind the wildtype but not the edited sequences to provide signal. One of each target molecules, Drop-off probes, reference probes are allocated into one droplet. The signal intensity for each probe was measured for each droplet. In the wildtype control (WT) sample, most droplets showed high fluorescent intensity for both probes. In the edited sample, about 85% of the droplets showed decreased fluorescent intensity in the Drop-off probe, suggesting that an equivalent percentage of sequences were edited.

FIG. 24 show using the gRNA$^{Q}$ assay in FIG. 23 to measure gRNA abundance.

FIG. 25 show using different RNA editing using gRNAs with different structures.

DETAILED DESCRIPTION

Figure 1:
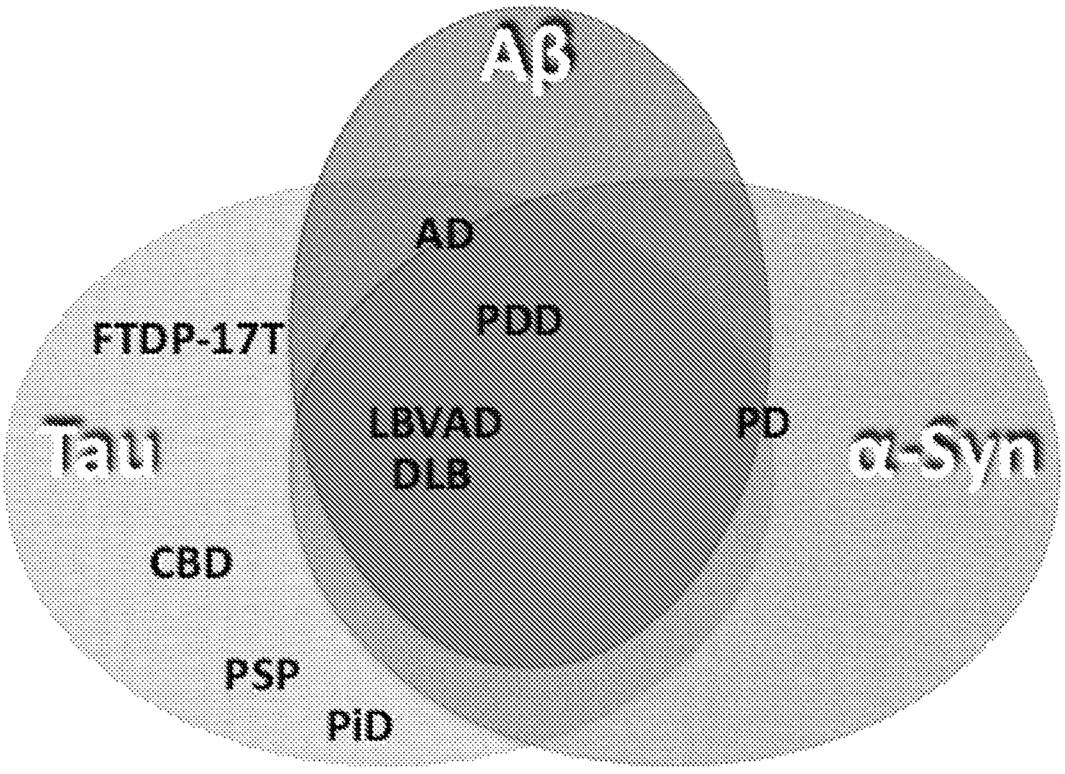
FIG. 1 shows a Venn diagram of diseases caused by different pathogenic proteins. Abeta plaques, alpha-synuclein Lewy bodies and Tau NFT pathologies in combination can confer a worse prognosis for a subject. Alzheimer's disease can share protein pathologies with other neurodegenerative diseases. For example, Alzheimer's disease (AD) can share protein pathologies with one or more of: CBD: Corticobasal degeneration; DLB: Dementia with Lewy bodies; FTDP-17T: Fronto-temporal dementia with Parkinsonism linked to Tau mutations on chromosome 17; LBVAD: Lewy body variant of Alzheimer's Disease; PD: Parkinson's Disease; PDD: Parkinson's Disease with dementia; PiD: Pick's Disease; or PSP: Progressive supranuclear palsy.

The practice of some embodiments disclosed herein employ, unless otherwise indicated, conventional techniques of immunology, biochemistry, chemistry, molecular biology, microbiology, cell biology, genomics and recombinant DNA, which are within the skill of the art. Unless defined otherwise, all technical and scientific terms used herein have the same meaning as is commonly understood by one of skill in the art.

The term "a" and "an" refers to one or to more than one (i.e., to at least one) of the grammatical object of the article. By way of example, "an element" means one element or more than one element.

The term "about" or "approximately" as used herein when referring to a measurable value such as an amount or concentration and the like, is meant to encompass variations of 20%, 10%, 5%, 1%, 0.5%, or even 0.1% of the specified amount. For example, "about" can mean plus or minus 10%, per the practice in the art. Alternatively, "about" can mean a range of plus or minus 20%, plus or minus 10%, plus or minus 5%, or plus or minus 1% of a given value. Alternatively, particularly with respect to biological systems or processes, the term can mean within an order of magnitude, up to 5-fold, or up to 2-fold, of a value. Where particular values can be described in the application and claims, unless otherwise stated the term "about" meaning up to an acceptable error range for the particular value should be assumed. Also, where ranges, subranges, or both, of values can be provided, the ranges or subranges can include the endpoints of the ranges or subranges. The terms "substantially", "substantially no", "substantially free", and "approximately" can be used when describing a magnitude, a position or both to indicate that the value described can be up to a reasonable expected range of values. For example, a numeric value can have a value that can be +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein can be intended to include all subranges subsumed therein.

The term "partially", "at least partially", or as used herein can refer to a value approaching 100% of a given value. In some cases, the term can refer to an amount that can be at least about 60%, 65%, 70%, 75%, 80%, 85%, 90%, 91%, 92%, 93%, 94%, 95%, 96%, 97%, 98%, 99%, 99.9%, or 99.99% of a total amount. In some cases, the term can refer to an amount that can be about 100% of a total amount.

The term "and/or" as used in a phrase such as "A and/or B" herein is intended to include both A and B; A or B; A (alone); and B (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

As used herein, the term "comprising" is intended to mean that the compositions and methods include the recited elements, but do not exclude others. "Consisting essentially of" when used to define compositions and methods, shall mean excluding other elements of any essential significance to the combination for the intended use. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this disclosure. Embodiments defined by each of these transition terms are within the scope of this disclosure.

The term "subject," "host," "individual," and "patient" are as used interchangeably herein to refer to animals, typically mammalian animals. Any suitable mammal can be treated by a method, cell or composition described herein. A mammal can be administered a vector, an engineered guide RNA, a precursor guide RNA, a nucleic acid, or a pharmaceutical composition, as described herein. Non-limiting examples of mammals include humans, non-human primates (e.g., apes, gibbons, chimpanzees, orangutans, monkeys, macaques, and the like), domestic animals (e.g., dogs and cats), farm animals (e.g., horses, cows, goats, sheep, pigs) and experimental animals (e.g., mouse, rat, rabbit, guinea pig). In some embodiments a mammal is a human. A mammal can be any age or at any stage of development (e.g., an adult, teen, child, infant, or a mammal in utero). A mammal can be male or female. A mammal can be a pregnant female. In some embodiments a subject is a human. In some embodiments, a subject has or is suspected of having a disease such as a neurodegenerative disease. In some embodiments, a subject has or can be suspected of having a cancer or neoplastic disorder. In other embodiments, a subject has or can be suspected of having a disease or disorder associated with aberrant protein expression. In some cases, a human can be more than about: 1 day to about 10 months old, from about 9 months to about 24 months old, from about 1 year to about 8 years old, from about 5 years to about 25 years old, from about 20 years to about 50 years old, from about 1 year old to about 130 years old or from about 30 years to about 100 years old. Humans can be more than about: 1, 2, 5, 10, 20, 30, 40, 50, 60, 70, 80, 90, 100, 110, or 120 years of age. Humans can be less than about: 1, 2, 5, 10, 20, 30, 40, 50, 60, 70, 80, 90, 100, 110, 120 or 130 years of age.

The term "subject," "host," "individual," and "patient" are as used interchangeably herein to refer to animals, typically mammalian animals. Any suitable mammal can be administered a composition as described herein (such as an engineered guide RNA) or treated by a method as described herein. A subject can be a vertebrate or an invertebrate. A subject can be a laboratory animal. Non-limiting examples of mammals include humans, non-human primates (e.g., apes, gibbons, chimpanzees, orangutans, monkeys, macaques, and the like), domestic animals (e.g., dogs and cats), farm animals (e.g., horses, cows, goats, sheep, pigs) and experimental animals (e.g., mouse, rat, rabbit, guinea pig). In some embodiments a mammal is a human. A mammal can be any age or at any stage of development (e.g., an adult, teen, child, infant, or a mammal in utero). A mammal can be male or female. In some embodiments a subject is a human. A subject can be a patient. A subject can be suffering from a disease. A subject can display symptoms of a disease. A subject may not display symptoms of a disease, but still have a disease. A subject can be under medical care of a caregiver (e.g., the subject is hospitalized and is treated by a physician).

The term "protein", "peptide", and "polypeptide" are used interchangeably and in their broadest sense to refer to a compound of two or more subunit amino acids, amino acid analogs or peptidomimetics. The terms also encompass an amino acid polymer that has been modified; for example, disulfide bond formation, glycosylation, lipidation, acetylation, phosphorylation, or any other manipulation, such as conjugation with a labeling component. As used herein the term "amino acid" refers to either natural and/or unnatural or synthetic amino acids, including glycine and both the D or L optical isomers, and amino acid analogs and peptidomimetics. The subunits may be linked by peptide bonds. In another embodiment, the subunit may be linked by other bonds, e.g., ester, ether, etc. A protein or peptide must contain at least two amino acids and no limitation is placed on the maximum number of amino acids which may comprise a protein's or peptide's sequence. As used herein the term "amino acid" refers to either natural and/or unnatural or synthetic amino acids, including glycine and both the D and L optical isomers, amino acid analogs and peptidomimetics. As used herein, the term "fusion protein" refers to a protein comprised of domains from more than one naturally occurring or recombinantly produced protein, where generally each domain serves a different function. In this regard, the term "linker" refers to a protein fragment that is used to link these domains together—optionally to preserve the conformation of the fused protein domains and/or prevent unfavorable interactions between the fused protein domains which may compromise their respective functions.

"Homology" or "identity" or "similarity" can refer to sequence similarity between two peptides or between two nucleic acid molecules. Homology can be determined by comparing a position in each sequence which can be aligned for purposes of comparison. When a position in the compared sequence can be occupied by the same base or amino acid, then the molecules can be homologous at that position. A degree of homology between sequences can be a function of the number of matching or homologous positions shared by the sequences. An "unrelated" or "non-homologous" sequence shares less than 40% identity, or alternatively less than 25% identity, with one of the sequences of the disclosure. Sequence homology can refer to a % identity of a sequence to a reference sequence. As a practical matter, whether any particular sequence can be at least 50%, 60%, 70%, 80%, 85%, 90%, 92%, 95%, 96%, 97%, 98% or 99% identical to any sequence described herein (which can correspond with a particular nucleic acid sequence described herein), such particular polypeptide sequence can be determined conventionally using known computer programs such the Bestfit program (Wisconsin Sequence Analysis Package, Version 8 for Unix, Genetics Computer Group, University Research Park, 575 Science Drive, Madison, Wis. 53711). When using Bestfit or any other sequence alignment program to determine whether a particular sequence is, for instance, 95% identical to a reference sequence, the parameters can be set such that the percentage of identity can be calculated over the full length of the reference sequence and that gaps in sequence homology of up to 5% of the total reference sequence can be allowed.

In some cases, the identity between a reference sequence (query sequence, i.e., a sequence of the disclosure) and a subject sequence, also referred to as a global sequence alignment, can be determined using the FASTDB computer program based on the algorithm of Brutlag et al. (Comp. App. Biosci. 6:237-245 (1990)). In some embodiments, parameters for a particular embodiment in which identity can be narrowly construed, used in a FASTDB amino acid alignment, can include: Scoring Scheme=PAM (Percent Accepted Mutations) 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject sequence, whichever can be shorter. According to this embodiment, if the subject sequence can be shorter than the query sequence due to N- or C-terminal deletions, not because of internal deletions, a manual correction can be made to the results to take into consideration the fact that the FASTDB program does not account for N- and C-terminal truncations of the subject sequence when calculating global percent identity. For subject sequences truncated at the N- and C-termini, relative to the query sequence, the percent identity can be corrected by calculating the number of residues of the query sequence that can be lateral to the N- and C-terminal of the subject sequence, which can be not matched/aligned with a corresponding subject residue, as a percent of the total bases of the query sequence. A determination of whether a residue can be matched/aligned can be determined by results of the FASTDB sequence alignment. This percentage can be then subtracted from the percent identity, calculated by the FASTDB program using the specified parameters, to arrive at a final percent identity score. This final percent identity score can be used for the purposes of this embodiment. In some cases, only residues to the N- and C-termini of the subject sequence, which can be not matched/aligned with the query sequence, can be considered for the purposes of manually adjusting the percent identity score. That is, only query residue positions outside the farthest N- and C-terminal residues of the subject sequence can be considered for this manual correction. For example, a 90-residue subject sequence can be aligned with a 100-residue query sequence to determine percent identity. The deletion occurs at the N-terminus of the subject sequence, and therefore, the FASTDB alignment does not show a matching/alignment of the first 10 residues at the N-terminus. The 10 unpaired residues represent 10% of the sequence (number of residues at the N- and C-termini not matched/total number of residues in the query sequence) so 10% can be subtracted from the percent identity score calculated by the FASTDB program. If the remaining 90 residues were perfectly matched, the final percent identity can be 90%. In another example, a 90-residue subject sequence can be compared with a 100-residue query sequence. This time the deletions can be internal deletions, so there can be no residues at the N- or C-termini of the subject sequence which can be not matched/aligned with the query. In this case, the percent identity calculated by FASTDB can be not manually corrected. Once again, only residue positions outside the N- and C-terminal ends of the subject sequence, as displayed in the FASTDB alignment, which can be not matched/aligned with the query sequence can be manually corrected for.

The terms "polynucleotide" and "oligonucleotide" are used interchangeably and refer to a polymeric form of nucleotides of any length, either deoxyribonucleotides or ribonucleotides or analogs thereof. Polynucleotides can have any three dimensional structure and may perform any function, known or unknown. The following are non-limiting examples of polynucleotides: a gene or gene fragment (for example, a probe, primer, EST or SAGE tag), an exon, an intron, intergenic DNA (including, without limitation, heterochromatic DNA), messenger RNA (mRNA), transfer RNA (tRNA), ribosomal RNA (rRNA), a ribozyme, cDNA, a recombinant polynucleotide, a branched polynucleotide, a plasmid, a vector, isolated DNA of a sequence, isolated RNA of a sequence, sgRNA, guide RNA, a nucleic acid probe, a primer, an snRNA, a long non-coding RNA, a snoRNA, a siRNA, a miRNA, a tRNA-derived small RNA (tsRNA), an antisense RNA, an shRNA, or a small rDNA-derived RNA (srRNA). A polynucleotide can comprise modified nucleotides, such as methylated nucleotides and nucleotide analogs. If present, modifications to the nucleotide structure can be imparted before or after assembly of the polynucleotide. The sequence of nucleotides can be interrupted by non-nucleotide components. A polynucleotide can be further modified after polymerization, such as by conjugation with a labeling component. The term also refers to both double and single stranded molecules. Nucleic acids, including e.g., nucleic acids with a phosphothioate backbone, can include one or more reactive moieties. As used herein, the term reactive moiety includes any group capable of reacting with another molecule, e.g., a nucleic acid or polypeptide through covalent, non-covalent or other interactions. By way of example, the nucleic acid can include an amino acid reactive moiety that reacts with an amino acid on a protein or polypeptide through a covalent, non-covalent, or other interaction. Unless otherwise specified or required, any embodiment of this disclosure that is a polynucleotide encompasses both the double stranded form and each of two complementary single stranded forms known or predicted to make up the double stranded form.

Polynucleotides useful in the methods of the disclosure can comprise natural nucleic acid sequences and variants thereof, artificial nucleic acid sequences, or a combination of such sequences. In some embodiments, polynucleotides of the disclosure refer to a DNA sequence. In some embodiments, the DNA sequence is interchangeable with a similar RNA sequence. In some embodiments, polynucleotides of the disclosure refer to an RNA sequence. In some embodiments, the RNA sequence is interchangeable with a similar DNA sequence. In some embodiments, Us and Ts of a polynucleotide may be interchanged in a sequence provided herein.

A polynucleotide is composed of a specific sequence of four nucleotide bases: adenine (A); cytosine (C); guanine (G); thymine (T); and uracil (U) for thymine when the polynucleotide is RNA. In some embodiments, the polynucleotide may comprise one or more other nucleotide bases, such as inosine (I), a nucleoside formed when hypoxanthine is attached to ribofuranose via a β-N9 glycosidic bond, resulting in the chemical structure:

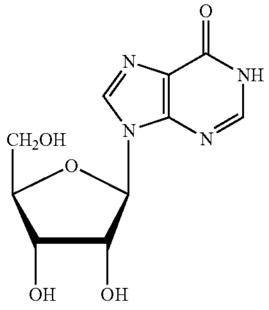

Inosine is read by the translation machinery as guanine (G).

The term "polynucleotide sequence" is the alphabetical representation of a polynucleotide molecule. This alphabetical representation can be input into databases in a computer having a central processing unit and used for bioinformatics applications such as functional genomics and homology searching.

As used herein, "expression" refers to the process by which polynucleotides are transcribed into mRNA and/or the process by which the transcribed mRNA is subsequently being translated into peptides, polypeptides, or proteins. If the polynucleotide is derived from genomic DNA, expression may include splicing of the mRNA in an eukaryotic cell.

The terms "equivalent" or "biological equivalent" are used interchangeably when referring to a particular molecule, biological, or cellular material and intend those having minimal homology while still maintaining desired structure or functionality.

The term "mutation" as used herein, refers to an alteration to a nucleic acid sequence encoding a protein relative to the consensus sequence of said protein. "Missense" mutations result in the substitution of one codon for another; "nonsense" mutations change a codon from one encoding a particular amino acid to a stop codon. Nonsense mutations often result in truncated translation of proteins. "Silent" mutations are those which have no effect on the resulting protein. As used herein the term "point mutation" refers to a mutation affecting only one nucleotide in a gene sequence. "Splice site mutations" are those mutations present premRNA (prior to processing to remove introns) resulting in mistranslation and often truncation of proteins from incorrect delineation of the splice site. A mutation can comprise a single nucleotide variation (SNV). A mutation can comprise a sequence variant, a sequence variation, a sequence alteration, or an allelic variant. The reference DNA sequence can be obtained from a reference database. A mutation can affect function. A mutation may not affect function. A mutation can occur at the DNA level in one or more nucleotides, at the ribonucleic acid (RNA) level in one or more nucleotides, at the protein level in one or more amino acids, or any combination thereof. The reference sequence can be obtained from a database such as the NCBI Reference Sequence Database (RefSeq) database. Specific changes that can constitute a mutation can include a substitution, a deletion, an insertion, an inversion, or a conversion in one or more nucleotides or one or more amino acids. A mutation can be a point mutation. A mutation can be a fusion gene. A fusion pair or a fusion gene can result from a mutation, such as a translocation, an interstitial deletion, a chromosomal inversion, or any combination thereof. A mutation can constitute variability in the number of repeated sequences, such as triplications, quadruplications, or others. For example, a mutation can be an increase or a decrease in a copy number associated with a given sequence (i.e., copy number variation, or CNV). A mutation can include two or more sequence changes in different alleles or two or more sequence changes in one allele. A mutation can include two different nucleotides at one position in one allele, such as a mosaic. A mutation can include two different nucleotides at one position in one allele, such as a chimeric. A mutation can be present in a malignant tissue. A presence or an absence of a mutation can indicate an increased risk to develop a disease or condition. A presence or an absence of a mutation can indicate a presence of a disease or condition. A mutation can be present in a benign tissue. Absence of a mutation may indicate that a tissue or sample is benign. As an alternative, absence of a mutation may not indicate that a tissue or sample is benign. Methods as described herein can comprise identifying a presence of a mutation in a sample.

"Canonical amino acids" refer to those 20 amino acids found naturally in the human body shown in the table below with each of their three letter abbreviations, one letter abbreviations, structures, and corresponding codons:

| non-polar, aliphatic residues | | | | |
|---|---|---|---|---|
| Glycine | Gly | G | 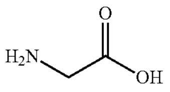 | GGU GGC GGA GGG |
| Alanine | Ala | A | 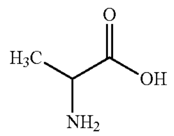 | GCU GCC GCA GCG |
| Valine | Val | V | 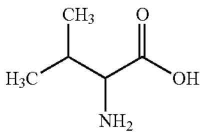 | GUU GUC GUA GUG |

-continued
| | | | | |
|---|---|---|---|---|
| Leucine | Leu | L | 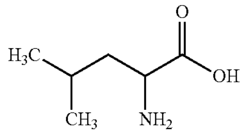 | UUA UUG CUU CUC CUA CUG |
| Isoleucine | Ile | I | 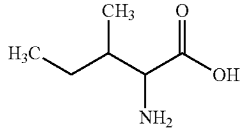 | AUU AUC AUA |
| Proline | Pro | P | 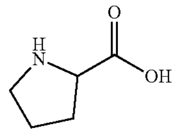 | CCU CCC CCA CCG |
| | | | aromatic residues | |
| Phenylalanine | Phe | F | 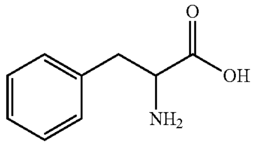 [SMILES: NC(Cc1ccccc1)C(=O)O] | UUU UUC |
| Tyrosine | Tyr | Y | 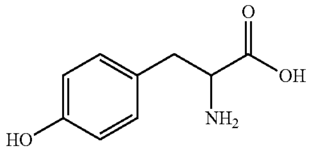 | UAU UAC |
| Tryptophan | Trp | W | 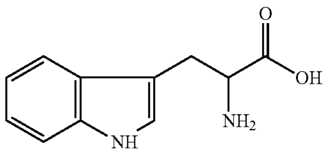 [SMILES: NC(Cc1c[nH]c2ccccc12)C(=O)O] | UGG |
| | | | polar, non-charged residues | |
| Serine | Ser | S | 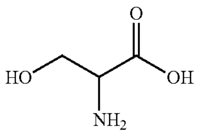 | UCU UCC UCA UCG AGU AGC |
| Threonine | Thr | T | 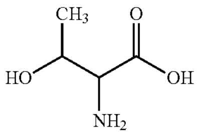 | ACU ACC ACA ACG |
| Cysteine | Cys | C | 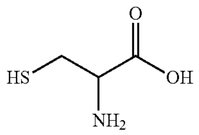 | UGU UGC |
| Methionine | Met | M | 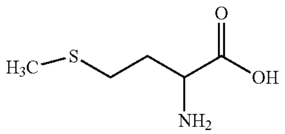 | AUG |

-continued

| | | | | |
|---|---|---|---|---|
| Asparagine | Asn | N | 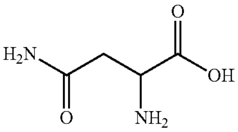 | AAU AAC |
| Glutamine | Gln | Q | 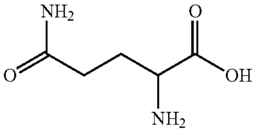 | CAA CAG |
| | | | positively charged residues | |
| Lysine | Lys | K | 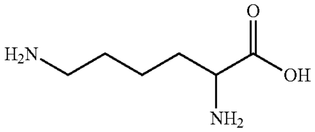 | AAA AAG |
| Arginine | Arg | R | 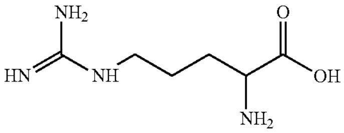 [SMILES: N=C(N)NCCCC(N)C(=O)O] | CGU CGC CGA CGG AGA AGG |
| Histidine | His | H | 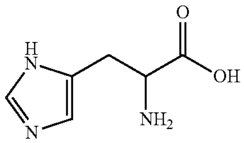 [SMILES: NC(Cc1cnc[nH]1)C(=O)O] | CAU CAC |
| | | | negatively charged residues | |
| Aspartate | Asp | D | 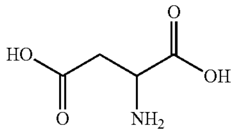 | GAU GAC |
| Glutamate | Glu | E | 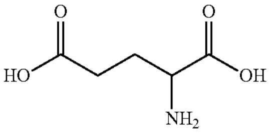 | GAA GAG |

The term "non-canonical amino acids" refers to those synthetic or otherwise modified amino acids that fall outside this group, typically generated by chemical synthesis or modification of canonical amino acids (e.g. amino acid analogs). The present disclosure employs proteinogenic non-canonical amino acids in some of the methods and vectors disclosed herein. A non-limiting exemplary non-canonical amino acid is pyrrolysine (Pyl or O), the chemical structure of which is provided below:

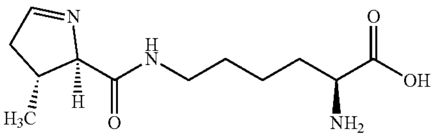 [SMILES: C[C@@H]1CC=N[C@H]1C(=O)NCCCC[C@H](N)C(=O)O]

Inosine (I) is another exemplary non-canonical amino acid, which is commonly found in tRNA and is essential for proper translation according to "wobble base pairing." The structure of inosine is provided above.

The term "complementary" or "complementarity" refers to the ability of a nucleic acid to form hydrogen bond(s) with another nucleic acid sequence by either traditional Watson-Crick or other non-traditional types. For example, the sequence A-G-T can be complementary to the sequence T-C-A. A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary, respectively). "Perfectly complementary" means that all the contiguous residues of a nucleic acid sequence will hydrogen bond with the same number of contiguous residues in a second nucleic acid sequence. "Substantially complementary", "partially complementary", "at least partially complementary", or as used herein refers to a degree of complementarity that can be at least 60%, 65%, 70%, 75%, 80%, 85%, 90%, 95%. 97%, 98%, 99%, or 100% over a region of 10, 15, 20, 25, 30, 35, 40, 45, 50, or more nucleotides, or refers to two nucleic acids that hybridize under stringent conditions (e.g., stringent hybridization conditions). Nucleic acids can include nonspecific sequences. As used herein, the term “nonspecific sequence” or “not specific” refers to a nucleic acid sequence that contains a series of residues that can be not designed to be complementary to or can be only partially complementary to any other nucleic acid sequence.

It is to be inferred without explicit recitation and unless otherwise intended, that when the present disclosure relates to a polypeptide, protein, polynucleotide or antibody, an equivalent or a biologically equivalent of such is intended within the scope of this disclosure. As used herein, the term “biological equivalent thereof” is intended to be synonymous with “equivalent thereof” when referring to a reference protein, antibody, polypeptide or nucleic acid, intends those having minimal homology while still maintaining desired structure or functionality. Unless specifically recited herein, it is contemplated that any polynucleotide, polypeptide or protein mentioned herein also includes equivalents thereof. For example, an equivalent intends at least about 70% homology or identity, or at least 80% homology or identity and alternatively, or at least about 85%, or alternatively at least about 90%, or alternatively at least about 95%, or alternatively 98% percent homology or identity and exhibits substantially equivalent biological activity to the reference protein, polypeptide or nucleic acid. Alternatively, when referring to polynucleotides, an equivalent thereof is a polynucleotide that hybridizes under stringent conditions to the reference polynucleotide or its complement. The section headings used herein are for organizational purposes and are not to be construed as limiting the subject matter described.

OVERVIEW

RNA editing has emerged as an attractive alternative to DNA editing. Unlike DNA editing, RNA editing can be less likely to cause a potentially dangerous immune reaction such as those reported utilizing CRISPR-based approaches. Indeed, unlike the DNA-editing enzyme Cas9, which comes from bacteria, RNA editing entities and biologically active fragments thereof such as Adenosine Deaminase Acting on RNA (ADAR) are human proteins that do not trigger the adaptive immune system. Additionally, RNA editing may be a safer approach to gene therapies because editing RNA does not contain a risk for permanent genomic changes as seen with DNA editing. Also, while off-site RNA editing may occur, the off-site edited mRNA is diluted out and/or degraded, unlike with off-site DNA editing that is permanent, e.g., the transient nature of mRNA compared to the permeance of DNA, off-site editing is likely far less consequential in the context of RNA vs DNA.

Provided herein are compositions of engineered polynucleotides (also referred to as “engineered guide RNAs (gRNAs)” or “guide RNAs”) and methods for use in targeting an RNA, particularly for the prevention, amelioration, and/or treatment of disease. Although many diseases can be targeted utilizing the compositions and methods provided herein, those associated with mutations in Amyloid Precursor Protein (APP) are preferentially targeted. APP mutations are associated with diseases arising in the central nervous system (CNS). In an aspect, the compositions and methods of the disclosure provide suitable means for which to treat CNS disease with improved targeting and reduced immunogenicity as compared to available technologies utilizing DNA editing.

In some cases, amyloid precursor protein (APP) can be cut by beta secretase (BACE) or gamma secretase, and the fragment resulting from such cuts can be Amyloid beta (referred to as “Aβ” or “Abeta”) peptides of 36-43 amino acids. Certain Abeta peptide metabolites of this cleavage can be crucially involved in Alzheimer’s disease pathology and progression.

Compositions described herein can edit the cleavage site in APP, so that beta/gamma secretases exhibit reduced cleavage of APP or can no longer cut APP and, therefore, reduced levels of Abeta 40/42 or no Abetas can be produced.

Also disclosed herein are compositions of engineered polynucleotides and methods of use thereof for targeting RNA to knockdown proteins implicated in a neurodegenerative disease. For example, engineered polynucleotides disclosed herein may target Tau (e.g., a microtubule-associated protein Tau (MAPT) encoded from a MAPT gene) or α-synuclein (SNCA) for knockdown. Compositions disclosed herein also include combinations of more than one engineered guide RNA, for example, engineered guides targeting a cleavage site in APP for RNA editing and engineered guides targeting Tau or SNCA for knockdown. These disclosed compositions can have synergistic effects to prevent and/or cure a neurodegenerative disease. The compositions and methods disclosed herein can yield results in editing and/or knockdown of targets without any of the resulting issues seen in small molecule or antibody therapy. Compositions can partially knockdown APP (instead of target cleavage site editing). Editing at the target cleavage site in APP and partial knockdown can be deployed singly or in combination.

Targeting of Ribonucleic Acid

Targeting an RNA can be a process by which RNA can be enzymatically modified post synthesis on specific nucleosides or bases.

Targeting of RNA can be a way to modulate expression of a polypeptide. For example, through modulation of polypeptide-encoding double stranded RNA (dsRNA) substrates that enter the RNA interference (RNAi) pathway. This modulation may then act at the chromatin level to modulate expression of the polypeptide.

Targeting of RNA can also be a way to regulate gene translation. RNA editing can be a mechanism in which to regulate transcript recoding by regulating the triplet codon to introduce silent mutations and/or non-synonymous mutations.

Specific RNA editing can lead to transcript recoding. Because inosine shares the base pairing properties of guanosine, the translational machinery interprets edited adenosines as guanosine, altering the triplet codon, which can result in amino acid substitutions in protein products. More than half the triplet codons in the genetic code could in theory be reassigned through RNA editing. Due to the degeneracy of the genetic code, RNA editing can cause both silent and non-synonymous amino acid substitutions.

Targeting an RNA can chemically transform a base of a nucleotide in a targeted RNA. In some cases, targeting an RNA can affect splicing. Adenosines targeted for editing may be disproportionately localized near splice junctions in pre-mRNA. Therefore, during formation of a dsRNA ADAR substrate, intronic cis-acting sequences can form RNA duplexes encompassing splicing sites and potentially obscuring them from the splicing machinery. Furthermore, through modification of select adenosines, ADARs can create or eliminate splicing sites, broadly affecting later splicing of the transcript. Similar to the translational machinery, the spliceosome interprets inosine as guanosine (G), and therefore, a canonical GU 5' splice site and AG 3' acceptor site can be created via the deamination of AU (IU=GU) and AA (AI=AG), respectively. Correspondingly, RNA editing can destroy a canonical AG 3' splice site (IG=GG).

In some embodiments, a engineered polynucleotide and a target RNA molecule can have at least one mismatch. In some embodiments, a engineered polynucleotide and a target RNA molecule can have one mismatch. In some embodiments, a engineered polynucleotide and a target RNA molecule can have an A/C, A/G, U/C, U/G, C/A, C/U, G/A, G/U mismatch, or any combination thereof. In some embodiments, a engineered polynucleotide and a target RNA molecule can have a A/C mismatch. In some embodiment, an A in an A/C, A/G, C/A, or G/A can be modified by the RNA editing entity. In other cases, a C in an A/C, C/A, C/U, or U/C can be modified by the RNA editing entity. In other cases, a U in a U/C, C/U, G/U, or U/G can be modified by the RNA editing entity. In other cases, a G in a U/G, G/U, G/A, or A/G can be modified by the RNA editing entity. In some embodiments, an A in an A/C mismatch can be modified by the RNA editing entity. Such modifications can comprise any modification, for example chemical modifications induced by any RNA editing entity described herein and thereof. In an embodiment, a modification reverts a mismatch in a target RNA to a residue present in an otherwise comparable WT RNA.

A chemical transformation of a targeted RNA can result in an increased level of a protein or fragment thereof after translation of the targeted RNA with the chemical transformation, relative to an otherwise comparable RNA lacking the chemical transformation. In some embodiments, a chemical transformation of a targeted RNA can result in a decreased level of a protein or fragment thereof after translation of the targeted RNA with the chemical transformation, relative to an otherwise comparable RNA lacking the chemical transformation. In some embodiments, a chemical transformation can convert a sense codon into a stop codon. In some cases, a chemical transformation can convert a stop codon into a sense codon. In some embodiments, a chemical transformation can convert a first sense codon into a second sense codon. In some instances, a chemical transformation can convert a first stop codon into a second stop codon. In some embodiments, a chemical transformation can alter the localization, folding, stability, or synthesis of a protein or fragment thereof after translation of a targeted RNA with the chemical transformation, relative to an otherwise comparable RNA lacking the chemical transformation. In some cases, a chemical transformation can alter the localization, folding, stability, or synthesis of a targeted RNA with the chemical transformation, relative to an otherwise comparable target RNA lacking the chemical transformation. In some embodiments, a target RNA can comprise a coding or a non-coding RNA.

Targeting of RNA can comprise any one of an insertion, deletion, or substitution of a base. Examples of RNA targeting include pseudouridylation (the isomerization of uridine residues) and deamination (removal of an amine group from cytidine to give rise to uridine, or C-to-U editing).

RNA Editing Entities and Biologically Active Fragments Thereof

Provided herein are compositions that comprise an RNA editing entity or a biologically active fragment thereof and methods of using the same. In an aspect, an RNA editing entity can comprise an adenosine Deaminase Acting on RNA (ADAR), Adenosine Deaminase Acting on tRNA (ADAT), and biologically active fragments thereof of either of these. ADARs and ADATs can be enzymes that catalyze the chemical conversion of adenosines to inosines in RNA. Because the properties of inosine mimic those of guanosine (inosine will form two hydrogen bonds with cytosine, for example), inosine can be recognized as guanosine by the translational cellular machinery. "Adenosine-to-inosine (A-to-I) RNA editing", therefore, effectively changes the primary sequence of RNA targets. In general, ADAR and ADAT enzymes share a common domain architecture comprising a variable number of amino-terminal dsRNA binding domains (dsRBDs) and a single carboxy-terminal catalytic deaminase domain. Human ADARs and ADATs possess two or three dsRBDs. Evidence suggests that ADARs and ADATs can form homodimer as well as heterodimer with other ADARs or and ADATs when bound to double-stranded RNA, however it is currently inconclusive if dimerization is required for editing to occur.

Three human ADAR genes have been identified (ADARs 1-3) with ADAR1 (official symbol ADAR) and ADAR2 (ADARB1) proteins having well-characterized adenosine deamination activity. ADARs have a typical modular domain organization that includes at least two copies of a dsRNA binding domain (dsRBD; ADAR1 with three dsRBDs; ADAR2 and ADAR3 each with two dsRBDs) in their N-terminal region followed by a C-terminal deaminase domain. ADAT catalyzes the deamination on tRNAs. ADAT is also named tadA in *E. coli*. Three human ADAT genes have been identified (ADATs 1-3).

Specific RNA editing can lead to transcript recoding. Because inosine shares the base pairing properties of guanosine, the translational machinery interprets edited adenosines as guanosine, altering the triplet codon, which can result in amino acid substitutions in protein products. More than half the triplet codons in the genetic code could be reassigned through RNA editing. Due to the degeneracy of the genetic code, RNA editing can cause both silent and non-synonymous amino acid substitutions.

In some cases, targeting an RNA can affect splicing. Adenosines targeted for editing may be disproportionately localized near splice junctions in pre-mRNA. Therefore, during formation of a dsRNA ADAR substrate, intronic cis-acting sequences can form RNA duplexes encompassing splicing sites and potentially obscuring them from the splicing machinery. Furthermore, through modification of select adenosines, ADARs can create or eliminate splicing sites, broadly affecting later splicing of the transcript. Similar to the translational machinery, the spliceosome interprets inosine as guanosine, and therefore, a canonical GU 5' splice site and AG 3' acceptor site can be created via the deamination of AU (IU=GU) and AA (AI=AG), respectively. Correspondingly, RNA editing can destroy a canonical AG 3' splice site (IG=GG).

In an aspect, an RNA editing entity comprises an ADAR. In some embodiments, an ADAR can comprise any one of: ADAR1, ADAR1p110, ADAR1p150, ADAR2, ADAR3, APOBEC protein, or any combination thereof. In some embodiments, the ADAR RNA editing entity is ADAR1. Additionally, or alternatively, the ADAR RNA editing entity is ADAR2. Additionally, or alternatively, the ADAR RNA editing entity is ADAR3. In an aspect, an RNA editing entity can be a non-ADAR In some cases, an RNA editing entity can comprise at least about 80% sequence homology to APOBEC1, APOBEC2, ADAR1, ADAR1p110, ADAR1p150, ADAR2, ADAR3, or any combination thereof. Alternate editing entities are also contemplated, such as those from a clustered regularly interspaced short palindromic repeats (CRISPR) system.

In some cases, an RNA editing entity can be a virus-encoded RNA-dependent RNA polymerase. In some cases, an RNA editing entity can be a virus-encoded RNA-dependent RNA polymerase from measles, mumps, or parainfluenza. In some instances, an RNA editing entity can be an enzyme from *Trypanosoma brucei* capable of adding or deleting a nucleotide or nucleotides in a target RNA. In some instances, an RNA editing entity can be an enzyme from *Trypanosoma brucei* capable of adding or deleting an Uracil or more than one Uracil in a target RNA. In some instances, an RNA editing entity can comprise a recombinant enzyme. In some cases, an RNA editing entity can comprise a fusion polypeptide.

In an aspect, an RNA editing entity can be recruiting by a subject engineered polynucleotide. In some embodiments, an engineered polynucleotide can recruit an RNA editing entity that, when associated with the engineered polynucleotide and the target RNA or not associated with the target RNA, facilitates: an editing of a base of a nucleotide of a polynucleotide of the region of the target RNA, a modulation of the expression of a polypeptide encoded by a subject target RNA, such as APP, SNCA, Tau; or a combination thereof. An engineered polynucleotide can contain an RNA editing entity recruiting domain to be capable of recruiting an RNA editing entity.

Engineered Polynucleotides

Provided herein are polynucleotides and compositions that comprise the same. In an aspect, a polynucleotide can be an engineered polynucleotide. In an embodiment, an engineered polynucleotide can be an engineered polynucleotide. In some embodiments, an engineered polynucleotide of the disclosure may be utilized for RNA editing, for example to prevent or treat a disease or condition. In some cases, an engineered polynucleotide can be used in association with a subject RNA editing entity to edit a target RNA or modulate expression of a polypeptide encoded by the target RNA. In an embodiment, compositions disclosed herein can include engineered polynucleotides capable of facilitating editing by subject RNA editing entities such as ADAR or ADAT polypeptides or biologically active fragments thereof.

Engineered polynucleotides can be engineered in any way suitable for RNA targeting. In an aspect, an engineered polynucleotide generally comprises at least a targeting sequence that allows it to hybridize to a region of a target RNA. In some cases, a targeting sequence may also be referred to as a targeting domain or a targeting region.

In an aspect, a targeting sequence of an engineered polynucleotide allows the engineered polynucleotide to target an RNA sequence through base paring, such as Watson Crick base pairing. In an embodiment, the targeting sequence can be located at either the N-terminus or C-terminus of the engineered polynucleotide. In some cases, the targeting sequence is located at both termini. The targeting sequence can be of any length. In some cases, the targeting sequence is at least about: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, or up to about 200 nucleotides in length. In an embodiment, an engineered polynucleotide comprises a targeting sequence that is about 75-100, 80-110, 90-120, or 95-115 nucleotides in length. In an embodiment, an engineered polynucleotide comprises a targeting sequence that is about 100 nucleotides in length.

In some cases, a subject targeting sequence comprises at least partial sequence complementarity to a region of a target RNA that at least partially encodes a subject polypeptide for example APP, SNCA, or Tau. In some cases, a targeting sequence comprises 95%, 96%, 97%, 98%, 99%, or 100% sequence complementarity to a target RNA. In some cases, a targeting sequence comprises less than 100% complementarity to a target RNA sequence. For example, a targeting sequence and a region of a target RNA that can be bound by the targeting sequence may have a single base mismatch. In other cases, the targeting sequence of a subject engineered polynucleotide comprises at least about 1, 2, 3, 4, 5, 6, 7, 8, 9, 10, 11, 12, 13, 14, 15, 16, 20, 30, 40 or up to about 50 base mismatches. In some aspects, nucleotide mismatches can be associated with structural features provided herein. In some aspects, a targeting sequence comprises at least about 1, 2, 3, 4, 5, 6, 7, 8, 9, 10, 11, 12, 13, 14, or up to about 15 nucleotides that differ in complementarity from a wildtype RNA of a subject target RNA.

In an aspect, a subject engineered polynucleotide comprises an RNA editing entity recruiting domain. An RNA editing entity can be recruited by an RNA editing entity recruiting domain on an engineered polynucleotide. In some cases, a subject engineered polynucleotide is configured to facilitate editing of a base of a nucleotide of a polynucleotide of a region of a subject target RNA, modulation expression of a polypeptide encoded by the subject target RNA, or both. In some cases, an engineered polynucleotide can be configured to facilitate an editing of a base of a nucleotide or polynucleotide of a region of an RNA by a subject RNA editing entity. In order to facilitate editing, an engineered polynucleotide of the disclosure may recruit an RNA editing entity. In certain embodiments, an engineered polynucleotide lacks an RNA editing entity recruiting domain. Either way, a subject engineered polynucleotide can be capable of binding an RNA editing entity, or be bound by it, and facilitate editing of a subject target RNA.

Various RNA editing entity recruiting domains can be utilized. In an embodiment, a recruiting domain comprises: Glutamate ionotropic receptor AMPA type subunit 2 (GluR2), APOBEC, MS2-bacteriophage-coat-protein-recruiting domain, Alu, a TALEN recruiting domain, a Zn-finger polypeptide recruiting domain, a mega-TAL recruiting domain, or a Cas13 recruiting domain, combinations thereof, or modified versions thereof. In certain embodiments, more than one recruiting domain can be included in an engineered polynucleotide of the disclosure. In cases where a recruiting sequence is present, the recruiting sequence can be utilized to position the RNA editing entity to effectively react with a subject target RNA after the targeting sequence, for example an antisense sequence, hybridizes to a target RNA. In some cases, a recruiting sequence can allow for transient binding of the RNA editing entity to the engineered polynucleotide. In other cases, the recruiting sequence allows for permanent binding of the RNA editing entity to the polynucleotide. A recruiting sequence can be of any length. In some cases, a recruiting sequence is from about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, up to about 80 nucleotides in length. In some cases, a recruiting sequence is about 45 nucleotides in length. In some cases, at least a portion of a recruiting sequence comprises at least 1 to about 75 nucleotides. In some cases, at least a portion of a recruiting sequence comprises about 45 nucleotides to about 60 nucleotides.

In an embodiment, an RNA editing entity recruiting domain comprises a GluR2 sequence or functional fragment thereof. In some cases, a GluR2 sequence can be recognized by an RNA editing entity, such as an ADAR or biologically active fragment thereof. In some embodiments, a GluR2 sequence can be a non-naturally occurring sequence. In some cases, a GluR2 sequence can be modified, for example for enhanced recruitment. In some embodiments, a GluR2 sequence can comprise a portion of a naturally occurring GluR2 sequence and a synthetic sequence.

In an embodiment, a recruiting domain comprises a GluR2 sequence, or a sequence having at least about 80%, 85%, 90%, 95%, 98%, 99%, or 100% identity to: GUGGAAUAGUAUAACAAUAUGCUAAAUGUUGUUAUAGUAUCCCAC (SEQ ID NO: 1). In some cases, a recruiting domain can comprise at least about 80% sequence homology to at least about 10, 15, 20, 25, or 30 nucleotides of SEQ ID NO: 1. In some embodiments, a recruiting domain can comprise at least about 90%, 95%, 96%, 97%, 98%, or 99% sequence homology to SEQ ID NO: 1.

Additional, RNA editing entity recruiting domains are also contemplated. In an embodiment, a recruiting domain comprises an apolipoprotein B mRNA editing enzyme, catalytic polypeptide-like (APOBEC) domain. In some cases, an APOBEC domain can comprise a non-naturally occurring sequence or naturally occurring sequence. In some embodiments, an APOBEC-domain-encoding sequence can comprise a modified portion. In some cases, an APOBEC-domain-encoding sequence can comprise a portion of a naturally occurring APOBEC-domain-encoding-sequence. In another embodiment, a recruiting domain can be from an MS2-bacteriophage-coat-protein-recruiting domain. In another embodiment, a recruiting domain can be from an Alu domain. In some cases, a recruiting domain can comprise at least about: 80%, 85%, 90%, or 95% sequence homology to at least about: 15, 20, 25, 30, or 35 nucleotides of an APOBEC, MS2-bacteriophage-coat-protein-recruiting domain, or Alu domain. Any number of recruiting sequences may be found in a polynucleotide of the present disclosure. In some cases, at least about 1, 2, 3, 4, 5, 6, 7, 8, 9, or up to about 10 recruiting sequences are included in a polynucleotide. Recruiting sequences may be located at any position of subject polynucleotides. In some cases, a recruiting sequence is on an N-terminus, middle, or C-terminus of a polynucleotide. A recruiting sequence can be upstream or downstream of a targeting sequence. In some cases, a recruiting sequence flanks a targeting sequence of a subject polynucleotide. A recruiting sequence can comprise all ribonucleotides or deoxyribonucleotides, although a recruiting sequence comprising both ribo- and deoxyribonucleotides is not excluded.

In cases where a recruiting sequence can be absent, an engineered polynucleotide can be still capable of associating with a subject RNA editing entity (e.g., ADAR) to facilitate editing of a target RNA and/or modulate expression of a polypeptide encoded by a subject target RNA. This can be achieved through structural features. Structural features can comprise any one of a: mismatch, symmetrical bulge, asymmetrical bulge, symmetrical internal loop, asymmetrical internal loop, hairpins, wobble base pairs, a structured motif, circularized RNA, chemical modification, or any combination thereof. In an aspect, a double stranded RNA (dsRNA) substrate, for example hybridized polynucleotide strands, can be formed upon hybridization of an engineered polynucleotide of the present disclosure to a target RNA. Described herein can be a feature, which corresponds to one of several structural features that can be present in a dsRNA substrate of the present disclosure. Examples of features include a mismatch, a bulge (symmetrical bulge or asymmetrical bulge), an internal loop (symmetrical internal loop or asymmetrical internal loop), or a hairpin (a recruiting hairpin or a hairpin comprising a non-targeting domain). Engineered polynucleotides of the present disclosure can have from 1 to 50 features. Engineered polynucleotides of the present disclosure can have from 1 to 5, from 5 to 10, from 10 to 15, from 15 to 20, from 20 to 25, from 25 to 30, from 30 to 35, from 35 to 40, from 40 to 45, from 45 to 50, from 5 to 20, from 1 to 3, from 4 to 5, from 2 to 10, from 20 to 40, from 10 to 40, from 20 to 50, from 30 to 50, from 4 to 7, or from 8 to 10 features.

As disclosed herein, a structured motif comprises two or more features in a dsRNA substrate.

A double stranded RNA (dsRNA) substrate can be formed upon hybridization of an engineered polynucleotide of the present disclosure to a target RNA. As disclosed herein, a mismatch refers to a nucleotide in a polynucleotide that can be unpaired to an opposing nucleotide in a target RNA within the dsRNA. A mismatch can comprise any two nucleotides that do not base pair, can be not complementary, or both. In some embodiments, a mismatch can be an A/C mismatch. An A/C mismatch can comprise a C in an engineered polynucleotide of the present disclosure opposite an A in a target RNA. An A/C mismatch can comprise a A in an engineered polynucleotide of the present disclosure opposite an C in a target RNA. In an embodiment, a G/G mismatch can comprise a G in an engineered polynucleotide of the present disclosure opposite a Gin a target RNA. In some embodiments, a mismatch positioned 5' of the edit site can facilitate base-flipping of the target A to be edited. A mismatch can also help confer sequence specificity. In an embodiment, a mismatch comprises a G/G mismatch. In an embodiment, a mismatch comprises an A/C mismatch, wherein the A can be in the target RNA and the C can be in the targeting sequence of the engineered polynucleotide. In another embodiment, the A in the A/C mismatch can be the base of the nucleotide in the target RNA edited by a subject RNA editing entity.

In an aspect, a structural feature can form in an engineered polynucleotide independently. In other cases, a structural feature can form when an engineered polynucleotide binds to a target RNA. A structural feature can also form when an engineered polynucleotide associates with other molecules such as a peptide, a nucleotide, or a small molecule. In certain embodiments, a structural feature of an engineered polynucleotide can be formed independent of a target RNA, and its structure can change as a result of the engineered polypeptide hybridization with a target RNA region. In certain embodiments, a structural feature can be present when an engineered polynucleotide can be in association with a target RNA.

In some cases, a structural feature can be a hairpin. In some cases, an engineered polynucleotide can lack a hairpin domain. In other cases, an engineered polynucleotide can contain a hairpin domain or more than one hairpin domain.

A hairpin can be located anywhere in a polynucleotide. As disclosed herein, a hairpin can be an RNA duplex wherein a single RNA strand has folded in upon itself to form the RNA duplex. The single RNA strand folds upon itself due to having nucleotide sequences upstream and downstream of the folding region base pairs to each other. A hairpin can have from 10 to 500 nucleotides in length of the entire duplex structure. The stem-loop structure of a hairpin can be from 3 to 15 nucleotides long. A hairpin can be present in any of the engineered polynucleotides disclosed herein. The engineered polynucleotides disclosed herein can have from 1 to 10 hairpins. In some embodiments, the engineered polynucleotides disclosed herein have 1 hairpin. In some embodiments, the engineered polynucleotides disclosed herein have 2 hairpins. As disclosed herein, a hairpin can refer to a recruitment hairpin or a hairpin or a non-recruitment hairpin. A hairpin can be located anywhere within the engineered polynucleotides of the present disclosure. In some embodiments, one or more hairpins can be present at the β' end of an engineered polynucleotide of the present disclosure, at the 5' end of an engineered polynucleotide of the present disclosure or within the targeting sequence of an engineered polynucleotide of the present disclosure, or any combination thereof.

In aspect, a structural feature comprises a recruitment hairpin, as disclosed herein. A recruitment hairpin can recruit an RNA editing entity, such as ADAR. In some embodiments, a recruitment hairpin comprises a GluR2 domain. In some embodiments, a recruitment hairpin comprises an Alu domain.

In yet another aspect, a structural feature comprises a non-recruitment hairpin. A non-recruitment hairpin, as disclosed herein, can exhibit functionality that improves localization of the engineered polynucleotide to the target RNA. In some embodiments, the non-recruitment hairpin improves nuclear retention. In some embodiments, the non-recruitment hairpin comprises a hairpin from U7 snRNA.

In another aspect, a structural feature comprises a wobble base. A wobble base pair refers to two bases that weakly pair. For example, a wobble base pair of the present disclosure can refer to a G paired with a U.

A hairpin of the present disclosure can be of any length. In an aspect, a hairpin can be from about 5-200 or more nucleotides. In some cases, a hairpin can comprise about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, or 400 or more nucleotides. In other cases, a hairpin can also comprise 5 to 10, 5 to 20, 5 to 30, 5 to 40, 5 to 50, 5 to 60, 5 to 70, 5 to 80, 5 to 90, 5 to 100, 5 to 110, 5 to 120, 5 to 130, 5 to 140, 5 to 150, 5 to 160, 5 to 170, 5 to 180, 5 to 190, 5 to 200, 5 to 210, 5 to 220, 5 to 230, 5 to 240, 5 to 250, 5 to 260, 5 to 270, 5 to 280, 5 to 290, 5 to 300, 5 to 310, 5 to 320, 5 to 330, 5 to 340, 5 to 350, 5 to 360, 5 to 370, 5 to 380, 5 to 390, or 5 to 400 nucleotides. A hairpin can be a structural feature formed from a single strand of RNA with sufficient complementarity to itself to hybridize into a double stranded RNA motif/structure consisting of double-stranded hybridized RNA separated by a nucleotide loop.

In some cases, a structural feature can be a bulge. A bulge can comprise a single (intentional) nucleic acid mismatch between the target strand and an engineered polynucleotide strand. In other cases, more than one consecutive mismatch between strands constitutes a bulge as long as the bulge region, mismatched stretch of bases, can be flanked on both sides with hybridized, complementary dsRNA regions. A bulge can be located at any location of a polynucleotide. In some cases, a bulge can be located from about 30 to about 70 nucleotides from a 5' hydroxyl or the β' hydroxyl.

In an embodiment, a double stranded RNA (dsRNA) substrate can be formed upon hybridization of an engineered polynucleotide of the present disclosure to a target RNA. As disclosed herein, a bulge refers to the structure formed upon formation of the dsRNA substrate, where nucleotides in either the engineered polynucleotide or the target RNA can be not complementary to their positional counterparts on the opposite strand. A bulge can change the secondary or tertiary structure of the dsRNA substrate. A bulge can have from 1 to 4 nucleotides on the engineered polynucleotide side of the dsRNA substrate or the target RNA side of the dsRNA substrate. In some embodiments, the engineered polynucleotides of the present disclosure have 2 bulges. In some embodiments, the engineered polynucleotides of the present disclosure have 3 bulges. In some embodiments, the engineered polynucleotides of the present disclosure have 4 bulges. In some embodiments, the presence of a bulge in a dsRNA substrate can position ADAR to selectively edit the target A in the target RNA and reduce off-target editing of non-targets. In some embodiments, the presence of a bulge in a dsRNA substrate can recruit additional ADAR. Bulges in dsRNA substrates disclosed herein can recruit other proteins, such as other RNA editing entities. In some embodiments, a bulge positioned 5' of the edit site can facilitate base-flipping of the target A to be edited. A bulge can also help confer sequence specificity. A bulge can help direct ADAR editing by constraining it in an orientation that yield selective editing of the target A.

In an aspect, a double stranded RNA (dsRNA) substrate can be formed upon hybridization of an engineered polynucleotide of the present disclosure to a target RNA. A bulge can be a symmetrical bulge or an asymmetrical bulge. A bulge can be formed by 1 to 4 participating nucleotides on either the polynucleotide side or the target RNA side of the dsRNA substrate. A symmetrical bulge can be formed when the same number of nucleotides can be present on each side of the bulge. A symmetrical bulge can have from 2 to 4 nucleotides on the engineered polynucleotide side of the dsRNA substrate or the target RNA side of the dsRNA substrate. For example, a symmetrical bulge in a dsRNA substrate of the present disclosure can have the same number of nucleotides on the engineered polynucleotide side and the target RNA side of the dsRNA substrate. A symmetrical bulge of the present disclosure can be formed by 2 nucleotides on the engineered polynucleotide side of the dsRNA target and 2 nucleotides on the target RNA side of the dsRNA substrate. A symmetrical bulge of the present disclosure can be formed by 3 nucleotides on the engineered polynucleotide side of the dsRNA target and 3 nucleotides on the target RNA side of the dsRNA substrate. A symmetrical bulge of the present disclosure can be formed by 4 nucleotides on the engineered polynucleotide side of the dsRNA target and 4 nucleotides on the target RNA side of the dsRNA substrate.

A double stranded RNA (dsRNA) substrate can be formed upon hybridization of an engineered polynucleotide of the present disclosure to a target RNA. A bulge can be a symmetrical bulge or an asymmetrical bulge. An asymmetrical bulge can be formed when a different number of nucleotides can be present on each side of the bulge. An asymmetrical bulge can have from 1 to 4 participating nucleotides on either the polynucleotide side or the target RNA side of the dsRNA substrate. For example, an asymmetrical bulge in a dsRNA substrate of the present disclosure can have different numbers of nucleotides on the engineered polynucleotide side and the target RNA side of the dsRNA substrate. An asymmetrical bulge of the present disclosure can be formed by 0 nucleotides on the engineered polynucleotide side of the dsRNA substrate and 1 nucleotide on the target RNA side of the dsRNA substrate. An asymmetrical bulge of the present disclosure can be formed by 0 nucleotides on the target RNA side of the dsRNA substrate and 1 nucleotide on the engineered polynucleotide side of the dsRNA substrate. An asymmetrical bulge of the present disclosure can be formed by 0 nucleotides on the engineered polynucleotide side of the dsRNA substrate and 2 nucleotides on the target RNA side of the dsRNA substrate. An asymmetrical bulge of the present disclosure can be formed by 0 nucleotides on the target RNA side of the dsRNA substrate and 2 nucleotides on the engineered polynucleotide side of the dsRNA substrate. An asymmetrical bulge of the present disclosure can be formed by 0 nucleotides on the engineered polynucleotide side of the dsRNA substrate and 3 nucleotides on the target RNA side of the dsRNA substrate. An asymmetrical bulge of the present disclosure can be formed by 0 nucleotides on the target RNA side of the dsRNA substrate and 3 nucleotides on the engineered polynucleotide side of the dsRNA substrate. An asymmetrical bulge of the present disclosure can be formed by 0 nucleotides on the engineered polynucleotide side of the dsRNA substrate and 4 nucleotides on the target RNA side of the dsRNA substrate. An asymmetrical bulge of the present disclosure can be formed by 0 nucleotides on the target RNA side of the dsRNA substrate and 4 nucleotides on the engineered polynucleotide side of the dsRNA substrate. An asymmetrical bulge of the present disclosure can be formed by 1 nucleotide on the engineered polynucleotide side of the dsRNA substrate and 2 nucleotides on the target RNA side of the dsRNA substrate. An asymmetrical bulge of the present disclosure can be formed by 1 nucleotide on the target RNA side of the dsRNA substrate and 2 nucleotides on the engineered polynucleotide side of the dsRNA substrate. An asymmetrical bulge of the present disclosure can be formed by 1 nucleotide on the engineered polynucleotide side of the dsRNA substrate and 3 nucleotides on the target RNA side of the dsRNA substrate. An asymmetrical bulge of the present disclosure can be formed by 1 nucleotide on the target RNA side of the dsRNA substrate and 3 nucleotides on the engineered polynucleotide side of the dsRNA substrate. An asymmetrical bulge of the present disclosure can be formed by 1 nucleotides on the engineered polynucleotide side of the dsRNA substrate and 4 nucleotides on the target RNA side of the dsRNA substrate. An asymmetrical bulge of the present disclosure can be formed by 1 nucleotide on the target RNA side of the dsRNA substrate and 4 nucleotides on the engineered polynucleotide side of the dsRNA substrate. An asymmetrical bulge of the present disclosure can be formed by 2 nucleotides on the engineered polynucleotide side of the dsRNA substrate and 3 nucleotides on the target RNA side of the dsRNA substrate. An asymmetrical bulge of the present disclosure can be formed by 2 nucleotides on the target RNA side of the dsRNA substrate and 3 nucleotides on the engineered polynucleotide side of the dsRNA substrate. An asymmetrical bulge of the present disclosure can be formed by 2 nucleotides on the engineered polynucleotide side of the dsRNA substrate and 4 nucleotides on the target RNA side of the dsRNA substrate. An asymmetrical bulge of the present disclosure can be formed by 2 nucleotides on the target RNA side of the dsRNA substrate and 4 nucleotides on the engineered polynucleotide side of the dsRNA substrate. An asymmetrical bulge of the present disclosure can be formed by 3 nucleotides on the engineered polynucleotide side of the dsRNA substrate and 4 nucleotides on the target RNA side of the dsRNA substrate. An asymmetrical bulge of the present disclosure can be formed by 3 nucleotides on the target RNA side of the dsRNA substrate and 4 nucleotides on the engineered polynucleotide side of the dsRNA substrate. In some cases, a structural feature can be a loop.

In an aspect, a double stranded RNA (dsRNA) substrate can be formed upon hybridization of an engineered polynucleotide of the present disclosure to a target RNA. As disclosed herein, an internal loop refers to the structure formed upon formation of the dsRNA substrate, where nucleotides in either the engineered polynucleotide or the target RNA can be not complementary to their positional counterparts on the opposite strand and where one side of the internal loop, either on the target RNA side or the engineered polynucleotide side of the dsRNA substrate, has greater than 5 nucleotides. An internal loop can be a symmetrical internal loop or an asymmetrical internal loop. Internal loops present in the vicinity of the edit site can help with base flipping of the target A in the target RNA to be edited. A double stranded RNA (dsRNA) substrate can be formed upon hybridization of an engineered polynucleotide of the present disclosure to a target RNA. An internal loop can be a symmetrical internal loop or an asymmetrical internal loop. A symmetrical internal loop can be formed when the same number of nucleotides can be present on each side of the internal loop. For example, a symmetrical internal loop in a dsRNA substrate of the present disclosure can have the same number of nucleotides on the engineered polynucleotide side and the target RNA side of the dsRNA substrate. A symmetrical internal loop of the present disclosure can be formed by 5 nucleotides on the engineered polynucleotide side of the dsRNA target and 5 nucleotides on the target RNA side of the dsRNA substrate. A symmetrical internal loop of the present disclosure can be formed by 6 nucleotides on the engineered polynucleotide side of the dsRNA target and 6 nucleotides on the target RNA side of the dsRNA substrate. A symmetrical internal loop of the present disclosure can be formed by 7 nucleotides on the engineered polynucleotide side of the dsRNA target and 7 nucleotides on the target RNA side of the dsRNA substrate. A symmetrical internal loop of the present disclosure can be formed by 8 nucleotides on the engineered polynucleotide side of the dsRNA target and 8 nucleotides on the target RNA side of the dsRNA substrate. A symmetrical internal loop of the present disclosure can be formed by 9 nucleotides on the engineered polynucleotide side of the dsRNA target and 9 nucleotides on the target RNA side of the dsRNA substrate. A symmetrical internal loop of the present disclosure can be formed by 10 nucleotides on the engineered polynucleotide side of the dsRNA target and 10 nucleotides on the target RNA side of the dsRNA substrate.

In an aspect, a double stranded RNA (dsRNA) substrate can be formed upon hybridization of an engineered polynucleotide of the present disclosure to a target RNA. An internal loop can be a symmetrical internal loop or an asymmetrical internal loop. An asymmetrical internal loop can be formed when a different number of nucleotides can be present on each side of the internal loop. For example, an asymmetrical internal loop in a dsRNA substrate of the present disclosure can have different numbers of nucleotides on the engineered polynucleotide side and the target RNA side of the dsRNA substrate. An asymmetrical internal loop of the present disclosure can be formed by 5 nucleotides on the engineered polynucleotide side of the dsRNA substrate and 6 nucleotides on the target RNA side of the dsRNA substrate. An asymmetrical internal loop of the present disclosure can be formed by 5 nucleotides on the target RNA side of the dsRNA substrate and 6 nucleotides on the engineered polynucleotide side of the dsRNA substrate. An asymmetrical internal loop of the present disclosure can be formed by 5 nucleotides on the engineered polynucleotide side of the dsRNA substrate and 7 nucleotides on the target RNA side of the dsRNA substrate. An asymmetrical internal loop of the present disclosure can be formed by 5 nucleotides on the target RNA side of the dsRNA substrate and 7 nucleotides on the engineered polynucleotide side of the dsRNA substrate. An asymmetrical internal loop of the present disclosure can be formed by 5 nucleotides on the engineered polynucleotide side of the dsRNA substrate and 8 nucleotides internal loop the target RNA side of the dsRNA substrate. An asymmetrical internal loop of the present disclosure can be formed by 5 nucleotides on the target RNA side of the dsRNA substrate and 8 nucleotides on the engineered polynucleotide side of the dsRNA substrate. An asymmetrical internal loop of the present disclosure can be formed by 5 nucleotides on the engineered polynucleotide side of the dsRNA substrate and 9 nucleotides internal loop the target RNA side of the dsRNA substrate. An asymmetrical internal loop of the present disclosure can be formed by 5 nucleotides on the target RNA side of the dsRNA substrate and 9 nucleotides on the engineered polynucleotide side of the dsRNA substrate. An asymmetrical internal loop of the present disclosure can be formed by 5 nucleotides on the engineered polynucleotide side of the dsRNA substrate and 10 nucleotides internal loop the target RNA side of the dsRNA substrate. An asymmetrical internal loop of the present disclosure can be formed by 5 nucleotides on the target RNA side of the dsRNA substrate and 10 nucleotides on the engineered polynucleotide side of the dsRNA substrate. An asymmetrical internal loop of the present disclosure can be formed by 6 nucleotides on the engineered polynucleotide side of the dsRNA substrate and 7 nucleotides internal loop the target RNA side of the dsRNA substrate. An asymmetrical internal loop of the present disclosure can be formed by 6 nucleotides on the target RNA side of the dsRNA substrate and 7 nucleotides on the engineered polynucleotide side of the dsRNA substrate. An asymmetrical internal loop of the present disclosure can be formed by 6 nucleotides on the engineered polynucleotide side of the dsRNA substrate and 8 nucleotides internal loop the target RNA side of the dsRNA substrate. An asymmetrical internal loop of the present disclosure can be formed by 6 nucleotides on the target RNA side of the dsRNA substrate and 8 nucleotides on the engineered polynucleotide side of the dsRNA substrate. An asymmetrical internal loop of the present disclosure can be formed by 6 nucleotides on the engineered polynucleotide side of the dsRNA substrate and 9 nucleotides internal loop the target RNA side of the dsRNA substrate. An asymmetrical internal loop of the present disclosure can be formed by 6 nucleotides on the target RNA side of the dsRNA substrate and 9 nucleotides on the engineered polynucleotide side of the dsRNA substrate. An asymmetrical internal loop of the present disclosure can be formed by 6 nucleotides on the engineered polynucleotide side of the dsRNA substrate and 10 nucleotides internal loop the target RNA side of the dsRNA substrate. An asymmetrical internal loop of the present disclosure can be formed by 6 nucleotides on the target RNA side of the dsRNA substrate and 10 nucleotides on the engineered polynucleotide side of the dsRNA substrate. An asymmetrical internal loop of the present disclosure can be formed by 7 nucleotides on the engineered polynucleotide side of the dsRNA substrate and 8 nucleotides internal loop the target RNA side of the dsRNA substrate. An asymmetrical internal loop of the present disclosure can be formed by 7 nucleotides on the target RNA side of the dsRNA substrate and 8 nucleotides on the engineered polynucleotide side of the dsRNA substrate. An asymmetrical internal loop of the present disclosure can be formed by 7 nucleotides on the engineered polynucleotide side of the dsRNA substrate and 9 nucleotides internal loop the target RNA side of the dsRNA substrate. An asymmetrical internal loop of the present disclosure can be formed by 7 nucleotides on the target RNA side of the dsRNA substrate and 9 nucleotides on the engineered polynucleotide side of the dsRNA substrate. An asymmetrical internal loop of the present disclosure can be formed by 7 nucleotides on the engineered polynucleotide side of the dsRNA substrate and 10 nucleotides internal loop the target RNA side of the dsRNA substrate. An asymmetrical internal loop of the present disclosure can be formed by 7 nucleotides on the target RNA side of the dsRNA substrate and 10 nucleotides on the engineered polynucleotide side of the dsRNA substrate. An asymmetrical internal loop of the present disclosure can be formed by 8 nucleotides on the engineered polynucleotide side of the dsRNA substrate and 9 nucleotides internal loop the target RNA side of the dsRNA substrate. An asymmetrical internal loop of the present disclosure can be formed by 8 nucleotides on the target RNA side of the dsRNA substrate and 9 nucleotides on the engineered polynucleotide side of the dsRNA substrate. An asymmetrical internal loop of the present disclosure can be formed by 8 nucleotides on the engineered polynucleotide side of the dsRNA substrate and 10 nucleotides internal loop the target RNA side of the dsRNA substrate. An asymmetrical internal loop of the present disclosure can be formed by 8 nucleotides on the target RNA side of the dsRNA substrate and 10 nucleotides on the engineered polynucleotide side of the dsRNA substrate. An asymmetrical internal loop of the present disclosure can be formed by 9 nucleotides on the engineered polynucleotide side of the dsRNA substrate and 10 nucleotides internal loop the target RNA side of the dsRNA substrate. An asymmetrical internal loop of the present disclosure can be formed by 9 nucleotides on the target RNA side of the dsRNA substrate and 10 nucleotides on the engineered polynucleotide side of the dsRNA substrate.

Structural features that comprise a bulge or loop can be of any size. In some cases, a bulge or loop comprise at least: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 bases. In some cases, a bulge or loop comprise at least about 1-10, 5-15, 10-20, 15-25, or 20-30 bases in total.

In some cases, a structural feature can be a structured motif. As disclosed herein, a structured motif comprises two or more structural features in a dsRNA substrate. A structured motif can comprise of any combination of structural features, such as in the above claims, to generate an ideal substrate for ADAR editing at a precise location(s). These structural motifs could be artificially engineered to maximized ADAR editing, and/or these structural motifs can be modeled to recapitulate known ADAR substrates.

In some cases, a structural feature comprises an at least partial circularization of a polynucleotide. In some cases, a polynucleotide provided herein can be circularized or in a circular configuration. In some aspects, an at least partially circular polynucleotide lacks a 5' hydroxyl or a 3' hydroxyl.

In some embodiments, an engineered polynucleotide can comprise a backbone comprising a plurality of sugar and phosphate moieties covalently linked together. In some cases, a backbone of an engineered polynucleotide can comprise a phosphodiester bond linkage between a first hydroxyl group in a phosphate group on a 5' carbon of a deoxyribose in DNA or ribose in RNA and a second hydroxyl group on a 3' carbon of a deoxyribose in DNA or ribose in RNA.

In some embodiments, a backbone of an engineered polynucleotide can lack a 5' reducing hydroxyl, a 3' reducing hydroxyl, or both, capable of being exposed to a solvent. In some embodiments, a backbone of an engineered polynucleotide can lack a 5' reducing hydroxyl, a 3' reducing hydroxyl, or both, capable of being exposed to nucleases. In some embodiments, a backbone of an engineered polynucleotide can lack a 5' reducing hydroxyl, a 3' reducing hydroxyl, or both, capable of being exposed to hydrolytic enzymes. In some instances, a backbone of an engineered polynucleotide can be represented as a polynucleotide sequence in a circular 2-dimensional format with one nucleotide after the other. In some instances, a backbone of an engineered polynucleotide can be represented as a polynucleotide sequence in a looped 2-dimensional format with one nucleotide after the other. In some cases, a 5' hydroxyl, a 3' hydroxyl, or both, are joined through a phosphorus-oxygen bond. In some cases, a 5' hydroxyl, a 3' hydroxyl, or both, are modified into a phosphoester with a phosphorus-containing moiety.

Subject polynucleotides can comprise modifications. A modification can be a substitution, insertion, deletion, chemical modification, physical modification, stabilization, purification, or any combination thereof. In some cases, a modification is a chemical modification. Suitable chemical modifications comprise any one of: 5'adenylate, 5' guanosine-triphosphate cap, 5'N7-Methylguanosine-triphosphate cap, 5'triphosphate cap, 3'phosphate, 3'thiophosphate, 5'phosphate, 5'thiophosphate, Cis-Syn thymidine dimer, trimers, C12 spacer, C3 spacer, C6 spacer, dSpacer, PC spacer, rSpacer, Spacer 18, Spacer 9,3'-3' modifications, 5'-5' modifications, abasic, acridine, azobenzene, biotin, biotin BB, biotin TEG, cholesteryl TEG, desthiobiotin TEG, DNP TEG, DNP-X, DOTA, dT-Biotin, dual biotin, PC biotin, psoralen C2, psoralen C6, TINA, 3'DABCYL, black hole quencher 1, black hole quencher 2, DABCYL SE, dT-DABCYL, IRDye QC-1, QSY-21, QSY-35, QSY-7, QSY-9, carboxyl linker, thiol linkers, 2'deoxyribonucleoside analog purine, 2'deoxyribonucleoside analog pyrimidine, ribonucleoside analog, 2'-O-methyl ribonucleoside analog, sugar modified analogs, wobble/universal bases, fluorescent dye label, 2'fluoro RNA, 2'O-methyl RNA, methylphosphonate, phosphodiester DNA, phosphodiester RNA, phosphothioate DNA, phosphorothioate RNA, UNA, pseudouridine-5'-triphosphate, 5-methylcytidine-5'-triphosphate, 2-O-methyl 3phosphorothioate or any combinations thereof.

A modification can be made at any location of a polynucleotide. In some cases, a modification is located in a 5' or 3' end. In some cases, a polynucleotide comprises a modification at a base selected from: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, or 150. More than one modification can be made to a polynucleotide. In some cases, a modification can be permanent. In other cases, a modification can be transient. In some cases, multiple modifications are made to a polynucleic acid. A polynucleic acid modification may alter physio-chemical properties of a nucleotide, such as their conformation, polarity, hydrophobicity, chemical reactivity, base-pairing interactions, or any combination thereof.

A modification can also be a phosphorothioate substitute. In some cases, a natural phosphodiester bond may be susceptible to rapid degradation by cellular nucleases and; a modification of internucleotide linkage using phosphorothioate (PS) bond substitutes can be more stable towards hydrolysis by cellular degradation. A modification can increase stability in a polynucleic acid. A modification can also enhance biological activity. In some cases, a phosphorothioate enhanced RNA polynucleic acid can inhibit RNase A, RNase T1, calf serum nucleases, or any combinations thereof. These properties can allow the use of PS-RNA polynucleic acids to be used in applications where exposure to nucleases is of high probability in vivo or in vitro. For example, phosphorothioate (PS) bonds can be introduced between the last 3-5 nucleotides at the 5'- or 3'-end of a polynucleic acid which can inhibit exonuclease degradation. In some cases, phosphorothioate bonds can be added throughout an entire polynucleic acid to reduce attack by endonucleases.

An engineered polynucleotide can have any frequency of bases. For example, a polynucleotide can have a percent adenine of 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 1-5%, 3-8%, 5-12%, 10- 15%, 8-20%, 15-25%, 20-30%, 25-35%, or up to about 30-40%. A polynucleotide can have a percent cytosine of 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 1-5%, 3-8%, 5-12%, 10-15%, 8-20%, 15-25%, 20-30%, 25-35%, or up to about 30-40%. A polynucleotide can have a percent thymine of 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 1-5%, 3-8%, 5-12%, 10-15%, 8-20%, 15-25%, 20-30%, 25-35%, or up to about 30-40%. A polynucleotide can have a percent guanine of 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 1-5%, 3-8%, 5-12%, 10-15%, 8-20%, 15-25%, 20-30%, 25-35%, or up to about 30-40%. A polynucleotide can have a percent uracil of 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 1-5%, 3-8%, 5-12%, 10-15%, 8-20%, 15-25%, 20-30%, 25-35%, or up to about 30-40%.

In some cases, an engineered polynucleotide can undergo quality control after a modification. In some cases, quality control may include PAGE, HPLC, MS, or any combination thereof. In some cases, a mass of a polynucleotide can be determined. A mass can be determined by LC-MS assay. A mass can be 30,000 amu, 50,000amu, 70,000 amu, 90,000 amu, 100,000 amu, 120,000 amu, 150,000 amu, 175,000 amu, 200,000 amu, 250,000 amu, 300,000 amu, 350,000 amu, 400,000 amu, to about 500,000 amu. A mass can be of a sodium salt of a polynucleotide.

In some cases, an endotoxin level of a polynucleotide can be determined. A clinically/therapeutically acceptable level of an endotoxin can be less than 3 EU/mL. A clinically/therapeutically acceptable level of an endotoxin can be less than 10 EU/mL. A clinically/therapeutically acceptable level of an endotoxin can be less than 8 EU/mL. A clinically/therapeutically acceptable level of an endotoxin can be less than 5 EU/mL. A clinically/therapeutically acceptable level of an endotoxin can be less than 4 EU/mL. A clinically/therapeutically acceptable level of an endotoxin can be less than 3 EU/mL. A clinically/therapeutically acceptable level of an endotoxin can be less than 2 EU/mL. A clinically/therapeutically acceptable level of an endotoxin can be less than 1 EU/mL. A clinically/therapeutically acceptable level of an endotoxin can be less than 0.5 EU/mL.

In some cases, a polynucleotide can undergo sterility testing. A clinically/therapeutically acceptable level of a sterility testing can be 0 or denoted by no growth on a culture. A clinically/therapeutically acceptable level of a sterility testing can be less than 0.5% growth. A clinically/therapeutically acceptable level of a sterility testing can be less than 1% growth.

In some cases, any one of the polynucleotides that comprise recruiting sequences may also comprise structural features described herein.

Also provided are linear engineered polynucleotides. Linear polynucleotides can substantially lack structural features provided herein. For example, a linear polynucleotide can lack a structural feature or can have less than about 2 structural features or partial structures. A partial structure can comprise a portion of the bases required to achieve a structural feature as described herein.

In other cases, a linear engineered polynucleotide can comprise any one of: 5' hydroxyl, a 3' hydroxyl, or both. Any one of these can be capable of being exposed to solvent and maintain linearization.

Compositions and methods provided herein can be utilized to modulate expression of a target. Modulation can refer to altering the expression of a gene or portion thereof at one of various stages, with a view to alleviate a disease or condition associated with the gene or a mutation in the gene. Modulation can be mediated at the level of transcription or post-transcriptionally. Modulating transcription can correct aberrant expression of splice variants generated by a mutation in a gene. In some cases, compositions and methods provided herein can be utilized to regulate gene translation of a target. Modulation can refer to decreasing or knocking down the expression of a gene or portion thereof by decreasing the abundance of a transcript. The decreasing the abundance of a transcript can be mediated by decreasing the processing, splicing, turnover or stability of the transcript; or by decreasing the accessibility of the transcript by translational machinery such as ribosome. In some cases, an engineered polynucleotide described herein can facilitate a knockdown. A knockdown can reduce the expression of a target RNA. In some cases, a knockdown can be accompanied by editing of an mRNA. In some cases, a knockdown can occur with substantially little to no editing of an mRNA. In some instances, a knockdown can occur by targeting an untranslated region of the target RNA, such as a 3' UTR, a 5' UTR or both. In some cases, a knockdown can occur by targeting a coding region of the target RNA. In some instances, a knockdown can be mediated by an RNA editing enzyme (e.g. ADAR). In some instances, an RNA editing enzyme can cause a knockdown by hydrolytic deamination of multiple adenosines in an RNA. Hydrolytic deamination of multiple adenosines in an RNA can be referred to as hyper-editing. In some cases, hyper-editing can occur in cis (e.g. in an Alu element) or in trans (e.g. in a target RNA by an engineered polynucleotide).

In an aspect, a subject engineered polynucleotide can be utilized to hyper-edit a target RNA or target RNA region. In some cases, hyper-editing can introduce edits in at least 2 or more nucleotides of a subject target RNA. In some cases, hyper-editing can introduce at least or at most about 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, or at least or at most about 100 edits in a region of a target RNA. In an embodiment, hyper-editing can occur in an untranslated region, translated region, 3'UTR, 5'UTR, or any combinations herein and thereof. In an embodiment, a target RNA of a subject APP mRNA can be hyper-edited to mutagenize the mRNA thereby generating a modified APP polypeptide that has reduced or eliminated cleavage as compared to an otherwise comparable APP polypeptide that is not modified. In an embodiment, a region of a target mRNA can be mutagenized at the β-Secretase cut site and the residues distal and proximal to it such that the modified polypeptide has reduced or eliminated cleavage by a β-Secretase. In an aspect, the reduced cleavage is at least about or at most about 1-fold, 3-fold, 5-fold, 7-fold, 10-fold, 15-fold, 20-fold, 40-fold, 60-fold, 80-fold, or 100-fold reduced as compared to an otherwise comparable target mRNA that does not under hyper-editing, for example using a subject engineered polypeptide system. In an embodiment, hyper-editing can modulate a driver event in disease by reducing or eliminating a substrate preference of β-Secretases (including but not limited to BACE1); and not majorly modulating APP expression which in turn can enable APP's primary cellular functions to remain largely unaffected. BACE1 substrate preferences are shown below, and also the APP mRNA sequence with putative adenosines that may be edited (singly or in combinations). Examples of this methodology are provided in Example 19 and 20.

In an aspect, a subject engineered polynucleotide can be designed utilizing methods that comprise tiling. For example, an engineered polynucleotide can be selected from a plurality of candidate engineered polynucleotides that have been tiled against a nucleic acid or polypeptide of a subject target RNA. In an embodiment, an engineered polynucleotide can be selected from a group of engineered polynucleotides that have been tiled against a nucleic acid or polypeptide of a subject target RNA, such as APP, SNCA, and/or Tau. In some cases, tiling can comprise tiling engineered polynucleotides across regulatory elements of subject targets. In some cases, tiling can comprise tiling engineered polynucleotides across any one of: a poly(A) tail, a microRNA response element (MRE), an AU-rich element (ARE), 5'UTR, 3'UTR, or any combination thereof of subject target sequence.

In an aspect, engineered polynucleotides that are tiled against a target RNA or nucleic acid can be pooled for use in a method described herein. In some cases, engineered polynucleotides can be pooled for detecting a target in a single assay. The pooling of engineered polynucleotides that are tiled against a single target can enhance the detection of a target RNA using the methods described herein. The tiling for example, can be sequential along the target nucleic acid or target polypeptide. Sometimes, the tiling can be overlapping along the target nucleic acid or target RNA. In some instances, the tiling comprises gaps between the tiled engineered polynucleotide along the target nucleic acid or target RNA. In some instances, the tiling of an engineered polynucleotide can be non-sequential. Often, a method for detecting a target nucleic acid and/or target RNA can comprise contacting a target nucleic acid or target RNA to a pool of engineered polynucleotides and an RNA editing entity and/or nuclease, wherein an engineered polynucleotide of the pool of engineered polynucleotides comprises a targeting sequence to a sequence of a target; and assaying for editing.

In some embodiments, engineered polynucleotides can include cis-regulatory elements. Such cis-regulatory elements can include specific RNA sequence. In some cases, the cis-regulatory elements can regulate the RNA abundance, RNA synthesis, RNA stability, RNA degradation, or RNA localization of engineered polynucleotides. Such cis-regulatory elements can comprise Malat1, Xist, Neat1, or snoRNAs sequence. Malat1 sequence can localize engineered polynucleotides to the nucleus. Malat1, Xist, Neat1, or snoRNAs sequence can also provide a nuclear retention signal for the polynucleotide.

In some cases, engineered polynucleotides can be expressed from a Polymerase I, II, or III promoter. In other cases, the promoter can be a tissue-specific promoter. In some cases, multiple engineered polynucleotides can be expressed by a Polymerase I, II, or III promoter. In some cases, multiple engineered polynucleotides can be expressed a Polymerase I, II, or III promoter from one direction by placing multiple engineered polynucleotides from one side of the Polymerase I, II, or III promoter. In other cases, multiple engineered polynucleotides can be expressed a Polymerase I, II, or III promoter from two directions by placing multiple engineered polynucleotides from both sides of the Polymerase I, II, or III promoter.

In some embodiments, a engineered polynucleotide can have a length of 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, or 500 nucleotides. In some embodiments, an engineered polynucleotide can have a length from about: 5-50, 10-50, 20-80, 30-100, 40-130, 50-150, 50-200, 50-300, 100-200, 100-150, 100-250, 150-300, 200-300, 300-400, 250-400, 250-500, 250-450, or 400-500 nucleotides in length.

In some embodiments, a reporter assay can be used to measure the editing efficiency of an engineered polynucleotides or a target RNA sequence. A reporter assay can comprise a reporter. A reporter can be a nucleic acid reporter or a protein reporter. A nucleic acid reporter can be maintained on a plasmid, viral vector, non-viral vector, a linear nucleic acid sequence, a circular nucleic acid, a nucleic acid with a 5' or a 3' reducing hydroxyl group. In some embodiments, a reporter can comprise a transcriptional, post-transcriptional, a translational, or a post-translational reporter. In some case, a reporter can comprise a luciferase reporter, fluorescence reporter, drug resistance reporter, cell viability reporter, protein activity reporter, enzymatic activity reporter, polypeptide or protein binding activity reporter, nucleic acid activity reporter, or any combinations described herein and thereof.

In some embodiments, a reporter can comprise two kozak start codons. In some embodiments, a reporter can comprise 0, 1, 2, 3, 4, 5, 6, 7, 8, 9, 10, or more kozak start codons. A start codon can comprise ATG. In some cases, a nucleic acid sequence including but not limited to DNA or RNA sequence can be placed upstream or 5' of a kozak start codon. In some cases, a nucleic acid sequence including but not limited to DNA or RNA sequence can be placed in-frame and/or downstream or 3' of a kozak start codon. In some embodiments, a sequence placed in-frame and/or downstream or 3' of a kozak start codon can be translationally initiated at the kozak start codon. In some cases, a sequenced placed in-frame and downstream or 3' of a kozak start codon may not be translationally initiated at the kozak start codon. In some embodiments, a reporter can comprise a first nucleic acid sequence placed upstream or 5' of a first kozak start codon and a second nucleic acid sequence placed in-frame and/or downstream or 3' of the first kozak start codon. In some embodiments, a reporter can comprise a first nucleic acid sequence placed upstream or 5' of a first kozak start codon and a second nucleic acid sequence placed in-frame and/or downstream or 3' of a second kozak start codon. In some cases, a first kozak start codon and a second kozak start codon can be separated by 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, or 500 nucleotides. In other cases, a first kozak start codon and a second kozak start codon can be separated by 0-10, 9-20, 19-30, 29-40, 39-50, 49-100, 99-150, 149-200, 199-250, 249-300, 299-350, 349-400, 399-450, or 499-500 nucleotides. In some cases, a first sequence placed upstream or 5' of a first kozak start codon can increase or decrease the translation of a second sequence placed in-frame and downstream or 3' of a second kozak start codon. In some cases, a first sequence placed downstream or 3' of a first kozak start codon but before a second kozak start codon can increase or decrease the translation of a second sequence placed in-frame and downstream or 3' of the second kozak start codon. In some embodiments, the sequence 5' and 3' of a kozak codon can comprise the sequence of a genomic locus or RNA. An RNA can comprise a precursor-mRNA, a pre-messenger RNA (mRNA), a messenger RNA (mRNA), a ribosomal RNA, a transfer RNA (tRNA), a long non-coding RNA, a small RNA, a nuclear RNA, a cytoplasmic RNA, a prokaryotic RNA, a synthesized RNA, a purified RNA, a single-stranded RNA, a double-stranded RNA, a mitochondrial RNA, and any combination thereof. In some embodiments, a suitable RNA to target can comprise a ribozyme, isolated RNA of a sequence, sgRNA, guide RNA, snRNA, long non-coding RNA, long intergenic non-coding RNA, enhancer RNA, extracellular RNA, Y RNA, hnRNA, scaRNA, circRNA, snoRNA, siRNA, miRNA, tRNA-derived small RNA (tsRNA), antisense RNA, shRNA, small rDNA-derived RNA (srRNA), a portion thereof, and any combination thereof. In some embodiment, a portion of an RNA can be coding or non-coding. In other cases, a portion of an RNA can comprise a 5'UTR or 3'UTR. In some instances, a portion of an RNA can comprise a sequence from a Charcot-Marie-Tooth Syndrome 1A, APP, tau, or alpha-synuclein mRNA. In some cases, a second sequence placed in-frame and downstream or 3' of a second kozak start codon can comprise a sequence encoding a reporter or a portion of a reporter described herein and thereof.

In some embodiments, an editing of a base of a nucleotide of a first sequence placed upstream/5' or downstream of a first kozak start codon can increase or decrease the translation of a second nucleic acid sequence placed in-frame and/or downstream or 3' of the first kozak start codon. In some cases, an increase or decrease of the translation of a second nucleic acid sequence placed in-frame and/or downstream or 3' of a first kozak start codon can comprise an increase or decrease in translational initiation, elongation, termination, re-initiation, or any combinations thereof of the second nucleic acid sequence. In some embodiments, an amount of an editing of a base of a nucleotide of a first sequence placed upstream/5' of a first kozak start codon can be linear to the translational initiation, elongation, termination, re-initiation, or any combinations thereof of a second nucleic acid sequence placed downstream or 3' of the first kozak codon. In some embodiments, an amount of an editing of a base of a nucleotide of a sequence placed upstream/5' or downstream/3' of a first kozak start codon may not be linear to the translational initiation, elongation, termination, re-initiation, or any combinations thereof of a second nucleic acid sequence placed downstream or 3' of the first kozak codon.

In some embodiments, an editing of a base of a nucleotide of a sequence placed upstream/5' or downstream/3' of a first kozak start codon can increase or decrease the translation of a second nucleic acid sequence placed in-frame and/or downstream or 3' of a second kozak start codon. In some cases, an increase or decrease of the translation of a second nucleic acid sequence placed in-frame and/or downstream or 3' of a second kozak start codon can comprise an increase or decrease in translational initiation, elongation, termination, re-initiation, or any combinations thereof of the second nucleic acid sequence. In some embodiments, an amount of an editing of a base of a nucleotide of a sequence placed upstream/5' or downstream/3' of a first kozak start codon can be linear to the translational initiation, elongation, termination, re-initiation, or any combinations thereof of a second nucleic acid sequence placed downstream or 3' of a second kozak codon. In some embodiments, an amount of an editing of a base of a nucleotide of a sequence placed upstream/5' or downstream/3' of a first kozak start codon may not be linear to the translational initiation, elongation, termination, re-initiation, or any combinations thereof of a second nucleic acid sequence placed downstream or 3' of a second kozak codon.

Suitable Targets

Compositions and methods provided herein can be utilized to target suitable RNA polypeptides and portions thereof. A suitable RNA can comprise a non-protein coding region or a protein coding region. Exemplary non-protein coding regions include but are not limited to a three prime untranslated region (3'UTR), five prime untranslated region (5'UTR), poly(A) tail, a microRNA response element (MRE), AU-rich element (ARE), or any combination thereof. A suitable RNA can also comprise an intron, exon, or any combination thereof. In some cases, the engineered guide RNAs disclosed herein target a non-protein coding region in order to facilitate target protein knockdown.

In some cases, a suitable RNA to target includes but is not limited to: a precursor-mRNA, a pre-messenger RNA (mRNA), a messenger RNA (mRNA), a ribosomal RNA, a transfer RNA (tRNA), a long non-coding RNA, a small RNA, a nuclear RNA, a cytoplasmic RNA, a prokaryotic RNA, a synthesized RNA, a purified RNA, a single-stranded RNA, a double-stranded RNA, a mitochondrial RNA, and any combination thereof. In some embodiments, a suitable RNA to target can comprise a ribozyme, isolated RNA of a sequence, sgRNA, guide RNA, snRNA, long non-coding RNA, long intergenic non-coding RNA, enhancer RNA, extracellular RNA, Y RNA, hnRNA, scaRNA, circRNA, snoRNA, siRNA, miRNA, tRNA-derived small RNA (tsRNA), antisense RNA, shRNA, small rDNA-derived RNA (srRNA), and any combination thereof.

A messenger RNA or mRNA can comprise a nucleic acid molecule that is transcribed from DNA and then processed to remove non-coding sections known as introns. The resulting mRNA can be exported from the nucleus (or another locus where the DNA is present) and translated into a protein. A pre-mRNA can comprise the nucleic acid strand prior to processing to remove non-coding sections.

Exemplary endogenous targets can also comprise amyloid precursor protein (APP), Tau, and Alpha-synuclein (SNCA).

In some embodiments, the engineered polynucleotides disclosed herein can target a secretase enzyme cleavage site in APP and edit said cleavage site in order to modulate processing and cleavage of APP by secretase enzymes (e.g., a beta secretase such as BACE1, cathepsin B or Meprin beta). In some embodiments, the engineered polynucleotides can modulate the expression of APP. In some cases, the engineered polynucleotides can modulate the transcription or post-transcriptional regulation of the APP mRNA or pre-mRNA. In other cases, the engineered polynucleotides can correct aberrant expression of splice variants generated by a mutation in APP. In some cases, the engineered polynucleotides can modulate the gene or protein translation of APP. In some embodiments, the engineered polynucleotides can decrease, down-regulate, or knock down the expression of APP by decreasing the abundance of the APP transcript. In some instances, the engineered polynucleotides can decrease or down-regulate the processing, splicing, turnover or stability of the APP transcript; or the accessibility of the APP transcript by translational machinery such as ribosome. In some cases, an engineered polynucleotide can facilitate a knockdown of APP. A knockdown can reduce the expression of APP. In some cases, a knockdown can be accompanied by editing of the APP mRNA or pre-mRNA. In some cases, a knockdown can occur with substantially little to no editing of the APP mRNA or pre-mRNA. In some instances, a knockdown can occur by targeting an untranslated region of the APP mRNA or pre-mRNA, such as a 3' UTR, a 5' UTR or both. In some cases, a knockdown can occur by targeting a coding region of the APP mRNA or pre-mRNA.

Compositions described herein can edit the cleavage site in APP, so that β/γ secretases exhibit reduced cleavage of APP or can no longer cut APP, and therefore reduced levels of Abeta 40/Abeta 42 or no Abetas can be produced. Compositions consistent with the present disclosure may combine compositions for target APP cleavage site editing with compositions for Tau (e.g., a microtubule-associated protein Tau (MAPT) encoded from a MAPT gene) knockdown or compositions for Alpha-synuclein (SNCA) knockdown and can have synergistic effects to prevent and/or cure a neurodegenerative disease. The compositions and methods disclosed herein can yield results in editing and/or knockdown of targets without any of the resulting issues seen in small molecule or antibody therapy. Compositions can knockdown APP (instead of target cleavage site editing). Editing at the target cleavage site in APP and knockdown can be deployed singly or in combination.

In some cases, a targeting sequence of an engineered polynucleotide provided herein can at least partially hybridize to a region of a target RNA. A region of a target RNA can comprise: (a) a sequence that at least partially encodes for a suitable target provided herein, (b) a sequence that is proximal to a sequence that at least partially encodes for a suitable target provided herein, (c) comprises (a) and (b). For example, a region of a target RNA can comprise (a) a sequence that at least partially encodes for an APP, (b) a sequence that is proximal to a sequence that at least partially encodes for an APP, or (c) comprises (a) and (b). Other suitable targets can be targeted with engineered polynucleotides disclosed herein.

Amyloid precursor protein (APP)

Pathogenic cleavage of amyloid precursor protein (APP) can create Amyloid beta (Abeta) fragments, which has been implicated in Alzheimer's disease. The accumulation of Abeta fragments can: impair synaptic functions and related signaling pathways, change neuronal activities, trigger the release of neurotoxic mediators from glial cells, or any combination thereof. Abeta can alter kinase function, leading to Tau hyperphosphorylation.

Figure 2A:
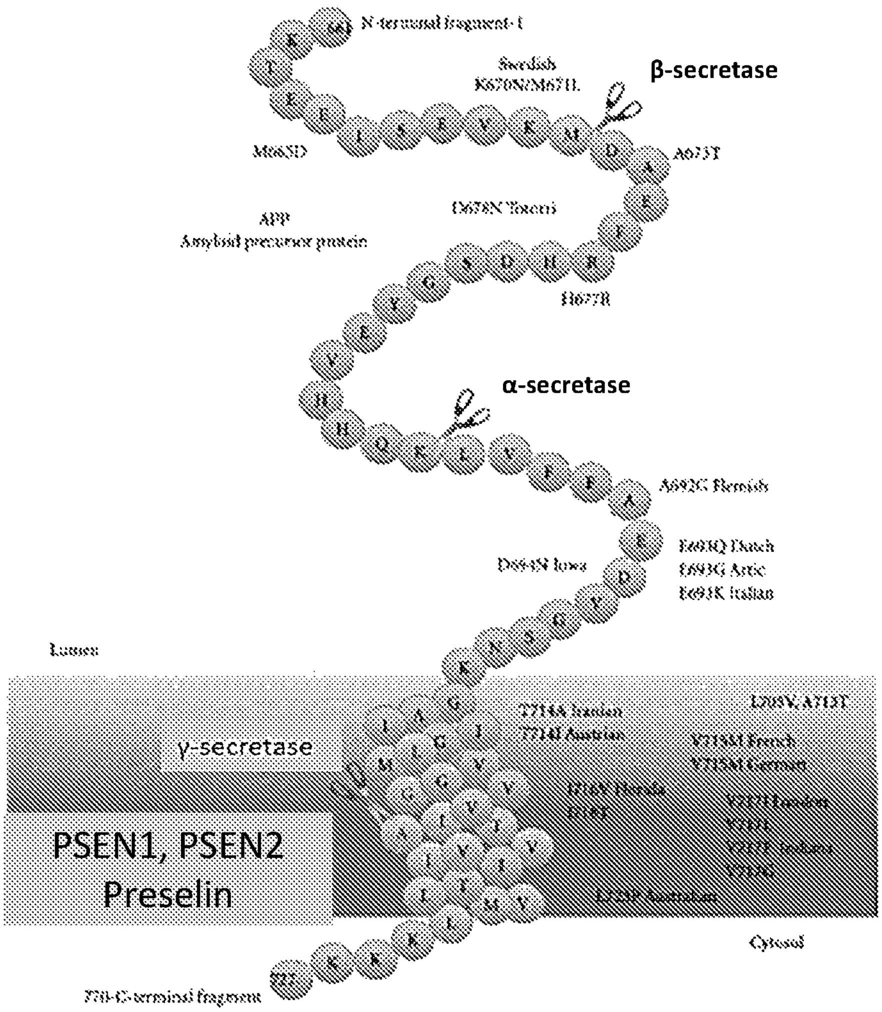
FIG. 2A shows an exemplary schematic of the processing of APP. It also shows the beta and gamma secretase cleavage sites on APP that can lead to Abeta fragment formation. Further, the pathogenic mutations that have been implicated in Alzheimer's diseases in different populations are shown. Autosomal dominant genetic mutations around β- and γ-secretase cleavage sites can cause either elevated levels of total Abeta metabolite production or can cause a specific increase in Abeta 42 peptides, which can be more hydrophobic, which may be associated with early onset Alzheimer's disease risk (both increased and decreased). These data have been used to support development and clinical testing of β- and γ-secretase inhibitors. Examples of such mutations are further described. For example, the A673V mutation can shift APP processing toward the amyloidogenic pathway, with increased production of Abeta peptides, and markedly can enhance the aggregation and fibrillogenic properties of both Abeta 40 and Abeta 42. The A673T mutation lies adjacent to the β-secretase cleavage site in the APP gene and can result in an about 40% reduction in the formation of Abeta peptides in vitro. This variant was found to be significantly more common in the aged control group than in AD cases, suggesting that A673T reduces the risk for AD. Genetics and genomic studies of APP have identified 52 pathogenic mutations in APP that can lead to Abeta deposition in the brain parenchyma and in cerebral blood vessels. Studies of these families have shown that over-expression of the normal APP sequence (trisomy 21 or APP duplication) or mutations that lead to elevated total Abeta, elevated Abeta 42, or increased Abeta aggregation can lead to dementia or AD neuropathology. Figure discloses SEQ ID NO: 197.
Figure 2B:
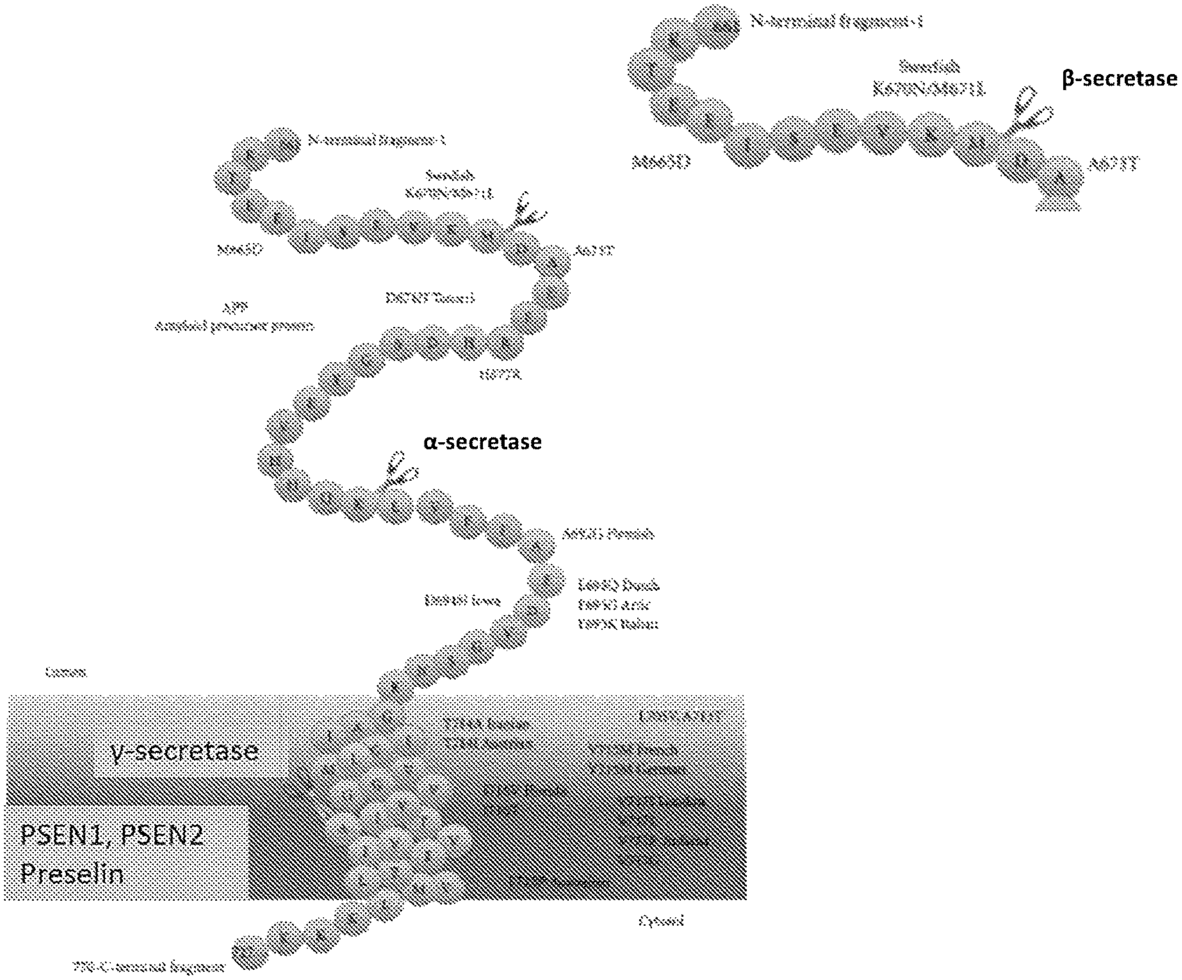
FIG. 2B shows an exemplary schematic showing possible sites for mRNA base editing of APP. Using mRNA base editing, the compositions as described herein can specifically alter amino acid residues that can be critical for BACE1-mediated proteolysis, thereby reducing or eliminating formation of Abeta fragments associated with increased Alzheimer's disease risk while preserving both BACE1 function and normal APP levels. Figure discloses SEQ ID NOS 197-198, respectively, in order of appearance.
Figure 2C:
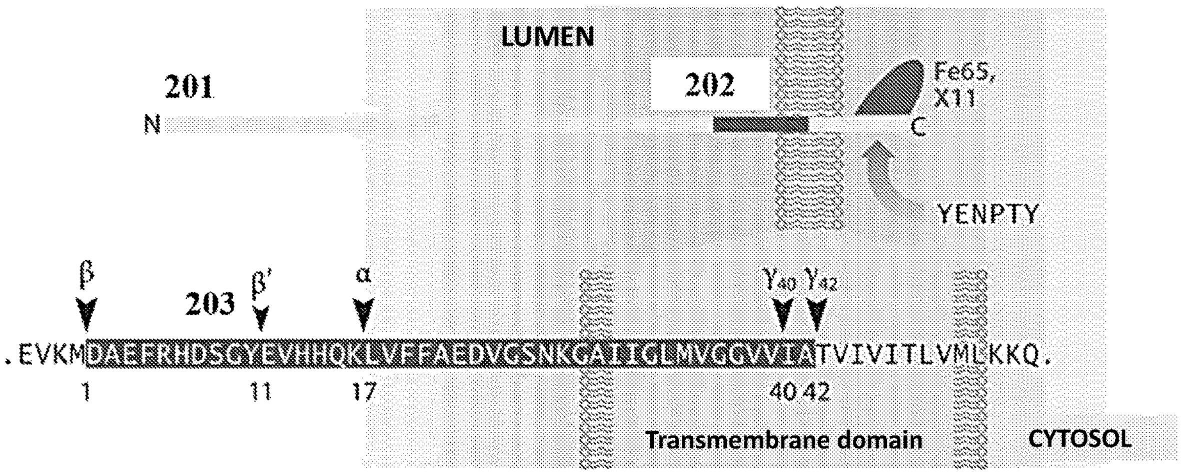
FIG. 2C shows a cartoon schematic of the APP processing in vivo. APP protein, 201, has a N-terminal ectodomains and a shorter C-terminus that contains a crucial Tyrosine—Glutamic Acid-Asparagine-Proline-Threonine-Tyrosine (YENPTY) (SEQ ID NO: 193) protein-sorting domain to which the adaptor proteins X11 and Fe65 bind. The fragment, 202, containing the Abeta peptide, from $672^{nd}$ to $727^{th}$ amino acid of SEQ ID NO: 2, is magnified in 203. The alpha, beta, beta', and gamma cleavage sites are listed on the amino acid sequence in 203. Figure also discloses SEQ ID NO: 199.
Figure 2D:
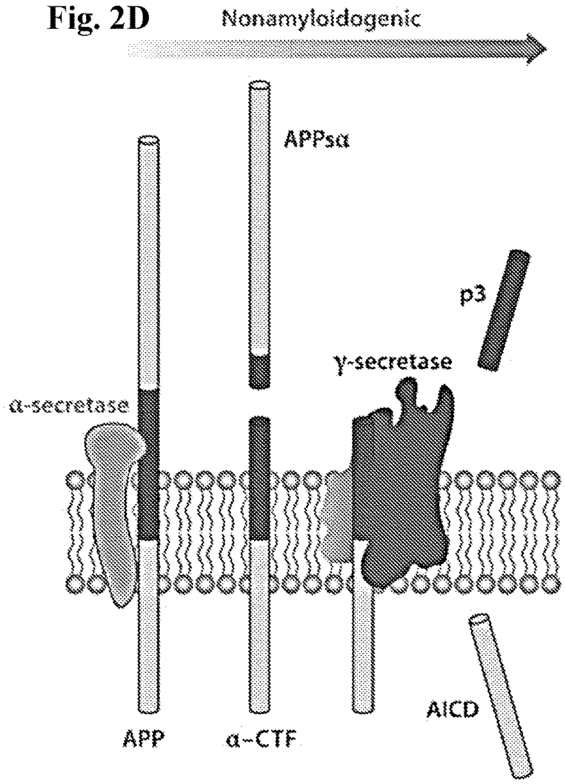
FIG. 2D and FIG. 2E depict cartoon schematic showing normal and pathogenic processing of APP.
Figure 2E:
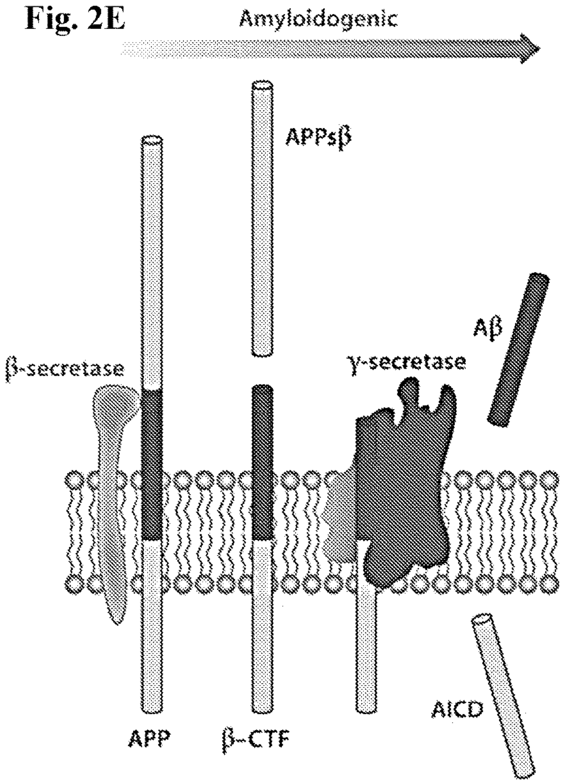
Figure 3:
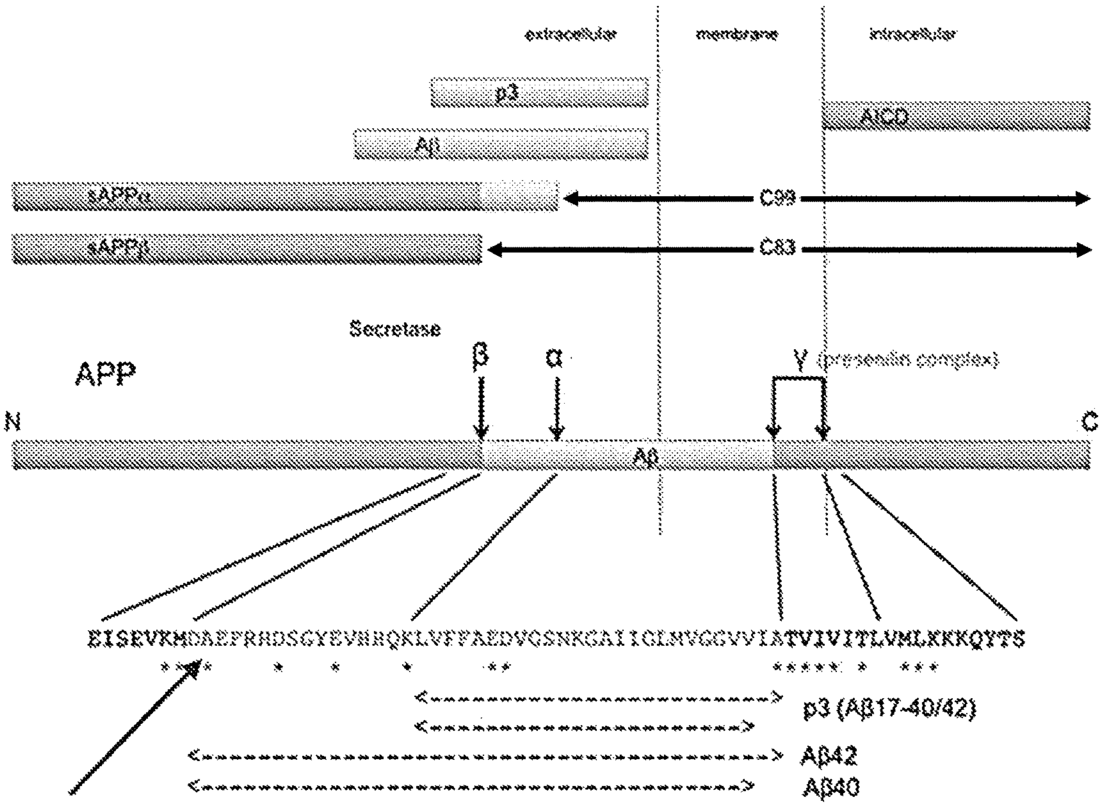
FIG. 3 shows APP, the generation of Abeta fragments, and the effects of the A673T and A673V mutations in APP processing. The amino acid sequence of a portion of APP is shown. The Abeta 40 length and Abeta 42 sequences are also shown. Additionally, the location of the A673T mutation is shown, a mutation that can be protective (reduced Abeta 1—Abeta 42 levels, improved cognition with age) and can suggest reduced BACE1 cleavage. The location of the A673V mutation is shown, a mutation that can confer increased risk (increased Abeta 1— Abeta 42 levels, impaired cognition) and can suggest increased BACE1 cleavage. The amino acid consensus sequence of full length APP is shown in SEQ ID NO: 2. Figure discloses SEQ ID NO: 200.

The generation of Abeta by enzymatic cleavages of the β-amyloid precursor protein (APP) is an important player in Alzheimer's disease. As shown in FIGS. 2D, 2E, and 3, the non-amyloidogenic APP processing pathway involves cleavages by alpha- and gamma-secretase. The cleavage by alpha-secretase generates a long form of secreted APP (APPs alpha) and a C-terminal fragment (alpha-CTF). Further processing of alpha-CTF by gamma-secretase generates a p3 and AICD fragment. The amyloidogenic APP processing pathway instead involves cleavages by beta- and gamma-secretase. The cleavage by beta-secretase generates a short form of secreted APP (APPs beta) and a C-terminal fragment (beta-CTF). Further processing of beta-CTF by gamma-secretase generates an Abeta and AICD fragment. The oligomerization and fibrillization of Abeta fragments lead to AD pathology.

FIGS. 2D and 2E was adapted from Thinakaran G, Koo EH. 2008 Amyloid precursor protein trafficking, processing, and function. J. Biol. Chem. 283:29615-19. Herein the methods of which are incorporated by reference.

In some cases, amyloid precursor protein (APP) can be cut by a beta secretase (e.g., BACE1, cathepsin B or Meprin beta) or gamma secretase, and the fragment resulting from such cuts can be Abeta peptides of 36-43 amino acids. Certain Abeta peptide metabolites of this cleavage can be crucially involved in Alzheimer's disease pathology and progression. The wild type sequence of the APP polypeptide is listed in SEQ ID NO: 2.

```
APP
                                             SEQ ID NO: 2
MLPGLALLLLAAWTARALEVPTDGNAGLLAEPQIAMFCGRLNMHMNVQNG

KWDSDPSGTKTCIDTKEGILQYCQEVYPELQITNVVEANQPVTIQNWCKR

GRKQCKTHPHFVIPYRCLVGEFVSDALLVPDKCKFLHQERMDVCETHLHW

HTVAKETCSEKSTNLHDYGMLLPCGIDKFRGVEFVCCPLAEESDNVDSAD

AEEDDSDVWWGGADTDYADGSEDKVVEVAEEEEVAEVEEEEADDDEDDED

GDEVEEEAEEPYEEATERTTSIATTTTTTTESVEEVVREVCSEQAETGPC

RAMISRWYFDVTEGKCAPFFYGGCGGNRNNFDTEEYCMAVCGSAMSQSLL

KTTQEPLARDPVKLPTTAASTPDAVDKYLETPGDENEHAHFQKAKERLEA

KHRERMSQVMREWEEAERQAKNLPKADKKAVIQHFQEKVESLEQEAANER

QQLVETHMARVEAMLNDRRRLALENYITALQAVPPRPRHVFNMLKKYVRA

EQKDRQHTLKHFEHVRMVDPKKAAQIRSQVMTHLRVIYERMNQSLSLLYN

VPAVAEEIQDEVDELLQKEQNYSDDVLANMISEPRISYGNDALMPSLTET

KTTVELLPVNGEFSLDDLQPWHSFGADSVPANTENEVEPVDARPAADRGL

TTRPGSGLTNIKTEEISEVKMDAEFRHDSGYEVHHQKLVFFAEDVGSNKG

AIIGLMVGGVVIATVIVITLVMLKKKQYTSIHHGVVEVDAAVTPEERHLS

KMQQNGYENPTYKFFEQMQN
```

The mRNA sequences of human APP are listed in TABLE 1.

TABLE 1

Human APP mRNA Isoform Sequences. Sequences obtained from NCBI APP gene ID: 381; Assembly GRCh38.p13 (GCF_000001405.39); NC_000021.9 (25880550 . . . 26171128, complement)

| SEQ ID NO | Isoform | mRNA Sequence |
|---|---|---|
| 3 | 1 | GUCAGUUUCCUCGGCAGCGGUAGGCGAGAGCACGC<br>GGAGGAGCGUGCGCGGGGGCCCCGGGAGACGGCGG<br>CGGUGGCGGCGCGGGCAGAGCAAGGACGCGGCGGA<br>UCCCACUCGCACAGCAGCGCACUCGGUGCCCCGCG<br>CAGGGUCGCGAUGCUGCCCGGUUUGGCACUGCUCC<br>UGCUGGCCGCCUGGACGGCUCGGGCGCUGGAGGUA<br>CCCACUGAUGGUAAUGCUGGCCUGCUGGCUGAACC<br>CCAGAUUGCCAUGUUCUGUGGCAGACUGAACAUGC<br>ACAUGAAUGUCCAGAAUGGGAAGUGGGAUUCAGAU<br>CCAUCAGGGACCAAAACCUGCAUUGAUACCAAGGA<br>AGGCAUCCUGCAGUAUUGCCAAGAAGUCUACCCUG<br>AACUGCAGAUCACCAAUGUGGUAGAAGCCAACCAA<br>CCAGUGACCAUCCAGAACUGGUGCAAGCGGGGCCG<br>CAAGCAGUGCAAGACCCAUCCCCACUUUGUGAUUC<br>CCUACCGCUGCUUAGUUGGUGAGUUUGUAAGUGAU<br>GCCCUUCUCGUUCCUGACAAGUGCAAAUUCUUACA<br>CCAGGAGAGGAUGGAUGUUUGCGAAACUCAUCUUC<br>ACUGGCACACCGUCGCCAAAGAGACAUGCAGUGAG<br>AAGAGUACCAACUUGCAUGACUACGGCAUGUUGCU<br>GCCCUGCGGAAUUGACAAGUUCCGAGGGGUAGAGU<br>UUGUGUGUUGCCCACUGGCUGAAGAAAGUGACAAU<br>GUGGAUUCUGCUGAUGCGGAGGAGGAUGACUCGGA<br>UGUCUGGUGGGGCGGAGCAGACACAGACUAUGCAG<br>AUGGGAGUGAAGACAAAGUAGUAGAAGUAGCAGAG<br>GAGGAAGAAGUGGCUGAGGUGGAAGAAGAAGAAGC<br>CGAUGAUGACGAGGACGAUGAGGAUGGUGAUGAGG<br>UAGAGGAAGAGGCUGAGGAACCCUACGAAGAAGCC<br>ACAGAGAGAACCACCAGCAUUGCCACCACCACCAC<br>CACCACCACAGAGUCUGUGGAAGAGGUGGUUCGAG<br>AGGUGUGCUCUGAACAAGCCGAGACGGGGCCGUGC<br>CGAGCAAUGAUCUCCCGCUGGUACUUUGAUGUGAC<br>UGAAGGGAAGUGUGCCCCAUUCUUUUACGGCGGAU<br>GUGGCGGCAACCGGAACAACUUUGACACAGAAGAG<br>UACUGCAUGGCCGUGUGUGGCAGCGCCAUGUCCCA<br>AAGUUUACUCAAGACUACCCAGGAACCUCUUGCCC<br>GAGAUCCUGUUAAACUUCCUACAACAGCAGCCAGU<br>ACCCCUGAUGCCGUUGACAAGUAUCUCGAGACACC<br>UGGGGAUGAGAAUGAACAUGCCCAUUUCCAGAAAG<br>CCAAAGAGAGGCUUGAGGCCAAGCACCGAGAGAGA<br>AUGUCCCAGGUCAUGAGAGAAUGGGAAGAGGCAGA<br>ACGUCAAGCAAAGAACUUGCCUAAAGCUGAUAAGA<br>AGGCAGUUAUCCAGCAUUUCCAGGAGAAAGUGGAA<br>UCUUUGGAACAGGAAGCAGCCAACGAGAGACAGCA<br>GCUGGUGGAGACACACAUGGCCAGAGUGGAAGCCA<br>UGCUCAAUGACCGCCGCCGCCUGGCCCUGGAGAAC<br>UACAUCACCGCUCUGCAGGCUGUUCCUCCUCGGCC<br>UCGUCACGUGUUCAAUAUGCUAAAGAAGUAUGUCC<br>GCGCAGAACAGAAGGACAGACAGCACACCCUAAAG<br>CAUUUCGAGCAUGUGCGCAUGGUGGAUCCCAAGAA<br>AGCCGCUCAGAUCCGGUCCCAGGUUAUGACACACC<br>UCCGUGUGAUUUAUGAGCGCAUGAAUCAGUCUCUC<br>UCCCUGCUCUACAACGUGCCUGCAGUGGCCGAGGA<br>GAUUCAGGAUGAAGUUGAUGAGCUGCUUCAGAAAG<br>AGCAAAACUAUUCAGAUGACGUCUUGGCCAACAUG<br>AUUAGUGAACCAAGGAUCAGUUACGGAAACGAUGC<br>UCUCAUGCCAUCUUUGACCGAAACGAAAACCACCG<br>UGGAGCUCCUUCCCGUGAAUGGAGAGUUCAGCCUG<br>GACGAUCUCCAGCCGUGGCAUUCUUUUGGGGCUGA<br>CUCUGUGCCAGCCAACACAGAAAACGAAGUUGAGC<br>CUGUUGAUGCCCGCCCUGCUGCCGACCGAGGACUG<br>ACCACUCGACCAGGUUCUGGGUUGACAAAUAUCAA<br>GACGGAGGAGAUCUCUGAAGUGAAGAUGGAUGCAG<br>AAUUCCGACAUGACUCAGGAUAUGAAGUUCAUCAU<br>CAAAAAUUGGUGUUCUUUGCAGAAGAUGUGGGUUC<br>AAACAAAGGUGCAAUCAUUGGACUCAUGGUGGGCG<br>GUGUUGUCAUAGCGACAGUGAUCGUCAUCACCUUG<br>GUGAUGCUGAAGAAGAAACAGUACACAUCCAUUCA<br>UCAUGGUGUGGUGGAGGUUGACGCCGCUGUCACCC |

TABLE 1-continued

Human APP mRNA Isoform Sequences. Sequences obtained from NCBI APP gene ID: 381; Assembly GRCh38.p13 (GCF_000001405.39); NC_000021.9 (25880550 . . . 26171128, complement)

| SEQ ID NO | Isoform | mRNA Sequence |
|---|---|---|
| | | CAGAGGAGCGCCACCUGUCCAAGAUGCAGCAGAAC<br>GGCUACGAAAAUCCAACCUACAAGUUCUUUGAGCA<br>GAUGCAGAACUAGACCCCCGCCACAGCAGCCUCUG<br>AAGUUGGACAGCAAAACCAUUGCUUCACUACCCAU<br>CGGUGUCCAUUUAUAGAAUAAUGUGGGAAGAAACA<br>AACCCGUUUUAUGAUUUACUCAUUAUCGCCUUUUG<br>ACAGCUGUGCUGUAACACAAGUAGAUGCCUGAACU<br>UGAAUUAAUCCACACAUCAGUAAUGUAUUCUAUCU<br>CUCUUUACAUUUUGGUCUCUAUACUACAUUAUUAA<br>UGGGUUUUGUGUACUGUAAAGAAUUUAGCUGUAUC<br>AAACUAGUGCAUGAAUAGAUUCUCUCCUGAUUAUU<br>UAUCACAUAGCCCCUUAGCCAGUUGUAUAUUAUUC<br>UUGUGGUUUGUGACCCAAUUAAGUCCUACUUUACA<br>UAUGCUUUAAGAAUCGAUGGGGGAUGCUUCAUGUG<br>AACGUGGGAGUUCAGCUGCUUCUCUUGCCUAAGUA<br>UUCCUUUCCUGAUCACUAUGCAUUUUAAAGUUAAA<br>CAUUUUUAAGUAUUUCAGAUGCUUUAGAGAGAUUU<br>UUUUUCCAUGACUGCAUUUUACUGUACAGAUUGCU<br>GCUUCUGCUAUAUUUGUGAUAUAGGAAUUAAGAGG<br>AUACACACGUUUGUUUCUUCGUGCCUGUUUUAUGU<br>GCACACAUUAGGCAUUGAGACUUCAAGCUUUUCUU<br>UUUUUGUCCACGUAUCUUUGGGUCUUUGAUAAAGA<br>AAAGAAUCCCUGUUCAUUGUAAGCACUUUUACGGG<br>GCGGGUGGGGAGGGGUGCUCUGCUGGUCUUCAAUU<br>ACCAAGAAUUCUCCAAAACAAUUUUCUGCAGGAUG<br>AUUGUACAGAAUCAUUGCUUAUGACAUGAUCGCUU<br>UCUACACUGUAUUACAUAAAUAAAUUAAAUAAAAU<br>AACCCCGGGCAAGACUUUUCUUUGAAGGAUGACUA<br>CAGACAUUAAAUAAUCGAAGUAAUUUUGGGUGGGG<br>AGAAGAGGCAGAUUCAAUUUUCUUUAACCAGUCUG<br>AAGUUUCAUUUAUGAUACAAAGAAGAUGAAAAUG<br>GAAGUGGCAAUAUAAGGGGAUGAGGAAGGCAUGCC<br>UGGACAAACCCUUCUUUUAAGAUGUGUCUUCAAUU<br>UGUAUAAAAUGGUGUUUUCAUGUAAAUAAAUACAU<br>UCUUGGAGGAGCA |
| 4 | 2 | GUCAGUUUCCUCGGCAGCGGUAGGCGAGAGCACGC<br>GGAGGAGCGUGCGCGGGGGCCCCGGGAGACGGCGG<br>CGGUGGCGGCGCGGGCAGAGCAAGGACGCGGCGGA<br>UCCCACUCGCACAGCAGCGCACUCGGUGCCCCGCG<br>CAGGGUCGCGAUGCUGCCCGGUUUGGCACUGCUCC<br>UGCUGGCCGCCUGGACGGCUCGGGCGCUGGAGGUA<br>CCCACUGAUGGUAAUGCUGGCCUGCUGGCUGAACC<br>CCAGAUUGCCAUGUUCUGUGGCAGACUGAACAUGC<br>ACAUGAAUGUCCAGAAUGGGAAGUGGGAUUCAGAU<br>CCAUCAGGGACCAAAACCUGCAUUGAUACCAAGGA<br>AGGCAUCCUGCAGUAUUGCCAAGAAGUCUACCCUG<br>AACUGCAGAUCACCAAUGUGGUAGAAGCCAACCAA<br>CCAGUGACCAUCCAGAACUGGUGCAAGCGGGGCCG<br>CAAGCAGUGCAAGACCCAUCCCCACUUUGUGAUUC<br>CCUACCGCUGCUUAGUUGGUGAGUUUGUAAGUGAU<br>GCCCUUCUCGUUCCUGACAAGUGCAAAUUCUUACA<br>CCAGGAGAGGAUGGAUGUUUGCGAAACUCAUCUUC<br>ACUGGCACACCGUCGCCAAAGAGACAUGCAGUGAG<br>AAGAGUACCAACUUGCAUGACUACGGCAUGUUGCU<br>GCCCUGCGGAAUUGACAAGUUCCGAGGGGUAGAGU<br>UUGUGUGUUGCCCACUGGCUGAAGAAAGUGACAAU<br>GUGGAUUCUGCUGAUGCGGAGGAGGAUGACUCGGA<br>UGUCUGGUGGGGCGGAGCAGACACAGACUAUGCAG<br>AUGGGAGUGAAGACAAAGUAGUAGAAGUAGCAGAG<br>GAGGAAGAAGUGGCUGAGGUGGAAGAAGAAGAAGC<br>CGAUGAUGACGAGGACGAUGAGGAUGGUGAUGAGG<br>UAGAGGAAGAGGCUGAGGAACCCUACGAAGAAGCC<br>ACAGAGAGAACCACCAGCAUUGCCACCACCACCAC<br>CACCACCACAGAGUCUGUGGAAGAGGUGGUUCGAG<br>AGGUGUGCUCUGAACAAGCCGAGACGGGGCCGUGC<br>CGAGCAAUGAUCUCCCGCUGGUACUUUGAUGUGAC<br>UGAAGGGAAGUGUGCCCCAUUCUUUUACGGCGGAU<br>GUGGCGGCAACCGGAACAACUUUGACACAGAAGAG<br>UACUGCAUGGCCGUGUGUGGCAGCGCCAUUCCUAC<br>AACAGCAGCCAGUACCCCUGAUGCCGUUGACAAGU<br>AUCUCGAGACACCUGGGGAUGAGAAUGAACAUGCC |

TABLE 1-continued

Human APP mRNA Isoform Sequences. Sequences obtained from NCBI APP gene ID: 381; Assembly GRCh38.p13 (GCF_000001405.39); NC_000021.9 (25880550 . . . 26171128, complement)

| SEQ ID NO | Iso-form | mRNA Sequence |
|---|---|---|
| | | CAUUUCCAGAAAGCCAAAGAGAGGCUUGAGGCCAA |
| | | GCACCGAGAGAGAAUGUCCCAGGUCAUGAGAGAAU |
| | | GGGAAGAGGCAGAACGUCAAGCAAAGAACUUGCCU |
| | | AAAGCUGAUAAGAAGGCAGUUAUCCAGCAUUUCCA |
| | | GGAGAAAGUGGAAUCUUUGGAACAGGAAGCAGCCA |
| | | ACGAGAGACAGCAGCUGGUGGAGACACACAUGGCC |
| | | AGAGUGGAAGCCAUGCUCAAUGACCGCCGCCGCCU |
| | | GGCCCUGGAGAACUACAUCACCGCUCUGCAGGCUG |
| | | UUCCUCCUCGGCCUCGUCACGUGUUCAAUAUGCUA |
| | | AAGAAGUAUGUCCGCGCAGAACAGAAGGACAGACA |
| | | GCACACCCUAAAGCAUUUCGAGCAUGUGCGCAUGG |
| | | UGGAUCCCAAGAAAGCCGCUCAGAUCCGGUCCCAG |
| | | GUUAUGACACACCUCCGUGUGAUUUAUGAGCGCAU |
| | | GAAUCAGUCUCUCUCCCUGCUCUACAACGUGCCUG |
| | | CAGUGGCCGAGGAGAUUCAGGAUGAAGUUGAUGAG |
| | | CUGCUUCAGAAAGAGCAAAACUAUUCAGAUGACGU |
| | | CUUGGCCAACAUGAUUAGUGAACCAAGGAUCAGUU |
| | | ACGGAAACGAUGCUCUCAUGCCAUCUUUGACCGAA |
| | | ACGAAAACCACCGUGGAGCUCCUUCCCGUGAAUGG |
| | | AGAGUUCAGCCUGGACGAUCUCCAGCCGUGGCAUU |
| | | CUUUUGGGGCUGACUCUGUGCCAGCCAACACAGAA |
| | | AACGAAGUUGAGCCUGUUGAUGCCCGCCCUGCUGC |
| | | CGACCGAGGACUGACCACUCGACCAGGUUCUGGGU |
| | | UGACAAAUAUCAAGACGGAGGAGAUCUCUGAAGUG |
| | | AAGAUGGAUGCAGAAUUCCGACAUGACUCAGGAUA |
| | | UGAAGUUCAUCAUCAAAAAUUGGUGUUCUUUGCAG |
| | | AAGAUGUGGGUUCAAACAAAGGUGCAAUCAUUGGA |
| | | CUCAUGGUGGGCGGUGUUGUCAUAGCGACAGUGAU |
| | | CGUCAUCACCUUGGUGAUGCUGAAGAAGAAACAGU |
| | | ACACAUCCAUUCAUCAUGGUGUGGUGGAGGUUGAC |
| | | GCCGCUGUCACCCCAGAGGAGCGCCACCUGUCCAA |
| | | GAUGCAGCAGAACGGCUACGAAAAUCCAACCUACA |
| | | AGUUCUUUGAGCAGAUGCAGAACUAGACCCCCGCC |
| | | ACAGCAGCCUCUGAAGUUGGACAGCAAAACCAUUG |
| | | CUUCACUACCCAUCGGUGUCCAUUUAUAGAAUAAU |
| | | GUGGGAAGAAACAAACCCGUUUUAUGAUUUACUCA |
| | | UUAUCGCCUUUUGACAGCUGUGCUGUAACACAAGU |
| | | AGAUGCCUGAACUUGAAUUAAUCCACACAUCAGUA |
| | | AUGUAUUCUAUCUCUCUUUACAUUUUGGUCUCUAU |
| | | ACUACAUUAUUAAUGGGUUUUGUGUACUGUAAAGA |
| | | AUUUAGCUGUAUCAAACUAGUGCAUGAAUAGAUUC |
| | | UCUCCUGAUUAUUUAUCACAUAGCCCCUUAGCCAG |
| | | UUGUAUAUUAUUCUUGUGGUUUGUGACCCAAUUAA |
| | | GUCCUACUUUACAUAUGCUUUAAGAAUCGAUGGGG |
| | | GAUGCUUCAUGUGAACGUGGGAGUUCAGCUGCUUC |
| | | UCUUGCCUAAGUAUUCCUUUCCUGAUCACUAUGCA |
| | | UUUUAAAGUUAAACAUUUUUAAGUAUUUCAGAUGC |
| | | UUUAGAGAGAUUUUUUUUCCAUGACUGCAUUUUAC |
| | | UGUACAGAUUGCUGCUUCUGCUAUAUUUGUGAUAU |
| | | AGGAAUUAAGAGGAUACACACGUUUGUUUCUUCGU |
| | | GCCUGUUUUAUGUGCACACAUUAGGCAUUGAGACU |
| | | UCAAGCUUUUCUUUUUUUGUCCACGUAUCUUUGGG |
| | | UCUUUGAUAAAGAAAAGAAUCCCUGUUCAUUGUAA |
| | | GCACUUUUACGGGGCGGGUGGGGAGGGGUGCUCUG |
| | | CUGGUCUUCAAUUACCAAGAAUUCUCCAAAACAAU |
| | | UUUCUGCAGGAUGAUUGUACAGAAUCAUUGCUUAU |
| | | GACAUGAUCGCUUUCUACACUGUAUUACAUAAAUA |
| | | AAUUAAAUAAAAUAACCCCGGGCAAGACUUUUCUU |
| | | UGAAGGAUGACUACAGACAUUAAAUAAUCGAAGUA |
| | | AUUUUGGGUGGGGAGAAGAGGCAGAUUCAAUUUUC |
| | | UUUAACCAGUCUGAAGUUUCAUUUAUGAUACAAAA |
| | | GAAGAUGAAAAUGGAAGUGGCAAUAUAAGGGGAUG |
| | | AGGAAGGCAUGCCUGGACAAACCCUUCUUUUAAGA |
| | | UGUGUCUUCAAUUUGUAUAAAAUGGUGUUUUCAUG |
| | | UAAAUAAAUACAUUCUUGGAGGAGCA |
| 5 | 3 | GUCAGUUUCCUCGGCAGCGGUAGGCGAGAGCACGC |
| | | GGAGGAGCGUGCGCGGGGGCCCCGGGAGACGGCGG |
| | | CGGUGGCGGCGCGGGCAGAGCAAGGACGCGGCGGA |
| | | UCCCACUCGCACAGCAGCGCACUCGGUGCCCCGCG |
| | | CAGGGUCGCGAUGCUGCCCGGUUUGGCACUGCUCC |
| | | UGCUGGCCGCCUGGACGGCUCGGGCGCUGGAGGUA |
| | | CCCACUGAUGGUAAUGCUGGCCUGCUGGCUGAACC |
| | | CCAGAUUGCCAUGUUCUGUGGCAGACUGAACAUGC |
| | | ACAUGAAUGUCCAGAAUGGGAAGUGGGAUUCAGAU |
| | | CCAUCAGGGACCAAAACCUGCAUUGAUACCAAGGA |
| | | AGGCAUCCUGCAGUAUUGCCAAGAAGUCUACCCUG |
| | | AACUGCAGAUCACCAAUGUGGUAGAAGCCAACCAA |
| | | CCAGUGACCAUCCAGAACUGGUGCAAGCGGGGCCG |
| | | CAAGCAGUGCAAGACCCAUCCCCACUUUGUGAUUC |
| | | CCUACCGCUGCUUAGUUGGUGAGUUUGUAAGUGAU |
| | | GCCCUUCUCGUUCCUGACAAGUGCAAAUUCUUACA |
| | | CCAGGAGAGGAUGGAUGUUUGCGAAACUCAUCUUC |
| | | ACUGGCACACCGUCGCCAAAGAGACAUGCAGUGAG |
| | | AAGAGUACCAACUUGCAUGACUACGGCAUGUUGCU |
| | | GCCCUGCGGAAUUGACAAGUUCCGAGGGGUAGAGU |
| | | UUGUGUGUUGCCCACUGGCUGAAGAAAGUGACAAU |
| | | GUGGAUUCUGCUGAUGCGGAGGAGGAUGACUCGGA |
| | | UGUCUGGUGGGGCGGAGCAGACACAGACUAUGCAG |
| | | AUGGGAGUGAAGACAAAGUAGUAGAAGUAGCAGAG |
| | | GAGGAAGAAGUGGCUGAGGUGGAAGAAGAAGAAGC |
| | | CGAUGAUGACGAGGACGAUGAGGAUGGUGAUGAGG |
| | | UAGAGGAAGAGGCUGAGGAACCCUACGAAGAAGCC |
| | | ACAGAGAGAACCACCAGCAUUGCCACCACCACCAC |
| | | CACCACCACAGAGUCUGUGGAAGAGGUGGUUCGAG |
| | | UUCCUACAACAGCAGCCAGUACCCCUGAUGCCGUU |
| | | GACAAGUAUCUCGAGACACCUGGGGAUGAGAAUGA |
| | | ACAUGCCCAUUUCCAGAAAGCCAAAGAGAGGCUUG |
| | | AGGCCAAGCACCGAGAGAGAAUGUCCCAGGUCAUG |
| | | AGAGAAUGGGAAGAGGCAGAACGUCAAGCAAAGAA |
| | | CUUGCCUAAAGCUGAUAAGAAGGCAGUUAUCCAGC |
| | | AUUUCCAGGAGAAAGUGGAAUCUUUGGAACAGGAA |
| | | GCAGCCAACGAGAGACAGCAGCUGGUGGAGACACA |
| | | CAUGGCCAGAGUGGAAGCCAUGCUCAAUGACCGCC |
| | | GCCGCCUGGCCCUGGAGAACUACAUCACCGCUCUG |
| | | CAGGCUGUUCCUCCUCGGCCUCGUCACGUGUUCAA |
| | | UAUGCUAAAGAAGUAUGUCCGCGCAGAACAGAAGG |
| | | ACAGACAGCACACCCUAAAGCAUUUCGAGCAUGUG |
| | | CGCAUGGUGGAUCCCAAGAAAGCCGCUCAGAUCCG |
| | | GUCCCAGGUUAUGACACACCUCCGUGUGAUUUAUG |
| | | AGCGCAUGAAUCAGUCUCUCUCCCUGCUCUACAAC |
| | | GUGCCUGCAGUGGCCGAGGAGAUUCAGGAUGAAGU |
| | | UGAUGAGCUGCUUCAGAAAGAGCAAAACUAUUCAG |
| | | AUGACGUCUUGGCCAACAUGAUUAGUGAACCAAGG |
| | | AUCAGUUACGGAAACGAUGCUCUCAUGCCAUCUUU |
| | | GACCGAAACGAAAACCACCGUGGAGCUCCUUCCCG |
| | | UGAAUGGAGAGUUCAGCCUGGACGAUCUCCAGCCG |
| | | UGGCAUUCUUUUGGGGCUGACUCUGUGCCAGCCAA |
| | | CACAGAAAACGAAGUUGAGCCUGUUGAUGCCCGCC |
| | | CUGCUGCCGACCGAGGACUGACCACUCGACCAGGU |
| | | UCUGGGUUGACAAAUAUCAAGACGGAGGAGAUCUC |
| | | UGAAGUGAAGAUGGAUGCAGAAUUCCGACAUGACU |
| | | CAGGAUAUGAAGUUCAUCAUCAAAAAUUGGUGUUC |
| | | UUUGCAGAAGAUGUGGGUUCAAACAAAGGUGCAAU |
| | | CAUUGGACUCAUGGUGGGCGGUGUUGUCAUAGCGA |
| | | CAGUGAUCGUCAUCACCUUGGUGAUGCUGAAGAAG |
| | | AAACAGUACACAUCCAUUCAUCAUGGUGUGGUGGA |
| | | GGUUGACGCCGCUGUCACCCCAGAGGAGCGCCACC |
| | | UGUCCAAGAUGCAGCAGAACGGCUACGAAAAUCCA |
| | | ACCUACAAGUUCUUUGAGCAGAUGCAGAACUAGAC |
| | | CCCCGCCACAGCAGCCUCUGAAGUUGGACAGCAAA |
| | | ACCAUUGCUUCACUACCCAUCGGUGUCCAUUUAUA |
| | | GAAUAAUGUGGGAAGAAACAAACCCGUUUUAUGAU |
| | | UUACUCAUUAUCGCCUUUUGACAGCUGUGCUGUAA |
| | | CACAAGUAGAUGCCUGAACUUGAAUUAAUCCACAC |
| | | AUCAGUAAUGUAUUCUAUCUCUCUUUACAUUUUGG |
| | | UCUCUAUACUACAUUAUUAAUGGGUUUUGUGUACU |
| | | GUAAAGAAUUUAGCUGUAUCAAACUAGUGCAUGAA |
| | | UAGAUUCUCUCCUGAUUAUUUAUCACAUAGCCCCU |
| | | UAGCCAGUUGUAUAUUAUUCUUGUGGUUUGUGACC |
| | | CAAUUAAGUCCUACUUUACAUAUGCUUUAAGAAUC |
| | | GAUGGGGGAUGCUUCAUGUGAACGUGGGAGUUCAG |
| | | CUGCUUCUCUUGCCUAAGUAUUCCUUUCCUGAUCA |
| | | CUAUGCAUUUUAAAGUUAAACAUUUUUAAGUAUUU |

TABLE 1-continued

Human APP mRNA Isoform Sequences. Sequences obtained from NCBI APP gene ID: 381; Assembly GRCh38.p13 (GCF_000001405.39); NC_000021.9 (25880550 . . . 26171128, complement)

| SEQ ID NO | Iso-form | mRNA Sequence |
|---|---|---|
| | | CAGAUGCUUUAGAGAGAUUUUUUUUCCAUGACUGC<br>AUUUUACUGUACAGAUUGCUGCUUCUGCUAUAUUU<br>GUGAUAUAGGAAUUAAGAGGAUACACACGUUUGUU<br>UCUUCGUGCCUGUUUUAUGUGCACACAUUAGGCAU<br>UGAGACUUCAAGCUUUUCUUUUUUUGUCCACGUAU<br>CUUUGGGUCUUUGAUAAAGAAAAGAAUCCCUGUUC<br>AUUGUAAGCACUUUUACGGGGCGGGUGGGGAGGGG<br>UGCUCUGCUGGUCUUCAAUUACCAAGAAUUCUCCA<br>AAACAAUUUUCUGCAGGAUGAUUGUACAGAAUCAU<br>UGCUUAUGACAUGAUCGCUUUCUACACUGUAUUAC<br>AUAAAUAAAUUAAAUAAAAUAACCCCGGGCAAGAC<br>UUUUCUUUGAAGGAUGACUACAGACAUUAAAUAAU<br>CGAAGUAAUUUUGGGUGGGGAGAAGAGGCAGAUUC<br>AAUUUUCUUUAACCAGUCUGAAGUUUCAUUUAUGA<br>UACAAAAGAAGAUGAAAAUGGAAGUGGCAAUAUAA<br>GGGGAUGAGGAAGGCAUGCCUGGACAAACCCUUCU<br>UUUAAGAUGUGUCUUCAAUUUGUAUAAAAUGGUGU<br>UUUCAUGUAAAUAAAUACAUUCUUGGAGGAGCA |
| 6 | 4 | AAAUAGCACAGCCUUGCUGUGCGUGGUAGAAGUUG<br>GGUUAGUGUUGACAUGCUGUUGACUCACCCUCCCG<br>AGGAUGGAAGCUCUGGCCUGGGUCAAGUUGUGGUC<br>ACUGCAGUUAACAGUUUGUUGAUCUCAGGGAGUAU<br>UCCACAGUUGCUGAUGUAAUUGACAAUGAUUGGAG<br>CCAGCUCUUCCCCAGAUUCAAAUGGACCAAUUAGA<br>GGACUUGUUGGUUCUGUUUAUCAACUAUGUACCCA<br>CUGAUGGUAAUGCUGGCCUGCUGGCUGAACCCCAG<br>AUUGCCAUGUUCUGUGGCAGACUGAACAUGCACAU<br>GAAUGUCCAGAAUGGGAAGUGGGAUUCAGAUCCAU<br>CAGGGACCAAAACCUGCAUUGAUACCAAGGAAGGC<br>AUCCUGCAGUAUUGCCAAGAAGUCUACCCUGAACU<br>GCAGAUCACCAAUGUGGUAGAAGCCAACCAACCAG<br>UGACCAUCCAGAACUGGUGCAAGCGGGGCCGCAAG<br>CAGUGCAAGACCCAUCCCCACUUUGUGAUUCCCUA<br>CCGCUGCUUAGUUGGUGAGUUUGUAAGUGAUGCCC<br>UUCUCGUUCCUGACAAGUGCAAAUUCUUACACCAG<br>GAGAGGAUGGAUGUUUGCGAAACUCAUCUUCACUG<br>GCACACCGUCGCCAAAGAGACAUGCAGUGAGAAGA<br>GUACCAACUUGCAUGACUACGGCAUGUUGCUGCCC<br>UGCGGAAUUGACAAGUUCCGAGGGGUAGAGUUUGU<br>GUGUUGCCCACUGGCUGAAGAAAGUGACAAUGUGG<br>AUUCUGCUGAUGCGGAGGAGGAUGACUCGGAUGUC<br>UGGUGGGGCGGAGCAGACACAGACUAUGCAGAUGG<br>GAGUGAAGACAAAGUAGUAGAAGUAGCAGAGGAGG<br>AAGAAGUGGCUGAGGUGGAAGAAGAAGAAGCCGAU<br>GAUGACGAGGACGAUGAGGAUGGUGAUGAGGUAGA<br>GGAAGAGGCUGAGGAACCCUACGAAGAAGCCACAG<br>AGAGAACCACCAGCAUUGCCACCACCACCACCACC<br>ACCACAGAGUCUGUGGAAGAGGUGGUUCGAGAGGU<br>GUGCUCUGAACAAGCCGAGACGGGGCCGUGCCGAG<br>CAAUGAUCUCCCGCUGGUACUUUGAUGUGACUGAA<br>GGGAAGUGUGCCCCAUUCUUUUACGGCGGAUGUGG<br>CGGCAACCGGAACAACUUUGACACAGAAGAGUACU<br>GCAUGGCCGUGUGUGGCAGCGCCAUUCCUACAACA<br>GCAGCCAGUACCCCUGAUGCCGUUGACAAGUAUCU<br>CGAGACACCUGGGGAUGAGAAUGAACAUGCCCAUU<br>UCCAGAAAGCCAAAGAGAGGCUUGAGGCCAAGCAC<br>CGAGAGAGAAUGUCCCAGGUCAUGAGAGAAUGGGA<br>AGAGGCAGAACGUCAAGCAAAGAACUUGCCUAAAG<br>CUGAUAAGAAGGCAGUUAUCCAGCAUUUCCAGGAG<br>AAAGUGGAAUCUUUGGAACAGGAAGCAGCCAACGA<br>GAGACAGCAGCUGGUGGAGACACACAUGGCCAGAG<br>UGGAAGCCAUGCUCAAUGACCGCCGCCGCCUGGCC<br>CUGGAGAACUACAUCACCGCUCUGCAGGCUGUUCC<br>UCCUCGGCCUCGUCACGUGUUCAAUAUGCUAAAGA<br>AGUAUGUCCGCGCAGAACAGAAGGACAGACAGCAC<br>ACCCUAAAGCAUUUCGAGCAUGUGCGCAUGGUGGA<br>UCCCAAGAAAGCCGCUCAGAUCCGGUCCCAGGUUA<br>UGACACACCUCCGUGUGAUUUAUGAGCGCAUGAAU<br>CAGUCUCUCUCCCUGCUCUACAACGUGCCUGCAGU<br>GGCCGAGGAGAUUCAGGAUGAAGUUGAUGAGCUGC<br>UUCAGAAAGAGCAAAACUAUUCAGAUGACGUCUUG |

TABLE 1-continued

Human APP mRNA Isoform Sequences. Sequences obtained from NCBI APP gene ID: 381; Assembly GRCh38.p13 (GCF_000001405.39); NC_000021.9 (25880550 . . . 26171128, complement)

| SEQ ID NO | Iso-form | mRNA Sequence |
|---|---|---|
| | | GCCAACAUGAUUAGUGAACCAAGGAUCAGUUACGG<br>AAACGAUGCUCUCAUGCCAUCUUUGACCGAAACGA<br>AAACCACCGUGGAGCUCCUUCCCGUGAAUGGAGAG<br>UUCAGCCUGGACGAUCUCCAGCCGUGGCAUUCUUU<br>UGGGGCUGACUCUGUGCCAGCCAACACAGAAAACG<br>AAGUUGAGCCUGUUGAUGCCCGCCCUGCUGCCGAC<br>CGAGGACUGACCACUCGACCAGGUUCUGGGUUGAC<br>AAAUAUCAAGACGGAGGAGAUCUCUGAAGUGAAGA<br>UGGAUGCAGAAUUCCGACAUGACUCAGGAUAUGAA<br>GUUCAUCAUCAAAAAUUGGUGUUCUUUGCAGAAGA<br>UGUGGGUUCAAACAAAGGUGCAAUCAUUGGACUCA<br>UGGUGGGCGGUGUUGUCAUAGCGACAGUGAUCGUC<br>AUCACCUUGGUGAUGCUGAAGAAGAAACAGUACAC<br>AUCCAUUCAUCAUGGUGUGGUGGAGGUUGACGCCG<br>CUGUCACCCCAGAGGAGCGCCACCUGUCCAAGAUG<br>CAGCAGAACGGCUACGAAAAUCCAACCUACAAGUU<br>CUUUGAGCAGAUGCAGAACUAGACCCCCGCCACAG<br>CAGCCUCUGAAGUUGGACAGCAAAACCAUUGCUUC<br>ACUACCCAUCGGUGUCCAUUUAUAGAAUAAUGUGG<br>GAAGAAACAAACCCGUUUUAUGAUUUACUCAUUAU<br>CGCCUUUUGACAGCUGUGCUGUAACACAAGUAGAU<br>GCCUGAACUUGAAUUAAUCCACACAUCAGUAAUGU<br>AUUCUAUCUCUCUUUACAUUUUGGUCUCUAUACUA<br>CAUUAUUAAUGGGUUUUGUGUACUGUAAAGAAUUU<br>AGCUGUAUCAAACUAGUGCAUGAAUAGAUUCUCUC<br>CUGAUUAUUUAUCACAUAGCCCCUUAGCCAGUUGU<br>AUAUUAUUCUUGUGGUUUGUGACCCAAUUAAGUCC<br>UACUUUACAUAUGCUUUAAGAAUCGAUGGGGGAUG<br>CUUCAUGUGAACGUGGGAGUUCAGCUGCUUCUCUU<br>GCCUAAGUAUUCCUUUCCUGAUCACUAUGCAUUUU<br>AAAGUUAAACAUUUUUAAGUAUUUCAGAUGCUUUA<br>GAGAGAUUUUUUUUCCAUGACUGCAUUUUACUGUA<br>CAGAUUGCUGCUUCUGCUAUAUUUGUGAUAUAGGA<br>AUUAAGAGGAUACACACGUUUGUUUCUUCGUGCCU<br>GUUUUAUGUGCACACAUUAGGCAUUGAGACUUCAA<br>GCUUUUCUUUUUUUGUCCACGUAUCUUUGGGUCUU<br>UGAUAAAGAAAAGAAUCCCUGUUCAUUGUAAGCAC<br>UUUUACGGGGCGGGUGGGGAGGGGUGCUCUGCUGG<br>UCUUCAAUUACCAAGAAUUCUCCAAAACAAUUUUC<br>UGCAGGAUGAUUGUACAGAAUCAUUGCUUAUGACA<br>UGAUCGCUUUCUACACUGUAUUACAUAAAUAAAUU<br>AAAUAAAAUAACCCCGGGCAAGACUUUUCUUUGAA<br>GGAUGACUACAGACAUUAAAUAAUCGAAGUAAUUU<br>UGGGUGGGGAGAAGAGGCAGAUUCAAUUUUCUUUA<br>ACCAGUCUGAAGUUUCAUUUAUGAUACAAAAGAAG<br>AUGAAAAUGGAAGUGGCAAUAUAAGGGGAUGAGGA<br>AGGCAUGCCUGGACAAACCCUUCUUUUAAGAUGUG<br>UCUUCAAUUUGUAUAAAAUGGUGUUUUCAUGUAAA<br>UAAAUACAUUCUUGGAGGAGCAAAAAAAAAAAAAA<br>AA |
| 7 | 5 | GUCAGUUUCCUCGGCAGCGGUAGGCGAGAGCACGC<br>GGAGGAGCGUGCGCGGGGGCCCCGGGAGACGGCGG<br>CGGUGGCGGCGCGGGCAGAGCAAGGACGCGGCGGA<br>UCCCACUCGCACAGCAGCGCACUCGGUGCCCCGCG<br>CAGGGUCGCGAUGCUGCCCGGUUUGGCACUGCUCC<br>UGCUGGCCGCCUGGACGGCUCGGGCGCUGGAGGUC<br>UACCCUGAACUGCAGAUCACCAAUGUGGUAGAAGC<br>CAACCAACCAGUGACCAUCCAGAACUGGUGCAAGC<br>GGGGCCGCAAGCAGUGCAAGACCCAUCCCCACUUU<br>GUGAUUCCCUACCGCUGCUUAGUUGGUGAGUUUGU<br>AAGUGAUGCCCUUCUCGUUCCUGACAAGUGCAAAU<br>UCUUACACCAGGAGAGGAUGGAUGUUUGCGAAACU<br>CAUCUUCACUGGCACACCGUCGCCAAAGAGACAUG<br>CAGUGAGAAGAGUACCAACUUGCAUGACUACGGCA<br>UGUUGCUGCCCUGCGGAAUUGACAAGUUCCGAGGG<br>GUAGAGUUUGUGUGUUGCCCACUGGCUGAAGAAAG<br>UGACAAUGUGGAUUCUGCUGAUGCGGAGGAGGAUG<br>ACUCGGAUGUCUGGUGGGGCGGAGCAGACACAGAC<br>UAUGCAGAUGGGAGUGAAGACAAAGUAGUAGAAGU<br>AGCAGAGGAGGAAGAAGUGGCUGAGGUGGAAGAAG<br>AAGAAGCCGAUGAUGACGAGGACGAUGAGGAUGGU |

TABLE 1-continued

Human APP mRNA Isoform Sequences. Sequences obtained from NCBI APP gene ID: 381; Assembly GRCh38.p13 (GCF_000001405.39); NC_000021.9 (25880550 . . . 26171128, complement)

| SEQ ID NO | Iso-form | mRNA Sequence |
|---|---|---|
| | | GAUGAGGUAGAGGAAGAGGCUGAGGAACCCUACGA |
| | | AGAAGCCACAGAGAGAACCACCAGCAUUGCCACCA |
| | | CCACCACCACCACCACAGAGUCUGUGGAAGAGGUG |
| | | GUUCGAGUUCCUACAACAGCAGCCAGUACCCCUGA |
| | | UGCCGUUGACAAGUAUCUCGAGACACCUGGGGAUG |
| | | AGAAUGAACAUGCCCAUUUCCAGAAAGCCAAAGAG |
| | | AGGCUUGAGGCCAAGCACCGAGAGAGAAUGUCCCA |
| | | GGUCAUGAGAGAAUGGGAAGAGGCAGAACGUCAAG |
| | | CAAAGAACUUGCCUAAAGCUGAUAAGAAGGCAGUU |
| | | AUCCAGCAUUUCCAGGAGAAAGUGGAAUCUUUGGA |
| | | ACAGGAAGCAGCCAACGAGAGACAGCAGCUGGUGG |
| | | AGACACACAUGGCCAGAGUGGAAGCCAUGCUCAAU |
| | | GACCGCCGCCGCCUGGCCCUGGAGAACUACAUCAC |
| | | CGCUCUGCAGGCUGUUCCUCCUCGGCCUCGUCACG |
| | | UGUUCAAUAUGCUAAAGAAGUAUGUCCGCGCAGAA |
| | | CAGAAGGACAGACAGCACACCCUAAAGCAUUUCGA |
| | | GCAUGUGCGCAUGGUGGAUCCCAAGAAAGCCGCUC |
| | | AGAUCCGGUCCCAGGUUAUGACACACCUCCGUGUG |
| | | AUUUAUGAGCGCAUGAAUCAGUCUCUCUCCCUGCU |
| | | CUACAACGUGCCUGCAGUGGCCGAGGAGAUUCAGG |
| | | AUGAAGUUGAUGAGCUGCUUCAGAAAGAGCAAAAC |
| | | UAUUCAGAUGACGUCUUGGCCAACAUGAUUAGUGA |
| | | ACCAAGGAUCAGUUACGGAAACGAUGCUCUCAUGC |
| | | CAUCUUUGACCGAAACGAAAACCACCGUGGAGCUC |
| | | CUUCCCGUGAAUGGAGAGUUCAGCCUGGACGAUCU |
| | | CCAGCCGUGGCAUUCUUUUGGGGCUGACUCUGUGC |
| | | CAGCCAACACAGAAAACGAAGUUGAGCCUGUUGAU |
| | | GCCCGCCCUGCUGCCGACCGAGGACUGACCACUCG |
| | | ACCAGGUUCUGGGUUGACAAAUAUCAAGACGGAGG |
| | | AGAUCUCUGAAGUGAAGAUGGAUGCAGAAUUCCGA |
| | | CAUGACUCAGGAUAUGAAGUUCAUCAUCAAAAAUU |
| | | GGUGUUCUUUGCAGAAGAUGUGGGUUCAAACAAAG |
| | | GUGCAAUCAUUGGACUCAUGGUGGGCGGUGUUGUC |
| | | AUAGCGACAGUGAUCGUCAUCACCUUGGUGAUGCU |
| | | GAAGAAGAAACAGUACACAUCCAUUCAUCAUGGUG |
| | | UGGUGGAGGUUGACGCCGCUGUCACCCCAGAGGAG |
| | | CGCCACCUGUCCAAGAUGCAGCAGAACGGCUACGA |
| | | AAAUCCAACCUACAAGUUCUUUGAGCAGAUGCAGA |
| | | ACUAGACCCCCGCCACAGCAGCCUCUGAAGUUGGA |
| | | CAGCAAAACCAUUGCUUCACUACCCAUCGGUGUCC |
| | | AUUUAUAGAAUAAUGUGGGAAGAAACAAACCCGUU |
| | | UUAUGAUUUACUCAUUAUCGCCUUUUGACAGCUGU |
| | | GCUGUAACACAAGUAGAUGCCUGAACUUGAAUUAA |
| | | UCCACACAUCAGUAAUGUAUUCUAUCUCUCUUUAC |
| | | AUUUUGGUCUCUAUACUACAUUAUUAAUGGGUUUU |
| | | GUGUACUGUAAAGAAUUUAGCUGUAUCAAACUAGU |
| | | GCAUGAAUAGAUUCUCUCCUGAUUAUUUAUCACAU |
| | | AGCCCCUUAGCCAGUUGUAUAUUAUUCUUGUGGUU |
| | | UGUGACCCAAUUAAGUCCUACUUUACAUAUGCUUU |
| | | AAGAAUCGAUGGGGGAUGCUUCAUGUGAACGUGGG |
| | | AGUUCAGCUGCUUCUCUUGCCUAAGUAUUCCUUUC |
| | | CUGAUCACUAUGCAUUUUAAAGUUAAACAUUUUUA |
| | | AGUAUUUCAGAUGCUUUAGAGAGAUUUUUUUUCCA |
| | | UGACUGCAUUUUACUGUACAGAUUGCUGCUUCUGC |
| | | UAUAUUUGUGAUAUAGGAAUUAAGAGGAUACACAC |
| | | GUUUGUUUCUUCGUGCCUGUUUUAUGUGCACACAU |
| | | UAGGCAUUGAGACUUCAAGCUUUUCUUUUUUUGUC |
| | | CACGUAUCUUUGGGUCUUUGAUAAAGAAAAGAAUC |
| | | CCUGUUCAUUGUAAGCACUUUUACGGGGCGGGUGG |
| | | GGAGGGGUGCUCUGCUGGUCUUCAAUUACCAAGAA |
| | | UUCUCCAAAACAAUUUUCUGCAGGAUGAUUGUACA |
| | | GAAUCAUUGCUUAUGACAUGAUCGCUUUCUACACU |
| | | GUAUUACAUAAAUAAAUUAAAUAAAAUAACCCCGG |
| | | GCAAGACUUUUCUUUGAAGGAUGACUACAGACAUU |
| | | AAAUAAUCGAAGUAAUUUUGGGUGGGGAGAAGAGG |
| | | CAGAUUCAAUUUUCUUUAACCAGUCUGAAGUUUCA |
| | | UUUAUGAUACAAAAGAAGAUGAAAAUGGAAGUGGC |
| | | AAUAUAAGGGGAUGAGGAAGGCAUGCCUGGACAAA |
| | | CCCUUCUUUUAAGAUGUGUCUUCAAUUUGUAUAAA |
| | | AUGGUGUUUUCAUGUAAAUAAAUACAUUCUUGGAG |
| | | GAGCA |
| 8 | 6 | GUCAGUUUCCUCGGCAGCGGUAGGCGAGAGCACGC |
| | | GGAGGAGCGUGCGCGGGGGCCCCGGGAGACGGCGG |
| | | CGGUGGCGGCGCGGGCAGAGCAAGGACGCGGCGGA |
| | | UCCCACUCGCACAGCAGCGCACUCGGUGCCCCGCG |
| | | CAGGGUCGCGAUGCUGCCCGGUUUGGCACUGCUCC |
| | | UGCUGGCCGCCUGGACGGCUCGGGCGCUGGAGGUC |
| | | UACCCUGAACUGCAGAUCACCAAUGUGGUAGAAGC |
| | | CAACCAACCAGUGACCAUCCAGAACUGGUGCAAGC |
| | | GGGGCCGCAAGCAGUGCAAGACCCAUCCCCACUUU |
| | | GUGAUUCCCUACCGCUGCUUAGUUGGUGAGUUUGU |
| | | AAGUGAUGCCCUUCUCGUUCCUGACAAGUGCAAAU |
| | | UCUUACACCAGGAGAGGAUGGAUGUUUGCGAAACU |
| | | CAUCUUCACUGGCACACCGUCGCCAAAGAGACAUG |
| | | CAGUGAGAAGAGUACCAACUUGCAUGACUACGGCA |
| | | UGUUGCUGCCCUGCGGAAUUGACAAGUUCCGAGGG |
| | | GUAGAGUUUGUGUGUUGCCCACUGGCUGAAGAAAG |
| | | UGACAAUGUGGAUUCUGCUGAUGCGGAGGAGGAUG |
| | | ACUCGGAUGUCUGGUGGGGCGGAGCAGACACAGAC |
| | | UAUGCAGAUGGGAGUGAAGACAAAGUAGUAGAAGU |
| | | AGCAGAGGAGGAAGAAGUGGCUGAGGUGGAAGAAG |
| | | AAGAAGCCGAUGAUGACGAGGACGAUGAGGAUGGU |
| | | GAUGAGGUAGAGGAAGAGGCUGAGGAACCCUACGA |
| | | AGAAGCCACAGAGAGAACCACCAGCAUUGCCACCA |
| | | CCACCACCACCACCACAGAGUCUGUGGAAGAGGUG |
| | | GUUCGAGAGGUGUGCUCUGAACAAGCCGAGACGGG |
| | | GCCGUGCCGAGCAAUGAUCUCCCGCUGGUACUUUG |
| | | AUGUGACUGAAGGGAAGUGUGCCCCAUUCUUUUAC |
| | | GGCGGAUGUGGCGGCAACCGGAACAACUUUGACAC |
| | | AGAAGAGUACUGCAUGGCCGUGUGUGGCAGCGCCA |
| | | UGUCCCAAAGUUUACUCAAGACUACCCAGGAACCU |
| | | CUUGCCCGAGAUCCUGUUAAACUUCCUACAACAGC |
| | | AGCCAGUACCCCUGAUGCCGUUGACAAGUAUCUCG |
| | | AGACACCUGGGGAUGAGAAUGAACAUGCCCAUUUC |
| | | CAGAAAGCCAAAGAGAGGCUUGAGGCCAAGCACCG |
| | | AGAGAGAAUGUCCCAGGUCAUGAGAGAAUGGGAAG |
| | | AGGCAGAACGUCAAGCAAAGAACUUGCCUAAAGCU |
| | | GAUAAGAAGGCAGUUAUCCAGCAUUUCCAGGAGAA |
| | | AGUGGAAUCUUUGGAACAGGAAGCAGCCAACGAGA |
| | | GACAGCAGCUGGUGGAGACACACAUGGCCAGAGUG |
| | | GAAGCCAUGCUCAAUGACCGCCGCCGCCUGGCCCU |
| | | GGAGAACUACAUCACCGCUCUGCAGGCUGUUCCUC |
| | | CUCGGCCUCGUCACGUGUUCAAUAUGCUAAAGAAG |
| | | UAUGUCCGCGCAGAACAGAAGGACAGACAGCACAC |
| | | CCUAAAGCAUUUCGAGCAUGUGCGCAUGGUGGAUC |
| | | CCAAGAAAGCCGCUCAGAUCCGGUCCCAGGUUAUG |
| | | ACACACCUCCGUGUGAUUUAUGAGCGCAUGAAUCA |
| | | GUCUCUCUCCCUGCUCUACAACGUGCCUGCAGUGG |
| | | CCGAGGAGAUUCAGGAUGAAGUUGAUGAGCUGCUU |
| | | CAGAAAGAGCAAAACUAUUCAGAUGACGUCUUGGC |
| | | CAACAUGAUUAGUGAACCAAGGAUCAGUUACGGAA |
| | | ACGAUGCUCUCAUGCCAUCUUUGACCGAAACGAAA |
| | | ACCACCGUGGAGCUCCUUCCCGUGAAUGGAGAGUU |
| | | CAGCCUGGACGAUCUCCAGCCGUGGCAUUCUUUUG |
| | | GGGCUGACUCUGUGCCAGCCAACACAGAAAACGAA |
| | | GUUGAGCCUGUUGAUGCCCGCCCUGCUGCCGACCG |
| | | AGGACUGACCACUCGACCAGGUUCUGGGUUGACAA |
| | | AUAUCAAGACGGAGGAGAUCUCUGAAGUGAAGAUG |
| | | GAUGCAGAAUUCCGACAUGACUCAGGAUAUGAAGU |
| | | UCAUCAUCAAAAAUUGGUGUUCUUUGCAGAAGAUG |
| | | UGGGUUCAAACAAAGGUGCAAUCAUUGGACUCAUG |
| | | GUGGGCGGUGUUGUCAUAGCGACAGUGAUCGUCAU |
| | | CACCUUGGUGAUGCUGAAGAAGAAACAGUACACAU |
| | | CCAUUCAUCAUGGUGUGGUGGAGGUUGACGCCGCU |
| | | GUCACCCCAGAGGAGCGCCACCUGUCCAAGAUGCA |
| | | GCAGAACGGCUACGAAAAUCCAACCUACAAGUUCU |
| | | UUGAGCAGAUGCAGAACUAGACCCCCGCCACAGCA |
| | | GCCUCUGAAGUUGGACAGCAAAACCAUUGCUUCAC |
| | | UACCCAUCGGUGUCCAUUUAUAGAAUAAUGUGGGA |
| | | AGAAACAAACCCGUUUUAUGAUUUACUCAUUAUCG |
| | | CCUUUUGACAGCUGUGCUGUAACACAAGUAGAUGC |
| | | CUGAACUUGAAUUAAUCCACACAUCAGUAAUGUAU |
| | | UCUAUCUCUCUUUACAUUUUGGUCUCUAUACUACA |

TABLE 1-continued

Human APP mRNA Isoform Sequences. Sequences obtained from NCBI APP gene ID: 381; Assembly GRCh38.p13 (GCF_000001405.39); NC_000021.9 (25880550 . . . 26171128, complement)

| SEQ ID NO | Iso-form | mRNA Sequence |
|---|---|---|
| | | UUAUUAAUGGGUUUUGUGUACUGUAAAGAAUUUAG<br>CUGUAUCAAACUAGUGCAUGAAUAGAUUCUCUCCU<br>GAUUAUUUAUCACAUAGCCCCUUAGCCAGUUGUAU<br>AUUAUUCUUGUGGUUUGUGACCCAAUUAAGUCCUA<br>CUUUACAUAUGCUUUAAGAAUCGAUGGGGGAUGCU<br>UCAUGUGAACGUGGGAGUUCAGCUGCUUCUCUUGC<br>CUAAGUAUUCCUUUCCUGAUCACUAUGCAUUUUAA<br>AGUUAAACAUUUUUAAGUAUUUCAGAUGCUUUAGA<br>GAGAUUUUUUUUCCAUGACUGCAUUUUACUGUACA<br>GAUUGCUGCUUCUGCUAUAUUUGUGAUAUAGGAAU<br>UAAGAGGAUACACACGUUUGUUUCUUCGUGCCUGU<br>UUUAUGUGCACACAUUAGGCAUUGAGACUUCAAGC<br>UUUUCUUUUUUUGUCCACGUAUCUUUGGGUCUUUG<br>AUAAAGAAAAGAAUCCCUGUUCAUUGUAAGCACUU<br>UUACGGGGCGGGUGGGGAGGGGUGCUCUGCUGGUC<br>UUCAAUUACCAAGAAUUCUCCAAAACAAUUUUCUG<br>CAGGAUGAUUGUACAGAAUCAUUGCUUAUGACAUG<br>AUCGCUUUCUACACUGUAUUACAUAAAUAAAUUAA<br>AUAAAAUAACCCCGGGCAAGACUUUUCUUUGAAGG<br>AUGACUACAGACAUUAAAUAAUCGAAGUAAUUUUG<br>GGUGGGGAGAAGAGGCAGAUUCAAUUUUCUUUAAC<br>CAGUCUGAAGUUUCAUUUAUGAUACAAAAGAAGAU<br>GAAAAUGGAAGUGGCAAUAUAAGGGGAUGAGGAAG<br>GCAUGCCUGGACAAACCCUUCUUUUAAGAUGUGUC<br>UUCAAUUUGUAUAAAAUGGUGUUUUCAUGUAAAUA<br>AAUACAUUCUUGGAGGAGCA |
| 9 | 7 | GUCGGAUGAUUCAAGCUCACGGGGACGAGCAGGAG<br>CGCUCUCGACUUUUCUAGAGCCUCAGCGUCCUAGG<br>ACUCACCUUUCCCUGAUCCUGCACCGUCCCUCUCC<br>UGGCCCCAGACUCUCCCUCCCACUGUUCACGAAGC<br>CCAGGUACCCACUGAUGGUAAUGCUGGCCUGCUGG<br>CUGAACCCCAGAUUGCCAUGUUCUGUGGCAGACUG<br>AACAUGCACAUGAAUGUCCAGAAUGGGAAGUGGGA<br>UUCAGAUCCAUCAGGGACCAAAACCUGCAUUGAUA<br>CCAAGGAAGGCAUCCUGCAGUAUUGCCAAGAAGUC<br>UACCCUGAACUGCAGAUCACCAAUGUGGUAGAAGC<br>CAACCAACCAGUGACCAUCCAGAACUGGUGCAAGC<br>GGGGCCGCAAGCAGUGCAAGACCCAUCCCCACUUU<br>GUGAUUCCCUACCGCUGCUUAGUUGGUGAGUUUGU<br>AAGUGAUGCCCUUCUCGUUCCUGACAAGUGCAAAU<br>UCUUACACCAGGAGAGGAUGGAUGUUUGCGAAACU<br>CAUCUUCACUGGCACACCGUCGCCAAAGAGACAUG<br>CAGUGAGAAGAGUACCAACUUGCAUGACUACGGCA<br>UGUUGCUGCCCUGCGGAAUUGACAAGUUCCGAGGG<br>GUAGAGUUUGUGUGUUGCCCACUGGCUGAAGAAAG<br>UGACAAUGUGGAUUCUGCUGAUGCGGAGGAGGAUG<br>ACUCGGAUGUCUGGUGGGGCGGAGCAGACACAGAC<br>UAUGCAGAUGGGAGUGAAGACAAAGUAGUAGAAGU<br>AGCAGAGGAGGAAGAAGUGGCUGAGGUGGAAGAAG<br>AAGAAGCCGAUGAUGACGAGGACGAUGAGGAUGGU<br>GAUGAGGUAGAGGAAGAGGCUGAGGAACCCUACGA<br>AGAAGCCACAGAGAGAACCACCAGCAUUGCCACCA<br>CCACCACCACCACCACAGAGUCUGUGGAAGAGGUG<br>GUUCGAGUUCCUACAACAGCAGCCAGUACCCCUGA<br>UGCCGUUGACAAGUAUCUCGAGACACCUGGGGAUG<br>AGAAUGAACAUGCCCAUUUCCAGAAAGCCAAAGAG<br>AGGCUUGAGGCCAAGCACCGAGAGAGAAUGUCCCA<br>GGUCAUGAGAGAAUGGGAAGAGGCAGAACGUCAAG<br>CAAAGAACUUGCCUAAAGCUGAUAAGAAGGCAGUU<br>AUCCAGCAUUUCCAGGAGAAAGUGGAAUCUUUGGA<br>ACAGGAAGCAGCCAACGAGAGACAGCAGCUGGUGG<br>AGACACACAUGGCCAGAGUGGAAGCCAUGCUCAAU<br>GACCGCCGCCGCCUGGCCCUGGAGAACUACAUCAC<br>CGCUCUGCAGGCUGUUCCUCCUCGGCCUCGUCACG<br>UGUUCAAUAUGCUAAAGAAGUAUGUCCGCGCAGAA<br>CAGAAGGACAGACAGCACACCCUAAAGCAUUUCGA<br>GCAUGUGCGCAUGGUGGAUCCCAAGAAAGCCGCUC<br>AGAUCCGGUCCCAGGUUAUGACACACCUCCGUGUG<br>AUUUAUGAGCGCAUGAAUCAGUCUCUCUCCCUGCU<br>CUACAACGUGCCUGCAGUGGCCGAGGAGAUUCAGG<br>AUGAAGUUGAUGAGCUGCUUCAGAAAGAGCAAAAC |

TABLE 1-continued

Human APP mRNA Isoform Sequences. Sequences obtained from NCBI APP gene ID: 381; Assembly GRCh38.p13 (GCF_000001405.39); NC_000021.9 (25880550 . . . 26171128, complement)

| SEQ ID NO | Iso-form | mRNA Sequence |
|---|---|---|
| | | UAUUCAGAUGACGUCUUGGCCAACAUGAUUAGUGA<br>ACCAAGGAUCAGUUACGGAAACGAUGCUCUCAUGC<br>CAUCUUUGACCGAAACGAAAACCACCGUGGAGCUC<br>CUUCCCGUGAAUGGAGAGUUCAGCCUGGACGAUCU<br>CCAGCCGUGGCAUUCUUUUGGGGCUGACUCUGUGC<br>CAGCCAACACAGAAAACGAAGUUGAGCCUGUUGAU<br>GCCCGCCCUGCUGCCGACCGAGGACUGACCACUCG<br>ACCAGGUUCUGGGUUGACAAAUAUCAAGACGGAGG<br>AGAUCUCUGAAGUGAAGAUGGAUGCAGAAUUCCGA<br>CAUGACUCAGGAUAUGAAGUUCAUCAUCAAAAAUU<br>GGUGUUCUUUGCAGAAGAUGUGGGUUCAAACAAAG<br>GUGCAAUCAUUGGACUCAUGGUGGGCGGUGUUGUC<br>AUAGCGACAGUGAUCGUCAUCACCUUGGUGAUGCU<br>GAAGAAGAAACAGUACACAUCCAUUCAUCAUGGUG<br>UGGUGGAGGUUGACGCCGCUGUCACCCCAGAGGAG<br>CGCCACCUGUCCAAGAUGCAGCAGAACGGCUACGA<br>AAAUCCAACCUACAAGUUCUUUGAGCAGAUGCAGA<br>ACUAGACCCCCGCCACAGCAGCCUCUGAAGUUGGA<br>CAGCAAAACCAUUGCUUCACUACCCAUCGGUGUCC<br>AUUUAUAGAAUAAUGUGGGAAGAAACAAACCCGUU<br>UUAUGAUUUACUCAUUAUCGCCUUUUGACAGCUGU<br>GCUGUAACACAAGUAGAUGCCUGAACUUGAAUUAA<br>UCCACACAUCAGUAAUGUAUUCUAUCUCUCUUUAC<br>AUUUUGGUCUCUAUACUACAUUAUUAAUGGGUUUU<br>GUGUACUGUAAAGAAUUUAGCUGUAUCAAACUAGU<br>GCAUGAAUAGAUUCUCUCCUGAUUAUUUAUCACAU<br>AGCCCCUUAGCCAGUUGUAUAUUAUUCUUGUGGUU<br>UGUGACCCAAUUAAGUCCUACUUUACAUAUGCUUU<br>AAGAAUCGAUGGGGGAUGCUUCAUGUGAACGUGGG<br>AGUUCAGCUGCUUCUCUUGCCUAAGUAUUCCUUUC<br>CUGAUCACUAUGCAUUUUAAAGUUAAACAUUUUUA<br>AGUAUUUCAGAUGCUUUAGAGAGAUUUUUUUUCCA<br>UGACUGCAUUUUACUGUACAGAUUGCUGCUUCUGC<br>UAUAUUUGUGAUAUAGGAAUUAAGAGGAUACACAC<br>GUUUGUUUCUUCGUGCCUGUUUUAUGUGCACACAU<br>UAGGCAUUGAGACUUCAAGCUUUUCUUUUUUUGUC<br>CACGUAUCUUUGGGUCUUUGAUAAAGAAAAGAAUC<br>CCUGUUCAUUGUAAGCACUUUUACGGGGCGGGUGG<br>GGAGGGGUGCUCUGCUGGUCUUCAAUUACCAAGAA<br>UUCUCCAAAACAAUUUUCUGCAGGAUGAUUGUACA<br>GAAUCAUUGCUUAUGACAUGAUCGCUUUCUACACU<br>GUAUUACAUAAAUAAAUUAAAUAAAAUAACCCCGG<br>GCAAGACUUUUCUUUGAAGGAUGACUACAGACAUU<br>AAAUAAUCGAAGUAAUUUUGGGUGGGGAGAAGAGG<br>CAGAUUCAAUUUUCUUUAACCAGUCUGAAGUUUCA<br>UUUAUGAUACAAAAGAAGAUGAAAAUGGAAGUGGC<br>AAUAUAAGGGGAUGAGGAAGGCAUGCCUGGACAAA<br>CCCUUCUUUUAAGAUGUGUCUUCAAUUUGUAUAAA<br>AUGGUGUUUUCAUGUAAAUAAAUACAUUCUUGGAG<br>GAGCA |
| 10 | 8 | GUCAGUUUCCUCGGCAGCGGUAGGCGAGAGCACGC<br>GGAGGAGCGUGCGCGGGGGCCCCGGGAGACGGCGG<br>CGGUGGCGGCGCGGGCAGAGCAAGGACGCGGCGGA<br>UCCCACUCGCACAGCAGCGCACUCGGUGCCCCGCG<br>CAGGGUCGCGAUGCUGCCCGGUUUGGCACUGCUCC<br>UGCUGGCCGCCUGGACGGCUCGGGCGCUGGAGGUA<br>CCCACUGAUGGUAAUGCUGGCCUGCUGGCUGAACC<br>CCAGAUUGCCAUGUUCUGUGGCAGACUGAACAUGC<br>ACAUGAAUGUCCAGAAUGGGAAGUGGGAUUCAGAU<br>CCAUCAGGGACCAAAACCUGCAUUGAUACCAAGGA<br>AGGCAUCCUGCAGUAUUGCCAAGAAGUCUACCCUG<br>AACUGCAGAUCACCAAUGUGGUAGAAGCCAACCAA<br>CCAGUGACCAUCCAGAACUGGUGCAAGCGGGGCCG<br>CAAGCAGUGCAAGACCCAUCCCCACUUUGUGAUUC<br>CCUACCGCUGCUUAGUUGGUGAGUUUGUAAGUGAU<br>GCCCUUCUCGUUCCUGACAAGUGCAAAUUCUUACA<br>CCAGGAGAGGAUGGAUGUUUGCGAAACUCAUCUUC<br>ACUGGCACACCGUCGCCAAAGAGACAUGCAGUGAG<br>AAGAGUACCAACUUGCAUGACUACGGCAUGUUGCU<br>GCCCUGCGGAAUUGACAAGUUCCGAGGGUAGAGU<br>UUGUGUGUUGCCCACUGGCUGAAGAAAGUGACAAU |

TABLE 1-continued

Human APP mRNA Isoform Sequences. Sequences obtained from NCBI APP gene ID: 381; Assembly GRCh38.p13 (GCF_000001405.39); NC_000021.9 (25880550 . . . 26171128, complement)

| SEQ ID NO | Iso-form | mRNA Sequence |
|---|---|---|
| | | GUGGAUUCUGCUGAUGCGGAGGAGGAUGACUCGGA |
| | | UGUCUGGUGGGGCGGAGCAGACACAGACUAUGCAG |
| | | AUGGGAGUGAAGACAAAGUAGUAGAAGUAGCAGAG |
| | | GAGGAAGAAGUGGCUGAGGUGGAAGAAGAAGAAGC |
| | | CGAUGAUGACGAGGACGAUGAGGAUGGUGAUGAGG |
| | | UAGAGGAAGAGGCUGAGGAACCCUACGAAGAAGCC |
| | | ACAGAGAGAACCACCAGCAUUGCCACCACCACCAC |
| | | CACCACCACAGAGUCUGUGGAAGAGGUGGUUCGAG |
| | | AGGUGUGCUCUGAACAAGCCGAGACGGGGCCGUGC |
| | | CGAGCAAUGAUCUCCCGCUGGUACUUUGAUGUGAC |
| | | UGAAGGGAAGUGUGCCCCAUUCUUUUACGGCGGAU |
| | | GUGGCGGCAACCGGAACAACUUUGACACAGAAGAG |
| | | UACUGCAUGGCCGUGUGUGGCAGCGCCAUGUCCCA |
| | | AAGUUUACUCAAGACUACCCAGGAACCUCUUGCCC |
| | | GAGAUCCUGUUAAACUUCCUACAACAGCAGCCAGU |
| | | ACCCCUGAUGCCGUUGACAAGUAUCUCGAGACACC |
| | | UGGGGAUGAGAAUGAACAUGCCCAUUUCCAGAAAG |
| | | CCAAAGAGAGGCUUGAGGCCAAGCACCGAGAGAGA |
| | | AUGUCCCAGGUCAUGAGAGAAUGGGAAGAGGCAGA |
| | | ACGUCAAGCAAAGAACUUGCCUAAAGCUGAUAAGA |
| | | AGGCAGUUAUCCAGCAUUUCCAGGAGAAAGUGGAA |
| | | UCUUUGGAACAGGAAGCAGCCAACGAGAGACAGCA |
| | | GCUGGUGGAGACACACAUGGCCAGAGUGGAAGCCA |
| | | UGCUCAAUGACCGCCGCCGCCUGGCCCUGGAGAAC |
| | | UACAUCACCGCUCUGCAGGCUGUUCCUCCUCGGCC |
| | | UCGUCACGUGUUCAAUAUGCUAAAGAAGUAUGUCC |
| | | GCGCAGAACAGAAGGACAGACAGCACACCCUAAAG |
| | | CAUUUCGAGCAUGUGCGCAUGGUGGAUCCCAAGAA |
| | | AGCCGCUCAGAUCCGGUCCCAGGUUAUGACACACC |
| | | UCCGUGUGAUUUAUGAGCGCAUGAAUCAGUCUCUC |
| | | UCCCUGCUCUACAACGUGCCUGCAGUGGCCGAGGA |
| | | GAUUCAGGAUGAAGUUGAUGAGCUGCUUCAGAAAG |
| | | AGCAAAACUAUUCAGAUGACGUCUUGGCCAACAUG |
| | | AUUAGUGAACCAAGGAUCAGUUACGGAAACGAUGC |
| | | UCUCAUGCCAUCUUUGACCGAAACGAAAACCACCG |
| | | UGGAGCUCCUUCCCGUGAAUGGAGAGUUCAGCCUG |
| | | GACGAUCUCCAGCCGUGGCAUUCUUUUGGGGCUGA |
| | | CUCUGUGCCAGCCAACACAGAAAACGAAGGUUCUG |
| | | GGUUGACAAAUAUCAAGACGGAGGAGAUCUCUGAA |
| | | GUGAAGAUGGAUGCAGAAUUCCGACAUGACUCAGG |
| | | AUAUGAAGUUCAUCAUCAAAAAUUGGUGUUCUUUG |
| | | CAGAAGAUGUGGGUUCAAACAAAGGUGCAAUCAUU |
| | | GGACUCAUGGUGGGCGGUGUUGUCAUAGCGACAGU |
| | | GAUCGUCAUCACCUUGGUGAUGCUGAAGAAGAAAC |
| | | AGUACACAUCCAUUCAUCAUGGUGUGGUGGAGGUU |
| | | GACGCCGCUGUCACCCCAGAGGAGCGCCACCUGUC |
| | | CAAGAUGCAGCAGAACGGCUACGAAAAUCCAACCU |
| | | ACAAGUUCUUUGAGCAGAUGCAGAACUAGACCCCC |
| | | GCCACAGCAGCCUCUGAAGUUGGACAGCAAAACCA |
| | | UUGCUUCACUACCCAUCGGUGUCCAUUUAUAGAAU |
| | | AAUGUGGGAAGAAACAAACCCGUUUUAUGAUUUAC |
| | | UCAUUAUCGCCUUUUGACAGCUGUGCUGUAACACA |
| | | AGUAGAUGCCUGAACUUGAAUUAAUCCACACAUCA |
| | | GUAAUGUAUUCUAUCUCUCUUUACAUUUUGGUCUC |
| | | UAUACUACAUUAUUAAUGGGUUUUGUGUACUGUAA |
| | | AGAAUUUAGCUGUAUCAAACUAGUGCAUGAAUAGA |
| | | UUCUCUCCUGAUUAUUUAUCACAUAGCCCCUUAGC |
| | | CAGUUGUAUAUUAUUCUUGUGGUUUGUGACCCAAU |
| | | UAAGUCCUACUUUACAUAUGCUUUAAGAAUCGAUG |
| | | GGGGAUGCUUCAUGUGAACGUGGGAGUUCAGCUGC |
| | | UUCUCUUGCCUAAGUAUUCCUUUCCUGAUCACUAU |
| | | GCAUUUUAAAGUUAAACAUUUUUAAGUAUUUCAGA |
| | | UGCUUUAGAGAGAUUUUUUUUCCAUGACUGCAUUU |
| | | UACUGUACAGAUUGCUGCUUCUGCUAUAUUUGUGA |
| | | UAUAGGAAUUAAGAGGAUACACACGUUUGUUUCUU |
| | | CGUGCCUGUUUUAUGUGCACACAUUAGGCAUUGAG |
| | | ACUUCAAGCUUUUCUUUUUUUGUCCACGUAUCUUU |
| | | GGGUCUUUGAUAAAGAAAAGAAUCCCUGUUCAUUG |
| | | UAAGCACUUUUACGGGGCGGGUGGGGAGGGGUGCU |
| | | CUGCUGGUCUUCAAUUACCAAGAAUUCUCCAAAAC |
| | | AAUUUUCUGCAGGAUGAUUGUACAGAAUCAUUGCU |
| | | UAUGACAUGAUCGCUUUCUACACUGUAUUACAUAA |
| | | AUAAAUUAAAUAAAAUAACCCCGGGCAAGACUUUU |
| | | CUUUGAAGGAUGACUACAGACAUUAAAUAAUCGAA |
| | | GUAAUUUUGGGUGGGGAGAAGAGGCAGAUUCAAUU |
| | | UUCUUUAACCAGUCUGAAGUUUCAUUUAUGAUACA |
| | | AAAGAAGAUGAAAAUGGAAGUGGCAAUAUAAGGGG |
| | | AUGAGGAAGGCAUGCCUGGACAAACCCUUCUUUUA |
| | | AGAUGUGUCUUCAAUUUGUAUAAAAUGGUGUUUUC |
| | | AUGUAAAUAAAUACAUUCUUGGAGGAGCA |
| 11 | 9 | GUCAGUUUCCUCGGCAGCGGUAGGCGAGAGCACGC |
| | | GGAGGAGCGUGCGCGGGGGCCCCGGGAGACGGCGG |
| | | CGGUGGCGGCGCGGGCAGAGCAAGGACGCGGCGGA |
| | | UCCCACUCGCACAGCAGCGCACUCGGUGCCCCGCG |
| | | CAGGGUCGCGAUGCUGCCCGGUUUGGCACUGCUCC |
| | | UGCUGGCCGCCUGGACGGCUCGGGCGCUGGAGGUA |
| | | CCCACUGAUGGUAAUGCUGGCCUGCUGGCUGAACC |
| | | CCAGAUUGCCAUGUUCUGUGGCAGACUGAACAUGC |
| | | ACAUGAAUGUCCAGAAUGGGAAGUGGGAUUCAGAU |
| | | CCAUCAGGGACCAAAACCUGCAUUGAUACCAAGGA |
| | | AGGCAUCCUGCAGUAUUGCCAAGAAGUCUACCCUG |
| | | AACUGCAGAUCACCAAUGUGGUAGAAGCCAACCAA |
| | | CCAGUGACCAUCCAGAACUGGUGCAAGCGGGGCCG |
| | | CAAGCAGUGCAAGACCCAUCCCCACUUUGUGAUUC |
| | | CCUACCGCUGCUUAGUUGGUGAGUUUGUAAGUGAU |
| | | GCCCUUCUCGUUCCUGACAAGUGCAAAUUCUUACA |
| | | CCAGGAGAGGAUGGAUGUUUGCGAAACUCAUCUUC |
| | | ACUGGCACACCGUCGCCAAAGAGACAUGCAGUGAG |
| | | AAGAGUACCAACUUGCAUGACUACGGCAUGUUGCU |
| | | GCCCUGCGGAAUUGACAAGUUCCGAGGGGUAGAGU |
| | | UUGUGUGUUGCCCACUGGCUGAAGAAAGUGACAAU |
| | | GUGGAUUCUGCUGAUGCGGAGGAGGAUGACUCGGA |
| | | UGUCUGGUGGGGCGGAGCAGACACAGACUAUGCAG |
| | | AUGGGAGUGAAGACAAAGUAGUAGAAGUAGCAGAG |
| | | GAGGAAGAAGUGGCUGAGGUGGAAGAAGAAGAAGC |
| | | CGAUGAUGACGAGGACGAUGAGGAUGGUGAUGAGG |
| | | UAGAGGAAGAGGCUGAGGAACCCUACGAAGAAGCC |
| | | ACAGAGAGAACCACCAGCAUUGCCACCACCACCAC |
| | | CACCACCACAGAGUCUGUGGAAGAGGUGGUUCGAG |
| | | AGGUGUGCUCUGAACAAGCCGAGACGGGGCCGUGC |
| | | CGAGCAAUGAUCUCCCGCUGGUACUUUGAUGUGAC |
| | | UGAAGGGAAGUGUGCCCCAUUCUUUUACGGCGGAU |
| | | GUGGCGGCAACCGGAACAACUUUGACACAGAAGAG |
| | | UACUGCAUGGCCGUGUGUGGCAGCGCCAUUCCUAC |
| | | AACAGCAGCCAGUACCCCUGAUGCCGUUGACAAGU |
| | | AUCUCGAGACACCUGGGGAUGAGAAUGAACAUGCC |
| | | CAUUUCCAGAAAGCCAAAGAGAGGCUUGAGGCCAA |
| | | GCACCGAGAGAGAAUGUCCCAGGUCAUGAGAGAAU |
| | | GGGAAGAGGCAGAACGUCAAGCAAAGAACUUGCCU |
| | | AAAGCUGAUAAGAAGGCAGUUAUCCAGCAUUUCCA |
| | | GGAGAAAGUGGAAUCUUUGGAACAGGAAGCAGCCA |
| | | ACGAGAGACAGCAGCUGGUGGAGACACACAUGGCC |
| | | AGAGUGGAAGCCAUGCUCAAUGACCGCCGCCGCCU |
| | | GGCCCUGGAGAACUACAUCACCGCUCUGCAGGCUG |
| | | UUCCUCCUCGGCCUCGUCACGUGUUCAAUAUGCUA |
| | | AAGAAGUAUGUCCGCGCAGAACAGAAGGACAGACA |
| | | GCACACCCUAAAGCAUUUCGAGCAUGUGCGCAUGG |
| | | UGGAUCCCAAGAAAGCCGCUCAGAUCCGGUCCCAG |
| | | GUUAUGACACACCUCCGUGUGAUUUAUGAGCGCAU |
| | | GAAUCAGUCUCUCUCCCUGCUCUACAACGUGCCUG |
| | | CAGUGGCCGAGGAGAUUCAGGAUGAAGUUGAUGAG |
| | | CUGCUUCAGAAAGAGCAAAACUAUUCAGAUGACGU |
| | | CUUGGCCAACAUGAUUAGUGAACCAAGGAUCAGUU |
| | | ACGGAAACGAUGCUCUCAUGCCAUCUUUGACCGAA |
| | | ACGAAAACCACCGUGGAGCUCCUUCCCGUGAAUGG |
| | | AGAGUUCAGCCUGGACGAUCUCCAGCCGUGGCAUU |
| | | CUUUUGGGGCUGACUCUGUGCCAGCCAACACAGAA |
| | | AACGAAGGUUCUGGGUUGACAAAUAUCAAGACGGA |
| | | GGAGAUCUCUGAAGUGAAGAUGGAUGCAGAAUUCC |
| | | GACAUGACUCAGGAUAUGAAGUUCAUCAUCAAAAA |
| | | UUGGUGUUCUUUGCAGAAGAUGUGGGUUCAAACAA |
| | | AGGUGCAAUCAUUGGACUCAUGGUGGGCGGUGUUG |
| | | UCAUAGCGACAGUGAUCGUCAUCACCUUGGUGAUG |

TABLE 1-continued

Human APP mRNA Isoform Sequences. Sequences obtained from NCBI APP gene ID: 381; Assembly GRCh38.p13 (GCF_000001405.39); NC_000021.9 (25880550 . . . 26171128, complement)

| SEQ ID NO | Iso-form | mRNA Sequence |
|---|---|---|
| | | CUGAAGAAGAAACAGUACACAUCCAUUCAUCAUGGUGUGGUGGAGGUUGACGCCGCUGUCACCCCAGAGGAGCGCCACCUGUCCAAGAUGCAGCAGAACGGCUACGAAAAUCCAACCUACAAGUUCUUUGAGCAGAUGCAGAACUAGACCCCCGCCACAGCAGCCUCUGAAGUUGGACAGCAAAACCAUUGCUUCACUACCCAUCGGUGUCCAUUUAUAGAAUAAUGUGGGAAGAAACAAACCCGUUUUAUGAUUUACUCAUUAUCGCCUUUUGACAGCUGUGCUGUAACACAAGUAGAUGCCUGAACUUGAAUUAAUCCACACAUCAGUAAUGUAUUCUAUCUCUCUUUACAUUUUGGUCUCUAUACUACAUUAUUAAUGGGUUUUGUGUACUGUAAAGAAUUUAGCUGUAUCAAACUAGUGCAUGAAUAGAUUCUCUCCUGAUUAUUUAUCACAUAGCCCCUUAGCCAGUUGUAUAUUAUUCUUGUGGUUUGUGACCCAAUUAAGUCCUACUUUACAUAUGCUUUAAGAAUCGAUGGGGGAUGCUUCAUGUGAACGUGGGAGUUCAGCUGCUUCUCUUGCCUAAGUAUUCCUUUCCUGAUCACUAUGCAUUUUAAAGUUAAACAUUUUUAAGUAUUUCAGAUGCUUUAGAGAGAUUUUUUUUCCAUGACUGCAUUUUACUGUACAGAUUGCUGCUUCUGCUAUAUUUGUGAUAUAGGAAUUAAGAGGAUACACACGUUUGUUUCUUCGUGCCUGUUUUAUGUGCACACAUUAGGCAUUGAGACUUCAAGCUUUUCUUUUUUUGUCCACGUAUCUUUGGGUCUUUGAUAAAGAAAAGAAUCCCUGUUCAUUGUAAGCACUUUUACGGGGCGGGUGGGGAGGGGUGCUCUGCUGGUCUUCAAUUACCAAGAAUUCUCCAAAACAAUUUUCUGCAGGAUGAUUGUACAGAAUCAUUGCUUAUGACAUGAUCGCUUUCUACACUGUAUUACAUAAAUAAAUUAAAUAAAAUAACCCCGGGCAAGACUUUUCUUUGAAGGAUGACUACAGACAUUAAAUAAUCGAAGUAAUUUUGGGUGGGGAGAAGAGGCAGAUUCAAUUUUCUUUAACCAGUCUGAAGUUUCAUUUAUGAUACAAAGAAGAUGAAAAUGGAAGUGGCAAUAUAAGGGGAUGAGGAAGGCAUGCCUGGACAAACCCUUCUUUUAAGAUGUGUCUUCAAUUUGUAUAAAAUGGUGUUUUCAUGUAAAUAAAUACAUUCUUGGAGGAGCA |
| 12 | 10 | GUCAGUUUCCUCGGCAGCGGUAGGCGAGAGCACGCGGAGGAGCGUGCGCGGGGGCCCCGGGAGACGGCGGCGGUGGCGGCGCGGGCAGAGCAAGGACGCGGCGGAUCCCACUCGCACAGCAGCGCACUCGGUGCCCCGCGCAGGGUCGCGAUGCUGCCCGGUUUGGCACUGCUCCUGCUGGCCGCCUGGACGGCUCGGGCGCUGGAGGUACCCACUGAUGGUAAUGCUGGCCUGCUGGCUGAACCCCAGAUUGCCAUGUUCUGUGGCAGACUGAACAUGCACAUGAAUGUCCAGAAUGGGAAGUGGGAUUCAGAUCCAUCAGGGACCAAAACCUGCAUUGAUACCAAGGAAGGCAUCCUGCAGUAUUGCCAAGAAGUCUACCCUGAACUGCAGAUCACCAAUGUGGUAGAAGCCAACCAACCAGUGACCAUCCAGAACUGGUGCAAGCGGGGCCGCAAGCAGUGCAAGACCCAUCCCCACUUUGUGAUUCCCUACCGCUGCUUAGUUGGUGAGUUUGUAAGUGAUGCCCUUCUCGUUCCUGACAAGUGCAAAUUCUUACACCAGGAGAGGAUGGAUGUUUGCGAAACUCAUCUUCACUGGCACACCGUCGCCAAAGAGACAUGCAGUGAGAAGAGUACCAACUUGCAUGACUACGGCAUGUUGCUGCCCUGCGGAAUUGACAAGUUCCGAGGGGUAGAGUUUGUGUGUUGCCCACUGGCUGAAGAAAGUGACAAUGUGGAUUCUGCUGAUGCGGAGGAGGAUGACUCGGAUGUCUGGUGGGGCGGAGCAGACACAGACUAUGCAGAUGGGAGUGAAGACAAAGUAGUAGAAGUAGCAGAGGAGGAAGAAGUGGCUGAGGUGGAAGAAGAAGAAGCCGAUGAUGACGAGGACGAUGAGGAUGGUGAUGAGGUAGAGGAAGAGGCUGAGGAACCCUACGAAGAAGCCACAGAGAGAACCACCAGCAUUGCCACCACCACCACCACCACCACAGAGUCUGUGGAAGAGGUGGUUCGAGUUCCUACAACAGCAGCCAGUACCCCUGAUGCCGUUGACAAGUAUCUCGAGACACCUGGGGAUGAGAAUGAACAUGCCCAUUUCCAGAAAGCCAAAGAGAGGCUUGAGGCCAAGCACCGAGAGAGAAUGUCCCAGGUCAUGAGAGAAUGGGAAGAGGCAGAACGUCAAGCAAAGAA |

TABLE 1-continued

Human APP mRNA Isoform Sequences. Sequences obtained from NCBI APP gene ID: 381; Assembly GRCh38.p13 (GCF_000001405.39); NC_000021.9 (25880550 . . . 26171128, complement)

| SEQ ID NO | Iso-form | mRNA Sequence |
|---|---|---|
| | | CUUGCCUAAAGCUGAUAAGAAGGCAGUUAUCCAGCAUUUCCAGGAGAAAGUGGAAUCUUUGGAACAGGAAGCAGCCAACGAGAGACAGCAGCUGGUGGAGACACACAUGGCCAGAGUGGAAGCCAUGCUCAAUGACCGCCGCCGCCUGGCCCUGGAGAACUACAUCACCGCUCUGCAGGCUGUUCCUCCUCGGCCUCGUCACGUGUUCAAUAUGCUAAAGAAGUAUGUCCGCGCAGAACAGAAGGACAGACAGCACACCCUAAAGCAUUUCGAGCAUGUGCGCAUGGUGGAUCCCAAGAAAGCCGCUCAGAUCCGGUCCCAGGUUAUGACACACCUCCGUGUGAUUUAUGAGCGCAUGAAUCAGUCUCUCUCCCUGCUCUACAACGUGCCUGCAGUGGCCGAGGAGAUUCAGGAUGAAGUUGAUGAGCUGCUUCAGAAAGAGCAAAACUAUUCAGAUGACGUCUUGGCCAACAUGAUUAGUGAACCAAGGAUCAGUUACGGAAACGAUGCUCUCAUGCCAUCUUUGACCGAAACGAAAACCACCGUGGAGCUCCUUCCCGUGAAUGGAGAGUUCAGCCUGGACGAUCUCCAGCCGUGGCAUUCUUUUGGGGCUGACUCUGUGCCAGCCAACACAGAAAACGAAGGUUCUGGGUUGACAAAUAUCAAGACGGAGGAGAUCUCUGAAGUGAAGAUGGAUGCAGAAUUCCGACAUGACUCAGGAUAUGAAGUUCAUCAUCAAAAAUUGGUGUUCUUUGCAGAAGAUGUGGGUUCAAACAAAGGUGCAAUCAUUGGACUCAUGGUGGGCGGUGUUGUCAUAGCGACAGUGAUCGUCAUCACCUUGGUGAUGCUGAAGAAGAAACAGUACACAUCCAUUCAUCAUGGUGUGGUGGAGGUUGACGCCGCUGUCACCCCAGAGGAGCGCCACCUGUCCAAGAUGCAGCAGAACGGCUACGAAAAUCCAACCUACAAGUUCUUUGAGCAGAUGCAGAACUAGACCCCCGCCACAGCAGCCUCUGAAGUUGGACAGCAAAACCAUUGCUUCACUACCCAUCGGUGUCCAUUUAUAGAAUAAUGUGGGAAGAAACAAACCCGUUUUAUGAUUUACUCAUUAUCGCCUUUUGACAGCUGUGCUGUAACACAAGUAGAUGCCUGAACUUGAAUUAAUCCACACAUCAGUAAUGUAUUCUAUCUCUCUUUACAUUUUGGUCUCUAUACUACAUUAUUAAUGGGUUUUGUGUACUGUAAAGAAUUUAGCUGUAUCAAACUAGUGCAUGAAUAGAUUCUCUCCUGAUUAUUUAUCACAUAGCCCCUUAGCCAGUUGUAUAUUAUUCUUGUGGUUUGUGACCCAAUUAAGUCCUACUUUACAUAUGCUUUAAGAAUCGAUGGGGGAUGCUUCAUGUGAACGUGGGAGUUCAGCUGCUUCUCUUGCCUAAGUAUUCCUUUCCUGAUCACUAUGCAUUUUAAAGUUAAACAUUUUUAAGUAUUUCAGAUGCUUUAGAGAGAUUUUUUUUCCAUGACUGCAUUUUACUGUACAGAUUGCUGCUUCUGCUAUAUUUGUGAUAUAGGAAUUAAGAGGAUACACACGUUUGUUUCUUCGUGCCUGUUUUAUGUGCACACAUUAGGCAUUGAGACUUCAAGCUUUUCUUUUUUUGUCCACGUAUCUUUGGGUCUUUGAUAAAGAAAAGAAUCCCUGUUCAUUGUAAGCACUUUUACGGGGCGGGUGGGGAGGGGUGCUCUGCUGGUCUUCAAUUACCAAGAAUUCUCCAAAACAAUUUUCUGCAGGAUGAUUGUACAGAAUCAUUGCUUAUGACAUGAUCGCUUUCUACACUGUAUUACAUAAAUAAAUUAAAUAAAAUAACCCCGGGCAAGACUUUUCUUUGAAGGAUGACUACAGACAUUAAAUAAUCGAAGUAAUUUUGGGUGGGGAGAAGAGGCAGAUUCAAUUUUCUUUAACCAGUCUGAAGUUUCAUUUAUGAUACAAAGAAGAUGAAAAUGGAAGUGGCAAUAUAAGGGGAUGAGGAAGGCAUGCCUGGACAAACCCUUCUUUUAAGAUGUGUCUUCAAUUUGUAUAAAAUGGUGUUUUCAUGUAAAUAAAUACAUUCUUGGAGGAGCA |
| 13 | 11 | GUCAGUUUCCUCGGCAGCGGUAGGCGAGAGCACGCGGAGGAGCGUGCGCGGGGGCCCCGGGAGACGGCGGCGGUGGCGGCGCGGGCAGAGCAAGGACGCGGCGGAUCCCACUCGCACAGCAGCGCACUCGGUGCCCCGCGCAGGGUCGCGAUGCUGCCCGGUUUGGCACUGCUCCUGCUGGCCGCCUGGACGGCUCGGGCGCUGGAGGUACCCACUGAUGGUAAUGCUGGCCUGCUGGCUGAACCCCAGAUUGCCAUGUUCUGUGGCAGACUGAACAUGCACAUGAAUGUCCAGAAUGGGAAGUGGGAUUCAGAUCCAUCAGGGACCAAAACCUGCAUUGAUACCAAGGA |

TABLE 1-continued

Human APP mRNA Isoform Sequences. Sequences obtained from NCBI APP gene ID: 381; Assembly GRCh38.p13 (GCF_000001405.39); NC_000021.9 (25880550 . . . 26171128, complement)

| SEQ ID NO | Isoform | mRNA Sequence |
|---|---|---|
| | | AGGCAUCCUGCAGUAUUGCCAAGAAGUCUACCCUG<br>AACUGCAGAUCACCAAUGUGGUAGAAGCCAACCAA<br>CCAGUGACCAUCCAGAACUGGUGCAAGCGGGGCCG<br>CAAGCAGUGCAAGACCCAUCCCCACUUUGUGAUUC<br>CCUACCGCUGCUUAGUUGGUGAGUUUGUAAGUGAU<br>GCCCUUCUCGUUCCUGACAAGUGCAAAUUCUUACA<br>CCAGGAGAGGAUGGAUGUUUGCGAAACUCAUCUUC<br>ACUGGCACACCGUCGCCAAAGAGACAUGCAGUGAG<br>AAGAGUACCAACUUGCAUGACUACGGCAUGUUGCU<br>GCCCUGCGGAAUUGACAAGUUCCGAGGGGUAGAGU<br>UUGUGUGUUGCCCACUGGCUGAAGAAAGUGACAAU<br>GUGGAUUCUGCUGAUGCGGAGGAGGAUGACUCGGA<br>UGUCUGGUGGGGCGGAGCAGACACAGACUAUGCAG<br>AUGGGAGUGAAGACAAAGUAGUAGAAGUAGCAGAG<br>GAGGAAGAAGUGGCUGAGGUGGAAGAAGAAGAAGC<br>CGAUGAUGACGAGGACGAUGAGGAUGGUGAUGAGG<br>UAGAGGAAGAGGCUGAGGAACCCUACGAAGAAGCC<br>ACAGAGAGAACCACCAGCAUUGCCACCACCACCAC<br>CACCACCACAGAGUCUGUGGAAGAGGUGGUUCGAG<br>UGUCCCAAAGUUUACUCAAGACUACCCAGGAACCU<br>CUUGCCCGAGAUCCUGUUAAACUUCCUACAACAGC<br>AGCCAGUACCCCUGAUGCCGUUGACAAGUAUCUCG<br>AGACACCUGGGGAUGAGAAUGAACAUGCCCAUUUC<br>CAGAAAGCCAAAGAGAGGCUUGAGGCCAAGCACCG<br>AGAGAGAAUGUCCCAGGUCAUGAGAGAAUGGGAAG<br>AGGCAGAACGUCAAGCAAAGAACUUGCCUAAAGCU<br>GAUAAGAAGGCAGUUAUCCAGCAUUUCCAGGAGAA<br>AGUGGAAUCUUUGGAACAGGAAGCAGCCAACGAGA<br>GACAGCAGCUGGUGGAGACACACAUGGCCAGAGUG<br>GAAGCCAUGCUCAAUGACCGCCGCCGCCUGGCCCU<br>GGAGAACUACAUCACCGCUCUGCAGGCUGUUCCUC<br>CUCGGCCUCGUCACGUGUUCAAUAUGCUAAAGAAG<br>UAUGUCCGCGCAGAACAGAAGGACAGACAGCACAC<br>CCUAAAGCAUUUCGAGCAUGUGCGCAUGGUGGAUC<br>CCAAGAAAGCCGCUCAGAUCCGGUCCCAGGUUAUG<br>ACACACCUCCGUGUGAUUUAUGAGCGCAUGAAUCA<br>GUCUCUCUCCCUGCUCUACAACGUGCCUGCAGUGG<br>CCGAGGAGAUUCAGGAUGAAGUUGAUGAGCUGCUU<br>CAGAAAGAGCAAAACUAUUCAGAUGACGUCUUGGC<br>CAACAUGAUUAGUGAACCAAGGAUCAGUUACGGAA<br>ACGAUGCUCUCAUGCCAUCUUUGACCGAAACGAAA<br>ACCACCGUGGAGCUCCUUCCCGUGAAUGGAGAGUU<br>CAGCCUGGACGAUCUCCAGCCGUGGCAUUCUUUUG<br>GGGCUGACUCUGUGCCAGCCAACACAGAAAACGAA<br>GUUGAGCCUGUUGAUGCCCGCCCUGCUGCCGACCG<br>AGGACUGACCACUCGACCAGGUUCUGGGUUGACAA<br>AUAUCAAGACGGAGGAGAUCUCUGAAGUGAAGAUG<br>GAUGCAGAAUUCCGACAUGACUCAGGAUAUGAAGU<br>UCAUCAUCAAAAAUUGGUGUUCUUUGCAGAAGAUG<br>UGGGUUCAAACAAAGGUGCAAUCAUUGGACUCAUG<br>GUGGGCGGUGUUGUCAUAGCGACAGUGAUCGUCAU<br>CACCUUGGUGAUGCUGAAGAAGAAACAGUACACAU<br>CCAUUCAUCAUGGUGUGGUGGAGGUUGACGCCGCU<br>GUCACCCCAGAGGAGCGCCACCUGUCCAAGAUGCA<br>GCAGAACGGCUACGAAAAUCCAACCUACAAGUUCU<br>UUGAGCAGAUGCAGAACUAGACCCCCGCCACAGCA<br>GCCUCUGAAGUUGGACAGCAAAACCAUUGCUUCAC<br>UACCCAUCGGUGUCCAUUUAUAGAAUAAUGUGGGA<br>AGAAACAAACCCGUUUUAUGAUUUACUCAUUAUCG<br>CCUUUUGACAGCUGUGCUGUAACACAAGUAGAUGC<br>CUGAACUUGAAUUAAUCCACACAUCAGUAAUGUAU<br>UCUAUCUCUCUUUACAUUUUGGUCUCUAUACUACA<br>UUAUUAAUGGGUUUUGUGUACUGUAAAGAAUUUAG<br>CUGUAUCAAACUAGUGCAUGAAUAGAUUCUCUCCU<br>GAUUAUUUAUCACAUAGCCCCUUAGCCAGUUGUAU<br>AUUAUUCUUGUGGUUUGUGACCCAAUUAAGUCCUA<br>CUUUACAUAUGCUUUAAGAAUCGAUGGGGGAUGCU<br>UCAUGUGAACGUGGGAGUUCAGCUGCUUCUCUUGC<br>CUAAGUAUUCCUUUCCUGAUCACUAUGCAUUUUAA<br>AGUUAAACAUUUUUAAGUAUUUCAGAUGCUUUAGA<br>GAGAUUUUUUUUCCAUGACUGCAUUUUACUGUACA<br>GAUUGCUGCUUCUGCUAUAUUUGUGAUAUAGGAAU<br>UAAGAGGAUACACACGUUUGUUUCUUCGUGCCUGU<br>UUUAUGUGCACACAUUAGGCAUUGAGACUUCAAGC<br>UUUUCUUUUUUUGUCCACGUAUCUUUGGGUCUUUG<br>AUAAAGAAAAGAAUCCCUGUUCAUUGUAAGCACUU<br>UUACGGGGCGGGUGGGGAGGGGUGCUCUGCUGGUC<br>UUCAAUUACCAAGAAUUCUCCAAAACAAUUUUCUG<br>CAGGAUGAUUGUACAGAAUCAUUGCUUAUGACAUG<br>AUCGCUUUCUACACUGUAUUACAUAAAUAAAUUAA<br>AUAAAAUAACCCCGGGCAAGACUUUUCUUUGAAGG<br>AUGACUACAGACAUUAAAUAAUCGAAGUAAUUUUG<br>GGUGGGGAGAAGAGGCAGAUUCAAUUUUCUUUAAC<br>CAGUCUGAAGUUUCAUUUAUGAUACAAAAGAAGAU<br>GAAAAUGGAAGUGGCAAUAUAAGGGGAUGAGGAAG<br>GCAUGCCUGGACAAACCCUUCUUUUAAGAUGUGUC<br>UUCAAUUUGUAUAAAAUGGUGUUUUCAUGUAAAUA<br>AAUACAUUCUUGGAGGAGCA |

An Abeta fragment can be formed by cleaving a portion of an APP. An enzyme can cleave the APP. The enzyme can be a gamma secretase, a beta secretase (e.g., BACE1, cathepsin B or Meprin beta), or a combination thereof. An Abeta fragment can be from about 30 to about 50 amino acids in length. An Abeta fragment can be from about 35 to about 45 amino acids in length. An Abeta fragment can be from about 38 to about 42 amino acids in length. An Abeta fragment can be from about 36 to about 42 amino acids in length. An Abeta fragment can be from about 40 to about 45 amino acids in length. An Abeta fragment can be from about 33 to about 40 amino acids in length. mRNA base editing on an APP can prevent cleavage of an Abeta fragment or substantially reduce cleavage of an Abeta fragment. An Abeta fragment can comprise at least about: 80%, 85%, 90%, 95%, 96%, 97%, 98%, or 99% sequence homology to SEQ ID NO: 14. An Abeta fragment can comprise at least about 80%, 85%, 90%, 95%, 96%, 97%, 98%, or 99% sequence homology to SEQ ID NO: 15.

```
Abeta 40-
SEQ ID NO: 14:
DAEFRHDSGYEVHHQKLVFFAEDVGSNKGAIIGLMVGGVV

Abeta 42-
SEQ ID NO. 15:
DAEFRHDSGYEVHHQKLVFFAEDVGSNKGAIIGLMVGGVVIA
```

A polynucleotide at least partially encoding an amyloid precursor protein is modified by the compositions disclosed herein (e.g., an engineered guide RNA targeting a cleavage site in APP) to produce a modified polynucleotide at least partially encoding a modified amyloid precursor protein. In some cases, the modified amyloid precursor protein has an altered susceptibility to protease cleavage relative to the amyloid precursor protein encoded by the unedited polynucleotide. In some cases, the unedited polynucleotide encodes at least a portion of the wild type sequence of amyloid precursor protein. In some cases, the unedited polynucleotide encodes at least a portion of the amyloid precursor protein sequence of SEQ ID NO: 2. In some embodiments, Abeta fragment can also comprise Abeta 1, Abeta 2, Abeta 3, Abeta 4, Abeta 5, Abeta 6, Abeta 7, Abeta 8, Abeta 9, Abeta 10, Abeta 11, Abeta 12, Abeta 13, Abeta 14, Abeta 15, Abeta 16, Abeta 17, Abeta 18, Abeta 19, Abeta 20, Abeta 21, Abeta 22, Abeta 23, Abeta 24, Abeta 25, Abeta 26, Abeta 27, Abeta 28, Abeta 29, Abeta 30, Abeta 31, Abeta 32, Abeta 33, Abeta 34, Abeta 35, Abeta 36, Abeta 37, Abeta 38, Abeta 39, Abeta 40, Abeta 41, Abeta 42, any derivatives herein or thereof, or any combinations herein and thereof. Aggregations of Abeta fragments can create Abeta or amyloid-beta plaques. Abeta or amyloid-beta plaques can comprise Abeta 1, Abeta 2, Abeta 3, Abeta 4, Abeta 5, Abeta 6, Abeta 7, Abeta 8, Abeta 9, Abeta 10, Abeta 11, Abeta 12, Abeta 13, Abeta 14, Abeta 15, Abeta 16, Abeta 17, Abeta 18, Abeta 19, Abeta 20, Abeta 21, Abeta 22, Abeta 23, Abeta 24, Abeta 25, Abeta 26, Abeta 27, Abeta 28, Abeta 29, Abeta 30, Abeta 31, Abeta 32, Abeta 33, Abeta 34, Abeta 35, Abeta 36, Abeta 37, Abeta 38, Abeta 39, Abeta 40, Abeta 41, Abeta 42, any derivatives herein or thereof, or any combinations herein and thereof. In some embodiments, an Abeta or amyloid-beta plaque can comprise one 1, 1×10^1, 1×10^2, 1×10^3, 1×10^4, 1×10^5, 1×10^6, 1×10^7, 1×10^8, 1×10^9, 1×10^10, 1×10^11, 1×10^12, 1×10^13, 1×10^14, 1×10^15, 1×10^16, 1×10^17, 1×10^18, 1×10^19, 1×10^20, 1×10^21, 1×10^22, 1×10^23, 1×10^24, 1×10^25, 1×10^26, 1×10^27, 1×10^28, 1×10^29, 1×10^30, 1×10^31, 1×10^32, 1×10^33, 1×10^34, 1×10^35, 1×10^36, 1×10^37, 1×10^38, 1×10^39, 1×10^40, 1×10^41, 1×10^42, 1×10^43, 1×10^44, 1×10^45, 1×10^46, 1×10^47, 1×10^48, 1×10^49, 1×10^50, 1×10^51, 1×10^52, 1×10^53, 1×10^54, 1×10^55, 1×10^56, 1×10^57, 1×10^58, 1×10^59, 1×10^60, 1×10^61, 1×10^62, 1×10^63, 1×10^64, 1×10^65, 1×10^66, 1×10^67, 1×10^68, 1×10^69, 1×10^70, 1×10^71, 1×10^72, 1×10^73, 1×10^74, 1×10^75, 1×10^76, 1×10^77, 1×10^78, 1×10^79, 1×10^80, 1×10^81, 1×10^82, 1×10^83, 1×10^84, 1×10^85, 1×10^86, 1×10^87, 1×10^88, 1×10^89, 1×10^90, 1×10^91, 1×10^92, 1×10^93, 1×10^94, 1×10^95, 1×10^96, 1×10^97, 1×10^98, 1×10^99, or 1×10^100 Abeta fragments or molecules. In other cases, an Abeta or amyloid-beta plaque can comprise from 1 to 1×10^1, from 9 to 1×10^2, from 0.99×10^2 to 1×10^3, from 0.99×10^3 to 1×10^4, from 0.99×10^4 to 1×10^5, from 0.99×10^5 to 1×10^6, from 0.99×10^6 to 1×10^7, from 0.99×10^7 to 1×10^8, from 0.99×10^8 to 1×10^9, from 0.99×10^9 to 1×10^10, from 0.99×10^10 to 1×10^11, from 0.99×10^11 to 1×10^12, from 0.99×10^12 to 1×10^13, from 0.99×10^13 to 1×10^14, from 0.99×10^14 to 1×10^15, from 0.99×10^15 to 1×10^16, from 0.99×10^16 to 1×10^17, from 0.99×10^17 to 1×10^18, from 0.99×10^18 to 1×10^19, from 0.99×10^19 to 1×10^20, from 0.99×10^20 to 1×10^21, from 0.99×10^21 to 1×10^22, from 0.99×10^22 to 1×10^23, from 0.99×10^23 to 1×10^24, from 0.99×10^24 to 1×10^25, from 0.99×10^25 to 1×10^26, from 0.99×10^26 to 1×10^27, from 0.99×10^27 to 1×10^28, from 0.99×10^28 to 1×10^29, from 0.99×10^29 to 1×10^30, from 0.99×10^30 to 1×10^31, from 0.99×10^31 to 1×10^32, from 0.99×10^32 to 1×10^33, from 0.99×10^33 to 1×10^34, from 0.99×10^34 to 1×10^35, from 0.99×10^35 to 1×10^36, from 0.99×10^36 to 1×10^37, from 0.99×10^37 to 1×10^38, from 0.99×10^38 to 1×10^39, from 0.99×10^39 to 1×10^40, from 0.99×10^40 to 1×10^41, from 0.99×10^41 to 1×10^42, from 0.99×10^42 to 1×10^43, from 0.99×10^43 to 1×10^44, from 0.99×10^44 to 1×10^45, from 0.99×10^45 to 1×10^46, from 0.99×10^46 to 1×10^47, from 0.99×10^47 to 1×10^48, from 0.99×10^48 to 1×10^49, from 0.99×10^49 to 1×10^50, from 0.99×10^50 to 1×10^51, from 0.99×10^51 to 1×10^52, from 0.99×10^52 to 1×10^53, from 0.99×10^53 to 1×10^54, from 0.99×10^54 to 1×10^55, from 0.99×10^55 to 1×10^56, from 0.99×10^56 to 1×10^57, from 0.99×10^57 to 1×10^58, from 0.99×10^58 to 1×10^59, from 0.99×10^59 to 1×10^60, from 0.99×10^60 to 1×10^61, from 0.99×10^61 to 1×10^62, from 0.99×10^62 to 1×10^63, from 0.99×10^63 to 1×10^64, from 0.99×10^64 to 1×10^65, from 0.99×10^65 to 1×10^66, from 0.99×10^66 to 1×10^67, from 0.99×10^67 to 1×10^68, from 0.99×10^68 to 1×10^69, from 0.99×10^69 to 1×10^70, from 0.99×10^70 to 1×10^71, from 0.99×10^71 to 1×10^72, from 0.99×10^72 to 1×10^73, from 0.99×10^73 to 1×10^74, from 0.99×10^74 to 1×10^75, from 0.99×10^75 to 1×10^76, from 0.99×10^76 to 1×10^77, from 0.99×10^77 to 1×10^78, from 0.99×10^78 to 1×10^79, from 0.99×10^79 to 1×10^80, from 0.99×10^80 to 1×10^81, from 0.99×10^81 to 1×10^82, from 0.99×10^82 to 1×10^83, from 0.99×10^83 to 1×10^84, from 0.99×10^84 to 1×10^85, from 0.99×10^85 to 1×10^86, from 0.99×10^86 to 1×10^87, from 0.99×10^87 to 1×10^88, from 0.99×10^88 to 1×10^89, from 0.99×10^89 to 1×10^90, from 0.99×10^90 to 1×10^91, from 0.99×10^91 to 1×10^92, from 0.99×10^92 to 1×10^93, from 0.99×10^93 to 1×10^94, from 0.99×10^94 to 1×10^95, from 0.99×10^95 to 1×10^96, from 0.99×10^96 to 1×10^97, from 0.99×10^97 to 1×10^98, from 0.99×10^98 to 1×10^99, or from 0.99×10^99 to 1×10^100 Abeta fragments or molecules.

In some cases, the unedited polynucleotide encodes at least a portion of an amyloid precursor protein having at least about 65%, 70%, 75%, 80%, 85%, 90%, 95%, 97%, 98%, or 99% sequence homology to SEQ ID NO: 3-13. An APP mRNA sequence can be targeted. In an embodiment, a specific residue can be targeted utilizing compositions and methods provided herein. Specific residues can comprise point mutations as compared to a wildtype sequence such as that provided in TABLE 2, FIG. 7, and FIG. 8. In some cases, any one of the 3,583 residues of the sequence may be targeted utilizing the compositions and method provided herein. In some cases, a target residue may be located among residues 1 to 100, from 99 to 200, from 199 to 300, from 299 to 400, from 399 to 500, from 499 to 600, from 599 to 700, from 699 to 800, from 799 to 900, from 899 to 1000, from 999 to 1100, from 1099 to 1200, from 1199 to 1300, from 1299 to 1400, from 1399 to 1500, from 1499 to 1600, from 1599 to 1700, from 1699 to 1800, from 1799 to 1900, from 1899 to 2000, from 1999 to 2100, from 2099 to 2200, from 2199 to 2300, from 2299 to 2400, from 2399 to 2500, from 2499 to 2600, from 2599 to 2700, from 2699 to 2800, from 2799 to 2900, from 2899 to 3000, from 2999 to 3100, from 3099 to 3200, from 3199 to 3300, from 3299 to 3400, from 3399 to 3583, or any combination thereof. A target residue may be located at residue 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, and/or 714. In some embodiments, the engineered polynucleotides disclosed herein can target a secretase enzyme cleavage site in APP and edit said cleavage site in order to modulate processing and cleavage of APP by secretase enzymes (e.g., a beta secretase such as BACE1, cathepsin B or Meprin beta). Examples of specific residues that can be targeted by engineered polynucleotide are provided in TABLE 3.

TABLE 2

Exemplary mutations that can be targeted along with the nearest cleavage site

| # | Mutation | Nearest Cleavage Site |
|---|---|---|
| 1 | K670E | BACE (β-site) |
| 2 | K670R | BACE (β-site) |
| 3 | K670G | BACE (β-site) |
| 4 | K670E + M671V | BACE (β-site) |
| 5 | K670R + M671V | BACE (β-site) |

TABLE 2-continued

| Exemplary mutations that can be targeted along with the nearest cleavage site | | |
|---|---|---|
| # | Mutation | Nearest Cleavage Site |
| 6 | K670G + M671V | BACE (β-site) |
| 7 | M671V | BACE (β-site) |
| 8 | D672G | BACE (β-site) |
| 9 | E682G | BACE (β'-site) |
| 10 | H684R | BACE (β'-site) |
| 11 | K687E | α-secretase |
| 12 | K687R | α-secretase |
| 13 | K687G | α-secretase |
| 14 (Control) | A673V | Influences BACE, known pathogenic mutation |
| 15 (Control) | A673T | Influences BACE, known protective mutation |

TABLE 3

| Exemplary residues in APP polypeptide that can be targeted | | |
|---|---|---|
| # | Amino Acid | Residue |
| 1 | K670 | 670 |
| 2 | M671 | 671 |
| 3 | D672 | 672 |
| 4 | A673 | 673 |
| 5 | E682 | 682 |
| 6 | H684 | 684 |
| 7 | K687 | 687 |
| 8 | I712 | 712 |
| 9 | T714 | 714 |

Figure 5:
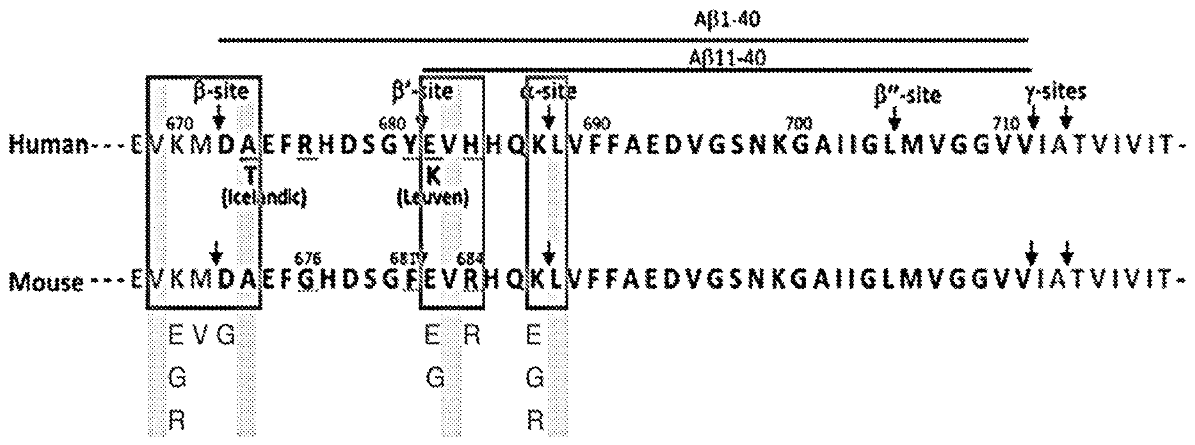
FIG. 5 shows an APP amino acid schematic carton denoting the non-limiting examples of target mutation sites in the APP protein sequence to modulate cleavage by proteases and lower production of Abeta fragments. APP contains numerous cleavage sites which are cleaved by endogenous proteases, such as beta-secretase 1 (BACE1) and alpha secretases (e.g., ADAM10). Mutations near the β-site, β'-site, and α-site as indicated in FIG. 5 were identified as amenable to editing by ADAR and were selected for further analysis. The 15 target mutations are shown in TABLE 1 below, along with the nearest cleavage site. Figure discloses SEQ ID NOS 201 and 203, respectively, in order of appearance.

In some cases, the altered susceptibility to protease cleavage comprises a reduced susceptibility by the protease. In some cases, the reduced susceptibility to protease cleavage comprises reduced susceptibility to cleavage at a position cleaved by a beta-secretase. A reduced susceptibility by the protease can be 0.001%, 0.01%, 0.1%, 1%, 10%, 20%, 30%, 40%, 50%, 60%, 70%, 80%, 90%, from 0.00099% to 0.01%, from 0.0099% to 0.1%, from 0.099% to 1%, from 0.99% to 10%, from 9.99% to 20%, from 19.99% to 30%, from 29.99% to 40%, from 39.99% to 50%, from 49.99% to 60%, from 59.99% to 70%, from 69.99% to 80%, or from 79.99% to 90%, of that of a wild-type control. A reduced susceptibility by the protease can also be 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, or 60% of that of a wild-type control. In some cases, the reduced susceptibility to protease cleavage comprises reduced susceptibility to cleavage at a position cleaved by a Beta-secretase (e.g., BACE1, cathepsin B or Meprin beta). In some cases, the reduced susceptibility to cleavage is at one or more cleavage sites of the amyloid precursor protein. In some cases, the reduced susceptibility to cleavage is at the β-site or the β'-site of the amyloid precursor protein as indicated in FIG. 5. In some cases, the reduced susceptibility to cleavage is at the β-site. For example, upon administration of an engineered guide RNA of the present disclosure, the engineered guide RNA results in ADAR-mediated editing of the β cleavage site in APP, resulting in reduced cleavage of APP by a Beta-secretase (e.g., BACE1, cathepsin B or Meprin beta) at the β cleavage site.

In some cases, the altered susceptibility to protease cleavage comprises an enhanced susceptibility. An enhanced susceptibility by the protease can be 1-fold, at least 2-fold, at least 3-fold, at least 4-fold, at least 5-fold, at least 6-fold, at least 7-fold, at least 8-fold, at least 9-fold, at least 10-fold, at least 11-fold, at least 12-fold, at least 13-fold, at least 14-fold, at least 15-fold, at least 16-fold, at least 17-fold, at least 18-fold, at least 19-fold, at least 20-fold, at least 21-fold, at least 22-fold, at least 23-fold, at least 24-fold, at least 25-fold, at least 26-fold, at least 27-fold, at least 28-fold, at least 29-fold, at least 30-fold, at least 31-fold, at least 32-fold, at least 33-fold, at least 34-fold, at least 35-fold, at least 36-fold, at least 37-fold, at least 38-fold, at least 39-fold, at least 40-fold, at least 41-fold, at least 42-fold, at least 43-fold, at least 44-fold, at least 45-fold, at least 46-fold, at least 47-fold, at least 48-fold, at least 49-fold, at least 50-fold, at least 51-fold, at least 52-fold, at least 53-fold, at least 54-fold, at least 55-fold, at least 56-fold, at least 57-fold, at least 58-fold, at least 59-fold, at least 60-fold, at least 61-fold, at least 62-fold, at least 63-fold, at least 64-fold, at least 65-fold, at least 66-fold, at least 67-fold, at least 68-fold, at least 69-fold, at least 70-fold, at least 71-fold, at least 72-fold, at least 73-fold, at least 74-fold, at least 75-fold, at least 76-fold, at least 77-fold, at least 78-fold, at least 79-fold, at least 80-fold, at least 81-fold, at least 82-fold, at least 83-fold, at least 84-fold, at least 85-fold, at least 86-fold, at least 87-fold, at least 88-fold, at least 89-fold, at least 90-fold, at least 91-fold, at least 92-fold, at least 93-fold, at least 94-fold, at least 95-fold, at least 96-fold, at least 97-fold, at least 98-fold, at least 99-fold, at least 100-fold, 1-20-fold, 2-21-fold, 3-22-fold, 4-23-fold, 5-24-fold, 6-25-fold, 7-26-fold, 8-27-fold, 9-28-fold, 10-29-fold, 11-30-fold, 12-31-fold, 13-32-fold, 14-33-fold, 15-34-fold, 16-35-fold, 17-36-fold, 18-37-fold, 19-38-fold, 20-39-fold, 21-40-fold, 22-41-fold, 23-42-fold, 24-43 fold, 25-44-fold, 26-45-fold, 27-46-fold, 28-47-fold, 29-48-fold, 30-49-fold, 31-50-fold, 32-51-fold, 33-52-fold, 34-53-fold, 35-54-fold, 36-55-fold, 37-56-fold, 38-57-fold, 39-58-fold, 40-59-fold, 41-60-fold, 42-61-fold, 43-62-fold, 44-63-fold, 45-64-fold, 46-65-fold, 47-66-fold, 48-67-fold, 49-68-fold, 50-69-fold, 51-70-fold, 52-71-fold, 53-72-fold, 54-73-fold, 55-74-fold, 56-75-fold, 57-76-fold, 58-77-fold, 59-78-fold, 60-79-fold, 61-80-fold, 62-81-fold, 63-82-fold, 64-83-fold, 65-84-fold, 66-85-fold, 67-86-fold, 68-87-fold, 69-88-fold, 70-89-fold, 71-90-fold, 72-91-fold, 73-92-fold, 74-93-fold, 75-94-fold, 76-95-fold, 77-96-fold, 78-97-fold, 79-98-fold, 80-99-fold, or 81-100-fold of that of a wild-type control. In some cases, the enhanced susceptibility to protease cleavage comprises enhanced susceptibility to cleavage at a position cleaved by an α-secretase or γ-secretase. In some cases, the enhanced susceptibility to cleavage is at an α-site of the amyloid precursor protein as indicated in FIG. 5.

In some cases, the altered susceptibility to protease cleavage comprises a reduced susceptibility to cleavage at one cleavage site (e.g., the β-site or the β'-site) and an enhanced susceptibility to cleavage at another cleavage site (e.g., the α-site), wherein the β-site, the β'-site, and the α-site are as indicated in FIG. 5. As such, engineered polynucleotides of the present disclosure may target a β-site to decrease Beta-secretase (e.g., BACE1, cathepsin B or Meprin beta) cleavage. Additionally, or alternatively, engineered polynucleotides of the present disclosure may target an α-site to increase cleavage by an alpha secretase, thereby indirectly reducing Beta-secretase (e.g., BACE1, cathepsin B or Meprin beta) cleavage. Compositions with more than one engineered polynucleotides targeting the α-site and the β-site are contemplated, thereby allowing for multiplexed therapies. In some cases, the modified amyloid precursor protein contains multiple amino acid substitutions. In some cases, the multiple amino acid substitutions are in proximity to different cleavage sites. Proximity or in proximity can mean being separated by at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, or 500 nucleotides.

In some embodiments, the engineered polynucleotides disclosed herein can target a secretase enzyme cleavage site in APP and edit said cleavage site in order to modulate processing and cleavage of APP by secretase enzymes (e.g., a beta secretase such as BACE1, cathepsin B or Meprin beta). In some cases, the modified amyloid precursor protein comprises a substitution of an amino acid compared to the unedited amyloid precursor protein. The present disclosure provides engineered guide RNAs that target and mediate substitution of the amino acid in the modified APP as compared to unedited APP. Such substitutions are made via ADAR-mediated RNA editing using the disclosed engineered guide RNAs. In some cases, the substitution is at a position in proximity to a cleavage site of the amyloid precursor protein. In some cases, the substitution is at a position up to 2, 3, 4, 5, 6, 7, 8, 9, or 10 amino acids away from the cleavage site. In some cases, the substitution is at a position up to 5 amino acids away from the cleavage site. In some cases, the substitution is at a position up to 3 amino acids away from the cleavage site. In some cases, the substitution is at a position up to 2 amino acids away from the cleavage site. In some cases, the substitution is at the same amino acid position as the cleavage site. In some cases, the substitution is at a position up to 5, 10, 15, 20, or 25 angstroms from the cleavage site. In some cases, the distance from the cleavage site is measured in a folded amyloid precursor protein. In some cases, the cleavage site is the β-site. In some cases, the cleavage site is the β'-site. In some cases, the cleavage site is the α-site. In some cases, the cleavage site is a γ-site. In some cases, the cleavage site is a β-site, β'-site, α-site, γ-site, or any combination thereof. An engineered guide polynucleotide of the present disclosure may facilitate editing of a β-site, β'-site, α-site, γ-site, or any combination thereof by ADAR-mediated editing of an mRNA (pre-mRNA or mRNA) encoding an Abeta polypeptide, wherein the substitution of an amino acid affected by the editing is up to 2, 3, 4, 5, 6, 7, 8, 9, or 10 amino acids from the β-site, β'-site, α-site, γ-site, or any combination thereof.

In some cases, the substitution in the amino acid comprises a substitution that results in a change in charge, hydrophobicity, or polarity of the amino acid, or any combination thereof. In some cases, the substitution in the amino acid comprises a substitution that results in a change in charge of the amino acid. In some cases, the change in charge is from positive to negative, negative to positive, neutral to positive, or neutral to negative. In some cases, the substitution in the amino acid comprises a conservative substitution. In some cases, the substitution in the amino acid comprises a charge neutral substitution. In some cases, the substitution in the amino acid comprises a radical substitution. In some cases, the change in the amino acid comprises a K to E change, a K to R change, a K to G change, an M to V change, a D to G change, an E to G change, an H to R change, or any combination thereof.

In some cases, the substitution in the amino acid is at a position corresponding to position 670, 671, 672, 673, 682, 684, 687, 712, or 714 of the amyloid precursor protein. In some cases, the substitution in the amino acid is at a position corresponding to position 670, 671, 672, 673, 682, 684, 687, 712, or 714 of a polynucleotide sequence encoding for the amyloid precursor protein. In some cases, the substitution in the amino acid is at a position corresponding to position 670, 671, 672, 673, 682, 684, 687, 712, or 714 of the amyloid precursor protein of SEQ ID NO: 2. In some cases, the substitution in the amino acid is at a position corresponding to position 670, 671, 672, 673, 682, 684, 687, 712, or 714 of the amyloid precursor protein of SEQ ID NO: 2 as determined by a Smith-Waterman alignment algorithm. In some cases, the substitution is at a position corresponding to position 670 or 671 of a polynucleotide sequence encoding for an amyloid precursor protein. In some cases, modified amyloid precursor protein comprises a substitution corresponding to position 670 and 671 of a polynucleotide sequence encoding for an amyloid precursor protein. In some cases, the substitution is at a position corresponding to position 670 of a polynucleotide sequence encoding for an amyloid precursor protein. In some cases, the substitution is at a position corresponding to position 671 of a polynucleotide sequence encoding for an amyloid precursor protein.

In some cases, the modified amyloid precursor protein comprises multiple amino acid substitutions. In some cases, the modified amyloid precursor protein comprises an amino acid substitution at a position corresponding to position 670 or 671 of a polynucleotide sequence encoding for the amyloid precursor protein and an additional substitution. In some cases, the modified amyloid precursor protein comprises an amino acid substitution at a position corresponding to position 670 and 671 of a polynucleotide sequence encoding for the amyloid precursor protein and an additional substitution. In some cases, the modified amyloid precursor protein comprises an amino acid substitution at a position corresponding to position 670 of a polynucleotide sequence encoding for the amyloid precursor protein and an additional substitution. In some cases, the modified amyloid precursor protein comprises an amino acid substitution at a position corresponding to position 671 of a polynucleotide sequence encoding for the amyloid precursor protein and an additional substitution. In some cases, the additional amino acid substitution is at a position corresponding to, 670, 671, 672, 673, 682, 684, 687, 712, or 714 of a polynucleotide sequence encoding for the amyloid precursor protein.

In some cases, the amino acid substitution of the modified polynucleotide sequence encoding for amyloid precursor protein comprises K670E, K670R, K670G, M671V, D672G, E682G, H684R, K687R, K687E, or K687G, wherein the position is determined by comparing the sequence of the modified amyloid precursor protein to the amyloid precursor protein of SEQ ID NO: 2 as determined by a Smith-Waterman alignment algorithm. In some cases, the amyloid precursor protein is the amyloid precursor protein of SEQ ID NO: 2. In some cases, the amino acid substitution comprises K670G or M671V. In some cases, the amino acid substitution comprises K670G. In some cases, the amino acid substitution comprises M671V.

In some cases, the engineered guide RNA facilitates an edit in a polynucleotide at least partially encoding for amyloid precursor protein. In some cases, the engineered guide RNA is at least partially complementary to at least a portion of the polynucleotide. In some cases, at least a portion of the engineered polynucleotide forms an at least partially double-stranded oligonucleotide with the targeted polynucleotide/RNA. This at least partially double-stranded oligonucleotide may also be referred to as a double-stranded RNA (dsRNA) substrate. For example, the engineered guide RNA may have a sequence that hybridizes to a sequence of the polynucleotide encoding for APP. The double-stranded oligonucleotide or dsRNA substrate refers to the sequence and structure formed upon hybridization of the sequence of the engineered guide RNA to the sequence of the polynucleotide encoding for APP. The double stranded oligonucleotide may comprise a single base mismatch between the sequence of the polynucleotide and the corresponding sequence of the engineered guide RNA. The single base mismatch may be at the target base to be edited, for example the adenosine in the target polynucleotide to be edited by an RNA editing protein. In some cases, the engineered guide RNA associates with an editing protein (e.g., an RNA editing protein such as ADAR). In some cases, the editing protein in association with the at least partially double-stranded oligonucleotide is capable of recruiting the editing protein. The RNA editing protein (e.g., ADAR) may comprise one or two polypeptide chains. Two polypeptide chains may be identical. Two polypeptide chains may not be identical. Two ADAR polypeptide chains may form a homodimer. Two ADAR polypeptide chains may form a heterodimer. Upon formation of the at least partially double stranded oligonucleotide, a first monomer (one of the polypeptide chains) of the homodimer or heterodimer may associate with the at least partially double stranded oligonucleotide followed by a second monomer (the other polypeptide chain) of the homodimer or heterodimer. In some embodiments, a preformed homodimer or heterodimer associate with the at least partially double stranded oligonucleotide. In some cases, a monomer of ADAR may associate with the at least partially double stranded oligonucleotide. In other cases, a first monomer and a second monomer may bind the at least partially double stranded oligonucleotide independently. Upon binding to the at least partially double stranded oligonucleotide, the first and second monomer may form a homodimer or a heterodimer. In some cases, the editing protein, once bound to an engineered polynucleotide provided herein, modifies a base of a nucleotide in the targeted polynucleotide/RNA. In particular, the editing protein is an RNA editing protein and modifies an RNA base of an RNA nucleotide in a target RNA. In some cases, modifying the base produces a modified polynucleotide at least partially encoding the modified amyloid precursor protein.

In some cases, the engineered guide RNAs disclosed herein facilitate editing (e.g., via ADAR) of a base of a nucleotide comprised in a codon which encodes an amino acid in proximity to a secretase cleavage site of the amyloid precursor protein. The amino acid in proximity to the secretase cleavage site of the amyloid precursor protein can be any of the amino acids provided herein. In some cases, the base of the nucleotide is comprised in a codon which encodes an amino acid in proximity to: an alpha-secretase cleavage site, a beta-secretase cleavage site (e.g., a ®- or ®'-cleavage site), or a gamma-secretase cleavage site of the amyloid precursor protein, or any combination thereof. In some embodiments, the base of the nucleotide is comprised in a codon which encodes an amino acid in proximity to the ®- or ®'-cleavage site. In some cases, the engineered guide RNAs disclosed herein facilitate editing (e.g., via ADAR) of a base of a nucleotide comprised in a codon which encodes an amino acid in proximity to a position corresponding to position 670, 671, 672, 673, 682, 684, 687, 712, or 714 of a sequence encoding for an amyloid precursor. In some cases, the engineered guide RNAs disclosed herein facilitate editing (e.g., via ADAR) of a base of a nucleotide comprised in a codon which encodes an amino acid in proximity to a position corresponding to position 670, 671, 672, 673, 682, 684, 687, 712, or 714 of the amyloid precursor protein of SEQ ID NO: 2, as determined by a Smith-Waterman alignment algorithm. In some cases, the base of the nucleotide is comprised in a codon which encodes an amino acid at a position corresponding to position 670, 671, 672, 673, 682, 684, 687, 712, or 714 of the amyloid precursor protein of SEQ ID NO: 2 as determined by a Smith-Waterman alignment algorithm. The base of the nucleotide may be comprised in a codon encoding an amino acid at a position corresponding to position 670 of the amyloid precursor protein of SEQ ID NO: 2, as determined by a Smith-Waterman alignment algorithm. The base of the nucleotide may be comprised in a codon encoding an amino acid at a position corresponding to position 671 of the amyloid precursor protein of SEQ ID NO: 2, as determined by a Smith-Waterman alignment algorithm. In some cases, modifying the base of the nucleotide results in a change in the amino acid sequence of the modified amyloid precursor protein translated from the modified RNA as compared to an amyloid precursor protein translated from the unedited RNA. The change in the amino acid can be any of the amino acid substitutions provided herein.

In some cases, the editing protein in association with the engineered guide RNA and the polynucleotide modifies a second base on a second nucleotide of the polynucleotide. In some embodiments, the first and second nucleotide can belong to the same codon. In some cases, the first and second nucleotide can belong to two different codons. In some instances, the first nucleotide and the second nucleotide are consecutive.

In some cases, the engineered guide RNAs of the present disclosure modify a polynucleotide encoding for APP via an RNA editing protein (e.g., ADAR). Said modification of the base of a nucleotide in a sequence of the polynucleotide is a chemical modification. In some cases, the chemical modification is a deamination. In some cases, the modification results in the cell's translational machinery reading the original, unedited base as a different base. In some cases, the base is an adenosine. In some cases, the base is an adenosine and the engineered guide RNAs of the present disclosure facilitate modification of the adenosine to inosine. In some cases, the base is an adenosine and the engineered guide RNAs of the present disclosure recruit ADAR, which modifies the adenosine to inosine.

In some cases, the polynucleotide at least partially encoding the amyloid precursor protein is mRNA or pre-mRNA. In some cases, the polynucleotide is mRNA. In some cases, the polynucleotide is pre-mRNA. In some cases, the polynucleotide at least partially encoding the amyloid precursor protein is DNA. The engineered guide RNAs of the present disclosure, thus, may facilitate editing of mRNA or pre-mRNA by recruiting an RNA editing protein such as ADAR to the mRNA or the pre-mRNA and modifying adenosines to inosines. The engineered guide RNAs of the present disclosure, thus, may facilitate editing of mRNA by recruiting an RNA editing protein such as ADAR to the mRNA and modifying adenosines to inosines. The engineered guide RNAs of the present disclosure, thus, may facilitate editing of pre-mRNA by recruiting an RNA editing protein such as ADAR to the pre-mRNA and modifying adenosines to inosines.

In some cases, the modified amyloid precursor protein encoded by the modified polynucleotide as facilitated by the engineered guide RNA does not otherwise inhibit protease cleavage of other substrates even as proteases have less activity on the modified amyloid precursor protein compared to the unedited amyloid precursor protein. For example, while engineered guide RNAs of the present disclosure may facilitate an edit in APP resulting in reduced cleavage at the Beta-secretase (e.g., BACE1, cathepsin B or Meprin beta) cleavage site cleavage site within APP, Beta-secretase (e.g., BACE1, cathepsin B or Meprin beta) cleaving activity may not be diminished on other endogenous targets of a Beta-secretase (e.g., BACE1, cathepsin B or Meprin beta). This can be measured by ascertaining the amount of cleavage metabolites of other such endogenous targets of a Beta-secretase (e.g., BACE1, cathepsin B or Meprin beta) in a) a cell expressing the modified amyloid precursor protein, and b) a cell expressing the unedited amyloid precursor protein and comparing the values. The values can optionally be normalized to expression of the endogenous protein in each cell, or to another suitable marker. Measurement of the other endogenous targets of a Beta-secretase (e.g., BACE1, cathepsin B or Meprin beta) and cleavage metabolites can be performed by a variety of in vitro assays, including without limitation enzyme-linked immunosorbent assays (ELISAs) or mass spectrometry techniques, such as LC-MS or MALDI. Non-limiting examples of other endogenous targets of a Beta-secretase, which can be suitable for measurement of metabolites indicative of protease activity amyloid-like protein 1 (APLP1), amyloid-like protein 2 (APLP2), Contactin 2, Jagged 1, neural cell adhesion molecule L1 (CHL1), Neurexin 1α, Neurexin 3β, neuregulin 1 (NRG1), seizure related protein 6 (SEZ6), seizure related protein 6 precursor protein (SEZ6L), a 13 (131-4) Auxiliary subunit of the voltage-gated sodium ion channel (VGSC) subtype Nav1, VGSC Accessory Subunits KCNE1 or KCNE2, a functional portion of any of these, or any combination of thereof. In some cases, the endogenous substrate examined to determine the extent to which beta secretase activity has been inhibited is NRG1, SEZ6, or CHL1.

In some cases, the engineered guide RNA capable of facilitating a modification on a base of a nucleotide comprised in a polynucleotide encoding at least a portion of the amyloid precursor protein produces a modified amyloid precursor protein comprising at least one amino acid substitution compared to an unedited polynucleotide. In some cases, the modified amyloid precursor protein (containing modifications of the cleavage site cleavage site) produces a lower amount of Abeta 40, Abeta 42 when cleaved by a Beta-secretase (e.g., BACE1, cathepsin B or Meprin beta), or both when expressed in a cell compared to a corresponding cell expressing the unedited amyloid precursor protein for a comparable period of time. In some cases, the amount of Abeta 40, Abeta 42, or both is measured by an Abeta 40 or Abeta 42 ELISA, or both. In some cases, the modified amyloid precursor protein produces an increased amount of secreted ectodomain APP alpha (sAPPa) when expressed in a cell compared to the unedited amyloid precursor protein for a comparable period of time. In some cases, the amount of sAPPa or the beta-COOH-terminal fragment is measured by a sAPPa ELISA. In some cases, amounts of Abeta 40, Abeta 42, or both, and amounts of sAPPa are measured. The engineered guide RNAs of the present disclosure may be used to facilitate an edit at a Beta-secretase (e.g., BACE1, cathepsin B or Meprin beta) cleavage site in APP, resulting in a decreased production of Abeta 40 and Abeta42 metabolites. In some embodiments, the engineered guide RNAs and methods of using said engineered guide RNAs disclosed herein can result in at least 1-fold, at least 2-fold, at least 3-fold, at least 4-fold, at least 5-fold, at least 6-fold, at least 7-fold, at least 8-fold, at least 9-fold, at least 10-fold, at least 11-fold, at least 12-fold, at least 13-fold, at least 14-fold, at least 15-fold, at least 16-fold, at least 17-fold, at least 18-fold, at least 19-fold, at least 20-fold, at least 21-fold, at least 22-fold, at least 23-fold, at least 24-fold, at least 25-fold, at least 26-fold, at least 27-fold, at least 28-fold, at least 29-fold, at least 30-fold, at least 31-fold, at least 32-fold, at least 33-fold, at least 34-fold, at least 35-fold, at least 36-fold, at least 37-fold, at least 38-fold, at least 39-fold, at least 40-fold, at least 41-fold, at least 42-fold, at least 43-fold, at least 44-fold, at least 45-fold, at least 46-fold, at least 47-fold, at least 48-fold, at least 49-fold, at least 50-fold, at least 51-fold, at least 52-fold, at least 53-fold, at least 54-fold, at least 55-fold, at least 56-fold, at least 57-fold, at least 58-fold, at least 59-fold, at least 60-fold, at least 61-fold, at least 62-fold, at least 63-fold, at least 64-fold, at least 65-fold, at least 66-fold, at least 67-fold, at least 68-fold, at least 69-fold, at least 70-fold, at least 71-fold, at least 72-fold, at least 73-fold, at least 74-fold, at least 75-fold, at least 76-fold, at least 77-fold, at least 78-fold, at least 79-fold, at least 80-fold, at least 81-fold, at least 82-fold, at least 83-fold, at least 84-fold, at least 85-fold, at least 86-fold, at least 87-fold, at least 88-fold, at least 89-fold, at least 90-fold, at least 91-fold, at least 92-fold, at least 93-fold, at least 94-fold, at least 95-fold, at least 96-fold, at least 97-fold, at least 98-fold, at least 99-fold, at least 100-fold, 1-20-fold, 2-21-fold, 3-22-fold, 4-23-fold, 5-24-fold, 6-25-fold, 7-26-fold, 8-27-fold, 9-28-fold, 10-29-fold, 11-30-fold, 12-31-fold, 13- 32-fold, 14-33-fold, 15-34-fold, 16-35-fold, 17-36-fold, 18-37-fold, 19-38-fold, 20-39-fold, 21-40-fold, 22-41-fold, 23-42-fold, 24-43 fold, 25-44-fold, 26-45-fold, 27-46-fold, 28-47-fold, 29-48-fold, 30-49-fold, 31-50-fold, 32-51-fold, 33-52-fold, 34-53-fold, 35-54-fold, 36-55-fold, 37-56-fold, 38-57-fold, 39-58-fold, 40-59-fold, 41-60-fold, 42-61-fold, 43-62-fold, 44-63-fold, 45-64-fold, 46-65-fold, 47-66-fold, 48-67-fold, 49-68-fold, 50-69-fold, 51-70-fold, 52-71-fold, 53-72-fold, 54-73-fold, 55-74-fold, 56-75-fold, 57-76-fold, 58-77-fold, 59-78-fold, 60-79-fold, 61-80-fold, 62-81-fold, 63-82-fold, 64-83-fold, 65-84-fold, 66-85-fold, 67-86-fold, 68-87-fold, 69-88-fold, 70-89-fold, 71-90-fold, 72-91-fold, 73-92-fold, 74-93-fold, 75-94-fold, 76-95-fold, 77-96-fold, 78-97-fold, 79-98-fold, 80-99-fold, or 81-100-fold decrease in the protein level of Abeta 40, 42, or both, as compared to that generated upon Beta-secretase (e.g., BACE1, cathepsin B or Meprin beta) cleavage of unedited APP.

Methods of mRNA base editing can result in at least partially reducing an amount of peptide bond cleavage of a protein (such as APP). Methods can include altering a cleavage site, such as a BACE cleavage site, including the ®-site, the ®'-site, or a combination thereof. Methods can include altering BACE-mediated degradation of APP. A reduced amount of peptide bond cleavage can be adjacent to an alanine, a cysteine, an aspartic acid, a glutamic acid, a phenylalanine, a glycine, a histidine, an isoleucine, a lysine, a leucine, a methionine, an asparagine, a proline, a glutamine, an arginine, a serine, a threonine, a tryptophan, a tyrosine, or a valine or the protein. The reduced amount of peptide bond cleavage can be adjacent to a methionine or an aspartate of the protein.

Methods to monitor the efficacy of the engineered nucleotide targeting APP can comprise in vitro demonstration of molecular efficiency in APP base editing, reduction in Abeta 1, Abeta 2, Abeta 3, Abeta 4, Abeta 5, Abeta 6, Abeta 7, Abeta 8, Abeta 9, Abeta 10, Abeta 11, Abeta 12, Abeta 13, Abeta 14, Abeta 15, Abeta 16, Abeta 17, Abeta 18, Abeta 19, Abeta 20, Abeta 21, Abeta 22, Abeta 23, Abeta 24, Abeta 25, Abeta 26, Abeta 27, Abeta 28, Abeta 29, Abeta 30, Abeta 31, Abeta 32, Abeta 33, Abeta 34, Abeta 35, Abeta 36, Abeta 37, Abeta 38, Abeta 39, Abeta 40, Abeta 41, Abeta 42 production using cells naturally expressing sufficient levels of APP, model cell lines where APP is knocked out, cells transfected with WT APP, or other cell types including, but not limited to human neuroblastoma cells, human iPSCs and derived cell types, human neural progenitor cells and derived cell types, LUHMES cells, NTera-2 cells, and/or primary cells cultured from mice containing a humanized APP sequence. Model cell lines include, but are not limited to, 293 cells, COS cells, HeLa cells, Vero cells, 3T3 mouse fibroblasts, C3H10T1/2 fibroblasts, CHO cells, and the like. Exemplary host cells include, without limitation, HeLa cells (e.g., American Type Culture Collection (ATCC) No. CCL-2), CHO cells (e.g., ATCC Nos. CRL9618, CCL61, CRL9096), 293 cells (e.g., ATCC No. CRL-1573), Vero cells, NIH 3T3 cells (e.g., ATCC No. CRL-1658), Huh-7 cells, BHK cells (e.g., ATCC No. CCL10), PC12 cells (ATCC No. CRL1721), COS cells, COS-7 cells (ATCC No. CRL1651), RAT1 cells, mouse L cells (ATCC No. CCLI.3), human embryonic kidney (HEK) cells (ATCC No. CRL1573), HLHepG2 cells, and the like.

Abeta oligomers can initiate pathogenesis in Alzheimer's disease, however, their suppression cannot be sufficient to reduce disease progression. Targeting insoluble Abeta and Abeta aggregates can ignore the toxicity of soluble Abeta and/or C-terminal fragments, which can be highly toxic as well. Expectations of an effect with only Abeta reduction can ignore other identified pathogenic drivers (e.g., p-Tau, alpha-synuclein).

In some embodiments, the editing of a base of the APP mRNA results in a decreased gene translation of the APP polypeptide. In other cases, the editing of a base of the 5'UTR of the APP mRNA results in a decreased gene translation of the APP polypeptide. The decreased gene translation of the APP polypeptide can be measure by an in vitro assay. Such in vitro assay can comprise an in vitro translation assay. An in vitro translation assay can comprise a cell extract. A cell extract can comprise rabbit reticulocyte lysate, wheat germ extract, insect cells, yeast *Kluyveromyces*, or *E. coli* cell-free extract. An in vitro translation assay can comprise mixing a cell extract with a nucleic acid template, ATP, and amino acids. A nucleic acid template can comprise a mRNA template or a cDNA template. A nucleic acid template can comprise a mRNA sequence listed in TABLE 1 or 13. A nucleic acid template can comprise a cDNA sequence complementary to the mRNA sequence listed in TABLE 1 or 13. When using an in vitro translation system with a cDNA template, the cDNA can be converted to a mRNA by in vitro transcription. A cDNA can be maintained in a circular vector. A cDNA can be maintained as a linear sequence.

Therefore, a multi-targeted combination therapy, such as described in the compositions and methods herein, can provide the necessary disease modification in Alzheimer's disease.

Tau

Tau proteins (Tau-p) are encoded by six mRNA isoforms of Tau MAPT. Tau-p is a microtubule-binding protein, important for microtubule stability and transport. It is primarily expressed in the neurons of the CNS. The aggregation of hyperphosphorylated mutant Tau proteins into neurofibrillary tangles (NFTs) in the human brain causes a group of neurodegenerative diseases named Tauopathies, including Alzheimer's Disease. Proteolytic Tau cleavage fragments (that can be formed by calpain-mediated proteolysis, activated downstream of Abeta production) can also be directly neurotoxic. Therefore, a multiplex strategy to substantially reduce Tau formation can be important in effectively treating neurodegenerative diseases.

In an embodiment, a specific residue can be targeted utilizing compositions and methods provided herein. Complete Tau mRNA sequence are shown in TABLE 4. In some cases, a target residue can be any one position of the 6,644 residues of the sequence may be targeted utilizing the compositions and method provided herein. In some cases, a target residue may be located among residues from 1 to 100, from 99 to 200, from 199 to 300, from 299 to 400, from 399 to 500, from 499 to 600, from 599 to 700, from 699 to 800, from 799 to 900, from 899 to 1000, from 999 to 1100, from 1099 to 1200, from 1199 to 1300, from 1299 to 1400, from 1399 to 1500, from 1499 to 1600, from 1599 to 1700, from 1699 to 1800, from 1799 to 1900, from 1899 to 2000, from 1999 to 2100, from 2099 to 2200, from 2199 to 2300, from 2299 to 2400, from 2399 to 2500, from 2499 to 2600, from 2599 to 2700, from 2699 to 2800, from 2799 to 2900, from 2899 to 3000, from 2999 to 3100, from 3099 to 3200, from 3199 to 3300, from 3299 to 3400, from 3399 to 3500, from 3499 to 3600, from 3599 to 3700, from 3699 to 3800, from 3799 to 3900, from 3899 to 4000, from 3999 to 4100, from 4099 to 4200, from 4199 to 4300, from 4299 to 4400, from 4399 to 4500, from 4499 to 4600, from 4599 to 4700, from 4699 to 4800, from 4799 to 4900, from 4899 to 5000, from 4999 to 5100, from 5099 to 5200, from 5199 to 5300, from 5299 to 5400, from 5399 to 5500, from 5499 to 5600, from 5599 to 5700, from 5699 to 5800, from 5799 to 5900, from 5899 to 6000, from 5999 to 6100, from 6099 to 6200, from 6199 to 6300, from 6299 to 6400, from 6399 to 6444, or any combination thereof of the Tau mRNA.

TABLE 4

Human MAPT mRNA Isoform Sequences. Sequences obtained from NCBI MAPT gene ID: 4137; Assembly GRCh38.p13 (GCF_000001405.39); NC_000017.11 (45894538 . . . 46028334)

| SEQ ID NO | Isoform | mRNA Sequence |
|---|---|---|
| 16 | 1 | GCAGUCACCGCCACCCACCAGCUCCGGCACCAACAGCAGCGCCGCUG<br>CCACCGCCCACCUUCUGCCGCCGCCACCACAGCCACCUUCUCCUCCU<br>CCGCUGUCCUCUCCCGUCCUCGCCUCUGUCGACUAUCAGGUGAACU<br>UUGAACCAGGAUGGCUGAGCCCCGCCAGGAGUUCGAAGUGAUGGAA<br>GAUCACGCUGGGACGUACGGGUUGGGGGACAGGAAAGAUCAGGGG<br>GGCUACACCAUGCACCAAGACCAAGAGGGUGACACGGACGCUGGCC<br>UGAAAGAAUCUCCCCUGCAGACCCCCACUGAGGACGGAUCUGAGGA<br>ACCGGGCUCUGAAACCUCUGAUGCUAAGAGCACUCCAACAGCGGAA<br>GAUGUGACAGCACCCUUAGUGGAUGAGGGAGCUCCCGGCAAGCAGG<br>CUGCCGCGCAGCCCCACACGGAGAUCCCAGAAGGAACCACAGCUGA<br>AGAAGCAGGCAUUGGAGACACCCCCAGCCUGGAAGACGAAGCUGCU<br>GGUCACGUGACCCAAGAGCCUGAAAGUGGUAAGGUGGUCCAGGAAG<br>GCUUCCUCCGAGAGCCAGGCCCCCCAGGUCUGAGCCACCAGCUCAU<br>GUCCGGCAUGCCUGGGGCUCCCCUCCUGCCUGAGGGCCCCAGAGAG<br>GCCACACGCCAACCUUCGGGGACAGGACCUGAGGACACAGAGGGCG<br>GCCGCCACGCCCCUGAGCUGCUCAAGCACCAGCUUCUAGGAGACCU<br>GCACCAGGAGGGGCCGCCGCUGAAGGGGGCAGGGGGCAAAGAGAGG<br>CCGGGGAGCAAGGAGGAGGUGGAUGAAGACCGCGACGUCGAUGAGU<br>CCUCCCCCCAAGACUCCCCUCCCUCCAAGGCCUCCCCAGCCCAAGAU<br>GGGCGGCCUCCCCAGACAGCCGCCAGAGAAGCCACCAGCAUCCCAG<br>GCUUCCCAGCGGAGGGUGCCAUCCCCCUCCCUGUGGAUUUCCUCUC<br>CAAAGUUUCCACAGAGAUCCCAGCCUCAGAGCCCGACGGGCCCAGU<br>GUAGGGCGGGCCAAAGGGCAGGAUGCCCCCCUGGAGUUCACGUUUC<br>ACGUGGAAAUCACACCCAACGUGCAGAAGGAGCAGGCGCACUCGGA<br>GGAGCAUUUGGGAAGGGCUGCAUUUCCAGGGGCCCCUGGAGAGGGG<br>CCAGAGGCCCGGGGCCCCUCUUUGGGAGAGGACACAAAAGAGGCUG<br>ACCUUCCAGAGCCCUCUGAAAAGCAGCCUGCUGCUGCUCCGCGGGG<br>GAAGCCCGUCAGCCGGGUCCCUCAACUCAAAGCUCGCAUGGUCAGU<br>AAAAGCAAAGACGGGACUGGAAGCGAUGACAAAAAAGCCAAGACAU<br>CCACACGUUCCUCUGCUAAAACCUUGAAAAAUAGGCCUUGCCUUAG<br>CCCCAAACACCCCACUCCUGGUAGCUCAGACCCUCUGAUCCAACCCU<br>CCAGCCCUGCUGUGUGCCCAGAGCCACCUUCCUCUCCUAAAUACGU<br>CUCUUCUGUCACUUCCCGAACUGGCAGUUCUGGAGCAAAGGAGAUG<br>AAACUCAAGGGGGCUGAUGGUAAAACGAAGAUCGCCACACCGCGGG<br>GAGCAGCCCCUCCAGGCCAGAAGGGCCAGGCCAACGCCACCAGGAU<br>UCCAGCAAAAACCCCGCCCGCUCCAAAGACACCACCCAGCUCUGGUG<br>AACCUCCAAAAUCAGGGGAUCGCAGCGGCUACAGCAGCCCCGGCUC<br>CCCAGGCACUCCCGGCAGCCGCUCCCGCACCCCGUCCCUUCCAACCC<br>CACCCACCCGGGAGCCCAAGAAGGUGGCAGUGGUCCGUACUCCACC<br>CAAGUCGCCGUCUUCCGCCAAGAGCCGCCUGCAGACAGCCCCCGUGC<br>CCAUGCCAGACCUGAAGAAUGUCAAGUCCAAGAUCGGCUCCACUGA<br>GAACCUGAAGCACCAGCCGGGAGGCGGGAAGGUGCAGAUAAUUAAU<br>AAGAAGCUGGAUCUUAGCAACGUCCAGUCCAAGUGUGGCUCAAAGG<br>AUAAUAUCAAACACGUCCCGGGAGGCGGCAGUGUGCAAAUAGUCUA<br>CAAACCAGUUGACCUGAGCAAGGUGACCUCCAAGUGUGGCUCAUUA<br>GGCAACAUCCAUCAUAAACCAGGAGGUGGCCAGGUGGAAGUAAAAU<br>CUGAGAAGCUUGACUUCAAGGACAGAGUCCAGUCGAAGAUUGGGUC<br>CCUGGACAAUAUCACCCACGUCCCUGGCGGAGGAAAUAAAAAGAUU<br>GAAACCCACAAGCUGACCUUCCGCGAGAACGCCAAAGCCAAGACAG<br>ACCACGGGGCGGAGAUCGUGUACAAGUCGCCAGUGGUGUCUGGGGA<br>CACGUCUCCACGGCAUCUCAGCAAUGUCUCCUCCACCGGCAGCAUC<br>GACAUGGUAGACUCGCCCCAGCUCGCCACGCUAGCUGACGAGGUGU<br>CUGCCUCCCUGGCCAAGCAGGGUUUGUGAUCAGGCCCCUGGGGCGG<br>UCAAUAAUUGUGGAGAGGAGAGAAUGAGAGAGUGUGGAAAAAAAA<br>AGAAUAAUGACCCGGCCCCCGCCCUCUGCCCCCAGCUGCUCCUCGCA<br>GUUCGGUUAAUUGGUUAAUCACUUAACCUGCUUUUGUCACUCGGCU<br>UUGGCUCGGGACUUCAAAAUCAGUGAUGGGAGUAAGAGCAAAUUU<br>CAUCUUUCCAAAUUGAUGGGUGGGCUAGUAAUAAAAUAUUUAAAA<br>AAAAACAUUCAAAAACAUGGCCACAUCCAACAUUUCCUCAGGCAAU<br>UCCUUUUGAUUCUUUUUUCUUCCCCCUCCAUGUAGAAGAGGGAGAA<br>GGAGAGGCUCUGAAAGCUGCUUCUGGGGGAUUUCAAGGGACUGGG<br>GGUGCCAACCACCUCUGGCCCUGUUGUGGGGGUGUCACAGAGGCAG<br>UGGCAGCAACAAAGGAUUUGAAACUUGGUGUGUUCGUGGAGCCACA<br>GGCAGACGAUGUCAACCUUGUGUGAGUGUGACGGGGGUUGGGGUG<br>GGGCGGGAGGCCACGGGGGAGGCCGAGGCAGGGGCUGGGCAGAGGG<br>GAGAGGAAGCACAAGAAGUGGGAGUGGGAGAGGAAGCCACGUGCU<br>GGAGAGUAGACAUCCCCCUCCUUGCCGCUGGGAGAGCCAAGGCCUA<br>UGCCACCUGCAGCGUCUGAGCGGCCGCCUGUCCUUGGUGGCCGGGG<br>GUGGGGGCCUGCUGUGGGUCAGUGUGCCACCCUCUGCAGGGCAGCC<br>UGUGGGAGAAGGGACAGCGGGUAAAAAGAGAAGGCAAGCUGGCAG<br>GAGGGUGGCACUUCGUGGAUGACCUCCUUAGAAAAGACUGACCUUG<br>AUGUCUUGAGAGCGCUGGCCUCUUCCUCCCUCCCUGCAGGUAGGG |

TABLE 4-continued

Human MAPT mRNA Isoform Sequences. Sequences obtained from NCBI MAPT gene ID: 4137; Assembly GRCh38.p13 (GCF_000001405.39); NC_000017.11 (45894538 . . . 46028334)

| SEQ ID NO | Isoform | mRNA Sequence |
|---|---|---|
| | | GGCCUGAGUUGAGGGGCUUCCCUCUGCUCCACAGAAACCCUGUUUU<br>AUUGAGUUCUGAAGGUUGGAACUGCUGCCAUGAUUUUGGCCACUUU<br>GCAGACCUGGGACUUUAGGGCUAACCAGUUCUCUUUGUAAGGACUU<br>GUGCCUCUUGGGAGACGUCCACCCGUUUCCAAGCCUGGGCCACUGG<br>CAUCUCUGGAGUGUGUGGGGGUCUGGGAGGCAGGUCCCGAGCCCCC<br>UGUCCUUCCCACGGCCACUGCAGUCACCCCGUCUGCGCCGCUGUGCU<br>GUUGUCUGCCGUGAGAGCCCAAUCACUGCCUAUACCCCUCAUCACA<br>CGUCACAAUGUCCCGAAUUCCCAGCCUCACCACCCCUUCUCAGUAA<br>UGACCCUGGUUGGUUGCAGGAGGUACCUACUCCAUACUGAGGGUGA<br>AAUUAAGGGAAGGCAAAGUCCAGGCACAAGAGUGGGACCCCAGCCU<br>CUCACUCUCAGUUCCACUCAUCCAACUGGGACCCUCACCACGAAUC<br>UCAUGAUCUGAUUCGGUUCCCUGUCUCCUCCUCCCGUCACAGAUGU<br>GAGCCAGGGCACUGCUCAGCUGUGACCCUAGGUGUUUCUGCCUUGU<br>UGACAUGGAGAGAGCCCUUUCCCCUGAGAAGGCCUGGCCCCUUCCU<br>GUGCUGAGCCCACAGCAGCAGGCUGGGUGUCUUGGUUGUCAGUGGU<br>GGCACCAGGAUGGAAGGGCAAGGCACCCAGGGCAGGCCCACAGUCC<br>CGCUGUCCCCCACUUGCACCCUAGCUUGUAGCUGCCAACCUCCCAGA<br>CAGCCCAGCCCGCUGCUCAGCUCCACAUGCAUAGUAUCAGCCCUCCA<br>CACCCGACAAAGGGGAACACACCCCCUUGGAAAUGGUUCUUUUCCC<br>CCAGUCCCAGCUGGAAGCCAUGCUGUCUGUUCUGCUGGAGCAGCUG<br>AACAUAUACAUAGAUGUUGCCCUGCCCUCCCCAUCUGCACCCUGUU<br>GAGUUGUAGUUGGAUUUGUCUGUUUAUGCUUGGAUUCACCAGAGU<br>GACUAUGAUAGUGAAAAGAAAAAAAAAAAAAAAAAAAGGACGCAUG<br>UAUCUUGAAAUGCUUGUAAAGAGGUUUCUAACCCACCCUCACGAGG<br>UGUCUCUCACCCCCACACUGGGACUCGUGUGGCCUGUGUGGUGCCA<br>CCCUGCUGGGGCCUCCCAAGUUUUGAAAGGCUUUCCUCAGCACCUG<br>GGACCCAACAGAGACCAGCUUCUAGCAGCUAAGGAGGCCGUUCAGC<br>UGUGACGAAGGCCUGAAGCACAGGAUUAGGACUGAAGCGAUGAUG<br>UCCCCUUCCCUACUUCCCCUUGGGGCUCCCUGUGUCAGGGCACAGA<br>CUAGGUCUUGUGGCUGGUCUGGCUUGCGGCGCGAGGAUGGUUCUCU<br>CUGGUCAUAGCCCGAAGUCUCAUGGCAGUCCCAAAGGAGGCUUACA<br>ACUCCUGCAUCACAAGAAAAAGGAAGCCACUGCCAGCUGGGGGGAU<br>CUGCAGCUCCCAGAAGCUCCGUGAGCCUCAGCCACCCCUCAGACUG<br>GGUUCCUCUCCAAGCUCGCCCUCUGGAGGGGCAGCGCAGCCUCCCA<br>CCAAGGGCCCUGCGACCACAGCAGGGAUUGGGAUGAAUUGCCUGUC<br>CUGGAUCUGCUCUAGAGGCCCAAGCUGCCUGCCUGAGGAAGGAUGA<br>CUUGACAAGUCAGGAGACACUGUUCCCAAAGCCUUGACCAGAGCAC<br>CUCAGCCCGCUGACCUUGCACAAACUCCAUCUGCUGCCAUGAGAAA<br>AGGGAAGCCGCCUUUGCAAAACAUUGCUGCCUAAAGAAACUCAGCA<br>GCCUCAGGCCCAAUUCUGCCACUUCUGGUUUGGGUACAGUUAAAGG<br>CAACCCUGAGGGACUUGGCAGUAGAAAUCCAGGGCCUCCCCUGGGG<br>CUGGCAGCUUCGUGUGCAGCUAGAGCUUUACCUGAAAGGAAGUCUC<br>UGGGCCCAGAACUCUCCACCAAGAGCCUCCCUGCCGUUCGCUGAGU<br>CCCAGCAAUUCUCCUAAGUUGAAGGGAUCUGAGAAGGAGAAGGAAA<br>UGUGGGGUAGAUUUGGUGGUGGUUAGAGAUAUGCCCCCCUCAUUAC<br>UGCCAACAGUUUCGGCUGCAUUUCUUCACGCACCUCGGUUCCUCUU<br>CCUGAAGUUCUUGUGCCCUGCUCUUCAGCACCAUGGGCCUUCUUAU<br>ACGGAAGGCUCUGGGAUCUCCCCCUUGUGGGGCAGGCUCUUGGGGC<br>CAGCCUAAGAUCAUGGUUUAGGGUGAUCAGUGCUGGCAGAUAAAU<br>UGAAAAGGCACGCUGGCUUGUGAUCUUAAAUGAGGACAAUCCCCCC<br>AGGGCUGGGCACUCCUCCCCUCCCCUCACUUCUCCCACCUGCAGAGC<br>CAGUGUCCUUGGGUGGGCUAGAUAGGAUAUACUGUAUGCCGGCUCC<br>UUCAAGCUGCUGACUCACUUUAUCAAUAGUUCCAUUUAAAUUGACU<br>UCAGUGGUGAGACUGUAUCCUGUUUGCUAUUGCUUGUUGUGCUAU<br>GGGGGGAGGGGGGAGGAAUGUGUAAGAUAGUUAACAUGGGCAAAG<br>GGAGAUCUUGGGGUGCAGCACUUAAACUGCCUCGUAACCCUUUUCA<br>UGAUUUCAACCACAUUUGCUAGAGGGAGGGAGCAGCCACGGAGUUA<br>GAGGCCCUUGGGGUUUCUCUUUUCCACUGACAGGCUUUCCCAGGCA<br>GCUGGCUAGUUCAUUCCCUCCCCAGCCAGGUGCAGGCGUAGGAAUA<br>UGGACAUCUGGUUGCUUUGGCCUGCUGCCCUCUUUCAGGGGUCCUA<br>AGCCCACAAUCAUGCCUCCCUAAGACCUUGGCAUCCUUCCCUCUAA<br>GCCGUUGGCACCUCUGUGCCACCUCUCACACUGGCUCCAGACACAC<br>AGCCUGUGCUUUUGGAGCUGAGAUCACUCGCUUCACCCUCCUCAUC<br>UUUGUUCUCCAAGUAAAGCCACGAGGUCGGGGCGAGGGCAGAGGUG<br>AUCACCUGCGUGUCCCAUCUACAGACCUGCAGCUUCAUAAAACUUC<br>UGAUUUCUCUUCAGCUUUGAAAAGGGUUACCCUGGGCACUGGCCUA<br>GAGCCUCACCUCCUAAUAGACUUAGCCCCAUGAGUUUGCCAUGUUG<br>AGCAGGACUAUUUCUGGCACUUGCAAGUCCCAUGAUUUCUUCGGUA<br>AUUCUGAGGGUGGGGGGAGGGACAUGAAAUCAUCUUAGCUUAGCU<br>UUCUGUCUGUGAAUGUCUAUAUAGUGUAUUGUGUGUUUUAACAAA<br>UGAUUUACACUGACUGUUGCUGUAAAAGUGAAUUUGGAAAUAAAG<br>UUAUUACUCUGAUUAAA |

TABLE 4-continued

Human MAPT mRNA Isoform Sequences. Sequences obtained from NCBI MAPT gene ID: 4137; Assembly GRCh38.p13 (GCF_000001405.39); NC_000017.11 (45894538 . . . 46028334)

| SEQ ID NO | Isoform | mRNA Sequence |
|---|---|---|
| 17 | 2 | GCAGUCACCGCCACCCACCAGCUCCGGCACCAACAGCAGCGCCGCUG<br>CCACCGCCCACCUUCUGCCGCCGCCACCACAGCCACCUUCUCCUCCU<br>CCGCUGUCCUCUCCCGUCCUCGCCUCUGUCGACUAUCAGGUGAACU<br>UUGAACCAGGAUGGCUGAGCCCCGCCAGGAGUUCGAAGUGAUGGAA<br>GAUCACGCUGGGACGUACGGGUUGGGGGACAGGAAAGAUCAGGGG<br>GGCUACACCAUGCACCAAGACCAAGAGGGUGACACGGACGCUGGCC<br>UGAAAGAAUCUCCCCUGCAGACCCCCACUGAGGACGGAUCUGAGGA<br>ACCGGGCUCUGAAACCUCUGAUGCUAAGAGCACUCCAACAGCGGAA<br>GAUGUGACAGCACCCUUAGUGGAUGAGGGAGCUCCCGGCAAGCAGG<br>CUGCCGCGCAGCCCCACACGGAGAUCCCAGAAGGAACCACAGCUGA<br>AGAAGCAGGCAUUGGAGACACCCCCAGCCUGGAAGACGAAGCUGCU<br>GGUCACGUGACCCAAGCUCGCAUGGUCAGUAAAAGCAAAGACGGGA<br>CUGGAAGCGAUGACAAAAAAGCCAAGGGGGCUGAUGGUAAAACGA<br>AGAUCGCCACACCGCGGGGAGCAGCCCCUCCAGGCCAGAAGGGCCA<br>GGCCAACGCCACCAGGAUUCCAGCAAAAACCCCGCCCGCUCCAAAG<br>ACACCACCCAGCUCUGGUGAACCUCCAAAAUCAGGGGAUCGCAGCG<br>GCUACAGCAGCCCCGGCUCCCCAGGCACUCCCGGCAGCCGCUCCCGC<br>ACCCCGUCCCUUCCAACCCCACCCACCCGGGAGCCCAAGAAGGUGGC<br>AGUGGUCCGUACUCCACCCAAGUCGCCGUCUUCCGCCAAGAGCCGC<br>CUGCAGACAGCCCCCGUGCCCAUGCCAGACCUGAAGAAUGUCAAGU<br>CCAAGAUCGGCUCCACUGAGAACCUGAAGCACCAGCCGGGAGGCGG<br>GAAGGUGCAGAUAAUUAAUAAGAAGCUGGAUCUUAGCAACGUCCA<br>GUCCAAGUGUGGCUCAAAGGAUAAUAUCAAACACGUCCCGGGAGGC<br>GGCAGUGUGCAAAUAGUCUACAAACCAGUUGACCUGAGCAAGGUGA<br>CCUCCAAGUGUGGCUCAUUAGGCAACAUCCAUCAUAAACCAGGAGG<br>UGGCCAGGUGGAAGUAAAAUCUGAGAAGCUUGACUUCAAGGACAG<br>AGUCCAGUCGAAGAUUGGGUCCCUGGACAAUAUCACCCACGUCCCU<br>GGCGGAGGAAAUAAAAAGAUUGAAACCCACAAGCUGACCUUCCGCG<br>AGAACGCCAAAGCCAAGACAGACCACGGGGCGGAGAUCGUGUACAA<br>GUCGCCAGUGGUGUCUGGGGACACGUCUCCACGGCAUCUCAGCAAU<br>GUCUCCUCCACCGGCAGCAUCGACAUGGUAGACUCGCCCCAGCUCG<br>CCACGCUAGCUGACGAGGUGUCUGCCUCCCUGGCCAAGCAGGGUUU<br>GUGAUCAGGCCCCUGGGGCGGUCAAUAAUUGUGGAGAGGAGAGAA<br>UGAGAGAGUGUGGAAAAAAAAAGAAUAAUGACCCGGCCCCCGCCCU<br>CUGCCCCCAGCUGCUCCUCGCAGUUCGGUUAAUUGGUUAAUCACUU<br>AACCUGCUUUUGUCACUCGGCUUUGGCUCGGGACUUCAAAAUCAGU<br>GAUGGGAGUAAGAGCAAAUUUCAUCUUUCCAAAUUGAUGGGUGGG<br>CUAGUAAUAAAAUAUUUAAAAAAAAACAUUCAAAAACAUGGCCAC<br>AUCCAACAUUUCCUCAGGCAAUUCCUUUUGAUUCUUUUUUCUUCCC<br>CCUCCAUGUAGAAGAGGGAGAAGGAGAGGCUCUGAAAGCUGCUUCU<br>GGGGGAUUUCAAGGGACUGGGGGUGCCAACCACCUCUGGCCCUGUU<br>GUGGGGGUGUCACAGAGGCAGUGGCAGCAACAAAGGAUUUGAAAC<br>UUGGUGUGUUCGUGGAGCCACAGGCAGACGAUGUCAACCUUGUGUG<br>AGUGUGACGGGGGUUGGGGUGGGGCGGGAGGCCACGGGGGAGGCC<br>GAGGCAGGGGCUGGGCAGAGGGGAGAGGAAGCACAAGAAGUGGGA<br>GUGGGAGAGGAAGCCACGUGCUGGAGAGUAGACAUCCCCCUCCUUG<br>CCGCUGGGAGAGCCAAGGCCUAUGCCACCUGCAGCGUCUGAGCGGC<br>CGCCUGUCCUUGGUGGCCGGGGGUGGGGGCCUGCUGUGGGUCAGUG<br>UGCCACCCUCUGCAGGGCAGCCUGUGGGAGAAGGGACAGCGGGUAA<br>AAAGAGAAGGCAAGCUGGCAGGAGGGUGGCACUUCGUGGAUGACCU<br>CCUUAGAAAAGACUGACCUUGAUGUCUUGAGAGCGCUGGCCUCUUC<br>CUCCCUCCCUGCAGGGUAGGGGGCCUGAGUUGAGGGGCUUCCCUCU<br>GCUCCACAGAAACCCUGUUUUAUUGAGUUCUGAAGGUUGGAACUGC<br>UGCCAUGAUUUUGGCCACUUUGCAGACCUGGGACUUUAGGGCUAAC<br>CAGUUCUCUUUGUAAGGACUUGUGCCUCUUGGGAGACGUCCACCCG<br>UUUCCAAGCCUGGGCCACUGGCAUCUCUGGAGUGUGUGGGGGUCUG<br>GGAGGCAGGUCCCGAGCCCCCUGUCCUUCCCACGGCCACUGCAGUC<br>ACCCCGUCUGCGCCGCUGUGCUGUUGUCUGCCGUGAGAGCCCAAUC<br>ACUGCCUAUACCCCUCAUCACACGUCACAAUGUCCCGAAUUCCCAG<br>CCUCACCACCCCUUCUCAGUAAUGACCCUGGUUGGUUGCAGGAGGU<br>ACCUACUCCAUACUGAGGGUGAAAUUAAGGGAAGGCAAAGUCCAGG<br>CACAAGAGUGGGACCCCAGCCUCUCACUCUCAGUUCCACUCAUCCA<br>ACUGGGACCCUCACCACGAAUCUCAUGAUCUGAUUCGGUUCCCUGU<br>CUCCUCCUCCCGUCACAGAUGUGAGCCAGGGCACUGCUCAGCUGUG<br>ACCCUAGGUGUUUCUGCCUUGUUGACAUGGAGAGAGCCCUUUCCCC<br>UGAGAAGGCCUGGCCCCUUCCUGUGCUGAGCCCACAGCAGCAGGCU<br>GGGUGUCUUGGUUGUCAGUGGUGGCACCAGGAUGGAAGGGCAAGG<br>CACCCAGGGCAGGCCCACAGUCCCGCUGUCCCCCACUUGCACCCUAG<br>CUUGUAGCUGCCAACCUCCCAGACAGCCCAGCCCGCUGCUCAGCUCC<br>ACAUGCAUAGUAUCAGCCCUCCACACCCGACAAAGGGGAACACACC<br>CCCUUGGAAAUGGUUCUUUUCCCCCAGUCCCAGCUGGAAGCCAUGC |

TABLE 4-continued

Human MAPT mRNA Isoform Sequences. Sequences obtained from NCBI MAPT gene ID: 4137; Assembly GRCh38.p13 (GCF_000001405.39); NC_000017.11 (45894538 . . . 46028334)

| SEQ ID NO | Isoform | mRNA Sequence |
|---|---|---|
| | | UGUCUGUUCUGCUGGAGCAGCUGAACAUAUACAUAGAUGUUGCCCU |
| | | GCCCUCCCCAUCUGCACCCUGUUGAGUUGUAGUUGGAUUUGUCUGU |
| | | UUAUGCUUGGAUUCACCAGAGUGACUAUGAUAGUGAAAAGAAAAA |
| | | AAAAAAAAAAAAAGGACGCAUGUAUCUUGAAAUGCUUGUAAAGAG |
| | | GUUUCUAACCCACCCUCACGAGGUGUCUCUCACCCCCACACUGGGA |
| | | CUCGUGUGGCCUGUGUGGUGCCACCCUGCUGGGGCCUCCCAAGUUU |
| | | UGAAAGGCUUUCCUCAGCACCUGGGACCCAACAGAGACCAGCUUCU |
| | | AGCAGCUAAGGAGGCCGUUCAGCUGUGACGAAGGCCUGAAGCACAG |
| | | GAUUAGGACUGAAGCGAUGAUGUCCCCUUCCCUACUUCCCCUUGGG |
| | | GCUCCCUGUGUCAGGGCACAGACUAGGUCUUGUGGCUGGUCUGGCU |
| | | UGCGGCGCGAGGAUGGUUCUCUCUGGUCAUAGCCCGAAGUCUCAUG |
| | | GCAGUCCCAAAGGAGGCUUACAACUCCUGCAUCACAAGAAAAAGGA |
| | | AGCCACUGCCAGCUGGGGGGAUCUGCAGCUCCCAGAAGCUCCGUGA |
| | | GCCUCAGCCACCCCUCAGACUGGGUUCCUCUCCAAGCUCGCCCUCUG |
| | | GAGGGGCAGCGCAGCCUCCCACCAAGGGCCCUGCGACCACAGCAGG |
| | | GAUUGGGAUGAAUUGCCUGUCCUGGAUCUGCUCUAGAGGCCCAAGC |
| | | UGCCUGCCUGAGGAAGGAUGACUUGACAAGUCAGGAGACACUGUUC |
| | | CCAAAGCCUUGACCAGAGCACCUCAGCCCGCUGACCUUGCACAAAC |
| | | UCCAUCUGCUGCCAUGAGAAAAGGGAAGCCGCCUUUGCAAAACAUU |
| | | GCUGCCUAAAGAAACUCAGCAGCCUCAGGCCCAAUUCUGCCACUUC |
| | | UGGUUUGGGUACAGUUAAAGGCAACCCUGAGGGACUUGGCAGUAG |
| | | AAAUCCAGGGCCUCCCCUGGGGCUGGCAGCUUCGUGUGCAGCUAGA |
| | | GCUUUACCUGAAAGGAAGUCUCUGGGCCCAGAACUCUCCACCAAGA |
| | | GCCUCCCUGCCGUUCGCUGAGUCCCAGCAAUUCUCCUAAGUUGAAG |
| | | GGAUCUGAGAAGGAGAAGGAAAUGUGGGGUAGAUUUGGUGGUGGU |
| | | UAGAGAUAUGCCCCCCUCAUUACUGCCAACAGUUUCGGCUGCAUUU |
| | | CUUCACGCACCUCGGUUCCUCUUCCUGAAGUUCUUGUGCCCUGCUC |
| | | UUCAGCACCAUGGGCCUUCUUAUACGGAAGGCUCUGGGAUCUCCCC |
| | | CUUGUGGGGCAGGCUCUUGGGGCCAGCCUAAGAUCAUGGUUUAGGG |
| | | UGAUCAGUGCUGGCAGAUAAAUUGAAAAGGCACGCUGGCUUGUGA |
| | | UCUUAAAUGAGGACAAUCCCCCCAGGGCUGGGCACUCCUCCCCUCC |
| | | CCUCACUUCUCCCACCUGCAGAGCCAGUGUCCUUGGGUGGGCUAGA |
| | | UAGGAUAUACUGUAUGCCGGCUCCUUCAAGCUGCUGACUCACUUUA |
| | | UCAAUAGUUCCAUUUAAAUUGACUUCAGUGGUGAGACUGUAUCCUG |
| | | UUUGCUAUUGCUUGUUGUGCUAUGGGGGGAGGGGGGAGGAAUGUG |
| | | UAAGAUAGUUAACAUGGGCAAAGGGAGAUCUUGGGGUGCAGCACU |
| | | UAAACUGCCUCGUAACCCUUUUCAUGAUUUCAACCACAUUUGCUAG |
| | | AGGGAGGGAGCAGCCACGGAGUUAGAGGCCCUUGGGGUUUCUCUUU |
| | | UCCACUGACAGGCUUUCCCAGGCAGCUGGCUAGUUCAUUCCCUCCC |
| | | CAGCCAGGUGCAGGCGUAGGAAUAUGGACAUCUGGUUGCUUUGGCC |
| | | UGCUGCCCUCUUUCAGGGGUCCUAAGCCCACAAUCAUGCCUCCCUA |
| | | AGACCUUGGCAUCCUUCCCUCUAAGCCGUUGGCACCUCUGUGCCAC |
| | | CUCUCACACUGGCUCCAGACACACAGCCUGUGCUUUUGGAGCUGAG |
| | | AUCACUCGCUUCACCCUCCUCAUCUUUGUUCUCCAAGUAAAGCCAC |
| | | GAGGUCGGGGCGAGGGCAGAGGUGAUCACCUGCGUGUCCCAUCUAC |
| | | AGACCUGCAGCUUCAUAAAACUUCUGAUUUCUCUUCAGCUUUGAAA |
| | | AGGGUUACCCUGGGCACUGGCCUAGAGCCUCACCUCCUAAUAGACU |
| | | UAGCCCCAUGAGUUUGCCAUGUUGAGCAGGACUAUUUCUGGCACUU |
| | | GCAAGUCCCAUGAUUUCUUCGGUAAUUCUGAGGGUGGGGGGAGGG |
| | | ACAUGAAAUCAUCUUAGCUUAGCUUUCUGUCUGUGAAUGUCUAUAU |
| | | AGUGUAUUGUGUGUUUUAACAAAUGAUUUACACUGACUGUUGCUG |
| | | UAAAAGUGAAUUUGGAAAUAAAGUUAUUACUCUGAUUAAA |
| 18 | 3 | GCAGUCACCGCCACCCACCAGCUCCGGCACCAACAGCAGCGCCGCUG |
| | | CCACCGCCCACCUUCUGCCGCCGCCACCACAGCCACCUUCUCCUCCU |
| | | CCGCUGUCCUCUCCCGUCCUCGCCUCUGUCGACUAUCAGGUGAACU |
| | | UUGAACCAGGAUGGCUGAGCCCCGCCAGGAGUUCGAAGUGAUGGAA |
| | | GAUCACGCUGGGACGUACGGGUUGGGGGACAGGAAAGAUCAGGGG |
| | | GGCUACACCAUGCACCAAGACCAAGAGGGUGACACGGACGCUGGCC |
| | | UGAAAGCUGAAGAAGCAGGCAUUGGAGACACCCCCAGCCUGGAAGA |
| | | CGAAGCUGCUGGUCACGUGACCCAAGCUCGCAUGGUCAGUAAAAGC |
| | | AAAGACGGGACUGGAAGCGAUGACAAAAAAGCCAAGGGGGCUGAU |
| | | GGUAAAACGAAGAUCGCCACACCGCGGGGAGCAGCCCCUCCAGGCC |
| | | AGAAGGGCCAGGCCAACGCCACCAGGAUUCCAGCAAAAACCCCGCC |
| | | CGCUCCAAAGACACCACCCAGCUCUGGUGAACCUCCAAAAUCAGGG |
| | | GAUCGCAGCGGCUACAGCAGCCCCGGCUCCCCAGGCACUCCCGGCAG |
| | | CCGCUCCCGCACCCCGUCCCUUCCAACCCCACCCACCCGGGAGCCCA |
| | | AGAAGGUGGCAGUGGUCCGUACUCCACCCAAGUCGCCGUCUUCCGC |
| | | CAAGAGCCGCCUGCAGACAGCCCCCGUGCCCAUGCCAGACCUGAAG |
| | | AAUGUCAAGUCCAAGAUCGGCUCCACUGAGAACCUGAAGCACCAGC |
| | | CGGGAGGCGGGAAGGUGCAGAUAAUUAAUAAGAAGCUGGAUCUUA |
| | | GCAACGUCCAGUCCAAGUGUGGCUCAAAGGAUAAUAUCAAACACGU |

TABLE 4-continued

Human MAPT mRNA Isoform Sequences. Sequences obtained from NCBI MAPT gene ID: 4137; Assembly GRCh38.p13 (GCF_000001405.39); NC_000017.11 (45894538 . . . 46028334)

| SEQ ID NO | Isoform | mRNA Sequence |
|---|---|---|
| | | CCCGGGAGGCGGCAGUGUGCAAAUAGUCUACAAACCAGUUGACCUG<br>AGCAAGGUGACCUCCAAGUGUGGCUCAUUAGGCAACAUCCAUCAUA<br>AACCAGGAGGUGGCCAGGUGGAAGUAAAAUCUGAGAAGCUUGACU<br>UCAAGGACAGAGUCCAGUCGAAGAUUGGGUCCCUGGACAAUAUCAC<br>CCACGUCCCUGGCGGAGGAAAUAAAAAGAUUGAAACCCACAAGCUG<br>ACCUUCCGCGAGAACGCCAAAGCCAAGACAGACCACGGGGCGGAGA<br>UCGUGUACAAGUCGCCAGUGGUGUCUGGGGACACGUCUCCACGGCA<br>UCUCAGCAAUGUCUCCUCCACCGGCAGCAUCGACAUGGUAGACUCG<br>CCCCAGCUCGCCACGCUAGCUGACGAGGUGUCUGCCUCCCUGGCCA<br>AGCAGGGUUUGUGAUCAGGCCCCUGGGGCGGUCAAUAAUUGUGGAG<br>AGGAGAGAAUGAGAGAGUGUGGAAAAAAAAAGAAUAAUGACCCGG<br>CCCCCGCCCUCUGCCCCCAGCUGCUCCUCGCAGUUCGGUUAAUUGGU<br>UAAUCACUUAACCUGCUUUUGUCACUCGGCUUUGGCUCGGGACUUC<br>AAAAUCAGUGAUGGGAGUAAGAGCAAAUUUCAUCUUUCCAAAUUG<br>AUGGGUGGGCUAGUAAUAAAAUAUUUAAAAAAAAACAUUCAAAAA<br>CAUGGCCACAUCCAACAUUUCCUCAGGCAAUUCCUUUUGAUUCUUU<br>UUUCUUCCCCCUCCAUGUAGAAGAGGGAGAAGGAGAGGCUCUGAAA<br>GCUGCUUCUGGGGGAUUUCAAGGGACUGGGGGUGCCAACCACCUCU<br>GGCCCUGUUGUGGGGGUGUCACAGAGGCAGUGGCAGCAACAAAGGA<br>UUUGAAACUUGGUGUGUUCGUGGAGCCACAGGCAGACGAUGUCAAC<br>CUUGUGUGAGUGUGACGGGGGUUGGGGUGGGGCGGGAGGCCACGG<br>GGGAGGCCGAGGCAGGGGCUGGGCAGAGGGGAGAGGAAGCACAAG<br>AAGUGGGAGUGGGAGAGGAAGCCACGUGCUGGAGAGUAGACAUCCC<br>CCUCCUUGCCGCUGGGAGAGCCAAGGCCUAUGCCACCUGCAGCGUC<br>UGAGCGGCCGCCUGUCCUUGGUGGCCGGGGGUGGGGGCCUGCUGUG<br>GGUCAGUGUGCCACCCUCUGCAGGGCAGCCUGUGGGAGAAGGGACA<br>GCGGGUAAAAAGAGAAGGCAAGCUGGCAGGAGGGUGGCACUUCGU<br>GGAUGACCUCCUUAGAAAAGACUGACCUUGAUGUCUUGAGAGCGCU<br>GGCCUCUUCCUCCCUCCCUGCAGGGUAGGGGGCCUGAGUUGAGGGG<br>CUUCCCUCUGCUCCACAGAAACCCUGUUUUAUUGAGUUCUGAAGGU<br>UGGAACUGCUGCCAUGAUUUUGGCCACUUUGCAGACCUGGGACUUU<br>AGGGCUAACCAGUUCUCUUUGUAAGGACUUGUGCCUCUUGGGAGAC<br>GUCCACCCGUUUCCAAGCCUGGGCCACUGGCAUCUCUGGAGUGUGU<br>GGGGGUCUGGGAGGCAGGUCCCGAGCCCCCUGUCCUUCCCACGGCC<br>ACUGCAGUCACCCCGUCUGCGCCGCUGUGCUGUUGUCUGCCGUGAG<br>AGCCCAAUCACUGCCUAUACCCCUCAUCACACGUCACAAUGUCCCG<br>AAUUCCCAGCCUCACCACCCCUUCUCAGUAAUGACCCUGGUUGGUU<br>GCAGGAGGUACCUACUCCAUACUGAGGGUGAAAUUAAGGGAAGGCA<br>AAGUCCAGGCACAAGAGUGGGACCCCAGCCUCUCACUCUCAGUUCC<br>ACUCAUCCAACUGGGACCCUCACCACGAAUCUCAUGAUCUGAUUCG<br>GUUCCCUGUCUCCUCCUCCCGUCACAGAUGUGAGCCAGGGCACUGC<br>UCAGCUGUGACCCUAGGUGUUUCUGCCUUGUUGACAUGGAGAGAGC<br>CCUUUCCCCUGAGAAGGCCUGGCCCCUUCCUGUGCUGAGCCCACAG<br>CAGCAGGCUGGGUGUCUUGGUUGUCAGUGGUGGCACCAGGAUGGAA<br>GGGCAAGGCACCCAGGGCAGGCCCACAGUCCCGCUGUCCCCCACUU<br>GCACCCUAGCUUGUAGCUGCCAACCUCCCAGACAGCCCAGCCCGCUG<br>CUCAGCUCCACAUGCAUAGUAUCAGCCCUCCACACCCGACAAAGGG<br>GAACACACCCCCUUGGAAAUGGUUCUUUUCCCCCAGUCCCAGCUGG<br>AAGCCAUGCUGUCUGUUCUGCUGGAGCAGCUGAACAUAUACAUAGA<br>UGUUGCCCUGCCCUCCCCAUCUGCACCCUGUUGAGUUGUAGUUGGA<br>UUUGUCUGUUUAUGCUUGGAUUCACCAGAGUGACUAUGAUAGUGA<br>AAAGAAAAAAAAAAAAAAAAAAAGGACGCAUGUAUCUUGAAAUGCU<br>UGUAAAGAGGUUUCUAACCCACCCUCACGAGGUGUCUCUCACCCCC<br>ACACUGGGACUCGUGUGGCCUGUGUGGUGCCACCCUGCUGGGGCCU<br>CCCAAGUUUUGAAAGGCUUUCCUCAGCACCUGGGACCCAACAGAGA<br>CCAGCUUCUAGCAGCUAAGGAGGCCGUUCAGCUGUGACGAAGGCCU<br>GAAGCACAGGAUUAGGACUGAAGCGAUGAUGUCCCCUUCCCUACUU<br>CCCCUUGGGGCUCCCUGUGUCAGGGCACAGACUAGGUCUUGUGGCU<br>GGUCUGGCUUGCGGCGCGAGGAUGGUUCUCUCUGGUCAUAGCCCGA<br>AGUCUCAUGGCAGUCCCAAAGGAGGCUUACAACUCCUGCAUCACAA<br>GAAAAAGGAAGCCACUGCCAGCUGGGGGGAUCUGCAGCUCCCAGAA<br>GCUCCGUGAGCCUCAGCCACCCCUCAGACUGGGUUCCUCUCCAAGC<br>UCGCCCUCUGGAGGGGCAGCGCAGCCUCCCACCAAGGGCCCUGCGA<br>CCACAGCAGGGAUUGGGAUGAAUUGCCUGUCCUGGAUCUGCUCUAG<br>AGGCCCAAGCUGCCUGCCUGAGGAAGGAUGACUUGACAAGUCAGGA<br>GACACUGUUCCCAAAGCCUUGACCAGAGCACCUCAGCCCGCUGACC<br>UUGCACAAACUCCAUCUGCUGCCAUGAGAAAAGGGAAGCCGCCUUU<br>GCAAAACAUUGCUGCCUAAAGAAACUCAGCAGCCUCAGGCCCAAUU<br>CUGCCACUUCUGGUUUGGGUACAGUUAAAGGCAACCCUGAGGGACU<br>UGGCAGUAGAAAUCCAGGGCCUCCCCUGGGGCUGGCAGCUUCGUGU<br>GCAGCUAGAGCUUUACCUGAAAGGAAGUCUCUGGGCCCAGAACUCU<br>CCACCAAGAGCCUCCCUGCCGUUCGCUGAGUCCCAGCAAUUCUCCU |

TABLE 4-continued

Human MAPT mRNA Isoform Sequences. Sequences obtained from NCBI MAPT gene ID: 4137; Assembly GRCh38.p13 (GCF_000001405.39); NC_000017.11 (45894538 . . . 46028334)

| SEQ ID NO | Isoform | mRNA Sequence |
|---|---|---|
| | | AAGUUGAAGGAUCUGAGAAGGAGAAGGAAAUGUGGGGUAGAUUU<br>GGUGGUGGUUAGAGAUAUGCCCCCCUCAUUACUGCCAACAGUUUCG<br>GCUGCAUUUCUUCACGCACCUCGGUUCCUCUUCCUGAAGUUCUUGU<br>GCCCUGCUCUUCAGCACCAUGGGCCUUCUUAUACGGAAGGCUCUGG<br>GAUCUCCCCCUUGUGGGGCAGGCUCUUGGGGCCAGCCUAAGAUCAU<br>GGUUUAGGGUGAUCAGUGCUGGCAGAUAAAUUGAAAAGGCACGCU<br>GGCUUGUGAUCUUAAAUGAGGACAAUCCCCCCAGGGCUGGGCACUC<br>CUCCCCUCCCCUCACUUCUCCCACCUGCAGAGCCAGUGUCCUUGGGU<br>GGGCUAGAUAGGAUAUACUGUAUGCCGGCUCCUUCAAGCUGCUGAC<br>UCACUUUAUCAAUAGUUCCAUUUAAAUUGACUUCAGUGGUGAGACU<br>GUAUCCUGUUUGCUAUUGCUUGUUGUGCUAUGGGGGGAGGGGGA<br>GGAAUGUGUAAGAUAGUUAACAUGGGCAAAGGAGAUCUUGGGGU<br>GCAGCACUUAAACUGCCUCGUAACCCUUUUCAUGAUUUCAACCACA<br>UUUGCUAGAGGGAGGGAGCAGCCACGGAGUUAGAGGCCCUUGGGGU<br>UUCUCUUUUCCACUGACAGGCUUUCCCAGGCAGCUGGCUAGUUCAU<br>UCCCUCCCCAGCCAGGUGCAGGCGUAGGAAUAUGGACAUCUGGUUG<br>CUUUGGCCUGCUGCCCUCUUUCAGGGGUCCUAAGCCCACAAUCAUG<br>CCUCCCUAAGACCUUGGCAUCCUUCCCUCUAAGCCGUUGGCACCUC<br>UGUGCCACCUCUCACACUGGCUCCAGACACACAGCCUGUGCUUUUG<br>GAGCUGAGAUCACUCGCUUCACCCUCCUCAUCUUUGUUCUCCAAGU<br>AAAGCCACGAGGUCGGGGCGAGGGCAGAGGUGAUCACCUGCGUGUC<br>CCAUCUACAGACCUGCAGCUUCAUAAAACUUCUGAUUUCUCUUCAG<br>CUUUGAAAAGGGUUACCCUGGGCACUGGCCUAGAGCCUCACCUCCU<br>AAUAGACUUAGCCCCAUGAGUUUGCCAUGUUGAGCAGGACUAUUUC<br>UGGCACUUGCAAGUCCCAUGAUUUCUUCGGUAAUUCUGAGGGUGGG<br>GGGAGGGACAUGAAAUCAUCUUAGCUUAGCUUUCUGUCUGUGAAU<br>GUCUAUAUAGUGUAUUGUGUGUUUUAACAAAUGAUUUACACUGAC<br>UGUUGCUGUAAAAGUGAAUUUGGAAAUAAAGUUAUUACUCUGAUU<br>AAA |
| 19 | 4 | GCAGUCACCGCCACCCACCAGCUCCGGCACCAACAGCAGCGCCGCUG<br>CCACCGCCCACCUUCUGCCGCCGCCACCACAGCCACCUUCUCCUCCU<br>CCGCUGUCCUCUCCCGUCCUCGCCUCUGUCGACUAUCAGGUGAACU<br>UUGAACCAGGAUGGCUGAGCCCCGCCAGGAGUUCGAAGUGAUGGAA<br>GAUCACGCUGGGACGUACGGGUUGGGGGACAGGAAAGAUCAGGGG<br>GGCUACACCAUGCACCAAGACCAAGAGGGUGACACGGACGCUGGCC<br>UGAAAGCUGAAGAAGCAGGCAUUGGAGACACCCCCAGCCUGGAAGA<br>CGAAGCUGCUGGUCACGUGACCCAAGCUCGCAUGGUCAGUAAAAGC<br>AAAGACGGGACUGGAAGCGAUGACAAAAAAGCCAAGGGGGCUGAU<br>GGUAAAACGAAGAUCGCCACACCGCGGGGAGCAGCCCCUCCAGGCC<br>AGAAGGGCCAGGCCAACGCCACCAGGAUUCCAGCAAAAACCCCGCC<br>CGCUCCAAAGACACCACCCAGCUCUGGUGAACCUCCAAAAUCAGGG<br>GAUCGCAGCGGCUACAGCAGCCCCGGCUCCCCAGGCACUCCCGGCAG<br>CCGCUCCCGCACCCCGUCCCUUCCAACCCCACCCACCCGGGAGCCCA<br>AGAAGGUGGCAGUGGUCCGUACUCCACCCAAGUCGCCGUCUUCCGC<br>CAAGAGCCGCCUGCAGACAGCCCCCGUGCCCAUGCCAGACCUGAAG<br>AAUGUCAAGUCCAAGAUCGGCUCCACUGAGAACCUGAAGCACCAGC<br>CGGGAGGCGGGAAGGUGCAAAUAGUCUACAAACCAGUUGACCUGAG<br>CAAGGUGACCUCCAAGUGUGGCUCAUUAGGCAACAUCCAUCAUAAA<br>CCAGGAGGUGGCCAGGUGGAAGUAAAAUCUGAGAAGCUUGACUUCA<br>AGGACAGAGUCCAGUCGAAGAUUGGGUCCCUGGACAAUAUCACCCA<br>CGUCCCUGGCGGAGGAAAUAAAAAGAUUGAAACCCACAAGCUGACC<br>UUCCGCGAGAACGCCAAAGCCAAGACAGACCACGGGGCGGAGAUCG<br>UGUACAAGUCGCCAGUGGUGUCUGGGGACACGUCUCCACGGCAUCU<br>CAGCAAUGUCUCCUCCACCGGCAGCAUCGACAUGGUAGACUCGCCC<br>CAGCUCGCCACGCUAGCUGACGAGGUGUCUGCCUCCCUGGCCAAGC<br>AGGGUUUGUGAUCAGGCCCCUGGGGCGGUCAAUAAUUGUGGAGAG<br>GAGAGAAUGAGAGAGUGUGGAAAAAAAAAGAAUAAUGACCCGGCC<br>CCCGCCCUCUGCCCCCAGCUGCUCCUCGCAGUUCGGUUAAUUGGUU<br>AAUCACUUAACCUGCUUUUGUCACUCGGCUUUGGCUCGGGACUUCA<br>AAAUCAGUGAUGGGAGUAAGAGCAAAUUUCAUCUUUCCAAAUUGA<br>UGGGUGGGCUAGUAAUAAAAUAUUUAAAAAAAAACAUUCAAAAAC<br>AUGGCCACAUCCAACAUUUCCUCAGGCAAUUCCUUUUGAUUCUUUU<br>UUCUUCCCCCUCCAUGUAGAAGAGGGAGAAGGAGAGGCUCUGAAAG<br>CUGCUUCUGGGGGAUUUCAAGGGACUGGGGGUGCCAACCACCUCUG<br>GCCCUGUUGUGGGGGUGUCACAGAGGCAGUGGCAGCAACAAAGGAU<br>UUGAAACUUGGUGUGUUCGUGGAGCCACAGGCAGACGAUGUCAACC<br>UUGUGUGAGUGUGACGGGGGUUGGGGUGGGGCGGGAGGCCACGGG<br>GGAGGCCGAGGCAGGGGCUGGGCAGAGGGGAGAGGAAGCACAAGA<br>AGUGGGAGUGGGAGAGGAAGCCACGUGCUGGAGAGUAGACAUCCCC<br>CUCCUUGCCGCUGGGAGAGCCAAGGCCUAUGCCACCUGCAGCGUCU<br>GAGCGGCCGCCUGUCCUUGGUGGCCGGGGGUGGGGGCCUGCUGUGG |

TABLE 4-continued

Human MAPT mRNA Isoform Sequences. Sequences obtained from NCBI MAPT gene ID: 4137; Assembly GRCh38.p13 (GCF_000001405.39); NC_000017.11 (45894538 . . . 46028334)

| SEQ ID NO | Isoform | mRNA Sequence |
|---|---|---|
| | | GUCAGUGUGCCACCCUCUGCAGGGCAGCCUGUGGGAGAAGGGACAG<br>CGGGUAAAAAGAGAAGGCAAGCUGGCAGGAGGGUGGCACUUCGUG<br>GAUGACCUCCUUAGAAAAGACUGACCUUGAUGUCUUGAGAGCGCUG<br>GCCUCUUCCUCCCUCCCUGCAGGGUAGGGGGCCUGAGUUGAGGGGC<br>UUCCCUCUGCUCCACAGAAACCCUGUUUUAUUGAGUUCUGAAGGUU<br>GGAACUGCUGCCAUGAUUUUGGCCACUUUGCAGACCUGGGACUUUA<br>GGGCUAACCAGUUCUCUUUGUAAGGACUUGUGCCUCUUGGGAGACG<br>UCCACCCGUUUCCAAGCCUGGGCCACUGGCAUCUCUGGAGUGUGUG<br>GGGGUCUGGGAGGCAGGUCCCGAGCCCCCUGUCCUUCCCACGGCCA<br>CUGCAGUCACCCCGUCUGCGCCGCUGUGCUGUUGUCUGCCGUGAGA<br>GCCCAAUCACUGCCUAUACCCCUCAUCACACGUCACAAUGUCCCGA<br>AUUCCCAGCCUCACCACCCCUUCUCAGUAAUGACCCUGGUUGGUUG<br>CAGGAGGUACCUACUCCAUACUGAGGGUGAAAUUAAGGGAAGGCAA<br>AGUCCAGGCACAAGAGUGGGACCCCAGCCUCUCACUCUCAGUUCCA<br>CUCAUCCAACUGGGACCCUCACCACGAAUCUCAUGAUCUGAUUCGG<br>UUCCCUGUCUCCUCCUCCCGUCACAGAUGUGAGCCAGGGCACUGCU<br>CAGCUGUGACCCUAGGUGUUUCUGCCUUGUUGACAUGGAGAGAGCC<br>CUUUCCCCUGAGAAGGCCUGGCCCCUUCCUGUGCUGAGCCCACAGC<br>AGCAGGCUGGGUGUCUUGGUUGUCAGUGGUGGCACCAGGAUGGAA<br>GGGCAAGGCACCCAGGGCAGGCCCACAGUCCCGCUGUCCCCCACUU<br>GCACCCUAGCUUGUAGCUGCCAACCUCCCAGACAGCCCAGCCCGCUG<br>CUCAGCUCCACAUGCAUAGUAUCAGCCCUCCACACCCGACAAAGGG<br>GAACACACCCCCUUGGAAAUGGUUCUUUUCCCCCAGUCCCAGCUGG<br>AAGCCAUGCUGUCUGUUCUGCUGGAGCAGCUGAACAUAUACAUAGA<br>UGUUGCCCUGCCCUCCCCAUCUGCACCCUGUUGAGUUGUAGUUGGA<br>UUUGUCUGUUUAUGCUUGGAUUCACCAGAGUGACUAUGAUAGUGA<br>AAAGAAAAAAAAAAAAAAAAAAAGGACGCAUGUAUCUUGAAAUGCU<br>UGUAAAGAGGUUUCUAACCCACCCUCACGAGGUGUCUCUCACCCCC<br>ACACUGGGACUCGUGUGGCCUGUGUGGUGCCACCCUGCUGGGGCCU<br>CCCAAGUUUUGAAAGGCUUUCCUCAGCACCUGGGACCCAACAGAGA<br>CCAGCUUCUAGCAGCUAAGGAGGCCGUUCAGCUGUGACGAAGGCCU<br>GAAGCACAGGAUUAGGACUGAAGCGAUGAUGUCCCCUUCCCUACUU<br>CCCCUUGGGGCUCCCUGUGUCAGGGCACAGACUAGGUCUUGUGGCU<br>GGUCUGGCUUGCGGCGCGAGGAUGGUUCUCUCUGGUCAUAGCCCGA<br>AGUCUCAUGGCAGUCCCAAAGGAGGCUUACAACUCCUGCAUCACAA<br>GAAAAAGGAAGCCACUGCCAGCUGGGGGGAUCUGCAGCUCCCAGAA<br>GCUCCGUGAGCCUCAGCCACCCCUCAGACUGGGUUCCUCUCCAAGC<br>UCGCCCUCUGGAGGGGCAGCGCAGCCUCCCACCAAGGGCCCUGCGA<br>CCACAGCAGGGAUUGGGAUGAAUUGCCUGUCCUGGAUCUGCUCUAG<br>AGGCCCAAGCUGCCUGCCUGAGGAAGGAUGACUUGACAAGUCAGGA<br>GACACUGUUCCCAAAGCCUUGACCAGAGCACCUCAGCCCGCUGACC<br>UUGCACAAACUCCAUCUGCUGCCAUGAGAAAAGGGAAGCCGCCUUU<br>GCAAAACAUUGCUGCCUAAAGAAACUCAGCAGCCUCAGGCCCAAUU<br>CUGCCACUUCUGGUUUGGGUACAGUUAAAGGCAACCCUGAGGGACU<br>UGGCAGUAGAAAUCCAGGGCCUCCCCUGGGGCUGGCAGCUUCGUGU<br>GCAGCUAGAGCUUUACCUGAAAGGAAGUCUCUGGGCCCAGAACUCU<br>CCACCAAGAGCCUCCCUGCCGUUCGCUGAGUCCCAGCAAUUCUCCU<br>AAGUUGAAGGGAUCUGAGAAGGAGAAGGAAAUGUGGGGUAGAUUU<br>GGUGGUGGUUAGAGAUAUGCCCCCCUCAUUACUGCCAACAGUUUCG<br>GCUGCAUUUCUUCACGCACCUCGGUUCCUCUUCCUGAAGUUCUUGU<br>GCCCUGCUCUUCAGCACCAUGGGCCUUCUUAUACGGAAGGCUCUGG<br>GAUCUCCCCCUUGUGGGGCAGGCUCUUGGGGCCAGCCUAAGAUCAU<br>GGUUUAGGGUGAUCAGUGCUGGCAGAUAAAUUGAAAAGGCACGCU<br>GGCUUGUGAUCUUAAAUGAGGACAAUCCCCCCAGGGCUGGGCACUC<br>CUCCCCUCCCCUCACUUCUCCCACCUGCAGAGCCAGUGUCCUUGGGU<br>GGGCUAGAUAGGAUAUACUGUAUGCCGGCUCCUUCAAGCUGCUGAC<br>UCACUUUAUCAAUAGUUCCAUUUAAAUUGACUUCAGUGGUGAGACU<br>GUAUCCUGUUUGCUAUUGCUUGUUGUGCUAUGGGGGGAGGGGGA<br>GGAAUGUGUAAGAUAGUUAACAUGGGCAAAGGGAGAUCUUGGGGU<br>GCAGCACUUAAACUGCCUCGUAACCCUUUUCAUGAUUUCAACCACA<br>UUUGCUAGAGGGAGGGAGCAGCCACGGAGUUAGAGGCCCUUGGGGU<br>UUCUCUUUUCCACUGACAGGCUUUCCCAGGCAGCUGGCUAGUUCAU<br>UCCCUCCCCAGCCAGGUGCAGGCGUAGGAAUAUGGACAUCUGGUUG<br>CUUUGGCCUGCUGCCCUCUUUCAGGGGUCCUAAGCCCACAAUCAUG<br>CCUCCCUAAGACCUUGGCAUCCUUCCCUCUAAGCCGUUGGCACCUC<br>UGUGCCACCUCUCACACUGGCUCCAGACACACAGCCUGUGCUUUUG<br>GAGCUGAGAUCACUCGCUUCACCCUCCUCAUCUUUGUUCUCCAAGU<br>AAAGCCACGAGGUCGGGGCGAGGGCAGAGGUGAUCACCUGCGUGUC<br>CCAUCUACAGACCUGCAGCUUCAUAAAACUUCUGAUUUCUCUUCAG<br>CUUUGAAAAGGGUUACCCUGGGCACUGGCCUAGAGCCUCACCUCCU<br>AAUAGACUUAGCCCCAUGAGUUUGCCAUGUUGAGCAGGACUAUUUC<br>UGGCACUUGCAAGUCCCAUGAUUUCUUCGGUAAUUCUGAGGGUGGG |

TABLE 4-continued

Human MAPT mRNA Isoform Sequences. Sequences obtained from NCBI MAPT gene ID: 4137; Assembly GRCh38.p13 (GCF_000001405.39); NC_000017.11 (45894538 . . . 46028334)

| SEQ ID NO | Isoform | mRNA Sequence |
|---|---|---|
| | | GGGAGGGACAUGAAAUCAUCUUAGCUUAGCUUUCUGUCUGUGAAU<br>GUCUAUAUAGUGUAUUGUGUGUUUUAACAAAUGAUUUACACUGAC<br>UGUUGCUGUAAAAGUGAAUUUGGAAAUAAAGUUAUUACUCUGAUU<br>AAA |
| 20 | 5 | GCAGUCACCGCCACCCACCAGCUCCGGCACCAACAGCAGCGCCGCUG<br>CCACCGCCCACCUUCUGCCGCCGCCACCACAGCCACCUUCUCCUCCU<br>CCGCUGUCCUCUCCCGUCCUCGCCUCUGUCGACUAUCAGGUGAACU<br>UUGAACCAGGAUGGCUGAGCCCCGCCAGGAGUUCGAAGUGAUGGAA<br>GAUCACGCUGGGACGUACGGGUUGGGGGACAGGAAAGAUCAGGGG<br>GGCUACACCAUGCACCAAGACCAAGAGGGUGACACGGACGCUGGCC<br>UGAAAGAAUCUCCCCUGCAGACCCCCACUGAGGACGGAUCUGAGGA<br>ACCGGGCUCUGAAACCUCUGAUGCUAAGAGCACUCCAACAGCGGAA<br>GCUGAAGAAGCAGGCAUUGGAGACACCCCCAGCCUGGAAGACGAAG<br>CUGCUGGUCACGUGACCCAAGCUCGCAUGGUCAGUAAAAGCAAAGA<br>CGGGACUGGAAGCGAUGACAAAAAAGCCAAGGGGGCUGAUGGUAA<br>AACGAAGAUCGCCACACCGCGGGGAGCAGCCCCUCCAGGCCAGAAG<br>GGCCAGGCCAACGCCACCAGGAUUCCAGCAAAAACCCCGCCCGCUCC<br>AAAGACACCACCCAGCUCUGGUGAACCUCCAAAAUCAGGGGAUCGC<br>AGCGGCUACAGCAGCCCCGGCUCCCCAGGCACUCCCGGCAGCCGCUC<br>CCGCACCCCGUCCCUUCCAACCCCACCCACCCGGGAGCCCAAGAAGG<br>UGGCAGUGGUCCGUACUCCACCCAAGUCGCCGUCUUCCGCCAAGAG<br>CCGCCUGCAGACAGCCCCCGUGCCCAUGCCAGACCUGAAGAAUGUC<br>AAGUCCAAGAUCGGCUCCACUGAGAACCUGAAGCACCAGCCGGGAG<br>GCGGGAAGGUGCAGAUAAUUAAUAAGAAGCUGGAUCUUAGCAACG<br>UCCAGUCCAAGUGUGGCUCAAAGGAUAAUAUCAAACACGUCCCGGG<br>AGGCGGCAGUGUGCAAAUAGUCUACAAACCAGUUGACCUGAGCAAG<br>GUGACCUCCAAGUGUGGCUCAUUAGGCAACAUCCAUCAUAAACCAG<br>GAGGUGGCCAGGUGGAAGUAAAAUCUGAGAAGCUUGACUUCAAGG<br>ACAGAGUCCAGUCGAAGAUUGGGUCCCUGGACAAUAUCACCCACGU<br>CCCUGGCGGAGGAAAUAAAAAGAUUGAAACCCACAAGCUGACCUUC<br>CGCGAGAACGCCAAAGCCAAGACAGACCACGGGGCGGAGAUCGUGU<br>ACAAGUCGCCAGUGGUGUCUGGGGACACGUCUCCACGGCAUCUCAG<br>CAAUGUCUCCUCCACCGGCAGCAUCGACAUGGUAGACUCGCCCCAG<br>CUCGCCACGCUAGCUGACGAGGUGUCUGCCUCCCUGGCCAAGCAGG<br>GUUUGUGAUCAGGCCCCUGGGGCGGUCAAUAAUUGUGGAGAGGAG<br>AGAAUGAGAGAGUGUGGAAAAAAAAAGAAUAAUGACCCGGCCCCCG<br>CCCUCUGCCCCCAGCUGCUCCUCGCAGUUCGGUUAAUUGGUUAAUC<br>ACUUAACCUGCUUUUGUCACUCGGCUUUGGCUCGGGACUUCAAAAU<br>CAGUGAUGGGAGUAAGAGCAAAUUUCAUCUUUCCAAAUUGAUGGG<br>UGGGCUAGUAAUAAAAUAUUUAAAAAAAAACAUUCAAAAACAUGG<br>CCACAUCCAACAUUUCCUCAGGCAAUUCCUUUUGAUUCUUUUUUCU<br>UCCCCCUCCAUGUAGAAGAGGGAGAAGGAGAGGCUCUGAAAGCUGC<br>UUCUGGGGGAUUUCAAGGGACUGGGGGUGCCAACCACCUCUGGCCC<br>UGUUGUGGGGGUGUCACAGAGGCAGUGGCAGCAACAAAGGAUUUG<br>AAACUUGGUGUGUUCGUGGAGCCACAGGCAGACGAUGUCAACCUUG<br>UGUGAGUGUGACGGGGGUUGGGGUGGGGCGGGAGGCCACGGGGA<br>GGCCGAGGCAGGGGCUGGGCAGAGGGGAGAGGAAGCACAAGAAGU<br>GGGAGUGGGAGAGGAAGCCACGUGCUGGAGAGUAGACAUCCCCCUC<br>CUUGCCGCUGGGAGAGCCAAGGCCUAUGCCACCUGCAGCGUCUGAG<br>CGGCCGCCUGUCCUUGGUGGCCGGGGGUGGGGGCCUGCUGUGGGUC<br>AGUGUGCCACCCUCUGCAGGGCAGCCUGUGGGAGAAGGGACAGCGG<br>GUAAAAAGAGAAGGCAAGCUGGCAGGAGGGUGGCACUUCGUGGAU<br>GACCUCCUUAGAAAAGACUGACCUUGAUGUCUUGAGAGCGCUGGCC<br>UCUUCCUCCCUCCCUGCAGGGUAGGGGGCCUGAGUUGAGGGGCUUC<br>CCUCUGCUCCACAGAAACCCUGUUUUAUUGAGUUCUGAAGGUUGGA<br>ACUGCUGCCAUGAUUUUGGCCACUUUGCAGACCUGGGACUUUAGGG<br>CUAACCAGUUCUCUUUGUAAGGACUUGUGCCUCUUGGGAGACGUCC<br>ACCCGUUUCCAAGCCUGGGCCACUGGCAUCUCUGGAGUGUGUGGGG<br>GUCUGGGAGGCAGGUCCCGAGCCCCCUGUCCUUCCCACGGCCACUG<br>CAGUCACCCCGUCUGCGCCGCUGUGCUGUUGUCUGCCGUGAGAGCC<br>CAAUCACUGCCUAUACCCCUCAUCACACGUCACAAUGUCCCGAAUU<br>CCCAGCCUCACCACCCCUUCUCAGUAAUGACCCUGGUUGGUUGCAG<br>GAGGUACCUACUCCAUACUGAGGGUGAAAUUAAGGGAAGGCAAAG<br>UCCAGGCACAAGAGUGGGACCCCAGCCUCUCACUCUCAGUUCCACU<br>CAUCCAACUGGGACCCUCACCACGAAUCUCAUGAUCUGAUUCGGUU<br>CCCUGUCUCCUCCUCCCGUCACAGAUGUGAGCCAGGGCACUGCUCA<br>GCUGUGACCCUAGGUGUUUCUGCCUUGUUGACAUGGAGAGAGCCCU<br>UUCCCCUGAGAAGGCCUGGCCCCUUCCUGUGCUGAGCCCACAGCAG<br>CAGGCUGGGUGUCUUGGUUGUCAGUGGUGGCACCAGGAUGGAAGG<br>GCAAGGCACCCAGGGCAGGCCCACAGUCCCGCUGUCCCCCACUUGCA<br>CCCUAGCUUGUAGCUGCCAACCUCCCAGACAGCCCAGCCCGCUGCUC |

TABLE 4-continued

Human MAPT mRNA Isoform Sequences. Sequences obtained from NCBI MAPT gene ID: 4137; Assembly GRCh38.p13 (GCF_000001405.39); NC_000017.11 (45894538 . . . 46028334)

| SEQ ID NO | Isoform | mRNA Sequence |
|---|---|---|
| | | AGCUCCACAUGCAUAGUAUCAGCCCUCCACACCCGACAAAGGGGAA |
| | | CACACCCCCUUGGAAAUGGUUCUUUUCCCCCAGUCCCAGCUGGAAG |
| | | CCAUGCUGUCUGUUCUGCUGGAGCAGCUGAACAUAUACAUAGAUGU |
| | | UGCCCUGCCCUCCCCAUCUGCACCCUGUUGAGUUGUAGUUGGAUUU |
| | | GUCUGUUUAUGCUUGGAUUCACCAGAGUGACUAUGAUAGUGAAAA |
| | | GAAAAAAAAAAAAAAAAAAGGACGCAUGUAUCUUGAAAUGCUUGU |
| | | AAAGAGGUUUCUAACCCACCCUCACGAGGUGUCUCUCACCCCCACA |
| | | CUGGGACUCGUGUGGCCUGUGUGGUGCCACCCUGCUGGGGCCUCCC |
| | | AAGUUUUGAAAGGCUUUCCUCAGCACCUGGGACCCAACAGAGACCA |
| | | GCUUCUAGCAGCUAAGGAGGCCGUUCAGCUGUGACGAAGGCCUGAA |
| | | GCACAGGAUUAGGACUGAAGCGAUGAUGUCCCCUUCCCUACUUCCC |
| | | CUUGGGGCUCCCUGUGUCAGGGCACAGACUAGGUCUUGUGGCUGGU |
| | | CUGGCUUGCGGCGCGAGGAUGGUUCUCUCUGGUCAUAGCCCGAAGU |
| | | CUCAUGGCAGUCCCAAAGGAGGCUUACAACUCCUGCAUCACAAGAA |
| | | AAAGGAAGCCACUGCCAGCUGGGGGGAUCUGCAGCUCCCAGAAGCU |
| | | CCGUGAGCCUCAGCCACCCCUCAGACUGGGUUCCUCUCCAAGCUCGC |
| | | CCUCUGGAGGGGCAGCGCAGCCUCCCACCAAGGGCCCUGCGACCAC |
| | | AGCAGGGAUUGGGAUGAAUUGCCUGUCCUGGAUCUGCUCUAGAGGC |
| | | CCAAGCUGCCUGCCUGAGGAAGGAUGACUUGACAAGUCAGGAGACA |
| | | CUGUUCCCAAAGCCUUGACCAGAGCACCUCAGCCCGCUGACCUUGC |
| | | ACAAACUCCAUCUGCUGCCAUGAGAAAAGGGAAGCCGCCUUUGCAA |
| | | AACAUUGCUGCCUAAAGAAACUCAGCAGCCUCAGGCCCAAUUCUGC |
| | | CACUUCUGGUUUGGGUACAGUUAAAGGCAACCCUGAGGGACUUGGC |
| | | AGUAGAAAUCCAGGGCCUCCCCUGGGGCUGGCAGCUUCGUGUGCAG |
| | | CUAGAGCUUUACCUGAAAGGAAGUCUCUGGGCCCAGAACUCUCCAC |
| | | CAAGAGCCUCCCUGCCGUUCGCUGAGUCCCAGCAAUUCUCCUAAGU |
| | | UGAAGGGAUCUGAGAAGGAGAAGGAAAUGUGGGGUAGAUUUGGUG |
| | | GUGGUUAGAGAUAUGCCCCCCUCAUUACUGCCAACAGUUUCGGCUG |
| | | CAUUUCUUCACGCACCUCGGUUCCUCUUCCUGAAGUUCUUGUGCCC |
| | | UGCUCUUCAGCACCAUGGGCCUUCUUAUACGGAAGGCUCUGGGAUC |
| | | UCCCCCUUGUGGGGCAGGCUCUUGGGGCCAGCCUAAGAUCAUGGUU |
| | | UAGGGUGAUCAGUGCUGGCAGAUAAAUUGAAAAGGCACGCUGGCU |
| | | UGUGAUCUUAAAUGAGGACAAUCCCCCCAGGGCUGGGCACUCCUCC |
| | | CCUCCCCUCACUUCUCCCACCUGCAGAGCCAGUGUCCUUGGGUGGG |
| | | CUAGAUAGGAUAUACUGUAUGCCGGCUCCUUCAAGCUGCUGACUCA |
| | | CUUUAUCAAUAGUUCCAUUUAAAUUGACUUCAGUGGUGAGACUGU |
| | | AUCCUGUUUGCUAUUGCUUGUUGUGCUAUGGGGGGAGGGGGGAGG |
| | | AAUGUGUAAGAUAGUUAACAUGGGCAAAGGGAGAUCUUGGGGUGC |
| | | AGCACUUAAACUGCCUCGUAACCCUUUUCAUGAUUUCAACCACAUU |
| | | UGCUAGAGGGAGGGAGCAGCCACGGAGUUAGAGGCCCUUGGGGUUU |
| | | CUCUUUUCCACUGACAGGCUUUCCCAGGCAGCUGGCUAGUUCAUUC |
| | | CCUCCCCAGCCAGGUGCAGGCGUAGGAAUAUGGACAUCUGGUUGCU |
| | | UUGGCCUGCUGCCCUCUUUCAGGGGUCCUAAGCCCACAAUCAUGCC |
| | | UCCCUAAGACCUUGGCAUCCUUCCCUCUAAGCCGUUGGCACCUCUG |
| | | UGCCACCUCUCACACUGGCUCCAGACACACAGCCUGUGCUUUUGGA |
| | | GCUGAGAUCACUCGCUUCACCCUCCUCAUCUUUGUUCUCCAAGUAA |
| | | AGCCACGAGGUCGGGGCGAGGGCAGAGGUGAUCACCUGCGUGUCCC |
| | | AUCUACAGACCUGCAGCUUCAUAAAACUUCUGAUUUCUCUUCAGCU |
| | | UUGAAAAGGGUUACCCUGGGCACUGGCCUAGAGCCUCACCUCCUAA |
| | | UAGACUUAGCCCCAUGAGUUUGCCAUGUUGAGCAGGACUAUUUCUG |
| | | GCACUUGCAAGUCCCAUGAUUUCUUCGGUAAUUCUGAGGGUGGGGG |
| | | GAGGGACAUGAAAUCAUCUUAGCUUAGCUUUCUGUCUGUGAAUGUC |
| | | UAUAUAGUGUAUUGUGUGUUUUAACAAAUGAUUUACACUGACUGU |
| | | UGCUGUAAAAGUGAAUUUGGAAAUAAAGUUAUUACUCUGAUUAAA |
| 21 | 6 | GCAGUCACCGCCACCCACCAGCUCCGGCACCAACAGCAGCGCCGCUG |
| | | CCACCGCCCACCUUCUGCCGCCGCCACCACAGCCACCUUCUCCUCCU |
| | | CCGCUGUCCUCUCCCGUCCUCGCCUCUGUCGACUAUCAGGUGAACU |
| | | UUGAACCAGGAUGGCUGAGCCCCGCCAGGAGUUCGAAGUGAUGGAA |
| | | GAUCACGCUGGGACGUACGGGUUGGGGACAGGAAAGAUCAGGGG |
| | | GGCUACACCAUGCACCAAGACCAAGAGGGUGACACGGACGCUGGCC |
| | | UGAAAGAAUCUCCCCUGCAGACCCCCACUGAGGACGGAUCUGAGGA |
| | | ACCGGGCUCUGAAACCUCUGAUGCUAAGAGCACUCCAACAGCGGAA |
| | | GAUGUGACAGCACCCUUAGUGGAUGAGGGAGCUCCCGGCAAGCAGG |
| | | CUGCCGCGCAGCCCCACACGGAGAUCCCAGAAGGAACCACAGCUGA |
| | | AGAAGCAGGCAUUGGAGACACCCCCAGCCUGGAAGACGAAGCUGCU |
| | | GGUCACGUGACCCAAGAGCCUGAAAGUGGUAAGGUGGUCCAGGAAG |
| | | GCUUCCUCCGAGAGCCAGGCCCCCCAGGUCUGAGCCACCAGCUCAU |
| | | GUCCGGCAUGCCUGGGGCUCCCCUCCUGCCUGAGGGCCCCAGAGAG |
| | | GCCACACGCCAACCUUCGGGGACAGGACCUGAGGACACAGAGGGCG |
| | | GCCGCCACGCCCCUGAGCUGCUCAAGCACCAGCUUCUAGGAGACCU |
| | | GCACCAGGAGGGGCCGCCGCUGAAGGGGGCAGGGGGCAAAGAGAGG |

TABLE 4-continued

Human MAPT mRNA Isoform Sequences. Sequences obtained from NCBI MAPT gene ID: 4137; Assembly GRCh38.p13 (GCF_000001405.39); NC_000017.11 (45894538 . . . 46028334)

| SEQ ID NO | Isoform | mRNA Sequence |
|---|---|---|
| | | CCGGGGAGCAAGGAGGAGGUGGAUGAAGACCGCGACGUCGAUGAGU<br>CCUCCCCCCAAGACUCCCCUCCCUCCAAGGCCUCCCCAGCCCAAGAU<br>GGGCGGCCUCCCCAGACAGCCGCCAGAGAAGCCACCAGCAUCCCAG<br>GCUUCCCAGCGGAGGGUGCCAUCCCCCUCCCUGUGGAUUUCCUCUC<br>CAAAGUUUCCACAGAGAUCCCAGCCUCAGAGCCCGACGGGCCCAGU<br>GUAGGGCGGGCCAAAGGGCAGGAUGCCCCCCUGGAGUUCACGUUUC<br>ACGUGGAAAUCACACCCAACGUGCAGAAGGAGCAGGCGCACUCGGA<br>GGAGCAUUUGGGAAGGGCUGCAUUUCCAGGGGCCCCUGGAGAGGGG<br>CCAGAGGCCCGGGGCCCCUCUUUGGGAGAGGACACAAAAGAGGCUG<br>ACCUUCCAGAGCCCUCUGAAAAGCAGCCUGCUGCUGCUCCGCGGGG<br>GAAGCCCGUCAGCCGGGUCCCUCAACUCAAAGCUCGCAUGGUCAGU<br>AAAAGCAAAGACGGGACUGGAAGCGAUGACAAAAAAGCCAAGACAU<br>CCACACGUUCCUCUGCUAAAACCUUGAAAAAUAGGCCUUGCCUUAG<br>CCCCAAACACCCCACUCCUGGUAGCUCAGACCCUCUGAUCCAACCCU<br>CCAGCCCUGCUGUGUGCCCAGAGCCACCUUCCUCUCCUAAAUACGU<br>CUCUUCUGUCACUUCCCGAACUGGCAGUUCUGGAGCAAAGGAGAUG<br>AAACUCAAGGGGGCUGAUGGUAAAACGAAGAUCGCCACACCGCGGG<br>GAGCAGCCCCUCCAGGCCAGAAGGGCCAGGCCAACGCCACCAGGAU<br>UCCAGCAAAAACCCCGCCCGCUCCAAAGACACCACCCAGCUCUGCGA<br>CUAAGCAAGUCCAGAGAAGACCACCCCCUGCAGGGCCCAGAUCUGA<br>GAGAGGUGAACCUCCAAAAUCAGGGGAUCGCAGCGGCUACAGCAGC<br>CCCGGCUCCCCAGGCACUCCCGGCAGCCGCUCCCGCACCCCGUCCCU<br>UCCAACCCCACCCACCCGGGAGCCCAAGAAGGUGGCAGUGGUCCGU<br>ACUCCACCCAAGUCGCCGUCUUCCGCCAAGAGCCGCCUGCAGACAGC<br>CCCCGUGCCCAUGCCAGACCUGAAGAAUGUCAAGUCCAAGAUCGGC<br>UCCACUGAGAACCUGAAGCACCAGCCGGGAGGCGGGAAGGUGCAGA<br>UAAUUAAUAAGAAGCUGGAUCUUAGCAACGUCCAGUCCAAGUGUGG<br>CUCAAAGGAUAAUAUCAAACACGUCCCGGGAGGCGGCAGUGUGCAA<br>AUAGUCUACAAACCAGUUGACCUGAGCAAGGUGACCUCCAAGUGUG<br>GCUCAUUAGGCAACAUCCAUCAUAAACCAGGAGGUGGCCAGGUGGA<br>AGUAAAAUCUGAGAAGCUUGACUUCAAGGACAGAGUCCAGUCGAAG<br>AUUGGGUCCCUGGACAAUAUCACCCACGUCCCUGGCGGAGGAAAUA<br>AAAAGAUUGAAACCCACAAGCUGACCUUCCGCGAGAACGCCAAAGC<br>CAAGACAGACCACGGGGCGGAGAUCGUGUACAAGUCGCCAGUGGUG<br>UCUGGGGACACGUCUCCACGGCAUCUCAGCAAUGUCUCCUCCACCG<br>GCAGCAUCGACAUGGUAGACUCGCCCCAGCUCGCCACGCUAGCUGA<br>CGAGGUGUCUGCCUCCCUGGCCAAGCAGGGUUUGUGAUCAGGCCCC<br>UGGGGCGGUCAAUAAUUGUGGAGAGGAGAGAAUGAGAGAGUGUGG<br>AAAAAAAAAGAAUAAUGACCCGGCCCCCGCCCUCUGCCCCCAGCUG<br>CUCCUCGCAGUUCGGUUAAUUGGUUAAUCACUUAACCUGCUUUUGU<br>CACUCGGCUUUGGCUCGGGACUUCAAAAUCAGUGAUGGGAGUAAGA<br>GCAAAUUUCAUCUUUCCAAAUUGAUGGGUGGGCUAGUAAUAAAAU<br>AUUUAAAAAAAAACAUUCAAAAACAUGGCCACAUCCAACAUUUCCU<br>CAGGCAAUUCCUUUUGAUUCUUUUUUCUUCCCCCUCCAUGUAGAAG<br>AGGGAGAAGGAGAGGCUCUGAAAGCUGCUUCUGGGGGAUUUCAAG<br>GGACUGGGGGUGCCAACCACCUCUGGCCCUGUUGUGGGGGUGUCAC<br>AGAGGCAGUGGCAGCAACAAAGGAUUUGAAACUUGGUGUGUUCGU<br>GGAGCCACAGGCAGACGAUGUCAACCUUGUGUGAGUGUGACGGGGG<br>UUGGGGUGGGGCGGGAGGCCACGGGGGAGGCCGAGGCAGGGGCUGG<br>GCAGAGGGGAGAGGAAGCACAAGAAGUGGGAGUGGGAGAGGAAGC<br>CACGUGCUGGAGAGUAGACAUCCCCCUCCUUGCCGCUGGGAGAGCC<br>AAGGCCUAUGCCACCUGCAGCGUCUGAGCGGCCGCCUGUCCUUGGU<br>GGCCGGGGGUGGGGGCCUGCUGUGGGUCAGUGUGCCACCCUCUGCA<br>GGGCAGCCUGUGGGAGAAGGGACAGCGGGUAAAAAGAGAAGGCAA<br>GCUGGCAGGAGGGUGGCACUUCGUGGAUGACCUCCUUAGAAAAGAC<br>UGACCUUGAUGUCUUGAGAGCGCUGGCCUCUUCCUCCCUCCCUGCA<br>GGGUAGGGGGCCUGAGUUGAGGGGCUUCCCUCUGCUCCACAGAAAC<br>CCUGUUUUAUUGAGUUCUGAAGGUUGGAACUGCUGCCAUGAUUUU<br>GGCCACUUUGCAGACCUGGGACUUUAGGGCUAACCAGUUCUCUUUG<br>UAAGGACUUGUGCCUCUUGGGAGACGUCCACCCGUUUCCAAGCCUG<br>GGCCACUGGCAUCUCUGGAGUGUGUGGGGGUCUGGGAGGCAGGUCC<br>CGAGCCCCCUGUCCUUCCCACGGCCACUGCAGUCACCCCGUCUGCGC<br>CGCUGUGCUGUUGUCUGCCGUGAGAGCCCAAUCACUGCCUAUACCC<br>CUCAUCACACGUCACAAUGUCCCGAAUUCCCAGCCUCACCACCCCUU<br>CUCAGUAAUGACCCUGGUUGGUUGCAGGAGGUACCUACUCCAUACU<br>GAGGGUGAAAUUAAGGGAAGGCAAAGUCCAGGCACAAGAGUGGGA<br>CCCCAGCCUCUCACUCUCAGUUCCACUCAUCCAACUGGGACCCUCAC<br>CACGAAUCUCAUGAUCUGAUUCGGUUCCCUGUCUCCUCCUCCCGUC<br>ACAGAUGUGAGCCAGGGCACUGCUCAGCUGUGACCCUAGGUGUUUC<br>UGCCUUGUUGACAUGGAGAGAGCCCUUUCCCCUGAGAAGGCCUGGC<br>CCCUUCCUGUGCUGAGCCCACAGCAGCAGGCUGGGUGUCUUGGUUG<br>UCAGUGGUGGCACCAGGAUGGAAGGGCAAGGCACCCAGGGCAGGCC |

TABLE 4-continued

Human MAPT mRNA Isoform Sequences. Sequences obtained from NCBI MAPT gene ID: 4137; Assembly GRCh38.p13 (GCF_000001405.39); NC_000017.11 (45894538 . . . 46028334)

| SEQ ID NO | Isoform | mRNA Sequence |
|---|---|---|
| | | CACAGUCCCGCUGUCCCCCACUUGCACCCUAGCUUGUAGCUGCCAAC |
| | | CUCCCAGACAGCCCAGCCCGCUGCUCAGCUCCACAUGCAUAGUAUC |
| | | AGCCCUCCACACCCGACAAAGGGGAACACACCCCCUUGGAAAUGGU |
| | | UCUUUUCCCCCAGUCCCAGCUGGAAGCCAUGCUGUCUGUUCUGCUG |
| | | GAGCAGCUGAACAUAUACAUAGAUGUUGCCCUGCCCUCCCCAUCUG |
| | | CACCCUGUUGAGUUGUAGUUGGAUUUGUCUGUUUAUGCUUGGAUU |
| | | CACCAGAGUGACUAUGAUAGUGAAAAGAAAAAAAAAAAAAAAAA |
| | | GGACGCAUGUAUCUUGAAAUGCUUGUAAAGAGGUUUCUAACCCACC |
| | | CUCACGAGGUGUCUCUCACCCCCACACUGGGACUCGUGUGGCCUGU |
| | | GUGGUGCCACCCUGCUGGGGCCUCCCAAGUUUUGAAAGGCUUUCCU |
| | | CAGCACCUGGGACCCAACAGAGACCAGCUUCUAGCAGCUAAGGAGG |
| | | CCGUUCAGCUGUGACGAAGGCCUGAAGCACAGGAUUAGGACUGAAG |
| | | CGAUGAUGUCCCCUUCCCUACUUCCCCUUGGGGCUCCCUGUGUCAG |
| | | GGCACAGACUAGGUCUUGUGGCUGGUCUGGCUUGCGGCGCGAGGAU |
| | | GGUUCUCUCUGGUCAUAGCCCGAAGUCUCAUGGCAGUCCCAAAGGA |
| | | GGCUUACAACUCCUGCAUCACAAGAAAAAGGAAGCCACUGCCAGCU |
| | | GGGGGGAUCUGCAGCUCCCAGAAGCUCCGUGAGCCUCAGCCACCCC |
| | | UCAGACUGGGUUCCUCUCCAAGCUCGCCCUCUGGAGGGGCAGCGCA |
| | | GCCUCCCACCAAGGGCCCUGCGACCACAGCAGGGAUUGGGAUGAAU |
| | | UGCCUGUCCUGGAUCUGCUCUAGAGGCCCAAGCUGCCUGCCUGAGG |
| | | AAGGAUGACUUGACAAGUCAGGAGACACUGUUCCCAAAGCCUUGAC |
| | | CAGAGCACCUCAGCCCGCUGACCUUGCACAAACUCCAUCUGCUGCC |
| | | AUGAGAAAAGGGAAGCCGCCUUUGCAAAACAUUGCUGCCUAAAGAA |
| | | ACUCAGCAGCCUCAGGCCCAAUUCUGCCACUUCUGGUUUGGGUACA |
| | | GUUAAAGGCAACCCUGAGGGACUUGGCAGUAGAAAUCCAGGGCCUC |
| | | CCCUGGGGCUGGCAGCUUCGUGUGCAGCUAGAGCUUUACCUGAAAG |
| | | GAAGUCUCUGGGCCCAGAACUCUCCACCAAGAGCCUCCCUGCCGUU |
| | | CGCUGAGUCCCAGCAAUUCUCCUAAGUUGAAGGGAUCUGAGAAGGA |
| | | GAAGGAAAUGUGGGGUAGAUUUGGUGGUGGUUAGAGAUAUGCCCC |
| | | CCUCAUUACUGCCAACAGUUUCGGCUGCAUUUCUUCACGCACCUCG |
| | | GUUCCUCUUCCUGAAGUUCUUGUGCCCUGCUCUUCAGCACCAUGGG |
| | | CCUUCUUAUACGGAAGGCUCUGGGAUCUCCCCCUUGUGGGGCAGGC |
| | | UCUUGGGGCCAGCCUAAGAUCAUGGUUUAGGGUGAUCAGUGCUGGC |
| | | AGAUAAAUUGAAAAGGCACGCUGGCUUGUGAUCUUAAAUGAGGAC |
| | | AAUCCCCCCAGGGCUGGGCACUCCUCCCCUCCCCUCACUUCUCCCAC |
| | | CUGCAGAGCCAGUGUCCUUGGGUGGGCUAGAUAGGAUAUACUGUAU |
| | | GCCGGCUCCUUCAAGCUGCUGACUCACUUUAUCAAUAGUUCCAUUU |
| | | AAAUUGACUUCAGUGGUGAGACUGUAUCCUGUUUGCUAUUGCUUG |
| | | UUGUGCUAUGGGGGGAGGGGGGAGGAAUGUGUAAGAUAGUUAACA |
| | | UGGGCAAAGGGAGAUCUUGGGGUGCAGCACUUAAACUGCCUCGUAA |
| | | CCCUUUUCAUGAUUUCAACCACAUUUGCUAGAGGGAGGGAGCAGCC |
| | | ACGGAGUUAGAGGCCCUUGGGGUUUCUCUUUUCCACUGACAGGCUU |
| | | UCCCAGGCAGCUGGCUAGUUCAUUCCCUCCCCAGCCAGGUGCAGGC |
| | | GUAGGAAUAUGGACAUCUGGUUGCUUUGGCCUGCUGCCCUCUUUCA |
| | | GGGGUCCUAAGCCCACAAUCAUGCCUCCCUAAGACCUUGGCAUCCU |
| | | UCCCUCUAAGCCGUUGGCACCUCUGUGCCACCUCUCACACUGGCUCC |
| | | AGACACACAGCCUGUGCUUUUGGAGCUGAGAUCACUCGCUUCACCC |
| | | UCCUCAUCUUUGUUCUCCAAGUAAAGCCACGAGGUCGGGGCGAGGG |
| | | CAGAGGUGAUCACCUGCGUGUCCCAUCUACAGACCUGCAGCUUCAU |
| | | AAAACUUCUGAUUUCUCUUCAGCUUUGAAAAGGGUUACCCUGGGCA |
| | | CUGGCCUAGAGCCUCACCUCCUAAUAGACUUAGCCCCAUGAGUUUG |
| | | CCAUGUUGAGCAGGACUAUUUCUGGCACUUGCAAGUCCCAUGAUUU |
| | | CUUCGGUAAUUCUGAGGGUGGGGGGAGGGACAUGAAAUCAUCUUA |
| | | GCUUAGCUUUCUGUCUGUGAAUGUCUAUAUAGUGUAUUGUGUGUU |
| | | UUAACAAAUGAUUUACACUGACUGUUGCUGUAAAAGUGAAUUUGG |
| | | AAAUAAAGUUAUUACUCUGAUUAAA |
| 22 | 7 | GCAGUCACCGCCACCCACCAGCUCCGGCACCAACAGCAGCGCCGCUG |
| | | CCACCGCCCACCUUCUGCCGCCGCCACCACAGCCACCUUCUCCUCCU |
| | | CCGCUGUCCUCUCCCGUCCUCGCCUCUGUCGACUAUCAGGUGAACU |
| | | UUGAACCAGGAUGGCUGAGCCCCGCCAGGAGUUCGAAGUGAUGGAA |
| | | GAUCACGCUGGGACGUACGGGUUGGGGGACAGGAAAGAUCAGGGG |
| | | GGCUACACCAUGCACCAAGACCAAGAGGGUGACACGGACGCUGGCC |
| | | UGAAAGAAUCUCCCCUGCAGACCCCCACUGAGGACGGAUCUGAGGA |
| | | ACCGGGCUCUGAAACCUCUGAUGCUAAGAGCACUCCAACAGCGGAA |
| | | GCUGAAGAAGCAGGCAUUGGAGACACCCCCAGCCUGGAAGACGAAG |
| | | CUGCUGGUCACGUGACCCAAGCUCGCAUGGUCAGUAAAAGCAAAGA |
| | | CGGGACUGGAAGCGAUGACAAAAAAGCCAAGGGGGCUGAUGGUAA |
| | | AACGAAGAUCGCCACACCGCGGGGAGCAGCCCCUCCAGGCCAGAAG |
| | | GGCCAGGCCAACGCCACCAGGAUUCCAGCAAAAACCCCGCCCGCUCC |
| | | AAAGACACCACCCAGCUCUGGUGAACCUCCAAAAUCAGGGGAUCGC |
| | | AGCGGCUACAGCAGCCCCGGCUCCCCAGGCACUCCCGGCAGCCGCUC |

TABLE 4-continued

Human MAPT mRNA Isoform Sequences. Sequences obtained from NCBI MAPT gene ID: 4137; Assembly GRCh38.p13 (GCF_000001405.39); NC_000017.11 (45894538 . . . 46028334)

| SEQ ID NO | Isoform | mRNA Sequence |
|---|---|---|
| | | CCGCACCCCGUCCCUUCCAACCCCACCCACCCGGGAGCCCAAGAAGG<br>UGGCAGUGGUCCGUACUCCACCCAAGUCGCCGUCUUCCGCCAAGAG<br>CCGCCUGCAGACAGCCCCCGUGCCCAUGCCAGACCUGAAGAAUGUC<br>AAGUCCAAGAUCGGCUCCACUGAGAACCUGAAGCACCAGCCGGGAG<br>GCGGGAAGGUGCAAAUAGUCUACAAACCAGUUGACCUGAGCAAGGU<br>GACCUCCAAGUGUGGCUCAUUAGGCAACAUCCAUCAUAAACCAGGA<br>GGUGGCCAGGUGGAAGUAAAAUCUGAGAAGCUUGACUUCAAGGAC<br>AGAGUCCAGUCGAAGAUUGGGUCCCUGGACAAUAUCACCCACGUCC<br>CUGGCGGAGGAAAUAAAAAGAUUGAAACCCACAAGCUGACCUUCCG<br>CGAGAACGCCAAAGCCAAGACAGACCACGGGGCGGAGAUCGUGUAC<br>AAGUCGCCAGUGGUGUCUGGGGACACGUCUCCACGGCAUCUCAGCA<br>AUGUCUCCUCCACCGGCAGCAUCGACAUGGUAGACUCGCCCCAGCU<br>CGCCACGCUAGCUGACGAGGUGUCUGCCUCCCUGGCCAAGCAGGGU<br>UUGUGAUCAGGCCCCUGGGGCGGUCAAUAAUUGUGGAGAGGAGAG<br>AAUGAGAGAGUGUGGAAAAAAAAAGAAUAAUGACCCGGCCCCCGCC<br>CUCUGCCCCCAGCUGCUCCUCGCAGUUCGGUUAAUUGGUUAAUCAC<br>UUAACCUGCUUUUGUCACUCGGCUUUGGCUCGGGACUUCAAAAUCA<br>GUGAUGGGAGUAAGAGCAAAUUUCAUCUUUCCAAAUUGAUGGGUG<br>GGCUAGUAAUAAAAUAUUUAAAAAAAAACAUUCAAAAACAUGGCC<br>ACAUCCAACAUUUCCUCAGGCAAUUCCUUUUGAUUCUUUUUUCUUC<br>CCCCUCCAUGUAGAAGAGGGAGAAGGAGAGGCUCUGAAAGCUGCUU<br>CUGGGGGAUUUCAAGGGACUGGGGGUGCCAACCACCUCUGGCCCUG<br>UUGUGGGGGUGUCACAGAGGCAGUGGCAGCAACAAAGGAUUUGAA<br>ACUUGGUGUGUUCGUGGAGCCACAGGCAGACGAUGUCAACCUUGUG<br>UGAGUGUGACGGGGGUUGGGGUGGGGCGGGAGGCCACGGGGGAGG<br>CCGAGGCAGGGGCUGGGCAGAGGGGAGAGGAAGCACAAGAAGUGG<br>GAGUGGGAGAGGAAGCCACGUGCUGGAGAGUAGACAUCCCCCUCCU<br>UGCCGCUGGGAGAGCCAAGGCCUAUGCCACCUGCAGCGUCUGAGCG<br>GCCGCCUGUCCUUGGUGGCCGGGGGUGGGGGCCUGCUGUGGGUCAG<br>UGUGCCACCCUCUGCAGGGCAGCCUGUGGGAGAAGGGACAGCGGGU<br>AAAAAGAGAAGGCAAGCUGGCAGGAGGGUGGCACUUCGUGGAUGA<br>CCUCCUUAGAAAAGACUGACCUUGAUGUCUUGAGAGCGCUGGCCUC<br>UUCCUCCCUCCCUGCAGGGUAGGGGGCCUGAGUUGAGGGGCUUCCC<br>UCUGCUCCACAGAAACCCUGUUUUAUUGAGUUCUGAAGGUUGGAAC<br>UGCUGCCAUGAUUUUGGCCACUUUGCAGACCUGGGACUUUAGGGCU<br>AACCAGUUCUCUUUGUAAGGACUUGUGCCUCUUGGGAGACGUCCAC<br>CCGUUUCCAAGCCUGGGCCACUGGCAUCUCUGGAGUGUGUGGGGGU<br>CUGGGAGGCAGGUCCCGAGCCCCCUGUCCUUCCCACGGCCACUGCA<br>GUCACCCCGUCUGCGCCGCUGUGCUGUUGUCUGCCGUGAGAGCCCA<br>AUCACUGCCUAUACCCCUCAUCACACGUCACAAUGUCCCGAAUUCC<br>CAGCCUCACCACCCCUUCUCAGUAAUGACCCUGGUUGGUUGCAGGA<br>GGUACCUACUCCAUACUGAGGGUGAAAUUAAGGGAAGGCAAAGUCC<br>AGGCACAAGAGUGGGACCCCAGCCUCUCACUCUCAGUUCCACUCAU<br>CCAACUGGGACCCUCACCACGAAUCUCAUGAUCUGAUUCGGUUCCC<br>UGUCUCCUCCUCCCGUCACAGAUGUGAGCCAGGGCACUGCUCAGCU<br>GUGACCCUAGGUGUUUCUGCCUUGUUGACAUGGAGAGAGCCCUUUC<br>CCCUGAGAAGGCCUGGCCCCUUCCUGUGCUGAGCCCACAGCAGCAG<br>GCUGGGUGUCUUGGUUGUCAGUGGUGGCACCAGGAUGGAAGGGCA<br>AGGCACCCAGGGCAGGCCCACAGUCCCGCUGUCCCCCACUUGCACCC<br>UAGCUUGUAGCUGCCAACCUCCCAGACAGCCCAGCCCGCUGCUCAG<br>CUCCACAUGCAUAGUAUCAGCCCUCCACACCCGACAAAGGGGAACA<br>CACCCCCUUGGAAAUGGUUCUUUUCCCCCAGUCCCAGCUGGAAGCC<br>AUGCUGUCUGUUCUGCUGGAGCAGCUGAACAUAUACAUAGAUGUUG<br>CCCUGCCCUCCCCAUCUGCACCCUGUUGAGUUGUAGUUGGAUUUGU<br>CUGUUUAUGCUUGGAUUCACCAGAGUGACUAUGAUAGUGAAAAGA<br>AAAAAAAAAAAAAAAAAGGACGCAUGUAUCUUGAAAUGCUUGUAA<br>AGAGGUUUCUAACCCACCCUCACGAGGUGUCUCUCACCCCCACACU<br>GGGACUCGUGUGGCCUGUGUGGUGCCACCCUGCUGGGGCCUCCCAA<br>GUUUUGAAAGGCUUUCCUCAGCACCUGGGACCCAACAGAGACCAGC<br>UUCUAGCAGCUAAGGAGGCCGUUCAGCUGUGACGAAGGCCUGAAGC<br>ACAGGAUUAGGACUGAAGCGAUGAUGUCCCCUUCCCUACUUCCCCU<br>UGGGGCUCCCUGUGUCAGGGCACAGACUAGGUCUUGUGGCUGGUCU<br>GGCUUGCGGCGCGAGGAUGGUUCUCUCUGGUCAUAGCCCGAAGUCU<br>CAUGGCAGUCCCAAAGGAGGCUUACAACUCCUGCAUCACAAGAAAA<br>AGGAAGCCACUGCCAGCUGGGGGGAUCUGCAGCUCCCAGAAGCUCC<br>GUGAGCCUCAGCCACCCCUCAGACUGGGUUCCUCUCCAAGCUCGCCC<br>UCUGGAGGGGCAGCGCAGCCUCCCACCAAGGGCCCUGCGACCACAG<br>CAGGGAUUGGGAUGAAUUGCCUGUCCUGGAUCUGCUCUAGAGGCCC<br>AAGCUGCCUGCCUGAGGAAGGAUGACUUGACAAGUCAGGAGACACU<br>GUUCCCAAAGCCUUGACCAGAGCACCUCAGCCCGCUGACCUUGCAC<br>AAACUCCAUCUGCUGCCAUGAGAAAAGGGAAGCCGCCUUUGCAAAA<br>CAUUGCUGCCUAAAGAAACUCAGCAGCCUCAGGCCCAAUUCUGCCA |

TABLE 4-continued

Human MAPT mRNA Isoform Sequences. Sequences obtained from NCBI MAPT gene ID: 4137; Assembly GRCh38.p13 (GCF_000001405.39); NC_000017.11 (45894538 . . . 46028334)

| SEQ ID NO | Isoform | mRNA Sequence |
| --- | --- | --- |
| | | CUUCUGGUUUGGGUACAGUUAAAGGCAACCCUGAGGGACUUGGCAG |
| | | UAGAAAUCCAGGGCCUCCCCUGGGGCUGGCAGCUUCGUGUGCAGCU |
| | | AGAGCUUUACCUGAAAGGAAGUCUCUGGGCCCAGAACUCUCCACCA |
| | | AGAGCCUCCCUGCCGUUCGCUGAGUCCCAGCAAUUCUCCUAAGUUG |
| | | AAGGGAUCUGAGAAGGAGAAGGAAAUGUGGGGUAGAUUUGGUGGU |
| | | GGUUAGAGAUAUGCCCCCCUCAUUACUGCCAACAGUUUCGGCUGCA |
| | | UUUCUUCACGCACCUCGGUUCCUCUUCCUGAAGUUCUUGUGCCCUG |
| | | CUCUUCAGCACCAUGGGCCUUCUUAUACGGAAGGCUCUGGGAUCUC |
| | | CCCCUUGUGGGGCAGGCUCUUGGGGCCAGCCUAAGAUCAUGGUUUA |
| | | GGGUGAUCAGUGCUGGCAGAUAAAUUGAAAAGGCACGCUGGCUUG |
| | | UGAUCUUAAAUGAGGACAAUCCCCCCAGGGCUGGGCACUCCUCCCC |
| | | UCCCCUCACUUCUCCCACCUGCAGAGCCAGUGUCCUUGGGUGGGCU |
| | | AGAUAGGAUAUACUGUAUGCCGGCUCCUUCAAGCUGCUGACUCACU |
| | | UUAUCAAUAGUUCCAUUUAAAUUGACUUCAGUGGUGAGACUGUAU |
| | | CCUGUUUGCUAUUGCUUGUUGUGCUAUGGGGGGAGGGGGGAGGAA |
| | | UGUGUAAGAUAGUUAACAUGGGCAAAGGGAGAUCUUGGGGUGCAG |
| | | CACUUAAACUGCCUCGUAACCCUUUUCAUGAUUUCAACCACAUUUG |
| | | CUAGAGGGAGGGAGCAGCCACGGAGUUAGAGGCCCUUGGGGUUUCU |
| | | CUUUUCCACUGACAGGCUUUCCCAGGCAGCUGGCUAGUUCAUUCCC |
| | | UCCCCAGCCAGGUGCAGGCGUAGGAAUAUGGACAUCUGGUUGCUUU |
| | | GGCCUGCUGCCCUCUUUCAGGGGUCCUAAGCCCACAAUCAUGCCUC |
| | | CCUAAGACCUUGGCAUCCUUCCCUCUAAGCCGUUGGCACCUCUGUG |
| | | CCACCUCUCACACUGGCUCCAGACACACAGCCUGUGCUUUUGGAGC |
| | | UGAGAUCACUCGCUUCACCCUCCUCAUCUUUGUUCUCCAAGUAAAG |
| | | CCACGAGGUCGGGGCGAGGGCAGAGGUGAUCACCUGCGUGUCCCAU |
| | | CUACAGACCUGCAGCUUCAUAAAACUUCUGAUUUCUCUUCAGCUUU |
| | | GAAAAGGGUUACCCUGGGCACUGGCCUAGAGCCUCACCUCCUAAUA |
| | | GACUUAGCCCCAUGAGUUUGCCAUGUUGAGCAGGACUAUUUCUGGC |
| | | ACUUGCAAGUCCCAUGAUUUCUUCGGUAAUUCUGAGGGUGGGGGA |
| | | GGGACAUGAAAUCAUCUUAGCUUAGCUUUCUGUCUGUGAAUGUCUA |
| | | UAUAGUGUAUUGUGUGUUUUAACAAAUGAUUUACACUGACUGUUG |
| | | CUGUAAAAGUGAAUUUGGAAAUAAAGUUAUUACUCUGAUUAAA |
| 23 | 8 | GCAGUCACCGCCACCCACCAGCUCCGGCACCAACAGCAGCGCCGCUG |
| | | CCACCGCCCACCUUCUGCCGCCGCCACCACAGCCACCUUCUCCUCCU |
| | | CCGCUGUCCUCUCCCGUCCUCGCCUCUGUCGACUAUCAGGUGAACU |
| | | UUGAACCAGGAUGGCUGAGCCCCGCCAGGAGUUCGAAGUGAUGGAA |
| | | GAUCACGCUGGGACGUACGGGUUGGGGACAGGAAAGAUCAGGGG |
| | | GGCUACACCAUGCACCAAGACCAAGAGGGUGACACGGACGCUGGCC |
| | | UGAAAGAAUCUCCCCUGCAGACCCCCACUGAGGACGGAUCUGAGGA |
| | | ACCGGGCUCUGAAACCUCUGAUGCUAAGAGCACUCCAACAGCGGAA |
| | | GAUGUGACAGCACCCUUAGUGGAUGAGGGAGCUCCCGGCAAGCAGG |
| | | CUGCCGCGCAGCCCCACACGGAGAUCCCAGAAGGAACCACAGCUGA |
| | | AGAAGCAGGCAUUGGAGACACCCCCAGCCUGGAAGACGAAGCUGCU |
| | | GGUCACGUGACCCAAGCUCGCAUGGUCAGUAAAAGCAAAGACGGGA |
| | | CUGGAAGCGAUGACAAAAAAGCCAAGGGGGCUGAUGGUAAAACGA |
| | | AGAUCGCCACACCGCGGGGAGCAGCCCCUCCAGGCCAGAAGGGCCA |
| | | GGCCAACGCCACCAGGAUUCCAGCAAAAACCCCGCCCGCUCCAAAG |
| | | ACACCACCCAGCUCUGGUGAACCUCCAAAAUCAGGGGAUCGCAGCG |
| | | GCUACAGCAGCCCCGGCUCCCCAGGCACUCCCGGCAGCCGCUCCCGC |
| | | ACCCCGUCCCUUCCAACCCCACCCACCCGGGAGCCCAAGAAGGUGGC |
| | | AGUGGUCCGUACUCCACCCAAGUCGCCGUCUUCCGCCAAGAGCCGC |
| | | CUGCAGACAGCCCCCGUGCCCAUGCCAGACCUGAAGAAUGUCAAGU |
| | | CCAAGAUCGGCUCCACUGAGAACCUGAAGCACCAGCCGGGAGGCGG |
| | | GAAGGUGCAAAUAGUCUACAAACCAGUUGACCUGAGCAAGGUGACC |
| | | UCCAAGUGUGGCUCAUUAGGCAACAUCCAUCAUAAACCAGGAGGUG |
| | | GCCAGGUGGAAGUAAAAUCUGAGAAGCUUGACUUCAAGGACAGAG |
| | | UCCAGUCGAAGAUUGGGUCCCUGGACAAUAUCACCCACGUCCCUGG |
| | | CGGAGGAAAUAAAAAGAUUGAAACCCACAAGCUGACCUUCCGCGAG |
| | | AACGCCAAAGCCAAGACAGACCACGGGGCGGAGAUCGUGUACAAGU |
| | | CGCCAGUGGUGUCUGGGGACACGUCUCCACGGCAUCUCAGCAAUGU |
| | | CUCCUCCACCGGCAGCAUCGACAUGGUAGACUCGCCCCAGCUCGCCA |
| | | CGCUAGCUGACGAGGUGUCUGCCUCCCUGGCCAAGCAGGGUUUGUG |
| | | AUCAGGCCCCUGGGGCGGUCAAUAAUUGUGGAGAGGAGAGAAUGA |
| | | GAGAGUGUGGAAAAAAAAAGAAUAAUGACCCGGCCCCCGCCCUCUG |
| | | CCCCCAGCUGCUCCUCGCAGUUCGGUUAAUUGGUUAAUCACUUAAC |
| | | CUGCUUUUGUCACUCGGCUUUGGCUCGGGACUUCAAAAUCAGUGAU |
| | | GGGAGUAAGAGCAAAUUUCAUCUUUCCAAAUUGAUGGGUGGGCUA |
| | | GUAAUAAAAUAUUUAAAAAAAAACAUUCAAAAACAUGGCCACAUCC |
| | | AACAUUUCCUCAGGCAAUUCCUUUUGAUUCUUUUUUCUUCCCCCUC |
| | | CAUGUAGAAGAGGGAGAAGGAGAGGCUCUGAAAGCUGCUUCUGGG |
| | | GGAUUUCAAGGACUGGGGGUGCCAACCACCUCUGGCCCUGUUGUG |

TABLE 4-continued

Human MAPT mRNA Isoform Sequences. Sequences obtained from NCBI MAPT gene ID: 4137; Assembly GRCh38.p13 (GCF_000001405.39); NC_000017.11 (45894538 . . . 46028334)

| SEQ ID NO | Isoform | mRNA Sequence |
|---|---|---|
| | | GGGGUGUCACAGAGGCAGUGGCAGCAACAAAGGAUUUGAAACUUG |
| | | GUGUGUUCGUGGAGCCACAGGCAGACGAUGUCAACCUUGUGUGAGU |
| | | GUGACGGGGGUUGGGGUGGGGCGGGAGGCCACGGGGGAGGCCGAG |
| | | GCAGGGGCUGGGCAGAGGGGAGAGGAAGCACAAGAAGUGGGAGUG |
| | | GGAGAGGAAGCCACGUGCUGGAGAGUAGACAUCCCCCUCCUUGCCG |
| | | CUGGGAGAGCCAAGGCCUAUGCCACCUGCAGCGUCUGAGCGGCCGC |
| | | CUGUCCUUGGUGGCCGGGGGUGGGGGCCUGCUGUGGGUCAGUGUGC |
| | | CACCCUCUGCAGGGCAGCCUGUGGGAGAAGGGACAGCGGGUAAAAA |
| | | GAGAAGGCAAGCUGGCAGGAGGGUGGCACUUCGUGGAUGACCUCCU |
| | | UAGAAAAGACUGACCUUGAUGUCUUGAGAGCGCUGGCCUCUUCCUC |
| | | CCUCCCUGCAGGGUAGGGGGCCUGAGUUGAGGGGCUUCCCUCUGCU |
| | | CCACAGAAACCCUGUUUUAUUGAGUUCUGAAGGUUGGAACUGCUGC |
| | | CAUGAUUUUGGCCACUUUGCAGACCUGGGACUUUAGGGCUAACCAG |
| | | UUCUCUUUGUAAGGACUUGUGCCUCUUGGGAGACGUCCACCCGUUU |
| | | CCAAGCCUGGGCCACUGGCAUCUCUGGAGUGUGUGGGGGUCUGGGA |
| | | GGCAGGUCCCGAGCCCCCUGUCCUUCCCACGGCCACUGCAGUCACCC |
| | | CGUCUGCGCCGCUGUGCUGUUGUCUGCCGUGAGAGCCCAAUCACUG |
| | | CCUAUACCCCUCAUCACACGUCACAAUGUCCCGAAUUCCCAGCCUCA |
| | | CCACCCCUUCUCAGUAAUGACCCUGGUUGGUUGCAGGAGGUACCUA |
| | | CUCCAUACUGAGGGUGAAAUUAAGGGAAGGCAAAGUCCAGGCACAA |
| | | GAGUGGGACCCCAGCCUCUCACUCUCAGUUCCACUCAUCCAACUGG |
| | | GACCCUCACCACGAAUCUCAUGAUCUGAUUCGGUUCCCUGUCUCCU |
| | | CCUCCCGUCACAGAUGUGAGCCAGGGCACUGCUCAGCUGUGACCCU |
| | | AGGUGUUUCUGCCUUGUUGACAUGGAGAGAGCCCUUUCCCCUGAGA |
| | | AGGCCUGGCCCCUUCCUGUGCUGAGCCCACAGCAGCAGGCUGGGUG |
| | | UCUUGGUUGUCAGUGGUGGCACCAGGAUGGAAGGGCAAGGCACCCA |
| | | GGGCAGGCCCACAGUCCCGCUGUCCCCCACUUGCACCCUAGCUUGU |
| | | AGCUGCCAACCUCCCAGACAGCCCAGCCCGCUGCUCAGCUCCACAUG |
| | | CAUAGUAUCAGCCCUCCACACCCGACAAAGGGGAACACACCCCCUU |
| | | GGAAAUGGUUCUUUUCCCCCAGUCCCAGCUGGAAGCCAUGCUGUCU |
| | | GUUCUGCUGGAGCAGCUGAACAUAUACAUAGAUGUUGCCCUGCCCU |
| | | CCCCAUCUGCACCCUGUUGAGUUGUAGUUGGAUUUGUCUGUUUAUG |
| | | CUUGGAUUCACCAGAGUGACUAUGAUAGUGAAAAGAAAAAAAAAA |
| | | AAAAAAAAGGACGCAUGUAUCUUGAAAUGCUUGUAAAGAGGUUUC |
| | | UAACCCACCCUCACGAGGUGUCUCUCACCCCCACACUGGGACUCGU |
| | | GUGGCCUGUGUGGUGCCACCCUGCUGGGGCCUCCCAAGUUUUGAAA |
| | | GGCUUUCCUCAGCACCUGGGACCCAACAGAGACCAGCUUCUAGCAG |
| | | CUAAGGAGGCCGUUCAGCUGUGACGAAGGCCUGAAGCACAGGAUUA |
| | | GGACUGAAGCGAUGAUGUCCCCUUCCCUACUUCCCCUUGGGGCUCC |
| | | CUGUGUCAGGGCACAGACUAGGUCUUGUGGCUGGUCUGGCUUGCGG |
| | | CGCGAGGAUGGUUCUCUCUGGUCAUAGCCCGAAGUCUCAUGGCAGU |
| | | CCCAAAGGAGGCUUACAACUCCUGCAUCACAAGAAAAAGGAAGCCA |
| | | CUGCCAGCUGGGGGGAUCUGCAGCUCCCAGAAGCUCCGUGAGCCUC |
| | | AGCCACCCCUCAGACUGGGUUCCUCUCCAAGCUCGCCCUCUGGAGG |
| | | GGCAGCGCAGCCUCCCACCAAGGGCCCUGCGACCACAGCAGGGAUU |
| | | GGGAUGAAUUGCCUGUCCUGGAUCUGCUCUAGAGGCCCAAGCUGCC |
| | | UGCCUGAGGAAGGAUGACUUGACAAGUCAGGAGACACUGUUCCCAA |
| | | AGCCUUGACCAGAGCACCUCAGCCCGCUGACCUUGCACAAACUCCA |
| | | UCUGCUGCCAUGAGAAAAGGGAAGCCGCCUUUGCAAAACAUUGCUG |
| | | CCUAAAGAAACUCAGCAGCCUCAGGCCCAAUUCUGCCACUUCUGGU |
| | | UUGGGUACAGUUAAAGGCAACCCUGAGGGACUUGGCAGUAGAAAUC |
| | | CAGGGCCUCCCCUGGGGCUGGCAGCUUCGUGUGCAGCUAGAGCUUU |
| | | ACCUGAAAGGAAGUCUCUGGGCCCAGAACUCUCCACCAAGAGCCUC |
| | | CCUGCCGUUCGCUGAGUCCCAGCAAUUCUCCUAAGUUGAAGGGAUC |
| | | UGAGAAGGAGAAGGAAAUGUGGGGUAGAUUUGGUGGUGGUUAGAG |
| | | AUAUGCCCCCCUCAUUACUGCCAACAGUUUCGGCUGCAUUUCUUCA |
| | | CGCACCUCGGUUCCUCUUCCUGAAGUUCUUGUGCCCUGCUCUUCAG |
| | | CACCAUGGGCCUUCUUAUACGGAAGGCUCUGGGAUCUCCCCCUUGU |
| | | GGGGCAGGCUCUUGGGGCCAGCCUAAGAUCAUGGUUUAGGGUGAUC |
| | | AGUGCUGGCAGAUAAAUUGAAAAGGCACGCUGGCUUGUGAUCUUA |
| | | AAUGAGGACAAUCCCCCCAGGGCUGGGCACUCCUCCCCUCCCCUCAC |
| | | UUCUCCCACCUGCAGAGCCAGUGUCCUUGGGUGGGCUAGAUAGGAU |
| | | AUACUGUAUGCCGGCUCCUUCAAGCUGCUGACUCACUUUAUCAAUA |
| | | GUUCCAUUUAAAUUGACUUCAGUGGUGAGACUGUAUCCUGUUUGCU |
| | | AUUGCUUGUUGUGCUAUGGGGGGAGGGGGGAGGAAUGUGUAAGAU |
| | | AGUUAACAUGGGCAAAGGGAGAUCUUGGGGUGCAGCACUUAAACU |
| | | GCCUCGUAACCCUUUUCAUGAUUUCAACCACAUUUGCUAGAGGGAG |
| | | GGAGCAGCCACGGAGUUAGAGGCCCUUGGGGUUUCUCUUUUCCACU |
| | | GACAGGCUUUCCCAGGCAGCUGGCUAGUUCAUUCCCUCCCCAGCCA |
| | | GGUGCAGGCGUAGGAAUAUGGACAUCUGGUUGCUUUGGCCUGCUGC |
| | | CCUCUUUCAGGGGUCCUAAGCCCACAAUCAUGCCUCCCUAAGACCU |
| | | UGGCAUCCUUCCCUCUAAGCCGUUGGCACCUCUGUGCCACCUCUCA |

TABLE 4-continued

Human MAPT mRNA Isoform Sequences. Sequences obtained from NCBI MAPT gene ID: 4137; Assembly GRCh38.p13 (GCF_000001405.39); NC_000017.11 (45894538 . . . 46028334)

| SEQ ID NO | Isoform | mRNA Sequence |
| --- | --- | --- |
| | | CACUGGCUCCAGACACACAGCCUGUGCUUUUGGAGCUGAGAUCACU<br>CGCUUCACCCUCCUCAUCUUUGUUCUCCAAGUAAAGCCACGAGGUC<br>GGGGCGAGGGCAGAGGUGAUCACCUGCGUGUCCCAUCUACAGACCU<br>GCAGCUUCAUAAAACUUCUGAUUUCUCUUCAGCUUUGAAAAGGGUU<br>ACCCUGGGCACUGGCCUAGAGCCUCACCUCCUAAUAGACUUAGCCC<br>CAUGAGUUUGCCAUGUUGAGCAGGACUAUUUCUGGCACUUGCAAGU<br>CCCAUGAUUUCUUCGGUAAUUCUGAGGGUGGGGGGAGGGACAUGA<br>AAUCAUCUUAGCUUAGCUUUCUGUCUGUGAAUGUCUAUAUAGUGU<br>AUUGUGUGUUUUAACAAAUGAUUUACACUGACUGUUGCUGUAAAA<br>GUGAAUUUGGAAAUAAAGUUAUUACUCUGAUUAAA |
| 24 | 9 | GCAGUCACCGCCACCCACCAGCUCCGGCACCAACAGCAGCGCCGCUG<br>CCACCGCCCACCUUCUGCCGCCGCCACCACAGCCACCUUCUCCUCCU<br>CCGCUGUCCUCUCCCGUCCUCGCCUCUGUCGACUAUCAGGUGAACU<br>UUGAACCAGGAUGGCUGAGCCCCGCCAGGAGUUCGAAGUGAUGGAA<br>GAUCACGCUGGGACGUACGGGUUGGGGACAGGAAAGAUCAGGGG<br>GGCUACACCAUGCACCAAGACCAAGAGGGUGACACGGACGCUGGCC<br>UGAAAGAAUCUCCCCUGCAGACCCCCACUGAGGACGGAUCUGAGGA<br>ACCGGGCUCUGAAACCUCUGAUGCUAAGAGCACUCCAACAGCGGAA<br>GCUGAAGAAGCAGGCAUUGGAGACACCCCCAGCCUGGAAGACGAAG<br>CUGCUGGUCACGUGACCCAAGAGGAGUUGAGAGUUCCGGGCCGGCA<br>GAGGAAGGCGCCUGAAAGGCCCCUGGCCAAUGAGAUUAGCGCCCAC<br>GUCCAGCCUGGACCCUGCGGAGAGGCCUCUGGGGUCUCUGGGCCGU<br>GCCUCGGGGAGAAAGAGCCAGAAGCUCCCGUCCCGCUGACCGCGAG<br>CCUUCCUCAGCACCGUCCCGUUUGCCCAGCGCCUCCUCCAACAGGAG<br>GCCCUCAGGAGCCCUCCCUGGAGUGGGGACAAAAAGGCGGGGACUG<br>GGCCGAGAAGGGUCCGGCCUUUCCGAAGCCCGCCACCACUGCGUAU<br>CUCCACACAGAGCCUGAAAGUGGUAAGGUGGUCCAGGAAGGCUUCC<br>UCCGAGAGCCAGGCCCCCCAGGUCUGAGCCACCAGCUCAUGUCCGG<br>CAUGCCUGGGGCUCCCCUCCUGCCUGAGGGCCCCAGAGAGGCCACA<br>CGCCAACCUUCGGGGACAGGACCUGAGGACACAGAGGGCGGCCGCC<br>ACGCCCCUGAGCUGCUCAAGCACCAGCUUCUAGGAGACCUGCACCA<br>GGAGGGGCCGCCGCUGAAGGGGGCAGGGGGCAAAGAGAGGCCGGGG<br>AGCAAGGAGGAGGUGGAUGAAGACCGCGACGUCGAUGAGUCCUCCC<br>CCCAAGACUCCCCUCCCUCCAAGGCCUCCCCAGCCCAAGAUGGGCGG<br>CCUCCCCAGACAGCCGCCAGAGAAGCCACCAGCAUCCCAGGCUUCCC<br>AGCGGAGGGUGCCAUCCCCCUCCCUGUGGAUUUCCUCUCCAAAGUU<br>UCCACAGAGAUCCCAGCCUCAGAGCCCGACGGGCCCAGUGUAGGGC<br>GGGCCAAAGGGCAGGAUGCCCCCUGGAGUUCACGUUUCACGUGGA<br>AAUCACACCCAACGUGCAGAAGGAGCAGGCGCACUCGGAGGAGCAU<br>UUGGGAAGGGCUGCAUUUCCAGGGGCCCCUGGAGAGGGGCCAGAGG<br>CCCGGGGCCCCUCUUUGGGAGAGGACACAAAAGAGGCUGACCUUCC<br>AGAGCCCUCUGAAAAGCAGCCUGCUGCUGCUCCGCGGGGGAAGCCC<br>GUCAGCCGGGUCCCUCAACUCAAAGCUCGCAUGGUCAGUAAAAGCA<br>AAGACGGGACUGGAAGCGAUGACAAAAAAGCCAAGACAUCCACACG<br>UUCCUCUGCUAAAACCUUGAAAAAUAGGCCUUGCCUUAGCCCCAAA<br>CACCCCACUCCUGGUAGCUCAGACCCUCUGAUCCAACCCUCCAGCCC<br>UGCUGUGUGCCCAGAGCCACCUUCCUCUCCUAAAUACGUCUCUUCU<br>GUCACUUCCCGAACUGGCAGUUCUGGAGCAAAGGAGAUGAAACUCA<br>AGGGGGCUGAUGGUAAAACGAAGAUCGCCACACCGCGGGGAGCAGC<br>CCCUCCAGGCCAGAAGGGCCAGGCCAACGCCACCAGGAUUCCAGCA<br>AAAACCCCGCCCGCUCCAAAGACACCACCCAGCUCUGGUGAACCUCC<br>AAAAUCAGGGGAUCGCAGCGGCUACAGCAGCCCCGGCUCCCCAGGC<br>ACUCCCGGCAGCCGCUCCCGCACCCCGUCCCUUCCAACCCCACCCAC<br>CCGGGAGCCCAAGAAGGUGGCAGUGGUCCGUACUCCACCCAAGUCG<br>CCGUCUUCCGCCAAGAGCCGCCUGCAGACAGCCCCCGUGCCCAUGCC<br>AGACCUGAAGAAUGUCAAGUCCAAGAUCGGCUCCACUGAGAACCUG<br>AAGCACCAGCCGGGAGGCGGGAAGGUGCAGAUAAUUAAUAAGAAGC<br>UGGAUCUUAGCAACGUCCAGUCCAAGUGUGGCUCAAAGGAUAAUAU<br>CAAACACGUCCCGGGAGGCGGCAGUGUGCAAAUAGUCUACAAACCA<br>GUUGACCUGAGCAAGGUGACCUCCAAGUGUGGCUCAUUAGGCAACA<br>UCCAUCAUAAACCAGGAGGUGGCCAGGUGGAAGUAAAAUCUGAGAA<br>GCUUGACUUCAAGGACAGAGUCCAGUCGAAGAUUGGGUCCCUGGAC<br>AAUAUCACCCACGUCCCUGGCGGAGGAAAUAAAAAGAUUGAAACCC<br>ACAAGCUGACCUUCCGCGAGAACGCCAAAGCCAAGACAGACCACGG<br>GGCGGAGAUCGUGUACAAGUCGCCAGUGGUGUCUGGGGACACGUCU<br>CCACGGCAUCUCAGCAAUGUCUCCUCCACCGGCAGCAUCGACAUGG<br>UAGACUCGCCCCAGCUCGCCACGCUAGCUGACGAGGUGUCUGCCUC<br>CCUGGCCAAGCAGGGUUUGUGAUCAGGCCCCUGGGGCGGUCAAUAA<br>UUGUGGAGAGGAGAGAAUGAGAGAGUGUGGAAAAAAAAAGAAUAA<br>UGACCCGGCCCCCGCCCUCUGCCCCCAGCUGCUCCUCGCAGUUCGGU<br>UAAUUGGUUAAUCACUUAACCUGCUUUUGUCACUCGGCUUUGGCUC |

TABLE 4-continued

Human MAPT mRNA Isoform Sequences. Sequences obtained from NCBI MAPT gene ID: 4137; Assembly GRCh38.p13 (GCF_000001405.39); NC_000017.11 (45894538 . . . 46028334)

| SEQ ID NO | Isoform | mRNA Sequence |
|---|---|---|
| | | GGGACUUCAAAAUCAGUGAUGGGAGUAAGAGCAAAUUUCAUCUUU<br>CCAAAUUGAUGGGUGGGCUAGUAAUAAAAUAUUUAAAAAAAAACA<br>UUCAAAAACAUGGCCACAUCCAACAUUUCCUCAGGCAAUUCCUUUU<br>GAUUCUUUUUUCUUCCCCCUCCAUGUAGAAGAGGGAGAAGGAGAGG<br>CUCUGAAAGCUGCUUCUGGGGGAUUUCAAGGGACUGGGGGUGCCAA<br>CCACCUCUGGCCCUGUUGUGGGGGUGUCACAGAGGCAGUGGCAGCA<br>ACAAAGGAUUUGAAACUUGGUGUGUUCGUGGAGCCACAGGCAGACG<br>AUGUCAACCUUGUGUGAGUGUGACGGGGGUUGGGGUGGGGCGGGA<br>GGCCACGGGGGAGGCCGAGGCAGGGGCUGGGCAGAGGGGAGAGGAA<br>GCACAAGAAGUGGGAGUGGGAGAGGAAGCCACGUGCUGGAGAGUA<br>GACAUCCCCCUCCUUGCCGCUGGGAGAGCCAAGGCCUAUGCCACCU<br>GCAGCGUCUGAGCGGCCGCCUGUCCUUGGUGGCCGGGGGUGGGGGC<br>CUGCUGUGGGUCAGUGUGCCACCCUCUGCAGGGCAGCCUGUGGGAG<br>AAGGGACAGCGGGUAAAAAGAGAAGGCAAGCUGGCAGGAGGGUGG<br>CACUUCGUGGAUGACCUCCUUAGAAAAGACUGACCUUGAUGUCUUG<br>AGAGCGCUGGCCUCUUCCUCCCUCCCUGCAGGGUAGGGGGCCUGAG<br>UUGAGGGGCUUCCCUCUGCUCCACAGAAACCCUGUUUUAUUGAGUU<br>CUGAAGGUUGGAACUGCUGCCAUGAUUUUGGCCACUUUGCAGACCU<br>GGGACUUUAGGGCUAACCAGUUCUCUUUGUAAGGACUUGUGCCUCU<br>UGGGAGACGUCCACCCGUUUCCAAGCCUGGGCCACUGGCAUCUCUG<br>GAGUGUGUGGGGGUCUGGGAGGCAGGUCCCGAGCCCCCUGUCCUUC<br>CCACGGCCACUGCAGUCACCCCGUCUGCGCCGCUGUGCUGUUGUCU<br>GCCGUGAGAGCCCAAUCACUGCCUAUACCCCUCAUCACACGUCACA<br>AUGUCCCGAAUUCCCAGCCUCACCACCCCUUCUCAGUAAUGACCCU<br>GGUUGGUUGCAGGAGGUACCUACUCCAUACUGAGGGUGAAAUUAA<br>GGGAAGGCAAAGUCCAGGCACAAGAGUGGGACCCCAGCCUCUCACU<br>CUCAGUUCCACUCAUCCAACUGGGACCCUCACCACGAAUCUCAUGA<br>UCUGAUUCGGUUCCCUGUCUCCUCCUCCCGUCACAGAUGUGAGCCA<br>GGGCACUGCUCAGCUGUGACCCUAGGUGUUUCUGCCUUGUUGACAU<br>GGAGAGAGCCCUUUCCCCUGAGAAGGCCUGGCCCCUUCCUGUGCUG<br>AGCCCACAGCAGCAGGCUGGGUGUCUUGGUUGUCAGUGGUGGCACC<br>AGGAUGGAAGGGCAAGGCACCCAGGGCAGGCCCACAGUCCCGCUGU<br>CCCCCACUUGCACCCUAGCUUGUAGCUGCCAACCUCCCAGACAGCCC<br>AGCCCGCUGCUCAGCUCCACAUGCAUAGUAUCAGCCCUCCACACCCG<br>ACAAAGGGGAACACACCCCCUUGGAAAUGGUUCUUUUCCCCCAGUC<br>CCAGCUGGAAGCCAUGCUGUCUGUUCUGCUGGAGCAGCUGAACAUA<br>UACAUAGAUGUUGCCCUGCCCUCCCCAUCUGCACCCUGUUGAGUUG<br>UAGUUGGAUUUGUCUGUUUAUGCUUGGAUUCACCAGAGUGACUAU<br>GAUAGUGAAAAGAAAAAAAAAAAAAAAAAAAGGACGCAUGUAUCUU<br>GAAAUGCUUGUAAAGAGGUUUCUAACCCACCCUCACGAGGUGUCUC<br>UCACCCCCACACUGGGACUCGUGUGGCCUGUGUGGUGCCACCCUGC<br>UGGGGCCUCCCAAGUUUUGAAAGGCUUUCCUCAGCACCUGGGACCC<br>AACAGAGACCAGCUUCUAGCAGCUAAGGAGGCCGUUCAGCUGUGAC<br>GAAGGCCUGAAGCACAGGAUUAGGACUGAAGCGAUGAUGUCCCCUU<br>CCCUACUUCCCCUUGGGGCUCCCUGUGUCAGGGCACAGACUAGGUC<br>UUGUGGCUGGUCUGGCUUGCGGCGCGAGGAUGGUUCUCUCUGGUCA<br>UAGCCCGAAGUCUCAUGGCAGUCCCAAAGGAGGCUUACAACUCCUG<br>CAUCACAAGAAAAAGGAAGCCACUGCCAGCUGGGGGGAUCUGCAGC<br>UCCCAGAAGCUCCGUGAGCCUCAGCCACCCCUCAGACUGGGUUCCU<br>CUCCAAGCUCGCCCUCUGGAGGGGCAGCGCAGCCUCCCACCAAGGG<br>CCCUGCGACCACAGCAGGGAUUGGGAUGAAUUGCCUGUCCUGGAUC<br>UGCUCUAGAGGCCCAAGCUGCCUGCCUGAGGAAGGAUGACUUGACA<br>AGUCAGGAGACACUGUUCCCAAAGCCUUGACCAGAGCACCUCAGCC<br>CGCUGACCUUGCACAAACUCCAUCUGCUGCCAUGAGAAAAGGGAAG<br>CCGCCUUUGCAAAACAUUGCUGCCUAAAGAAACUCAGCAGCCUCAG<br>GCCCAAUUCUGCCACUUCUGGUUUGGGUACAGUUAAAGGCAACCCU<br>GAGGGACUUGGCAGUAGAAAUCCAGGGCCUCCCCUGGGGCUGGCAG<br>CUUCGUGUGCAGCUAGAGCUUUACCUGAAAGGAAGUCUCUGGGCCC<br>AGAACUCUCCACCAAGAGCCUCCCUGCCGUUCGCUGAGUCCCAGCA<br>AUUCUCCUAAGUUGAAGGGAUCUGAGAAGGAGAAGGAAAUGUGGG<br>GUAGAUUUGGUGGUGGUUAGAGAUAUGCCCCCCUCAUUACUGCCAA<br>CAGUUUCGGCUGCAUUUCUUCACGCACCUCGGUUCCUCUUCCUGAA<br>GUUCUUGUGCCCUGCUCUUCAGCACCAUGGGCCUUCUUAUACGGAA<br>GGCUCUGGGAUCUCCCCCUUGUGGGGCAGGCUCUUGGGGCCAGCCU<br>AAGAUCAUGGUUUAGGGUGAUCAGUGCUGGCAGAUAAAUUGAAAA<br>GGCACGCUGGCUUGUGAUCUUAAAUGAGGACAAUCCCCCCAGGGCU<br>GGGCACUCCUCCCCUCCCCUCACUUCUCCCACCUGCAGAGCCAGUGU<br>CCUUGGGUGGGCUAGAUAGGAUAUACUGUAUGCCGGCUCCUUCAAG<br>CUGCUGACUCACUUUAUCAAUAGUUCCAUUUAAAUUGACUUCAGUG<br>GUGAGACUGUAUCCUGUUUGCUAUUGCUUGUUGUGCUAUGGGGGG<br>AGGGGGGAGGAAUGUGUAAGAUAGUUAACAUGGGCAAAGGGAGAU<br>CUUGGGGUGCAGCACUUAAACUGCCUCGUAACCCUUUUCAUGAUUU |

TABLE 4-continued

Human MAPT mRNA Isoform Sequences. Sequences obtained from NCBI MAPT gene ID: 4137; Assembly GRCh38.p13 (GCF_000001405.39); NC_000017.11 (45894538 . . . 46028334)

| SEQ ID NO | Isoform | mRNA Sequence |
|---|---|---|
| | | CAACCACAUUUGCUAGAGGGAGGGAGCAGCCACGGAGUUAGAGGCC<br>CUUGGGGUUUCUCUUUUCCACUGACAGGCUUUCCCAGGCAGCUGGC<br>UAGUUCAUUCCCUCCCCAGCCAGGUGCAGGCGUAGGAAUAUGGACA<br>UCUGGUUGCUUUGGCCUGCUGCCCUCUUUCAGGGGUCCUAAGCCCA<br>CAAUCAUGCCUCCCUAAGACCUUGGCAUCCUUCCCUCUAAGCCGUU<br>GGCACCUCUGUGCCACCUCUCACACUGGCUCCAGACACACAGCCUG<br>UGCUUUUGGAGCUGAGAUCACUCGCUUCACCCUCCUCAUCUUUGUU<br>CUCCAAGUAAAGCCACGAGGUCGGGGCGAGGGCAGAGGUGAUCACC<br>UGCGUGUCCCAUCUACAGACCUGCAGCUUCAUAAAACUUCUGAUUU<br>CUCUUCAGCUUUGAAAAGGGUUACCCUGGGCACUGGCCUAGAGCCU<br>CACCUCCUAAUAGACUUAGCCCCAUGAGUUUGCCAUGUUGAGCAGG<br>ACUAUUUCUGGCACUUGCAAGUCCCAUGAUUUCUUCGGUAAUUCUG<br>AGGGUGGGGGGAGGGACAUGAAAUCAUCUUAGCUUAGCUUUCUGU<br>CUGUGAAUGUCUAUAUAGUGUAUUGUGUGUUUUAACAAAUGAUUU<br>ACACUGACUGUUGCUGUAAAAGUGAAUUUGGAAAUAAAGUUAUUA<br>CUCUGAUUAAA |
| 25 | 10 | GCAGUCACCGCCACCCACCAGCUCCGGCACCAACAGCAGCGCCGCUG<br>CCACCGCCCACCUUCUGCCGCCGCCACCACAGCCACCUUCUCCUCCU<br>CCGCUGUCCUCUCCCGUCCUCGCCUCUGUCGACUAUCAGGUGAACU<br>UUGAACCAGGAUGGCUGAGCCCCGCCAGGAGUUCGAAGUGAUGGAA<br>GAUCACGCUGGGACGUACGGGUUGGGGGACAGGAAAGAUCAGGGG<br>GGCUACACCAUGCACCAAGACCAAGAGGGUGACACGGACGCUGGCC<br>UGAAAGAAUCUCCCCUGCAGACCCCCACUGAGGACGGAUCUGAGGA<br>ACCGGGCUCUGAAACCUCUGAUGCUAAGAGCACUCCAACAGCGGAA<br>GCUGAAGAAGCAGGCAUUGGAGACACCCCCAGCCUGGAAGACGAAG<br>CUGCUGGUCACGUGACCCAAGAGGAGUUGAGAGUUCCGGGCCGGCA<br>GAGGAAGGCGCCUGAAAGGCCCCUGGCCAAUGAGAUUAGCGCCCAC<br>GUCCAGCCUGGACCCUGCGGAGAGGCCUCUGGGGUCUCUGGGCCGU<br>GCCUCGGGGAGAAAGAGCCAGAAGCUCCCGUCCCGCUGACCGCGAG<br>CCUUCCUCAGCACCGUCCCGUUUGCCCAGCGCCUCCUCCAACAGGAG<br>GCCCUCAGGAGCCCUCCCUGGAGUGGGGACAAAAAGGCGGGGACUG<br>GGCCGAGAAGGGUCCGGCCUUUCCGAAGCCCGCCACCACUGCGUAU<br>CUCCACACAGAGCCUGAAAGUGGUAAGGUGGUCCAGGAAGGCUUCC<br>UCCGAGAGCCAGGCCCCCCAGGUCUGAGCCACCAGCUCAUGUCCGG<br>CAUGCCUGGGGCUCCCCUCCUGCCUGAGGGCCCCAGAGAGGCCACA<br>CGCCAACCUUCGGGGACAGGACCUGAGGACACAGAGGGCGGCCGCC<br>ACGCCCCUGAGCUGCUCAAGCACCAGCUUCUAGGAGACCUGCACCA<br>GGAGGGGCCGCCGCUGAAGGGGGCAGGGGGCAAAGAGAGGCCGGGG<br>AGCAAGGAGGAGGUGGAUGAAGACCGCGACGUCGAUGAGUCCUCCC<br>CCCAAGACUCCCCUCCCUCCAAGGCCUCCCCAGCCCAAGAUGGGCGG<br>CCUCCCCAGACAGCCGCCAGAGAAGCCACCAGCAUCCCAGGCUUCCC<br>AGCGGAGGGUGCCAUCCCCCUCCCUGUGGAUUUCCUCUCCAAAGUU<br>UCCACAGAGAUCCCAGCCUCAGAGCCCGACGGGCCCAGUGUAGGGC<br>GGGCCAAAGGGCAGGAUGCCCCCUGGAGUUCACGUUUCACGUGGA<br>AAUCACACCCAACGUGCAGAAGGAGCAGGCGCACUCGGAGGAGCAU<br>UUGGGAAGGGCUGCAUUUCCAGGGGCCCCUGGAGAGGGGCCAGAGG<br>CCCGGGGCCCCUCUUUGGGAGAGGACACAAAAGAGGCUGACCUUCC<br>AGAGCCCUCUGAAAAGCAGCCUGCUGCUGCUCCGCGGGGGAAGCCC<br>GUCAGCCGGGUCCCUCAACUCAAAGCUCGCAUGGUCAGUAAAAGCA<br>AAGACGGGACUGGAAGCGAUGACAAAAAAGCCAAGGGGGCUGAUG<br>GUAAAACGAAGAUCGCCACACCGCGGGGAGCAGCCCCUCCAGGCCA<br>GAAGGGCCAGGCCAACGCCACCAGGAUUCCAGCAAAAACCCCGCCC<br>GCUCCAAAGACACCACCCAGCUCUGGUGAACCUCCAAAAUCAGGGG<br>AUCGCAGCGGCUACAGCAGCCCCGGCUCCCCAGGCACUCCCGGCAGC<br>CGCUCCCGCACCCCGUCCCUUCCAACCCCACCCACCCGGGAGCCCAA<br>GAAGGUGGCAGUGGUCCGUACUCCACCCAAGUCGCCGUCUUCCGCC<br>AAGAGCCGCCUGCAGACAGCCCCCGUGCCCAUGCCAGACCUGAAGA<br>AUGUCAAGUCCAAGAUCGGCUCCACUGAGAACCUGAAGCACCAGCC<br>GGGAGGCGGGAAGGUGCAAAUAGUCUACAAACCAGUUGACCUGAGC<br>AAGGUGACCUCCAAGUGUGGCUCAUUAGGCAACAUCCAUCAUAAAC<br>CAGGAGGUGGCCAGGUGGAAGUAAAAUCUGAGAAGCUUGACUUCA<br>AGGACAGAGUCCAGUCGAAGAUUGGGUCCCUGGACAAUAUCACCCA<br>CGUCCCUGGCGGAGGAAAUAAAAAGAUUGAAACCCACAAGCUGACC<br>UUCCGCGAGAACGCCAAAGCCAAGACAGACCACGGGGCGGAGAUCG<br>UGUACAAGUCGCCAGUGGUGUCUGGGGACACGUCUCCACGGCAUCU<br>CAGCAAUGUCUCCUCCACCGGCAGCAUCGACAUGGUAGACUCGCCC<br>CAGCUCGCCACGCUAGCUGACGAGGUGUCUGCCUCCCUGGCCAAGC<br>AGGGUUUGUGAUCAGGCCCCUGGGGCGGUCAAUAAUUGUGGAGAG<br>GAGAGAAUGAGAGAGUGUGGAAAAAAAAAGAAUAAUGACCCGGCC<br>CCCGCCCUCUGCCCCCAGCUGCUCCUCGCAGUUCGGUUAAUUGGUU<br>AAUCACUUAACCUGCUUUUGUCACUCGGCUUUGGCUCGGGACUUCA |

TABLE 4-continued

Human MAPT mRNA Isoform Sequences. Sequences obtained from NCBI MAPT gene ID: 4137; Assembly GRCh38.p13 (GCF_000001405.39); NC_000017.11 (45894538 . . . 46028334)

| SEQ ID NO | Isoform | mRNA Sequence |
|---|---|---|
| | | AAAUCAGUGAUGGGAGUAAGAGCAAAUUUCAUCUUUCCAAAUUGA |
| | | UGGGUGGGCUAGUAAUAAAAUAUUUAAAAAAAAACAUUCAAAAAC |
| | | AUGGCCACAUCCAACAUUUCCUCAGGCAAUUCCUUUUGAUUCUUUU |
| | | UUCUUCCCCCUCCAUGUAGAAGAGGGAGAAGGAGAGGCUCUGAAAG |
| | | CUGCUUCUGGGGGAUUUCAAGGGACUGGGGGUGCCAACCACCUCUG |
| | | GCCCUGUUGUGGGGGUGUCACAGAGGCAGUGGCAGCAACAAAGGAU |
| | | UUGAAACUUGGUGUGUUCGUGGAGCCACAGGCAGACGAUGUCAACC |
| | | UUGUGUGAGUGUGACGGGGGUUGGGGUGGGGCGGGAGGCCACGGG |
| | | GGAGGCCGAGGCAGGGGCUGGGCAGAGGGGAGAGGAAGCACAAGA |
| | | AGUGGGAGUGGGAGAGGAAGCCACGUGCUGGAGAGUAGACAUCCCC |
| | | CUCCUUGCCGCUGGGAGAGCCAAGGCCUAUGCCACCUGCAGCGUCU |
| | | GAGCGGCCGCCUGUCCUUGGUGGCCGGGGGUGGGGGCCUGCUGUGG |
| | | GUCAGUGUGCCACCCUCUGCAGGGCAGCCUGUGGGAGAAGGGACAG |
| | | CGGGUAAAAAGAGAAGGCAAGCUGGCAGGAGGGUGGCACUUCGUG |
| | | GAUGACCUCCUUAGAAAAGACUGACCUUGAUGUCUUGAGAGCGCUG |
| | | GCCUCUUCCUCCCUCCCUGCAGGGUAGGGGGCCUGAGUUGAGGGGC |
| | | UUCCCUCUGCUCCACAGAAACCCUGUUUUAUUGAGUUCUGAAGGUU |
| | | GGAACUGCUGCCAUGAUUUUGGCCACUUUGCAGACCUGGGACUUUA |
| | | GGGCUAACCAGUUCUCUUUGUAAGGACUUGUGCCUCUUGGGAGACG |
| | | UCCACCCGUUUCCAAGCCUGGGCCACUGGCAUCUCUGGAGUGUGUG |
| | | GGGGUCUGGGAGGCAGGUCCCGAGCCCCCUGUCCUUCCCACGGCCA |
| | | CUGCAGUCACCCCGUCUGCGCCGCUGUGCUGUUGUCUGCCGUGAGA |
| | | GCCCAAUCACUGCCUAUACCCCUCAUCACACGUCACAAUGUCCCGA |
| | | AUUCCCAGCCUCACCACCCCUUCUCAGUAAUGACCCUGGUUGGUUG |
| | | CAGGAGGUACCUACUCCAUACUGAGGGUGAAAUUAAGGGAAGGCAA |
| | | AGUCCAGGCACAAGAGUGGGACCCCAGCCUCUCACUCUCAGUUCCA |
| | | CUCAUCCAACUGGGACCCUCACCACGAAUCUCAUGAUCUGAUUCGG |
| | | UUCCCUGUCUCCUCCUCCCGUCACAGAUGUGAGCCAGGGCACUGCU |
| | | CAGCUGUGACCCUAGGUGUUUCUGCCUUGUUGACAUGGAGAGAGCC |
| | | CUUUCCCCUGAGAAGGCCUGGCCCCUUCCUGUGCUGAGCCCACAGC |
| | | AGCAGGCUGGGUGUCUUGGUUGUCAGUGGUGGCACCAGGAUGGAA |
| | | GGGCAAGGCACCCAGGGCAGGCCCACAGUCCCGCUGUCCCCCACUU |
| | | GCACCCUAGCUUGUAGCUGCCAACCUCCCAGACAGCCCAGCCCGCUG |
| | | CUCAGCUCCACAUGCAUAGUAUCAGCCCUCCACACCCGACAAAGGG |
| | | GAACACACCCCCUUGGAAAUGGUUCUUUUCCCCCAGUCCCAGCUGG |
| | | AAGCCAUGCUGUCUGUUCUGCUGGAGCAGCUGAACAUAUACAUAGA |
| | | UGUUGCCCUGCCCUCCCCAUCUGCACCCUGUUGAGUUGUAGUUGGA |
| | | UUUGUCUGUUUAUGCUUGGAUUCACCAGAGUGACUAUGAUAGUGA |
| | | AAAGAAAAAAAAAAAAAAAAAAAGGACGCAUGUAUCUUGAAAUGCU |
| | | UGUAAAGAGGUUUCUAACCCACCCUCACGAGGUGUCUCUCACCCCC |
| | | ACACUGGGACUCGUGUGGCCUGUGUGGUGCCACCCUGCUGGGGCCU |
| | | CCCAAGUUUUGAAAGGCUUUCCUCAGCACCUGGGACCCAACAGAGA |
| | | CCAGCUUCUAGCAGCUAAGGAGGCCGUUCAGCUGUGACGAAGGCCU |
| | | GAAGCACAGGAUUAGGACUGAAGCGAUGAUGUCCCCUUCCCUACUU |
| | | CCCCUUGGGGCUCCCUGUGUCAGGGCACAGACUAGGUCUUGUGGCU |
| | | GGUCUGGCUUGCGGCGCGAGGAUGGUUCUCUCUGGUCAUAGCCCGA |
| | | AGUCUCAUGGCAGUCCCAAAGGAGGCUUACAACUCCUGCAUCACAA |
| | | GAAAAAGGAAGCCACUGCCAGCUGGGGGGAUCUGCAGCUCCCAGAA |
| | | GCUCCGUGAGCCUCAGCCACCCCUCAGACUGGGUUCCUCUCCAAGC |
| | | UCGCCCUCUGGAGGGGCAGCGCAGCCUCCCACCAAGGGCCCUGCGA |
| | | CCACAGCAGGGAUUGGGAUGAAUUGCCUGUCCUGGAUCUGCUCUAG |
| | | AGGCCCAAGCUGCCUGCCUGAGGAAGGAUGACUUGACAAGUCAGGA |
| | | GACACUGUUCCCAAAGCCUUGACCAGAGCACCUCAGCCCGCUGACC |
| | | UUGCACAAACUCCAUCUGCUGCCAUGAGAAAAGGGAAGCCGCCUUU |
| | | GCAAAACAUUGCUGCCUAAAGAAACUCAGCAGCCUCAGGCCCAAUU |
| | | CUGCCACUUCUGGUUUGGGUACAGUUAAAGGCAACCCUGAGGGACU |
| | | UGGCAGUAGAAAUCCAGGGCCUCCCCUGGGGCUGGCAGCUUCGUGU |
| | | GCAGCUAGAGCUUUACCUGAAAGGAAGUCUCUGGGCCCAGAACUCU |
| | | CCACCAAGAGCCUCCCUGCCGUUCGCUGAGUCCCAGCAAUUCUCCU |
| | | AAGUUGAAGGGAUCUGAGAAGGAGAAGGAAAUGUGGGGUAGAUUU |
| | | GGUGGUGGUUAGAGAUAUGCCCCCCUCAUUACUGCCAACAGUUUCG |
| | | GCUGCAUUUCUUCACGCACCUCGGUUCCUCUUCCUGAAGUUCUUGU |
| | | GCCCUGCUCUUCAGCACCAUGGGCCUUCUUAUACGGAAGGCUCUGG |
| | | GAUCUCCCCCUUGUGGGGCAGGCUCUUGGGGCCAGCCUAAGAUCAU |
| | | GGUUUAGGGUGAUCAGUGCUGGCAGAUAAAUUGAAAAGGCACGCU |
| | | GGCUUGUGAUCUUAAAUGAGGACAAUCCCCCCAGGGCUGGGCACUC |
| | | CUCCCCUCCCCUCACUUCUCCCACCUGCAGAGCCAGUGUCCUUGGGU |
| | | GGGCUAGAUAGGAUAUACUGUAUGCCGGCUCCUUCAAGCUGCUGAC |
| | | UCACUUUAUCAAUAGUUCCAUUUAAAUUGACUUCAGUGGUGAGACU |
| | | GUAUCCUGUUUGCUAUUGCUUGUUGUGCUAUGGGGGGAGGGGGA |
| | | GGAAUGUGUAAGAUAGUUAACAUGGGCAAAGGAGAUCUUGGGGU |
| | | GCAGCACUUAAACUGCCUCGUAACCCUUUUCAUGAUUUCAACCACA |

TABLE 4-continued

Human MAPT mRNA Isoform Sequences. Sequences obtained from NCBI MAPT gene ID: 4137; Assembly GRCh38.p13 (GCF_000001405.39); NC_000017.11 (45894538 . . . 46028334)

| SEQ ID NO | Isoform | mRNA Sequence |
|---|---|---|
| | | UUUGCUAGAGGGAGGGAGCAGCCACGGAGUUAGAGGCCCUUGGGGU<br>UUCUCUUUUCCACUGACAGGCUUUCCCAGGCAGCUGGCUAGUUCAU<br>UCCCUCCCCAGCCAGGUGCAGGCGUAGGAAUAUGGACAUCUGGUUG<br>CUUUGGCCUGCUGCCCUCUUUCAGGGGUCCUAAGCCCACAAUCAUG<br>CCUCCCUAAGACCUUGGCAUCCUUCCCUCUAAGCCGUUGGCACCUC<br>UGUGCCACCUCUCACACUGGCUCCAGACACACAGCCUGUGCUUUUG<br>GAGCUGAGAUCACUCGCUUCACCCUCCUCAUCUUUGUUCUCCAAGU<br>AAAGCCACGAGGUCGGGGCGAGGGCAGAGGUGAUCACCUGCGUGUC<br>CCAUCUACAGACCUGCAGCUUCAUAAAACUUCUGAUUUCUCUUCAG<br>CUUUGAAAAGGGUUACCCUGGGCACUGGCCUAGAGCCUCACCUCCU<br>AAUAGACUUAGCCCCAUGAGUUUGCCAUGUUGAGCAGGACUAUUUC<br>UGGCACUUGCAAGUCCCAUGAUUUCUUCGGUAAUUCUGAGGGUGGG<br>GGGAGGGACAUGAAAUCAUCUUAGCUUAGCUUUCUGUCUGUGAAU<br>GUCUAUAUAGUGUAUUGUGUGUUUUAACAAAUGAUUUACACUGAC<br>UGUUGCUGUAAAAGUGAAUUUGGAAAUAAAGUUAUUACUCUGAUU<br>AAA |
| 26 | 11 | GCAGUCACCGCCACCCACCAGCUCCGGCACCAACAGCAGCGCCGCUG<br>CCACCGCCCACCUUCUGCCGCCGCCACCACAGCCACCUUCUCCUCCU<br>CCGCUGUCCUCUCCCGUCCUCGCCUCUGUCGACUAUCAGGUGAACU<br>UUGAACCAGGAUGGCUGAGCCCCGCCAGGAGUUCGAAGUGAUGGAA<br>GAUCACGCUGGGACGUACGGGUUGGGGGACAGGAAAGAUCAGGGG<br>GGCUACACCAUGCACCAAGACCAAGAGGGUGACACGGACGCUGGCC<br>UGAAAGAAUCUCCCCUGCAGACCCCCACUGAGGACGGAUCUGAGGA<br>ACCGGGCUCUGAAACCUCUGAUGCUAAGAGCACUCCAACAGCGGAA<br>GCUGAAGAAGCAGGCAUUGGAGACACCCCCAGCCUGGAAGACGAAG<br>CUGCUGGUCACGUGACCCAAGCUCGCAUGGUCAGUAAAAGCAAAGA<br>CGGGACUGGAAGCGAUGACAAAAAAGCCAAGGGGGCUGAUGGUAA<br>AACGAAGAUCGCCACACCGCGGGGAGCAGCCCCUCCAGGCCAGAAG<br>GGCCAGGCCAACGCCACCAGGAUUCCAGCAAAAACCCCGCCCGCUCC<br>AAAGACACCACCCAGCUCUGGUGAACCUCCAAAAUCAGGGGAUCGC<br>AGCGGCUACAGCAGCCCCGGCUCCCCAGGCACUCCCGGCAGCCGCUC<br>CCGCACCCCGUCCCUUCCAACCCCACCCACCCGGGAGCCCAAGAAGG<br>UGGCAGUGGUCCGUACUCCACCCAAGUCGCCGUCUUCCGCCAAGAG<br>CCGCCUGCAGACAGCCCCCGUGCCCAUGCCAGACCUGAAGAAUGUC<br>AAGUCCAAGAUCGGCUCCACUGAGAACCUGAAGCACCAGCCGGGAG<br>GCGGGAAGGUGCAAAUAGUCUACAAACCAGUUGACCUGAGCAAGGU<br>UGGAACUGCUGCCAUGAUUUUGGCCACUUUGCAGACCUGGGACUUU<br>AGGGCUAACCAGUUCUCUUUGUAAGGACUUGUGCCUCUUGGGAGAC<br>GUCCACCCGUUUCCAAGCCUGGGCCACUGGCAUCUCUGGAGUGUGU<br>GGGGGUCUGGGAGGCAGGUCCCGAGCCCCCUGUCCUUCCCACGGCC<br>ACUGCAGUCACCCCGUCUGCGCCGCUGUGCUGUUGUCUGCCGUGAG<br>AGCCCAAUCACUGCCUAUACCCCUCAUCACACGUCACAAUGUCCCG<br>AAUUCCCAGCCUCACCACCCCUUCUCAGUAAUGACCCUGGUUGGUU<br>GCAGGAGGUACCUACUCCAUACUGAGGGUGAAAUUAAGGGAAGGCA<br>AAGUCCAGGCACAAGAGUGGGACCCCAGCCUCUCACUCUCAGUUCC<br>ACUCAUCCAACUGGGACCCUCACCACGAAUCUCAUGAUCUGAUUCG<br>GUUCCCUGUCUCCUCCUCCCGUCACAGAUGUGAGCCAGGGCACUGC<br>UCAGCUGUGACCCUAGGUGUUUCUGCCUUGUUGACAUGGAGAGAGC<br>CCUUUCCCCUGAGAAGGCCUGGCCCCUUCCUGUGCUGAGCCCACAG<br>CAGCAGGCUGGGUGUCUUGGUUGUCAGUGGUGGCACCAGGAUGGAA<br>GGGCAAGGCACCCAGGGCAGGCCCACAGUCCCGCUGUCCCCCACUU<br>GCACCCUAGCUUGUAGCUGCCAACCUCCCAGACAGCCCAGCCCGCUG<br>CUCAGCUCCACAUGCAUAGUAUCAGCCCUCCACACCCGACAAAGGG<br>GAACACACCCCCUUGGAAAUGGUUCUUUUCCCCCAGUCCCAGCUGG<br>AAGCCAUGCUGUCUGUUCUGCUGGAGCAGCUGAACAUAUACAUAGA<br>UGUUGCCCUGCCCUCCCCAUCUGCACCCUGUUGAGUUGUAGUUGGA<br>UUUGUCUGUUUAUGCUUGGAUUCACCAGAGUGACUAUGAUAGUGA<br>AAAGAAAAAAAAAAAAAAAAAAAGGACGCAUGUAUCUUGAAAUGCU<br>UGUAAAGAGGUUUCUAACCCACCCUCACGAGGUGUCUCUCACCCCC<br>ACACUGGGACUCGUGUGGCCUGUGUGGUGCCACCCUGCUGGGGCCU<br>CCCAAGUUUUGAAAGGCUUUCCUCAGCACCUGGGACCCAACAGAGA<br>CCAGCUUCUAGCAGCUAAGGAGGCCGUUCAGCUGUGACGAAGGCCU<br>GAAGCACAGGAUUAGGACUGAAGCGAUGAUGUCCCCUUCCCUACUU<br>CCCCUUGGGGCUCCCUGUGUCAGGGCACAGACUAGGUCUUGUGGCU<br>GGUCUGGCUUGCGGCGCGAGGAUGGUUCUCUGGUCAUAGCCCGA<br>AGUCUCAUGGCAGUCCCAAAGGAGGCUUACAACUCCUGCAUCACAA<br>GAAAAAGGAAGCCACUGCCAGCUGGGGGGAUCUGCAGCUCCCAGAA<br>GCUCCGUGAGCCUCAGCCACCCCUCAGACUGGGUUCCUCUCCAAGC<br>UCGCCCUCUGGAGGGGCAGCGCAGCCUCCCACCAAGGGCCCUGCGA<br>CCACAGCAGGGAUUGGGAUGAAUUGCCUGUCCUGGAUCUGCUCUAG<br>AGGCCCAAGCUGCCUGCCUGAGGAAGGAUGACUUGACAAGUCAGGA |

TABLE 4-continued

Human MAPT mRNA Isoform Sequences. Sequences obtained from NCBI MAPT gene ID: 4137; Assembly GRCh38.p13 (GCF_000001405.39); NC_000017.11 (45894538 . . . 46028334)

| SEQ ID NO | Isoform | mRNA Sequence |
|---|---|---|
| | | GACACUGUUCCCAAAGCCUUGACCAGAGCACCUCAGCCCGCUGACC<br>UUGCACAAACUCCAUCUGCUGCCAUGAGAAAAGGGAAGCCGCCUUU<br>GCAAAACAUUGCUGCCUAAAGAAACUCAGCAGCCUCAGGCCCAAUU<br>CUGCCACUUCUGGUUUGGGUACAGUUAAAGGCAACCCUGAGGGACU<br>UGGCAGUAGAAAUCCAGGGCCUCCCCUGGGGCUGGCAGCUUCGUGU<br>GCAGCUAGAGCUUUACCUGAAAGGAAGUCUCUGGGCCCAGAACUCU<br>CCACCAAGAGCCUCCCUGCCGUUCGCUGAGUCCCAGCAAUUCUCCU<br>AAGUUGAAGGGAUCUGAGAAGGAGAAGGAAAUGUGGGGUAGAUUU<br>GGUGGUGGUUAGAGAUAUGCCCCCCUCAUUACUGCCAACAGUUUCG<br>GCUGCAUUUCUUCACGCACCUCGGUUCCUCUUCCUGAAGUUCUUGU<br>GCCCUGCUCUUCAGCACCAUGGGCCUUCUUAUACGGAAGGCUCUGG<br>GAUCUCCCCCUUGUGGGGCAGGCUCUUGGGGCCAGCCUAAGAUCAU<br>GGUUUAGGGUGAUCAGUGCUGGCAGAUAAAUUGAAAAGGCACGCU<br>GGCUUGUGAUCUUAAAUGAGGACAAUCCCCCCAGGGCUGGGCACUC<br>CUCCCCUCCCCUCACUUCUCCCACCUGCAGAGCCAGUGUCCUUGGGU<br>GGGCUAGAUAGGAUAUACUGUAUGCCGGCUCCUUCAAGCUGCUGAC<br>UCACUUUAUCAAUAGUUCCAUUUAAAUUGACUUCAGUGGUGAGACU<br>GUAUCCUGUUUGCUAUUGCUUGUUGUGCUAUGGGGGGAGGGGGA<br>GGAAUGUGUAAGAUAGUUAACAUGGGCAAAGGAGAUCUUGGGGU<br>GCAGCACUUAAACUGCCUCGUAACCCUUUUCAUGAUUUCAACCACA<br>UUUGCUAGAGGGAGGGAGCAGCCACGGAGUUAGAGGCCCUUGGGGU<br>UUCUCUUUUCCACUGACAGGCUUUCCCAGGCAGCUGGCUAGUUCAU<br>UCCCUCCCCAGCCAGGUGCAGGCGUAGGAAUAUGGACAUCUGGUUG<br>CUUUGGCCUGCUGCCCUCUUUCAGGGGUCCUAAGCCCACAAUCAUG<br>CCUCCCUAAGACCUUGGCAUCCUUCCCUCUAAGCCGUUGGCACCUC<br>UGUGCCACCUCUCACACUGGCUCCAGACACACAGCCUGUGCUUUUG<br>GAGCUGAGAUCACUCGCUUCACCCUCCUCAUCUUUGUUCUCCAAGU<br>AAAGCCACGAGGUCGGGGCGAGGGCAGAGGUGAUCACCUGCGUGUC<br>CCAUCUACAGACCUGCAGCUUCAUAAAACUUCUGAUUUCUCUUCAG<br>CUUUGAAAAGGGUUACCCUGGGCACUGGCCUAGAGCCUCACCUCCU<br>AAUAGACUUAGCCCCAUGAGUUUGCCAUGUUGAGCAGGACUAUUUC<br>UGGCACUUGCAAGUCCCAUGAUUUCUUCGGUAAUUCUGAGGGUGGG<br>GGGAGGGACAUGAAAUCAUCUUAGCUUAGCUUUCUGUCUGUGAAU<br>GUCUAUAUAGUGUAUUGUGUGUUUUAACAAAUGAUUUACACUGAC<br>UGUUGCUGUAAAAGUGAAUUUGGAAAUAAAGUUAUUACUCUGAUU<br>AAA |
| 27 | 12 | GCAGUCACCGCCACCCACCAGCUCCGGCACCAACAGCAGCGCCGCUG<br>CCACCGCCCACCUUCUGCCGCCGCCACCACAGCCACCUUCUCCUCCU<br>CCGCUGUCCUCUCCCGUCCUCGCCUCUGUCGACUAUCAGACAGGCUC<br>UGCUGAUGCUGUCCCUCUCCUGUUCAGUCGUGCCCUCACCGUUAAA<br>GAGAAAGAGCAAACUGCUGGGCAGCAGCAUUGAUUUUUUUAAUGA<br>AGUGGAAAGAGAGCUGGGAAUAACAAGUCGGGCCCACCUCACCUGC<br>CUCACCUGGUGAACUUUGAACCAGGAUGGCUGAGCCCCGCCAGGAG<br>UUCGAAGUGAUGGAAGAUCACGCUGGGACGUACGGGUUGGGGGAC<br>AGGAAAGAUCAGGGGGGCUACACCAUGCACCAAGACCAAGAGGGUG<br>ACACGGACGCUGGCCUGAAAGCUGAAGAAGCAGGCAUUGGAGACAC<br>CCCCAGCCUGGAAGACGAAGCUGCUGGUCACGUGACCCAAGCUCGC<br>AUGGUCAGUAAAAGCAAAGACGGGACUGGAAGCGAUGACAAAAAA<br>GCCAAGGGGGCUGAUGGUAAAACGAAGAUCGCCACACCGCGGGGAG<br>CAGCCCCUCCAGGCCAGAAGGGCCAGGCCAACGCCACCAGGAUUCC<br>AGCAAAAACCCCGCCCGCUCCAAAGACACCACCCAGCUCUGGUGAA<br>CCUCCAAAAUCAGGGGAUCGCAGCGGCUACAGCAGCCCCGGCUCCC<br>CAGGCACUCCCGGCAGCCGCUCCCGCACCCCGUCCCUUCCAACCCCA<br>CCCACCCGGGAGCCCAAGAAGGUGGCAGUGGUCCGUACUCCACCCA<br>AGUCGCCGUCUUCCGCCAAGAGCCGCCUGCAGACAGCCCCCGUGCCC<br>AUGCCAGACCUGAAGAAUGUCAAGUCCAAGAUCGGCUCCACUGAGA<br>ACCUGAAGCACCAGCCGGGAGGCGGGAAGGUGCAAAUAGUCUACAA<br>ACCAGUUGACCUGAGCAAGGUGACCUCCAAGUGUGGCUCAUUAGGC<br>AACAUCCAUCAUAAACCAGGAGGUGGCCAGGUGGAAGUAAAAUCUG<br>AGAAGCUUGACUUCAAGGACAGAGUCCAGUCGAAGAUUGGGUCCCU<br>GGACAAUAUCACCCACGUCCCUGGCGGAGGAAAUAAAAAGAUUGAA<br>ACCCACAAGCUGACCUUCCGCGAGAACGCCAAAGCCAAGACAGACC<br>ACGGGGCGGAGAUCGUGUACAAGUCGCCAGUGGUGUCUGGGGACAC<br>GUCUCCACGGCAUCUCAGCAAUGUCUCCUCCACCGGCAGCAUCGAC<br>AUGGUAGACUCGCCCCAGCUCGCCACGCUAGCUGACGAGGUGUCUG<br>CCUCCCUGGCCAAGCAGGGUUUGUGAUCAGGCCCCUGGGGCGGUCA<br>AUAAUUGUGGAGAGGAGAGAAUGAGAGAGUGUGGAAAAAAAAAGA<br>AUAAUGACCCGGCCCCCGCCCUCUGCCCCCAGCUGCUCCUCGCAGUU<br>CGGUUAAUUGGUUAAUCACUUAACCUGCUUUUGUCACUCGGCUUUG<br>GCUCGGGACUUCAAAAUCAGUGAUGGGAGUAAGAGCAAAUUUCAUC<br>UUUCCAAAUUGAUGGGUGGGCUAGUAAUAAAAUAUUUAAAAAAAA |

TABLE 4-continued

Human MAPT mRNA Isoform Sequences. Sequences obtained from NCBI MAPT gene ID: 4137; Assembly GRCh38.p13 (GCF_000001405.39); NC_000017.11 (45894538 . . . 46028334)

| SEQ ID NO | Isoform | mRNA Sequence |
|---|---|---|
| | | ACAUUCAAAAACAUGGCCACAUCCAACAUUUCCUCAGGCAAUUCCU |
| | | UUUGAUUCUUUUUUCUUCCCCCUCCAUGUAGAAGAGGGAGAAGGAG |
| | | AGGCUCUGAAAGCUGCUUCUGGGGGAUUUCAAGGGACUGGGGGUGC |
| | | CAACCACCUCUGGCCCUGUUGUGGGGGUGUCACAGAGGCAGUGGCA |
| | | GCAACAAAGGAUUUGAAACUUGGUGUGUUCGUGGAGCCACAGGCAG |
| | | ACGAUGUCAACCUUGUGUGAGUGUGACGGGGGUUGGGGUGGGGCG |
| | | GGAGGCCACGGGGGAGGCCGAGGCAGGGGCUGGGCAGAGGGGAGAG |
| | | GAAGCACAAGAAGUGGGAGUGGGAGAGGAAGCCACGUGCUGGAGA |
| | | GUAGACAUCCCCCUCCUUGCCGCUGGGAGAGCCAAGGCCUAUGCCA |
| | | CCUGCAGCGUCUGAGCGGCCGCCUGUCCUUGGUGGCCGGGGGUGGG |
| | | GGCCUGCUGUGGGUCAGUGUGCCACCCUCUGCAGGGCAGCCUGUGG |
| | | GAGAAGGGACAGCGGGUAAAAAGAGAAGGCAAGCUGGCAGGAGGG |
| | | UGGCACUUCGUGGAUGACCUCCUUAGAAAAGACUGACCUUGAUGUC |
| | | UUGAGAGCGCUGGCCUCUUCCUCCCUCCCUGCAGGGUAGGGGGCCU |
| | | GAGUUGAGGGGCUUCCCUCUGCUCCACAGAAACCCUGUUUUAUUGA |
| | | GUUCUGAAGGUUGGAACUGCUGCCAUGAUUUUGGCCACUUUGCAGA |
| | | CCUGGGACUUUAGGGCUAACCAGUUCUCUUUGUAAGGACUUGUGCC |
| | | UCUUGGGAGACGUCCACCCGUUUCCAAGCCUGGGCCACUGGCAUCU |
| | | CUGGAGUGUGUGGGGGUCUGGGAGGCAGGUCCCGAGCCCCCUGUCC |
| | | UUCCCACGGCCACUGCAGUCACCCCGUCUGCGCCGCUGUGCUGUUG |
| | | UCUGCCGUGAGAGCCCAAUCACUGCCUAUACCCCUCAUCACACGUC |
| | | ACAAUGUCCCGAAUUCCCAGCCUCACCACCCCUUCUCAGUAAUGAC |
| | | CCUGGUUGGUUGCAGGAGGUACCUACUCCAUACUGAGGGUGAAAUU |
| | | AAGGGAAGGCAAAGUCCAGGCACAAGAGUGGGACCCCAGCCUCUCA |
| | | CUCUCAGUUCCACUCAUCCAACUGGGACCCUCACCACGAAUCUCAU |
| | | GAUCUGAUUCGGUUCCCUGUCUCCUCCUCCCGUCACAGAUGUGAGC |
| | | CAGGGCACUGCUCAGCUGUGACCCUAGGUGUUUCUGCCUUGUUGAC |
| | | AUGGAGAGAGCCCUUUCCCCUGAGAAGGCCUGGCCCCUUCCUGUGC |
| | | UGAGCCCACAGCAGCAGGCUGGGUGUCUUGGUUGUCAGUGGUGGCA |
| | | CCAGGAUGGAAGGGCAAGGCACCCAGGGCAGGCCCACAGUCCCGCU |
| | | GUCCCCCACUUGCACCCUAGCUUGUAGCUGCCAACCUCCCAGACAGC |
| | | CCAGCCCGCUGCUCAGCUCCACAUGCAUAGUAUCAGCCCUCCACACC |
| | | CGACAAAGGGGAACACACCCCCUUGGAAAUGGUUCUUUUCCCCCAG |
| | | UCCCAGCUGGAAGCCAUGCUGUCUGUUCUGCUGGAGCAGCUGAACA |
| | | UAUACAUAGAUGUUGCCCUGCCCUCCCCAUCUGCACCCUGUUGAGU |
| | | UGUAGUUGGAUUUGUCUGUUUAUGCUUGGAUUCACCAGAGUGACU |
| | | AUGAUAGUGAAAAGAAAAAAAAAAAAAAAAAAAGGACGCAUGUAUC |
| | | UUGAAAUGCUUGUAAAGAGGUUUCUAACCCACCCUCACGAGGUGUC |
| | | UCUCACCCCCACACUGGGACUCGUGUGGCCUGUGUGGUGCCACCCU |
| | | GCUGGGGCCUCCCAAGUUUUGAAAGGCUUUCCUCAGCACCUGGGAC |
| | | CCAACAGAGACCAGCUUCUAGCAGCUAAGGAGGCCGUUCAGCUGUG |
| | | ACGAAGGCCUGAAGCACAGGAUUAGGACUGAAGCGAUGAUGUCCCC |
| | | UUCCCUACUUCCCCUUGGGGCUCCCUGUGUCAGGGCACAGACUAGG |
| | | UCUUGUGGCUGGUCUGGCUUGCGGCGCGAGGAUGGUUCUCUCUGGU |
| | | CAUAGCCCGAAGUCUCAUGGCAGUCCCAAAGGAGGCUUACAACUCC |
| | | UGCAUCACAAGAAAAAGGAAGCCACUGCCAGCUGGGGGGAUCUGCA |
| | | GCUCCCAGAAGCUCCGUGAGCCUCAGCCACCCCUCAGACUGGGUUC |
| | | CUCUCCAAGCUCGCCCUCUGGAGGGGCAGCGCAGCCUCCCACCAAG |
| | | GGCCCUGCGACCACAGCAGGGAUUGGGAUGAAUUGCCUGUCCUGGA |
| | | UCUGCUCUAGAGGCCCAAGCUGCCUGCCUGAGGAAGGAUGACUUGA |
| | | CAAGUCAGGAGACACUGUUCCCAAAGCCUUGACCAGAGCACCUCAG |
| | | CCCGCUGACCUUGCACAAACUCCAUCUGCUGCCAUGAGAAAAGGGA |
| | | AGCCGCCUUUGCAAAACAUUGCUGCCUAAAGAAACUCAGCAGCCUC |
| | | AGGCCCAAUUCUGCCACUUCUGGUUUGGGUACAGUUAAAGGCAACC |
| | | CUGAGGGACUUGGCAGUAGAAAUCCAGGGCCUCCCCUGGGGCUGGC |
| | | AGCUUCGUGUGCAGCUAGAGCUUUACCUGAAAGGAAGUCUCUGGGC |
| | | CCAGAACUCUCCACCAAGAGCCUCCCUGCCGUUCGCUGAGUCCCAGC |
| | | AAUUCUCCUAAGUUGAAGGGAUCUGAGAAGGAGAAGGAAAUGUGG |
| | | GGUAGAUUUGGUGGUGGUUAGAGAUAUGCCCCCCUCAUUACUGCCA |
| | | ACAGUUUCGGCUGCAUUUCUUCACGCACCUCGGUUCCUCUUCCUGA |
| | | AGUUCUUGUGCCCUGCUCUUCAGCACCAUGGGCCUUCUUAUACGGA |
| | | AGGCUCUGGGAUCUCCCCCUUGUGGGGCAGGCUCUUGGGGCCAGCC |
| | | UAAGAUCAUGGUUUAGGGUGAUCAGUGCUGGCAGAUAAAUUGAAA |
| | | AGGCACGCUGGCUUGUGAUCUUAAAUGAGGACAAUCCCCCCAGGGC |
| | | UGGGCACUCCUCCCCUCCCCUCACUUCUCCCACCUGCAGAGCCAGUG |
| | | UCCUUGGGUGGGCUAGAUAGGAUAUACUGUAUGCCGGCUCCUUCAA |
| | | GCUGCUGACUCACUUUAUCAAUAGUUCCAUUUAAAUUGACUUCAGU |
| | | GGUGAGACUGUAUCCUGUUUGCUAUUGCUUGUUGUGCUAUGGGGG |
| | | GAGGGGGGAGGAAUGUGUAAGAUAGUUAACAUGGGCAAAGGGAGA |
| | | UCUUGGGGUGCAGCACUUAAACUGCCUCGUAACCCUUUUCAUGAUU |
| | | UCAACCACAUUUGCUAGAGGGAGGGAGCAGCCACGGAGUUAGAGGC |
| | | CCUUGGGGUUUCUCUUUUCCACUGACAGGCUUUCCCAGGCAGCUGG |

TABLE 4-continued

Human MAPT mRNA Isoform Sequences. Sequences obtained from NCBI MAPT gene ID: 4137; Assembly GRCh38.p13 (GCF_000001405.39); NC_000017.11 (45894538 . . . 46028334)

| SEQ ID NO | Isoform | mRNA Sequence |
|---|---|---|
| | | CUAGUUCAUUCCCUCCCCAGCCAGGUGCAGGCGUAGGAAUAUGGAC<br>AUCUGGUUGCUUUGGCCUGCUGCCCUCUUUCAGGGGUCCUAAGCCC<br>ACAAUCAUGCCUCCCUAAGACCUUGGCAUCCUUCCCUCUAAGCCGU<br>UGGCACCUCUGUGCCACCUCUCACACUGGCUCCAGACACACAGCCU<br>GUGCUUUUGGAGCUGAGAUCACUCGCUUCACCCUCCUCAUCUUUGU<br>UCUCCAAGUAAAGCCACGAGGUCGGGGCGAGGGCAGAGGUGAUCAC<br>CUGCGUGUCCCAUCUACAGACCUGCAGCUUCAUAAAACUUCUGAUU<br>UCUCUUCAGCUUUGAAAAGGGUUACCCUGGGCACUGGCCUAGAGCC<br>UCACCUCCUAAUAGACUUAGCCCCAUGAGUUUGCCAUGUUGAGCAG<br>GACUAUUUCUGGCACUUGCAAGUCCCAUGAUUUCUUCGGUAAUUCU<br>GAGGGUGGGGGGAGGGACAUGAAAUCAUCUUAGCUUAGCUUUCUG<br>UCUGUGAAUGUCUAUAUAGUGUAUUGUGUGUUUUAACAAAUGAUU<br>UACACUGACUGUUGCUGUAAAAGUGAAUUUGGAAAUAAAGUUAUU<br>ACUCUGAUUAAA |

In some embodiments, the editing of a base of the Tau mRNA results in a decreased gene translation of the Tau polypeptide. In other cases, the editing of a base of the 5'UTR of the Tau mRNA results in a decreased gene translation of the Tau polypeptide. The decreased gene translation of the Tau polypeptide can be measure by an in vitro assay. Such in vitro assay can comprise an in vitro translation assay. An in vitro translation assay can comprise a cell extract. A cell extract can comprise rabbit reticulocyte lysate, wheat germ extract, insect cells, yeast *Kluyveromyces*, or *E. coli* cell-free extract. An in vitro translation assay can comprise mixing a cell extract with a nucleic acid template, ATP, and amino acids. A nucleic acid template can comprise a mRNA template or a cDNA template. A nucleic acid template can comprise a mRNA sequence listed in TABLE 4. A nucleic acid template can comprise a cDNA sequence complementary to the mRNA sequence listed in TABLE 4. When using an in vitro translation system with a cDNA template, the cDNA can be converted to a mRNA by in vitro transcription. A cDNA can be maintained in a circular vector. A cDNA can be maintained as a linear sequence.

A list of Tau polypeptides encoded by the mRNA in TABLE 4 is listed in TABLE 5.

TABLE 5

Human MAPT Protein Isoform Sequences.

| SEQ ID NO | Iso-form | Peptide Sequence |
|---|---|---|
| 28 | X1 | MAEPRQEFEVMEDHAGTYGLGDRKDQGGYTMHQDQEGDTD<br>AGLKESPLQTPTEDGSEEPGSETSDAKSTPTAEDVTAPLV<br>DEGAPGKQAAAQPHTEIPEGTTAEEAGIGDTPSLEDEAAG<br>HVTQEELRVPGRQRKAPERPLANEISAHVQPGPCGEASGV<br>SGPCLGEKEPEAPVPLTASLPQHRPVCPAPPPTGGPQEPS<br>LEWGQKGGDWAEKGPAFPKPATTAYLHTEPESGKVVQEGF<br>LREPGPPGLSHQLMSGMPGAPLLPEGPREATRQPSGTGPE<br>DTEGGRHAPELLKHQLLGDLHQEGPPLKGAGGKERPGSKE<br>EVDEDRDVDESSPQDSPPSKASPAQDGRPPQTAAREATSI<br>PGFPAEGAIPLPVDFLSKVSTEIPASEPDGPSVGRAKGQD<br>APLEFTFHVEITPNVQKEQAHSEEHLGRAAFPGAPGEGPE<br>ARGPSLGEDTKEADLPEPSEKQPAAAPRGKPVSRVPQLKA<br>RMVSKSKDGTGSDDKKAKTSTRSSAKTLKNRPCLSPKHPT<br>PGSSDPLIQPSSPAVCPEPPSSPKYVSSVTSRTGSSGAKE<br>MKLKGADGKTKIATPRGAAPPGQKGQANATRIPAKTPPAP |

TABLE 5-continued

Human MAPT Protein Isoform Sequences.

| SEQ ID NO | Iso-form | Peptide Sequence |
|---|---|---|
| | | KTPPSSGEPPKSGDRSGYSSPGSPGTPGSRSRTPSLPTPP<br>TREPKKVAVVRTPPKSPSSAKSRLQTAPVPMPDLKNVKSK<br>IGSTENLKHQPGGGKVQIINKKLDLSNVQSKCGSKDNIKH<br>VPGGGSVQIVYKPVDLSKVTSKCGSLGNIHHKPGGGQVEV<br>KSEKLDFKDRVQSKIGSLDNITHVPGGGNKKIETHKLTFR<br>ENAKAKTDHGAEIVYKSPVVSGDTSPRHLSNVSSTGSIDM<br>VDSPQLATLADEVSASLAKQGL |
| 29 | X3 | MAEPRQEFEVMEDHAGTYGLGDRKDQGGYTMHQDQEGDTD<br>AGLKESPLQTPTEDGSEEPGSETSDAKSTPTAEDVTAPLV<br>DEGAPGKQAAAQPHTEIPEGTTAEEAGIGDTPSLEDEAAG<br>HVTQEELRVPGRQRKAPERPLANEISAHVQPGPCGEASGV<br>SGPCLGEKEPEAPVPLTASLPQHRPVCPAPPPTGGPQEPS<br>LEWGQKGGDWAEKGPAFPKPATTAYLHTEPESGKVVQEGF<br>LREPGPPGLSHQLMSGMPGAPLLPEGPREATRQPSGTGPE<br>DTEGGRHAPELLKHQLLGDLHQEGPPLKGAGGKERPGSKE<br>EVDEDRDVDESSPQDSPPSKASPAQDGRPPQTAAREATSI<br>PGFPAEGAIPLPVDFLSKVSTEIPASEPDGPSVGRAKGQD<br>APLEFTFHVEITPNVQKEQAHSEEHLGRAAFPGAPGEGPE<br>ARGPSLGEDTKEADLPEPSEKQPAAAPRGKPVSRVPQLKA<br>RMVSKSKDGTGSDDKKAKTSTRSSAKTLKNRPCLSPKHPT<br>PGSSDPLIQPSSPAVCPEPPSSPKYVSSVTSRTGSSGAKE<br>MKLKGADGKTKIATPRGAAPPGQKGQANATRIPAKTPPAP<br>KTPPSSGEPPKSGDRSGYSSPGSPGTPGSRSRTPSLPTPP<br>TREPKKVAVVRTPPKSPSSAKSRLQTAPVPMPDLKNVKSK<br>IGSTENLKHQPGGGKVQIVYKPVDLSKVTSKCGSLGNIHH<br>KPGGGQVEVKSEKLDFKDRVQSKIGSLDNITHVPGGGNKK<br>IETHKLTFRENAKAKTDHGAEIVYKSPVVSGDTSPRHLSN<br>VSSTGSIDMVDSPQLATLADEVSASLAKQGL |
| 30 | X4 | MAEPRQEFEVMEDHAGTYGLGDRKDQGGYTMHQDQEGDTD<br>AGLKAEEAGIGDTPSLEDEAAGHVTQEELRVPGRQRKAPE<br>RPLANEISAHVQPGPCGEASGVSGPCLGEKEPEAPVPLTA<br>SLPQHRPVCPAPPPTGGPQEPSLEWGQKGGDWAEKGPAFP<br>KPATTAYLHTEPESGKVVQEGFLREPGPPGLSHQLMSGMP<br>GAPLLPEGPREATRQPSGTGPEDTEGGRHAPELLKHQLLG<br>DLHQEGPPLKGAGGKERPGSKEEVDEDRDVDESSPQDSPP<br>SKASPAQDGRPPQTAAREATSIPGFPAEGAIPLPVDFLSK<br>VSTEIPASEPDGPSVGRAKGQDAPLEFTFHVEITPNVQKE<br>QAHSEEHLGRAAFPGAPGEGPEARGPSLGEDTKEADLPEP<br>SEKQPAAAPRGKPVSRVPQLKARMVSKSKDGTGSDDKKAK<br>TSTRSSAKTLKNRPCLSPKHPTPGSSDPLIQPSSPAVCPE<br>PPSSPKYVSSVTSRTGSSGAKEMKLKGADGKTKIATPRGA<br>APPGQKGQANATRIPAKTPPAPKTPPSSGEPPKSGDRSGY<br>SSPGSPGTPGSRSRTPSLPTPPTREPKKVAVVRTPPKSPS<br>SAKSRLQTAPVPMPDLKNVKSKIGSTENLKHQPGGGKVQI |

TABLE 5-continued

Human MAPT Protein Isoform Sequences.

| SEQ ID NO | Isoform | Peptide Sequence |
|---|---|---|
| | | INKKLDLSNVQSKCGSKDNIKHVPGGGSVQIVYKPVDLSK VTSKCGSLGNIHHKPGGGQVEVKSEKLDFKDRVQSKIGSL DNITHVPGGGNKKIETHKLTFRENAKAKTDHGAEIVYKSP VVSGDTSPRHLSNVSSTGSIDMVDSPQLATLADEVSASLA KQGL |
| 31 | X5 | MAEPRQEFEVMEDHAGTYGLGDRKDQGGYTMHQDQEGDTD AGLKESPLQTPTEDGSEEPGSETSDAKSTPTAEDVTAPLV DEGAPGKQAAAQPHTEIPEGTTAEEAGIGDTPSLEDEAAG HVTQEELRVPGRQRKAPERPLANEISAHVQPGPCGEASGV SGPCLGEKEPEAPVPLTASLPQHRPVCPAPPPTGGPQEPS LEWGQKGGDWAEKGPAFPKPATTAYLHTEPESGKVVQEGF LREPGPPGLSHQLMSGMPGAPLLPEGPREATRQPSGTGPE DTEGGRHAPELLKHQLLGDLHQEGPPLKGAGGKERPGSKE EVDEDRDVDESSPQDSPPSKASPAQDGRPPQTAAREATSI PGFPAEGAIPLPVDFLSKVSTEIPASEPDGPSVGRAKGQD APLEFTFHVEITPNVQKEQAHSEEHLGRAAFPGAPGEGPE ARGPSLGEDTKEADLPEPSEKQPAAAPRGKPVSRVPQLKA RMVSKSKDGTGSDDKKAKGADGKTKIATPRGAAPPGQKGQ ANATRIPAKTPPAPKTPPSSGEPPKSGDRSGYSSPGSPGT PGSRSRTPSLPTPPTREPKKVAVVRTPPKSPSSAKSRLQT APVPMPDLKNVKSKIGSTENLKHQPGGGKVQIINKKLDLS NVQSKCGSKDNIKHVPGGGSVQIVYKPVDLSKVTSKCGSL GNIHHKPGGGQVEVKSEKLDFKDRVQSKIGSLDNITHVPG GGNKKIETHKLTFRENAKAKTDHGAEIVYKSPVVSGDTSP RHLSNVSSTGSIDMVDSPQLATLADEVSASLAKQGL |
| 32 | X6 | MAEPRQEFEVMEDHAGTYGLGDRKDQGGYTMHQDQEGDTD AGLKESPLQTPTEDGSEEPGSETSDAKSTPTAEDVTAPLV DEGAPGKQAAAQPHTEIPEGTTAEEAGIGDTPSLEDEAAG HVTQEELRVPGRQRKAPERPLANEISAHVQPGPCGEASGV SGPCLGEKEPEAPVPLTASLPQHRPVCPAPPPTGGPQEPS LEWGQKGGDWAEKGPAFPKPATTAYLHTEPESGKVVQEGF LREPGPPGLSHQLMSGMPGAPLLPEGPREATRQPSGTGPE DTEGGRHAPELLKHQLLGDLHQEGPPLKGAGGKERPGSKE EVDEDRDVDESSPQDSPPSKASPAQDGRPPQTAAREATSI PGFPAEGAIPLPVDFLSKVSTEIPASEPDGPSVGRAKGQD APLEFTFHVEITPNVQKEQAHSEEHLGRAAFPGAPGEGPE ARGPSLGEDTKEADLPEPSEKQPAAAPRGKPVSRVPQLKA RMVSKSKDGTGSDDKKAKGADGKTKIATPRGAAPPGQKGQ ANATRIPAKTPPAPKTPPSSGEPPKSGDRSGYSSPGSPGT PGSRSRTPSLPTPPTREPKKVAVVRTPPKSPSSAKSRLQT APVPMPDLKNVKSKIGSTENLKHQPGGGKVQIVYKPVDLS KVTSKCGSLGNIHHKPGGGQVEVKSEKLDFKDRVQSKIGS LDNITHVPGGGNKKIETHKLTFRENAKAKTDHGAEIVYKS PVVSGDTSPRHLSNVSSTGSIDMVDSPQLATLADEVSASL AKQGL |
| 33 | X7 | MAEPRQEFEVMEDHAGTYGLGDRKDQGGYTMHQDQEGDTD AGLKESPLQTPTEDGSEEPGSETSDAKSTPTAEDVTAPLV DEGAPGKQAAAQPHTEIPEGTTAEEAGIGDTPSLEDEAAG HVTQARMVSKSKDGTGSDDKKAKTSTRSSAKTLKNRPCLS PKHPTPGSSDPLIQPSSPAVCPEPPSSPKYVSSVTSRTGS SGAKEMKLKGADGKTKIATPRGAAPPGQKGQANATRIPAK TPPAPKTPPSSGEPPKSGDRSGYSSPGSPGTPGSRSRTPS LPTPPTREPKKVAVVRTPPKSPSSAKSRLQTAPVPMPDLK NVKSKIGSTENLKHQPGGGKVQIINKKLDLSNVQSKCGSK DNIKHVPGGGSVQIVYKPVDLSKVTSKCGSLGNIHHKPGG GQVEVKSEKLDFKDRVQSKIGSLDNITHVPGGGNKKIETH KLTFRENAKAKTDHGAEIVYKSPVVSGDTSPRHLSNVSST GSIDMVDSPQLATLADEVSASLAKQGL |
| 34 | X8 | MAEPRQEFEVMEDHAGTYGLGDRKDQGGYTMHQDQEGDTD AGLKESPLQTPTEDGSEEPGSETSDAKSTPTAEAEEAGIG DTPSLEDEAAGHVTQARMVSKSKDGTGSDDKKAKTSTRSS AKTLKNRPCLSPKHPTPGSSDPLIQPSSPAVCPEPPSSPK YVSSVTSRTGSSGAKEMKLKGADGKTKIATPRGAAPPGQK GQANATRIPAKTPPAPKTPPSSGEPPKSGDRSGYSSPGSP GTPGSRSRTPSLPTPPTREPKKVAVVRTPPKSPSSAKSRL QTAPVPMPDLKNVKSKIGSTENLKHQPGGGKVQIINKKLD LSNVQSKCGSKDNIKHVPGGGSVQIVYKPVDLSKVTSKCG SLGNIHHKPGGGQVEVKSEKLDFKDRVQSKIGSLDNITHV PGGGNKKIETHKLTFRENAKAKTDHGAEIVYKSPVVSGDT SPRHLSNVSSTGSIDMVDSPQLATLADEVSASLAKQGL |
| 35 | X9 | MAEPRQEFEVMEDHAGTYGLGDRKDQGGYTMHQDQEGDTD AGLKAEEAGIGDTPSLEDEAAGHVTQARMVSKSKDGTGSD DKKAKTSTRSSAKTLKNRPCLSPKHPTPGSSDPLIQPSSP AVCPEPPSSPKYVSSVTSRTGSSGAKEMKLKGADGKTKIA TPRGAAPPGQKGQANATRIPAKTPPAPKTPPSSGEPPKSG DRSGYSSPGSPGTPGSRSRTPSLPTPPTREPKKVAVVRTP PKSPSSAKSRLQTAPVPMPDLKNVKSKIGSTENLKHQPGG GKVQIINKKLDLSNVQSKCGSKDNIKHVPGGGSVQIVYKP VDLSKVTSKCGSLGNIHHKPGGGQVEVKSEKLDFKDRVQS KIGSLDNITHVPGGGNKKIETHKLTFRENAKAKTDHGAEI VYKSPVVSGDTSPRHLSNVSSTGSIDMVDSPQLATLADEV SASLAKQGL |

Alpha-synuclein (SNCA)

The Alpha-synuclein gene is made up of 5 exons and encodes a 140 amino-acid protein with a predicted molecular mass of ~14.5 kDa. The encoded product is an intrinsically disordered protein with unknown functions. Usually, Alpha-synuclein is a monomer. Under certain stress conditions or other unknown causes, α-synuclein self-aggregates into oligomers. Lewy-related pathology (LRP), primarily comprised of Alpha-synuclein in more than 50% of autopsy-confirmed Alzheimer's disease patients' brains. While the molecular mechanism of how Alpha-synuclein affects the development of Alzheimer's disease is unclear, experimental evidence has shown that Alpha-synuclein interacts with Tau-p and may seed the intracellular aggregation of Tau-p. Moreover, Alpha-synuclein could regulate the activity of GSK3β, which can mediate Tau-hyperphosphorylation. Alpha-synuclein can also self-assemble into pathogenic aggregates (Lewy bodies). Both Tau and α-synuclein can be released into the extracellular space and spread to other cells. Vascular abnormalities impair the supply of nutrients and removal of metabolic byproducts, cause microinfarcts, and promote the activation of glial cells. Therefore, a multiplex strategy to substantially reduce Tau formation, alpha-synuclein formation, or a combination thereof can be important in effectively treating neurodegenerative diseases.

The domain structure of Alpha-synuclein comprises an N-terminal A2 lipid-binding alpha-helix domain, a Non-amyloid β component (NAC) domain, and a C-terminal acidic domain. The lipid-binding domain consisting of five KXKEGV (SEQ ID NO: 194) imperfect repeats. The NAC domain consists of a GAV motif with a VGGAVVTGV (SEQ ID NO: 195) consensus sequence and three GXXX sub-motifs-where X is any of Gly, Ala, Val, Ile, Leu, Phe, Tyr, Trp, Thr, Ser or Met. The C-terminal acidic domain contains a copper-binding motif with a DPDNEA (SEQ ID NO: 196) consensus sequence. Molecularly, Alpha-synuclein is suggested to play a role in neuronal transmission and DNA repair. Complete mRNA sequences are shown in TABLE 6.

In some cases, a region of Alpha-synuclein can be targeted utilizing compositions provided herein. In some cases, a region of the Alpha-synuclein mRNA can be targeted with the engineered polynucleotides disclosed herein for knockdown. In some cases, a region of the exon or intron of the Alpha-synuclein mRNA can be targeted. In some embodiments, a region of the non-coding sequence of the Alpha-synuclein mRNA, such as the 5'UTR and 3'UTR, can be targeted. In other cases, a region of the coding sequence of the Alpha-synuclein mRNA can be targeted. In some cases, a polynucleotide comprises a targeting sequence that can hybridize to at least a portion of a sequence of TABLE 6. In some cases, a polynucleotide comprises a targeting sequence that can hybridize to at least a portion of a sequence that comprises at least about 80%, 85%, 90%, 95%, 97%, or 99% sequence identity to a sequence of TABLE 6 can be targeted. Suitable regions include but are not limited to a N-terminal A2 lipid-binding alpha-helix domain, a Non-amyloid β component (NAC) domain, or a C-terminal acidic domain.

In some aspects, an alpha-synuclein mRNA sequence is targeted. In some cases, any one of the 3,177 residues of the sequence may be targeted utilizing the compositions and method provided herein. In some cases, a target residue may be located among residues 1 to 100, from 99 to 200, from 199 to 300, from 299 to 400, from 399 to 500, from 499 to 600, from 599 to 700, from 699 to 800, from 799 to 900, from 899 to 1000, from 999 to 1100, from 1099 to 1200, from 1199 to 1300, from 1299 to 1400, from 1399 to 1500, from 1499 to 1600, from 1599 to 1700, from 1699 to 1800, from 1799 to 1900, from 1899 to 2000, from 1999 to 2100, from 2099 to 2200, from 2199 to 2300, from 2299 to 2400, from 2399 to 2500, from 2499 to 2600, from 2599 to 2700, from 2699 to 2800, from 2799 to 2900, from 2899 to 3000, from 2999 to 3100, from 3099 to 3177, or any combination thereof.

TABLE 6

Human Alpha-synuclein mRNA Isoform Sequences. Sequences derived from NCBI SNCA sequence corresponding to gene ID 6622; Assembly GRCh38.p13 (GCF_000001405.39); NC_000004.12 (89724099..89838324, complement).

| SEQ ID NO | Isoform | mRNA sequence |
|---|---|---|
| 36 | 1 | GGCGACGACCAGAAGGGGCCCAAGAGAGGGGGCGAGCGACCGAGCG<br>CCGCGACGCGGAAGUGAGGUGCGUGCGGGCUGCAGCGCAGACCCCG<br>GCCCGGCCCCUCCGAGAGCGUCCUGGGCGCUCCCUCACGCCUUGCCU<br>UCAAGCCUUCUGCCUUUCCACCCUCGUGAGCGGAGAACUGGGAGUG<br>GCCAUUCGACGACAGUGUGGUGUAAAGGAAUUCAUUAGCCAUGGAU<br>GUAUUCAUGAAAGGACUUUCAAAGGCCAAGGAGGGAGUUGUGGCU<br>GCUGCUGAGAAAACCAAACAGGGUGUGGCAGAAGCAGCAGGAAAGA<br>CAAAAGAGGGUGUUCUCUAUGUAGGCUCCAAAACCAAGGAGGGAGU<br>GGUGCAUGGUGUGGCAACAGUGGCUGAGAAGACCAAAGAGCAAGU<br>GACAAAUGUUGGAGGAGCAGUGGUGACGGGUGUGACAGCAGUAGC<br>CCAGAAGACAGUGGAGGGAGCAGGGAGCAUUGCAGCAGCCACUGGC<br>UUUGUCAAAAAGGACCAGUUGGGCAAGAAUGAAGAAGGAGCCCCAC<br>AGGAAGGAAUUCUGGAAGAUAUGCCUGUGGAUCCUGACAAUGAGG<br>CUUAUGAAAUGCCUUCUGAGGAAGGGUAUCAAGACUACGAACCUGA<br>AGCCUAAGAAAUAUCUUUGCUCCCAGUUUCUUGAGAUCUGCUGACA<br>GAUGUUCCAUCCUGUACAAGUGCUCAGUUCCAAUGUGCCCAGUCAU<br>GACAUUUCUCAAAGUUUUUACAGUGUAUCUCGAAGUCUUCCAUCAG<br>CAGUGAUUGAAGUAUCUGUACCUGCCCCCACUCAGCAUUUCGGUGC<br>UUCCCUUUCACUGAAGUGAAUACAUGGUAGCAGGGUCUUUGUGUGC<br>UGUGGAUUUUGUGGCUUCAAUCUACGAUGUUAAAACAAAUUAAAA<br>ACACCUAAGUGACUACCACUUAUUUCUAAAUCCUCACUAUUUUUUU<br>GUUGCUGUUGUUCAGAAGUUGUUAGUGAUUUGCUAUCAUAUAUUA<br>UAAGAUUUUUAGGUGUCUUUUAAUGAUACUGUCUAAGAAUAAUGA<br>CGUAUUGUGAAAUUUGUUAAUAUAUAUAAUACUUAAAAAUAUGUG<br>AGCAUGAAACUAUGCACCUAUAAAUACUAAAUAUGAAAUUUUACCA<br>UUUUGCGAUGUGUUUUAUUCACUUGUGUUUGUAUAUAAAUGGUGA<br>GAAUUAAAAUAAAACGUUAUCUCAUUGCAAAAAUAUUUUAUUUUU<br>AUCCCAUCUCACUUUAAUAAUAAAAAUCAUGCUUAUAAGCAACAUG<br>AAUUAAGAACUGACACAAAGGACAAAAAUAUAAAGUUAUUAAUAG<br>CCAUUUGAAGAAGGAGGAAUUUUAGAAGAGGUAGAGAAAAUGGAA<br>CAUUAACCCUACACUCGGAAUUCCCUGAAGCAACACUGCCAGAAGU<br>GUGUUUUGGUAUGCACUGGUUCCUUAAGUGGCUGUGAUUAAUUAU<br>UGAAAGUGGGGUGUUGAAGACCCCAACUACUAUUGUAGAGUGGUC<br>UAUUUCUCCCUUCAAUCCUGUCAAUGUUUGCUUUACGUAUUUUGGG<br>GAACUGUUGUUUGAUGUGUAUGUGUUUAUAAUUGUUAUACAUUUU<br>UAAUUGAGCCUUUUAUUAACAUAUAUUGUUAUUUUUGUCUCGAAA<br>UAAUUUUUUAGUUAAAAUCUAUUUUGUCUGAUAUUGGUGUGAAUG<br>CUGUACCUUUCUGACAAUAAAUAAUAUUCGACCAUGAAUAAAAAAA<br>AAAAAAAAGUGGGUUCCCGGGAACUAAGCAGUGUAGAAGAUGAUU<br>UUGACUACACCCUCCUUAGAGAGCCAUAAGACACAUUAGCACAUAU<br>UAGCACAUUCAAGGCUCUGAGAGAAUGUGGUUAACUUUGUUUAAC<br>UCAGCAUUCCUCACUUUUUUUUUUUAAUCAUCAGAAAUUCUCUCUC<br>UCUCUCUCUCUUUUUCUCUCGCUCUCUUUUUUUUUUUUUUUUUACA<br>GGAAAUGCCUUUAAACAUCGUUGGAACUACCAGAGUCACCUUAAAG<br>GAGAUCAAUUCUCUAGACUGAUAAAAAUUUCAUGGCCUCCUUUAAA<br>UGUUGCCAAAUAUAUGAAUUCUAGGAUUUUUCCUUAGGAAAGGUU<br>UUUCUCUUUCAGGGAAGAUCUAUUAACUCCCCAUGGGUGCUGAAAA<br>UAAACUUGAUGGUGAAAAACUCUGUAUAAAUUAAUUUAAAAAUUA<br>UUUGGUUUCUCUUUUUAAUUAUUCUGGGGCAUAGUCAUUUCUAAA<br>AGUCACUAGUAGAAAGUAUAAUUUCAAGACAGAAUAUUCUAGACA<br>UGCUAGCAGUUUAUAUGUAUUCAUGAGUAAUGUGAUAUAUAUUGG<br>GCGCUGGUGAGGAAGGAAGGAGGAAUGAGUGACUAUAAGGAUGGU<br>UACCAUAGAAACUUCCUUUUUUACCUAAUUGAAGAGAGACUACUAC |

TABLE 6-continued

Human Alpha-synuclein mRNA Isoform Sequences. Sequences derived from NCBI SNCA sequence corresponding to gene ID 6622; Assembly GRCh38.p13 (GCF_000001405.39); NC_000004.12 (89724099..89838324, complement).

| SEQ ID NO | Isoform | mRNA sequence |
|---|---|---|
| | | AGAGUGCUAAGCUGCAUGUGUCAUCUUACACUAGAGAGAAAUGGU<br>AAGUUUCUUGUUUUAUUUAAGUUAUGUUUAAGCAAGGAAAGGAUU<br>UGUUAUUGAACAGUAUAUUUCAGGAAGGUUAGAAAGUGGCGGUUA<br>GGAUAUAUUUUAAAUCUACCUAAAGCAGCAUAUUUUAAAAAUUUA<br>AAAGUAUUGGUAUUAAAUUAAGAAAUAGAGGACAGAACUAGACUG<br>AUAGCAGUGACCUAGAACAAUUUGAGAUUAGGAAAGUUGUGACCA<br>UGAAUUUAAGGAUUUAUGUGGAUACAAAUUCUCCUUUAAAGUGUU<br>UCUUCCCUUAAUAUUUAUCUGACGGUAAUUUUUGAGCAGUGAAUU<br>ACUUUAUAUAUCUUAAUAGUUUAUUUGGGACCAAACACUUAAACA<br>AAAAGUUCUUUAAGUCAUAUAAGCCUUUUCAGGAAGCUUGUCUCAU<br>AUUCACUCCCGAGACAUUCACCUGCCAAGUGGCCUGAGGAUCAAUC<br>CAGUCCUAGGUUUAUUUUGCAGACUUACAUUCUCCCAAGUUAUUCA<br>GCCUCAUAUGACUCCACGGUCGGCUUUACCAAAACAGUUCAGAGUG<br>CACUUUGGCACACAAUUGGGAACAGAACAAUCUAAUGUGUGGUUUG<br>GUAUUCCAAGUGGGGUCUUUUUCAGAAUCUCUGCACUAGUGUGAGA<br>UGCAAACAUGUUUCCUCAUCUUUCUGGCUUAUCCAGUAUGUAGCUA<br>UUUGUGACAUAAUAAAUAUAUACAUAUAUGAAAAUA |
| 37 | 2 | GGCGACGACCAGAAGGGGCCCAAGAGAGGGGGCGAGCGACCGAGCG<br>CCGCGACGCGGAAGUGAGGUGCGUGCGGGCUGCAGCGCAGACCCCG<br>GCCCGGCCCCUCCGAGAGCGUCCUGGGCGCUCCCUCACGCCUUGCCU<br>UCAAGCCUUCUGCCUUUCCACCCUCGUGAGCGGAGAACUGGGAGUG<br>GCCAUUCGACGACAGGUUAGCGGGUUUGCCUCCCACUCCCCCAGCC<br>UCGCGUCGCCGGCUCACAGCGGCCUCCUCUGGGGACAGUCCCCCCCG<br>GGUGCCGCCUCCGCCCUUCCUGUGCGCUCCUUUUCCUUCUUCUUUCC<br>UAUUAAAUAUUAUUUGGGAAUUGUUUAAAUUUUUUUUUAAAAAA<br>AGAGAGAGGCGGGGAGGAGUCGGAGUUGUGGAGAAGCAGAGGGAC<br>UCAGUGUGGUGUAAAGGAAUUCAUUAGCCAUGGAUGUAUUCAUGA<br>AAGGACUUUCAAAGGCCAAGGAGGGAGUUGUGGCUGCUGCUGAGA<br>AAACCAAACAGGGUGUGGCAGAAGCAGCAGGAAAGACAAAAGAGG<br>GUGUUCUCUAUGUAGGCUCCAAAACCAAGGAGGGAGUGGUGCAUGG<br>UGUGGCAACAGUGGCUGAGAAGACCAAAGAGCAAGUGACAAAUGU<br>UGGAGGAGCAGUGGUGACGGGUGUGACAGCAGUAGCCCAGAAGACA<br>GUGGAGGGAGCAGGGAGCAUUGCAGCAGCCACUGGCUUUGUCAAAA<br>AGGACCAGUUGGGCAAGAAUGAAGAAGGAGCCCCACAGGAAGGAAU<br>UCUGGAAGAUAUGCCUGUGGAUCCUGACAAUGAGGCUUAUGAAAU<br>GCCUUCUGAGGAAGGGUAUCAAGACUACGAACCUGAAGCCUAAGAA<br>AUAUCUUUGCUCCCAGUUUCUUGAGAUCUGCUGACAGAUGUUCCAU<br>CCUGUACAAGUGCUCAGUUCCAAUGUGCCCAGUCAUGACAUUUCUC<br>AAAGUUUUUACAGUGUAUCUCGAAGUCUUCCAUCAGCAGUGAUUGA<br>AGUAUCUGUACCUGCCCCCACUCAGCAUUUCGGUGCUUCCCUUUCA<br>CUGAAGUGAAUACAUGGUAGCAGGGUCUUUGUGUGCUGUGGAUUU<br>UGUGGCUUCAAUCUACGAUGUUAAAACAAAUUAAAAACACCUAAGU<br>GACUACCACUUAUUUCUAAAUCCUCACUAUUUUUUUGUUGCUGUUG<br>UUCAGAAGUUGUUAGUGAUUUGCUAUCAUAUAUUAUAAGAUUUUU<br>AGGUGUCUUUUAAUGAUACUGUCUAAGAAUAAUGACGUAUUGUGA<br>AAUUUGUUAAUAUAUAUAAUACUUAAAAAUAUGUGAGCAUGAAAC<br>UAUGCACCUAUAAAUACUAAAUAUGAAAUUUUACCAUUUUGCGAU<br>GUGUUUUAUUCACUUGUGUUUGUAUAUAAAUGGUGAGAAUUAAAA<br>UAAAACGUUAUCUCAUUGCAAAAAUAUUUAUUUUUAUCCCAUCUC<br>ACUUUAAUAAUAAAAAUCAUGCUUAUAAGCAACAUGAAUUAAGAA<br>CUGACACAAAGGACAAAAAUAUAAAGUUAUUAAUAGCCAUUUGAA<br>GAAGGAGGAAUUUUAGAAGAGGUAGAGAAAAUGGAACAUUAACCC<br>UACACUCGGAAUUCCCUGAAGCAACACUGCCAGAAGUGUGUUUUGG<br>UAUGCACUGGUUCCUUAAGUGGCUGUGAUUAAUUAUUGAAAGUGG<br>GGUGUUGAAGACCCCAACUACUAUUGUAGAGUGGUCUAUUUCUCCC<br>UUCAAUCCUGUCAAUGUUUGCUUUACGUAUUUUGGGGAACUGUUG<br>UUUGAUGUGUAUGUGUUUAUAAUUGUUAUACAUUUUUAAUUGAGC<br>CUUUUAUUAACAUAUAUUGUUAUUUUUGUCUCGAAAUAAUUUUUU<br>AGUUAAAAUCUAUUUUGUCUGAUAUUGGUGUGAAUGCUGUACCUU<br>UCUGACAAUAAAUAAUAUUCGACCAUGAAUAAAAAAAAAAAAAAA<br>GUGGGUUCCCGGGAACUAAGCAGUGUAGAAGAUGAUUUUGACUAC<br>ACCCUCCUUAGAGAGCCAUAAGACACAUUAGCACAUAUUAGCACAU<br>UCAAGGCUCUGAGAGAAUGUGGUUAACUUUGUUUAACUCAGCAUUC<br>CUCACUUUUUUUUUUUAAUCAUCAGAAAUUCUCUCUCUCUCUCU<br>CUUUUUCUCUCGCUCUCUUUUUUUUUUUUUUUUUACAGGAAAUGCC<br>UUUAAACAUCGUUGGAACUACCAGAGUCACCUUAAAGGAGAUCAAU<br>UCUCUAGACUGAUAAAAAUUUCAUGGCCUCCUUUAAAUGUUGCCAA<br>AUAUAUGAAUUCUAGGAUUUUUCCUUAGGAAAGGUUUUUCUCUUU<br>CAGGGAAGAUCUAUUAACUCCCCAUGGGUGCUGAAAAUAAACUUGA |

TABLE 6-continued

Human Alpha-synuclein mRNA Isoform Sequences. Sequences derived from NCBI SNCA sequence corresponding to gene ID 6622; Assembly GRCh38.p13 (GCF_000001405.39); NC_000004.12 (89724099..89838324, complement).

| SEQ ID NO | Isoform | mRNA sequence |
|---|---|---|
| | | UGGUGAAAAACUCUGUAUAAAUUAAUUUAAAAAUUAUUUGGUUUC<br>UCUUUUUAAUUAUUCUGGGGCAUAGUCAUUUCUAAAAGUCACUAG<br>UAGAAAGUAUAAUUUCAAGACAGAAUAUUCUAGACAUGCUAGCAG<br>UUUAUAUGUAUUCAUGAGUAAUGUGAUAUAUAUUGGGCGCUGGUG<br>AGGAAGGAAGGAGGAAUGAGUGACUAUAAGGAUGGUUACCAUAGA<br>AACUUCCUUUUUUACCUAAUUGAAGAGAGACUACUACAGAGUGCUA<br>AGCUGCAUGUGUCAUCUUACACUAGAGAGAAAUGGUAAGUUUCUU<br>GUUUUAUUUAAGUUAUGUUUAAGCAAGGAAAGGAUUUGUUAUUGA<br>ACAGUAUAUUUCAGGAAGGUUAGAAAGUGGCGGUUAGGAUAUAUU<br>UUAAAUCUACCUAAAGCAGCAUAUUUUAAAAAUUUAAAAGUAUUG<br>GUAUUAAAUUAAGAAAUAGAGGACAGAACUAGACUGAUAGCAGUG<br>ACCUAGAACAAUUUGAGAUUAGGAAAGUUGUGACCAUGAAUUUAA<br>GGAUUUAUGUGGAUACAAAUUCUCCUUUAAAGUGUUUCUUCCCUUA<br>AUAUUUAUCUGACGGUAAUUUUUGAGCAGUGAAUUACUUUAUAUA<br>UCUUAAUAGUUUAUUUGGGACCAAACACUUAAACAAAAAGUUCUU<br>UAAGUCAUAUAAGCCUUUUCAGGAAGCUUGUCUCAUAUUCACUCCC<br>GAGACAUUCACCUGCCAAGUGGCCUGAGGAUCAAUCCAGUCCUAGG<br>UUUAUUUUGCAGACUUACAUUCUCCCAAGUUAUUCAGCCUCAUAUG<br>ACUCCACGGUCGGCUUUACCAAAACAGUUCAGAGUGCACUUUGGCA<br>CACAAUUGGGAACAGAACAAUCUAAUGUGUGGUUUGGUAUUCCAA<br>GUGGGGUCUUUUUCAGAAUCUCUGCACUAGUGUGAGAUGCAAACAU<br>GUUUCCUCAUCUUUCUGGCUUAUCCAGUAUGUAGCUAUUUGUGACA<br>UAAUAAAUAUAUACAUAUAUGAAAAUA |
| 38 | 3 | GCUUCUCCAUUCUGGUGUGAUCCAGGAACAGCUGUCUUCCAGCUCU<br>GAAAGAGUGUGGUGUAAAGGAAUUCAUUAGCCAUGGAUGUAUUCA<br>UGAAAGGACUUUCAAAGGCCAAGGAGGGAGUUGUGGCUGCUGCUG<br>AGAAAACCAAACAGGGUGUGGCAGAAGCAGCAGGAAAGACAAAAG<br>AGGGUGUUCUCUAUGUAGGCUCCAAAACCAAGGAGGGAGUGGUGCA<br>UGGUGUGGCAACAGUGGCUGAGAAGACCAAAGAGCAAGUGACAAA<br>UGUUGGAGGAGCAGUGGUGACGGGUGUGACAGCAGUAGCCCAGAA<br>GACAGUGGAGGGAGCAGGGAGCAUUGCAGCAGCCACUGGCUUUGUC<br>AAAAAGGACCAGUUGGGCAAGAAUGAAGAAGGAGCCCCACAGGAAG<br>GAAUUCUGGAAGAUAUGCCUGUGGAUCCUGACAAUGAGGCUUAUG<br>AAAUGCCUUCUGAGGAAGGGUAUCAAGACUACGAACCUGAAGCCUA<br>AGAAAUAUCUUUGCUCCCAGUUUCUUGAGAUCUGCUGACAGAUGUU<br>CCAUCCUGUACAAGUGCUCAGUUCCAAUGUGCCCAGUCAUGACAUU<br>UCUCAAAGUUUUUACAGUGUAUCUCGAAGUCUUCCAUCAGCAGUGA<br>UUGAAGUAUCUGUACCUGCCCCCACUCAGCAUUUCGGUGCUUCCCU<br>UUCACUGAAGUGAAUACAUGGUAGCAGGGUCUUUGUGUGCUGUGG<br>AUUUUGUGGCUUCAAUCUACGAUGUUAAAACAAAUUAAAAACACCU<br>AAGUGACUACCACUUAUUUCUAAAUCCUCACUAUUUUUUUGUUGCU<br>GUUGUUCAGAAGUUGUUAGUGAUUUGCUAUCAUAUAUUAUAAGAU<br>UUUUAGGUGUCUUUUAAUGAUACUGUCUAAGAAUAAUGACGUAUU<br>GUGAAAUUUGUUAAUAUAUAUAAUACUUAAAAAUAUGUGAGCAUG<br>AAACUAUGCACCUAUAAAUACUAAAUAUGAAAUUUUACCAUUUUGC<br>GAUGUGUUUUAUUCACUUGUGUUUGUAUAUAAAUGGUGAGAAUUA<br>AAAUAAAACGUUAUCUCAUUGCAAAAAUAUUUUAUUUUUAUCCCA<br>UCUCACUUUAAUAAUAAAAAUCAUGCUUAUAAGCAACAUGAAUUA<br>AGAACUGACACAAAGGACAAAAAUAUAAAGUUAUUAAUAGCCAUU<br>UGAAGAAGGAGGAAUUUUAGAAGAGGUAGAGAAAAUGGAACAUUA<br>ACCCUACACUCGGAAUUCCCUGAAGCAACACUGCCAGAAGUGUGUU<br>UUGGUAUGCACUGGUUCCUUAAGUGGCUGUGAUUAAUUAUUGAAA<br>GUGGGGUGUUGAAGACCCCAACUACUAUUGUAGAGUGGUCUAUUUC<br>UCCCUUCAAUCCUGUCAAUGUUUGCUUUACGUAUUUUGGGGAACUG<br>UUGUUUGAUGUGUAUGUGUUUAUAAUUGUUAUACAUUUUUAAUUG<br>AGCCUUUUAUUAACAUAUAUUGUUAUUUUUGUCUCGAAAUAAUUU<br>UUUAGUUAAAAUCUAUUUUGUCUGAUAUUGGUGUGAAUGCUGUAC<br>CUUUCUGACAAUAAAUAAUAUUCGACCAUGAAUAAAAAAAAAAAA<br>AAAGUGGGUUCCCGGGAACUAAGCAGUGUAGAAGAUGAUUUUGAC<br>UACACCCUCCUUAGAGAGCCAUAAGACACAUUAGCACAUAUUAGCA<br>CAUUCAAGGCUCUGAGAGAAUGUGGUUAACUUUGUUUAACUCAGCA<br>UUCCUCACUUUUUUUUUUUAAUCAUCAGAAAUUCUCUCUCUCUCUC<br>UCUCUUUUUCUCUCGCUCUCUUUUUUUUUUUUUUUUUACAGGAAAU<br>GCCUUUAAACAUCGUUGGAACUACCAGAGUCACCUUAAAGGAGAUC<br>AAUUCUCUAGACUGAUAAAAAUUUCAUGGCCUCCUUUAAAUGUUGC<br>CAAAUAUAUGAAUUCUAGGAUUUUUCCUUAGGAAAGGUUUUUCUC<br>UUUCAGGGAAGAUCUAUUAACUCCCCAUGGGUGCUGAAAAUAAACU<br>UGAUGGUGAAAAACUCUGUAUAAAUUAAUUUAAAAAUUAUUUGGU<br>UUCUCUUUUUAAUUAUUCUGGGGCAUAGUCAUUUCUAAAAGUCACU |

TABLE 6-continued

Human Alpha-synuclein mRNA Isoform Sequences. Sequences derived from NCBI SNCA sequence corresponding to gene ID 6622; Assembly GRCh38.p13 (GCF_000001405.39); NC_000004.12 (89724099..89838324, complement).

| SEQ ID NO | Isoform | mRNA sequence |
|---|---|---|
| | | AGUAGAAAGUAUAAUUUCAAGACAGAAUAUUCUAGACAUGCUAGC<br>AGUUUAUAUGUAUUCAUGAGUAAUGUGAUAUAUAUUGGGCGCUGG<br>UGAGGAAGGAAGGAGGAAUGAGUGACUAUAAGGAUGGUUACCAUA<br>GAAACUUCCUUUUUUACCUAAUUGAAGAGAGACUACUACAGAGUGC<br>UAAGCUGCAUGUGUCAUCUUACACUAGAGAGAAAUGGUAAGUUUC<br>UUGUUUUAUUUAAGUUAUGUUUAAGCAAGGAAAGGAUUUGUUAUU<br>GAACAGUAUAUUUCAGGAAGGUUAGAAAGUGGCGGUUAGGAUAUA<br>UUUUAAAUCUACCUAAAGCAGCAUAUUUUAAAAAUUUAAAAGUAU<br>UGGUAUUAAAUUAAGAAAUAGAGGACAGAACUAGACUGAUAGCAG<br>UGACCUAGAACAAUUUGAGAUUAGGAAAGUUGUGACCAUGAAUUU<br>AAGGAUUUAUGUGGAUACAAAUUCUCCUUUAAAGUGUUUCUUCCCU<br>UAAUAUUUAUCUGACGGUAAUUUUUGAGCAGUGAAUUACUUUAUA<br>UAUCUUAAUAGUUUAUUUGGGACCAAACACUUAAACAAAAAGUUC<br>UUUAAGUCAUAUAAGCCUUUUCAGGAAGCUUGUCUCAUAUUCACUC<br>CCGAGACAUUCACCUGCCAAGUGGCCUGAGGAUCAAUCCAGUCCUA<br>GGUUUAUUUUGCAGACUUACAUUCUCCCAAGUUAUUCAGCCUCAUA<br>UGACUCCACGGUCGGCUUUACCAAAACAGUUCAGAGUGCACUUUGG<br>CACACAAUUGGGAACAGAACAAUCUAAUGUGUGGUUUGGUAUUCCA<br>AGUGGGGUCUUUUUCAGAAUCUCUGCACUAGUGUGAGAUGCAAACA<br>UGUUUCCUCAUCUUUCUGGCUUAUCCAGUAUGUAGCUAUUUGUGAC<br>AUAAUAAAUAUAUACAUAUAUGAAAAUA |
| 39 | 4 | GGCGACGACCAGAAGGGGCCCAAGAGAGGGGGCGAGCGACCGAGCG<br>CCGCGACGCGGAAGUGAGGUGCGUGCGGGCUGCAGCGCAGACCCCG<br>GCCCGGCCCCUCCGAGAGCGUCCUGGGCGCUCCCUCACGCCUUGCCU<br>UCAAGCCUUCUGCCUUUCCACCCUCGUGAGCGGAGAACUGGGAGUG<br>GCCAUUCGACGACAGGUUAGCGGGUUUGCCUCCCACUCCCCCAGCC<br>UCGCGUCGCCGGCUCACAGCGGCCUCCUCUGGGGACAGUCCCCCCCG<br>GGUGCCGCCUCCGCCCUUCCUGUGCGCUCCUUUUCCUUCUUCUUUCC<br>UAUUAAAUAUUAUUUGGGAAUUGUUUAAAUUUUUUUUUUAAAAAA<br>AGAGAGAGGCGGGGAGGAGUCGGAGUUGUGGAGAAGCAGAGGGAC<br>UCAGUGUGGUGUAAAGGAAUUCAUUAGCCAUGGAUGUAUUCAUGA<br>AAGGACUUUCAAAGGCCAAGGAGGGAGUUGUGGCUGCUGCUGAGA<br>AAACCAAACAGGGUGUGGCAGAAGCAGCAGGAAAGACAAAAGAGG<br>GUGUUCUCUAUGUAGGCUCCAAAACCAAGGAGGGAGUGGUGCAUGG<br>UGUGGCAACAGUGGCUGAGAAGACCAAAGAGCAAGUGACAAAUGU<br>UGGAGGAGCAGUGGUGACGGGUGUGACAGCAGUAGCCCAGAAGACA<br>GUGGAGGGAGCAGGGAGCAUUGCAGCAGCCACUGGCUUUGUCAAAA<br>AGGACCAGUUGGGCAAGGAAGGGUAUCAAGACUACGAACCUGAAGC<br>CUAAGAAAUAUCUUUGCUCCCAGUUUCUUGAGAUCUGCUGACAGAU<br>GUUCCAUCCUGUACAAGUGCUCAGUUCCAAUGUGCCCAGUCAUGAC<br>AUUUCUCAAAGUUUUUACAGUGUAUCUCGAAGUCUUCCAUCAGCAG<br>UGAUUGAAGUAUCUGUACCUGCCCCCACUCAGCAUUUCGGUGCUUC<br>CCUUUCACUGAAGUGAAUACAUGGUAGCAGGGUCUUUGUGUGCUGU<br>GGAUUUUGUGGCUUCAAUCUACGAUGUUAAAACAAAUUAAAAACA<br>CCUAAGUGACUACCACUUAUUUCUAAAUCCUCACUAUUUUUUUGUU<br>GCUGUUGUUCAGAAGUUGUUAGUGAUUUGCUAUCAUAUAUUAUAA<br>GAUUUUUAGGUGUCUUUUAAUGAUACUGUCUAAGAAUAAUGACGU<br>AUUGUGAAAUUUGUUAAUAUAUAUAAUACUUAAAAAUAUGUGAGC<br>AUGAAACUAUGCACCUAUAAAUACUAAAUAUGAAAUUUUACCAUU<br>UUGCGAUGUGUUUUAUUCACUUGUGUUUGUAUAUAAAUGGUGAGA<br>AUUAAAAUAAAACGUUAUCUCAUUGCAAAAAUAUUUUAUUUUUAU<br>CCCAUCUCACUUUAAUAAUAAAAAUCAUGCUUAUAAGCAACAUGAA<br>UUAAGAACUGACACAAAGGACAAAAAUAUAAAGUUAUUAAUAGCC<br>AUUUGAAGAAGGAGGAAUUUUAGAAGAGGUAGAGAAAAUGGAACA<br>UUAACCCUACACUCGGAAUUCCCUGAAGCAACACUGCCAGAAGUGU<br>GUUUUGGUAUGCACUGGUUCCUUAAGUGGCUGUGAUUAAUUAUUG<br>AAAGUGGGGUGUUGAAGACCCCAACUACUAUUGUAGAGUGGUCUA<br>UUUCUCCCUUCAAUCCUGUCAAUGUUUGCUUUACGUAUUUUGGGGA<br>ACUGUUGUUUGAUGUGUAUGUGUUUAUAAUUGUUAUACAUUUUUA<br>AUUGAGCCUUUUAUUAACAUAUAUUGUUAUUUUUGUCUCGAAAUA<br>AUUUUUUAGUUAAAAUCUAUUUUGUCUGAUAUUGGUGUGAAUGCU<br>GUACCUUUCUGACAAUAAAUAAUAUUCGACCAUGAAUAAAAAAAA<br>AAAAAAAGUGGGUUCCCGGGAACUAAGCAGUGUAGAAGAUGAUUU<br>UGACUACACCCUCCUUAGAGAGCCAUAAGACACAUUAGCACAUAUU<br>AGCACAUUCAAGGCUCUGAGAGAAUGUGGUUAACUUUGUUUAACUC<br>AGCAUUCCUCACUUUUUUUUUUUAAUCAUCAGAAAUUCUCUCUCUC<br>UCUCUCUCUUUUUCUCUCGCUCUCUUUUUUUUUUUUUUUUUACAGG<br>AAAUGCCUUUAAACAUCGUUGGAACUACCAGAGUCACCUUAAAGGA<br>GAUCAAUUCUCUAGACUGAUAAAAAUUUCAUGGCCUCCUUUAAAUG |

TABLE 6-continued

Human Alpha-synuclein mRNA Isoform Sequences. Sequences derived from NCBI SNCA sequence corresponding to gene ID 6622; Assembly GRCh38.p13 (GCF_000001405.39); NC_000004.12 (89724099..89838324, complement).

| SEQ ID NO | Isoform | mRNA sequence |
|---|---|---|
| | | UUGCCAAAUAUAUGAAUUCUAGGAUUUUUCCUUAGGAAAGGUUUU<br>UCUCUUUCAGGGAAGAUCUAUUAACUCCCCAUGGGUGCUGAAAAUA<br>AACUUGAUGGUGAAAAACUCUGUAUAAAUUAAUUUAAAAAUUAUU<br>UGGUUUCUCUUUUUAAUUAUUCUGGGGCAUAGUCAUUUCUAAAAG<br>UCACUAGUAGAAAGUAUAAUUUCAAGACAGAAUAUUCUAGACAUG<br>CUAGCAGUUUAUAUGUAUUCAUGAGUAAUGUGAUAUAUAUUGGGC<br>GCUGGUGAGGAAGGAAGGAGGAAUGAGUGACUAUAAGGAUGGUUA<br>CCAUAGAAACUUCCUUUUUUACCUAAUUGAAGAGAGACUACUACAG<br>AGUGCUAAGCUGCAUGUGUCAUCUUACACUAGAGAGAAAUGGUAA<br>GUUUCUUGUUUUAUUUAAGUUAUGUUUAAGCAAGGAAAGGAUUUG<br>UUAUUGAACAGUAUAUUUCAGGAAGGUUAGAAAGUGGCGGUUAGG<br>AUAUAUUUUAAAUCUACCUAAAGCAGCAUAUUUUAAAAAUUUAAA<br>AGUAUUGGUAUUAAAUUAAGAAAUAGAGGACAGAACUAGACUGAU<br>AGCAGUGACCUAGAACAAUUUGAGAUUAGGAAAGUUGUGACCAUG<br>AAUUUAAGGAUUUAUGUGGAUACAAAUUCUCCUUUAAAGUGUUUC<br>UUCCCUUAAUAUUUAUCUGACGGUAAUUUUUGAGCAGUGAAUUAC<br>UUUAUAUAUCUUAAUAGUUUAUUUGGGACCAAACACUUAAACAAA<br>AAGUUCUUUAAGUCAUAUAAGCCUUUUCAGGAAGCUUGUCUCAUAU<br>UCACUCCCGAGACAUUCACCUGCCAAGUGGCCUGAGGAUCAAUCCA<br>GUCCUAGGUUUAUUUUGCAGACUUACAUUCUCCCAAGUUAUUCAGC<br>CUCAUAUGACUCCACGGUCGGCUUUACCAAAACAGUUCAGAGUGCA<br>CUUUGGCACACAAUUGGGAACAGAACAAUCUAAUGUGUGGUUUGG<br>UAUUCCAAGUGGGGUCUUUUUCAGAAUCUCUGCACUAGUGUGAGAU<br>GCAAACAUGUUUCCUCAUCUUUCUGGCUUAUCCAGUAUGUAGCUAU<br>UUGUGACAUAAUAAAUAUAUACAUAUAUGAAAAUA |
| 40 | 5 | GCUUCUCCAUUCUGGUGUGAUCCAGGAACAGCUGUCUUCCAGCUCU<br>GAAAGAGGGCUGAGAGAUUAGGCUGCUUCUCCGGGAUCCGCUUUUC<br>CCCGGGAAACGCGAGGAUGCUCCAUGGAGCUGUGGUGUAAAGGAAU<br>UCAUUAGCCAUGGAUGUAUUCAUGAAAGGACUUUCAAAGGCCAAGG<br>AGGGAGUUGUGGCUGCUGCUGAGAAAACCAAACAGGGUGUGGCAG<br>AAGCAGCAGGAAAGACAAAAGAGGGUGUUCUCUAUGUAGGCUCCAA<br>AACCAAGGAGGGAGUGGUGCAUGGUGUGGCAACAGUGGCUGAGAA<br>GACCAAAGAGCAAGUGACAAAUGUUGGAGGAGCAGUGGUGACGGG<br>UGUGACAGCAGUAGCCCAGAAGACAGUGGAGGGAGCAGGGAGCAUU<br>GCAGCAGCCACUGGCUUUGUCAAAAAGGACCAGUUGGGCAAGAAUG<br>AAGAAGGAGCCCCACAGGAAGGAAUUCUGGAAGAUAUGCCUGUGGA<br>UCCUGACAAUGAGGCUUAUGAAAUGCCUUCUGAGGAAGGGUAUCAA<br>GACUACGAACCUGAAGCCUAAGAAAUAUCUUUGCUCCCAGUUUCUU<br>GAGAUCUGCUGACAGAUGUUCCAUCCUGUACAAGUGCUCAGUUCCA<br>AUGUGCCCAGUCAUGACAUUUCUCAAAGUUUUUACAGUGUAUCUCG<br>AAGUCUUCCAUCAGCAGUGAUUGAAGUAUCUGUACCUGCCCCCACU<br>CAGCAUUUCGGUGCUUCCCUUUCACUGAAGUGAAUACAUGGUAGCA<br>GGGUCUUUGUGUGCUGUGGAUUUUGUGGCUUCAAUCUACGAUGUU<br>AAAACAAAUUAAAAACACCUAAGUGACUACCACUUAUUUCUAAAUC<br>CUCACUAUUUUUUUGUUGCUGUUGUUCAGAAGUUGUUAGUGAUUU<br>GCUAUCAUAUAUUAUAAGAUUUUUAGGUGUCUUUUAAUGAUACUG<br>UCUAAGAAUAAUGACGUAUUGUGAAAUUUGUUAAUAUAUAUAAUA<br>CUUAAAAAUAUGUGAGCAUGAAACUAUGCACCUAUAAAUACUAAA<br>UAUGAAAUUUUACCAUUUUGCGAUGUGUUUUAUUCACUUGUGUUU<br>GUAUAUAAAUGGUGAGAAUUAAAAUAAAACGUUAUCUCAUUGCAA<br>AAAUAUUUUAUUUUUAUCCCAUCUCACUUUAAUAAUAAAAAUCAU<br>GCUUAUAAGCAACAUGAAUUAAGAACUGACACAAAGGACAAAAAU<br>AUAAAGUUAUUAAUAGCCAUUUGAAGAAGGAGGAAUUUUAGAAGA<br>GGUAGAGAAAAUGGAACAUUAACCCUACACUCGGAAUUCCCUGAAG<br>CAACACUGCCAGAAGUGUGUUUUGGUAUGCACUGGUUCCUUAAGUG<br>GCUGUGAUUAAUUAUUGAAAGUGGGGUGUUGAAGACCCCAACUAC<br>UAUUGUAGAGUGGUCUAUUUCUCCCUUCAAUCCUGUCAAUGUUUGC<br>UUUACGUAUUUUGGGGAACUGUUGUUUGAUGUGUAUGUGUUUAUA<br>AUUGUUAUACAUUUUUAAUUGAGCCUUUUAUUAACAUAUAUUGUU<br>AUUUUUGUCUCGAAAUAAUUUUUUAGUUAAAAUCUAUUUUGUCUG<br>AUAUUGGUGUGAAUGCUGUACCUUUCUGACAAUAAAUAAUAUUCG<br>ACCAUGAAUAAAAAAAAAAAAAAAAGUGGGUUCCCGGGAACUAAGC<br>AGUGUAGAAGAUGAUUUUGACUACACCCUCCUUAGAGAGCCAUAAG<br>ACACAUUAGCACAUAUUAGCACAUUCAAGGCUCUGAGAGAAUGUGG<br>UUAACUUUGUUUAACUCAGCAUUCCUCACUUUUUUUUUUUAAUCAU<br>CAGAAAUUCUCUCUCUCUCUCUCUCUUUUUCUCUCGCUCUCUUUUU<br>UUUUUUUUUUUACAGGAAAUGCCUUUAAACAUCGUUGGAACUACC<br>AGAGUCACCUUAAAGGAGAUCAAUUCUCUAGACUGAUAAAAAUUUC<br>AUGGCCUCCUUUAAAUGUUGCCAAAUAUAUGAAUUCUAGGAUUUU |

TABLE 6-continued

Human Alpha-synuclein mRNA Isoform Sequences. Sequences derived from NCBI SNCA sequence corresponding to gene ID 6622; Assembly GRCh38.p13 (GCF_000001405.39); NC_000004.12 (89724099..89838324, complement).

| SEQ ID NO | Isoform | mRNA sequence |
|---|---|---|
| | | UCCUUAGGAAAGGUUUUUCUCUUUCAGGGAAGAUCUAUUAACUCCC<br>CAUGGGUGCUGAAAAUAAACUUGAUGGUGAAAAACUCUGUAUAAA<br>UUAAUUUAAAAAUUAUUUGGUUUCUCUUUUUAAUUAUUCUGGGGC<br>AUAGUCAUUUCUAAAAGUCACUAGUAGAAAGUAUAAUUUCAAGAC<br>AGAAUAUUCUAGACAUGCUAGCAGUUUAUAUGUAUUCAUGAGUAA<br>UGUGAUAUAUAUUGGGCGCUGGUGAGGAAGGAAGGAGGAAUGAGU<br>GACUAUAAGGAUGGUUACCAUAGAAACUUCCUUUUUUACCUAAUUG<br>AAGAGAGACUACUACAGAGUGCUAAGCUGCAUGUGUCAUCUUACAC<br>UAGAGAGAAAUGGUAAGUUUCUUGUUUUAUUUAAGUUAUGUUUAA<br>GCAAGGAAAGGAUUUGUUAUUGAACAGUAUAUUUCAGGAAGGUUA<br>GAAAGUGGCGGUUAGGAUAUAUUUUAAAUCUACCUAAAGCAGCAU<br>AUUUUAAAAAUUUAAAAGUAUUGGUAUUAAAUUAAGAAAUAGAGG<br>ACAGAACUAGACUGAUAGCAGUGACCUAGAACAAUUUGAGAUUAG<br>GAAAGUUGUGACCAUGAAUUUAAGGAUUUAUGUGGAUACAAAUUC<br>UCCUUUAAAGUGUUUCUUCCCUUAAUAUUUAUCUGACGGUAAUUUU<br>UGAGCAGUGAAUUACUUUAUAUAUCUUAAUAGUUUAUUUGGGACC<br>AAACACUUAAACAAAAAGUUCUUUAAGUCAUAUAAGCCUUUUCAGG<br>AAGCUUGUCUCAUAUUCACUCCCGAGACAUUCACCUGCCAAGUGGC<br>CUGAGGAUCAAUCCAGUCCUAGGUUUAUUUUGCAGACUUACAUUCU<br>CCCAAGUUAUUCAGCCUCAUAUGACUCCACGGUCGGCUUUACCAAA<br>ACAGUUCAGAGUGCACUUUGGCACACAAUUGGGAACAGAACAAUCU<br>AAUGUGUGGUUUGGUAUUCCAAGUGGGGUCUUUUUCAGAAUCUCU<br>GCACUAGUGUGAGAUGCAAACAUGUUUCCUCAUCUUUCUGGCUUAU<br>CCAGUAUGUAGCUAUUUGUGACAUAAUAAAUAUAUACAUAUAUGA<br>AAAUA |
| 41 | 6 | GGCGACGACCAGAAGGGGCCCAAGAGAGGGGGCGAGCGACCGAGCG<br>CCGCGACGCGGAAGUGAGUGUGGUGUAAAGGAAUUCAUUAGCCAUG<br>GAUGUAUUCAUGAAAGGACUUUCAAAGGCCAAGGAGGGAGUUGUG<br>GCUGCUGCUGAGAAAACCAAACAGGGUGUGGCAGAAGCAGCAGGAA<br>AGACAAAAGAGGGUGUUCUCUAUGUAGGCUCCAAAACCAAGGAGGG<br>AGUGGUGCAUGGUGUGGCAACAGUGGCUGAGAAGACCAAAGAGCA<br>AGUGACAAAUGUUGGAGGAGCAGUGGUGACGGGUGUGACAGCAGU<br>AGCCCAGAAGACAGUGGAGGGAGCAGGGAGCAUUGCAGCAGCCACU<br>GGCUUUGUCAAAAAGGACCAGUUGGGCAAGAAUGAAGAAGGAGCCC<br>CACAGGAAGGAAUUCUGGAAGAUAUGCCUGUGGAUCCUGACAAUGA<br>GGCUUAUGAAAUGCCUUCUGAGGAAGGGUAUCAAGACUACGAACCU<br>GAAGCCUAAGAAAUAUCUUUGCUCCCAGUUUCUUGAGAUCUGCUGA<br>CAGAUGUUCCAUCCUGUACAAGUGCUCAGUUCCAAUGUGCCCAGUC<br>AUGACAUUUCUCAAAGUUUUUACAGUGUAUCUCGAAGUCUUCCAUC<br>AGCAGUGAUUGAAGUAUCUGUACCUGCCCCCACUCAGCAUUUCGGU<br>GCUUCCCUUUCACUGAAGUGAAUACAUGGUAGCAGGGUCUUUGUGU<br>GCUGUGGAUUUUGUGGCUUCAAUCUACGAUGUUAAAACAAAUUAA<br>AAACACCUAAGUGACUACCACUUAUUUCUAAAUCCUCACUAUUUUU<br>UUGUUGCUGUUGUUCAGAAGUUGUUAGUGAUUUGCUAUCAUAUAU<br>UAUAAGAUUUUUAGGUGUCUUUUAAUGAUACUGUCUAAGAAUAAU<br>GACGUAUUGUGAAAUUUGUUAAUAUAUAUAAUACUUAAAAAUAUG<br>UGAGCAUGAAACUAUGCACCUAUAAAUACUAAAUAUGAAAUUUUA<br>CCAUUUUGCGAUGUGUUUUAUUCACUUGUGUUUGUAUAUAAAUGG<br>UGAGAAUUAAAAUAAAACGUUAUCUCAUUGCAAAAAUAUUUUAUU<br>UUUAUCCCAUCUCACUUUAAUAAUAAAAAUCAUGCUUAUAAGCAAC<br>AUGAAUUAAGAACUGACACAAAGGACAAAAAUAUAAAGUUAUUAA<br>UAGCCAUUUGAAGAAGGAGGAAUUUUAGAAGAGGUAGAGAAAAUG<br>GAACAUUAACCCUACACUCGGAAUUCCCUGAAGCAACACUGCCAGA<br>AGUGUGUUUUGGUAUGCACUGGUUCCUUAAGUGGCUGUGAUUAAU<br>UAUUGAAAGUGGGGUGUUGAAGACCCCAACUACUAUUGUAGAGUG<br>GUCUAUUUCUCCCUUCAAUCCUGUCAAUGUUUGCUUUACGUAUUUU<br>GGGGAACUGUUGUUUGAUGUGUAUGUGUUUAUAAUUGUUAUACAU<br>UUUUAAUUGAGCCUUUUAUUAACAUAUAUUGUUAUUUUUGUCUCG<br>AAAUAAUUUUUUAGUUAAAAUCUAUUUUGUCUGAUAUUGGUGUGA<br>AUGCUGUACCUUUCUGACAAUAAAUAAUAUUCGACCAUGAAUAAAA<br>AAAAAAAAAAAGUGGGUUCCCGGGAACUAAGCAGUGUAGAAGAUG<br>AUUUUGACUACACCCUCCUUAGAGAGCCAUAAGACACAUUAGCACA<br>UAUUAGCACAUUCAAGGCUCUGAGAGAAUGUGGUUAACUUUGUUU<br>AACUCAGCAUUCCUCACUUUUUUUUUUUAAUCAUCAGAAAUUCUCU<br>CUCUCUCUCUCUCUUUUUCUCUCGCUCUCUUUUUUUUUUUUUUUUU<br>ACAGGAAAUGCCUUUAAACAUCGUUGGAACUACCAGAGUCACCUUA<br>AAGGAGAUCAAUUCUCUAGACUGAUAAAAAUUUCAUGGCCUCCUUU<br>AAAUGUUGCCAAAUAUAUGAAUUCUAGGAUUUUUCCUUAGGAAAG<br>GUUUUUCUCUUUCAGGGAAGAUCUAUUAACUCCCCAUGGGUGCUGA |

TABLE 6-continued

Human Alpha-synuclein mRNA Isoform Sequences. Sequences derived from NCBI SNCA sequence corresponding to gene ID 6622; Assembly GRCh38.p13 (GCF_000001405.39); NC_000004.12 (89724099..89838324, complement).

| SEQ ID NO | Isoform | mRNA sequence |
|---|---|---|
| | | AAAUAAACUUGAUGGUGAAAAACUCUGUAUAAAUUAAUUUAAAAA<br>UUAUUUGGUUUCUCUUUUUAAUUAUUCUGGGGCAUAGUCAUUUCU<br>AAAAGUCACUAGUAGAAAGUAUAAUUUCAAGACAGAAUAUUCUAG<br>ACAUGCUAGCAGUUUAUAUGUAUUCAUGAGUAAUGUGAUAUAUAU<br>UGGGCGCUGGUGAGGAAGGAAGGAGGAAUGAGUGACUAUAAGGAU<br>GGUUACCAUAGAAACUUCCUUUUUUACCUAAUUGAAGAGAGACUAC<br>UACAGAGUGCUAAGCUGCAUGUGUCAUCUUACACUAGAGAGAAAUG<br>GUAAGUUUCUUGUUUUAUUUAAGUUAUGUUUAAGCAAGGAAAGGA<br>UUUGUUAUUGAACAGUAUAUUUCAGGAAGGUUAGAAAGUGGCGGU<br>UAGGAUAUAUUUUAAAUCUACCUAAAGCAGCAUAUUUUAAAAAUU<br>UAAAAGUAUUGGUAUUAAAUUAAGAAAUAGAGGACAGAACUAGAC<br>UGAUAGCAGUGACCUAGAACAAUUUGAGAUUAGGAAAGUUGUGAC<br>CAUGAAUUUAAGGAUUUAUGUGGAUACAAAUUCUCCUUUAAAGUG<br>UUUCUUCCCUUAAUAUUUAUCUGACGGUAAUUUUUGAGCAGUGAA<br>UUACUUUAUAUAUCUUAAUAGUUUAUUUGGGACCAAACACUUAAA<br>CAAAAAGUUCUUUAAGUCAUAUAAGCCUUUUCAGGAAGCUUGUCUC<br>AUAUUCACUCCCGAGACAUUCACCUGCCAAGUGGCCUGAGGAUCAA<br>UCCAGUCCUAGGUUUAUUUUGCAGACUUACAUUCUCCCAAGUUAUU<br>CAGCCUCAUAUGACUCCACGGUCGGCUUUACCAAAACAGUUCAGAG<br>UGCACUUUGGCACACAAUUGGGAACAGAACAAUCUAAUGUGUGGUU<br>UGGUAUUCCAAGUGGGGUCUUUUUCAGAAUCUCUGCACUAGUGUGA<br>GAUGCAAACAUGUUUCCUCAUCUUUCUGGCUUAUCCAGUAUGUAGC<br>UAUUUGUGACAUAAUAAAUAUAUACAUAUAUGAAAAUA |
| 42 | 7 | GGCGACGACCAGAAGGGGCCCAAGAGAGGGGGCGAGCGACCGAGCG<br>CCGCGACGCGGAAGUGAGGUGCGUGCGGGCUGCAGCGCAGACCCCG<br>GCCCGGCCCCUCCGAGAGCGUCCUGGGCGCUCCCUCACGCCUUGCCU<br>UCAAGCCUUCUGCCUUUCCACCCUCGUGAGCGGAGAACUGGGAGUG<br>GCCAUUCGACGACAGGUUAGCGGGUUUGCCUCCCACUCCCCCAGCC<br>UCGCGUCGCCGGCUCACAGCGGCCUCCUCUGGGGACAGUCCCCCCCG<br>GGUGCCGCCUCCGCCCUUCCUGUGCGCUCCUUUUCCUUCUUCUUUCC<br>UAUUAAAUAUUAUUUGGGAAUUGUUUAAAUUUUUUUUUUAAAAAA<br>AGAGAGAGGCGGGGAGGAGUCGGAGUUGUGGAGAAGCAGAGGGAC<br>UCAGGGCUGAGAGAUUAGGCUGCUUCUCCGGGAUCCGCUUUUCCCC<br>GGGAAACGCGAGGAUGCUCCAUGGAGCUGUGGUGUAAAGGAAUUC<br>AUUAGCCAUGGAUGUAUUCAUGAAAGGACUUUCAAAGGCCAAGGA<br>GGGAGUUGUGGCUGCUGCUGAGAAAACCAAACAGGGUGUGGCAGA<br>AGCAGCAGGAAAGACAAAAGAGGGUGUUCUCUAUGUAGGCUCCAAA<br>ACCAAGGAGGGAGUGGUGCAUGGUGUGGCAACAGUGGCUGAGAAG<br>ACCAAAGAGCAAGUGACAAAUGUUGGAGGAGCAGUGGUGACGGGU<br>GUGACAGCAGUAGCCCAGAAGACAGUGGAGGGAGCAGGGAGCAUUG<br>CAGCAGCCACUGGCUUUGUCAAAAAGGACCAGUUGGGCAAGAAUGA<br>AGAAGGAGCCCCACAGGAAGGAAUUCUGGAAGAUAUGCCUGUGGAU<br>CCUGACAAUGAGGCUUAUGAAAUGCCUUCUGAGGAAGGGUAUCAAG<br>ACUACGAACCUGAAGCCUAAGAAAUAUCUUUGCUCCCAGUUUCUUG<br>AGAUCUGCUGACAGAUGUUCCAUCCUGUACAAGUGCUCAGUUCCAA<br>UGUGCCCAGUCAUGACAUUUCUCAAAGUUUUUACAGUGUAUCUCGA<br>AGUCUUCCAUCAGCAGUGAUUGAAGUAUCUGUACCUGCCCCCACUC<br>AGCAUUUCGGUGCUUCCCUUUCACUGAAGUGAAUACAUGGUAGCAG<br>GGUCUUUGUGUGCUGUGGAUUUUGUGGCUUCAAUCUACGAUGUUA<br>AAACAAAUUAAAAACACCUAAGUGACUACCACUUAUUUCUAAAUCC<br>UCACUAUUUUUUUGUUGCUGUUGUUCAGAAGUUGUUAGUGAUUUG<br>CUAUCAUAUAUUAUAAGAUUUUUAGGUGUCUUUUAAUGAUACUGU<br>CUAAGAAUAAUGACGUAUUGUGAAAUUUGUUAAUAUAUAUAAUAC<br>UUAAAAAUAUGUGAGCAUGAAACUAUGCACCUAUAAAUACUAAAU<br>AUGAAAUUUUACCAUUUUGCGAUGUGUUUUAUUCACUUGUGUUUG<br>UAUAUAAAUGGUGAGAAUUAAAAUAAAACGUUAUCUCAUUGCAAA<br>AAUAUUUUAUUUUUAUCCCAUCUCACUUUAAUAAUAAAAAUCAUGC<br>UUAUAAGCAACAUGAAUUAAGAACUGACACAAAGGACAAAAAUAU<br>AAAGUUAUUAAUAGCCAUUUGAAGAAGGAGGAAUUUUAGAAGAGG<br>UAGAGAAAAUGGAACAUUAACCCUACACUCGGAAUUCCCUGAAGCA<br>ACACUGCCAGAAGUGUGUUUUGGUAUGCACUGGUUCCUUAAGUGGC<br>UGUGAUUAAUUAUUGAAAGUGGGGUGUUGAAGACCCCAACUACUA<br>UUGUAGAGUGGUCUAUUUCUCCCUUCAAUCCUGUCAAUGUUUGCUU<br>UACGUAUUUUGGGGAACUGUUGUUUGAUGUGUAUGUGUUUAUAAU<br>UGUUAUACAUUUUUAAUUGAGCCUUUUAUUAACAUAUAUUGUUAU<br>UUUUGUCUCGAAAUAAUUUUUUAGUUAAAAUCUAUUUUGUCUGAU<br>AUUGGUGUGAAUGCUGUACCUUUCUGACAAUAAAUAAUAUUCGACC<br>AUGAAUAAAAAAAAAAAAAAAGUGGGUUCCCGGGAACUAAGCAGU<br>GUAGAAGAUGAUUUUGACUACACCCUCCUUAGAGAGCCAUAAGACA |

TABLE 6-continued

Human Alpha-synuclein mRNA Isoform Sequences. Sequences derived from NCBI SNCA sequence corresponding to gene ID 6622; Assembly GRCh38.p13 (GCF_000001405.39); NC_000004.12 (89724099..89838324, complement).

| SEQ ID NO | Isoform | mRNA sequence |
|---|---|---|
| | | CAUUAGCACAUAUUAGCACAUUCAAGGCUCUGAGAGAAUGUGGUUA<br>ACUUUGUUUAACUCAGCAUUCCUCACUUUUUUUUUUUAAUCAUCAG<br>AAAUUCUCUCUCUCUCUCUCUUUUUCUCUCGCUCUCUUUUUUUU<br>UUUUUUUUUACAGGAAAUGCCUUUAAACAUCGUUGGAACUACCAGA<br>GUCACCUUAAAGGAGAUCAAUUCUCUAGACUGAUAAAAAUUUCAUG<br>GCCUCCUUUAAAUGUUGCCAAAUAUAUGAAUUCUAGGAUUUUUCCU<br>UAGGAAAGGUUUUUCUCUUUCAGGGAAGAUCUAUUAACUCCCCAUG<br>GGUGCUGAAAAUAAACUUGAUGGUGAAAAACUCUGUAUAAAUUAA<br>UUUAAAAAUUAUUUGGUUUCUCUUUUUAAUUAUUCUGGGGCAUAG<br>UCAUUUCUAAAAGUCACUAGUAGAAAGUAUAAUUUCAAGACAGAA<br>UAUUCUAGACAUGCUAGCAGUUUAUAUGUAUUCAUGAGUAAUGUG<br>AUAUAUAUUGGGCGCUGGUGAGGAAGGAAGGAGGAAUGAGUGACU<br>AUAAGGAUGGUUACCAUAGAAACUUCCUUUUUUACCUAAUUGAAG<br>AGAGACUACUACAGAGUGCUAAGCUGCAUGUGUCAUCUUACACUAG<br>AGAGAAAUGGUAAGUUUCUUGUUUUAUUUAAGUUAUGUUUAAGCA<br>AGGAAAGGAUUUGUUAUUGAACAGUAUAUUUCAGGAAGGUUAGAA<br>AGUGGCGGUUAGGAUAUAUUUUAAAUCUACCUAAAGCAGCAUAUU<br>UUAAAAAUUUAAAAGUAUUGGUAUUAAAUUAAGAAAUAGAGGACA<br>GAACUAGACUGAUAGCAGUGACCUAGAACAAUUUGAGAUUAGGAA<br>AGUUGUGACCAUGAAUUUAAGGAUUUAUGUGGAUACAAAUUCUCC<br>UUUAAAGUGUUUCUUCCCUUAAUAUUUAUCUGACGGUAAUUUUUG<br>AGCAGUGAAUUACUUUAUAUAUCUUAAUAGUUUAUUUGGGACCAA<br>ACACUUAAACAAAAAGUUCUUUAAGUCAUAUAAGCCUUUUCAGGAA<br>GCUUGUCUCAUAUUCACUCCCGAGACAUUCACCUGCCAAGUGGCCU<br>GAGGAUCAAUCCAGUCCUAGGUUUAUUUUGCAGACUUACAUUCUCC<br>CAAGUUAUUCAGCCUCAUAUGACUCCACGGUCGGCUUUACCAAAAC<br>AGUUCAGAGUGCACUUUGGCACACAAUUGGGAACAGAACAAUCUAA<br>UGUGUGGUUUGGUAUUCCAAGUGGGGUCUUUUUCAGAAUCUCUGC<br>ACUAGUGUGAGAUGCAAACAUGUUUCCUCAUCUUUCUGGCUUAUCC<br>AGUAUGUAGCUAUUUGUGACAUAAUAAAUAUAUACAUAUAUGAAA<br>AUA |
| 43 | 8 | GAGUGUGAGCGGCGCCUGCUCAGGGUAGAUAGCUGAGGGCGGGGGU<br>GGAUGUUGGAUGGAUUAGAACCAUCACACUUGGGCCUGCUGUUUGC<br>CUGAGUUUGAACCACACCCCGAUGUGGUGUAAAGGAAUUCAUUAGC<br>CAUGGAUGUAUUCAUGAAAGGACUUUCAAAGGCCAAGGAGGGAGU<br>UGUGGCUGCUGCUGAGAAAACCAAACAGGGUGUGGCAGAAGCAGCA<br>GGAAAGACAAAAGAGGGUGUUCUCUAUGUAGGCUCCAAAACCAAGG<br>AGGGAGUGGUGCAUGGUGUGGCAACAGUGGCUGAGAAGACCAAAG<br>AGCAAGUGACAAAUGUUGGAGGAGCAGUGGUGACGGGUGUGACAG<br>CAGUAGCCCAGAAGACAGUGGAGGGAGCAGGGAGCAUUGCAGCAGC<br>CACUGGCUUUGUCAAAAAGGACCAGUUGGGCAAGAAUGAAGAAGG<br>AGCCCCACAGGAAGGAAUUCUGGAAGAUAUGCCUGUGGAUCCUGAC<br>AAUGAGGCUUAUGAAAUGCCUUCUGAGGAAGGGUAUCAAGACUAC<br>GAACCUGAAGCCUAAGAAAUAUCUUUGCUCCCAGUUUCUUGAGAUC<br>UGCUGACAGAUGUUCCAUCCUGUACAAGUGCUCAGUUCCAAUGUGC<br>CCAGUCAUGACAUUUCUCAAAGUUUUUACAGUGUAUCUCGAAGUCU<br>UCCAUCAGCAGUGAUUGAAGUAUCUGUACCUGCCCCCACUCAGCAU<br>UUCGGUGCUUCCCUUUCACUGAAGUGAAUACAUGGUAGCAGGGUCU<br>UUGUGUGCUGUGGAUUUUGUGGCUUCAAUCUACGAUGUUAAAACA<br>AAUUAAAAACACCUAAGUGACUACCACUUAUUUCUAAAUCCUCACU<br>AUUUUUUUGUUGCUGUUGUUCAGAAGUUGUUAGUGAUUUGCUAUC<br>AUAUAUUAUAAGAUUUUUAGGUGUCUUUUAAUGAUACUGUCUAAG<br>AAUAAUGACGUAUUGUGAAAUUUGUUAAUAUAUAUAAUACUUAAA<br>AAUAUGUGAGCAUGAAACUAUGCACCUAUAAAUACUAAAUAUGAA<br>AUUUUACCAUUUUGCGAUGUGUUUUAUUCACUUGUGUUUGUAUAU<br>AAAUGGUGAGAAUUAAAAUAAAACGUUAUCUCAUUGCAAAAAUAU<br>UUUAUUUUUAUCCCAUCUCACUUUAAUAAUAAAAAUCAUGCUUAUA<br>AGCAACAUGAAUUAAGAACUGACACAAAGGACAAAAAUAUAAAGU<br>UAUUAAUAGCCAUUUGAAGAAGGAGGAAUUUUAGAAGAGGUAGAG<br>AAAAUGGAACAUUAACCCUACACUCGGAAUUCCCUGAAGCAACACU<br>GCCAGAAGUGUGUUUUGGUAUGCACUGGUUCCUUAAGUGGCUGUG<br>AUUAAUUAUUGAAAGUGGGGUGUUGAAGACCCCAACUACUAUUGU<br>AGAGUGGUCUAUUUCUCCCUUCAAUCCUGUCAAUGUUUGCUUUACG<br>UAUUUUGGGGAACUGUUGUUUGAUGUGUAUGUGUUUAUAAUUGUU<br>AUACAUUUUUAAUUGAGCCUUUUAUUAACAUAUAUUGUUAUUUUU<br>GUCUCGAAAUAAUUUUUUAGUUAAAAUCUAUUUUGUCUGAUAUUG<br>GUGUGAAUGCUGUACCUUUCUGACAAUAAAUAAUAUUCGACCAUGA<br>AUAAAAAAAAAAAAAAAGUGGGUUCCCGGGAACUAAGCAGUGUAG<br>AAGAUGAUUUUGACUACACCCUCCUUAGAGAGCCAUAAGACACAUU |

TABLE 6-continued

Human Alpha-synuclein mRNA Isoform Sequences. Sequences derived from NCBI SNCA sequence corresponding to gene ID 6622; Assembly GRCh38.p13 (GCF_000001405.39); NC_000004.12 (89724099..89838324, complement).

| SEQ ID NO | Isoform | mRNA sequence |
|---|---|---|
| | | AGCACAUAUUAGCACAUUCAAGGCUCUGAGAGAAUGUGGUUAACUU<br>UGUUUAACUCAGCAUUCCUCACUUUUUUUUUUUAAUCAUCAGAAAU<br>UCUCUCUCUCUCUCUCUUUUUCUCUCGCUCUCUUUUUUUUUUUU<br>UUUUUACAGGAAAUGCCUUUAAACAUCGUUGGAACUACCAGAGUCA<br>CCUUAAAGGAGAUCAAUUCUCUAGACUGAUAAAAAUUUCAUGGCCU<br>CCUUUAAAUGUUGCCAAAUAUAUGAAUUCUAGGAUUUUUCCUUAG<br>GAAAGGUUUUUCUCUUUCAGGGAAGAUCUAUUAACUCCCCAUGGGU<br>GCUGAAAAUAAACUUGAUGGUGAAAAACUCUGUAUAAAUUAAUUU<br>AAAAAUUAUUUGGUUUCUCUUUUUAAUUAUUCUGGGGCAUAGUCA<br>UUUCUAAAAGUCACUAGUAGAAAGUAUAAUUUCAAGACAGAAUAU<br>UCUAGACAUGCUAGCAGUUUAUAUGUAUUCAUGAGUAAUGUGAUA<br>UAUAUUGGGCGCUGGUGAGGAAGGAAGGAGGAAUGAGUGACUAUA<br>AGGAUGGUUACCAUAGAAACUUCCUUUUUUACCUAAUUGAAGAGA<br>GACUACUACAGAGUGCUAAGCUGCAUGUGUCAUCUUACACUAGAGA<br>GAAAUGGUAAGUUUCUUGUUUUAUUUAAGUUAUGUUUAAGCAAGG<br>AAAGGAUUUGUUAUUGAACAGUAUAUUUCAGGAAGGUUAGAAAGU<br>GGCGGUUAGGAUAUAUUUUAAAUCUACCUAAAGCAGCAUAUUUUA<br>AAAAUUUAAAAGUAUUGGUAUUAAAUUAAGAAAUAGAGGACAGAA<br>CUAGACUGAUAGCAGUGACCUAGAACAAUUUGAGAUUAGGAAAGU<br>UGUGACCAUGAAUUUAAGGAUUUAUGUGGAUACAAAUUCUCCUUU<br>AAAGUGUUUCUUCCCUUAAUAUUUAUCUGACGGUAAUUUUUGAGC<br>AGUGAAUUACUUUAUAUAUCUUAAUAGUUUAUUUGGGACCAAACA<br>CUUAAACAAAAAGUUCUUUAAGUCAUAUAAGCCUUUUCAGGAAGCU<br>UGUCUCAUAUUCACUCCCGAGACAUUCACCUGCCAAGUGGCCUGAG<br>GAUCAAUCCAGUCCUAGGUUUAUUUUGCAGACUUACAUUCUCCCAA<br>GUUAUUCAGCCUCAUAUGACUCCACGGUCGGCUUUACCAAAACAGU<br>UCAGAGUGCACUUUGGCACACAAUUGGGAACAGAACAAUCUAAUGU<br>GUGGUUUGGUAUUCCAAGUGGGGUCUUUUUCAGAAUCUCUGCACUA<br>GUGUGAGAUGCAAACAUGUUUCCUCAUCUUUCUGGCUUAUCCAGUA<br>UGUAGCUAUUUGUGACAUAAUAAAUAUAUACAUAUAUGAAAAUA |
| 44 | 9 | GCUCUAAUUCUCUGCACCUUCUCAAGCAUUGUGCAGAUUGGUUUUC<br>UGGAUUAUCAGCCUGAAGGACAAAACGAAGAAACAGCCAUUAGCUC<br>CUGUCUCCCAUUGUCUGAGAGCUGCCACUAGGAUAUUAACUUCCUG<br>AAAUUCUGCAGAAAUCUCCUCUUACUUUGGCACUGGAGAUGCCCAU<br>ACGCAGAAAGCAAAAAGGCACAGCAUAUUUAAGGAAGCUCAUAAGA<br>AACAGUGCAUCCAGAAGUGGCGAGAAUUGGAGGAAUGGACAUGAG<br>ACUCUAAGAACCAGCGCCUUUGAUGUUCCUUUUGAUCUGUUAUGUA<br>GCUCUUCUUGUACACAGAAUGAAGAAGGAGCCCCACAGGAAGGAAU<br>UCUGGAAGAUAUGCCUGUGGAUCCUGACAAUGAGGCUUAUGAAAU<br>GCCUUCUGAGGAAGGGUAUCAAGACUACGAACCUGAAGCCUAAGAA<br>AUAUCUUUGCUCCCAGUUUCUUGAGAUCUGCUGACAGAUGUUCCAU<br>CCUGUACAAGUGCUCAGUUCCAAUGUGCCCAGUCAUGACAUUUCUC<br>AAAGUUUUUACAGUGUAUCUCGAAGUCUUCCAUCAGCAGUGAUUGA<br>AGUAUCUGUACCUGCCCCCACUCAGCAUUUCGGUGCUUCCCUUUCA<br>CUGAAGUGAAUACAUGGUAGCAGGGUCUUUGUGUGCUGUGGAUUU<br>UGUGGCUUCAAUCUACGAUGUUAAAACAAAUUAAAAACACCUAAGU<br>GACUACCACUUAUUUCUAAAUCCUCACUAUUUUUUUGUUGCUGUUG<br>UUCAGAAGUUGUUAGUGAUUUGCUAUCAUAUAUUAUAAGAUUUUU<br>AGGUGUCUUUUAAUGAUACUGUCUAAGAAUAAUGACGUAUUGUGA<br>AAUUUGUUAAUAUAUAUAAUACUUAAAAAUAUGUGAGCAUGAAAC<br>UAUGCACCUAUAAAUACUAAAUAUGAAAUUUUACCAUUUUGCGAU<br>GUGUUUUAUUCACUUGUGUUUGUAUAUAAAUGGUGAGAAUUAAAA<br>UAAAACGUUAUCUCAUUGCAAAAAUAUUUUAUUUUUAUCCCAUCUC<br>ACUUUAAUAAUAAAAAUCAUGCUUAUAAGCAACAUGAAUUAAGAA<br>CUGACACAAAGGACAAAAAUAUAAAGUUAUUAAUAGCCAUUUGAA<br>GAAGGAGGAAUUUUAGAAGAGGUAGAGAAAAUGGAACAUUAACCC<br>UACACUCGGAAUUCCCUGAAGCAACACUGCCAGAAGUGUGUUUUGG<br>UAUGCACUGGUUCCUUAAGUGGCUGUGAUUAAUUAUUGAAAGUGG<br>GGUGUUGAAGACCCCAACUACUAUUGUAGAGUGGUCUAUUUCUCCC<br>UUCAAUCCUGUCAAUGUUUGCUUUACGUAUUUUGGGGAACUGUUG<br>UUUGAUGUGUAUGUGUUUAUAAUUGUUAUACAUUUUUAAUUGAGC<br>CUUUUAUUAACAUAUAUUGUUAUUUUUGUCUCGAAAUAAUUUUUU<br>AGUUAAAAUCUAUUUUGUCUGAUAUUGGUGUGAAUGCUGUACCUU<br>UCUGACAAUAAAUAAUAUUCGACCAUGAAUAAAAAAAAAAAAAAA<br>GUGGGUUCCCGGGAACUAAGCAGUGUAGAAGAUGAUUUUGACUAC<br>ACCCUCCUUAGAGAGCCAUAAGACACAUUAGCACAUAUUAGCACAU<br>UCAAGGCUCUGAGAGAAUGUGGUUAACUUUGUUUAACUCAGCAUUC<br>CUCACUUUUUUUUUUUAAUCAUCAGAAAUUCUCUCUCUCUCUCU<br>CUUUUUCUCUCGCUCUCUUUUUUUUUUUUUUUUUACAGGAAAUGCC |

TABLE 6-continued

Human Alpha-synuclein mRNA Isoform Sequences. Sequences derived from NCBI SNCA sequence corresponding to gene ID 6622; Assembly GRCh38.p13 (GCF_000001405.39); NC_000004.12 (89724099..89838324, complement).

| SEQ ID NO | Isoform | mRNA sequence |
|---|---|---|
| | | UUUAAACAUCGUUGGAACUACCAGAGUCACCUUAAAGGAGAUCAAU<br>UCUCUAGACUGAUAAAAAUUUCAUGGCCUCCUUUAAAUGUUGCCAA<br>AUAUAUGAAUUCUAGGAUUUUUCCUUAGGAAAGGUUUUUCUCUUU<br>CAGGGAAGAUCUAUUAACUCCCCAUGGGUGCUGAAAAUAAACUUGA<br>UGGUGAAAAACUCUGUAUAAAUUAAUUUAAAAAUUAUUUGGUUUC<br>UCUUUUUAAUUAUUCUGGGGCAUAGUCAUUUCUAAAAGUCACUAG<br>UAGAAAGUAUAAUUUCAAGACAGAAUAUUCUAGACAUGCUAGCAG<br>UUUAUAUGUAUUCAUGAGUAAUGUGAUAUAUAUUGGGCGCUGGUG<br>AGGAAGGAAGGAGGAAUGAGUGACUAUAAGGAUGGUUACCAUAGA<br>AACUUCCUUUUUUACCUAAUUGAAGAGAGACUACUACAGAGUGCUA<br>AGCUGCAUGUGUCAUCUUACACUAGAGAGAAAUGGUAAGUUUCUU<br>GUUUUAUUUAAGUUAUGUUUAAGCAAGGAAAGGAUUUGUUAUUGA<br>ACAGUAUAUUUCAGGAAGGUUAGAAAGUGGCGGUUAGGAUAUAUU<br>UUAAAUCUACCUAAAGCAGCAUAUUUUAAAAAUUUAAAAGUAUUG<br>GUAUUAAAUUAAGAAAUAGAGGACAGAACUAGACUGAUAGCAGUG<br>ACCUAGAACAAUUUGAGAUUAGGAAAGUUGUGACCAUGAAUUUAA<br>GGAUUUAUGUGGAUACAAAUUCUCCUUUAAAGUGUUUCUUCCCUUA<br>AUAUUUAUCUGACGGUAAUUUUUGAGCAGUGAAUUACUUUAUAUA<br>UCUUAAUAGUUUAUUUGGGACCAAACACUUAAACAAAAAGUUCUU<br>UAAGUCAUAUAAGCCUUUUCAGGAAGCUUGUCUCAUAUUCACUCCC<br>GAGACAUUCACCUGCCAAGUGGCCUGAGGAUCAAUCCAGUCCUAGG<br>UUUAUUUUGCAGACUUACAUUCUCCCAAGUUAUUCAGCCUCAUAUG<br>ACUCCACGGUCGGCUUUACCAAAACAGUUCAGAGUGCACUUUGGCA<br>CACAAUUGGGAACAGAACAAUCUAAUGUGUGGUUUGGUAUUCCAA<br>GUGGGGUCUUUUUCAGAAUCUCUGCACUAGUGUGAGAUGCAAACAU<br>GUUUCCUCAUCUUUCUGGCUUAUCCAGUAUGUAGCUAUUUGUGACA<br>UAAUAAAUAUAUACAUAUAUGAAAAUA |

In some cases, a region of Alpha-synuclein polypeptide can be targeted utilizing compositions provided herein. Suitable regions include but are not limited to a N-terminal A2 lipid-binding alpha-helix domain, a Non-amyloid β component (NAC) domain, or a C-terminal acidic domain.

In some aspects, an alpha-synuclein polypeptide sequence is targeted, complete polypeptide sequences are shown in TABLE 7. In some cases, any one of the residues of an isoform sequence may be targeted utilizing the compositions and methods provided herein. In some cases, a target residue may be located among residues 1-10, 10-20, 20-40, 40-60, 60-80, 80-100, 100-120, or 120-140, overlapping portions thereof, and combinations thereof.

TABLE 7

Human alpha-synuclein polypeptide sequences associated with isoform of TABLE 6

| SEQ ID NO | Isoform | SNCA Polypeptide Sequence |
|---|---|---|
| 45 | Isoform 1-3; 5-8 | MDVFMKGLSKAKEGVVAAAEKTKQGVAEAAG<br>KTKEGVLYVGSKTKEGVVHGVATVAEKTKEQ<br>VTNVGGAVVTGVTAVAQKTVEGAGSIAAATG<br>FVKKDQLGKNEEGAPQEGILEDMPVDPDNEA<br>YEMPSEEGYQDYEPEA |
| 46 | Isoform 4 | MDVFMKGLSKAKEGVVAAAEKTKQGVAEAAG<br>KTKEGVLYVGSKTKEGVVHGVATVAEKTKEQ<br>VTNVGGAVVTGVTAVAQKTVEGAGSIAAATG<br>FVKKDQLGKEGYQDYEPEA |

TABLE 7-continued

Human alpha-synuclein polypeptide sequences associated with isoform of TABLE 6

| SEQ ID NO | Isoform | SNCA Polypeptide Sequence |
|---|---|---|
| 47 | Isoform 9 | MPIRRKQKGTAYLRKLIRNSASRSGENWRNG<br>HETLRTSAFDVPFDLLCSSSCTQNEEGAPQE<br>GILEDMPVDPDNEAYEMPSEEGYQDYEPEA |

Exemplary regions that can be targeted utilizing compositions provided herein can include but are not limited to a target residue of an SNCA polypeptide sequence is any one of: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, and/or 140. In some cases, exemplary residues that can be targeted can comprise Ml, V40, K85, S125, K129, or any combination thereof.

In some embodiments, the editing of a base of the SNCA mRNA results in a decreased gene translation of the SNCA polypeptide. In other cases, the editing of a base of the 5'UTR of the SNCA mRNA results in a decreased gene translation of the SNCA polypeptide. The decreased gene translation of the SNCA polypeptide can be measured by an in vitro assay. Such in vitro assay can comprise an in vitro translation assay. An in vitro translation assay can comprise a cell extract. A cell extract can comprise rabbit reticulocyte lysate, wheat germ extract, insect cells, yeast *Kluyveromyces*, or *E. coli* cell-free extract. An in vitro translation assay can comprise mixing a cell extract with a nucleic acid template, ATP, and amino acids. A nucleic acid template can comprise a mRNA template or a cDNA template. A nucleic acid template can comprise a mRNA sequence listed in TABLE 6. A nucleic acid template can comprise a cDNA sequence complementary to the mRNA sequence listed in TABLE 6. When using an in vitro translation system with a cDNA template, the cDNA can be converted to a mRNA by in vitro transcription. A cDNA can be maintained in a circular vector. A cDNA can be maintained as a linear sequence.

In some cases, the engineered polynucleotide capable of facilitating a modification of a base of a nucleotide comprised in a SNCA pre-mRNA or mRNA can down-regulate or knockdown the expression of the SNCA protein. In some embodiments, the editing of the SNCA pre-mRNA or mRNA can inhibit or down-regulate the splicing, mRNA export, mRNA localization, mRNA stability, mRNA degradation, polyadenylation, 5' cap modification, assembly of messenger ribonucleoprotein (mRNP), or translation of the SNCA pre-mRNA or mRNA. In some cases, the editing of the SNCA pre-mRNA or mRNA can result in a generation of an edited SNCA mRNA encoding a polypeptide comprising at least one amino acid substitution compared to a polypeptide encoded by an unedited polynucleotide. In other cases, the editing of the SNCA pre-mRNA or mRNA may not result in a generation of an edited SNCA mRNA encoding a polypeptide comprising at least one amino acid substitution compared to a polypeptide encoded by an unedited polynucleotide. In some cases, a modified SNCA mRNA can encode for a SNCA polypeptide, with or without an amino acid substitution, having lower amount than a SNCA protein encoded by an unedited SNCA mRNA. In some cases, the amount of SNCA polypeptide, with or without an amino acid substitution, can be measured by a SNCA ELISA. In an embodiment, the lower abundance of SNCA polypeptide or fragment thereof can be least or at most about: 1-fold, 8-fold, 15-fold, 22-fold, 29-fold, 36-fold, 43-fold, 50-fold, 57-fold, 64-fold, 71-fold, 78-fold, 85-fold, 92-fold, 99-fold, 106-fold, 113-fold, 120-fold, 127-fold, 134-fold, 141-fold, 148-fold, 155-fold, 162-fold, 169-fold, 176-fold, 183-fold, 190-fold, 197-fold, 204-fold, 211-fold, 218-fold, 225-fold, 232-fold, 239-fold, 246-fold, 253-fold, 260-fold, 267-fold, 274-fold, 281-fold, 288-fold, 295-fold, or up to about 350-fold.

In an embodiment, the lower abundance of SNCA polypeptide or fragment thereof can be least or at most about: 0.1-0.2 fold, 0.19-0.3 fold, 0.29-0.4 fold, 0.39-0.5 fold, 0.49-0.6 fold, 0.59-0.7 fold, 0.69-0.8 fold, 0.79-09 fold, 0.89-1 fold, 0.99-1 fold, 0.1-0.3 fold, 0.1-0.4 fold, 0.1-0.5 fold, 0.1-0.6 fold, 0.1-0.7 fold, 0.1-0.8 fold, 0.1-0.9 fold, 1-20-fold, 2-21-fold, 3-22-fold, 4-23-fold, 5-24-fold, 6-25-fold, 7-26-fold, 8-27-fold, 9-28-fold, 10-29-fold, 11-30-fold, 12-31-fold, 13-32-fold, 14-33-fold, 15-34-fold, 16-35-fold, 17-36-fold, 18-37-fold, 19-38-fold, 20-39-fold, 21-40-fold, 22-41-fold, 23-42-fold, 24-43 fold, 25-44-fold, 26-45-fold, 27-46-fold, 28-47-fold, 29-48-fold, 30-49-fold, 31-50-fold, 32-51-fold, 33-52-fold, 34-53-fold, 35-54-fold, 36-55-fold, 37-56-fold, 38-57-fold, 39-58-fold, 40-59-fold, 41-60-fold, 42-61-fold, 43-62-fold, 44-63-fold, 45-64-fold, 46-65-fold, 47-66-fold, 48-67-fold, 49-68-fold, 50-69-fold, 51-70-fold, 52-71-fold, 53-72-fold, 54-73-fold, 55-74-fold, 56-75-fold, 57-76-fold, 58-77-fold, 59-78-fold, 60-79-fold, 61-80-fold, 62-81-fold, 63-82-fold, 64-83-fold, 65-84-fold, 66-85-fold, 67-86-fold, 68-87-fold, 69-88-fold, 70-89-fold, 71-90-fold, 72-91-fold, 73-92-fold, 74-93-fold, 75-94-fold, 76-95-fold, 77-96-fold, 78-97-fold, 79-98-fold, 80-99-fold, or 81-100-fold decrease in the protein level of SNCA, as compared to that encoded by the unedited SNCA mRNA.

Genome Editing of APP

In some embodiments, the APP gene can be altered using genome editing. Genome editing can comprise a CRISPR/Cas associated protein, RNA guided endonuclease, zinc finger nuclease, transcription activator-like effector nuclease (TALEN), meganuclease, functional portion of any of these, fusion protein of any of these, or any combination thereof. In some embodiments, a CRISPR/Cas associated protein can comprise a CRISPR/Cas endonuclease. In some embodiments, a CRISPR/Cas associated protein can comprise class 1 or class 2 CRISPR/Cas protein. A class 2 CRISPR/Cas associated protein can comprise a type II CRISPR/Cas protein, a type V CRISPR/Cas protein, a type VI CRISPR/Cas protein. A CRISPR/Cas associated protein can comprise a Cas9 protein, Cas 12 protein, functional portion of any of these, fusion protein of any of these, or any combinations thereof. A CRISPR/Cas associated protein can comprise a wildtype or a variant CRISPR/Cas associated protein, functional portion of any of these, fusion protein of any of these, or any combinations thereof. A CRISPR/Cas associated protein can comprise a base editor. A base editor can comprise a cytidine deaminase, a deoxyadenosine deaminase, functional portion of any of these, fusion protein of any of these, or any combinations thereof. A CRISPR/Cas associated protein can comprise a reverse transcriptase. A reverse transcriptase can comprise a Moloney murine leukemia virus (M-MLV) reverse transcriptase or an Avian Myeloblastosis Virus (AMV) reverse transcriptase.

A CRISPR/Cas associated protein as described herein are targeted to a specific target DNA sequence in a genome by a guide RNA to which it is bound. The guide RNA comprises a sequence that is complementary to a target sequence within the target DNA, thus targeting the bound CRISPR/Cas protein to a specific location within the target DNA (the target sequence). A CRISPR/Cas associated protein, when targeted to the specific target DNA sequence, can create a single-strand break, two single-strand breaks, a double-strand break, two double-strand breaks, or any combinations thereof in the genome. A CRISPR/Cas associated protein, when targeted to the specific target DNA sequence, may not create any breaks in the genome. A CRISPR/Cas associated protein-guide RNA complex can make a blunt-ended double-stranded break, a 1-base pair (bp) staggered cut, a 2-bp staggered cut, a staggered cut with more than 2 base pairs, or any combination thereof in the genome. A double-strand DNA break can be repaired by end-joining mechanism or homologous directed repair. A double-strand DNA break can also be repaired by end-joining mechanism or homologous directed repair with a double strand donor DNA or a single-stranded oligonucleotide donor DNA. An edit in the genome can comprise stochastic or pre-selected insertions, deletions, base substitutions, inversion, chromosomal translocation, insertion.

A guide RNA can comprise a single guide RNA (sgRNA), a double guide RNA, or an engineered prime editing guide RNA (pegRNA). A guide RNA can comprise a crRNA and a tracrRNA. A crRNA can comprise a targeting sequence that hybridizes to a target sequence in the target DNA or locus. A tracrRNA can comprise a sequence that can form a stem-loop structure. Such a stem-loop structure can bind a CRISPR/Cas associated protein to activate the nuclease activity of the CRISPR/Cas associated protein. A sgRNA can comprise a crRNA and a tracrRNA in one RNA molecule. A double guide RNA can comprise a crRNA and a tracrRNA in two RNA molecules. A pegRNA can comprise a sequence that comprises a pre-selected edit or sequence in the genome. In such editing, the pre-selected sequence hybridizes to a cut and liberated 3' end of a nicked/cut DNA strand to form a primer-template complex, wherein the cut, liberated, and hybridized 3' end of the nicked/cut DNA strand can serve as a primer while the pre-selected edit or sequence of the pegRNA can serve as a template for the subsequent reactions, including but not limited to reverse transcription.

Suppressing of Pathogenic Mutations with a Suppressor tRNA

In some embodiments, the translation of a mRNA with a pathogenic mutation can be read through by an engineered tRNA with an engineered anticodon region. For example, a wild type codon can code for amino acid A while a pathogenic mutation can create a mutated codon that codes for a premature stop codon. An engineered tRNA can have an engineered anticodon region capable of recognizing and reading through the stop codon. In some embodiments, the anti-codon loop, arm length, tRNA-ribosome affinity in position 32/38, or other tRNA features can be optimized to increase the codon usage of the engineered tRNA. In other cases, the promoter, copy number, or other features can also be optimized to increase the codon usage of the engineered tRNA. In some embodiments, engineered polynucleotides of the present disclosure can be administered to a subject in need thereof in combination with a suppressor tRNA.

Manipulating the Phosphorylation of the APP, Tau, SNCA Polypeptide by RNA Editing In some embodiments, RNA editing of a target RNA can increase or decrease the amount of phosphorylation of a polypeptide encoded by the edited target RNA, compared to a polypeptide encoded by an unedited target RNA. RNA editing can effect an amino substitution that results in a deletion of an endogenous phosphorylation site. An endogenous phosphorylation can be identified by a polypeptide-specific antibody, phosphorylated site—specific antibody, phosphorylated fragment—specific antibody, a phosphorylated polypeptide—specific antibody, any derivatives herein and thereof, or any combinations herein and thereof. In other cases, a phosphorylation site of a polypeptide can be identified by a computer algorithm. A phosphorylation identification computer algorithm can comprise DISPHOS 1.3, ELM, GPS, NetPhorest, NetPhos, NetworKIN, P3DB, PHOSIDA, PhosphoregDB, PhosphoSitePlus, PREDIKIN, RLIMS, Scansite, any derivatives herein and thereof, or any combinations herein and thereof. In other cases, a phosphorylation site of a polypeptide can comprise mass-spectroscopy any derivatives herein and thereof, or any combinations herein and thereof. In some embodiments, RNA editing can effect an amino substitution outside of an endogenous phosphorylation site. An amino substitution outside of an endogenous phosphorylation site can increase or decrease a phosphorylation amount of the endogenous phosphorylation site. In other cases, an amino substitution may create a phosphorylation site. A created phosphorylation site can be identified by means that can identify an endogenous phosphorylation described herein and thereof. In some embodiments, an amino acid substitution can mimic a phosphorylation. A mimic of a phosphorylation can comprise a phosphomimetic. A phosphomimetic can comprise an amino substitution to aspartic acid. Aspartic acid can mimic a serine with phosphorylation.

A phosphorylation of a polypeptide can increase or decrease the enzymatic activity, stability, intracellular localization, extracellular localization, protein-binding activity, oligomerization activity, enzymatic processing, secretion, antimicrobial activity, degradation, chemical binding, or any endogenous or artificial activity of the polypeptide. In some embodiments, a phosphorylation of a polypeptide can increase or decrease the enzymatic activity, stability, intracellular localization, extracellular localization, protein-binding activity, oligomerization activity, enzymatic processing, secretion, antimicrobial activity, degradation, chemical binding, or any endogenous or artificial activity of a different polypeptide.

A phosphorylation of a polypeptide can be measured by a western blot with a polypeptide-specific antibody, phosphorylated site-specific antibody, phosphorylated fragment-specific antibody, a phosphorylated polypeptide-specific antibody. In other cases, a phosphorylation of a polypeptide can be measure by mass spectroscopy. A phosphorylation of a polypeptide can also be measured by an endogenous function of the polypeptide described herein and thereof. In some cases, a phosphorylation of a polypeptide can be measured by an in vitro assay with A protein is first phosphorylated using radioactive $^{32}$P-labeled ATP.

Phosphorylation of an APP or Abeta peptide can increaser or decrease an enzymatic cleavage of the APP or Abeta peptide by alpha, beta, beta', gamma-secretase, any derivatives thereof, or any combinations thereof. Phosphorylation of an APP or Abeta peptide can also increaser or decrease an enzymatic cleavage of the APP or Abeta peptide by BACE1, cathepsin B or Meprin beta. In other cases, phosphorylation of an APP or Abeta peptide can increaser or decrease an oligomerization or the APP/Abeta binding ability of the APP or Abeta peptide. In some cases, phosphorylation of an APP or Abeta peptide can increaser or decrease the formation, aggregation, or stability of a beta amyloid plaque.

A phosphorylation site can comprise position 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, or any combinations thereof of SEQ ID NO: 2, 14, or 15. In some cases, A phosphorylation site can be from position 1 to 10, from position 9 to 20, from position 19 to 30, from position 29 to 40, from position 39 to 50, from position 49 to 60, from position 59 to 70, from position 69 to 80, from position 79 to 90, from position 89 to 100, from position 99 to 110, from position 109 to 120, from position 119 to 130, from position 129 to 140, from position 139 to 150, from position 149 to 160, from position 159 to 170, from position 169 to 180, from position 179 to 190, from position 189 to 200, from position 199 to 210, from position 209 to 220, from position 219 to 230, from position 229 to 240, from position 239 to 250, from position 249 to 260, from position 259 to 270, from position 269 to 280, from position 279 to 290, from position 289 to 300, from position 299 to 310, from position 309 to 320, from position 319 to 330, from position 329 to 340, from position 339 to 350, from position 349 to 360, from position 359 to 370, from position 369 to 380, from position 379 to 390, from position 389 to 400, from position 399 to 410, from position 409 to 420, from position 419 to 430, from position 429 to 440, from position 439 to 450, from position 449 to 460, from position 459 to 470, from position 469 to 480, from position 479 to 490, from position 489 to 500, from position 499 to 510, from position 509 to 520, from position 519 to 530, from position 529 to 540, from position 539 to 550, from position 549 to 560, from position 559 to 570, from position 569 to 580, from position 579 to 590, from position 589 to 600, from position 599 to 610, from position 609 to 620, from position 619 to 630, from position 629 to 640, from position 639 to 650, from position 649 to 660, from position 659 to 670, from position 669 to 680, from position 679 to 690, from position 689 to 700, from position 699 to 710, from position 709 to 720, from position 719 to 730, from position 729 to 740, from position 739 to 750, from position 749 to 760, from position 759 to 770, or any combinations herein and thereof SEQ ID NO: 2, 14, or 15. A phosphorylation site can comprise position threonine 668 (T668), serine 198 (S198), S8, S26, S206, T10, T111, Y115, T153, S184, S185, S198, T205, S206, S208, T217, S262, S285 T381, S441, S679, S697, Y728, T729, S730, T743, Y757, T761, Y762, or any combinations herein and thereof of SEQ ID NO: 2.

Phosphorylation of a Tau polypeptide can increase or decrease formation, aggregation, or stability of neurofibrillary tangles (NFTs). In some cases, a phosphorylation site can comprise position of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, or any combinations herein and thereof of SEQ ID NO: 28-35. In some cases, a phosphorylation site can comprise from position 1 to 50, from position 49 to 100, from position 99 to 150, from position 149 to 200, from position 199 to 250, from position 249 to 300, from position 299 to 350, from position 349 to 400, from position 399 to 450, from position 449 to 500, from position 499 to 550, from position 549 to 600, from position 599 to 650, from position 649 to 700, from position 699 to 750, from position 749 to 800, from position 799 to 850, from position 849 to 862, or any combinations herein and thereof of SEQ ID NO: 28-35. A phosphorylation can comprise Y18, T39, S46, T50, T52, S56, S61, S64, T69, T111, S131, T149, T153, S171, T173, T175, T181, S191, S195, S199, S202, S205, S208, S210, S212, S214, S217, S231, S232, S235, S237, S238, S241, S258, S285, S289, S316, S320, S352, S355, S369, T373, T386, S388, S411, T466, T470, S396, S400, S404, S409, S412, T498, S501, S502, S508, S512, Y514, S515, S516, T522, S525, S527, T529, S531, T534, T548, S552, S554, S555, S558, S579, T580, S602, S610, S622, Y627, S633, T636, S641, S673, T694, Y711, S713, S717, T720, S721, S726, S729, S730, T731, S733, S739, T744, or any combinations herein and thereof of SEQ ID NO: 28-35.

Phosphorylation of a SNCA polypeptide can increase or decrease formation, aggregation, or stability of the SNCA polypeptide. In some cases, a phosphorylation site can comprise position of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, or any combinations herein and thereof of SEQ ID NO: 45-47. A phosphorylation site can be from position 1 to 10, from position 9 to 20, from position 19 to 30, from position 29 to 40, from position 39 to 50, from position 49 to 60, from position 59 to 70, from position 69 to 80, from position 79 to 90, from position 89 to 100, from position 99 to 110, from position 109 to 120, from position 119 to 130, from position 129 to 140 or any combinations herein and thereof of SEQ ID NO: 45-47. A phosphorylation can comprise Y39, S42, S87, Y125, S129, Y133, Y136, or any combinations herein and thereof of SEQ ID NO: 45-47.

Vectors

The present disclosure also provides for vectors that encode for the engineered guide RNAs disclosed herein.

The compositions provided herein can be delivered by any suitable means. In some cases, a suitable means comprises a vector. Any vector system can be used utilized, including but not limited to: plasmid vectors, minicircle vectors, linear DNA vectors, doggy bone vectors, retroviral vectors, lentiviral vectors, adenovirus vectors, poxvirus vectors; herpesvirus vectors and adeno-associated virus vectors, a liposome, a nanoparticle, an exosome, an extracellular vesicle, a nanomesh, modified versions thereof, good manufacturing practices versions thereof, chimeras thereof, and any combination thereof. In some cases, a vector can be used to introduce a polynucleotide provided herein. In some cases, the polynucleotide comprises a targeting sequence that hybridizes to a region of an RNA provided herein. In some embodiments, a nanoparticle vector can comprise a polymeric-based nanoparticle, an amino lipid-based nanoparticle, a metallic nanoparticle (such as gold-based nanoparticle), a portion of any of these, or any combination thereof.

Vectors provided herein can be used to deliver polynucleotide compositions provided herein. In some cases, at least about 2, 3, 4, or up to 5 different polynucleotides are delivered using a single vector. In some cases, multiple vectors are delivered. In some cases, multiple vector delivery can be co-current or sequential. In some cases, at least two engineered polynucleotides are delivered in a single vector. In other cases, at least two engineered polynucleotides are delivered on separate vectors. Engineered polynucleotides may also be delivered as naked polynucleotides. Any combination of vector and/or a non-vector approach can be taken.

A vector can be employed to deliver a nucleic acid. A vector can comprise DNA, such as double stranded DNA or single stranded DNA. A vector can comprise RNA. In some cases, the RNA can comprise a base modification. The vector can comprise a recombinant vector. The vector can be a vector that is modified from a naturally occurring vector. The vector can comprise at least a portion of a non-naturally occurring vector. Any vector can be utilized. A viral vector can comprise an adenoviral vector, an adeno-associated viral vector (AAV), a lentiviral vector, a retroviral vector, a portion of any of these, or any combination thereof. In some cases, a vector can comprise an AAV vector. A vector can be modified to include a modified VP1 protein (such as an AAV vector modified to include a VP1 protein). In an aspect an AAV vector is a recombinant AAV (rAAV) vector. rAAVs can be composed of substantially similar capsid sequence and structure as found in wild-type AAVs (wtAAVs). However, rAAVs encapsidate genomes that are substantially devoid of AAV protein-coding sequences and have therapeutic gene expression cassettes, such as subject polynucleotides, designed in their place. In some cases, sequences of viral origin can be the ITRs, which may be needed to guide genome replication and packaging during vector production. Suitable AAV vectors can be selected from any AAV serotype or combination of serotypes. For example, an AAV vector can be any one of: AAV1, AAV2, AAV3, AAV4, AAV5, AAV6, AAV7, AAV8, AAV9, AAV 10, AAV11, AAV12, or any combination thereof. In some cases, a vector is selected based on its natural tropism. In some cases, a vector serotype is selected based on its ability to cross the blood brain barrier. AAV9 and AAV10 have been shown to cross the blood brain barrier to transduce neurons and glia. In an aspect, an AAV vector is AAV2, AAV5, AAV6, AAV8, or AAV9. In some cases, an AAV vector is a chimera of at least two serotypes. In an aspect, an AAV vector is of serotypes AAV2, AAV5, and AAV9. In some cases, a chimeric AAV vector comprises rep and ITR sequences from AAV2 and a cap sequence from AAV5. In some cases, rep, cap, and ITR sequences can be mixed and matched from all the of the different AAV serotypes provided herein. In some cases, a suitable AAV vector can be further modified to encompass modifications such as in a capsid or rep protein. Modifications can also include deletions, insertions, mutations, and combinations thereof. In some cases, a modification to a vector is made to reduce immunogenicity to allow for repeated dosing. In some cases, a serotype of a vector that is utilized is changed when repeated dosing is performed to reduce and/or eliminate immunogenicity.

A vector can be used to deliver an engineered guide RNA provided herein and an additional polynucleotide targeting a therapeutic target, such as a second polynucleotide. In some cases, the vector comprises or encodes an additional RNA polynucleotide that associates with a second polynucleotide (e.g. an additional therapeutic target). Such vectors can be used to deliver multiplex therapeutics that simultaneously target multiple therapeutic targets, such as, in the case of Alzheimer' and other neurodegenerative disease, amyloid precursor protein and an additional target implicated in the disease such as a Tau protein (e.g. a microtubule-associated protein Tau (MAPT) encoded from a MAPT gene), or an alpha-synuclein protein. Alternatively, or in addition, the additional target can be a further edit site on the polynucleotide encoding the amyloid precursor protein (e.g. on the same polynucleotide). The vector polynucleotide encoding the engineered guide RNA and the second vector polynucleotide encoding the additional RNA polynucleotide can be contiguous or not contiguous. When the first and second vector polynucleotides are contiguous with each other, they can be operatively linked to the same promoter sequence.

Non-Viral Vector Approaches

In some cases, a vector may not be a viral vector. Non-viral methods can comprise naked delivery of compositions comprising polynucleotides and the like. In some cases, modifications provided herein can be incorporated into polynucleotides to increase stability and combat degradation when being delivered as naked polynucleotides. In other cases, a non-viral approach can harness use of nanoparticles, liposomes, and the like.

Therapeutic Applications

The engineered guide RNAs provided herein can be used as therapeutics. In one aspect herein is a method of treating or preventing a condition comprising administering a therapeutic that facilitates an edit of an RNA at least partially encoding an amyloid precursor protein (APP), wherein the edited RNA encodes a BACE protease-resistant APP, as compared to an otherwise comparable APP produced from an otherwise comparable RNA that does not comprise the edit, as determined by in vitro assay comprising contacting the BACE protease-resistant APP and the otherwise comparable APP with a beta-secretase (e.g., BACE1, cathepsin B or Meprin beta), a γ-secretase, or a beta secretase and a γ-secretase. In some cases, the therapeutic directly facilitates the edit. In some cases, the therapeutic indirectly facilitates the edit. In some cases, the conditions can comprise a neurodegenerative condition.

Methods can include mRNA base editing of one or more targets associated with a neurodegenerative disease. A neurodegenerative disease can include Alzheimer, Parkinson's, or other conditions mediated via Abeta fragments, Tau, alpha-synuclein, or combinations thereof. Methods can include editing a portion of a polynucleotide encoding for an amyloid precursor protein (APP) such that an enzyme (such as a beta secretase (BACE) or a gamma secretase) cannot cut APP at the edited sites. Methods can include editing a portion of a polynucleotide encoding for an APP such that a fragment (such as an Abeta fragment) cannot form. Editing a portion of the polynucleotide encoding for APP can result in a substantial reduction in an amount of Abeta fragment formed. In some embodiments, the edited RNA or the BACE protease-resistant APP is generated in at least 5%, 8%, 10%, 15%, 20%, 30%, 40%, or 50% of the subjects administered the therapeutic in a clinical trial.

In some embodiments, the present disclosure also provides for combination therapies. For example, a therapeutic method may include RNA editing of target cleavage sites in APP using an engineered guide RNA of the present disclosure in combination with another therapeutic agent that may have the same target (APP) or different targets. Said additional therapeutic agents may include guide RNAs for editing or knockout of polynucleotides encoding other therapeutic targets (e.g., Tau, alpha-synuclein) or may include antibodies that clear unwanted metabolites of Beta-secretase (e.g., BACE1, cathepsin B or Meprin beta) cleavage of APP. Methods can include knockdown of APP, knockdown of Tau, knockdown of alpha-synuclein, or any combination thereof. Methods can include delivery of one or more anti-Abeta antibodies for clearing of Abeta fragments already present in a tissue space. When in combination with an mRNA base editing approach, dosing amounts of an antibody can be lower as compared to a dosing amount in the absence of an mRNA base editing approach. Methods can include delivery of one or more secretase inhibitors to reduce cleavage and thus Abeta fragment formation. When in combination with an mRNA base editing approach, dosing amounts of a secretase inhibitor can be lower as compared to a dosing amount in the absence of an mRNA base editing approach. Methods can include delivery or combination delivery of one or more compositions as described herein.

The therapeutic applications described in this invention can be used in a treatment to obtain a desired pharmacologic effect, physiologic effect, or any combination thereof. In some instances, a treatment can reverse an adverse effect attributable to the disease or condition. In some cases, the treatment can stabilize the disease or condition. In some cases, the treatment can delay progression of the disease or condition. In some instances, the treatment can cause regression of the disease or condition. In some instances, a treatment can at least partially prevent the occurrence of the disease, condition, or a symptom of any of these. In some embodiments, a treatment's effect can be measured. In some cases, measurements can be compared before and after administration of the composition. For example, a subject can have medical images prior to treatment compared to images after treatment to show cancer regression. In some instances, a subject can have an improved blood test result after treatment compared to a blood test before treatment. In some instances, measurements can be compared to a standard.

Multiplexed Therapy

In some cases, the present disclosure encompasses multiplexed therapy, including multiplexed editing of multiple target RNAs, editing of multiple target sites within a target RNA, editing of RNA and knockdown, or any combination thereof. In some cases, use of vectors that contains multiple targeting guide RNAs can allow for simultaneous targeting of the Abeta generation and other proteins associated with neurodegeneration. Specifically, multiple unique, independent activities can be performed that regulate expression of complementary pathways affecting Alzheimer's, Tauopathies, Parkinson's, or neurodegeneration mediated via Tau, alpha-synuclein, and Abeta. Targeting more than one target RNA simultaneously may be important and the combination of Tau knockdown and editing of a cleavage site (e.g., a β-cleavage site) in APP may work in synergy. In some cases, use of mRNA base editing to knockdown (as opposed to just editing the cleavage site) expression of APP can be another approach for decreasing Abeta generation. As the compositions can be applied to gene expression knockdown, they could also include a combination of start-site editing to reduce expression, steric hinderance because the guide could block ribosomal activity, increased degradation of the targeted mRNA, or any combination thereof. The compositions and methods disclosed herein, thus, may suppress expression in an ADAR-dependent and ADAR-independent manner.

Both Abeta and Tau or SNCA are implicated in Alzheimer's disease initiation/progression. The compositions and methods disclosed herein can target both and, thus, may involve a multiplexed targeting approach. A multiplexed targeting approach can target 2, 3, 4, 5, 6, or more proteinopathies by independent mechanisms of action. For example, mRNA base editing using the engineered guide RNAs of the present disclosure can edit one or more cleavage sites of an APP protein preventing or substantially reducing Abeta fragment formation and mRNA base editing using the engineered guide RNAs of the present disclosure can knockdown Tau protein formation. In some cases, mRNA base editing using the guide RNAs of the present disclosure can edit one or more cleavage sites of an APP protein preventing or substantially reducing Abeta fragment formation and an additional therapeutic agent (e.g., an additional RNA polynucleotide, such as a siRNA, a shRNA, a miRNA, a piRNA, or an antisense oligonucleotide), which can knockdown Tau protein formation.

In some embodiments, a vector of the present disclosure may be a multiplex vector that contain multiple engineered guide polynucleotides targeting multiple target RNAs. In other cases, different engineered guide polynucleotide targeting different target RNAs can be maintained on different vectors. Vectors encoding for compositions that can (a) facilitate an edit to a cleavage site of a protein target (e.g., via association with an RNA editing protein such as ADAR), (b) reduce an amount of a protein target produced, (c) regulate the activity of a protein target produced, or (d) a combination thereof. A vector or a multiplex vector or vectors can be formulated in unit dose form. A multiplex vector can be configured to modulate more than one protein target implicated in a neurodegenerative disease. A vector can reduce an amount of the protein target by (i) performing an edit to a sequence that encodes for the protein, (ii) performing an edit to a sequence that does not encode for the protein, (iii) sterically hindering a promoter region associated with the protein target, or (iv) any combination thereof. The protein target can comprise amyloid beta, Tau, alpha-synuclein, or any combination thereof.

In some embodiments, a target RNA subjected to a multiplex targeting or edit can have at least 1-fold, at least 2-fold, at least 3-fold, at least 4-fold, at least 5-fold, at least 6-fold, at least 7-fold, at least 8-fold, at least 9-fold, at least 10-fold, at least 11-fold, at least 12-fold, at least 13-fold, at least 14-fold, at least 15-fold, at least 16-fold, at least 17-fold, at least 18-fold, at least 19-fold, at least 20-fold, at least 21-fold, at least 22-fold, at least 23-fold, at least 24-fold, at least 25-fold, at least 26-fold, at least 27-fold, at least 28-fold, at least 29-fold, at least 30-fold, at least 31-fold, at least 32-fold, at least 33-fold, at least 34-fold, at least 35-fold, at least 36-fold, at least 37-fold, at least 38-fold, at least 39-fold, at least 40-fold, at least 41-fold, at least 42-fold, at least 43-fold, at least 44-fold, at least 45-fold, at least 46-fold, at least 47-fold, at least 48-fold, at least 49-fold, at least 50-fold, at least 51-fold, at least 52-fold, at least 53-fold, at least 54-fold, at least 55-fold, at least 56-fold, at least 57-fold, at least 58-fold, at least 59-fold, at least 60-fold, at least 61-fold, at least 62-fold, at least 63-fold, at least 64-fold, at least 65-fold, at least 66-fold, at least 67-fold, at least 68-fold, at least 69-fold, at least 70-fold, at least 71-fold, at least 72-fold, at least 73-fold, at least 74-fold, at least 75-fold, at least 76-fold, at least 77-fold, at least 78-fold, at least 79-fold, at least 80-fold, at least 81-fold, at least 82-fold, at least 83-fold, at least 84-fold, at least 85-fold, at least 86-fold, at least 87-fold, at least 88-fold, at least 89-fold, at least 90-fold, at least 91-fold, at least 92-fold, at least 93-fold, at least 94-fold, at least 95-fold, at least 96-fold, at least 97-fold, at least 98-fold, at least 99-fold, at least 100-fold, 1-20-fold, 2-21-fold, 3-22-fold, 4-23-fold, 5-24-fold, 6-25-fold, 7-26-fold, 8-27-fold, 9-28-fold, 10-29-fold, 11-30-fold, 12-31-fold, 13-32-fold, 14-33-fold, 15-34-fold, 16-35-fold, 17-36-fold, 18-37-fold, 19-38-fold, 20-39-fold, 21-40-fold, 22-41-fold, 23-42-fold, 24-43 fold, 25-44-fold, 26-45-fold, 27-46-fold, 28-47-fold, 29-48-fold, 30-49-fold, 31-50-fold, 32-51-fold, 33-52-fold, 34-53-fold, 35-54-fold, 36-55-fold, 37-56-fold, 38-57-fold, 39-58-fold, 40-59-fold, 41-60-fold, 42-61-fold, 43-62-fold, 44-63-fold, 45-64-fold, 46-65-fold, 47-66-fold, 48-67-fold, 49-68-fold, 50-69-fold, 51-70-fold, 52-71-fold, 53-72-fold, 54-73-fold, 55-74-fold, 56-75-fold, 57-76-fold, 58-77-fold, 59-78-fold, 60-79-fold, 61-80-fold, 62-81-fold, 63-82-fold, 64-83-fold, 65-84-fold, 66-85-fold, 67-86-fold, 68-87-fold, 69-88-fold, 70-89-fold, 71-90-fold, 72-91-fold, 73-92-fold, 74-93-fold, 75-94-fold, 76-95-fold, 77-96-fold, 78-97-fold, 79-98-fold, 80-99-fold, or 81-100-fold decrease in the protein level of Abeta 40, 42, or both, as compared to that generated upon beta secretase (e.g., BACE1, cathepsin B or Meprin beta) cleavage of unedited APP.

A composition with multiplexed targeting of target RNAs can be at least at least 1-fold, at least 2-fold, at least 3-fold, at least 4-fold, at least 5-fold, at least 6-fold, at least 7-fold, at least 8-fold, at least 9-fold, at least 10-fold, at least 11-fold, at least 12-fold, at least 13-fold, at least 14-fold, at least 15-fold, at least 16-fold, at least 17-fold, at least 18-fold, at least 19-fold, at least 20-fold, at least 21-fold, at least 22-fold, at least 23-fold, at least 24-fold, at least 25-fold, at least 26-fold, at least 27-fold, at least 28-fold, at least 29-fold, at least 30-fold, at least 31-fold, at least 32-fold, at least 33-fold, at least 34-fold, at least 35-fold, at least 36-fold, at least 37-fold, at least 38-fold, at least 39-fold, at least 40-fold, at least 41-fold, at least 42-fold, at least 43-fold, at least 44-fold, at least 45-fold, at least 46-fold, at least 47-fold, at least 48-fold, at least 49-fold, at least 50-fold, at least 51-fold, at least 52-fold, at least 53-fold, at least 54-fold, at least 55-fold, at least 56-fold, at least 57-fold, at least 58-fold, at least 59-fold, at least 60-fold, at least 61-fold, at least 62-fold, at least 63-fold, at least 64-fold, at least 65-fold, at least 66-fold, at least 67-fold, at least 68-fold, at least 69-fold, at least 70-fold, at least 71-fold, at least 72-fold, at least 73-fold, at least 74-fold, at least 75-fold, at least 76-fold, at least 77-fold, at least 78-fold, at least 79-fold, at least 80-fold, at least 81-fold, at least 82-fold, at least 83-fold, at least 84-fold, at least 85-fold, at least 86-fold, at least 87-fold, at least 88-fold, at least 89-fold, at least 90-fold, at least 91-fold, at least 92-fold, at least 93-fold, at least 94-fold, at least 95-fold, at least 96-fold, at least 97-fold, at least 98-fold, at least 99-fold, at least 100-fold more effective in halting or inhibiting Alzheimer's disease progression or development.

In some cases, polynucleotide base editing can be used in conjunction with an additional method of knocking down gene expression of either the same gene targeted by the polynucleotide base editing or an additional gene implicated in a disease, such as a neurodegenerative disease. For example, mRNA base editing (e.g. using the engineered guide RNAs disclosed herein) can be used in conjunction with an RNA polynucleotide that associates with an mRNA sequence to minimize expression of a targeted gene. Examples of such RNA polynucleotides capable of minimizing expression of a targeted gene include small interfering RNA (siRNA), short hairpin RNA (shRNA), microRNA (miRNA), piwi-interacting RNA (piRNA), or an anti-sense oligonucleotide (ASO). In some cases, the ASO comprises a variant oligonucleotide structure that stabilizes the oligonucleotide and/or minimizes nuclease activity on the nucleotide. Examples of such variants oligonucleotides include morpholino oligomers. Thus, the present disclosure provides for compositions of engineered guides RNAs in combination with one or more additional therapeutic agents selected from small interfering RNA (siRNA), short hairpin RNA (shRNA), microRNA (miRNA), piwi-interacting RNA (piRNA), and an antisense oligonucleotide (ASO).

Abeta oligomers can initiate pathogenesis in Alzheimer's disease, however, their suppression cannot be sufficient to reduce disease progression. Targeting insoluble Abeta and Abeta aggregates can ignore the toxicity of soluble Abeta and/or C-terminal fragments, which can be highly toxic as well. Expectations of an effect with only Abeta reduction can ignore other identified pathogenic drivers (e.g., p-Tau, alpha-synuclein).

Genetic/neuropathologic evidence can link amyloid-beta aggregation (Abeta/amyloid-beta plaques) and Tau-p tangles with AD. Abeta can be derived from sequential proteolysis of amyloid precursor protein (APP) as variable-length fragments. Longer-length Abeta fragments (greater than 42 AA in length) can aggregate, forming plaques. Abeta fragments can drive Tau phosphorylation leading to aberrant Tau aggregation and gain-of-toxicity (synapse loss, or neurotoxicity). In an embodiment, a level of a beta amyloid plaque can be determined, for example using an in vivo diagnostic such as a PET scan, blood draw, and/or spinal tap. In another embodiment, a metabolite, including amyloid beta 40 (Abeta 40) and amyloid beta 42 (Abeta 42), can be measured.

Therefore, a multi-targeted combination therapy, such as described in the compositions and methods herein, can provide the necessary disease modification in Alzheimer's disease. A composition, including the disclosed engineered guide RNAs, as described herein may be administered with an additional therapeutic agent. An additional therapeutic agent can be a 5-HT 6 antagonist, 5-HT2A inverse agonist, an AB42 lowering agent, an acetylcholinesterase inhibitor, an alpha secretase enhancer, an alpha-1 adrenoreceptor antagonist, an alpha-2 adrenergic agonist, an angiotensin II receptor blocker, an angiotensin receptor blocker, an anti-amyloid antibody, an anti-aggregation agent, an anti-amyloid immunotherapy, an anti-inflammatory agent, an anti-malarial glial cell modulator, an antioxidant, an anti-Tau antibody, an anti-Tau immunotherapy, a BACE inhibitor, a beta-2 adrenergic receptor agonist, an arginase inhibitor, a beta-HSD1 inhibitor, a calcium channel blocker, a cannabinoid, a CB1 or CB2 endocannabinoid receptor agonist, a cholesterol lowering agent, a D2 receptor agonist, a dopamine-norepinephrine reuptake inhibitor, a FLNA inhibitor, a gamma secretase inhibitor, a GABA receptor modulator, a glucagon-like peptide 1 receptor agonist, a glutamate modulator, a glutamate receptor antagonist, a glycine transporter 1 inhibitor, a gonadotropin-releasing hormone receptor agonist, a GSK-3B inhibitor, a hepatocyte growth factor, a histone deacetylase inhibitor, a IgG1-Fc-GAIM fusion protein, an ion channel modulator, an iron chelating agent, a leukotriene receptor antagonist, a MAPT RNA inhibitor, a mast cell stabilizer, a melatonin receptor agonist, a microtubule protein modulator, a mitochondrial ATP synthase inhibitor, a monoamine oxidase B inhibitor, a muscarinic agonist, a nicotinic acetylcholine receptor agonist, an NMDA antagonist, an NMDA receptor modulator, a non-hormonal estrogen receptor B agonist, a non-nucleoside reverse transcriptase inhibitor, a nonsteroidal anti-inflammatory agent, an omega-3 fatty acid, a P38 MAPK inhibitor, a P75 neurotrophin receptor ligand, a PDE 5 inhibitor, a PDE-3 inhibitor, a PDE4D inhibitor, a positive allosteric modulator of GABA-A receptors, a PPAR-gamma agonist, a protein kinase C modulator, a RIPK1 inhibitor, a selective inhibitor of APP production, a selective norepinephrine reuptake inhibitor, a selective serotonin reuptake inhibitor, a selective tyrosine kinase inhibitor, a SGLT2 inhibitor, a SIGLEC-3 inhibitor, a sigma-1 receptor agonist, a sigma-2 receptor antagonist, a stem cell therapy, an SV2A modulator, a synthetic granulocyte colony stimulator, synthetic thiamine, a Tau protein aggregation inhibitor, a telomerase reverse transcriptase vaccine, a thrombin inhibitor, a transport protein ABCC1 activator, a TREM2 inhibitor, or any combination thereof. An additional therapeutic agent can be AADvac1, AAVrh.10hAPOE2, ABBV-8E12, ABvac40, AD-35, aducanumab, AGB101, AL002, AL003, allopregnanolone, amlopidine, AMX0035, ANAVEX 2-73, APH-1105, AR1001, AstroStem, atorvastatin, AVP-786, AXS-05, BAC, benfotiamine, BHV4157, BI425809, BIIB092, BIIP06, bioactive dietary polyphenol preparation, BPN14770, brexpiprazole, byrostatin, CAD106, candesartan, CERE-110, cilostazol, CKD-355, CNP520, COR388, crenezumab, cromolyn, CT1812, curcumin, dabigatran, DAOI, dapagliflozin, deferiprone, DHA, DHP1401, DNL747, dronabinol, efavirenz, elderberry juice, elenbecestat, escitalopram, formoterol, gantenerumab, *Ginkgo biloba*, grapeseed extract, GRF6019, guanfacine, GV1001, hUCB-MSCs, ibuprofen, icosapent ethyl, ID1201, insulin aspart, insulin glulisine, IONIS MAPTRx, J147, JNJ-63733657, lemborexant, leuprolide acetate depot, levetiracetam, liraglutide, lithium, LM11A-31-BHS, losartan, L-serine, Lu AF20513, LY3002813, LY3303560, LY3372993, masitinib, methylene blue, methylphenidate, mirtazapine, ML-4334, MLC901, montelukast, MP-101, nabilone, NDX-1017, neflamapimod, nicotinamide, nicotine, nilotinib, NPT08, octagam 10%, octohydroaminoacridine succinate, omega-3 PUFA, perindopril, pimavanserin, piromelatine, posiphen, prazosin, PTI-125, rasagiline, riluzole, R07105705, RPh201, sagramostim, salsalate, S-equol, solanezumab, SUVN-502, telmisartan, TEP, THN201, TPI-287, traneurocin, TRx0237, UB-311, valacyclovir, venlafaxine hMSCs (human mesenchymal stem cells), vorinostat, xanamem, zolpidem, or any combination thereof. The additional therapeutic agent can be administered concurrently, consecutively, or in any order.

An mRNA base editing approach using an engineered polynucleotide, such as guide RNA, of the present disclosure can be combined with an antibody-based approach (such as anti-Abeta antibodies). Disadvantages to employing an antibody-based approach alone can include low/inefficient transfer across the blood-brain-barrier and development of ARIA (neuroinflammation) in patients treated with these therapies constrain the therapeutic dose. It is likely that more than one Abeta species (including soluble Abeta)

contribute to disease progression. Thus, multiple different antibodies to the different species can be needed. Antibodies that may be combined with the engineered guide RNAs disclosed herein for combination treatment of a subject in need thereof can include bapineuzumab, solanezumab, gantenerumab, crenezumab, ponezumab, aducanumab, BAN2401, or any combination thereof.

An mRNA base editing approach using the engineered polynucleotides of the present disclosure can be combined with a secretase inhibitor approach (such as a beta secretase and γ-secretase inhibitors). Both enzymes appear to have proteolytic activity necessary for maintenance of synaptic function/neuronal health and thus severely or completely reducing function can led to poor long-term outcomes. Utilizing a combined approach of an mRNA base editing and secretase inhibitor approach can permit reducing dosing of the secretase inhibitor as compared to a solitary approach of delivering the secretase inhibitor alone. Inhibitors that may be combined with the engineered guide RNAs disclosed herein for combination treatment of a subject in need thereof can include verubecestat, atabecestat, lanabecestat, elenbecestat, umibecestat, avagacestat, semagacestat, or any combination thereof.

Compositions and methods as described herein can provide improvements over existing technologies and therapeutics, such as secretase inhibitors. Non-limiting and exemplary benefits and advantages of the compositions and methods as described herein can include (a) being capable of simultaneously targeting any and/or all forms of Abeta fragments (including those of varying length, and those that can be soluble or aggregated) and (b) without altering (i) the endogenous APP function, (ii) the endogenous β/γ-secretase function, or (iii) inflammation (e.g., ARIA).

Pharmaceutical Compositions

Compositions can include any editing entity described herein. A pharmaceutical composition can comprise a first active ingredient. The first active ingredient can comprise a viral vector as described herein, a non-naturally occurring RNA as described herein, or a nucleic acid as described herein. The pharmaceutical composition can be formulated in unit dose form. The pharmaceutical composition can comprise a pharmaceutically acceptable excipient, diluent, or carrier. The pharmaceutical composition can comprise a second, third, or fourth active ingredient—such as to provide multiplex targeting of related proteinopathies.

A composition described herein can compromise an excipient. An excipient can be added to a stem cell or can be co-isolated with the stem cell from its source. An excipient can comprise a cryo-preservative, such as DMSO, glycerol, polyvinylpyrrolidone (PVP), or any combination thereof. An excipient can comprise a cryo-preservative, such as a sucrose, a trehalose, a starch, a salt of any of these, a derivative of any of these, or any combination thereof. An excipient can comprise a pH agent (to minimize oxidation or degradation of a component of the composition), a stabilizing agent (to prevent modification or degradation of a component of the composition), a buffering agent (to enhance temperature stability), a solubilizing agent (to increase protein solubility), or any combination thereof. An excipient can comprise a surfactant, a sugar, an amino acid, an antioxidant, a salt, a non-ionic surfactant, a solubilizer, a trigylceride, an alcohol, or any combination thereof. An excipient can comprise sodium carbonate, acetate, citrate, phosphate, poly-ethylene glycol (PEG), human serum albumin (HSA), sorbitol, sucrose, trehalose, polysorbate 80, sodium phosphate, sucrose, disodium phosphate, mannitol, polysorbate 20, histidine, citrate, albumin, sodium hydroxide, glycine, sodium citrate, trehalose, arginine, sodium acetate, acetate, HCl, disodium edetate, lecithin, glycerine, xanthan rubber, soy isoflavones, polysorbate 80, ethyl alcohol, water, teprenone, or any combination thereof.

Compositions and methods disclosed herein can include multiplexed targeting via an mRNA base editing approach. For example, the present disclosure provides for multiplexed vectors for multiplexed targeting of Abeta generation and one or more additional proteins associated with a neurodegeneration disease or condition, such as Tau knockdown or alpha-synuclein knockdown. These multiplexed vectors may encode for engineered guide RNAs targeting APP (to affect Abeta generation) and one or more additional engineered guide RNAs or other therapeutic agents disclosed herein targeting one or more additional proteins associated with a neurodegeneration disease or condition. Compositions can perform multiple unique, independent bioactivities that regulate expression of complementary pathways affecting neurodegenerative conditions or Tau-pathologies (such as Alzheimer's, Parkinson's). Complementary pathways can include pathologies mediated via Tau, alpha-synuclein, and Abeta. In some cases, compositions can independently target more than one target RNA polynucleotide simultaneously such as a combination of Tau knockdown and APP editing. Compositions can include 2, 3, 4, 5, 6 vectors or more, independently targeting complementary pathways. Multiplexed targeting can result in additive therapeutic effects in subjects administered multiplexed vectors. Multiplexed targeting can provide a synergistic therapeutic effect in subjects administered multiplexed vectors, providing a greater therapeutic outcome than an individual targeting scheme.

Compositions can include mRNA base editing to (i) edit a cleavage site (such as to reduce or prevent Abeta fragment formation), (ii) knockdown protein expression (such as APP), or (iii) a combination thereof. Compositions can be designed to edit a base, edit a start-site (such as to reduce expression), create steric hindrance (such as a guide RNA that can block ribosomal activity), increase degradation of a targeted mRNA, or any combination thereof. The compositions and methods disclosed herein, thus, may suppress expression in an ADAR-dependent and -independent manner.

Editing can include editing of a target site (such as a BACE cleavage site) to prevent or substantially reduce cleavage of a protein by an enzyme. Editing can include knockdown of a protein (such as a protein implicated as a proteinopathy in a neurodegenerative disease) achieved by (i) start site editing (such as ATG), (ii) exon skipping (such as an exon that can contain the start site), (iii) blocking a region from promoter accessibility (such as an antisense-oligonucleotide (ASO)-based approach), or (iv) any combination thereof.

Compositions of the present disclosure can include an engineered guide RNA for editing a nucleotide in a target RNA polynucleotide sequence. Compositions can employ editing in an ADAR dependent or ADAR independent manner. Compositions can comprise a recruiting domain that recruits an RNA editing entity.

Compositions and methods described herein can allow for multiplexed targeting of both APP and Tau or SNCA mRNA to halt or prevent Alzheimer's disease progression. Delivery of a vector with multiple engineered polynucleotides targeting different target RNAs can allow for simultaneous or multiplexed targeting of the target RNAs. In some cases, delivery of vectors, each with an engineered polynucleotide targeting a specific target RNAs, can also allow for simultaneous or multiplexed targeting of the target RNAs.

An mRNA base editing approach can edit one or more BACE cleavage sites on APP, and thereby can mitigate toxic Abeta fragment formation or accumulation while maintaining normal or non-diseased APP/BACE function. A knockdown approach can simultaneously target Tau production to reduce Tau-p accumulation.

Compositions and methods provided herein can utilize pharmaceutical compositions. The compositions described throughout can be formulated into a pharmaceutical and be used to treat a human or mammal, in need thereof, diagnosed with a disease. In some cases, pharmaceutical compositions can be used prophylactically.

A disease or condition may include a neurodegenerative disease. A disease can include a disease associated with one or more proteinopathies (such as APP, Tau, or alpha-synuclein). A neurodegenerative disease can include Alzheimer's disease, amyotrophic lateral sclerosis, ataxia-telangiectasia, autosomal dominant cerebellar ataxia, autosomal recessive spastic ataxia of Chrlevoix-Saguenay, Baggio-Yoshinari syndrome, Batten disease, Cohen-Gibson syndrome, Corticobasal degeneration (CBD), corticobasal syndrome, Creutzfeldt-Jakob disease, dementia, fatal insomnia, fragile X-associated tremor/ataxia syndrome, Friedreich's ataxia, frontotemporal dementia, Fronto-temporal dementia with Parkinsonism linked to Tau mutations on chromosome 17 (FTDP-17T), heredetitary motor and sensory neuropathy with proximal dominance, Huntington's disease (HD), infantile refsum disease, JUNQ and IPOD, Kufor-Rakeb syndrome, Kufs disease, Lewy body disease, Lewy body variant of Alzheimer's disease (LBVAD), locomotor ataxia, Lyme disease, Machado-Joseph disease, motor neurone diseases (MND), multiple system atrophy, neuroacanthocytosis, Niemann-Pick disease, Parkinson's disease (PD), Parkinson's disease with dementia (PDD), Pick's disease (PiD), or Progressive supranuclear palsy (PSP), pontocerrebellar hypoplasia, prion disease, Refsum disease, Sandhoff disease, Shy-Drager syndrome, spinal muscular atrophy, spinocerebellar ataxia (SCA), spinocerrebellar ataxia, subacute combined degeneration of spinal cord, subacute sclerosing panencephalitis, tabes *dorsalis*, Tay-Sachs disease, toxic encephalapothay, toxic leukoencephalopathy, transneuronal degeneration, Wobbly Hedgehog syndrome or any combination thereof. A disease or condition can include a disease associated with Tau plaque formation including Alzheimer's disease, corticobasal degeneration, dementia pugilistica (chronic traumatic encephalopathy), frontotemporal dementia, frontotemporal lobar degeneration, gangliocytoma, ganglioglioma, lytico-bodig disease, meningioangiomatosis, Pick's disease, postencephalitic parkinsonism, primary age-related Tauopathy, progressive supranuclear palsy, Tauopathy, or any combination thereof. A disease or condition can include a disease associated with alpha-synuclein formation including Alzheimer's disease, dementia with Lewy bodies, Lewy body disease, multiple system atrophy, Parkinson's disease, or any combination thereof. A disease or condition can include a disease associated with Abeta fragment formation including Alzheimer's disease, cerebral amyloid angiopathy, inclusion body mitosis, Lew body dementia, or any combination thereof. A disease (or condition) can also include traumatic brain injury, Down's syndrome, a cancer, Fragile X Syndrome, autism, amyotrophic lateral sclerosis, multiple sclerosis, Lesch-Nyhan disease, a metabolic disorder, or any combination thereof. The disease can include a neurodegenerative disease.

The compositions provided herein can be utilized in methods provided herein. Any of the provided compositions provided herein can be utilized in methods provided herein. In some cases, a method comprises at least partially preventing, reducing, ameliorating, and/or treating a disease or condition, or a symptom of a disease or condition. In an embodiment, a composition can be utilized to reduce a level of a beta amyloid plaque in a subject, evaluated utilizing an in vivo diagnostic. A subject can be a human or non-human. A subject can be a mammal (e.g., rat, mouse, cow, dog, pig, sheep, horse). A subject can be a vertebrate or an invertebrate. A subject can be a laboratory animal. A subject can be a patient. A subject can be suffering from a disease. A subject can display symptoms of a disease. A subject may not display symptoms of a disease, but still have a disease. A subject can be under medical care of a caregiver (e.g., the subject is hospitalized and is treated by a physician). In an embodiment, a subject is over the age of 40, 50, 60, or 70.

Administration Routes and Dosing

Compositions described herein can employ an AAV (IV/CNS) vector for delivery to a subject. AAV vector delivery can achieve long-term benefits with single dose and can provide opportunity for multiplexed targeting. Methods can include identifying AAV serotypes that can promote central neuronal tropism and biodistribution with CNS/IV dosing.

In some cases, an administration can refer to methods that can be used to enable delivery of compounds or compositions to the desired site of biological action. Delivery can include direct application to the central nervous system (CNS). Delivery can include one that is permissive to cross the blood brain barrier. Delivery can include direct application to the affect tissue or region of the body. Delivery can include intracranial injection. Delivery can include a parenchymal injection, an intra-thecal injection, an intra-ventricular injection, or an intra-cisternal injection. A composition provided herein can be administered by any method. A method of administration can be by inhalation, intraarterial injection, intracerebroventricular injection, intracisternal injection, intramuscular injection, infraorbital injection, intraparenchymal injection, intraperitoneal injection, intraspinal injection, intrathecal injection, intravenous injection, intraventricular injection, stereotactic injection, subcutaneous injection, or any combination thereof. Delivery can include parenteral administration (including intravenous, subcutaneous, intrathecal, intraperitoneal, intramuscular, intravascular or infusion), oral administration, inhalation administration, intraduodenal administration, rectal administration. Delivery can include topical administration (such as a lotion, a cream, an ointment) to an external surface of a surface, such as a skin. In some cases, administration is by parenchymal injection, intra-thecal injection, intra-ventricular injection, intra-cisternal injection, intravenous injection, or intranasal administration or any combination thereof. In some instances, a subject can administer the composition in the absence of supervision. In some instances, a subject can administer the composition under the supervision of a medical professional (e.g., a physician, nurse, physician's assistant, orderly, hospice worker, etc.). A medical professional can administer the composition. In some cases, a cosmetic professional can administer the composition.

Administration or application of a composition, including any of the engineered guide RNAs, multiplexed vectors, or combination therapies, disclosed herein can be performed for a treatment duration of at least about at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 days consecutive or nonconsecutive days. A treatment duration can be from about 1 to about 30 days, from about 2 to about 30 days, from about 3 to about 30 days, from about 4 to about 30 days, from about 5 to about 30 days, from about 6 to about 30 days, from about 7 to about 30 days, from about 8 to about 30 days, from about 9 to about 30 days, from about 10 to about 30 days, from about 11 to about 30 days, from about 12 to about 30 days, from about 13 to about 30 days, from about 14 to about 30 days, from about 15 to about 30 days, from about 16 to about 30 days, from about 17 to about 30 days, from about 18 to about 30 days, from about 19 to about 30 days, from about 20 to about 30 days, from about 21 to about 30 days, from about 22 to about 30 days, from about 23 to about 30 days, from about 24 to about 30 days, from about 25 to about 30 days, from about 26 to about 30 days, from about 27 to about 30 days, from about 28 to about 30 days, or from about 29 to about 30 days.

Administration or application of a composition, including any of the engineered guide RNAs, multiplexed vectors, or combination therapies, disclosed herein can be performed for a treatment duration of at least about 1 week, at least about 1 month, at least about 1 year, at least about 2 years, at least about 3 years, at least about 4 years, at least about 5 years, at least about 6 years, at least about 7 years, at least about 8 years, at least about 9 years, at least about 10 years, at least about 15 years, at least about 20 years, or more. Administration can be performed repeatedly over a lifetime of a subject, such as once a month or once a year for the lifetime of a subject. Administration can be performed repeatedly over a substantial portion of a subject's life, such as once a month or once a year for at least about 1 year, 5 years, 10 years, 15 years, 20 years, 25 years, 30 years, or more.

In some cases, an administration of any composition provided herein, including pharmaceutical compositions can be in an effective amount, for example to reduce a symptom of a disease or condition and/or to reduce a disease or condition. An effective amount can be sufficient to achieve a desired effect. In the context of therapeutic or prophylactic applications, the effective amount will depend on the type and severity of the condition at issue and the characteristics of the individual subject, such as general health, age, sex, body weight, and tolerance to pharmaceutical compositions. In the context of an immunogenic composition, in some embodiments the effective amount is the amount sufficient to result in a protective response against a pathogen. In other embodiments, the effective amount of an immunogenic composition is the amount sufficient to result in antibody generation against the antigen. In some embodiments, the effective amount is the amount required to confer passive immunity on a subject in need thereof. With respect to immunogenic compositions, in some embodiments the effective amount will depend on the intended use, the degree of immunogenicity of a particular antigenic compound, and the health/responsiveness of the subject's immune system, in addition to the factors described above.

Administration or application of the compositions disclosed herein, including any of the engineered guide RNAs, multiplexed vectors, or combination therapies, can be performed at least 1, 2, 3, 4, 5, 6, 7, 8, 9, 10, 11, 12, 13, 14, 15, 16, 17, 18, 19, 20, 21, 22, 23, or 24 times a day. In some cases, administration or application of composition disclosed herein can be performed at least 1, 2, 3, 4, 5, 6, 7, 8, 9, 10, 11, 12, 13, 14, 15, 16, 17, 18, 19, 20, or 21 times a week. In some cases, administration or application of composition disclosed herein can be performed at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90 times a month.

A composition of the present disclosure, including any of the engineered guide RNAs, multiplexed vectors, or combination therapies, can be administered/applied as a single dose or as divided doses. In some cases, the compositions described herein can be administered at a first time point and a second time point. In some cases, a composition can be administered such that a first administration is administered before the other with a difference in administration time of 1 hour, 2 hours, 4 hours, 8 hours, 12 hours, 16 hours, 20 hours, 1 day, 2 days, 4 days, 7 days, 2 weeks, 4 weeks, 2 months, 3 months, 4 months, 5 months, 6 months, 7 months, 8 months, 9 months, 10 months, 11 months, 1 year or more.

Vectors of the disclosure can be administered at any suitable dose to a subject. Suitable doses can be at least about $5\times10^7$ to $50\times10^{13}$ genome copies/mL. In some cases, suitable doses can be at least about $5\times10^7$, $6\times10^7$, $7\times10^7$, $8\times10^7$, $9\times10^7$, $10\times10^7$, $11\times10^7$, $15\times10^7$, $20\times10^7$, $25\times10^7$, $30\times10^7$ or $50\times10^7$ genome copies/mL. In some embodiments, suitable doses can be about $5\times10^7$ to $6\times10^7$, $5.9\times10^7$ to $7\times10^7$, $6.9\times10^7$ to $8\times10^7$, $7.9\times10^7$ to $9\times10^7$, $8.9\times10^7$ to $10\times10^7$, $9.9\times10^7$ to $11\times10^7$, $10.9\times10^7$ to $15\times10^7$, $14.9\times10^7$ to $20\times10^7$, $19.9\times10^7$ to $25\times10^7$, $24.9\times10^7$ to $30\times10^7$, $29.9\times10^7$ to $50\times10^7$, or $49.9\times10^7$ to $100\times10^7$ genome copies/mL. In some cases, suitable doses can be about $5\times10^7$ to $10\times10^7$, $9.9\times10^7$ to $25\times10^7$, or $24.9\times10^7$ to $50\times10^7$ genome copies/mL. In some cases, suitable doses can be at least about $5\times10^8$, $6\times10^8$, $7\times10^8$, $8\times10^8$, $9\times10^8$, $10\times10^8$, $11\times10^8$, $15\times10^8$, $20\times10^8$, $25\times10^8$, $30\times10^8$ or $50\times10^8$ genome copies/mL. In some embodiments, suitable doses can be about $5\times10^8$ to $6\times10^8$, $5.9\times10^8$ to $7\times10^8$, $6.9\times10^8$ to $8\times10^8$, 7.9 to $9\times10^8$, $8.9\times10^8$ to $10\times10^8$, $9.9\times10^8$ to $11\times10^8$, $10.9\times10^8$ to $15\times10^8$, $14.9\times10^8$ to $20\times10^8$, $19.9\times10^8$ to $25\times10^8$, $24.9\times10^8$ to $30\times10^8$, $29.9\times10^8$ to $50\times10^8$, or $49.9\times10^8$ to $100\times10^8$ genome copies/mL. In some cases, suitable doses can be about $5\times10^8$ to $10\times10^8$, $9.9\times10^8$ to $25\times10^8$, or $24.9\times10^8$ to $50\times10^8$ genome copies/mL. In some cases, suitable doses can be at least about $5\times10^9$, $6\times10^9$, $7\times10^9$, $8\times10^9$, $9\times10^9$, $10\times10^9$, $11\times10^9$, $15\times10^9$, $20\times10^9$, $25\times10^9$, $30\times10^9$ or $50\times10^9$ genome copies/mL. In some embodiments, suitable doses can be about $5\times10^9$ to $6\times10^9$, $5.9\times10^9$ to $7\times10^9$, $6.9\times10^9$ to $8\times10^9$, $7.9\times10^9$ to $9\times10^9$, $8.9\times10^9$ to $10\times10^9$, $9.9\times10^9$ to $11\times10^9$, $10.9\times10^9$ to $15\times10^9$, $14.9\times10^9$ to $20\times10^9$, $19.9\times10^9$ to $25\times10^9$, $24.9\times10^9$ to $30\times10^9$, $29.9\times10^9$ to $50\times10^9$, or $49.9\times10^9$ to $100\times10^9$ genome copies/mL. In some cases, suitable doses can be about $5\times10^9$ to $10\times10^9$, $10\times10^9$ to $25\times10^9$, or $25\times10^9$ to $50\times10^9$ genome copies/mL. In some cases, suitable doses can be at least about $5\times10^{10}$, $6\times10^{10}$, $7\times10^{10}$, $8\times10^{10}$, $9\times10^{10}$, $10\times10^{10}$, $11\times10^{10}$, $15\times10^{10}$, $20\times10^{10}$, $25\times10^{10}$, $30\times10^{10}$ or $50\times10^{10}$ genome copies/mL. In some embodiments, suitable doses can be about $5\times10^{10}$ to $6\times10^{10}$, $5.9\times10^{10}$ to $7\times10^{10}$, 6.9 to $8\times10^{10}$, $7.9\times10^{10}$ to $9\times10^{10}$, $8.9\times10^{10}$ to $10\times10^{10}$, $9.9\times10^{10}$ to $11\times10^{10}$, $10.9\times10^{10}$ to $15\times10^{10}$, $14.9\times10^{10}$ to $20\times10^{10}$, $19.9\times10^{10}$ to $25\times10^{10}$, $24.9\times10^{10}$ to $30\times10^{10}$, $29.9\times10^{10}$ to $50\times10^{10}$, or $49.9\times10^{10}$ to $100\times10^{10}$ genome copies/mL. In some cases, suitable doses can be about $5\times10^{10}$ to $10\times10^{10}$, $10\times10^{10}$ to $25\times10^{10}$, or $25\times10^{10}$ to $50\times10^{10}$ genome copies/mL. In some cases, suitable doses can be at least about $5\times10^{11}$, $6\times10^{11}$, $7\times10^{11}$, $8\times10^{11}$, $9\times10^{11}$, $10\times10^{11}$, $11\times10^{11}$, $15\times10^{11}$, $20\times10^{11}$, $25\times10^{11}$, $30\times10^{11}$ or $50\times10^{11}$ genome copies/mL. In some embodiments, suitable doses can be about $5\times10^{11}$ to $6\times10^{11}$, $5.9\times10^{11}$ to $7\times10^{11}$, 6.9 to $8\times10^{11}$, $7.9\times10^{11}$ to $9\times10^{11}$, $8.9\times10^{11}$ to $10\times10^{11}$, $9.9\times10^{11}$ to $11\times10^{11}$, $10.9\times10^{11}$ to $15\times10^{11}$, $14.9\times10^{11}$ to $20\times10^{11}$, $19.9\times10^{11}$ to $25\times10^{11}$, $24.9\times10^{11}$ to $30\times10^{11}$, $29.9\times10^{11}$ to $50\times10^{11}$, or $49.9\times10^{11}$ to $100\times10^{11}$ genome copies/mL. In some cases, suitable doses can be about $5\times10^{11}$ to $10\times10^{11}$, $10\times10^{11}$ to $25\times10^{11}$, or $25\times10^{11}$ to $50\times10^{11}$ genome copies/mL. In some cases, suitable doses can be at least about $5\times10^{12}$, $6\times10^{12}$, $7\times10^{12}$, $8\times10^{12}$, $9\times10^{12}$, $10\times10^{12}$, $11\times10^{12}$, $15\times10^{12}$, $20\times10^{12}$, $25\times10^{12}$, $30\times10^{12}$ or $50\times10^{12}$ genome copies/mL. In some embodiments, suitable doses can be about 5x10'2 to $6\times10^{12}$, $5.9\times10^{12}$ to $7\times10^{12}$, 6.9 to $8\times10^{12}$, $7.9\times10^{12}$ to $9\times10^{12}$, $8.9\times10^{12}$ to $10\times10^{12}$, $9.9\times10^{12}$ to $12\times10^{12}$, $10.9\times10^{12}$ to $15\times10^{12}$, $14.9\times10^{12}$ to $20\times10^{12}$, $19.9\times10^{12}$ to $25\times10^{12}$, $24.9\times10^{12}$ to $30\times10^{12}$, $29.9\times10^{12}$ to $50\times10^{12}$, or $49.9\times10^{12}$ to $100\times10^{12}$ genome copies/mL. In some cases, suitable doses can be about $5\times10^{12}$ to $10\times10^{12}$, $9.9\times10^{12}$ to $25\times10^{12}$, or $24.9\times10^{12}$ to $50\times10^{12}$ genome copies/mL. In some cases, suitable doses can be at least about $5\times10^{13}$, $6\times10^{13}$, $7\times10^{13}$, $8\times10^{13}$, $9\times10^{13}$, $10\times10^{13}$, $11\times10^{13}$, $15\times10^{13}$, $20\times10^{13}$, $25\times10^{13}$, $30\times10^{13}$ or $50\times10^{13}$ genome copies/mL. In some embodiments, suitable doses can be about $5\times10^{13}$ to $6\times10^{13}$, $5.9\times10^{13}$ to $7\times10^{13}$, 6.9 to $8\times10^{13}$, $7.9\times10^{13}$ to $9\times10^{13}$, $8.9\times10^{13}$ to $10\times10^{13}$, $9.9\times10^{13}$ to $13\times10^{13}$, $10.9\times10^{13}$ to $15\times10^{13}$, $14.9\times10^{13}$ to $20\times10^{13}$, $19.9\times10^{13}$ to $25\times10^{13}$, $24.9\times10^{13}$ to $30\times10^{13}$, $29.9\times10^{13}$ to $50\times10^{13}$, or $49.9\times10^{13}$ to $100\times10^{13}$ genome copies/mL. In some cases, suitable doses can be about $5\times10^{13}$ to $10\times10^{13}$, $9.9\times10^{13}$ to $25\times10^{13}$, or $24.9\times10^{13}$ to $50\times10^{13}$ genome copies/mL. In some cases, suitable doses can be at least about $5\times10^{13}$, $6\times10^{13}$, $7\times10^{13}$, $8\times10^{13}$, $9\times10^{13}$, $10\times10^{13}$, $11\times10^{13}$, $15\times10^{13}$, $20\times10^{13}$, $25\times10^{13}$, $30\times10^{13}$ or $50\times10^{13}$ genome copies/mL. In some embodiments, suitable doses can be about $5\times10^{13}$ to $6\times10^{13}$, $5.9\times10^{13}$ to $7\times10^{13}$, 6.9 to $8\times10^{13}$, $7.9\times10^{13}$ to $9\times10^{13}$, $8.9\times10^{13}$ to $10\times10^{13}$, $9.9\times10^{13}$ to $13\times10^{13}$, $10.9\times10^{13}$ to $15\times10^{13}$, $14.9\times10^{13}$ to $20\times10^{13}$, $19.9\times10^{13}$ to $25\times10^{13}$, $24.9\times10^{13}$ to $30\times10^{13}$, $29.9\times10^{13}$ to $50\times10^{13}$, or $49.9\times10^{13}$ to $100\times10^{13}$ genome copies/mL. In some cases, suitable doses can be about $5\times10^{13}$ to $10\times10^{13}$, $9.9\times10^{13}$ to $25\times10^{13}$, or $24.9\times10^{13}$ to $50\times10^{13}$ genome copies/mL.

In some cases, the dose of virus particles administered to the individual can be any at least about $1\times10^{7}$ to about $1\times10^{13}$ genome copies/kg body weight. In some embodiments, the dose of virus particles administered to the individual can be $1\times10^{7}$, $2\times10^{7}$, $3\times10^{7}$, $4\times10^{7}$, $5\times10^{7}$, $6\times10^{7}$, $7\times10^{7}$, $8\times10^{7}$, or $9\times10^{7}$ genome copies/kg body weight. In some embodiments, the dose of virus particles administered to the individual can be $1\times10^{8}$, $2\times10^{8}$, $3\times10^{8}$, $4\times10^{8}$, $5\times10^{8}$, $6\times10^{8}$, $7\times10^{8}$, $8\times10^{8}$, or $9\times10^{8}$ genome copies/kg body weight. In some embodiments, the dose of virus particles administered to the individual can be $1\times10^{9}$, $2\times10^{9}$, $3\times10^{9}$, $4\times10^{9}$, $5\times10^{9}$, $6\times10^{9}$, $7\times10^{9}$, $8\times10^{9}$, or $9\times10^{9}$ genome copies/kg body weight. In some embodiments, the dose of virus particles administered to the individual can be $1\times10^{10}$, $2\times10^{10}$, $3\times10^{10}$, $4\times10^{10}$, $5\times10^{10}$, $6\times10^{10}$, $7\times10^{10}$, $8\times10^{10}$, or $9\times10^{10}$ genome copies/kg body weight. In some embodiments, the dose of virus particles administered to the individual can be $1\times10^{11}$, $2\times10^{11}$, $3\times10^{11}$, $4\times10^{11}$, $5\times10^{11}$, $6\times10^{11}$, $7\times10^{11}$, $8\times10^{11}$, or $9\times10^{11}$ genome copies/kg body weight. In some embodiments, the dose of virus particles administered to the individual can be $1\times10^{12}$, $2\times10^{12}$, $3\times10^{12}$, $4\times10^{12}$, $5\times10^{12}$, $6\times10^{12}$, $7\times10^{12}$, $8\times10^{12}$, or $9\times10^{12}$ genome copies/kg body weight. In some embodiments, the dose of virus particles administered to the individual can be $1\times10^{13}$, $2\times10^{13}$, $3\times10^{13}$, $4\times10^{13}$, $5\times10^{13}$, $6\times10^{13}$, $7\times10^{13}$, $8\times10^{13}$, or $9\times10^{13}$ genome copies/kg body weight.

Methods and Systems for Diagnosing a Disease or Monitoring a Disease Progression Doctors will use medical history, physical exam, neurological exam, mental status test, genetic test, and brain imaging to diagnose Alzheimer's disease. Medical history consultation can comprise examining whether there are current or past illness or if family members may have Alzheimer's disease. Physical exam can help identify medical issues causing dementia-like symptoms. Physical exam can comprise examining diet, nutrition, alcohol use, medications, blood pressure, temperature, pulse, heart and lung functions, or other health conditions. Physical exam can also comprise blood and urine test. Neurological exam can evaluate if a patient has other brain disorders other than Alzheimer's disease. Neurological exam can comprise testing reflexes, coordination, muscle tone/strength, eye movement, speech, or sensation. Neurological exam can also comprise brain imaging study including but not limited to Magnetic resonance imaging (MRI), computerized tomography (CT), or Positron emission tomography (PET). Mental status test can evaluate memory, problem-solving ability, or other cognitive abilities. Mental status test can comprise examining self-awareness, temporal or spatial awareness, memory, calculation ability, or others cognitive abilities. Mental status test can also comprise Mini-Mental State Exam (MA/ISE), the Mini-Cog test, FDA-approved computerized tests, mood assessment, or others. FDA-approved computerized tests can comprise the Cantab Mobile, Cognigram, Cognivue, Cognision and Automated Neuropsychological Assessment Metrics (ANAM) devices. Genetic testing can comprise testing APP, PSEN-1, PSEN-2, or apoE4. Other risk genes of Alzheimer's disease include ABCA7, CLU, CR1, PICALM, PLD3, TREM2, or SORL1. With all the information listed above, a doctor can determine if a patient has "possible Alzheimer's dementia" (dementia may be due to another cause), "probable Alzheimer's dementia" (no other cause for dementia can be found), or some other problems.

Kits

Any of the compositions described herein may be comprised in a kit. In a non-limiting example, a vector, a polynucleotide, a peptide, reagents to generate polynucleotides provided herein, and any combination thereof may be comprised in a kit. In some cases, kit components are provided in suitable container means.

Kits may comprise a suitably aliquoted composition. The components of the kits may be packaged either in aqueous media or in lyophilized form. The container means of the kits will generally include at least one vial, test tube, flask, bottle, syringe, or other container means, into which a component may be placed, and preferably, suitably aliquoted. Where there is more than one component in the kit, the kit also will generally contain a second, third or other additional container into which the additional components may be separately placed. However, various combinations of components may be comprised in a vial. The kits also will typically include a means for containing the components in close confinement for commercial sale. Such containers may include injection or blow-molded plastic containers into which the desired vials are retained.

However, the components of the kit may be provided as dried powder(s). When reagents and/or components are provided as a dry powder, the powder can be reconstituted by the addition of a suitable solvent. It is envisioned that the solvent may also be provided in another container means.

In some embodiments, a kit can comprise an engineered guide RNA, a precursor engineered guide RNA, a vector comprising the engineered guide RNA or the precursor engineered guide RNA, or a nucleic acid of the engineered guide RNA or the precursor engineered guide RNA, or a pharmaceutical composition and a container. In some instances, a container can be plastic, glass, metal, or any combination thereof.

In some instances, a packaged product comprising a composition described herein can be properly labeled. In some instances, the pharmaceutical composition described herein can be manufactured according to good manufacturing practice (cGMP) and labeling regulations. In some cases, a pharmaceutical composition disclosed herein can be aseptic.

EXAMPLES

Example 1: Treatment of Alzheimer's Disease

This example describes treatment of Alzheimer's disease using the engineered guide RNAs of the present disclosure.

Figure 4:
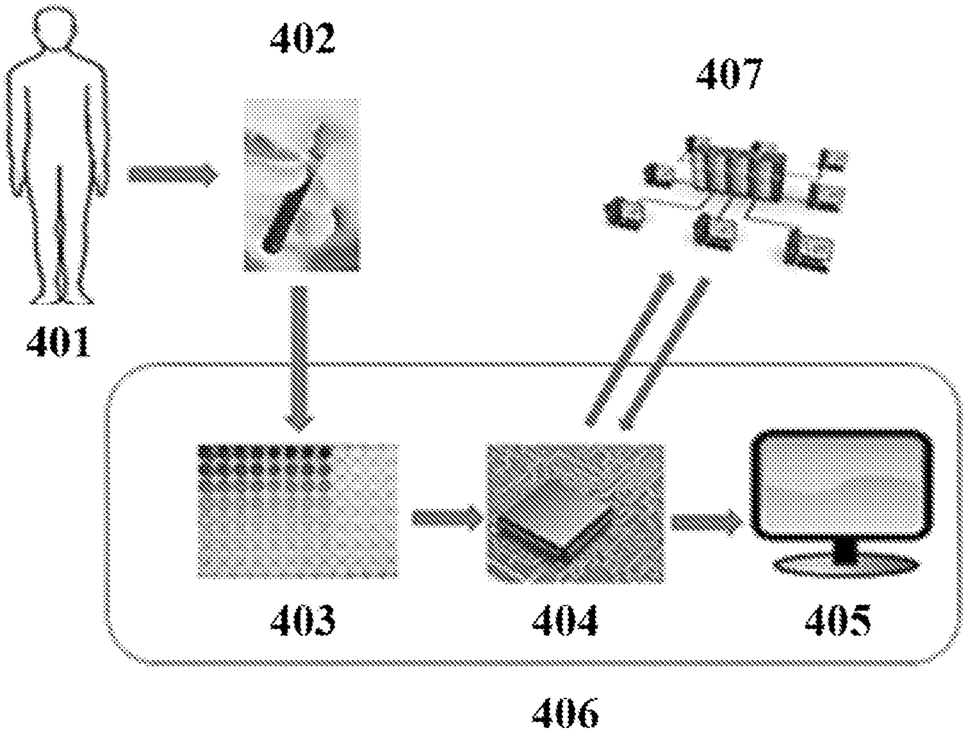
FIG. 4 shows an exemplary method for diagnosing a disease, condition, or for monitoring progression thereof. In the method, a sample 402 containing genetic material can be obtained from a subject 401, such as a human subject presumed to have a mutation in APP. A sample 402 can be subjected to one or more methods described herein. In some cases, a method can comprise performing sequencing (such as high-throughput sequencing), genotyping, hybridization, amplification, labeling, or any combination thereof (403). One or more results from a method can be input into a processing module 406. In 406, one or more input parameters such as a sample identification, subject identification, sample type, a reference, or other information can be input into a processor 404. One or more metrics from an assay can be input into the processor 404 such that the processor can produce a result, such as a diagnosis of a neurodegenerative condition, a risk of developing a neurodegenerative condition, an identification of a treatment for a neurodegenerative condition, a responsiveness to a treatment for a neurodegenerative condition, or any combination thereof. A processor can send a result, an input parameter, a metric, a reference, or any combination thereof to a display 405, such as a visual display or graphical user interface. The processor 404 can (i) send a result, an input parameter, a metric, or any combination thereof to a server 407, (ii) receive a result, an input parameter, a metric, or any combination thereof from the server 407, (iii) or a combination thereof.

A subject is diagnosed with Alzheimer's disease. FIG. 4 shows an example of such diagnosis.

The central idea is to mutagenize the beta-cleavage sites and the amino acids around them RNA editing. This approach has the dual advantages of: 1) directly modulating a driver event in the disease by diminishing the substrate preferences of beta-secretase (primarily BACE1 but also others); and 2) not interfering normal APP functions but leaving the endogenous APP expression largely unaffected. BACE1 substrate preferences are shown below in TABLE 8.

To target APP, engineered polynucleotides are designed based on a key APP target sequence region listed in SEQ ID NO: 48.

SEQ ID NO: 48
TATCAAGACGGAGGAGATCTCTGAAGTGAAGATGGATGCAGAATTCC

GACATGACTCAGGATATGAAGTTCATCATCAAAAATTGGTGTT

The antisense or complementary sequences (of lengths 20-100 bp) will include sequences complementary to all potential portions of the APP region in SEQ ID NO: 48. The regions opposite the target adenines will be paired with cytosines (as underlined in SEQ ID NO: 48). Examples of antisense sequences are listed in TABLE 9.

TABLE 9

Example antisense sequences for SEQ ID NO: 48.

| SEQ ID NO | SEQUENCE |
|---|---|
| 49 | TCTGCACCCATCTTCACTTC |
| 50 | TCATATCCTGAGTCATGTCGGAATTCTGCACCCATCTTCACTTCAGAGATCTCCTCCGTC |
| 51 | TCATATCCTGAGTCATGCCGGAATTCTGCACCCATCTTCACTTCAGAGACCTCCTCCGTC |

The underlined C corresponds to the cytosine paired with the adenine (the underlined A in SEQ ID NO: 48)

TABLE 8

Substrate Specificity of BACE1 (organized by the allotment of amino acids on each side of the cleavage bond at each position of the protein substrate (numbered from amino to carboxy terminus: P4, P3, P2, P1, P1', P2', P3', P4'; A > B A is more specific to BACE-1 than B; A = B, A is as specific to BACE-1 as B)

| Cleavage site | Terminus | Substrate Specificity of BACE-1 |
|---|---|---|
| P4 | N- | E > Q > D > N > M > G > L = T = H = P > R > V = W > F > A = S > I > Y |
| P3 | N- | I > V > L > E > H > M = A = T = P > K > S > F > D > Q > G = Y |
| P2 | N- | D > N > M > F > Y = L > S = E > A > Q > K > G |
| P1 | N- | L > F > M > Y >>> T > S > D > G > N > H > A |
| P1' | C- | M > E > Q > A > D > S >>> Y > L > T > V > I > F > R > K > G > N > W |
| P2' | C- | V > I > A > E > F > L > T > M > Y > S >> G > Q > N = D = W = K |
| P3' | C- | L > V > W > I > T > D > E > F > Y > M > R > K > A > G > S > Q > N > H > P |
| P4' | C- | D > E > W > F = Y = M > V > L > I > T > A > Q > G = S >> R > H > K > N |

The subject is prescribed a dosing regimen of a pharmaceutical composition. The pharmaceutical composition comprises an engineered polynucleotide or at least two engineered polynucleotides (e.g., any engineered guide RNA of the present disclosure) that edits a secretase cleavage site. The secretase cleavage site is a BACE secretase cleavage site. The cleavage site is the beta- or the beta'-cleavage site in APP (e.g., any of the APP isoforms disclosed herein). The pharmaceutical composition is administered to the subject by direct injection to cranial tissue, ICM injection, or ICV injection. The subject is a human or non-human animal. An amount of Abeta fragment formation following treatment with the engineered guide RNA is less (e.g., at least about 4-fold less) than an amount of Abeta fragment formation following treatment with a secretase inhibitor. Upon administration of the engineered guide RNA to the subject—for example but not limited to, through in vivo delivery of corresponding guide RNAs to the brain of the subject—a symptom of Alzheimer's disease is alleviated, or all symptoms are eliminated.

The engineered polynucleotide sequences, based on those listed in TABLE 9, are listed in TABLE 10.

TABLE 10

Example engineered polynucleotide sequences based on sequences in TABLE 9.

| SEQ ID NO | SEQUENCE |
|---|---|
| 52 | **GTGGAATAGTATAACAATATGCTAAATGTTGTTATAGTATCCCACN**$_S$ |
| 53 | **GTGGAATAGTATAACAATATGCTAAATGTTGTTATAGTATCCCACN**$_S$**GTGGAATAGTATAACAATATGCTAAATGTTGTTATAGTATCCCAC** |
| 54 | **GGCCGGGCGCGGTGGCTCACGCCTGTAATCCCAGCACTTTGGGAGGCCGAGGCGGGGAGATTGCTTGAGCCCAGGAGTTCGAGACCAGCCTGGGCAACATAGCGAGACCCCGTCTCN**$_S$**AGCCGGGCGTGGTGGCGCGCGCCTGTAGTCCCAGCTACTCGGGAGG** |

TABLE 10-continued

| Example engineered polynucleotide sequences based on sequences in TABLE 9. | |
|---|---|
| SEQ ID NO | SEQUENCE |
| | **CTGAGGCAGGAGGATCGCTTGAGCCCAGGAGTTCGAGGCTG CAGTGAGCTATGATCGCGCCACTGCACTCCAGCCTGGGCGA CAGAGCGAGACCCTGTCTC** |

Bold $N_S$ represent any of the sequences listed in TABLE 9.

Example 2: Multiplexed Compositions for Treatment of Alzheimer's Disease

This example describes multiplexed compositions (e.g., two engineered guide RNAs of the present disclosure targeting different RNA polynucleotides) for treatment of Alzheimer's disease. A subject is diagnosed with Alzheimer's disease. The subject is prescribed a dosing regimen of a pharmaceutical composition. The pharmaceutical composition comprises a multiplexed composition comprising an engineered guide RNA for editing of a BACE cleavage site (β- or the β'-cleavage site) in APP and an engineered guide RNA targeting a non-protein coding region (e.g., a start site) or causing exon skipping of a start site of the Tau gene, resulting in Tau knockdown in either cases. The pharmaceutical composition is administered to the subject by parenchymal injection, direct injection to cranial tissue, ICM injection, or ICV injection in an effective amount to treat Parkinson's disease. Upon administration of the multiplexed composition to the subject, a symptom of Alzheimer's disease is alleviated, or all symptoms are eliminated.

Example 3: Combination Treatment of Alzheimer's Disease

This example describes multiplexed compositions for treatment of Alzheimer's disease (e.g., two engineered guide RNAs of the present disclosure targeting different RNA polynucleotides). A subject will be diagnosed with Alzheimer's disease. The subject will be prescribed a dosing regimen of a pharmaceutical composition. The pharmaceutical composition will comprise the multiplexed composition comprising an engineered guide RNA for editing of a BACE cleavage site (β- or the β'-cleavage site) in APP and an engineered guide RNA targeting a non-protein coding region (e.g., a start site or promoter region) of SNCA resulting in alpha-synuclein knockdown. The engineered guide RNA and the antisense oligonucleotide are formulated in a single pharmaceutical composition or separate pharmaceutical compositions. The pharmaceutical composition or pharmaceutical compositions will be administered to the subject by parenchymal injection, direct injection to cranial tissue, ICM injection, or ICV injection in an effective amount to treat Alzheimer's disease. Upon administration of the multiplexed composition to the subject, a symptom of Alzheimer's disease is alleviated, or all symptoms are eliminated.

Example 4: Multiplexed Vectors for Treatment of Alzheimer's Disease

This example describes multiplexed vectors for treatment of Alzheimer's disease. A subject is diagnosed with Alzheimer's disease. The subject is prescribed a dosing regimen of a pharmaceutical composition. The pharmaceutical composition comprises a first vector comprising an engineered guide RNA targeting APP, and a second vector comprising a second engineered guide RNA targeting Tau-p. The pharmaceutical composition is administered to the subject by direct injection to the central nervous system (CNS), parenchymal injection, direct injection to cranial tissue, ICM injection, or ICV injection in an effective amount to treat Alzheimer's disease. Upon administration of the multiplexed vectors to the subject, a symptom of Alzheimer's disease is alleviated, or all symptoms are eliminated.

Example 5: Delivery of Multiplexed Engineered Polynucleotides with a Single Vector Because polymorphisms in different genes are associated with increased risk or severity of Alzheimer's disease, simultaneous manipulation of the expression of at least two target RNAs can be a useful treatment. RNA editing, as illustrated in the current invention, is modular: the RNA editing enzyme and the engineered polynucleotide are two different entities. Therefore, RNA editing can be multiplexed to correct multiple distinct targets simultaneously. For example, to treat Alzheimer's disease patients with contributing polymorphisms in APP and Tau or SNCA, two coding sequences are generated. The first coding sequence codes for any of the guide RNAs capable of binding to a target RNA sequence in any APP isoform, such as any one of those listed in TABLE 1 and 13 or any of the guide RNAs in TABLE 10 or 17. These guide RNAs can edit the cleavage sites in APP to inhibit the production of Abeta 40/42. The second coding sequence codes for a guide RNA that targets the start ATG of Tau or SNCA mRNA listed in TABLE 4 and 6 or any guide RNA listed in TABLEs 14-16. It can convert any nucleotide of the start ATG into any other nucleotide. Since the start ATG is removed, the expression of Tau or SNCA should decrease. These two coding sequences are each paired with a Polymerase III promoter and cloned into a single viral vector— such as an adenoviral vector, an adeno-associated viral vector (AAV), a lentiviral vector, or a retroviral vector—to express both coding sequences. The vector is injected into the brain of the patient by intracerebroventricular injection.

A subject is diagnosed with Alzheimer's disease. The subject is prescribed a dosing regimen of a pharmaceutical composition. The pharmaceutical composition comprises a multiplex targeting scheme of a vector comprising a first polynucleotide encoding a first engineered guide RNA that targets Abeta 40/42 and a second polynucleotide encoding a second engineered guide RNA that targets Tau/SNCA. The pharmaceutical composition is administered to the subject by direct injection to the central nervous system (CNS) in an effective amount to treat Alzheimer's disease.

Example 6: Delivery of Multiplexed Engineered Polynucleotides with Multiple Vectors The modularity of the RNA editing entity and the RNA targeting polynucleotide allows the multiplexed targeting to be carried out in various ways; for example, to treat Alzheimer's disease patients with contributing polymorphisms in APP and Tau or SNCA, two coding sequences are generated. The first coding sequence codes for any of the guide RNAs capable of binding to a target RNA sequence in any APP isoform, such as any one of those listed in TABLE 1 and 13 or any of the guide RNAs in TABLE 10 or 17. The second coding sequence codes for an engineered polynucleotide that targets the start ATG of any one of the Tau or SNCA mRNA listed in TABLE 4 and 6 or any guide RNA listed in TABLEs 14-16 and can convert any nucleotide of the start ATG into any other nucleotide. Since the start ATG is removed, the expression of Tau or SNCA should decrease. These two coding sequences are each paired with a Polymerase III promoter and each cloned into a single viral vector—such as an adenoviral vector, an adeno-associated viral vector (AAV), a lentiviral vector, or a retroviral vector—to express each coding sequence individually. The vectors are injected into the brain of the patient by intracerebroventricular injection.

A subject is diagnosed with Alzheimer's disease. The subject is prescribed a dosing regimen of a pharmaceutical composition. The pharmaceutical composition will comprise a multiplex targeting scheme of a first vector comprising a first polynucleotide encoding a first engineered guide RNA that targets Abeta 40/42 and a second vector comprising a second polynucleotide encoding a second engineered polynucleotide that targets Tau/SNCA. The pharmaceutical composition is administered to the subject by direct injection to the central nervous system (CNS) in an effective amount to treat Alzheimer's disease.

Example 7: Delivery of Multiplexed Engineered Polynucleotides with Multiple Vectors The engineered polynucleotides described in this invention can be maintained and administered without any viral vectors; for example, a first coding sequence coding for any of the guide RNAs capable of binding to a target RNA sequence in any APP isoform, such as any one of those listed in TABLE 1 and 13 or any of the guide RNAs in TABLE 10 or 17; and a second coding sequence coding for an engineered polynucleotide that targets the start ATG of any one of the Tau or SNCA mRNA listed in TABLE 4 and 6 or any guide RNA listed in TABLEs 14-16, each paired with a Polymerase III promoter, are injected into the brain of the patient by intracerebroventricular injection.

A subject is diagnosed with Alzheimer's disease. The subject is prescribed a dosing regimen of a pharmaceutical composition. The pharmaceutical composition comprises a multiplex targeting scheme of a first vector comprising a first polynucleotide encoding a first engineered guide RNA that targets Abeta 40/42 and a second vector comprising a second polynucleotide encoding a second engineered polynucleotide that targets Tau/SNCA. The pharmaceutical composition is administered to the subject by direct injection to the central nervous system (CNS) in an effective amount to treat Alzheimer's disease.

Example 8: Delivery of Multiplexed Engineered Polynucleotides with Multiple Vectors Any engineered polynucleotides described in Example 6, 7, and 8 are combined and injected into the brain of the patient by intracerebroventricular injection.

A subject is diagnosed with Alzheimer's disease. The subject is prescribed a dosing regimen of a pharmaceutical composition. The pharmaceutical composition w comprises a multiplex targeting scheme of a first vector comprising a first polynucleotide encoding a first engineered guide RNA that targets Abeta 40/42 and a second vector comprising a second polynucleotide encoding a second engineered polynucleotide that targets Tau/SNCA. The pharmaceutical composition is administered to the subject by direct injection to the central nervous system (CNS) in an effective amount to treat Alzheimer's disease.

Example 9: Identification of Target RNA Cleavage Sites within an RNA Encoding APP Identification of Target RNA Containing Mutations Target RNA sites were identified by analyzing human APP amino acid sequences and corresponding nucleotide sequences encoding said amino acid sequences at and/or near to the protease cleavage sites of APP. As can be seen in FIG. 5, APP contains numerous cleavage sites which are cleaved by endogenous proteases, such as beta-secretase (e.g., BACE1, cathepsin B or Meprin beta) and alpha secretases (e.g., ADAM10). Mutant APP proteins are selected that are non-amyloidogenic and/or can be made by ADAR-editing of endogenous APP. Levels of beta amyloid plaque forming metabolites, including amyloid beta 40 (Abeta 40) and amyloid beta 42 (Abeta 42), were measured. Mutations near the β-site, β'-site, and α-site as indicated in FIG. 5 were identified as amenable to editing by ADAR and were selected for further analysis.

Generation of Cell Lines Expressing Exemplary Mutant APP Polypeptide

Cell lines that express the wild type APP polypeptide provided in SEQ ID NO: 2 and the APP polypeptides with the mutations listed in TABLE 2 were generated. In an exemplary attempt, plasmids encoding the APP695 isoform with the desired mutation listed in TABLE 2 were generated. The APP695 isoform was chosen because it is the most highly expressed in neuron cells but other isoforms can be utilized. A mammalian codon-optimized APP695 isoform was synthesized as a single g-block gene fragment. APP695 was then cloned onto a pBI-CMV-mCherry backbone using Gibson assembly, provide in TABLE 11. A summary of the location of the features of the plasmid is provided in TABLE 12.

TABLE 11 pBI-CMV-mCherry backbone with wild type APP:

| SEQ ID NO | DNA |
|---|---|
| 55 | CTCGAGTAGTTATTAATAGTAATCAATTACGGGGTCATTAGTTCAT AGCCCATATATGGAGTTCCGCGTTACATAACTTACGGTAAATGGCC CGCCTGGCTGACCGCCCAACGACCCCCGCCCATTGACGTCAATAA TGACGTATGTTCCCATAGTAACGCCAATAGGGACTTTCCATTGACG TCAATGGGTGGAGTATTTACGGTAAACTGCCCACTTGGCAGTACAT CAAGTGTATCATATGCCAAGTACGCCCCCTATTGACGTCAATGACG GTAAATGGCCCGCCTGGCATTATGCCCAGTACATGACCTTATGGGA CTTTCCTACTTGGCAGTACATCTACGTATTAGTCATCGCTATTACC ATGGTGATGCGGTTTTGGCAGTACATCAATGGGCGTGGATAGCGG TTTGACTCACGGGGATTTCCAAGTCTCCACCCCATTGACGTCAATG GGAGTTTGTTTTGGCACCAAAATCAACGGGACTTTCCAAAATGTCG TAACAACTCCGCCCCATTGACGCAAATGGGCGGTAGGCGTGTACG GTGGGAGGTCTATATAAGCAGAGCTGGTTTAGTGAACCGTCAGAT CCGCTAGGGATCCTCTAGTCAGCTGACGCGTGCTAGCGCGGCCGC ATCGATAATGCTCCCTGGACTTGCTTTGCTGCTTTTGGCAGCCTGG ACTGCTCGAGCACTCGAGGTCCCAACGGATGGAAACGCGGGTCTT TTGGCAGAGCCTCAAATAGCAATGTTTTGCGGAAGACTCAACATGC ATATGAACGTTCAGAATGGGAAATGGGACTCCGACCCCAGTGGTA CGAAGACATGTATTGACACAAAGGAGGGAATACTCCAGTACTGCC AGGAAGTGTACCCGGAGCTTCAGATTACGAATGTGGTAGAGGCTA ATCAACCCGTAACTATCCAAAATTGGTGTAAGAGAGGCAGGAAGC AATGCAAGACTCATCCTCATTTCGTAATTCCGTATCGATGTTTGGT GGGAGAATTTGTCTCTGACGCATTGCTTGTTCCTGACAAGTGTAAG TTTCTTCACCAGGAACGCATGGACGTGTGCGAGACACACTTGCACT GGCATACCGTTGCGAAGGAGACGTGTTCCGAAAAGAGTACAAATC TCCATGACTACGGCATGTTGCTCCCGTGCGGAATAGATAAGTTCCG AGGCGTGGAGTTTGTATGCTGTCCGCTGGCAGAGGAGAGCGATAA TGTCGATTCCGCAGATGCCGAAGAGGACGACAGCGACGTCTGGTG GGGAGGAGCGGACACTGATTACGCTGATGGTAGTGAGGACAAAGT AGTCGAGGTGGCAGAAGAAGAAGAAGTGGCGGAGGTTGAAGAAG |

TABLE 11-continued pBI-CMV-mCherry backbone with wild type APP:

| SEQ ID NO | DNA |
|---|---|
| | AAGAGGCAGACGATGACGAAGACGATGAGGACGGTGATGAGGTAG AAGAAGAAGCGGAAGAACCGTACGAAGAAGCTACGGAACGCACTA CAAGTATTGCTACCACTACAACCACTACAACCGAATCAGTTGAGGA AGTGGTGCGAGTCCCCACTACGGCTGCCAGTACACCGGATGCCGT CGACAAATACCTGGAGACTCCTGGCGACGAAAACGAACATGCTCA TTTCCAGAAGGCGAAGGAACGCCTCGAAGCAAAGCACAGAGAGAG AATGTCACAGGTAATGAGGGAATGGGAGGAGGCGGAACGCCAAGC AAAGAACCTGCCTAAAGCGGACAAGAAGGCAGTTATCCAACATTTC CAAGAGAAAGTGGAGAGTCTCGAACAGGAGGCAGCGAACGAGAG GCAACAATTGGTAGAAACGCACATGGCGAGGGTGGAAGCTATGCT CAATGACCGAAGACGACTTGCCTTGGAAAATTACATTACTGCCCTT CAAGCCGTCCCACCGCGCCCACGCCATGTCTTTAACATGCTTAAGA AGTATGTTCGAGCTGAACAGAAGGATCGGCAACACACCCTGAAAC ACTTCGAACATGTCAGAATGGTTGACCCGAAGAAGGCTGCACAGA TTCGAAGTCAAGTTATGACCCATTTGAGGGTAATATATGAGAGAAT GAACCAAAGTCTGAGCCTTCTCTACAATGTCCCCGCTGTGGCCGAG GAAATTCAGGACGAAGTCGATGAGCTCCTGCAAAAGGAGCAGAAC TACTCTGACGATGTACTTGCTAATATGATTTCAGAGCCAAGGATCA GTTATGGAAACGACGCCCTGATGCCTAGTCTTACCGAAACCAAGAC TACGGTAGAACTCCTTCCCGTTAACGGAGAGTTCAGCTTGGACGAC CTTCAGCCTTGGCACTCATTCGGAGCTGATTCCGTACCAGCCAATA CGGAGAATGAAGTAGAGCCCGTAGACGCAAGACCTGCAGCGGACA GAGGGCTGACGACGAGACCCGGTAGCGGTTTGACAAATATCAAGA CGGAGGAGATCTCTGAAGTGAAGATGGATGCAGAATTCCGACATG ACTCAGGATATGAAGTTCATCATCAAAAATTGGTGTTCTTTGCAGA AGATGTCGGTTCTAACAAGGGTGCTATCATAGGCCTTATGGTGGGT GGCGTCGTGATTGCGACCGTGATAGTTATTACGCTTGTCATGCTGA AGAAGAAACAGTATACGTCCATCCATCACGGTGTGGTAGAGGTAG ATGCGGCCGTAACTCCCGAAGAGCGCCATCTTTCTAAGATGCAGC AGAATGGATACGAGAACCCCACGTACAAATTCTTTGAGCAAATGCA AAACTGATGTCGACGATATCTCCAGAGGATCATAATCAGCCATACC ACATTTGTAGAGGTTTTACTTGCTTTAAAAAACCTCCCACACCTCC CCCTGAACCTGAAACATAAAATGAATGCAATTGTTGTTGTTAACTT GTTTATTGCAGCTTATAATGGTTACAAATAAAGCAATAGCATCACA AATTTCACAAATAAAGCATTTTTTTCACTGCCCCGAGCTTCCTCGC TCACTGACTCGCTGCGCTCGGTCGTTCGGCTGCGGCGAGCGGTAT CAGCTCACTCAAAGGCGGTAATACGGTTATCCACAGAATCAGGGG ATAACGCAGGAAAGAACATGTGAGCAAAAGGCCAGCAAAAGGCCA GGAACCGTAAAAAGGCCGCGTTGCTGGCGTTTTTCCATAGGCTCC GCCCCCCTGACGAGCATCACAAAAATCGACGCTCAAGTCAGAGGT GGCGAAACCCGACAGGACTATAAAGATACCAGGCGTTTCCCCCTG GAAGCTCCCTCGTGCGCTCTCCTGTTCCGACCCTGCCGCTTACCGG ATACCTGTCCGCCTTTCTCCCTTCGGGAAGCGTGGCGCTTTCTCAT AGCTCACGCTGTAGGTATCTCAGTTCGGTGTAGGTCGTTCGCTCCA AGCTGGGCTGTGTGCACGAACCCCCCGTTCAGCCCGACCGCTGCG CCTTATCCGGTAACTATCGTCTTGAGTCCAACCCGGTAAGACACGA CTTATCGCCACTGGCAGCAGCCACTGGTAACAGGATTAGCAGAGC GAGGTATGTAGGCGGTGCTACAGAGTTCTTGAAGTGGTGGCCTAA CTACGGCTACACTAGAAGAACAGTATTTGGTATCTGCGCTCTGCTG AAGCCAGTTACCTTCGGAAAAAGAGTTGGTAGCTCTTGATCCGGCA AACAAACCACCGCTGGTAGCGGTGGTTTTTTTGTTTGCAAGCAGCA GATTACGCGCAGAAAAAAAGGATCTCAAGAAGATCCTTTGATCTTT TCTACGGGGTCTGACGCTCAGTGGAACGAAAACTCACGTTAAGGG ATTTTGGTCATGAGATTATCAAAAAGGATCTTCACCTAGATCCTTT TAAATTAAAAATGAAGTTTTAAATCAATCTAAAGTATATATGAGTA AACTTGGTCTGACAGTTACCAATGCTTAATCAGTGAGGCACCTATC TCAGCGATCTGTCTATTTCGTTCATCCATAGTTGCCTGACTCCCCG TCGTGTAGATAACTACGATACGGGAGGGCTTACCATCTGGCCCCA GTGCTGCAATGATACCGCGAGACCCACGCTCACCGGCTCCAGATT TATCAGCAATAAACCAGCCAGCCGGAAGGGCCGAGCGCAGAAGTG GTCCTGCAACTTTATCCGCCTCCATCCAGTCTATTAATTGTTGCCG GGAAGCTAGAGTAAGTAGTTCGCCAGTTAATAGTTTGCGCAACGTT GTTGCCATTGCTACAGGCATCGTGGTGTCACGCTCGTCGTTTGGTA TGGCTTCATTCAGCTCCGGTTCCCAACGATCAAGGCGAGTTACATG ATCCCCCATGTTGTGCAAAAAAGCGGTTAGCTCCTTCGGTCCTCCG ATCGTTGTCAGAAGTAAGTTGGCCGCAGTGTTATCACTCATGGTTA TGGCAGCACTGCATAATTCTCTTACTGTCATGCCATCCGTAAGATG CTTTTCTGTGACTGGTGAGTACTCAACCAAGTCATTCTGAGAATAG TGTATGCGGCGACCGAGTTGCTCTTGCCCGGCGTCAACACGGGAT AATACCGCGCCACATAGCAGAACTTTAAAAGTGCTCATCATTGGAA AACGTTCTTCGGGGCGAAAACTCTCAAGGATCTTACCGCTGTTGAG ATCCAGTTCGATGTAACCCACTCGTGCACCCAACTGATCTTCAGCA TCTTTTACTTTCACCAGCGTTTCTGGGTGAGCAAAAACAGGAAGGC AAAATGCCGCAAAAAAGGGAATAAGGGCGACACGGAAATGTTGAAT |

TABLE 11-continued pBI-CMV-mCherry backbone with wild type APP:

| SEQ ID NO | DNA |
|---|---|
| | ACTCATACTCTTCCTTTTTCAATATTATTGAAGCATTTATCAGGGT TATTGTCTCATGAGCGGATACATATTTGAATGTATTTAGAAAAATA AACAAATAGGGGTTCCGCGCACATTTCCCCGAAAAGTGCCACCTG ACGTCGGCAGTGAAAAAAATGCTTTATTTGTGAAATTTGTGATGCT ATTGCTTTATTTGTAACCATTATAAGCTGCAATAAACAAGTTAACA ACAACAATTGCATTCATTTTATGTTTCAGGTTCAGGGGGAGGTGTG GGAGGTTTTTTAAAGCAAGTAAAACCTCTACAAATGTGGTATGGCT GATTATGATCCTCTAGACTGCAGCCTCAGGAGATCTGGGCCCCCG CGGCATATGACCGGTGCTACTTGTACAGCTCGTCCATGCCGCCGG TGGAGTGTCTACCCTCGGCGCGTTCGTACTGTTCCACGATGGTGTA GTCCTCGTTGTGGGAGGTGATGTCCAACTTGATGTTGACGTTGTAG GCGCCGGGCAGCTGCACGGGCTTCTTGGCCTTGTAGGTGGTCTTG ACCTCAGCGTCGTAGTGGCCGCCGTCCTTCAGCTTCAGCCTCTGCT TGATCTCGCCCTTCAGGGCGCCGTCCTCGGGGTACATCCGCTCGG AGGAGGCCTCCCAGCCCATGGTCTTCTTCTGCATTACGGGGCCGT CGGAGGGGAAGTTGGTGCCGCGCAGCTTCACCTTGTAGATGAACT CGCCGTCTTGCAGGGAGGAGTCCTGGGTCACGGTCACCACGCCGC CGTCCTCGAAGTTCATCACGCGCTCCCACTTGAAGCCCTCGGGGA AGGACAGCTTCAAGTAGTCGGGGATGTCGGCGGGGTGCTTCACGT AGGCCTTGGAGCCGTACATGAATTGAGGGGACAGGATGTCCCAGG CGAAGGGCAGGGGGCCACCCTTGGTCACCTTCAGCTTGGCGGTCT GGGTGCCCTCGTAGGGGCGACCTTCACCCTCGCCCTCGATCTCGA ACTCGTGGCCGTTCACGGAGCCCTCCATGTGCACCTTGAAGCGCA TGAACTCCTTGATGATGGCCATGTTATCCTCCTCGCCCTTAGAAAC CATCTCCAGGCGATCTGACGGTTCACTAAACGAGCTCTGCTTATAT AGGCCTCCCACCGTACACGCCACCTCGACATA |

TABLE 12

Features of the pBI-CMV-mCherry backbone with wild type APP of SEQ ID NO 48

| Feature | Location of the feature (bp) |
|---|---|
| Enhancer | 64 to 473 |
| Minimal CMV Promoter #1 | 474 to 599 |
| MCS #1 | 601 to 646 |
| CDS1 (WT APP695 isoform) | 647 to 2734 |
| NM_201414.3 | 2393 to 2500 |
| BACE Cleavage Site | 2432 to 2437 |
| ADAM10 Cleavage Site | 2480 to 2482 |
| MCS #2 | 2735 to 2747 |
| SV40 polyA #1 | 2759 to 2946 |
| pUC origin | 3122 to 3721 |
| AmpR | 3883 to 4743 |
| SV40 polyA #2 | 4879 to 5066 |
| MCS #3 | 5070 to 5119 |
| CDS2 (mCherry) | 5120 to 5119 |
| MCS #4 | 5831 to 5834 |
| Minimal CMV Promoter #2 | 5837 to 5905 |

Figure 6:
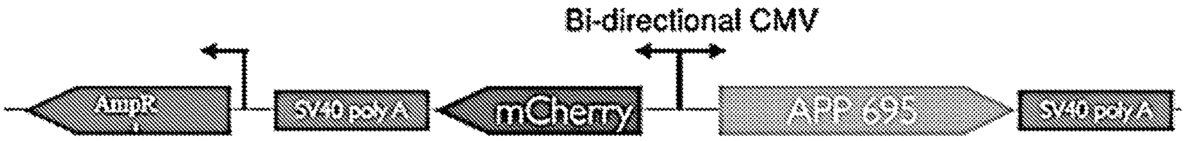
FIG. 6 shows exemplary plasmids encoding the APP695 isoform that each independently comprise a potential mutation, listed in TABLE 1, for use in expressing a mutant APPs in cells. The bi-directional CMV promoter can drive expression of mCherry and APP 695 from both sides of the promoter

Exemplary portions of plasmid sequences that each comprise a mutation that generates an APP polypeptide with the mutations listed in TABLE 2 are shown in FIG. 6. All plasmids containing these mutant APP gene sequences in the CDS1 region (bases 647 to 2734) of SEQ ID NO: 56-70, instead of the WT APP695 isoform are listed in the CDS1 of TABLE 12 in SEQ ID NO: 55. These sequences are listed in TABLE 13.

TABLE 13

Human Mutant APP mRNA Isoform Sequences

| SEQ ID NO | Mutation | mRNA Sequence |
|---|---|---|
| 56 | K670R | AUGCUCCCUGGACUUGCUUUGCUGCUUUUGGCAG |
| | | CCUGGACUGCUCGAGCACUCGAGGUCCCAACGGA |
| | | UGGAAACGCGGGUCUUUUGGCAGAGCCUCAAAUA |
| | | GCAAUGUUUUGCGGAAGACUCAACAUGCAUAUGAA |
| | | CGUUCAGAAUGGGAAAUGGACUCCGACCCCAGU |
| | | GGUACGAAGACAUGUAUUGACACAAAGGAGGGAA |
| | | UACUCCAGUACUGCCAGGAAGUGUACCCGGAGCU |
| | | UCAGAUUACGAAUGUGGUAGAGGCUAAUCAACCC |
| | | GUAACUAUCCAAAAUUGGUGUAAGAGAGGCAGGA |
| | | AGCAAUGCAAGACUCAUCCUCAUUUCGUAAUUCCG |
| | | UAUCGAUGUUUGGUGGGAGAAUUUGUCUCUGACG |
| | | CAUUGCUUGUUCCUGACAAGUGUAAGUUUCUUCAC |
| | | CAGGAACGCAUGGACGUGUGCGAGACACACUUGC |
| | | ACUGGCAUACCGUUGCGAAGGAGACGUGUUCCGA |
| | | AAAGAGUACAAAUCUCCAUGACUACGGCAUGUUGC |
| | | UCCCGUGCGGAAUAGAUAAGUUCCGAGGCGUGGA |
| | | GUUUGUAUGCUGUCCGCUGGCAGAGGAGAGCGAU |
| | | AAUGUCGAUUCCGCAGAUGCCGAAGAGGACGACA |
| | | GCGACGUCUGGUGGGGAGGAGCGGACACUGAUUA |
| | | CGCUGAUGGUAGUGAGGACAAAGUAGUCGAGGUG |
| | | GCAGAAGAAGAAGAAGUGGCGGAGGUUGAAGAAG |
| | | AAGAGGCAGACGAUGACGAAGACGAUGAGGACGG |
| | | UGAUGAGGUAGAAGAAGAAGCGGAAGAACCGUAC |
| | | GAAGAAGCUACGGAACGCACUACAAGUAUUGCUAC |
| | | CACUACAACCACUACAACCGAAUCAGUUGAGGAAG |
| | | UGGUGCGAGUCCCCACUACGGCUGCCAGUACACC |
| | | GGAUGCCGUCGACAAAUACCUGGAGACUCCUGGC |
| | | GACGAAAACGAACAUGCUCAUUUCCAGAAGGCGAA |
| | | GGAACGCCUCGAAGCAAAGCACAGAGAGAGAAUG |
| | | UCACAGGUAAUGAGGGAAUGGGAGGAGGCGGAAC |
| | | GCCAAGCAAAGAACCUGCCUAAAGCGGACAAGAA |
| | | GGCAGUUAUCCAACAUUUCCAAGAGAAAGUGGAG |
| | | AGUCUCGAACAGGAGGCAGCGAACGAGAGGCAAC |
| | | AAUUGGUAGAAACGCACAUGGCGAGGGUGGAAGC |
| | | UAUGCUCAAUGACCGAAGACGACUUGCCUUGGAAA |
| | | AUUACAUUACUGCCCUUCAAGCCGUCCCACCGCGC |
| | | CCACGCCAUGUCUUUAACAUGCUUAAGAAGUAUGU |
| | | UCGAGCUGAACAGAAGGAUCGGCAACACACCCUG |
| | | AAACACUUCGAACAUGUCAGAAUGGUUGACCCGAA |
| | | GAAGGCUGCACAGAUUCGAAGUCAAGUUAUGACC |
| | | CAUUUGAGGGUAAUAUAUGAGAGAAUGAACCAAA |
| | | GUCUGAGCCUUCUCUACAAUGUCCCCGCUGUGGCC |
| | | GAGGAAAUUCAGGACGAAGUCGAUGAGCUCCUGC |
| | | AAAAGGAGCAGAACUACUCUGACGAUGUACUUGCU |
| | | AAUAUGAUUUCAGAGCCAAGGAUCAGUUAUGGAAA |
| | | CGACGCCCUGAUGCCUAGUCUUACCGAAACCAAGA |
| | | CUACGGUAGAACUCCUUCCCGUUAACGGAGAGUUC |
| | | AGCUUGGACGACCUUCAGCCUUGGCACUCAUUCG |
| | | GAGCUGAUUCCGUACCAGCCAAUACGGAGAAUGA |
| | | AGUAGAGCCCGUAGACGCAAGACCUGCAGCGGAC |
| | | AGAGGGCUGACGACGAGACCCGGUAGCGGUUUGA |
| | | CAAAUAUCAAGACGGAGGAGAUCUCUGAAGUGAG |
| | | GAUGGAUGCAGAAUUCCGACAUGACUCAGGAUAU |
| | | GAAGUUCAUCAUCAAAAAUUGGUGUUCUUUGCAGA |
| | | AGAUGUCGGUUCUAACAAGGGUGCUAUCAUAGGC |
| | | CUUAUGGUGGGUGGCGUCGUGAUUGCGACCGUGA |
| | | UAGUUAUUACGCUUGUCAUGCUGAAGAAGAAACAG |
| | | UAUACGUCCAUCCAUCACGGUGUGGUAGAGGUAG |
| | | AUGCGGCCGUAACUCCCGAAGAGCGCCAUCUUUCU |
| | | AAGAUGCAGCAGAAUGGAUACGAGAACCCCACGU |
| | | ACAAAUUCUUUGAGCAAAUGCAAAACUGA |
| 57 | K670E | AUGCUCCCUGGACUUGCUUUGCUGCUUUUGGCAG |
| | | CCUGGACUGCUCGAGCACUCGAGGUCCCAACGGA |
| | | UGGAAACGCGGGUCUUUUGGCAGAGCCUCAAAUA |
| | | GCAAUGUUUUGCGGAAGACUCAACAUGCAUAUGAA |
| | | CGUUCAGAAUGGGAAAUGGACUCCGACCCCAGU |
| | | GGUACGAAGACAUGUAUUGACACAAAGGAGGGAA |
| | | UACUCCAGUACUGCCAGGAAGUGUACCCGGAGCU |
| | | UCAGAUUACGAAUGUGGUAGAGGCUAAUCAACCC |
| | | GUAACUAUCCAAAAUUGGUGUAAGAGAGGCAGGA |
| | | AGCAAUGCAAGACUCAUCCUCAUUUCGUAAUUCCG |
| | | UAUCGAUGUUUGGUGGGAGAAUUUGUCUCUGACG |
| | | CAUUGCUUGUUCCUGACAAGUGUAAGUUUCUUCAC |
| | | CAGGAACGCAUGGACGUGUGCGAGACACACUUGC |
| | | ACUGGCAUACCGUUGCGAAGGAGACGUGUUCCGA |
| | | AAAGAGUACAAAUCUCCAUGACUACGGCAUGUUGC |
| | | UCCCGUGCGGAAUAGAUAAGUUCCGAGGCGUGGA |
| | | GUUUGUAUGCUGUCCGCUGGCAGAGGAGAGCGAU |
| | | AAUGUCGAUUCCGCAGAUGCCGAAGAGGACGACA |
| | | GCGACGUCUGGUGGGGAGGAGCGGACACUGAUUA |
| | | CGCUGAUGGUAGUGAGGACAAAGUAGUCGAGGUG |
| | | GCAGAAGAAGAAGAAGUGGCGGAGGUUGAAGAAG |
| | | AAGAGGCAGACGAUGACGAAGACGAUGAGGACGG |
| | | UGAUGAGGUAGAAGAAGAAGCGGAAGAACCGUAC |
| | | GAAGAAGCUACGGAACGCACUACAAGUAUUGCUAC |
| | | CACUACAACCACUACAACCGAAUCAGUUGAGGAAG |
| | | UGGUGCGAGUCCCCACUACGGCUGCCAGUACACC |
| | | GGAUGCCGUCGACAAAUACCUGGAGACUCCUGGC |
| | | GACGAAAACGAACAUGCUCAUUUCCAGAAGGCGAA |
| | | GGAACGCCUCGAAGCAAAGCACAGAGAGAGAAUG |
| | | UCACAGGUAAUGAGGGAAUGGGAGGAGGCGGAAC |
| | | GCCAAGCAAAGAACCUGCCUAAAGCGGACAAGAA |
| | | GGCAGUUAUCCAACAUUUCCAAGAGAAAGUGGAG |
| | | AGUCUCGAACAGGAGGCAGCGAACGAGAGGCAAC |
| | | AAUUGGUAGAAACGCACAUGGCGAGGGUGGAAGC |
| | | UAUGCUCAAUGACCGAAGACGACUUGCCUUGGAAA |
| | | AUUACAUUACUGCCCUUCAAGCCGUCCCACCGCGC |
| | | CCACGCCAUGUCUUUAACAUGCUUAAGAAGUAUGU |
| | | UCGAGCUGAACAGAAGGAUCGGCAACACACCCUG |
| | | AAACACUUCGAACAUGUCAGAAUGGUUGACCCGAA |
| | | GAAGGCUGCACAGAUUCGAAGUCAAGUUAUGACC |
| | | CAUUUGAGGGUAAUAUAUGAGAGAAUGAACCAAA |
| | | GUCUGAGCCUUCUCUACAAUGUCCCCGCUGUGGCC |
| | | GAGGAAAUUCAGGACGAAGUCGAUGAGCUCCUGC |
| | | AAAAGGAGCAGAACUACUCUGACGAUGUACUUGCU |
| | | AAUAUGAUUUCAGAGCCAAGGAUCAGUUAUGGAAA |
| | | CGACGCCCUGAUGCCUAGUCUUACCGAAACCAAGA |
| | | CUACGGUAGAACUCCUUCCCGUUAACGGAGAGUUC |
| | | AGCUUGGACGACCUUCAGCCUUGGCACUCAUUCG |
| | | GAGCUGAUUCCGUACCAGCCAAUACGGAGAAUGA |
| | | AGUAGAGCCCGUAGACGCAAGACCUGCAGCGGAC |
| | | AGAGGGCUGACGACGAGACCCGGUAGCGGUUUGA |
| | | CAAAUAUCAAGACGGAGGAGAUCUCUGAAGUGGA |
| | | GAUGGAUGCAGAAUUCCGACAUGACUCAGGAUAU |
| | | GAAGUUCAUCAUCAAAAAUUGGUGUUCUUUGCAGA |
| | | AGAUGUCGGUUCUAACAAGGGUGCUAUCAUAGGC |
| | | CUUAUGGUGGGUGGCGUCGUGAUUGCGACCGUGA |
| | | UAGUUAUUACGCUUGUCAUGCUGAAGAAGAAACAG |
| | | UAUACGUCCAUCCAUCACGGUGUGGUAGAGGUAG |
| | | AUGCGGCCGUAACUCCCGAAGAGCGCCAUCUUUCU |
| | | AAGAUGCAGCAGAAUGGAUACGAGAACCCCACGU |
| | | ACAAAUUCUUUGAGCAAAUGCAAAACUGA |
| 58 | K670G | AUGCUCCCUGGACUUGCUUUGCUGCUUUUGGCAG |
| | | CCUGGACUGCUCGAGCACUCGAGGUCCCAACGGA |
| | | UGGAAACGCGGGUCUUUUGGCAGAGCCUCAAAUA |
| | | GCAAUGUUUUGCGGAAGACUCAACAUGCAUAUGAA |
| | | CGUUCAGAAUGGGAAAUGGACUCCGACCCCAGU |
| | | GGUACGAAGACAUGUAUUGACACAAAGGAGGGAA |
| | | UACUCCAGUACUGCCAGGAAGUGUACCCGGAGCU |
| | | UCAGAUUACGAAUGUGGUAGAGGCUAAUCAACCC |
| | | GUAACUAUCCAAAAUUGGUGUAAGAGAGGCAGGA |
| | | AGCAAUGCAAGACUCAUCCUCAUUUCGUAAUUCCG |
| | | UAUCGAUGUUUGGUGGGAGAAUUUGUCUCUGACG |
| | | CAUUGCUUGUUCCUGACAAGUGUAAGUUUCUUCAC |
| | | CAGGAACGCAUGGACGUGUGCGAGACACACUUGC |
| | | ACUGGCAUACCGUUGCGAAGGAGACGUGUUCCGA |
| | | AAAGAGUACAAAUCUCCAUGACUACGGCAUGUUGC |
| | | UCCCGUGCGGAAUAGAUAAGUUCCGAGGCGUGGA |
| | | GUUUGUAUGCUGUCCGCUGGCAGAGGAGAGCGAU |
| | | AAUGUCGAUUCCGCAGAUGCCGAAGAGGACGACA |
| | | GCGACGUCUGGUGGGGAGGAGCGGACACUGAUUA |
| | | CGCUGAUGGUAGUGAGGACAAAGUAGUCGAGGUG |
| | | GCAGAAGAAGAAGAAGUGGCGGAGGUUGAAGAAG |
| | | AAGAGGCAGACGAUGACGAAGACGAUGAGGACGG |
| | | UGAUGAGGUAGAAGAAGAAGCGGAAGAACCGUAC |
| | | GAAGAAGCUACGGAACGCACUACAAGUAUUGCUAC |
| | | CACUACAACCACUACAACCGAAUCAGUUGAGGAAG |
| | | UGGUGCGAGUCCCCACUACGGCUGCCAGUACACC |

TABLE 13-continued

Human Mutant APP mRNA Isoform Sequences

| SEQ ID NO | Mutation | mRNA Sequence |
|---|---|---|
| | | GGAUGCCGUCGACAAAUACCUGGAGACUCCUGGC<br>GACGAAAACGAACAUGCUCAUUUCCAGAAGGCGAA<br>GGAACGCCUCGAAGCAAAGCACAGAGAGAGAAUG<br>UCACAGGUAAUGAGGGAAUGGGAGGAGGCGGAAC<br>GCCAAGCAAAGAACCUGCCUAAAGCGGACAAGAA<br>GGCAGUUAUCCAACAUUUCCAAGAGAAAGUGGAG<br>AGUCUCGAACAGGAGGCAGCGAACGAGAGGCAAC<br>AAUUGGUAGAAACGCACAUGGCGAGGGUGGAAGC<br>UAUGCUCAAUGACCGAAGACGACUUGCCUUGGAAA<br>AUUACAUUACUGCCCUUCAAGCCGUCCCACCGCGC<br>CCACGCCAUGUCUUUAACAUGCUUAAGAAGUAUGU<br>UCGAGCUGAACAGAAGGAUCGGCAACACACCCUG<br>AAACACUUCGAACAUGUCAGAAUGGUUGACCCGAA<br>GAAGGCUGCACAGAUUCGAAGUCAAGUUAUGACC<br>CAUUUGAGGGUAAUAUAUGAGAGAAUGAACCAAA<br>GUCUGAGCCUUCUCUACAAUGUCCCCGCUGUGGCC<br>GAGGAAAUUCAGGACGAAGUCGAUGAGCUCCUGC<br>AAAAGGAGCAGAACUACUCUGACGAUGUACUUGCU<br>AAUAUGAUUUCAGAGCCAAGGAUCAGUUAUGGAAA<br>CGACGCCCUGAUGCCUAGUCUUACCGAAACCAAGA<br>CUACGGUAGAACUCCUUCCCGUUAACGGAGAGUUC<br>AGCUUGGACGACCUUCAGCCUUGGCACUCAUUCG<br>GAGCUGAUUCCGUACCAGCCAAUACGGAGAAUGA<br>AGUAGAGCCCGUAGACGCAAGACCUGCAGCGGAC<br>AGAGGGCUGACGACGAGACCCGGUAGCGGUUUGA<br>CAAAUAUCAAGACGGAGGAGAUCUCUGAAGUGGG<br>GAUGGAUGCAGAAUUCCGACAUGACUCAGGAUAU<br>GAAGUUCAUCAUCAAAAAUUGGUGUUCUUUGCAGA<br>AGAUGUCGGUUCUAACAAGGGUGCUAUCAUAGGC<br>CUUAUGGUGGGUGGCGUCGUGAUUGCGACCGUGA<br>UAGUUAUUACGCUUGUCAUGCUGAAGAAGAAACAG<br>UAUACGUCCAUCCAUCACGGUGUGGUAGAGGUAG<br>AUGCGGCCGUAACUCCCGAAGAGCGCCAUCUUUCU<br>AAGAUGCAGCAGAAUGGAUACGAGAACCCCACGU<br>ACAAAUUCUUUGAGCAAAUGCAAAACUGA |
| 59 | K670R + M671V | AUGCUCCCUGGACUUGCUUUGCUGCUUUUGGCAG<br>CCUGGACUGCUCGAGCACUCGAGGUCCCAACGGA<br>UGGAAACGCGGGUCUUUUGGCAGAGCCUCAAAUA<br>GCAAUGUUUUGCGGAAGACUCAACAUGCAUAUGAA<br>CGUUCAGAAUGGGAAAUGGGACUCCGACCCCAGU<br>GGUACGAAGACAUGUAUUGACACAAAGGAGGGAA<br>UACUCCAGUACUGCCAGGAAGUGUACCCGGAGCU<br>UCAGAUUACGAAUGUGGUAGAGGCUAAUCAACCC<br>GUAACUAUCCAAAAUUGGUGUAAGAGAGGCAGGA<br>AGCAAUGCAAGACUCAUCCUCAUUUCGUAAUUCCG<br>UAUCGAUGUUUGGUGGGAGAAUUUGUCUCUGACG<br>CAUUGCUUGUUCCUGACAAGUGUAAGUUUCUUCAC<br>CAGGAACGCAUGGACGUGUGCGAGACACACUUGC<br>ACUGGCAUACCGUUGCGAAGGAGACGUGUUCCGA<br>AAAGAGUACAAAUCUCCAUGACUACGGCAUGUUGC<br>UCCCGUGCGGAAUAGAUAAGUUCCGAGGCGUGGA<br>GUUUGUAUGCUGUCCGCUGGCAGAGGAGAGCGAU<br>AAUGUCGAUUCCGCAGAUGCCGAAGAGGACGACA<br>GCGACGUCUGGUGGGGAGGAGCGGACACUGAUUA<br>CGCUGAUGGUAGUGAGGACAAAGUAGUCGAGGUG<br>GCAGAAGAAGAAGAAGUGGCGGAGGUUGAAGAAG<br>AAGAGGCAGACGAUGACGAAGACGAUGAGGACGG<br>UGAUGAGGUAGAAGAAGAAGCGGAAGAACCGUAC<br>GAAGAAGCUACGGAACGCACUACAAGUAUUGCUAC<br>CACUACAACCACUACAACCGAAUCAGUUGAGGAAG<br>UGGUGCGAGUCCCCACUACGGCUGCCAGUACACC<br>GGAUGCCGUCGACAAAUACCUGGAGACUCCUGGC<br>GACGAAAACGAACAUGCUCAUUUCCAGAAGGCGAA<br>GGAACGCCUCGAAGCAAAGCACAGAGAGAGAAUG<br>UCACAGGUAAUGAGGGAAUGGGAGGAGGCGGAAC<br>GCCAAGCAAAGAACCUGCCUAAAGCGGACAAGAA<br>GGCAGUUAUCCAACAUUUCCAAGAGAAAGUGGAG<br>AGUCUCGAACAGGAGGCAGCGAACGAGAGGCAAC<br>AAUUGGUAGAAACGCACAUGGCGAGGGUGGAAGC<br>UAUGCUCAAUGACCGAAGACGACUUGCCUUGGAAA<br>AUUACAUUACUGCCCUUCAAGCCGUCCCACCGCGC<br>CCACGCCAUGUCUUUAACAUGCUUAAGAAGUAUGU<br>UCGAGCUGAACAGAAGGAUCGGCAACACACCCUG<br>AAACACUUCGAACAUGUCAGAAUGGUUGACCCGAA<br>GAAGGCUGCACAGAUUCGAAGUCAAGUUAUGACC<br>CAUUUGAGGGUAAUAUAUGAGAGAAUGAACCAAA<br>GUCUGAGCCUUCUCUACAAUGUCCCCGCUGUGGCC<br>GAGGAAAUUCAGGACGAAGUCGAUGAGCUCCUGC<br>AAAAGGAGCAGAACUACUCUGACGAUGUACUUGCU<br>AAUAUGAUUUCAGAGCCAAGGAUCAGUUAUGGAAA<br>CGACGCCCUGAUGCCUAGUCUUACCGAAACCAAGA<br>CUACGGUAGAACUCCUUCCCGUUAACGGAGAGUUC<br>AGCUUGGACGACCUUCAGCCUUGGCACUCAUUCG<br>GAGCUGAUUCCGUACCAGCCAAUACGGAGAAUGA<br>AGUAGAGCCCGUAGACGCAAGACCUGCAGCGGAC<br>AGAGGGCUGACGACGAGACCCGGUAGCGGUUUGA<br>CAAAUAUCAAGACGGAGGAGAUCUCUGAAGUGAG<br>GGUGGAUGCAGAAUUCCGACAUGACUCAGGAUAU<br>GAAGUUCAUCAUCAAAAAUUGGUGUUCUUUGCAGA<br>AGAUGUCGGUUCUAACAAGGGUGCUAUCAUAGGC<br>CUUAUGGUGGGUGGCGUCGUGAUUGCGACCGUGA<br>UAGUUAUUACGCUUGUCAUGCUGAAGAAGAAACAG<br>UAUACGUCCAUCCAUCACGGUGUGGUAGAGGUAG<br>AUGCGGCCGUAACUCCCGAAGAGCGCCAUCUUUCU<br>AAGAUGCAGCAGAAUGGAUACGAGAACCCCACGU<br>ACAAAUUCUUUGAGCAAAUGCAAAACUGA |
| 60 | K670E + M671V | AUGCUCCCUGGACUUGCUUUGCUGCUUUUGGCAG<br>CCUGGACUGCUCGAGCACUCGAGGUCCCAACGGA<br>UGGAAACGCGGGUCUUUUGGCAGAGCCUCAAAUA<br>GCAAUGUUUUGCGGAAGACUCAACAUGCAUAUGAA<br>CGUUCAGAAUGGGAAAUGGGACUCCGACCCCAGU<br>GGUACGAAGACAUGUAUUGACACAAAGGAGGGAA<br>UACUCCAGUACUGCCAGGAAGUGUACCCGGAGCU<br>UCAGAUUACGAAUGUGGUAGAGGCUAAUCAACCC<br>GUAACUAUCCAAAAUUGGUGUAAGAGAGGCAGGA<br>AGCAAUGCAAGACUCAUCCUCAUUUCGUAAUUCCG<br>UAUCGAUGUUUGGUGGGAGAAUUUGUCUCUGACG<br>CAUUGCUUGUUCCUGACAAGUGUAAGUUUCUUCAC<br>CAGGAACGCAUGGACGUGUGCGAGACACACUUGC<br>ACUGGCAUACCGUUGCGAAGGAGACGUGUUCCGA<br>AAAGAGUACAAAUCUCCAUGACUACGGCAUGUUGC<br>UCCCGUGCGGAAUAGAUAAGUUCCGAGGCGUGGA<br>GUUUGUAUGCUGUCCGCUGGCAGAGGAGAGCGAU<br>AAUGUCGAUUCCGCAGAUGCCGAAGAGGACGACA<br>GCGACGUCUGGUGGGGAGGAGCGGACACUGAUUA<br>CGCUGAUGGUAGUGAGGACAAAGUAGUCGAGGUG<br>GCAGAAGAAGAAGAAGUGGCGGAGGUUGAAGAAG<br>AAGAGGCAGACGAUGACGAAGACGAUGAGGACGG<br>UGAUGAGGUAGAAGAAGAAGCGGAAGAACCGUAC<br>GAAGAAGCUACGGAACGCACUACAAGUAUUGCUAC<br>CACUACAACCACUACAACCGAAUCAGUUGAGGAAG<br>UGGUGCGAGUCCCCACUACGGCUGCCAGUACACC<br>GGAUGCCGUCGACAAAUACCUGGAGACUCCUGGC<br>GACGAAAACGAACAUGCUCAUUUCCAGAAGGCGAA<br>GGAACGCCUCGAAGCAAAGCACAGAGAGAGAAUG<br>UCACAGGUAAUGAGGGAAUGGGAGGAGGCGGAAC<br>GCCAAGCAAAGAACCUGCCUAAAGCGGACAAGAA<br>GGCAGUUAUCCAACAUUUCCAAGAGAAAGUGGAG<br>AGUCUCGAACAGGAGGCAGCGAACGAGAGGCAAC<br>AAUUGGUAGAAACGCACAUGGCGAGGGUGGAAGC<br>UAUGCUCAAUGACCGAAGACGACUUGCCUUGGAAA<br>AUUACAUUACUGCCCUUCAAGCCGUCCCACCGCGC<br>CCACGCCAUGUCUUUAACAUGCUUAAGAAGUAUGU<br>UCGAGCUGAACAGAAGGAUCGGCAACACACCCUG<br>AAACACUUCGAACAUGUCAGAAUGGUUGACCCGAA<br>GAAGGCUGCACAGAUUCGAAGUCAAGUUAUGACC<br>CAUUUGAGGGUAAUAUAUGAGAGAAUGAACCAAA<br>GUCUGAGCCUUCUCUACAAUGUCCCCGCUGUGGCC<br>GAGGAAAUUCAGGACGAAGUCGAUGAGCUCCUGC<br>AAAAGGAGCAGAACUACUCUGACGAUGUACUUGCU<br>AAUAUGAUUUCAGAGCCAAGGAUCAGUUAUGGAAA<br>CGACGCCCUGAUGCCUAGUCUUACCGAAACCAAGA<br>CUACGGUAGAACUCCUUCCCGUUAACGGAGAGUUC<br>AGCUUGGACGACCUUCAGCCUUGGCACUCAUUCG<br>GAGCUGAUUCCGUACCAGCCAAUACGGAGAAUGA<br>AGUAGAGCCCGUAGACGCAAGACCUGCAGCGGAC<br>AGAGGGCUGACGACGAGACCCGGUAGCGGUUUGA<br>CAAAUAUCAAGACGGAGGAGAUCUCUGAAGUGGA |

TABLE 13-continued

Human Mutant APP mRNA Isoform Sequences

| SEQ ID NO | Mutation | mRNA Sequence |
|---|---|---|
| | | GGUGGAUGCAGAAUUCCGACAUGACUCAGGAUAU<br>GAAGUUCAUCAUCAAAAAUUGGUGUUCUUUGCAGA<br>AGAUGUCGGUUCUAACAAGGGUGCUAUCAUAGGC<br>CUUAUGGUGGGUGGCGUCGUGAUUGCGACCGUGA<br>UAGUUAUUACGCUUGUCAUGCUGAAGAAGAAACAG<br>UAUACGUCCAUCCAUCACGGUGUGGUAGAGGUAG<br>AUGCGGCCGUAACUCCCGAAGAGCGCCAUCUUUCU<br>AAGAUGCAGCAGAAUGGAUACGAGAACCCCACGU<br>ACAAAUUCUUUGAGCAAAUGCAAAACUGA |
| 61 | K670G + M671V | AUGCUCCCUGGACUUGCUUUGCUGCUUUUGGCAG<br>CCUGGACUGCUCGAGCACUCGAGGUCCCAACGGA<br>UGGAAACGCGGGUCUUUUGGCAGAGCCUCAAAUA<br>GCAAUGUUUUGCGGAAGACUCAACAUGCAUAUGAA<br>CGUUCAGAAUGGGAAAUGGGACUCCGACCCCAGU<br>GGUACGAAGACAUGUAUUGACACAAAGGAGGGAA<br>UACUCCAGUACUGCCAGGAAGUGUACCCGGAGCU<br>UCAGAUUACGAAUGUGGUAGAGGCUAAUCAACCC<br>GUAACUAUCCAAAAUUGGUGUAAGAGAGGCAGGA<br>AGCAAUGCAAGACUCAUCCUCAUUUCGUAAUUCCG<br>UAUCGAUGUUUGGUGGGAGAAUUUGUCUCUGACG<br>CAUUGCUUGUUCCUGACAAGUGUAAGUUUCUUCAC<br>CAGGAACGCAUGGACGUGUGCGAGACACACUUGC<br>ACUGGCAUACCGUUGCGAAGGAGACGUGUUCCGA<br>AAAGAGUACAAAUCUCCAUGACUACGGCAUGUUGC<br>UCCCGUGCGGAAUAGAUAAGUUCCGAGGCGUGGA<br>GUUUGUAUGCUGUCCGCUGGCAGAGGAGAGCGAU<br>AAUGUCGAUUCCGCAGAUGCCGAAGAGGACGACA<br>GCGACGUCUGGUGGGGAGGAGCGGACACUGAUUA<br>CGCUGAUGGUAGUGAGGACAAAGUAGUCGAGGUG<br>GCAGAAGAAGAAGAAGUGGCGGAGGUUGAAGAAG<br>AAGAGGCAGACGAUGACGAAGACGAUGAGGACGG<br>UGAUGAGGUAGAAGAAGAAGCGGAAGAACCGUAC<br>GAAGAAGCUACGGAACGCACUACAAGUAUUGCUAC<br>CACUACAACCACUACAACCGAAUCAGUUGAGGAAG<br>UGGUGCGAGUCCCCACUACGGCUGCCAGUACACC<br>GGAUGCCGUCGACAAAUACCUGGAGACUCCUGGC<br>GACGAAAACGAACAUGCUCAUUUCCAGAAGGCGAA<br>GGAACGCCUCGAAGCAAAGCACAGAGAGAGAAUG<br>UCACAGGUAAUGAGGGAAUGGGAGGAGGCGGAAC<br>GCCAAGCAAAGAACCUGCCUAAAGCGGACAAGAA<br>GGCAGUUAUCCAACAUUUCCAAGAGAAAGUGGAG<br>AGUCUCGAACAGGAGGCAGCGAACGAGAGGCAAC<br>AAUUGGUAGAAACGCACAUGGCGAGGGUGGAAGC<br>UAUGCUCAAUGACCGAAGACGACUUGCCUUGGAAA<br>AUUACAUUACUGCCCUUCAAGCCGUCCCACCGCGC<br>CCACGCCAUGUCUUUAACAUGCUUAAGAAGUAUGU<br>UCGAGCUGAACAGAAGGAUCGGCAACACACCCUG<br>AAACACUUCGAACAUGUCAGAAUGGUUGACCCGAA<br>GAAGGCUGCACAGAUUCGAAGUCAAGUUAUGACC<br>CAUUUGAGGGUAAUAUAUGAGAGAAUGAACCAAA<br>GUCUGAGCCUUCUCUACAAUGUCCCCGCUGUGGCC<br>GAGGAAAUUCAGGACGAAGUCGAUGAGCUCCUGC<br>AAAAGGAGCAGAACUACUCUGACGAUGUACUUGCU<br>AAUAUGAUUUCAGAGCCAAGGAUCAGUUAUGGAAA<br>CGACGCCCUGAUGCCUAGUCUUACCGAAACCAAGA<br>CUACGGUAGAACUCCUUCCCGUUAACGGAGAGUUC<br>AGCUUGGACGACCUUCAGCCUUGGCACUCAUUCG<br>GAGCUGAUUCCGUACCAGCCAAUACGGAGAAUGA<br>AGUAGAGCCCGUAGACGCAAGACCUGCAGCGGAC<br>AGAGGGCUGACGACGAGACCCGGUAGCGGUUUGA<br>CAAAUAUCAAGACGGAGGAGAUCUCUGAAGUGGG<br>GGUGGAUGCAGAAUUCCGACAUGACUCAGGAUAU<br>GAAGUUCAUCAUCAAAAAUUGGUGUUCUUUGCAGA<br>AGAUGUCGGUUCUAACAAGGGUGCUAUCAUAGGC<br>CUUAUGGUGGGUGGCGUCGUGAUUGCGACCGUGA<br>UAGUUAUUACGCUUGUCAUGCUGAAGAAGAAACAG<br>UAUACGUCCAUCCAUCACGGUGUGGUAGAGGUAG<br>AUGCGGCCGUAACUCCCGAAGAGCGCCAUCUUUCU<br>AAGAUGCAGCAGAAUGGAUACGAGAACCCCACGU<br>ACAAAUUCUUUGAGCAAAUGCAAAACUGA |
| 62 | M671V | AUGCUCCCUGGACUUGCUUUGCUGCUUUUGGCAG<br>CCUGGACUGCUCGAGCACUCGAGGUCCCAACGGA<br>UGGAAACGCGGGUCUUUUGGCAGAGCCUCAAAUA<br>GCAAUGUUUUGCGGAAGACUCAACAUGCAUAUGAA<br>CGUUCAGAAUGGGAAAUGGGACUCCGACCCCAGU<br>GGUACGAAGACAUGUAUUGACACAAAGGAGGGAA<br>UACUCCAGUACUGCCAGGAAGUGUACCCGGAGCU<br>UCAGAUUACGAAUGUGGUAGAGGCUAAUCAACCC<br>GUAACUAUCCAAAAUUGGUGUAAGAGAGGCAGGA<br>AGCAAUGCAAGACUCAUCCUCAUUUCGUAAUUCCG<br>UAUCGAUGUUUGGUGGGAGAAUUUGUCUCUGACG<br>CAUUGCUUGUUCCUGACAAGUGUAAGUUUCUUCAC<br>CAGGAACGCAUGGACGUGUGCGAGACACACUUGC<br>ACUGGCAUACCGUUGCGAAGGAGACGUGUUCCGA<br>AAAGAGUACAAAUCUCCAUGACUACGGCAUGUUGC<br>UCCCGUGCGGAAUAGAUAAGUUCCGAGGCGUGGA<br>GUUUGUAUGCUGUCCGCUGGCAGAGGAGAGCGAU<br>AAUGUCGAUUCCGCAGAUGCCGAAGAGGACGACA<br>GCGACGUCUGGUGGGGAGGAGCGGACACUGAUUA<br>CGCUGAUGGUAGUGAGGACAAAGUAGUCGAGGUG<br>GCAGAAGAAGAAGAAGUGGCGGAGGUUGAAGAAG<br>AAGAGGCAGACGAUGACGAAGACGAUGAGGACGG<br>UGAUGAGGUAGAAGAAGAAGCGGAAGAACCGUAC<br>GAAGAAGCUACGGAACGCACUACAAGUAUUGCUAC<br>CACUACAACCACUACAACCGAAUCAGUUGAGGAAG<br>UGGUGCGAGUCCCCACUACGGCUGCCAGUACACC<br>GGAUGCCGUCGACAAAUACCUGGAGACUCCUGGC<br>GACGAAAACGAACAUGCUCAUUUCCAGAAGGCGAA<br>GGAACGCCUCGAAGCAAAGCACAGAGAGAGAAUG<br>UCACAGGUAAUGAGGGAAUGGGAGGAGGCGGAAC<br>GCCAAGCAAAGAACCUGCCUAAAGCGGACAAGAA<br>GGCAGUUAUCCAACAUUUCCAAGAGAAAGUGGAG<br>AGUCUCGAACAGGAGGCAGCGAACGAGAGGCAAC<br>AAUUGGUAGAAACGCACAUGGCGAGGGUGGAAGC<br>UAUGCUCAAUGACCGAAGACGACUUGCCUUGGAAA<br>AUUACAUUACUGCCCUUCAAGCCGUCCCACCGCGC<br>CCACGCCAUGUCUUUAACAUGCUUAAGAAGUAUGU<br>UCGAGCUGAACAGAAGGAUCGGCAACACACCCUG<br>AAACACUUCGAACAUGUCAGAAUGGUUGACCCGAA<br>GAAGGCUGCACAGAUUCGAAGUCAAGUUAUGACC<br>CAUUUGAGGGUAAUAUAUGAGAGAAUGAACCAAA<br>GUCUGAGCCUUCUCUACAAUGUCCCCGCUGUGGCC<br>GAGGAAAUUCAGGACGAAGUCGAUGAGCUCCUGC<br>AAAAGGAGCAGAACUACUCUGACGAUGUACUUGCU<br>AAUAUGAUUUCAGAGCCAAGGAUCAGUUAUGGAAA<br>CGACGCCCUGAUGCCUAGUCUUACCGAAACCAAGA<br>CUACGGUAGAACUCCUUCCCGUUAACGGAGAGUUC<br>AGCUUGGACGACCUUCAGCCUUGGCACUCAUUCG<br>GAGCUGAUUCCGUACCAGCCAAUACGGAGAAUGA<br>AGUAGAGCCCGUAGACGCAAGACCUGCAGCGGAC<br>AGAGGGCUGACGACGAGACCCGGUAGCGGUUUGA<br>CAAAUAUCAAGACGGAGGAGAUCUCUGAAGUGAA<br>GGUGGAUGCAGAAUUCCGACAUGACUCAGGAUAU<br>GAAGUUCAUCAUCAAAAAUUGGUGUUCUUUGCAGA<br>AGAUGUCGGUUCUAACAAGGGUGCUAUCAUAGGC<br>CUUAUGGUGGGUGGCGUCGUGAUUGCGACCGUGA<br>UAGUUAUUACGCUUGUCAUGCUGAAGAAGAAACAG<br>UAUACGUCCAUCCAUCACGGUGUGGUAGAGGUAG<br>AUGCGGCCGUAACUCCCGAAGAGCGCCAUCUUUCU<br>AAGAUGCAGCAGAAUGGAUACGAGAACCCCACGU<br>ACAAAUUCUUUGAGCAAAUGCAAAACUGA |
| 63 | D672G | AUGCUCCCUGGACUUGCUUUGCUGCUUUUGGCAG<br>CCUGGACUGCUCGAGCACUCGAGGUCCCAACGGA<br>UGGAAACGCGGGUCUUUUGGCAGAGCCUCAAAUA<br>GCAAUGUUUUGCGGAAGACUCAACAUGCAUAUGAA<br>CGUUCAGAAUGGGAAAUGGGACUCCGACCCCAGU<br>GGUACGAAGACAUGUAUUGACACAAAGGAGGGAA<br>UACUCCAGUACUGCCAGGAAGUGUACCCGGAGCU<br>UCAGAUUACGAAUGUGGUAGAGGCUAAUCAACCC<br>GUAACUAUCCAAAAUUGGUGUAAGAGAGGCAGGA<br>AGCAAUGCAAGACUCAUCCUCAUUUCGUAAUUCCG<br>UAUCGAUGUUUGGUGGGAGAAUUUGUCUCUGACG<br>CAUUGCUUGUUCCUGACAAGUGUAAGUUUCUUCAC<br>CAGGAACGCAUGGACGUGUGCGAGACACACUUGC<br>ACUGGCAUACCGUUGCGAAGGAGACGUGUUCCGA<br>AAAGAGUACAAAUCUCCAUGACUACGGCAUGUUGC<br>UCCCGUGCGGAAUAGAUAAGUUCCGAGGCGUGGA |

TABLE 13-continued

Human Mutant APP mRNA Isoform Sequences

| SEQ ID NO | Mutation | mRNA Sequence |
|---|---|---|
| | | GUUUGUAUGCUGUCCGCUGGCAGAGGAGAGCGAU<br>AAUGUCGAUUCCGCAGAUGCCGAAGAGGACGACA<br>GCGACGUCUGGUGGGGAGGAGCGGACACUGAUUA<br>CGCUGAUGGUAGUGAGGACAAAGUAGUCGAGGUG<br>GCAGAAGAAGAAGAAGUGGCGGAGGUUGAAGAAG<br>AAGAGGCAGACGAUGACGAAGACGAUGAGGACGG<br>UGAUGAGGUAGAAGAAGAAGCGGAAGAACCGUAC<br>GAAGAAGCUACGGAACGCACUACAAGUAUUGCUAC<br>CACUACAACCACUACAACCGAAUCAGUUGAGGAAG<br>UGGUGCGAGUCCCCACUACGGCUGCCAGUACACC<br>GGAUGCCGUCGACAAAUACCUGGAGACUCCUGGC<br>GACGAAAACGAACAUGCUCAUUUCCAGAAGGCGAA<br>GGAACGCCUCGAAGCAAAGCACAGAGAGAGAAUG<br>UCACAGGUAAUGAGGGAAUGGGAGGAGGCGGAAC<br>GCCAAGCAAAGAACCUGCCUAAAGCGGACAAGAA<br>GGCAGUUAUCCAACAUUUCCAAGAGAAAGUGGAG<br>AGUCUCGAACAGGAGGCAGCGAACGAGAGGCAAC<br>AAUUGGUAGAAACGCACAUGGCGAGGGUGGAAGC<br>UAUGCUCAAUGACCGAAGACGACUUGCCUUGGAAA<br>AUUACAUUACUGCCCUUCAAGCCGUCCCACCGCGC<br>CCACGCCAUGUCUUUAACAUGCUUAAGAAGUAUGU<br>UCGAGCUGAACAGAAGGAUCGGCAACACACCCUG<br>AAACACUUCGAACAUGUCAGAAUGGUUGACCCGAA<br>GAAGGCUGCACAGAUUCGAAGUCAAGUUAUGACC<br>CAUUUGAGGGUAAUAUAUGAGAGAAUGAACCAAA<br>GUCUGAGCCUUCUCUACAAUGUCCCCGCUGUGGCC<br>GAGGAAAUUCAGGACGAAGUCGAUGAGCUCCUGC<br>AAAAGGAGCAGAACUACUCUGACGAUGUACUUGCU<br>AAUAUGAUUUCAGAGCCAAGGAUCAGUUAUGGAAA<br>CGACGCCCUGAUGCCUAGUCUUACCGAAACCAAGA<br>CUACGGUAGAACUCCUUCCCGUUAACGGAGAGUUC<br>AGCUUGGACGACCUUCAGCCUUGGCACUCAUUCG<br>GAGCUGAUUCCGUACCAGCCAAUACGGAGAAUGA<br>AGUAGAGCCCGUAGACGCAAGACCUGCAGCGGAC<br>AGAGGGCUGACGACGAGACCCGGUAGCGGUUUGA<br>CAAAUAUCAAGACGGAGGAGAUCUCUGAAGUGAA<br>GAUGGGUGCAGAAUUCCGACAUGACUCAGGAUAU<br>GAAGUUCAUCAUCAAAAAUUGGUGUUCUUUGCAGA<br>AGAUGUCGGUUCUAACAAGGGUGCUAUCAUAGGC<br>CUUAUGGUGGGUGGCGUCGUGAUUGCGACCGUGA<br>UAGUUAUUACGCUUGUCAUGCUGAAGAAGAAACAG<br>UAUACGUCCAUCCAUCACGGUGUGGUAGAGGUAG<br>AUGCGGCCGUAACUCCCGAAGAGCGCCAUCUUUCU<br>AAGAUGCAGCAGAAUGGAUACGAGAACCCCACGU<br>ACAAAUUCUUUGAGCAAAUGCAAAACUGA |
| 64 | A673V | AUGCUCCCUGGACUUGCUUUGCUGCUUUUGGCAG<br>CCUGGACUGCUCGAGCACUCGAGGUCCCAACGGA<br>UGGAAACGCGGGUCUUUUGGCAGAGCCUCAAAUA<br>GCAAUGUUUUGCGGAAGACUCAACAUGCAUAUGAA<br>CGUUCAGAAUGGGAAAUGGGACUCCGACCCCAGU<br>GGUACGAAGACAUGUAUUGACACAAAGGAGGGAA<br>UACUCCAGUACUGCCAGGAAGUGUACCCGGAGCU<br>UCAGAUUACGAAUGUGGUAGAGGCUAAUCAACCC<br>GUAACUAUCCAAAAUUGGUGUAAGAGAGGCAGGA<br>AGCAAUGCAAGACUCAUCCUCAUUUCGUAAUUCCG<br>UAUCGAUGUUUGGUGGGAGAAUUUGUCUCUGACG<br>CAUUGCUUGUUCCUGACAAGUGUAAGUUUCUUCAC<br>CAGGAACGCAUGGACGUGUGCGAGACACACUUGC<br>ACUGGCAUACCGUUGCGAAGGAGACGUGUUCCGA<br>AAAGAGUACAAAUCUCCAUGACUACGGCAUGUUGC<br>UCCCGUGCGGAAUAGAUAAGUUCCGAGGCGUGGA<br>GUUUGUAUGCUGUCCGCUGGCAGAGGAGAGCGAU<br>AAUGUCGAUUCCGCAGAUGCCGAAGAGGACGACA<br>GCGACGUCUGGUGGGGAGGAGCGGACACUGAUUA<br>CGCUGAUGGUAGUGAGGACAAAGUAGUCGAGGUG<br>GCAGAAGAAGAAGAAGUGGCGGAGGUUGAAGAAG<br>AAGAGGCAGACGAUGACGAAGACGAUGAGGACGG<br>UGAUGAGGUAGAAGAAGAAGCGGAAGAACCGUAC<br>GAAGAAGCUACGGAACGCACUACAAGUAUUGCUAC<br>CACUACAACCACUACAACCGAAUCAGUUGAGGAAG<br>UGGUGCGAGUCCCCACUACGGCUGCCAGUACACC<br>GGAUGCCGUCGACAAAUACCUGGAGACUCCUGGC<br>GACGAAAACGAACAUGCUCAUUUCCAGAAGGCGAA<br>GGAACGCCUCGAAGCAAAGCACAGAGAGAGAAUG<br>UCACAGGUAAUGAGGGAAUGGGAGGAGGCGGAAC<br>GCCAAGCAAAGAACCUGCCUAAAGCGGACAAGAA<br>GGCAGUUAUCCAACAUUUCCAAGAGAAAGUGGAG<br>AGUCUCGAACAGGAGGCAGCGAACGAGAGGCAAC<br>AAUUGGUAGAAACGCACAUGGCGAGGGUGGAAGC<br>UAUGCUCAAUGACCGAAGACGACUUGCCUUGGAAA<br>AUUACAUUACUGCCCUUCAAGCCGUCCCACCGCGC<br>CCACGCCAUGUCUUUAACAUGCUUAAGAAGUAUGU<br>UCGAGCUGAACAGAAGGAUCGGCAACACACCCUG<br>AAACACUUCGAACAUGUCAGAAUGGUUGACCCGAA<br>GAAGGCUGCACAGAUUCGAAGUCAAGUUAUGACC<br>CAUUUGAGGGUAAUAUAUGAGAGAAUGAACCAAA<br>GUCUGAGCCUUCUCUACAAUGUCCCCGCUGUGGCC<br>GAGGAAAUUCAGGACGAAGUCGAUGAGCUCCUGC<br>AAAAGGAGCAGAACUACUCUGACGAUGUACUUGCU<br>AAUAUGAUUUCAGAGCCAAGGAUCAGUUAUGGAAA<br>CGACGCCCUGAUGCCUAGUCUUACCGAAACCAAGA<br>CUACGGUAGAACUCCUUCCCGUUAACGGAGAGUUC<br>AGCUUGGACGACCUUCAGCCUUGGCACUCAUUCG<br>GAGCUGAUUCCGUACCAGCCAAUACGGAGAAUGA<br>AGUAGAGCCCGUAGACGCAAGACCUGCAGCGGAC<br>AGAGGGCUGACGACGAGACCCGGUAGCGGUUUGA<br>CAAAUAUCAAGACGGAGGAGAUCUCUGAAGUGAA<br>GAUGGAUGUGGAAUUCCGACAUGACUCAGGAUAU<br>GAAGUUCAUCAUCAAAAAUUGGUGUUCUUUGCAGA<br>AGAUGUCGGUUCUAACAAGGGUGCUAUCAUAGGC<br>CUUAUGGUGGGUGGCGUCGUGAUUGCGACCGUGA<br>UAGUUAUUACGCUUGUCAUGCUGAAGAAGAAACAG<br>UAUACGUCCAUCCAUCACGGUGUGGUAGAGGUAG<br>AUGCGGCCGUAACUCCCGAAGAGCGCCAUCUUUCU<br>AAGAUGCAGCAGAAUGGAUACGAGAACCCCACGU<br>ACAAAUUCUUUGAGCAAAUGCAAAACUGA |
| 65 | A673T | AUGCUCCCUGGACUUGCUUUGCUGCUUUUGGCAG<br>CCUGGACUGCUCGAGCACUCGAGGUCCCAACGGA<br>UGGAAACGCGGGUCUUUUGGCAGAGCCUCAAAUA<br>GCAAUGUUUUGCGGAAGACUCAACAUGCAUAUGAA<br>CGUUCAGAAUGGGAAAUGGGACUCCGACCCCAGU<br>GGUACGAAGACAUGUAUUGACACAAAGGAGGGAA<br>UACUCCAGUACUGCCAGGAAGUGUACCCGGAGCU<br>UCAGAUUACGAAUGUGGUAGAGGCUAAUCAACCC<br>GUAACUAUCCAAAAUUGGUGUAAGAGAGGCAGGA<br>AGCAAUGCAAGACUCAUCCUCAUUUCGUAAUUCCG<br>UAUCGAUGUUUGGUGGGAGAAUUUGUCUCUGACG<br>CAUUGCUUGUUCCUGACAAGUGUAAGUUUCUUCAC<br>CAGGAACGCAUGGACGUGUGCGAGACACACUUGC<br>ACUGGCAUACCGUUGCGAAGGAGACGUGUUCCGA<br>AAAGAGUACAAAUCUCCAUGACUACGGCAUGUUGC<br>UCCCGUGCGGAAUAGAUAAGUUCCGAGGCGUGGA<br>GUUUGUAUGCUGUCCGCUGGCAGAGGAGAGCGAU<br>AAUGUCGAUUCCGCAGAUGCCGAAGAGGACGACA<br>GCGACGUCUGGUGGGGAGGAGCGGACACUGAUUA<br>CGCUGAUGGUAGUGAGGACAAAGUAGUCGAGGUG<br>GCAGAAGAAGAAGAAGUGGCGGAGGUUGAAGAAG<br>AAGAGGCAGACGAUGACGAAGACGAUGAGGACGG<br>UGAUGAGGUAGAAGAAGAAGCGGAAGAACCGUAC<br>GAAGAAGCUACGGAACGCACUACAAGUAUUGCUAC<br>CACUACAACCACUACAACCGAAUCAGUUGAGGAAG<br>UGGUGCGAGUCCCCACUACGGCUGCCAGUACACC<br>GGAUGCCGUCGACAAAUACCUGGAGACUCCUGGC<br>GACGAAAACGAACAUGCUCAUUUCCAGAAGGCGAA<br>GGAACGCCUCGAAGCAAAGCACAGAGAGAGAAUG<br>UCACAGGUAAUGAGGGAAUGGGAGGAGGCGGAAC<br>GCCAAGCAAAGAACCUGCCUAAAGCGGACAAGAA<br>GGCAGUUAUCCAACAUUUCCAAGAGAAAGUGGAG<br>AGUCUCGAACAGGAGGCAGCGAACGAGAGGCAAC<br>AAUUGGUAGAAACGCACAUGGCGAGGGUGGAAGC<br>UAUGCUCAAUGACCGAAGACGACUUGCCUUGGAAA<br>AUUACAUUACUGCCCUUCAAGCCGUCCCACCGCGC<br>CCACGCCAUGUCUUUAACAUGCUUAAGAAGUAUGU<br>UCGAGCUGAACAGAAGGAUCGGCAACACACCCUG<br>AAACACUUCGAACAUGUCAGAAUGGUUGACCCGAA<br>GAAGGCUGCACAGAUUCGAAGUCAAGUUAUGACC<br>CAUUUGAGGGUAAUAUAUGAGAGAAUGAACCAAA<br>GUCUGAGCCUUCUCUACAAUGUCCCCGCUGUGGCC |

TABLE 13-continued

Human Mutant APP mRNA Isoform Sequences

| SEQ ID NO | Mutation | mRNA Sequence |
|---|---|---|
| | | GAGGAAAUUCAGGACGAAGUCGAUGAGCUCCUGC<br>AAAAGGAGCAGAACUACUCUGACGAUGUACUUGCU<br>AAUAUGAUUUCAGAGCCAAGGAUCAGUUAUGGAAA<br>CGACGCCCUGAUGCCUAGUCUUACCGAAACCAAGA<br>CUACGGUAGAACUCCUUCCCGUUAACGGAGAGUUC<br>AGCUUGGACGACCUUCAGCCUUGGCACUCAUUCG<br>GAGCUGAUUCCGUACCAGCCAAUACGGAGAAUGA<br>AGUAGAGCCCGUAGACGCAAGACCUGCAGCGGAC<br>AGAGGGCUGACGACGAGACCCGGUAGCGGUUUGA<br>CAAAUAUCAAGACGGAGGAGAUCUCUGAAGUGAA<br>GAUGGAUACAGAAUUCCGACAUGACUCAGGAUAU<br>GAAGUUCAUCAUCAAAAAUUGGUGUUCUUUGCAGA<br>AGAUGUCGGUUCUAACAAGGGUGCUAUCAUAGGC<br>CUUAUGGUGGGUGGCGUCGUGAUUGCGACCGUGA<br>UAGUUAUUACGCUUGUCAUGCUGAAGAAGAAACAG<br>UAUACGUCCAUCCAUCACGGUGUGGUAGAGGUAG<br>AUGCGGCCGUAACUCCCGAAGAGCGCCAUCUUUCU<br>AAGAUGCAGCAGAAUGGAUACGAGAACCCCACGU<br>ACAAAUUCUUUGAGCAAAUGCAAAACUGA |
| 66 | K687R | AUGCUCCCUGGACUUGCUUUGCUGCUUUUGGCAG<br>CCUGGACUGCUCGAGCACUCGAGGUCCCAACGGA<br>UGGAAACGCGGGUCUUUUGGCAGAGCCUCAAAUA<br>GCAAUGUUUUGCGGAAGACUCAACAUGCAUAUGAA<br>CGUUCAGAAUGGGAAAUGGGACUCCGACCCCAGU<br>GGUACGAAGACAUGUAUUGACACAAAGGAGGGAA<br>UACUCCAGUACUGCCAGGAAGUGUACCCGGAGCU<br>UCAGAUUACGAAUGUGGUAGAGGCUAAUCAACCC<br>GUAACUAUCCAAAAUUGGUGUAAGAGAGGCAGGA<br>AGCAAUGCAAGACUCAUCCUCAUUUCGUAAUUCCG<br>UAUCGAUGUUUGGUGGGAGAAUUUGUCUCUGACG<br>CAUUGCUUGUUCCUGACAAGUGUAAGUUUCUUCAC<br>CAGGAACGCAUGGACGUGUGCGAGACACACUUGC<br>ACUGGCAUACCGUUGCGAAGGAGACGUGUUCCGA<br>AAAGAGUACAAAUCUCCAUGACUACGGCAUGUUGC<br>UCCCGUGCGGAAUAGAUAAGUUCCGAGGCGUGGA<br>GUUUGUAUGCUGUCCGCUGGCAGAGGAGAGCGAU<br>AAUGUCGAUUCCGCAGAUGCCGAAGAGGACGACA<br>GCGACGUCUGGUGGGGAGGAGCGGACACUGAUUA<br>CGCUGAUGGUAGUGAGGACAAAGUAGUCGAGGUG<br>GCAGAAGAAGAAGAAGUGGCGGAGGUUGAAGAAG<br>AAGAGGCAGACGAUGACGAAGACGAUGAGGACGG<br>UGAUGAGGUAGAAGAAGAAGCGGAAGAACCGUAC<br>GAAGAAGCUACGGAACGCACUACAAGUAUUGCUAC<br>CACUACAACCACUACAACCGAAUCAGUUGAGGAAG<br>UGGUGCGAGUCCCCACUACGGCUGCCAGUACACC<br>GGAUGCCGUCGACAAAUACCUGGAGACUCCUGGC<br>GACGAAAACGAACAUGCUCAUUUCCAGAAGGCGAA<br>GGAACGCCUCGAAGCAAAGCACAGAGAGAGAAUG<br>UCACAGGUAAUGAGGGAAUGGGAGGAGGCGGAAC<br>GCCAAGCAAAGAACCUGCCUAAAGCGGACAAGAA<br>GGCAGUUAUCCAACAUUUCCAAGAGAAAGUGGAG<br>AGUCUCGAACAGGAGGCAGCGAACGAGAGGCAAC<br>AAUUGGUAGAAACGCACAUGGCGAGGGUGGAAGC<br>UAUGCUCAAUGACCGAAGACGACUUGCCUUGGAAA<br>AUUACAUUACUGCCCUUCAAGCCGUCCCACCGCGC<br>CCACGCCAUGUCUUUAACAUGCUUAAGAAGUAUGU<br>UCGAGCUGAACAGAAGGAUCGGCAACACACCCUG<br>AAACACUUCGAACAUGUCAGAAUGGUUGACCCGAA<br>GAAGGCUGCACAGAUUCGAAGUCAAGUUAUGACC<br>CAUUUGAGGGUAAUAUAUGAGAGAAUGAACCAAA<br>GUCUGAGCCUUCUCUACAAUGUCCCCGCUGUGGCC<br>GAGGAAAUUCAGGACGAAGUCGAUGAGCUCCUGC<br>AAAAGGAGCAGAACUACUCUGACGAUGUACUUGCU<br>AAUAUGAUUUCAGAGCCAAGGAUCAGUUAUGGAAA<br>CGACGCCCUGAUGCCUAGUCUUACCGAAACCAAGA<br>CUACGGUAGAACUCCUUCCCGUUAACGGAGAGUUC<br>AGCUUGGACGACCUUCAGCCUUGGCACUCAUUCG<br>GAGCUGAUUCCGUACCAGCCAAUACGGAGAAUGA<br>AGUAGAGCCCGUAGACGCAAGACCUGCAGCGGAC<br>AGAGGGCUGACGACGAGACCCGGUAGCGGUUUGA<br>CAAAUAUCAAGACGGAGGAGAUCUCUGAAGUGAA<br>GAUGGAUGCAGAAUUCCGACAUGACUCAGGAUAU<br>GAAGUUCAUCAUCAAAGAUUGGUGUUCUUUGCAGA<br>AGAUGUCGGUUCUAACAAGGGUGCUAUCAUAGGC<br>CUUAUGGUGGGUGGCGUCGUGAUUGCGACCGUGA<br>UAGUUAUUACGCUUGUCAUGCUGAAGAAGAAACAG<br>UAUACGUCCAUCCAUCACGGUGUGGUAGAGGUAG<br>AUGCGGCCGUAACUCCCGAAGAGCGCCAUCUUUCU<br>AAGAUGCAGCAGAAUGGAUACGAGAACCCCACGU<br>ACAAAUUCUUUGAGCAAAUGCAAAACUGA |
| 67 | K687E | AUGCUCCCUGGACUUGCUUUGCUGCUUUUGGCAG<br>CCUGGACUGCUCGAGCACUCGAGGUCCCAACGGA<br>UGGAAACGCGGGUCUUUUGGCAGAGCCUCAAAUA<br>GCAAUGUUUUGCGGAAGACUCAACAUGCAUAUGAA<br>CGUUCAGAAUGGGAAAUGGGACUCCGACCCCAGU<br>GGUACGAAGACAUGUAUUGACACAAAGGAGGGAA<br>UACUCCAGUACUGCCAGGAAGUGUACCCGGAGCU<br>UCAGAUUACGAAUGUGGUAGAGGCUAAUCAACCC<br>GUAACUAUCCAAAAUUGGUGUAAGAGAGGCAGGA<br>AGCAAUGCAAGACUCAUCCUCAUUUCGUAAUUCCG<br>UAUCGAUGUUUGGUGGGAGAAUUUGUCUCUGACG<br>CAUUGCUUGUUCCUGACAAGUGUAAGUUUCUUCAC<br>CAGGAACGCAUGGACGUGUGCGAGACACACUUGC<br>ACUGGCAUACCGUUGCGAAGGAGACGUGUUCCGA<br>AAAGAGUACAAAUCUCCAUGACUACGGCAUGUUGC<br>UCCCGUGCGGAAUAGAUAAGUUCCGAGGCGUGGA<br>GUUUGUAUGCUGUCCGCUGGCAGAGGAGAGCGAU<br>AAUGUCGAUUCCGCAGAUGCCGAAGAGGACGACA<br>GCGACGUCUGGUGGGGAGGAGCGGACACUGAUUA<br>CGCUGAUGGUAGUGAGGACAAAGUAGUCGAGGUG<br>GCAGAAGAAGAAGAAGUGGCGGAGGUUGAAGAAG<br>AAGAGGCAGACGAUGACGAAGACGAUGAGGACGG<br>UGAUGAGGUAGAAGAAGAAGCGGAAGAACCGUAC<br>GAAGAAGCUACGGAACGCACUACAAGUAUUGCUAC<br>CACUACAACCACUACAACCGAAUCAGUUGAGGAAG<br>UGGUGCGAGUCCCCACUACGGCUGCCAGUACACC<br>GGAUGCCGUCGACAAAUACCUGGAGACUCCUGGC<br>GACGAAAACGAACAUGCUCAUUUCCAGAAGGCGAA<br>GGAACGCCUCGAAGCAAAGCACAGAGAGAGAAUG<br>UCACAGGUAAUGAGGGAAUGGGAGGAGGCGGAAC<br>GCCAAGCAAAGAACCUGCCUAAAGCGGACAAGAA<br>GGCAGUUAUCCAACAUUUCCAAGAGAAAGUGGAG<br>AGUCUCGAACAGGAGGCAGCGAACGAGAGGCAAC<br>AAUUGGUAGAAACGCACAUGGCGAGGGUGGAAGC<br>UAUGCUCAAUGACCGAAGACGACUUGCCUUGGAAA<br>AUUACAUUACUGCCCUUCAAGCCGUCCCACCGCGC<br>CCACGCCAUGUCUUUAACAUGCUUAAGAAGUAUGU<br>UCGAGCUGAACAGAAGGAUCGGCAACACACCCUG<br>AAACACUUCGAACAUGUCAGAAUGGUUGACCCGAA<br>GAAGGCUGCACAGAUUCGAAGUCAAGUUAUGACC<br>CAUUUGAGGGUAAUAUAUGAGAGAAUGAACCAAA<br>GUCUGAGCCUUCUCUACAAUGUCCCCGCUGUGGCC<br>GAGGAAAUUCAGGACGAAGUCGAUGAGCUCCUGC<br>AAAAGGAGCAGAACUACUCUGACGAUGUACUUGCU<br>AAUAUGAUUUCAGAGCCAAGGAUCAGUUAUGGAAA<br>CGACGCCCUGAUGCCUAGUCUUACCGAAACCAAGA<br>CUACGGUAGAACUCCUUCCCGUUAACGGAGAGUUC<br>AGCUUGGACGACCUUCAGCCUUGGCACUCAUUCG<br>GAGCUGAUUCCGUACCAGCCAAUACGGAGAAUGA<br>AGUAGAGCCCGUAGACGCAAGACCUGCAGCGGAC<br>AGAGGGCUGACGACGAGACCCGGUAGCGGUUUGA<br>CAAAUAUCAAGACGGAGGAGAUCUCUGAAGUGAA<br>GAUGGAUGCAGAAUUCCGACAUGACUCAGGAUAU<br>GAAGUUCAUCAUCAAGAAUUGGUGUUCUUUGCAGA<br>AGAUGUCGGUUCUAACAAGGGUGCUAUCAUAGGC<br>CUUAUGGUGGGUGGCGUCGUGAUUGCGACCGUGA<br>UAGUUAUUACGCUUGUCAUGCUGAAGAAGAAACAG<br>UAUACGUCCAUCCAUCACGGUGUGGUAGAGGUAG<br>AUGCGGCCGUAACUCCCGAAGAGCGCCAUCUUUCU<br>AAGAUGCAGCAGAAUGGAUACGAGAACCCCACGU<br>ACAAAUUCUUUGAGCAAAUGCAAAACUGA |
| 68 | K687G | AUGCUCCCUGGACUUGCUUUGCUGCUUUUGGCAG<br>CCUGGACUGCUCGAGCACUCGAGGUCCCAACGGA<br>UGGAAACGCGGGUCUUUUGGCAGAGCCUCAAAUA<br>GCAAUGUUUUGCGGAAGACUCAACAUGCAUAUGAA<br>CGUUCAGAAUGGGAAAUGGGACUCCGACCCCAGU<br>GGUACGAAGACAUGUAUUGACACAAAGGAGGGAA |

TABLE 13-continued

Human Mutant APP mRNA Isoform Sequences

| SEQ ID NO | Mutation | mRNA Sequence |
|---|---|---|
| | | UACUCCAGUACUGCCAGGAAGUGUACCCGGAGCU<br>UCAGAUUACGAAUGUGGUAGAGGCUAAUCAACCC<br>GUAACUAUCCAAAAUUGGUGUAAGAGAGGCAGGA<br>AGCAAUGCAAGACUCAUCCUCAUUUCGUAAUUCCG<br>UAUCGAUGUUUGGUGGGAGAAUUUGUCUCUGACG<br>CAUUGCUUGUUCCUGACAAGUGUAAGUUUCUUCAC<br>CAGGAACGCAUGGACGUGUGCGAGACACACUUGC<br>ACUGGCAUACCGUUGCGAAGGAGACGUGUUCCGA<br>AAAGAGUACAAAUCUCCAUGACUACGGCAUGUUGC<br>UCCCGUGCGGAAUAGAUAAGUUCCGAGGCGUGGA<br>GUUUGUAUGCUGUCCGCUGGCAGAGGAGAGCGAU<br>AAUGUCGAUUCCGCAGAUGCCGAAGAGGACGACA<br>GCGACGUCUGGUGGGGAGGAGCGGACACUGAUUA<br>CGCUGAUGGUAGUGAGGACAAAGUAGUCGAGGUG<br>GCAGAAGAAGAAGAAGUGGCGGAGGUUGAAGAAG<br>AAGAGGCAGACGAUGACGAAGACGAUGAGGACGG<br>UGAUGAGGUAGAAGAAGAAGCGGAAGAACCGUAC<br>GAAGAAGCUACGGAACGCACUACAAGUAUUGCUAC<br>CACUACAACCACUACAACCGAAUCAGUUGAGGAAG<br>UGGUGCGAGUCCCCACUACGGCUGCCAGUACACC<br>GGAUGCCGUCGACAAAUACCUGGAGACUCCUGGC<br>GACGAAAACGAACAUGCUCAUUUCCAGAAGGCGAA<br>GGAACGCCUCGAAGCAAAGCACAGAGAGAGAAUG<br>UCACAGGUAAUGAGGGAAUGGGAGGAGGCGGAAC<br>GCCAAGCAAAGAACCUGCCUAAAGCGGACAAGAA<br>GGCAGUUAUCCAACAUUUCCAAGAGAAAGUGGAG<br>AGUCUCGAACAGGAGGCAGCGAACGAGAGGCAAC<br>AAUUGGUAGAAACGCACAUGGCGAGGGUGGAAGC<br>UAUGCUCAAUGACCGAAGACGACUUGCCUUGGAAA<br>AUUACAUUACUGCCCUUCAAGCCGUCCCACCGCGC<br>CCACGCCAUGUCUUUAACAUGCUUAAGAAGUAUGU<br>UCGAGCUGAACAGAAGGAUCGGCAACACACCCUG<br>AAACACUUCGAACAUGUCAGAAUGGUUGACCCGAA<br>GAAGGCUGCACAGAUUCGAAGUCAAGUUAUGACC<br>CAUUUGAGGGUAAUAUAUGAGAGAAUGAACCAAA<br>GUCUGAGCCUUCUCUACAAUGUCCCCGCUGUGGCC<br>GAGGAAAUUCAGGACGAAGUCGAUGAGCUCCUGC<br>AAAAGGAGCAGAACUACUCUGACGAUGUACUUGCU<br>AAUAUGAUUUCAGAGCCAAGGAUCAGUUAUGGAAA<br>CGACGCCCUGAUGCCUAGUCUUACCGAAACCAAGA<br>CUACGGUAGAACUCCUUCCCGUUAACGGAGAGUUC<br>AGCUUGGACGACCUUCAGCCUUGGCACUCAUUCG<br>GAGCUGAUUCCGUACCAGCCAAUACGGAGAAUGA<br>AGUAGAGCCCGUAGACGCAAGACCUGCAGCGGAC<br>AGAGGGCUGACGACGAGACCCGGUAGCGGUUUGA<br>CAAAUAUCAAGACGGAGGAGAUCUCUGAAGUGAA<br>GAUGGAUGCAGAAUUCCGACAUGACUCAGGAUAU<br>GAAGUUCAUCAUCAAGGAUUGGUGUUCUUUGCAG<br>AAGAUGUCGGUUCUAACAAGGGUGCUAUCAUAGG<br>CCUUAUGGUGGGUGGCGUCGUGAUUGCGACCGUG<br>AUAGUUAUUACGCUUGUCAUGCUGAAGAAGAAACA<br>GUAUACGUCCAUCCAUCACGGUGUGGUAGAGGUA<br>GAUGCGGCCGUAACUCCCGAAGAGCGCCAUCUUU<br>CUAAGAUGCAGCAGAAUGGAUACGAGAACCCCAC<br>GUACAAAUUCUUUGAGCAAAUGCAAAACUGA |
| 69 | H684R | AUGCUCCCUGGACUUGCUUUGCUGCUUUUGGCAG<br>CCUGGACUGCUCGAGCACUCGAGGUCCCAACGGA<br>UGGAAACGCGGGUCUUUUGGCAGAGCCUCAAAUA<br>GCAAUGUUUUGCGGAAGACUCAACAUGCAUAUGAA<br>CGUUCAGAAUGGGAAAUGGGACUCCGACCCCAGU<br>GGUACGAAGACAUGUAUUGACACAAAGGAGGGAA<br>UACUCCAGUACUGCCAGGAAGUGUACCCGGAGCU<br>UCAGAUUACGAAUGUGGUAGAGGCUAAUCAACCC<br>GUAACUAUCCAAAAUUGGUGUAAGAGAGGCAGGA<br>AGCAAUGCAAGACUCAUCCUCAUUUCGUAAUUCCG<br>UAUCGAUGUUUGGUGGGAGAAUUUGUCUCUGACG<br>CAUUGCUUGUUCCUGACAAGUGUAAGUUUCUUCAC<br>CAGGAACGCAUGGACGUGUGCGAGACACACUUGC<br>ACUGGCAUACCGUUGCGAAGGAGACGUGUUCCGA<br>AAAGAGUACAAAUCUCCAUGACUACGGCAUGUUGC<br>UCCCGUGCGGAAUAGAUAAGUUCCGAGGCGUGGA<br>GUUUGUAUGCUGUCCGCUGGCAGAGGAGAGCGAU<br>AAUGUCGAUUCCGCAGAUGCCGAAGAGGACGACA<br>GCGACGUCUGGUGGGGAGGAGCGGACACUGAUUA<br>CGCUGAUGGUAGUGAGGACAAAGUAGUCGAGGUG<br>GCAGAAGAAGAAGAAGUGGCGGAGGUUGAAGAAG<br>AAGAGGCAGACGAUGACGAAGACGAUGAGGACGG<br>UGAUGAGGUAGAAGAAGAAGCGGAAGAACCGUAC<br>GAAGAAGCUACGGAACGCACUACAAGUAUUGCUAC<br>CACUACAACCACUACAACCGAAUCAGUUGAGGAAG<br>UGGUGCGAGUCCCCACUACGGCUGCCAGUACACC<br>GGAUGCCGUCGACAAAUACCUGGAGACUCCUGGC<br>GACGAAAACGAACAUGCUCAUUUCCAGAAGGCGAA<br>GGAACGCCUCGAAGCAAAGCACAGAGAGAGAAUG<br>UCACAGGUAAUGAGGGAAUGGGAGGAGGCGGAAC<br>GCCAAGCAAAGAACCUGCCUAAAGCGGACAAGAA<br>GGCAGUUAUCCAACAUUUCCAAGAGAAAGUGGAG<br>AGUCUCGAACAGGAGGCAGCGAACGAGAGGCAAC<br>AAUUGGUAGAAACGCACAUGGCGAGGGUGGAAGC<br>UAUGCUCAAUGACCGAAGACGACUUGCCUUGGAAA<br>AUUACAUUACUGCCCUUCAAGCCGUCCCACCGCGC<br>CCACGCCAUGUCUUUAACAUGCUUAAGAAGUAUGU<br>UCGAGCUGAACAGAAGGAUCGGCAACACACCCUG<br>AAACACUUCGAACAUGUCAGAAUGGUUGACCCGAA<br>GAAGGCUGCACAGAUUCGAAGUCAAGUUAUGACC<br>CAUUUGAGGGUAAUAUAUGAGAGAAUGAACCAAA<br>GUCUGAGCCUUCUCUACAAUGUCCCCGCUGUGGCC<br>GAGGAAAUUCAGGACGAAGUCGAUGAGCUCCUGC<br>AAAAGGAGCAGAACUACUCUGACGAUGUACUUGCU<br>AAUAUGAUUUCAGAGCCAAGGAUCAGUUAUGGAAA<br>CGACGCCCUGAUGCCUAGUCUUACCGAAACCAAGA<br>CUACGGUAGAACUCCUUCCCGUUAACGGAGAGUUC<br>AGCUUGGACGACCUUCAGCCUUGGCACUCAUUCG<br>GAGCUGAUUCCGUACCAGCCAAUACGGAGAAUGA<br>AGUAGAGCCCGUAGACGCAAGACCUGCAGCGGAC<br>AGAGGGCUGACGACGAGACCCGGUAGCGGUUUGA<br>CAAAUAUCAAGACGGAGGAGAUCUCUGAAGUGAA<br>GAUGGAUGCAGAAUUCCGACAUGACUCAGGAUAU<br>GAAGUUCGUCAUCAAAAAUUGGUGUUCUUUGCAGA<br>AGAUGUCGGUUCUAACAAGGGUGCUAUCAUAGGC<br>CUUAUGGUGGGUGGCGUCGUGAUUGCGACCGUGA<br>UAGUUAUUACGCUUGUCAUGCUGAAGAAGAAACAG<br>UAUACGUCCAUCCAUCACGGUGUGGUAGAGGUAG<br>AUGCGGCCGUAACUCCCGAAGAGCGCCAUCUUUCU<br>AAGAUGCAGCAGAAUGGAUACGAGAACCCCACGU<br>ACAAAUUCUUUGAGCAAAUGCAAAACUGA |
| 70 | E682G | AUGCUCCCUGGACUUGCUUUGCUGCUUUUGGCAG<br>CCUGGACUGCUCGAGCACUCGAGGUCCCAACGGA<br>UGGAAACGCGGGUCUUUUGGCAGAGCCUCAAAUA<br>GCAAUGUUUUGCGGAAGACUCAACAUGCAUAUGAA<br>CGUUCAGAAUGGGAAAUGGGACUCCGACCCCAGU<br>GGUACGAAGACAUGUAUUGACACAAAGGAGGGAA<br>UACUCCAGUACUGCCAGGAAGUGUACCCGGAGCU<br>UCAGAUUACGAAUGUGGUAGAGGCUAAUCAACCC<br>GUAACUAUCCAAAAUUGGUGUAAGAGAGGCAGGA<br>AGCAAUGCAAGACUCAUCCUCAUUUCGUAAUUCCG<br>UAUCGAUGUUUGGUGGGAGAAUUUGUCUCUGACG<br>CAUUGCUUGUUCCUGACAAGUGUAAGUUUCUUCAC<br>CAGGAACGCAUGGACGUGUGCGAGACACACUUGC<br>ACUGGCAUACCGUUGCGAAGGAGACGUGUUCCGA<br>AAAGAGUACAAAUCUCCAUGACUACGGCAUGUUGC<br>UCCCGUGCGGAAUAGAUAAGUUCCGAGGCGUGGA<br>GUUUGUAUGCUGUCCGCUGGCAGAGGAGAGCGAU<br>AAUGUCGAUUCCGCAGAUGCCGAAGAGGACGACA<br>GCGACGUCUGGUGGGGAGGAGCGGACACUGAUUA<br>CGCUGAUGGUAGUGAGGACAAAGUAGUCGAGGUG<br>GCAGAAGAAGAAGAAGUGGCGGAGGUUGAAGAAG<br>AAGAGGCAGACGAUGACGAAGACGAUGAGGACGG<br>UGAUGAGGUAGAAGAAGAAGCGGAAGAACCGUAC<br>GAAGAAGCUACGGAACGCACUACAAGUAUUGCUAC<br>CACUACAACCACUACAACCGAAUCAGUUGAGGAAG<br>UGGUGCGAGUCCCCACUACGGCUGCCAGUACACC<br>GGAUGCCGUCGACAAAUACCUGGAGACUCCUGGC<br>GACGAAAACGAACAUGCUCAUUUCCAGAAGGCGAA<br>GGAACGCCUCGAAGCAAAGCACAGAGAGAGAAUG<br>UCACAGGUAAUGAGGGAAUGGGAGGAGGCGGAAC<br>GCCAAGCAAAGAACCUGCCUAAAGCGGACAAGAA<br>GGCAGUUAUCCAACAUUUCCAAGAGAAAGUGGAG |

TABLE 13-continued

Human Mutant APP mRNA Isoform Sequences

| SEQ ID NO | Mutation | mRNA Sequence |
|---|---|---|
| | | AGUCUCGAACAGGAGGCAGCGAACGAGAGGCAAC AAUUGGUAGAAACGCACAUGGCGAGGGUGGAAGC UAUGCUCAAUGACCGAAGACGACUUGCCUUGGAAA AUUACAUUACUGCCCUUCAAGCCGUCCCACCGCGC CCACGCCAUGUCUUUAACAUGCUUAAGAAGUAUGU UCGAGCUGAACAGAAGGAUCGGCAACACACCCUG AAACACUUCGAACAUGUCAGAAUGGUUGACCCGAA GAAGGCUGCACAGAUUCGAAGUCAAGUUAUGACC CAUUUGAGGGUAAUAUAUGAGAGAAUGAACCAAA GUCUGAGCCUUCUCUACAAUGUCCCCGCUGUGGCC GAGGAAAUUCAGGACGAAGUCGAUGAGCUCCUGC AAAAGGAGCAGAACUACUCUGACGAUGUACUUGCU AAUAUGAUUUCAGAGCCAAGGAUCAGUUAUGGAAA CGACGCCCUGAUGCCUAGUCUUACCGAAACCAAGA CUACGGUAGAACUCCUUCCCGUUAACGGAGAGUUC AGCUUGGACGACCUUCAGCCUUGGCACUCAUUCG GAGCUGAUUCCGUACCAGCCAAUACGGAGAAUGA AGUAGAGCCCGUAGACGCAAGACCUGCAGCGGAC AGAGGGCUGACGACGAGACCCGGUAGCGGUUUGA CAAAUAUCAAGACGGAGGAGAUCUCUGAAGUGAA GAUGGAUGCAGAAUUCCGACAUGACUCAGGAUAU GGAGUUCAUCAUCAAAAAUUGGUGUUCUUUGCAGA AGAUGUCGGUUCUAACAAGGGUGCUAUCAUAGGC CUUAUGGUGGGUGGCGUCGUGAUUGCGACCGUGA UAGUUAUUACGCUUGUCAUGCUGAAGAAGAAACAG UAUACGUCCAUCCAUCACGGUGUGGUAGAGGUAG AUGCGGCCGUAACUCCCGAAGAGCGCCAUCUUUCU AAGAUGCAGCAGAAUGGAUACGAGAACCCCACGU ACAAAUUCUUUGAGCAAAUGCAAAACUGA |

The APP695 plasmid was subjected to site-directed mutagenesis in order to make the desired APP mutants listed in TABLE 13. Nucleotide substitutions for each target mutant at or near the BACE cleavage site (β-site and β'-site) are shown in FIG. 7, along with nucleotide substitutions corresponding to the A673V mutation (pathogenic control) and A673T mutation (protective mutation control). Boxes in the nucleotide sequence indicate the target mutation. Nucleotide substitutions for each target mutant at or near the ADAM10 cleavage site (α-site) are shown in FIG. 8. Once prepared, plasmids comprising the desired target mutations were purified using a commercially available plasmid Midiprep kit.

In total, 15 APP constructs specified in TABLE 13 as well as wild type APP in the CDS1 of TABLE 12 in SEQ ID NO: 55 were prepared, and the identity of each construct was confirmed by sequencing.] Sequencing can comprise capillary sequencing, bisulfite-free sequencing, bisulfite sequencing, TET-assisted bisulfite (TAB) sequencing, ACE-sequencing, high-throughput sequencing, Maxam-Gilbert sequencing, massively parallel signature sequencing, Polony sequencing, 454 pyrosequencing, Sanger sequencing, Illumina sequencing, SOLiD sequencing, Ion Torrent semiconductor sequencing, DNA nanoball sequencing, Heliscope single molecule sequencing, single molecule real time (SMRT) sequencing, nanopore sequencing, shot gun sequencing, RNA sequencing, Enigma sequencing, or any combination thereof.

In vitro APP Cleavage Assay

Figure 9:
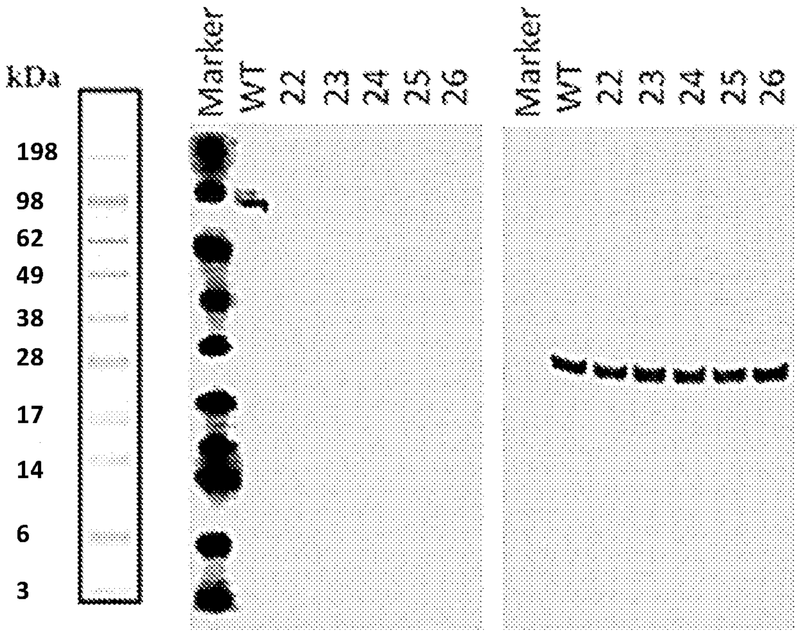
FIG. 9 shows western blots for isolated cell lines with successful APP knock out. On the left side of the image, treatment with antibodies for expressed APP (Biolegend clone LN27, 1:1000 dilution, expected size 110 kDa) is shown. The right side of the image shows treatment with antibodies for GAPDH for loading control (Biolegend clone FF26A/F9, 1:1000 dilution, expected size 36 kDa). Successful targeting utilizing a CRISPR/Cas9 ribonucleoprotein (RNP) reduces or eliminates the expression of APP, as shown in cell lines 22-26.

To evaluate the susceptibility of each APP mutant polypeptide to cleavage by endogenous proteases and production of Abeta 40 and Abeta 42 metabolites, a HEK293 APP knockout clone cell line was generated. In brief, HEK293 cells were nucleofected with a combination of 3 CRISPR/Cas9 ribonucleoproteins (RNPs) targeting the intron between exons 5 and 6 of the APP polypeptides. The cells were then cloned by limiting dilution and screened by Western blot to identify cells in which APP was knocked out. A resulting Western blot for isolated cell lines with successful APP knock out is shown FIG. 9. Western blots were visualized following treatment with secondary antibody (m-IgGk BP-HRP, Santa Cruz sc-516102, 1:1000 dilution).

Figure 10:
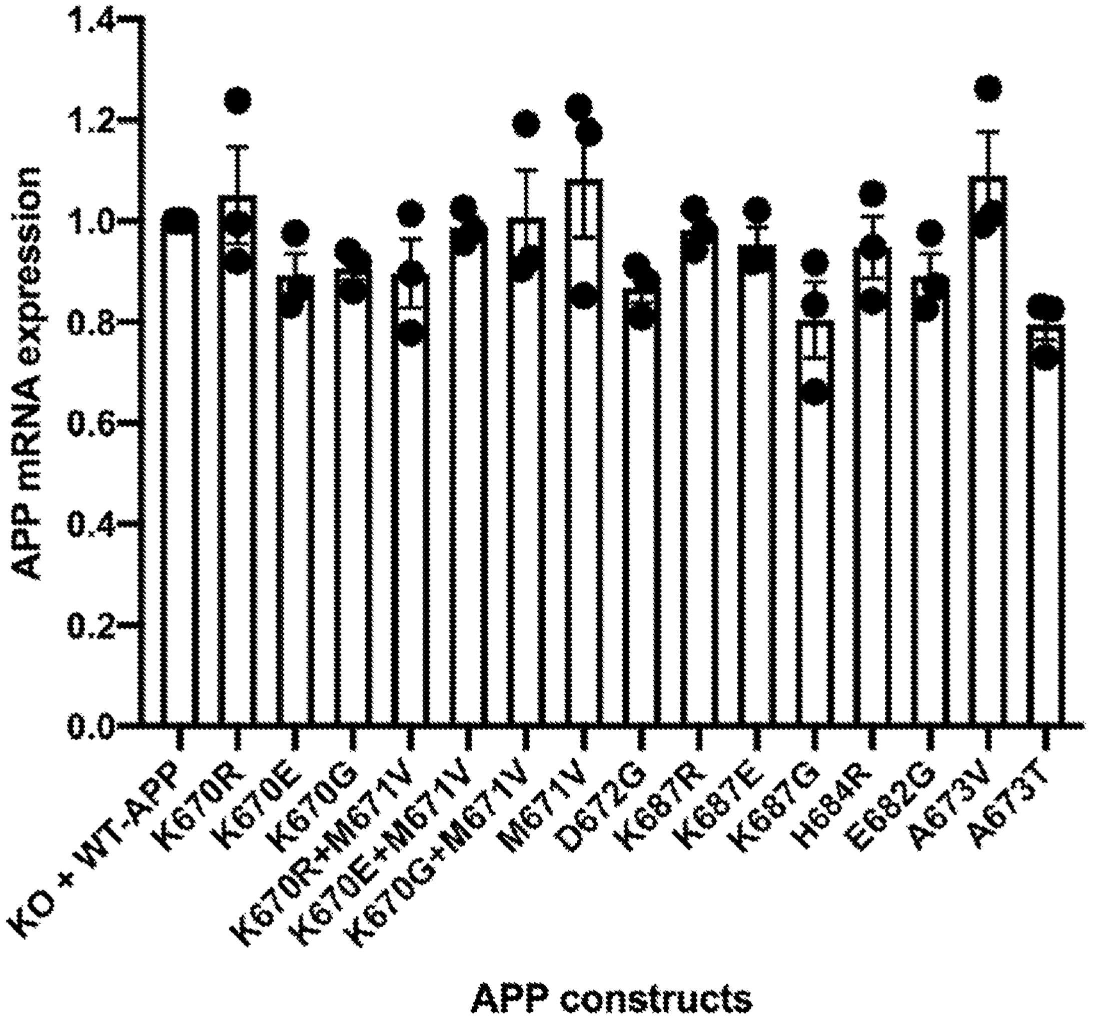
FIG. 10 shows mRNA expression levels of different APP constructs relative to those of HPRT in APP KO HEK293 cells (see FIG. 9) transfected with plasmids containing target APP variants.
Figure 11A:
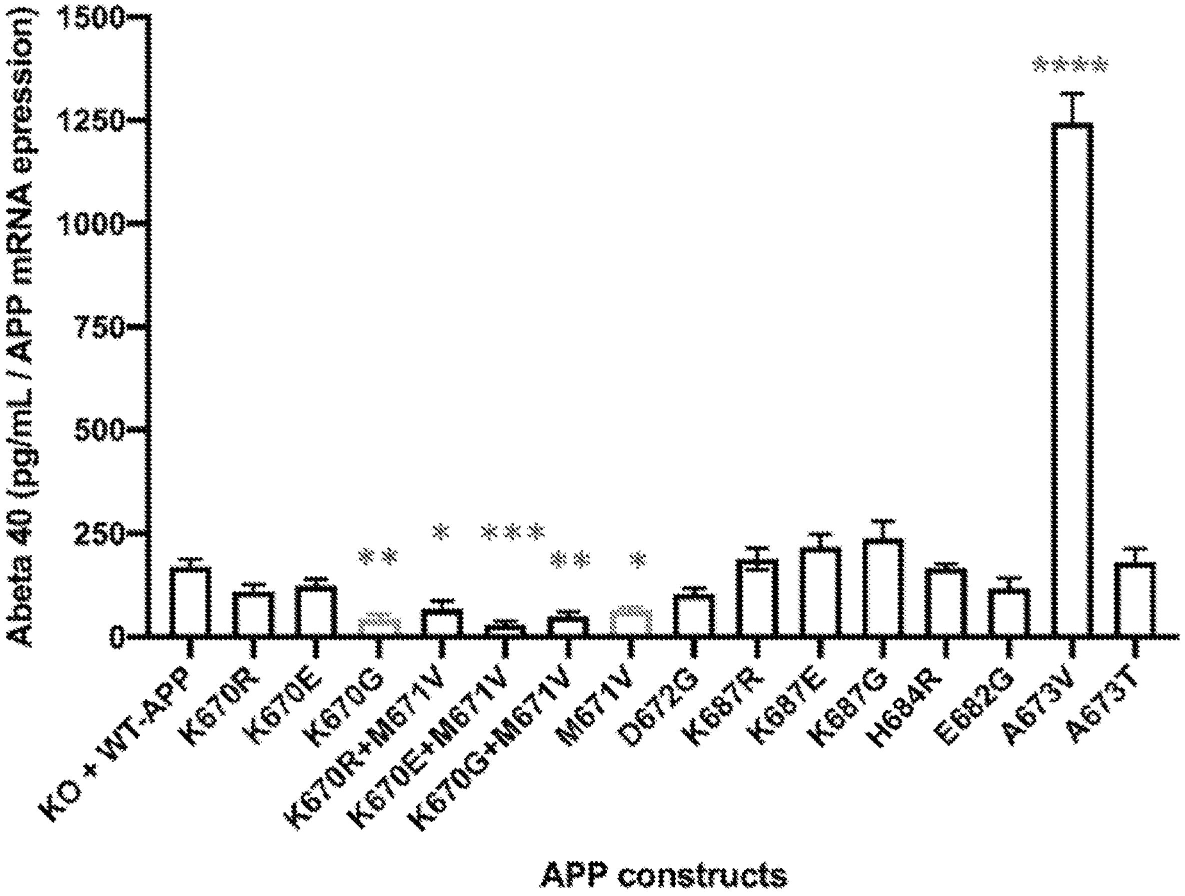
FIG. 11A shows a bar graph of the Abeta 40 protein expression levels (detected by ELISA) normalized to the APP mRNA expression level in APP KO HEK293 cells (see FIG. 9) transfected with plasmids containing target APP variants. The K670G, K670R+M671V, K670E+M671V, K670G+M671V, and M671V APP proteins exhibit statistically significant decreased expression level of Abeta 40 protein, as compared to the control (KO+WT-APP). The A673V APP protein exhibits statistically significant increased expression level, as compared to the control. Data represents mean+/−SEM. One-way ANOVA with Dunnett's posthoc test. *$p<0.05$; $p<0.005$, *$P<0.001$, ****$P<0.0001$.
Figure 11B:
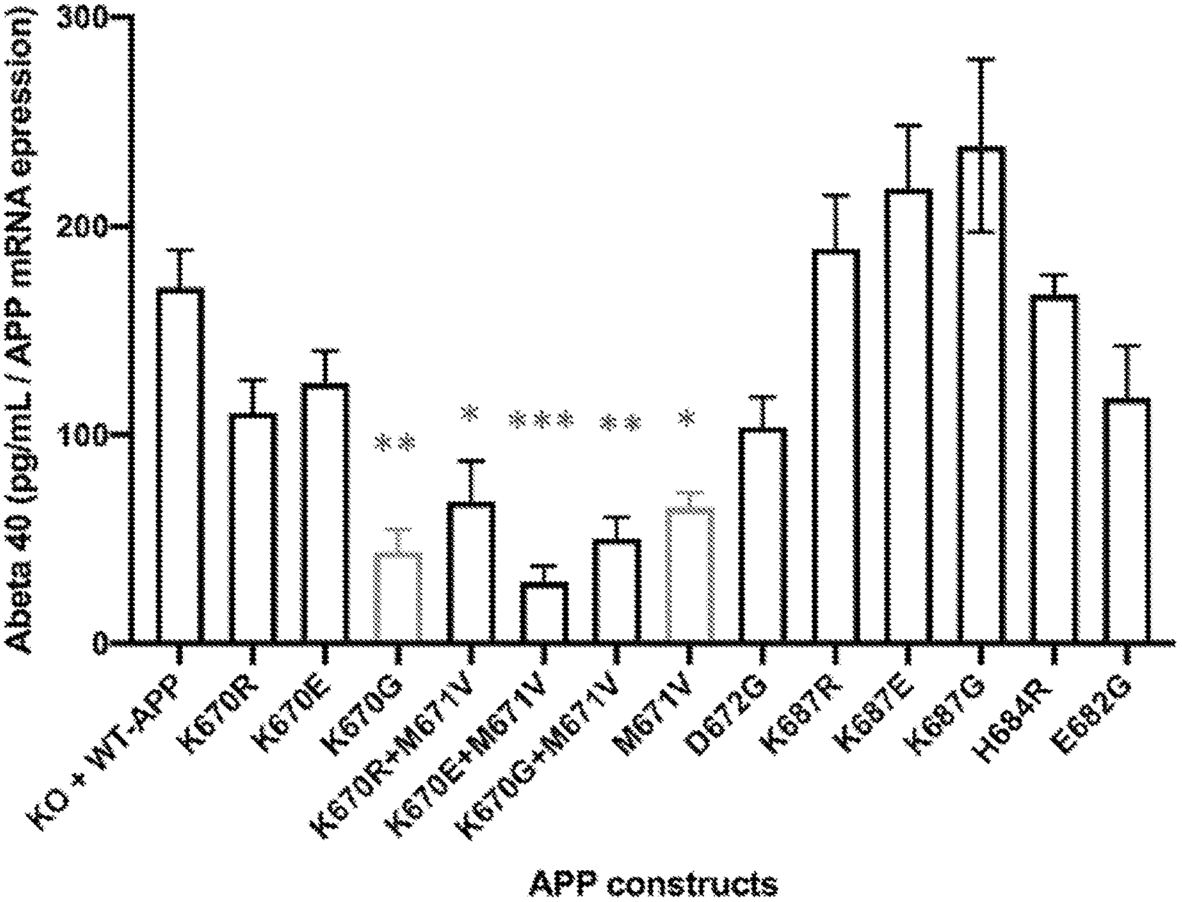
FIG. 11B is a magnified version of FIG. 11A, focusing on the five constructs with decreased expression compared to the control. Data represents mean +/−SEM. One-way ANOVA with Dunnett's posthoc test. *$p<0.05$; $p<0.005$, *$P<0.001$.
Figure 12A:
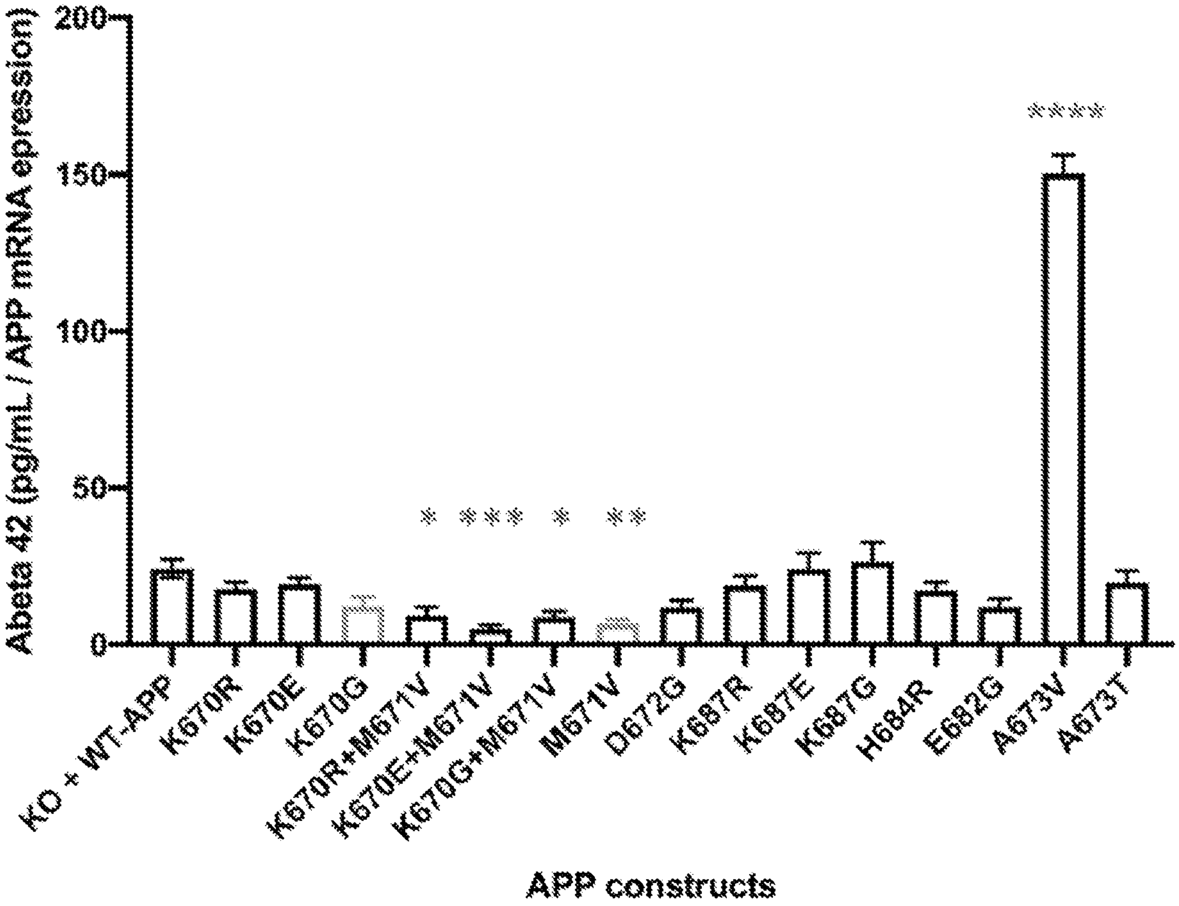
FIG. 12A shows a bar graph of the Abeta 42 protein expression levels (detected by ELISA) normalized to APP mRNA expression level in APP KO HEK293 cells (see FIG. 9) transfected with plasmids containing target APP variants. The K670E, K670R+M671V, K670E+M671V, K670G+M671V, and M671V APP proteins exhibit statistically significant decreased expression level, as compared to the control (KO+WT-APP). The A673V APP protein exhibits statistically significant increased expression level, as compared to the control. Data represents mean +/−SEM. One-way ANOVA with Dunnett's correction for multiple comparisons. *$p<0.05$; $p<0.005$, *$P<0.001$, ****$P<0.0001$.
Figure 12B:
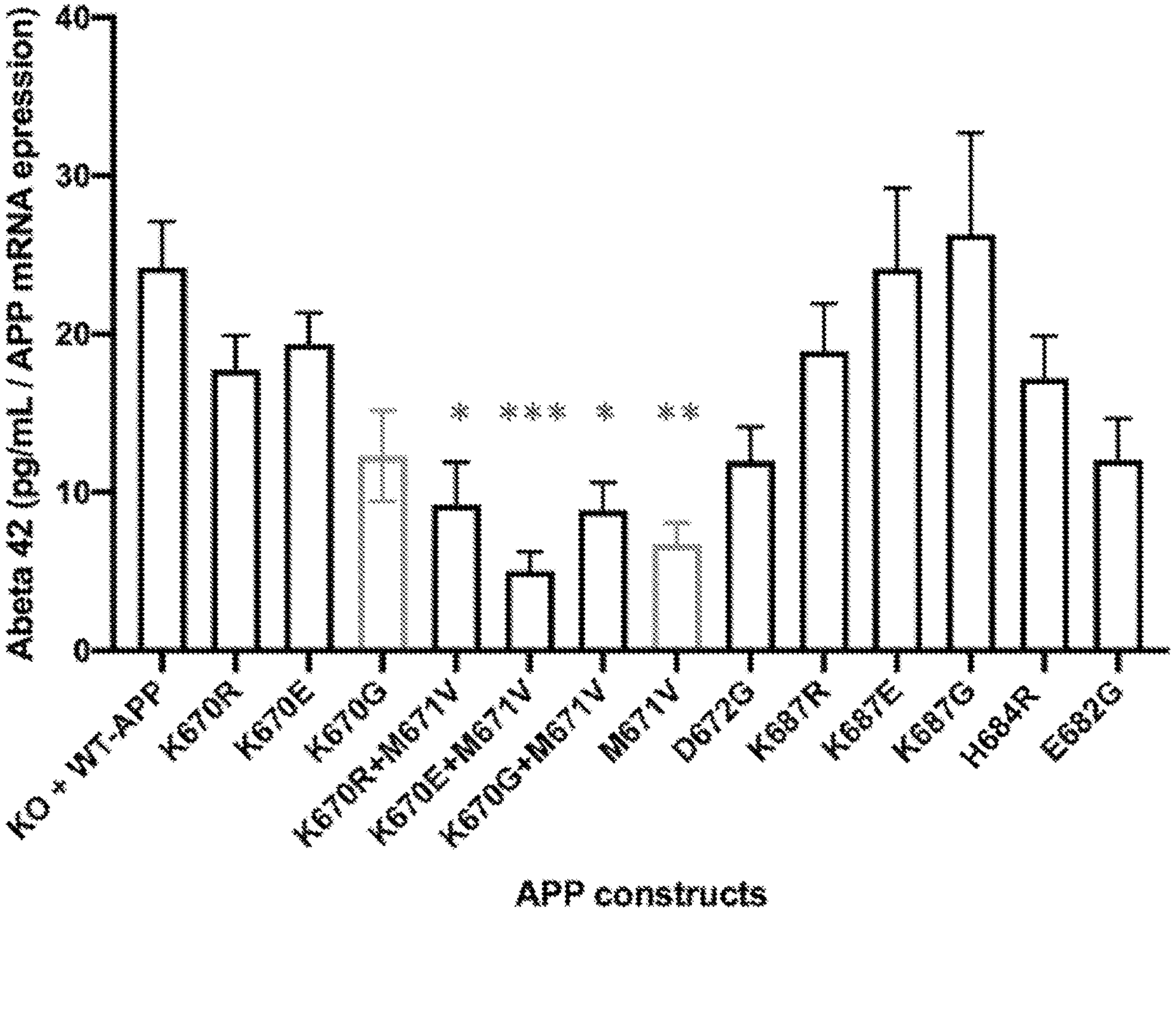
FIG. 12B is a magnified version of FIG. 12A, focusing on the five constructs with decreased expression compared to the control. Data represents mean +/−SEM. One-way ANOVA with Dunnett's correction for multiple comparisons. *$p<0.05$; $p<0.005$, *$P<0.001$.

The HEK293 APP knockout cell line was then transfected with 300 ng of the APP constructs (including wild type and controls) at 50,000 cells/well using Transit-293 in a 96-well format. Cells were then cultured for 48 hours post transfection, at which point media and cell lysates were collected. Secreted Abeta 40 and Abeta 42 levels were measured using Quantikine ELISAs (R&D Systems DAB140B and DAB142 kits). The experiment was performed with three separate transfections on three separate days (three screens) for a total of nine samples for each construct. Transfection efficiency was assessed by APP mRNA expression relative to HPRT mRNA levels in the same well using primers respectively conjugated to FAM and VIC. APP expression levels relative to HPRT levels measured this way from a representative well in each of the 3 screens is shown in FIG. 10. No significant difference in APP mRNA expression among constructs was observed (One-way ANOVA). FIG. 11A shows Abeta 40 levels normalized to APP mRNA expression detected upon each day of transfection for each of the tested constructs, including the wild-type APP. Each bar shows the mean +/−SEM. The construct containing the A673V pathogenic mutation showed greatly increased Abeta 40 levels compared to all other groups, as predicted. A One-way ANOVA ($P<0.0001$) comparing each sample to the knockout plus wild-type APP (KO+WT-APP) demonstrated significant differences. Stars represent statistical significance between the respective APP construct and the KO+WT-APP construct using Dunnett's post-hoc test. K670G and M671V appear to give the most statistically significant reduction in Abeta40 levels normalized to APP mRNA expression. FIG. 12A shows Abeta42 levels normalized to APP mRNA expression detected upon each day of transfection for each of the tested constructs, including the wild-type APP. Each bar shows the mean +/−SEM. The construct containing the A673V pathogenic mutation showed greatly increased Abeta 42 levels compared to all other groups, as predicted. A One-way ANOVA ($P<0.0001$) comparing each sample to the knockout plus wild-type APP (KO+WT-APP) demonstrated significant differences. Stars represent statistical significance between the respective APP construct and the KO+WT-APP construct using Dunnett's post-hoc test. The M671V mutation appears to give the most statistically significant reduction in Abeta42 levels normalized to APP mRNA expression.

Example 10: Engineered Polynucleotide Editing of Target RNA

Engineered polynucleotides, for example guide RNA, that comprise targeting sequence to Abeta 40 and/or Abeta 42 are used to correct APP mutation-comprising mRNA. EBV transformed B cells heterozygous for the mutation are treated with the polynucleotide.

In brief, guides are nucleofected in LCL cells using the Lonza X nucleofector, with program EH100. ~40 nmol or 60 nmol of each IVT guide RNA are nucleofected either into ~$2\times10^5$ LCL cells per reaction condition. The reaction is split into 2 wells, containing $1\times10^5$ each so that the cells can be collected for RNA isolation at either 3 hrs or 7 hrs. At collection, cells are spun at 1,500×g for 1 min. The media is removed. 180 ul of RLT buffer+BMe is added to each well. Qiagen RNeasy protocol and kit are used to isolate the RNAs from the cells. New England Biolabs (NEB) ProtoScript II First-Strand cDNA synthesis kit is used to synthesize cDNA from the isolated RNA. cDNA of APP was sequenced by Sanger sequencing. Sequencing was outsourced to Genewhiz. Sanger traces are analyzed to assess the editing efficiency of each IVT guide.

Example 11: Beta Secretase Cleavage of NRG1

This example describes beta secretase (e.g., BACE1, Cathepsin B, or Meprin beta) cleavage of another beta secretase substrate, Neuregulin1 (NRG1). A HEK293 APP knockout cell line is transfected with 300 ng of mutant APP constructs and a wild type APP construct at 50,000 cells/well using Transit-293 in a 96-well format. Cells are then cultured for 48 hours post transfection. Media and cell lysate are collected. Optionally, a beta secretase inhibitor is added to media and cell lysate immediately prior to sample processing. Secreted Abeta 40 and Abeta 42 levels are measured using Quantikine ELISAs (R&D Systems DAB140B and DAB142 kits) using a portion of the media and/or the lysate. A portion of the media and/or cell lysate is analyzed by liquid chromatography/mass spectrometry to quantify the amount of a peptide metabolite generated upon cleavage of neuregulin 1 (NRG1) by a beta secretase. For example, the cleavage product of NRG1 by a beta secretase between amino acid F237 and M238 is measured and quantified. The amount of peptide quantified is optionally normalized to the amount of full-length NRG1 present in the cell 48 hours post transfection. The amount of full-length NRG1 and the metabolites generated from beta secretase-mediated cleavage of NRG1 present in cells transfected with the APP constructs is measured by an NRG1 ELISA or other method suitable for quantifying the amount of NRG1 present. The amount of NRG1 cleavage product or the ratio of NRG1 cleavage product to the amount of NRG1 present in the cell transfected with the APP mutant is then compared to the amount of NRG1 cleavage product or the ratio of NRG1 cleavage product to the amount of NRG1 present in the cell transfected with the wild type APP construct. A desired APP mutant transfected in a cell has substantially the same profile of NRG1 cleavage product compared to the wild type APP transfected cell.

The experiment described in this example can be modified to measure cleavage products of other proteins targeted by beta secretase which produce metabolites indicative of beta secretase cleavage. Non-limiting examples of other such proteins include amyloid-like protein 1 (APLP1), amyloid-like protein 2 (APLP2), Contactin 2, Jagged 1, neural cell adhesion molecule L1 (CHL1), Neurexin 1α, Neurexin 3β, seizure related protein 6 (SEZ6), seizure related protein 6 precursor protein (SEZ6L), a (3 (β1-4) Auxiliary subunit of the voltage-gated sodium ion channel (VGSC) subtype Nav1, and VGSC Accessory Subunits KCNE1 or KCNE2.

While preferred embodiments have been shown and described herein, it will be obvious to those skilled in the art that such embodiments are provided by way of example only. Numerous variations, changes, and substitutions will now occur to those skilled in the art. It should be understood that various alternatives to the embodiments described herein may be employed. It is intended that the following claims define the scope and that methods and structures within the scope of these claims and their equivalents be covered herein.

Example 12: Editing RAB7a and SNCA mRNA

Figure 13A:
FIGS. 13A-13D show U7-driven expression of engineered guide RNAs with a 3' SmOPT and U7 hairpin that enhance specific guide RNA editing at additional gene targets with minimal unintended exon skipping.

In this example, different regions RAB7a and alpha-synuclein (SNCA) were edited using different guide RNA constructs. For RAB7a, exons 1, 2, and the 3' UTR were targeted for editing, whereas the start codon and the 3' UTR of SNCA were targeted. FIG. 13A shows a schematic of the exon structure of human RAB7A and SNCA. Exons are shown as gray segments; the coding region is denoted as a black line above. Locations of the guide RNA targeting sites are shown in purple; PCR primers are shown in green.

Figure 13B:
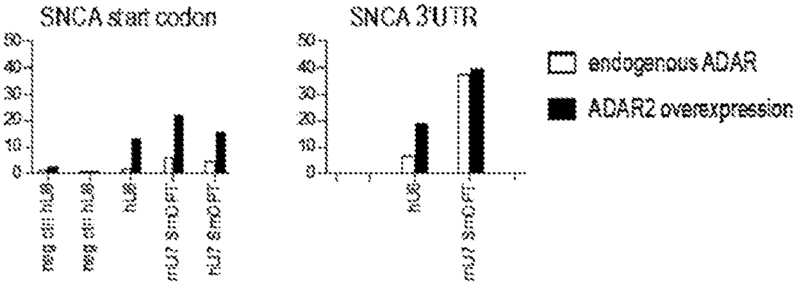

100 nt guide RNAs targeting human RAB7A exon 1, exon 3, or 3'UTR, or human SNCA start codon or 3' UTR were expressed using the hU6 promoter without a 3' hairpin or the mU7 or hU7 promoters with a 3' SmOPT U7 hairpin. FIG. 13B summarizes the results of the editing using the different guide RNA constructs in the presence or absence of ADAR2 overexpression. U7 promoters combined with a 3' SmOPT U7 hairpin enhanced ADAR editing at each target site (measured by Sanger sequencing). While constructs targeting the 3'UTRs worked equally well under endogenous versus overexpressed ADAR levels, constructs targeting other areas still benefited from ADAR2 overexpression.

Figure 13C:
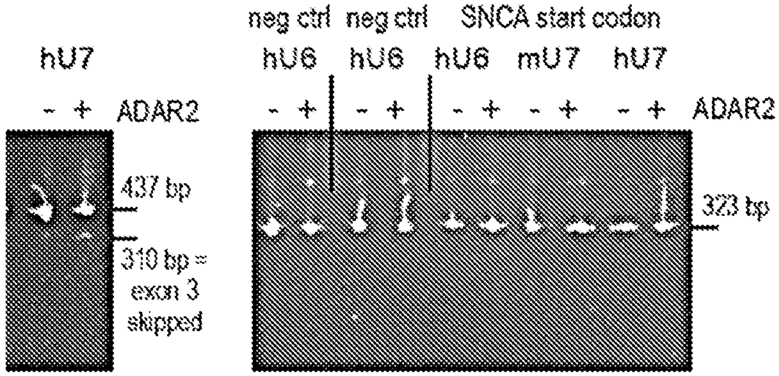
Figure 13D:
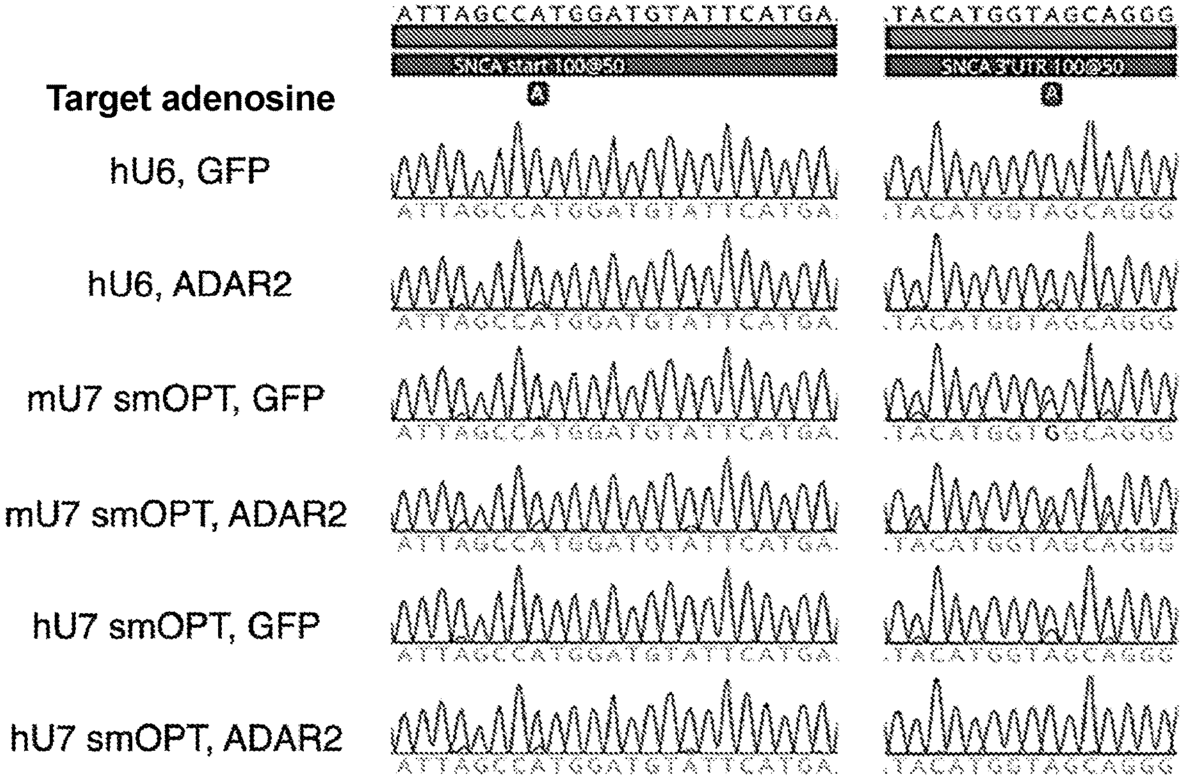

To confirm whether differential exon selection occurred, cDNA derived from the edited transcripts were isolated and PCR amplified using the denoted primers. The RAB7a primers, which span the coding determining sequence of RAB7a, generate a 437 bp amplicon if the exon structure is maintained. If exon 3 of RAB7a is skipped, a 310 bp amplicon is expected. Using the SNCA primers, a 323 bp PCR amplicon is expected. FIG. 13C shows minimal exon 3 skipping. FIG. 13D shows Sanger sequencing chromatograms show specific editing at the target adenosine of the indicated transcripts. The box indicates the on-target editing site. In some embodiments, disclosed herein are compositions of engineered guide RNAs under a U7 promoter and also comprising a smOpt hairpin sequence. Said engineered guide RNAs can hybridize to a target RNA sequence corresponding to SNCA, to facilitate ADAR-mediated editing of an adenosine (see FIG. 1). Editing of the SNCA gene was assessed by transfection in K562 cells highly overexpressing SNCA. At left is a Sanger sequence trace showing on target editing (as denoted by "Target A") of 91%.

Example 13: On and Off Target Editing of the 3' UTR of SNCA in K562 Cells

Figure 14A:
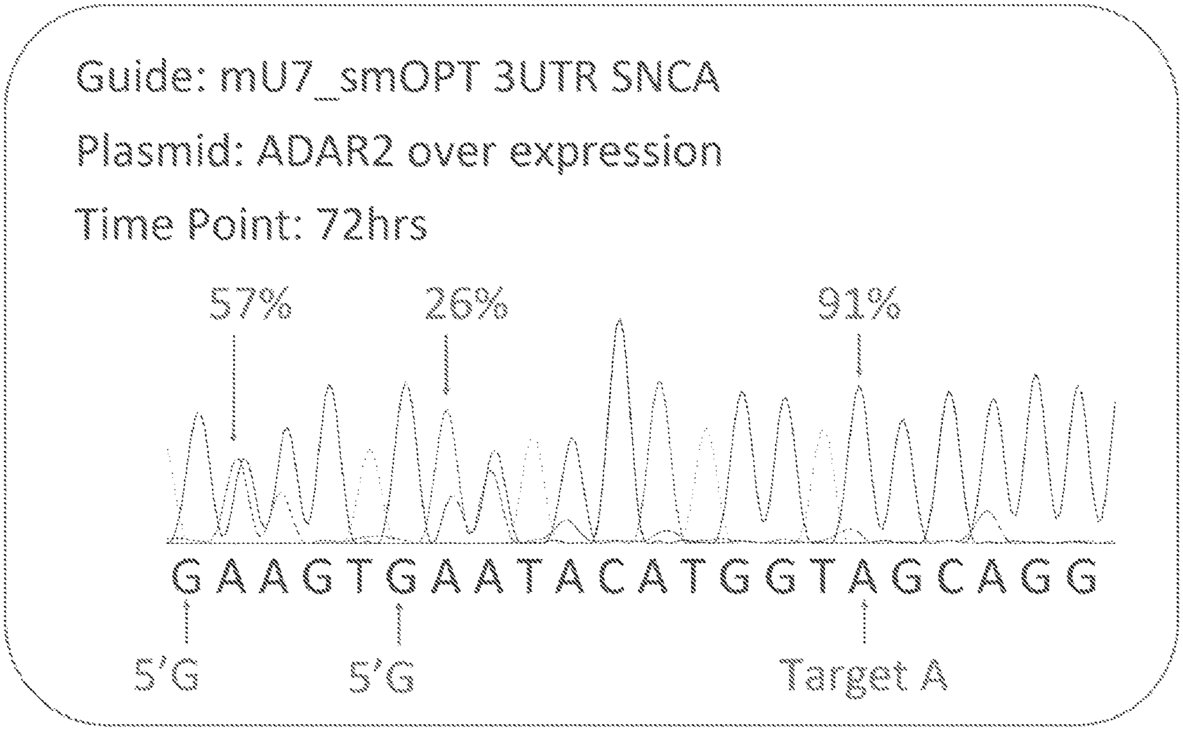
FIGS. 14A-14C show editing of the β' UTR of SNCA.
Figure 14B:
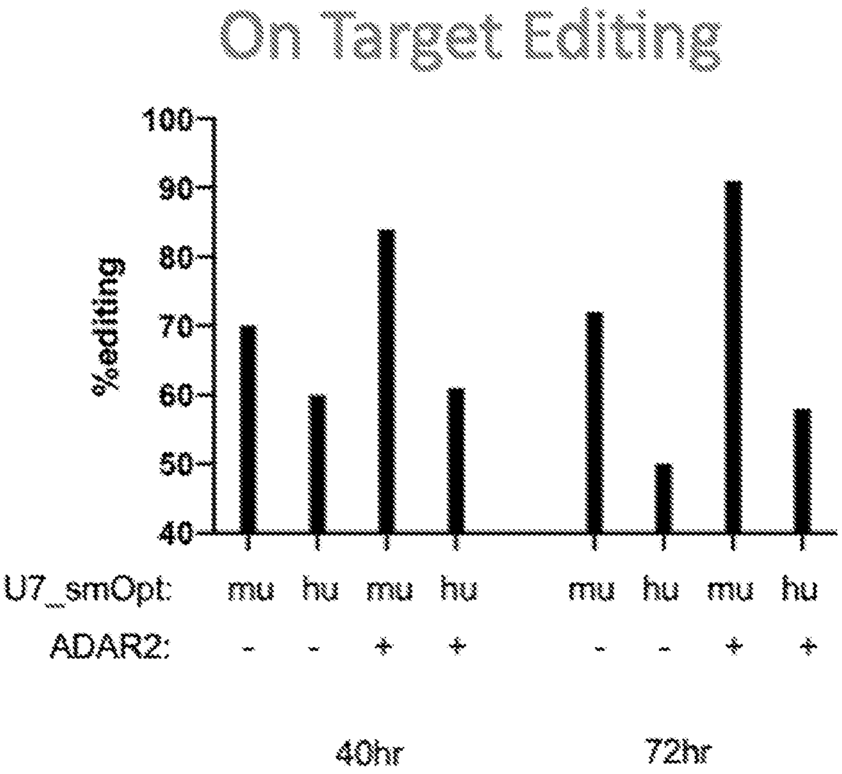
Figure 14C:
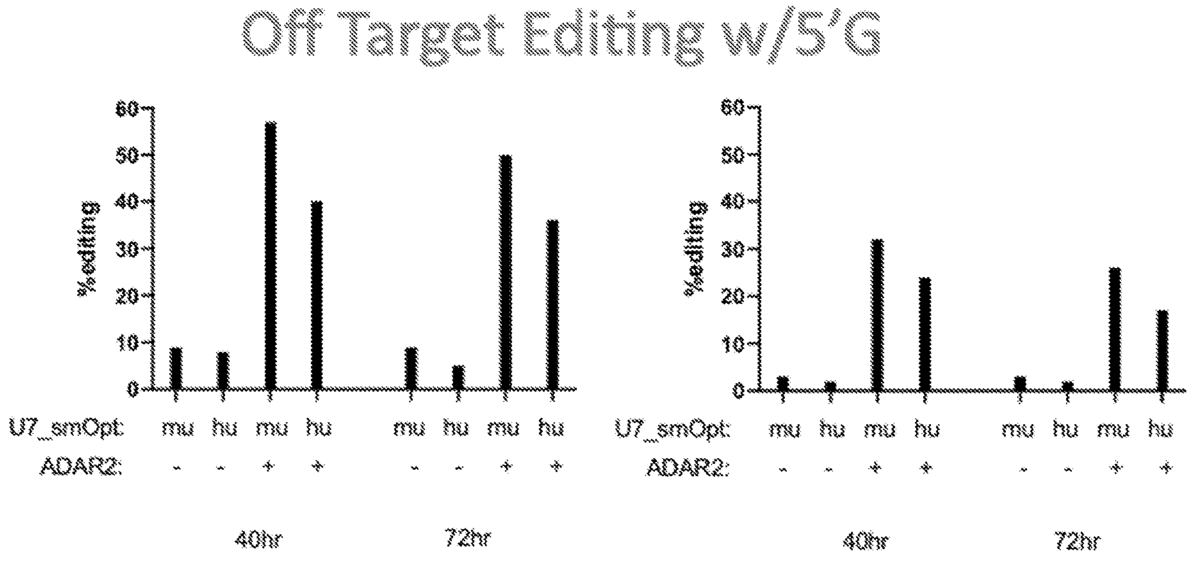

Disclosed herein are compositions of engineered guide RNAs under a U7 promoter and also comprising a smOpt hairpin sequence. Said engineered guide RNAs can hybridize to a target RNA sequence corresponding to SNCA, to facilitate ADAR-mediated editing of an adenosine (see FIG. 14). Editing of the SNCA gene was assessed by transfection of the engineered guide RNAS in K562 cells which overexpress SNCA. 1.5 μg of the engineered guide RNA was transfected into 2×10^5 SNCA-overexpressing K562 cells via nucleofection (Lonza). RNA editing was measured 40 and 72 hours after transfection. FIG. 14A is a Sanger sequence chromatogram showing on target editing (as denoted by "Target A") of 91%. FIG. 14B is a graph showing on target editing at the 40 hour and 72 hour timepoints in K562 cells with and without ADAR2 under either a mouse U7 promoter or a human U7 promoter. High levels of editing (greater than 40% for all constructs) over a sustained period of time were observed. FIG. 14C depicts graphs showing off-target editing of adenosines having a G directly

Example 14: Regulating the Protein Expression of SNCA with RNA Editing

Disclosed herein are methods for regulating the SNCA protein expression through RNA editing.

HEK293 cells were transfected with plasmids containing the target engineered polynucleotides (Guide A and Guide B) and shRNAs (shRNA1 and shRNA2) against the SNCA mRNA and mock gRNA (as a negative control). Guide A and Guide B target the start codon and 3'UTR of the SNCA mRNA, respectively. The two guides also contain different features. These features and the sequences of Guide A and Guide B are listed in TABLE 14.

TABLE 14

RNA sequence of exemplary anti-SNCA engineered polynucleotide to knockdown expression

| SEQ ID NO | Engineered Polynucleotide | RNA Sequence |
|---|---|---|
| 71 | Guide A targets start site | *GGUGCUCGCUUCGGCAGCACAU*<br>*AUACU*UUGUGAAAGAAGGACGG<br>GUCACCUUGUCUUUCCUGCUGC<br>UUCUGCCACACCCUGUUUGGUC<br>UUCUCAGCAGCAGCCACAACUC<br>CCUCCUUGGCCUUUGAAAGUCC<br>UUUCACGAAUACAUCCA"C"GG<br>CUAAUGAAUUCCUUUACACCAC<br>ACUGUCGUCGAAUGGCCACUCC<br>CAGUUCUCCGCUCACGAGGGUG<br>GAAAGGCAGAAGGCUUGAAGGC<br>AAGGCGUGAGUGGCCUGUGACU<br>AACUGUGCCAA*GCGGACUUCGG*<br>*UCCGC* |

TABLE 14-continued

RNA sequence of exemplary anti-SNCA engineered polynucleotide to knockdown expression

| SEQ ID NO | Engineered Polynucleotide | RNA Sequence |
|---|---|---|
| 72 | Guide B targets 3'UTR | GAACAUCGUAGAUUGAAGCCAC<br>AAAAUCCACAGCACACAAAGAC<br>CCUGC"C"ACCAUGUAUUCACU<br>UCAGUGAAAGGGAAGCACCGAA<br>AUGCUGAGUGGGGGCGUGG*AAU*<br>*UUUUGGAGCAGGUUUUUCUGACU*<br>*UCGGUCGGAAAACCCCU* |

(Italic font denotes U6 protective loops; underlined font denotes quantification tag; underlined and italic font denotes U7smOPT sequence; and "C" denotes the A/C mismatch in the guide)

Figure 15:
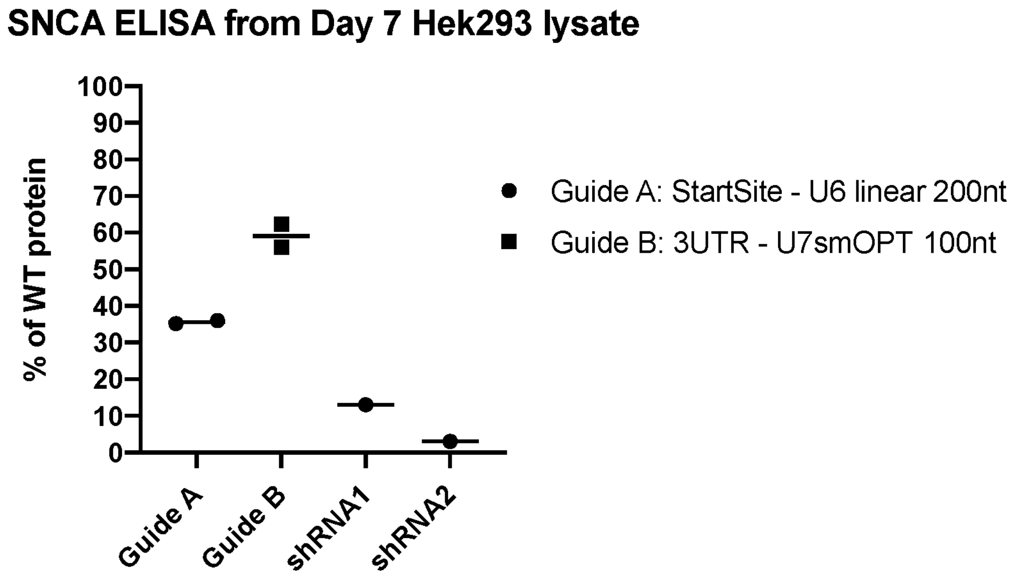
FIG. 15 shows a bar graph of the gRNA mediated SNCA protein expression reductions (detected by ELISA) normalized to the WT SNCA expression level in HEK293 cells with a mock gRNA. The cells were transfected with plasmids containing target engineered polynucleotides Guide A, Guide B, two shRNAs (shRNA1 and shRNA2) targeting the SNCA protein, and the mock gRNA. Guide A and Guide B target the start codon and 3'UTR of the SNCA mRNA, respectively. The two guides also contain different features. These features and the sequences of Guide A and Guide B are listed in TABLE 14. Guide A and Guide B decreased the abundance of the SNCA protein by about 65% and 40%, when compared to the wildtype SNCA protein, respectively. In comparison, two shRNAs (shRNA1 and shRNA2) targeting the SNCA protein knocked down its expression by about 90%-99%.

Guide A and Guide B were cloned into a U1 smOpt plasmid. Lysates were prepared 7 days after transfection, and the SNCA protein abundance from the lysate was measured by ELISA. The SNCA protein abundance of the HEK cell lysate without any transfection was used to normalize the SNCA abundance (% of WT protein). As shown by FIG. 15, Guide A and Guide B decreased the abundance of the SNCA protein by about 65% and 40%, respectively. shRNA1 and shRNA2 knocked down the SNCA protein expression by about 90%-99%.

Example 15: Tiled RNA Editing Against the SNCA mRNA

A gRNA tiling assay was performed to determine different gRNAs lengths and mismatch position, in a first assay focusing at the startsite. The guide RNAs are listed in TABLE 15.

TABLE 15

RNA Sequence of Engineered Polynucleotide Tiled Across SNCA Gene

| SEQ ID NO | RNA Sequence |
|---|---|
| 73 | AGGAGAAGGAGAAGGAGGAGGACUGGGAGGAGGAGGACGGCGACGACCA<br>GAAGGGGCCCA |
| 74 | CGACGACCAGAAGGGGCCCAAGAGAGGGGGCGGGCGACCGAGCGCCGCGA<br>CGCGGAAGUG |
| 75 | AGCGCCGCGACGCGGAAGUGAGGUGCGUGCGGGCUGCGGCGCAGACCCCG<br>GCCCGGCCCC |
| 76 | GCAGACCCCGGCCCGGCCCCUCCGAGGGCGUCCUGGGCGCUCCCUCACGC<br>CUUGCCUUCA |
| 77 | UCCCUCACGCCUUGCCUUCAAGCCUUCUGCCUUUCCGCCCUCGUGAGCGGA<br>GAACUGGGA |
| 78 | UCGUGAGCGGAGAACUGGGAGUGGCCAUUCGACGACGGUGUGGUGUAAAG<br>GAAUUCAUUA |
| 79 | UGGUGUAAAGGAAUUCAUUAGCCGUGGAUGUAUUCAUGAAAGGACUUUCA<br>AAGGCCGAGG |
| 80 | AGGACUUUCAAAGGCCGAGGAGGGAGUUGUGGCUGCUGCUGAGAAAUCCA<br>AACAGGGUGU |
| 81 | GAGAAAUCCAAACAGGGUGUGGCAGAAGCAGCAGGAAAGACAAAUGAGGG<br>UGUUCUCUAU |
| 82 | CAAAUGAGGGUGUUCUCUAUGUAGGCUCCGAAACCAAGGAGGGAGUGGUG<br>CAUGGUGUGG |

TABLE 15-continued

RNA Sequence of Engineered Polynucleotide Tiled Across SNCA Gene

| SEQ ID NO | RNA Sequence |
|---|---|
| 83 | GGGAGUGGUGCAUGGUGUGGCAACGGUGGCUGAGAAGACCAAAGAGCAAG UGACAAAUGU |
| 84 | AAAGAGCAAGUGACAAAUGUUGGAGGAGCGGUGGUGACGGGUGUGACAGC AGUAGCCCAG |
| 85 | GUGUGACAGCAGUAGCCCAGAAGACGGUGGAGGGAGCAGGGAGCAUUGCA GCAGCCACUG |
| 86 | GAGCAUUGCAGCAGCCACUGGCUUUGUCAAGAAGGACCAGUUGGGCAAGA AUGAAGAAGG |
| 87 | UUGGGCAAGAAUGAAGAAGGAGCCCCACGGGAAGGAAUUCUGGAAGAUAU GCCUGUGGAU |
| 88 | UGGAAGAUAUGCCUGUGGAUCCUGACGAUGAGGCUUAUGAAAUGCCUUCU GAGGAAGGGU |
| 89 | AAUGCCUUCUGAGGAAGGGUAUCAAGACUGCGAACCUGAAGCCUAAGAAA UAUCUUUGCU |
| 90 | GCCUAAGAAAUAUCUUUGCUCCCGGUUUCUUGAGAUCUGCUGACAGAUGUU CCAUCCUGU |
| 91 | UGACAGAUGUUCCAUCCUGUACAAGUGCUCGGUUCCAAUGUGCCCAGUCAU GACAUUUCU |
| 92 | UGCCCAGUCAUGACAUUUCUCAAAGUUUUUGCAGUGUAUCUCGAAGUCUUC CAUCAGCAG |
| 93 | UCGAAGUCUUCCAUCAGCAGUGAUUGAAGUGUCUGUACCUGCCCCCACUCA GCAUUUCGG |
| 94 | GCCCCCACUCAGCAUUUCGGUGCUUCCCUUUCGCUGAAGUGAAUACAUGGU AGCAGGGUC |
| 95 | GAAUACAUGGUAGCAGGGUCUUUGUGUGCUGUGGGUUUUGUGGCUUCAAU CUACGAUGUU |
| 96 | UGGCUUCAAUCUACGAUGUUAAGACAAAUUAAGAACACCUAAGUGACUACC ACUUAUUUC |
| 97 | AAGUGACUACCACUUAUUUCUAAAUCCUCGCUAUUUUUUUGUUGCUGUUGU UCAGAAGUU |
| 98 | GUUGCUGUUGUUCAGAAGUUGUUGGUGAUUUGCUAUCAUAUAUUAUAAGAU UUUUAGGUG |
| 99 | UAUUAUAAGAUUUUUAGGUGUCUUUUAAUGAUGCUGUCUAAGAAUAAUGAC GUAUUGUGA |
| 100 | AGAAUAAUGACGUAUUGUGAAAUUUGUUGAUAUAUAUAAUACUUAAUAAUA UGUGAGCAU |
| 101 | ACUUAAUAAUAUGUGAGCAUGAAACUAUGCGCCUAUAAAUACUAAAUAUGA AAUUUUACC |
| 102 | ACUAAAUAUGAAAUUUUACCGUUUUGCGAUGUGUUUUAUUCACUUGUGUUU GUAUAUAAA |
| 103 | CACUUGUGUUUGUAUAUAAAUGGUGAGAAUUAGAAUAAUACGUUAUCUCAU UGCAUAAAU |
| 104 | CGUUAUCUCAUUGCAUAAAUAUUUUAUUUUUAUCCCGUCUCACUUUAAUAA UAAUAAUCA |
| 105 | TGGGCCCCTTCTGGTCGTCGCCGTCCTCCTCCTCCCAGTCCTCCTCCTTCTCCTTCT CCT |
| 106 | CACTTCCGCGTCGCGGCGCTCGGTCGCCCGCCCCCTCTCTTGGGCCCCTTCTGGTC GTCG |

TABLE 15-continued

RNA Sequence of Engineered Polynucleotide Tiled Across SNCA Gene

| SEQ ID NO | RNA Sequence |
|---|---|
| 107 | ACCTCACTTCCGCGTCGCGGCGCTCGGTCGCTCGCCCCCTCTCTTGGGCCCCTTCTGGTC |
| 108 | GGGGCCGGGCCGGGGTCTGCGCCGCAGCCCGCACGCACCTCACTTCCGCGTCGCGGCGCT |
| 109 | GGACGCTCTCGGAGGGGCCGGGCCGGGGTCTGCGCCGCAGCCCGCACGCACCTCACTTCC |
| 110 | TGAAGGCAAGGCGTGAGGGAGCGCCCAGGACGCCCTCGGAGGGGCCGGGCCGGGGTCTGC |
| 111 | TCCCAGTTCTCCGCTCACGAGGGCGGAAAGGCAGAAGGCTTGAAGGCAAGGCGTGAGGGA |
| 112 | TAATGAATTCCTTTACACCACACCGTCGTCGAATGGCCACTCCCAGTTCTCCGCTCACGA |
| 113 | CCTCGGCCTTTGAAAGTCCTTTCATGAATACATCCACGGCTAATGAATTCCTTTACACCA |
| 114 | ACACCCTGTTTGGATTTCTCAGCAGCAGCCACAACTCCCTCCTCGGCCTTTGAAAGTCCT |
| 115 | ATAGAGAACACCCTCATTTGTCTTTCCTGCTGCTTCTGCCACACCCTGTTTGGATTTCTC |
| 116 | CCACACCATGCACCACTCCCTCCTTGGTTTCGGAGCCTACATAGAGAACACCCTCATTTG |
| 117 | ACATTTGTCACTTGCTCTTTGGTCTTCTCAGCCACCGTTGCCACACCATGCACCACTCCC |
| 118 | CTGGGCTACTGCTGTCACACCCGTCACCACCGCTCCTCCAACATTTGTCACTTGCTCTTT |
| 119 | CAGTGGCTGCTGCAATGCTCCCTGCTCCCTCCACCGTCTTCTGGGCTACTGCTGTCACAC |
| 120 | CCTTCTTCATTCTTGCCCAACTGGTCCTTCTTGACAAAGCCAGTGGCTGCTGCAATGCTC |
| 121 | ATCCACAGGCATATCTTCCAGAATTCCTTCCCGTGGGGCTCCTTCTTCATTCTTGCCCAA |
| 122 | ACCCTTCCTCAGAAGGCATTTCATAAGCCTCATCGTCAGGATCCACAGGCATATCTTCCA |
| 123 | AGCAAAGATATTTCTTAGGCTTCAGGTTCGCAGTCTTGATACCCTTCCTCAGAAGGCATT |
| 124 | ACAGGATGGAACATCTGTCAGCAGATCTCAAGAAACCGGGAGCAAAGATATTTCTTAGGC |
| 125 | AGAAATGTCATGACTGGGCACATTGGAACCGAGCACTTGTACAGGATGGAACATCTGTCA |
| 126 | CTGCTGATGGAAGACTTCGAGATACACTGCAAAAACTTTGAGAAATGTCATGACTGGGCA |
| 127 | CCGAAATGCTGAGTGGGGGCAGGTACAGACACTTCAATCACTGCTGATGGAAGACTTCGA |

TABLE 15-continued

RNA Sequence of Engineered Polynucleotide Tiled Across SNCA Gene

| SEQ ID NO | RNA Sequence |
|---|---|
| 128 | GACCCTGCTACCATGTATTCACTTCAGCGAAAGGGAAGCACCGAAATGCTGAGTGGGGGC |
| 129 | AACATCGTAGATTGAAGCCACAAAACCCACAGCACACAAAGACCCTGCTACCATGTATTC |
| 130 | GAAATAAGTGGTAGTCACTTAGGTGTTCTTAATTTGTCTTAACATCGTAGATTGAAGCCA |
| 131 | AACTTCTGAACAACAGCAACAAAAAAATAGCGAGGATTTAGAAATAAGTGGTAGTCACTT |
| 132 | CACCTAAAAATCTTATAATATATGATAGCAAATCACCAACAACTTCTGAACAACAGCAAC |
| 133 | TCACAATACGTCATTATTCTTAGACAGCATCATTAAAAGACACCTAAAAATCTTATAATA |
| 134 | ATGCTCACATATTATTAAGTATTATATATATCAACAAATTTCACAATACGTCATTATTCT |
| 135 | GGTAAAATTTCATATTTAGTATTTATAGGCGCATAGTTTCATGCTCACATATTATTAAGT |
| 136 | TTTATATACAAACACAAGTGAATAAAACACATCGCAAAACGGTAAAATTTCATATTTAGT |
| 137 | ATTTATGCAATGAGATAACGTATTATTCTAATTCTCACCATTTATATACAAACACAAGTG |
| 138 | TGATTATTATTATTAAAGTGAGACGGGATAAAAATAAAATATTTATGCAATGAGATAACG |
| 139 | GCTGGGGGAGTGGGAGGCAAACCCGCTAACCCGTCGTCGAATGGCCACTCCCAGTTCTCC |
| 140 | GCACCAAACTGACATTTGGGGTTTACCTACCCACATAGAGAACACCCTCTTGTGTCTTTC |
| 141 | ATCTTTGGATATAAGCACAATGGAGCTTACCCGTTGCCACACCATGCACCACTCCCTCCT |
| 142 | AAATGTAACACAAAACGTACACAGCCATACCTTGCCCAACTGGTCCTTGTTGACAAAGCC |
| 143 | TTGTTAGAAAGATTCAGCTTGGACTCCTACCCCAGAAGGCATTTCATAAGCCTCATTGTC |
| 144 | ATCCATGGCTAATGAATTCCTTTACACCACACCGGAAAACATAAAATACACTTTGAATGA |
| 145 | TGCACCACTCCCTCCTTGGTTTTGGAGCCCACAAAAACAAATTCAAGACATAAGTCTCAA |
| 146 | TTGTCACTTGCTCTTTGGTCTTCTCAGCCACTGGTACAAATAAAGAGCAACAACAGATTA |
| 147 | ATTCCTTCCTGTGGGGCTCCTTCTTCATTCCAATATTTAAAGTAAGAAGCACAAAAAGAA |
| 148 | CTTCAGGTTCGTAGTCTTGATACCCTTCCCAATATTAGAAAAATCAAAAAGACAGCACAC |

HEK392 cells were transfected with engineered polynucleotides cloned into a U1 smOpt plasmid and SNCA. The sequence of a human U1smOPT plasmid containing gRNA target the SNCA 3'UTR is listed in TABLE 16.

TABLE 16

The sequence of a human U1smOPT plasmid containing gRNA targeting the SNCA 3'UTR. The guide RNA is listed in bold.

| SEQ ID NO | SEQUENCE |
|---|---|
| 149 | TCGCGCGTTTCGGTGATGACGGTGAAAACCTCTGACACA |
| | TGCAGCTCCCGGAGACGGTCACAGCTTGTCTGTAAGCGG |
| | ATGCCGGGAGCAGACAAGCCCGTCAGGGCGCGTCAGCGG |
| | GTGTTGGCGGGTGTCGGGGCTGGCTTAACTATGCGGCAT |
| | CAGAGCAGATTGTACTGAGAGTGCACCATATGCGGTGTG |
| | AAATACCGCACAGATGCGTAAGGAGAAAATACCGCATCA |
| | GGCGCCATTCGCCATTCAGGCTGCGCAACTGTTGGGAAG |
| | GGCGATCGGTGCGGGCCTCTTCGCTATTACGCCAGCTGG |
| | CGAAAGGGGGATGTGCTGCAAGGCGATTAAGTTGGGTAA |
| | CGCCAGGGTTTTCCCAGTCACGACGTTGTAAAACGACGG |
| | CCAGTGAATTGACGCGCCATTGGGATGTTGTAAAACGAC |
| | GGCCAGTGAACCTGCAGGCAGCTGCGCGCTCGCTCGCTC |
| | ACTGAGGCCGCCCGGGCAAAGCCCGGGCGTCGGGCGACC |
| | TTTGGTCGCCCGGCCTCAGTGAGCGAGCGAGCGCGCAGA |
| | GAGGGAGTGGCCAACTCCATCACTAGGGGTTCCTGCGGC |
| | CGCACGCGTGGAGTAAGGACCAGCTTCTTTGGGAGAGAA |
| | CAGACGCAGGGGCGGGAGGGAAAAAGGGAGAGGCAGACG |
| | TCACTTCCTCTTGGCGACTCTGGCAGCAGATTGGTCGGT |
| | TGAGTGGCAGAAAGGCAGACGGGGACTGGGCAAGGCACT |
| | GTCGGTGACATCACGGACAGGGCGACTTCTATGTAGATG |
| | AGGCAGCGCAGAGGCTGCTGCTTCGCCACTTGCTGCTTC |
| | GCCACGAAGGGAGTTCCCGTGCCCTGGGAGCGGGTTCAG |
| | GACCGCTGATCGGAAGTGAGAATCCCAGCTGTGTGTCAG |
| | GGCTGGAAAGGGCTCGGGAGTGCGCGGGGCAAGTGACCG |
| | TGTGTGTAAAGAGTGAGGCGTATGAGGCTGTGTCGGGGC |
| | AGAGCCCGAAGATCTCACCGAACATCGTAGATCGAAGCC |
| | ACAAAACCCACAGCACACAAAGACCCTGCCACCATGCAT |
| | TCACTTCAGCGAAAGGGAAGCACCGAAATGCCGAGTGGG |
| | GGCGTGGAATTTTTGGAGCAGGTTTTCTGACTTCGGTCG |
| | GAAAACCCCTCCCAATTTCACTGGTCTACAATGAAAGCA |
| | AAACAGTTCTCTTCCCCGCTCCCCGGTGTGTGAGAGGGG |
| | CTTTGATCCTTCTCTGGTTTCCTAGGAAACGCGTATGTG |
| | CTAGCGTACTGAGTCGCCCAGTCTCAGATAGATCCGACG |
| | CCGCCATCTCTAGGCCCGCGCCGGCCCCCTCGCACAGAC |
| | TTGTGGGAGAAGCTCGGCTACTCCCCTGCCCCGGTTAAT |
| | TTGCATATAATATTTCCTAGTAACTATAGAGGCTTAATG |

TABLE 16-continued

The sequence of a human U1smOPT plasmid containing gRNA targeting the SNCA 3'UTR. The guide RNA is listed in bold.

| SEQ ID NO | SEQUENCE |
|---|---|
| | TGCGATAAAAGACAGATAATCTGTTCTTTTTAATACTAG |
| | CTACATTTTACATGATAGGCTTGGATTTCTATAAGAGAT |
| | ACAAATACTAAATTATTATTTTAAAAAACAGCACAAAGG |
| | AAACTCACCCTAACTGTAAAGTAATTGTGTGTTTTGAGA |
| | CTATAAATATCCCTTGGAGAAAAGCCTTGTTTGGAATTC |
| | ATACGCGTTGACATTGATTATTGACTAGTTATTAATAGT |
| | AATCAATTACGGGGTCATTAGTTCATAGCCCATATATGG |
| | AGTTCCGCGTTACATAACTTACGGTAAATGGCCCGCCTG |
| | GCTGACCGCCCAACGACCCCCGCCCATTGACGTCAATAA |
| | TGACGTATGTTCCCATAGTAACGCCAATAGGGACTTTCC |
| | ATTGACGTCAATGGGTGGAGTATTTACGGTAAACTGCCC |
| | ACTTGGCAGTACATCAAGTGTATCATATGCCAAGTACGC |
| | CCCCTATTGACGTCAATGACGGTAAATGGCCCGCCTGGC |
| | ATTATGCCCAGTACATGACCTTATGGGACTTTCCTACTT |
| | GGCAGTACATCTACGTATTAGTCATCGCTATTACCATGG |
| | TGATGCGGTTTTGGCAGTACATCAATGGGCGTGGATAGC |
| | GGTTTGACTCACGGGGATTTCCAAGTCTCCACCCCATTG |
| | ACGTCAATGGGAGTTTGTTTTGGCACCAAAATCAACGGG |
| | ACTTTCCAAAATGTCGTAACAACTCCGCCCCATTGACGC |
| | AAATGGGCGGTAGGCGTGTACGGTGGGAGGTCTATATAA |
| | GCAGAGCTCGTTTAGTGAACCGTCAGATCGCCTGGAGAC |
| | GCCATCCACGCTGTTTTGACCTCCATAGAAGACACCGGG |
| | ACCGATCCAGCCTCCGGACTCTAGAGGATCGAACCCTTA |
| | AGCCGCCACCATGGTGAGCAAGGGCGAGGAGCTGTTCAC |
| | CGGGGTGGTGCCCATCCTGGTCGAGCTGGACGGCGACGT |
| | AAACGGCCACAAGTTCAGCGTGTCCGGCGAGGGCGAGGG |
| | CGATGCCACCTACGGCAAGCTGACCCTGAAGTTCATCTG |
| | CACCACCGGCAAGCTGCCCGTGCCCTGGCCCACCCTCGT |
| | GACCACCCTGACCTACGGCGTGCAGTGCTTCAGCCGCTA |
| | CCCCGACCACATGAAGCAGCACGACTTCTTCAAGTCCGC |
| | CATGCCCGAAGGCTACGTCCAGGAGCGCACCATCTTCTT |
| | CAAGGACGACGGCAACTACAAGACCCGCGCCGAGGTGAA |
| | GTTCGAGGGCGACACCCTGGTGAACCGCATCGAGCTGAA |
| | GGGCATCGACTTCAAGGAGGACGGCAACATCCTGGGGCA |
| | CAAGCTGGAGTACAACTACAACAGCCACAACGTCTATAT |
| | CATGGCCGACAAGCAGAAGAACGGCATCAAGGTGAACTT |

TABLE 16-continued

The sequence of a human U1smOPT plasmid containing gRNA targeting the SNCA 3'UTR. The guide RNA is listed in bold.

| SEQ ID NO | SEQUENCE |
|---|---|
| | CAAGATCCGCCACAACATCGAGGACGGCAGCGTGCAGCT |
| | CGCCGACCACTACCAGCAGAACACCCCCATCGGCGACGG |
| | CCCCGTGCTGCTGCCCGACAACCACTACCTGAGCACCCA |
| | GTCCGCCCTGAGCAAAGACCCCAACGAGAAGCGCGATCA |
| | CATGGTCCTGCTGGAGTTCGTGACCGCCGCCGGGATCAC |
| | TCTCGGCATGGACGAGCTGTACAAGTACTCAGATCTCGA |
| | GCTCAAGTGAACCGGTCAGACATGATAAGATACATTGAT |
| | GAGTTTGGACAAACCACAACTAGAATGCAGTGAAAAAAA |
| | TGCTTTATTTGTGAAATTTGTGATGCTATTGCTTTATTT |
| | GTAACCATTATAAGCTGCAATAAACAAGTTAACAACAAC |
| | AATTGCATTCATTTTATGTTTCAGGTTCAGGGGGAGGTG |
| | TGGGAGGTTTTTTAAACACGTGCGGACCGAGCGGCCGCA |
| | GGAACCCCTAGTGATGGAGTTGGCCACTCCCTCTCTGCG |
| | CGCTCGCTCGCTCACTGAGGCCGGGCGACCAAAGGTCGC |
| | CCGACGCCCGGGCTTTGCCCGGGCGGCCTCAGTGAGCGA |
| | GCGAGCGCGCAGCTGCCTGCAGGCTTGGATCCCAATGGC |
| | GCGCCGAGCTTGGCTCGAGCATGGTCATAGCTGTTTCCT |
| | GTGTGAAATTGTTATCCGCTCACAATTCCACACAACATA |
| | CGAGCCGGAAGCATAAAGTGTAAAGCCTGGGGTGCCTAA |
| | TGAGTGAGCTAACTCACATTAATTGCGTTGCGCTCACTG |
| | CCCGCTTTCCAGTCGGGAAACCTGTCGTGCCAGCTGCAT |
| | TAATGAATCGGCCAACGCGCGGGGAGAGGCGGTTTGCGT |
| | ATTGGGCGCTCTTCCGCTTCCTCGCTCACTGACTCGCTG |
| | CGCTCGGTCGTTCGGCTGCGGCGAGCGGTATCAGCTCAC |
| | TCAAAGGCGGTAATACGGTTATCCACAGAATCAGGGGAT |
| | AACGCAGGAAAGAACATGTGAGCAAAAGGCCAGCAAAAG |
| | GCCAGGAACCGTAAAAAGGCCGCGTTGCTGGCGTTTTTC |
| | CATAGGCTCCGCCCCCCTGACGAGCATCACAAAAATCGA |
| | CGCTCAAGTCAGAGGTGGCGAAACCCGACAGGACTATAA |
| | AGATACCAGGCGTTTCCCCCTGGAAGCTCCCTCGTGCGC |
| | TCTCCTGTTCCGACCCTGCCGCTTACCGGATACCTGTCC |
| | GCCTTTCTCCCTTCGGGAAGCGTGGCGCTTTCTCATAGC |
| | TCACGCTGTAGGTATCTCAGTTCGGTGTAGGTCGTTCGC |
| | TCCAAGCTGGGCTGTGTGCACGAACCCCCCGTTCAGCCC |
| | GACCGCTGCGCCTTATCCGGTAACTATCGTCTTGAGTCC |
| | AACCCGGTAAGACACGACTTATCGCCACTGGCAGCAGCC |

TABLE 16-continued

The sequence of a human U1smOPT plasmid containing gRNA targeting the SNCA 3'UTR. The guide RNA is listed in bold.

| SEQ ID NO | SEQUENCE |
|---|---|
| | ACTGGTAACAGGATTAGCAGAGCGAGGTATGTAGGCGGT |
| | GCTACAGAGTTCTTGAAGTGGTGGCCTAACTACGGCTAC |
| | ACTAGAAGAACAGTATTTGGTATCTGCGCTCTGCTGAAG |
| | CCAGTTACCTTCGGAAAAAGAGTTGGTAGCTCTTGATCC |
| | GGCAAACAAACCACCGCTGGTAGCGGTGGTTTTTTTGTT |
| | TGCAAGCAGCAGATTACGCGCAGAAAAAAAGGATCTCAA |
| | GAAGATCCTTTGATCTTTTCTACGGGGTCTGACGCTCAG |
| | TGGAACGAAAACTCACGTTAAGGGATTTTGGTCATGAGA |
| | TTATCAAAAAGGATCTTCACCTAGATCCTTTTAAATTAA |
| | AAATGAAGTTTTAAATCAATCTAAAGTATATATGAGTAA |
| | ACTTGGTCTGACAGTTAGAAAAACTCATCGAGCATCAAA |
| | TGAAACTGCAATTTATTCATATCAGGATTATCAATACCA |
| | TATTTTTGAAAAAGCCGTTTCTGTAATGAAGGAGAAAAC |
| | TCACCGAGGCAGTTCCATAGGATGGCAAGATCCTGGTAT |
| | CGGTCTGCGATTCCGACTCGTCCAACATCAATACAACCT |
| | ATTAATTTCCCCTCGTCAAAAATAAGGTTATCAAGTGAG |
| | AAATCACCATGAGTGACGACTGAATCCGGTGAGAATGGC |
| | AAAAGTTTATGCATTTCTTTCCAGACTTGTTCAACAGGC |
| | CAGCCATTACGCTCGTCATCAAAATCACTCGCATCAACC |
| | AAACCGTTATTCATTCGTGATTGCGCCTGAGCGAGACGA |
| | AATACGCGATCGCTGTTAAAAGGACAATTACAAACAGGA |
| | ATCGAATGCAACCGGCGCAGGAACACTGCCAGCGCATCA |
| | ACAATATTTTCACCTGAATCAGGATATTCTTCTAATACC |
| | TGGAATGCTGTTTTCCCAGGGATCGCAGTGGTGAGTAAC |
| | CATGCATCATCAGGAGTACGGATAAAATGCTTGATGGTC |
| | GGAAGAGGCATAAATTCCGTCAGCCAGTTTAGTCTGACC |
| | ATCTCATCTGTAACATCATTGGCAACGCTACCTTTGCCA |
| | TGTTTCAGAAACAACTCTGGCGCATCGGGCTTCCCATAC |
| | AATCGATAGATTGTCGCACCTGATTGCCCGACATTATCG |
| | CGAGCCCATTTATACCCATATAAATCAGCATCCATGTTG |
| | GAATTTAATCGCGGCCTAGAGCAAGACGTTTCCCGTTGA |
| | ATATGGCTCATACTCTTCCTTTTTCAATATTATTGAAGC |
| | ATTTATCAGGGTTATTGTCTCATGAGCGGATACATATTT |
| | GAATGTATTTAGAAAAATAAACAAATAGGGGTTCCGCGC |
| | ACATTTCCCCGAAAAGTGCCACCTGACGTCTAAGAAACC |

TABLE 16-continued

The sequence of a human U1smOPT plasmid containing gRNA targeting the SNCA 3'UTR. The guide RNA is listed in bold.

| SEQ ID NO | SEQUENCE |
|---|---|
| | ATTATTATCATGACATTAACCTATAAAAATAGGCGTATC<br>ACGAGGCCCTTTCGTC |

The cell lysates were prepared 7 days after transfection. ELISA was used to measure the abundance of SNCA protein in the cell lysate. FIG. 15 shows that the engineered polynucleotide Guide A and Guide B decreased the abundance of the mutated SNCA protein by about 65% and 40%, when compared to the wildtype SNCA protein, respectively. In comparison, two shRNAs (shRNA1 and shRNA2) targeting the mutated SNCA protein knocked down its expression by about 90%-99%.

Example 16: Editing of a Target Adenosine in APP

This example describes editing of a target adenosine in APP using engineered guide RNAs of the present disclosure. Guides were designed to test whether endogenous ADAR could be harnessed to recognize the endogenous APP mRNA in the wildtype and programmed to edit an adenosine two nucleotides away from the clinically relevant adenosine of interest (M671V). The guide sequences targeting the adenosine in APP were designed and are summarized in TABLE 17.

TABLE 17

RNA Sequence of Exemplary anti-APP Engineered Polynucleotides and their Target RNA (underlining indicates the target adenosine)

| SEQ ID NO | Engineered Polynucleotide | Engineered Polynucleotide Sequence | Target RNA Sequence |
|---|---|---|---|
| 159 | 0.100.50 (Exon-Exon) | UUGAUGAUGAACUUCA<br>UAUCCUGAGUCAUGUC<br>GGAAUUCUGCAUCCAU<br>CCUCACUUCAGAGAUC<br>UCCUCCGUCUUGAUAU<br>UUGUCAACCCAGAACC<br>UGGU | ACCAGGUUCUGGGUUGAC<br>AAAUAUCAAGACGGAGGA<br>GAUCUCUGAAGUGAAGAU<br>GGAUGCAGAAUUCCGACA<br>UGACUCAGGAUAUGAAGU<br>UCAUCAUCAA<br>(SEQ ID NO: 150) |
| 160 | 0.100.50 (Exon-Intron) | UUGAUGAUGAACUUCA<br>UAUCCUGAGUCAUGUC<br>GGAAUUCUGCAUCCAU<br>CCUCACUUCAGAGAUC<br>UCCUCCGUCUUGAUAU<br>UUGUCAACCCAGAACC<br>UGUA | UACAGGUUCUGGGUUGAC<br>AAAUAUCAAGACGGAGGA<br>GAUCUCUGAAGUGAAGAU<br>GGAUGCAGAAUUCCGACA<br>UGACUCAGGAUAUGAAGU<br>UCAUCAUCAA<br>(SEQ ID NO: 151) |
| 161 | 0.90.45 (Exon only) | GAUGAACUUCAUAUCC<br>UGAGUCAUGUCGGAAU<br>UCUGCAUCCAUCCUCA<br>CUUCAGAGAUCUCCUC<br>CGUCUUGAUAUUUGUC<br>AACCCAGAAC | GUUCUGGGUUGACAAAUA<br>UCAAGACGGAGGAGAUCU<br>CUGAAGUGAAGAUGGAUG<br>CAGAAUUCCGACAUGACU<br>CAGGAUAUGAAGUUCAUC<br>(SEQ ID NO: 152) |
| 162 | 0.90.45 (01) | ATGATGAACTTCATAT<br>CCTGAGTCATGTCGGA<br>ATTCTGCATCCACCTT<br>CACTTCAGAGATCTCC<br>TCCGTCTTGATATTTG<br>TCAACCCAGA | TCTGGGTTGACAAATATCA<br>AGACGGAGGAGATCTCTG<br>AAGTGAAGATGGATGCAG<br>AATTCCGACATGACTCAG<br>GATATGAAGTTCATCAT<br>(SEQ ID NO: 153) |

TABLE 17-continued

RNA Sequence of Exemplary anti-APP Engineered Polynucleotides and their Target RNA (underlining indicates the target adenosine)

| SEQ ID NO | Engineered Polynucleotide | Engineered Polynucleotide Sequence | Target RNA Sequence |
|---|---|---|---|
| 163 | 0.90.70 (02) | CTTCTGCAAAGAACAC<br>CAATTTTTGATGATGA<br>ACTTCATATCCTGAGT<br>CATGTCGGAATTCTGC<br>ATCCACCTTCACTTCA<br>GAGATCTCCT | AGGAGATCTCTGAAGTGA<br>AGATGGATGCAGAATTCC<br>GACATGACTCAGGATATG<br>AAGTTCATCATCAAAAATT<br>GGTGTTCTTTGCAGAAG<br>(SEQ ID NO: 154) |
| 164 | 0.90.45 (03) | GATGATGAACTTCATA<br>TCCTGAGTCATGTCGG<br>AATTCTTCATCCACGT<br>TCACTTCCAGATCTCC<br>TCCGTCTTGATATTTG<br>TCAACCCAGA | TCTGGGTTGACAAATATCA<br>AGACGGAGGAGATCTGGA<br>AGTGAACATGGATGAAGA<br>ATTCCGACATGACTCAGG<br>ATATGAAGTTCATCATC<br>(SEQ ID NO: 155) |
| 165 | 0.90.70 (04) | TCTTCTGCAAAGAACA<br>CCAATTTTTGATGATG<br>AACTTCATATCCTGAG<br>TCATGTCGGAATTCTT<br>CATCCACGTTCACTTC<br>CAGATCTCCT | AGGAGATCTGGAAGTGAA<br>CATGGATGAAGAATTCCG<br>ACATGACTCAGGATATGA<br>AGTTCATCATCAAAAATTG<br>GTGTTCTTTGCAGAAGA<br>(SEQ ID NO: 156) |
| 166 | 0.60.50 (05) | ATCCTGAGTCATGTCG<br>GAATTCTTCATCCACG<br>TTCACTTCCAGATCTC<br>CTCCGTCTTGAT | ATCAAGACGGAGGAGATC<br>TGGAAGTGAACATGGATG<br>AAGAATTCCGACATGACT<br>CAGGAT<br>(SEQ ID NO: 157) |
| 167 | 0.60.40 (06) | TGAACTTCATATCCTG<br>AGTCATGTCGGAATTC<br>TTCATCCACGTTCACT<br>TCCAGATCTCCT | AGGAGATCTGGAAGTGAA<br>CATGGATGAAGAATTCCG<br>ACATGACTCAGGATATGA<br>AGTTCA<br>(SEQ ID NO: 158) |

Figure 16A:
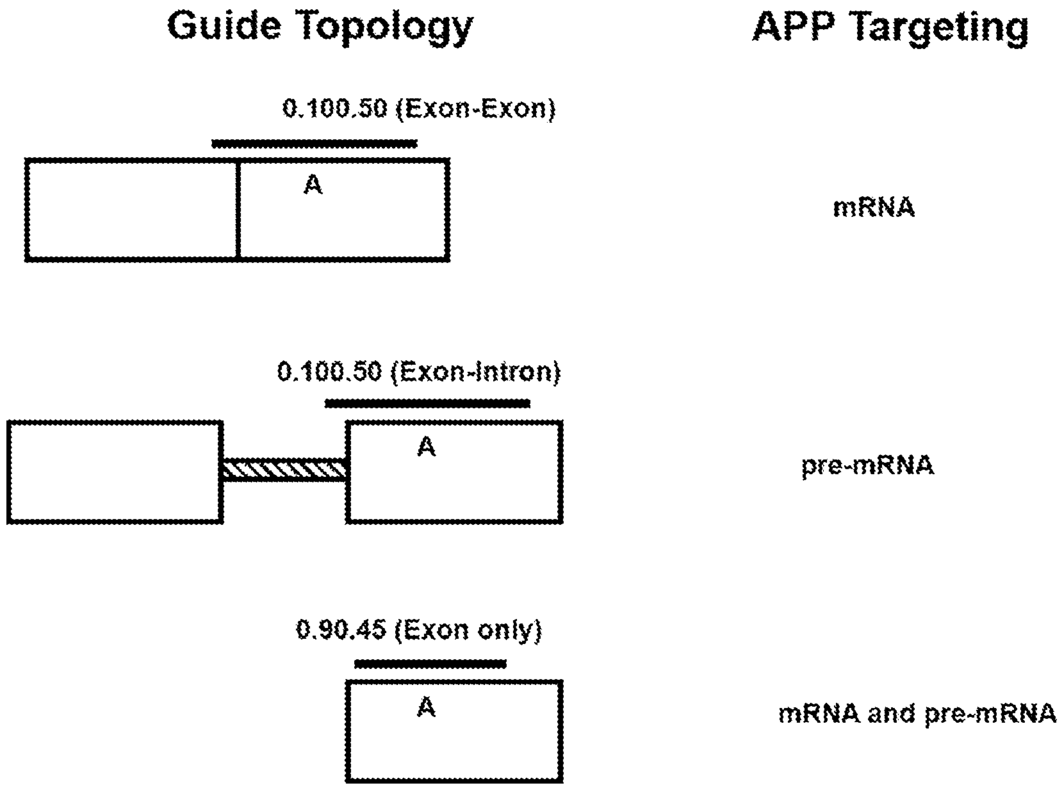
FIG. 16A-FIG. 16B show RNA editing of APP using engineered polynucleotides targeting different regions of the APP transcript.

Engineered polynucleotides were tested for recruitment and editing of a target adenosine by ADAR in a model cell line and compared to negative controls (a GFP plasmid and a no transfection control). The engineered guide RNAs were designed against pre-mRNA and mRNA, as shown in FIG. 16A. 0.100.50 (Exon-Exon) (SEQ ID NO: 159) is specific to the APP mRNA because it targets the continuous sequence across the exon with the target adenosine and its preceding exon. 0.100.50 (Exon-Intron) (SEQ ID NO: 160) is specific to the APP pre-mRNA because it targets the continuous sequence between the exon with the target adenosine and its preceding intron. 0.90.45 (Exon only) (SEQ ID NO: 161) can target both APP pre-mRNA and mRNA because it only targets the sequence of the target adenosine.

Each engineered polynucleotide was cloned onto a pAAV plasmid backbone (STX-364. The sequence of STX-364 is listed in TABLE 18.

TABLE 18

The complete sequence of STX-364

| SEQ ID NO | SEQUENCE |
|---|---|
| 168 | TCGCGCGTTTCGGTGATGACGGTGAAAACCTCTGACACATGC<br>AGCTCCCGGAGACGGTCACAGCTTGTCTGTAAGCGGATGCCG<br>GGAGCAGACAAGCCCGTCAGGGCGCGTCAGCGGGTGTTGGCG |

TABLE 18-continued

The complete sequence of STX-364

| SEQ ID NO | SEQUENCE |
|---|---|
| | GGTGTCGGGGCTGGCTTAACTATGCGGCATCAGAGCAGATTG |
| | TACTGAGAGTGCACCATATGCGGTGTGAAATACCGCACAGAT |
| | GCGTAAGGAGAAAATACCGCATCAGGCGCCATTCGCCATTCA |
| | GGCTGCGCAACTGTTGGGAAGGGCGATCGGTGCGGGCCTCTT |
| | CGCTATTACGCCAGCTGGCGAAAGGGGGATGTGCTGCAAGGC |
| | GATTAAGTTGGGTAACGCCAGGGTTTTCCCAGTCACGACGTT |
| | GTAAAACGACGGCCAGTGAATTGACGCGCCATTGGGATGTTG |
| | TAAAACGACGGCCAGTGAACCTGCAGGCAGCTGCGCGCTCGC |
| | TCGCTCACTGAGGCCGCCCGGGCAAAGCCCGGGCGTCGGGCG |
| | ACCTTTGGTCGCCCGGCCTCAGTGAGCGAGCGAGCGCGCAGA |
| | GAGGGAGTGGCCAACTCCATCACTAGGGGTTCCTGCGGCCGC |
| | ACGCGTGGAGGAGGGCCTATTTCCCATGATTCCTTCATATTT |
| | GCATATACGATACAAGGCTGTTAGAGAGATAATTAGAATTAA |
| | TTTGACTGTAAACACAAAGATATTAGTACAAAATACGTGACG |
| | TAGAAAGTAATAATTTCTTGGGTAGTTTGCAGTTTTAAAATT |
| | ATGTTTTAAAATGGACTATCATATGCTTACCGTAACTTGAAA |
| | GTATTTCGATTTCTTGGCTTTATATATCTTGTGGAAAGGACG |
| | AAACACCGAGAGACCAGCTGGATGGTCTCTTTTTTTTTCGTAC |
| | TGAGTCGCCCAGTCTCAGATAGATCCGACGCCGCCATCTCTA |
| | GGCCCGCGCCGGCCCCCTCGCACAGACTTGTGGGAGAAGCTC |
| | GGCTACTCCCCTGCCCCGGTTAATTTGCATATAATATTTCCT |
| | AGTAACTATAGAGGCTTAATGTGCGATAAAAGACAGATAATC |
| | TGTTCTTTTTAATACTAGCTACATTTTACATGATAGGCTTGG |
| | ATTTCTATAAGAGATACAAATACTAAATTATTATTTTAAAAA |
| | ACAGCACAAAAGGAAACTCACCCTAACTGTAAAGTAATTGTG |
| | TGTTTTGAGACTATAAATATCCCTTGGAGAAAAGCCTTGTTT |
| | GGATGTCTTCACAGGAAGACGCTTTTTTTGCGGCCGCATACG |
| | CGTTGACATTGATTATTGACTAGTTATTAATAGTAATCAATT |
| | ACGGGGTCATTAGTTCATAGCCCATATATGGAGTTCCGCGTT |
| | ACATAACTTACGGTAAATGGCCCGCCTGGCTGACCGCCCAAC |
| | GACCCCCGCCCATTGACGTCAATAATGACGTATGTTCCCATA |
| | GTAACGCCAATAGGGACTTTCCATTGACGTCAATGGGTGGAG |
| | TATTTACGGTAAACTGCCCACTTGGCAGTACATCAAGTGTAT |
| | CATATGCCAAGTACGCCCCCTATTGACGTCAATGACGGTAAA |
| | TGGCCCGCCTGGCATTATGCCCAGTACATGACCTTATGGGAC |
| | TTTCCTACTTGGCAGTACATCTACGTATTAGTCATCGCTATT |
| | ACCATGGTGATGCGGTTTTGGCAGTACATCAATGGGCGTGGA |

TABLE 18-continued

The complete sequence of STX-364

| SEQ ID NO | SEQUENCE |
|---|---|
| | TAGCGGTTTGACTCACGGGGATTTCCAAGTCTCCACCCCATT |
| | GACGTCAATGGGAGTTTGTTTTGGCACCAAAATCAACGGGAC |
| | TTTCCAAAATGTCGTAACAACTCCGCCCCATTGACGCAAATG |
| | GGCGGTAGGCGTGTACGGTGGGAGGTCTATATAAGCAGAGCT |
| | CGTTTAGTGAACCGTCAGATCGCCTGGAGACGCCATCCACGC |
| | TGTTTTGACCTCCATAGTAGACACCGGGACCGATCCAGCCTC |
| | CGGACTCTAGAGGATCGAACCCTTAAGCCGCCACCATGGTGA |
| | GCAAGGGCGAGGAGCTGTTCACCGGGGTGGTGCCCATCCTGG |
| | TCGAGCTGGACGGCGACGTAAACGGCCACAAGTTCAGCGTGT |
| | CCGGCGAGGGCGAGGGCGATGCCACCTACGGCAAGCTGACCC |
| | TGAAGTTCATCTGCACCACCGGCAAGCTGCCCGTGCCCTGGC |
| | CCACCCTCGTGACCACCCTGACCTACGGCGTGCAGTGCTTCA |
| | GCCGCTACCCCGACCACATGAAGCAGCACGACTTCTTCAAGT |
| | CCGCCATGCCCGAAGGCTACGTCCAGGAGCGCACCATCTTCT |
| | TCAAGGACGACGGCAACTACAAGACCCGCGCCGAGGTGAAGT |
| | TCGAGGGCGACACCCTGGTGAACCGCATCGAGCTGAAGGGCA |
| | TCGACTTCAAGGAGGACGGCAACATCCTGGGGCACAAGCTGG |
| | AGTACAACTACAACAGCCACAACGTCTATATCATGGCCGACA |
| | AGCAGAAGAACGGCATCAAGGTGAACTTCAAGATCCGCCACA |
| | ACATCGAGGACGGCAGCGTGCAGCTCGCCGACCACTACCAGC |
| | AGAACACCCCCATCGGCGACGGCCCCGTGCTGCTGCCCGACA |
| | ACCACTACCTGAGCACCCAGTCCGCCCTGAGCAAAGACCCCA |
| | ACGAGAAGCGCGATCACATGGTCCTGCTGGAGTTCGTGACCG |
| | CCGCCGGGATCACTCTCGGCATGGACGAGCTGTACAAGTACT |
| | CAGATCTCGAGCTCAAGTGAACCGGTCAGACATGATAAGATA |
| | CATTGATGAGTTTGGACAAACCACAACTAGAATGCAGTGAAA |
| | AAAATGCTTTATTTGTGAAATTTGTGATGCTATTGCTTTATT |
| | TGTAACCATTATAAGCTGCAATAAACAAGTTAACAACAACAA |
| | TTGCATTCATTTTATGTTTCAGGTTCAGGGGGAGGTGTGGGA |
| | GGTTTTTTAAACACGTGCGGACCGAGCGGCCGCAGGAACCCC |
| | TAGTGATGGAGTTGGCCACTCCCTCTCTGCGCGCTCGCTCGC |
| | TCACTGAGGCCGGGCGACCAAAGGTCGCCCGACGCCCGGGCT |
| | TTGCCCGGGCGGCCTCAGTGAGCGAGCGAGCGCGCAGCTGCC |
| | TGCAGGCTTGGATCCCAATGGCGCGCCGAGCTTGGCTCGAGC |
| | ATGGTCATAGCTGTTTCCTGTGTGAAATTGTTATCCGCTCAC |
| | AATTCCACACAACATACGAGCCGGAAGCATAAAGTGTAAAGC |
| | CTGGGGTGCCTAATGAGTGAGCTAACTCACATTAATTGCGTT |

TABLE 18-continued

The complete sequence of STX-364

| SEQ ID NO | SEQUENCE |
|---|---|
| | GCGCTCACTGCCCGCTTTCCAGTCGGGAAACCTGTCGTGCCA |
| | GCTGCATTAATGAATCGGCCAACGCGCGGGGAGAGGCGGTTT |
| | GCGTATTGGGCGCTCTTCCGCTTCCTCGCTCACTGACTCGCT |
| | GCGCTCGGTCGTTCGGCTGCGGCGAGCGGTATCAGCTCACTC |
| | AAAGGCGGTAATACGGTTATCCACAGAATCAGGGGATAACGC |
| | AGGAAAGAACATGTGAGCAAAAGGCCAGCAAAAGGCCAGGAA |
| | CCGTAAAAAGGCCGCGTTGCTGGCGTTTTTCCATAGGCTCCG |
| | CCCCCCTGACGAGCATCACAAAAATCGACGCTCAAGTCAGAG |
| | GTGGCGAAACCCGACAGGACTATAAAGATACCAGGCGTTTCC |
| | CCCTGGAAGCTCCCTCGTGCGCTCTCCTGTTCCGACCCTGCC |
| | GCTTACCGGATACCTGTCCGCCTTTCTCCCTTCGGGAAGCGT |
| | GGCGCTTTCTCATAGCTCACGCTGTAGGTATCTCAGTTCGGT |
| | GTAGGTCGTTCGCTCCAAGCTGGGCTGTGTGCACGAACCCCC |
| | CGTTCAGCCCGACCGCTGCGCCTTATCCGGTAACTATCGTCT |
| | TGAGTCCAACCCGGTAAGACACGACTTATCGCCACTGGCAGC |
| | AGCCACTGGTAACAGGATTAGCAGAGCGAGGTATGTAGGCGG |
| | TGCTACAGAGTTCTTGAAGTGGTGGCCTAACTACGGCTACAC |
| | TAGAAGAACAGTATTTGGTATCTGCGCTCTGCTGAAGCCAGT |
| | TACCTTCGGAAAAAGAGTTGGTAGCTCTTGATCCGGCAAACA |
| | AACCACCGCTGGTAGCGGTGGTTTTTTTGTTTGCAAGCAGCA |
| | GATTACGCGCAGAAAAAAAGGATCTCAAGAAGATCCTTTGAT |
| | CTTTTCTACGGGGTCTGACGCTCAGTGGAACGAAAACTCACG |
| | TTAAGGGATTTTGGTCATGAGATTATCAAAAAGGATCTTCAC |
| | CTAGATCCTTTTAAATTAAAAATGAAGTTTTAAATCAATCTA |
| | AAGTATATATGAGTAAACTTGGTCTGACAGTTAGAAAAACTC |
| | ATCGAGCATCAAATGAAACTGCAATTTATTCATATCAGGATT |
| | ATCAATACCATATTTTTGAAAAAGCCGTTTCTGTAATGAAGG |
| | AGAAAACTCACCGAGGCAGTTCCATAGGATGGCAAGATCCTG |
| | GTATCGGTCTGCGATTCCGACTCGTCCAACATCAATACAACC |
| | TATTAATTTCCCCTCGTCAAAAATAAGGTTATCAAGTGAGAA |
| | ATCACCATGAGTGACGACTGAATCCGGTGAGAATGGCAAAAG |
| | TTTATGCATTTCTTTCCAGACTTGTTCAACAGGCCAGCCATT |
| | ACGCTCGTCATCAAAATCACTCGCATCAACCAAACCGTTATT |
| | CATTCGTGATTGCGCCTGAGCGAGACGAAATACGCGATCGCT |
| | GTTAAAAGGACAATTACAAACAGGAATCGAATGCAACCGGCG |
| | CAGGAACACTGCCAGCGCATCAACAATATTTTCACCTGAATC |
| | AGGATATTCTTCTAATACCTGGAATGCTGTTTTCCCAGGGAT |
| | CGCAGTGGTGAGTAACCATGCATCATCAGGAGTACGGATAAA |
| | ATGCTTGATGGTCGGAAGAGGCATAAATTCCGTCAGCCAGTT |
| | TAGTCTGACCATCTCATCTGTAACATCATTGGCAACGCTACC |
| | TTTGCCATGTTTCAGAAACAACTCTGGCGCATCGGGCTTCCC |
| | ATACAATCGATAGATTGTCGCACCTGATTGCCCGACATTATC |
| | GCGAGCCCATTTATACCCATATAAATCAGCATCCATGTTGGA |
| | ATTTAATCGCGGCCTAGAGCAAGACGTTTCCCGTTGAATATG |
| | GCTCATACTCTTCCTTTTTCAATATTATTGAAGCATTTATCA |
| | GGGTTATTGTCTCATGAGCGGATACATATTTGAATGTATTTA |
| | GAAAAATAAACAAATAGGGGTTCCGCGCACATTTCCCCGAAA |
| | AGTGCCACCTGACGTCTAAGAAACCATTATTATCATGACATT |
| | AACCTATAAAAATAGGCGTATCACGAGGCCCTTTCGTC |

Figure 16B:
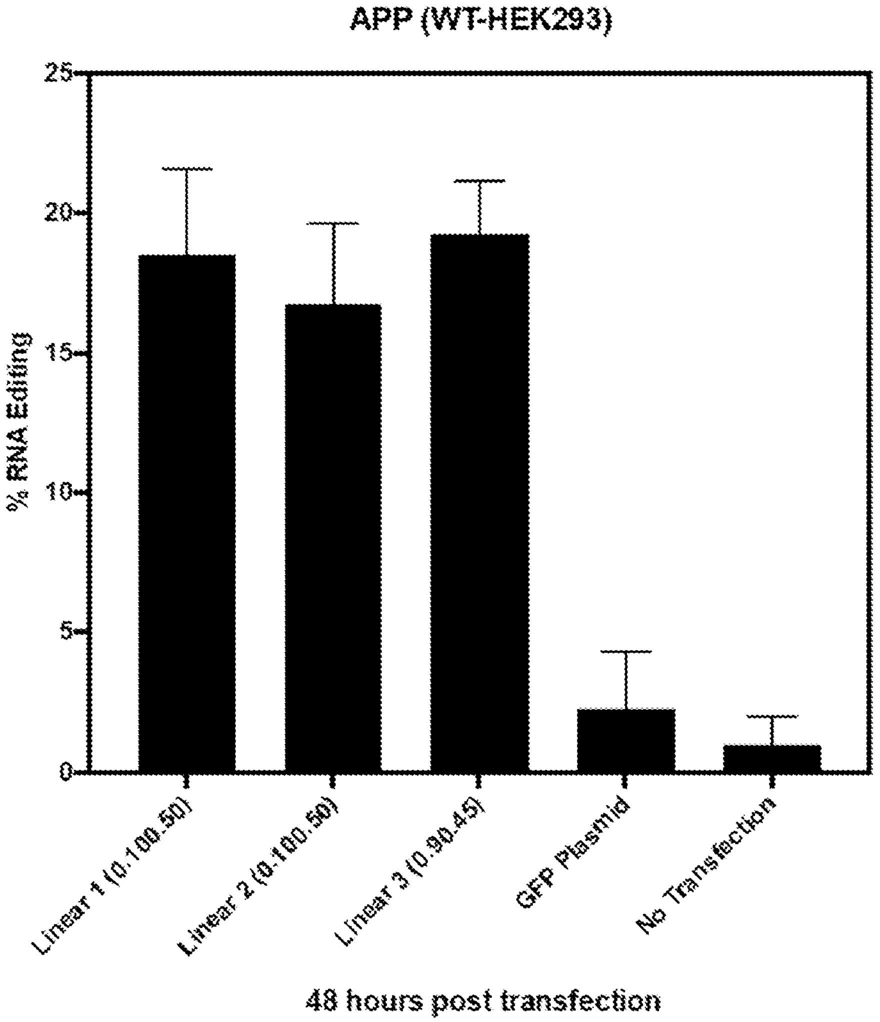

About 20,000 WT-HEK293 cells expressing ADAR1 were transfected with 500 ng of each plasmid and the control GFP plasmid. The transfected cells were lysed 48 hours post-transfection. The APP mRNAs were extracted and analyzed by Sanger sequencing. The editing efficiency was quantified using EditR software. As shown in FIG. 16B, about 15-20% editing of the target adenosine in APP was achieved, as compared to less than 3% editing in the negative controls.

Example 17: Methods for Optimizing Engineered Polynucleotide in Human Cells

Figure 17A:
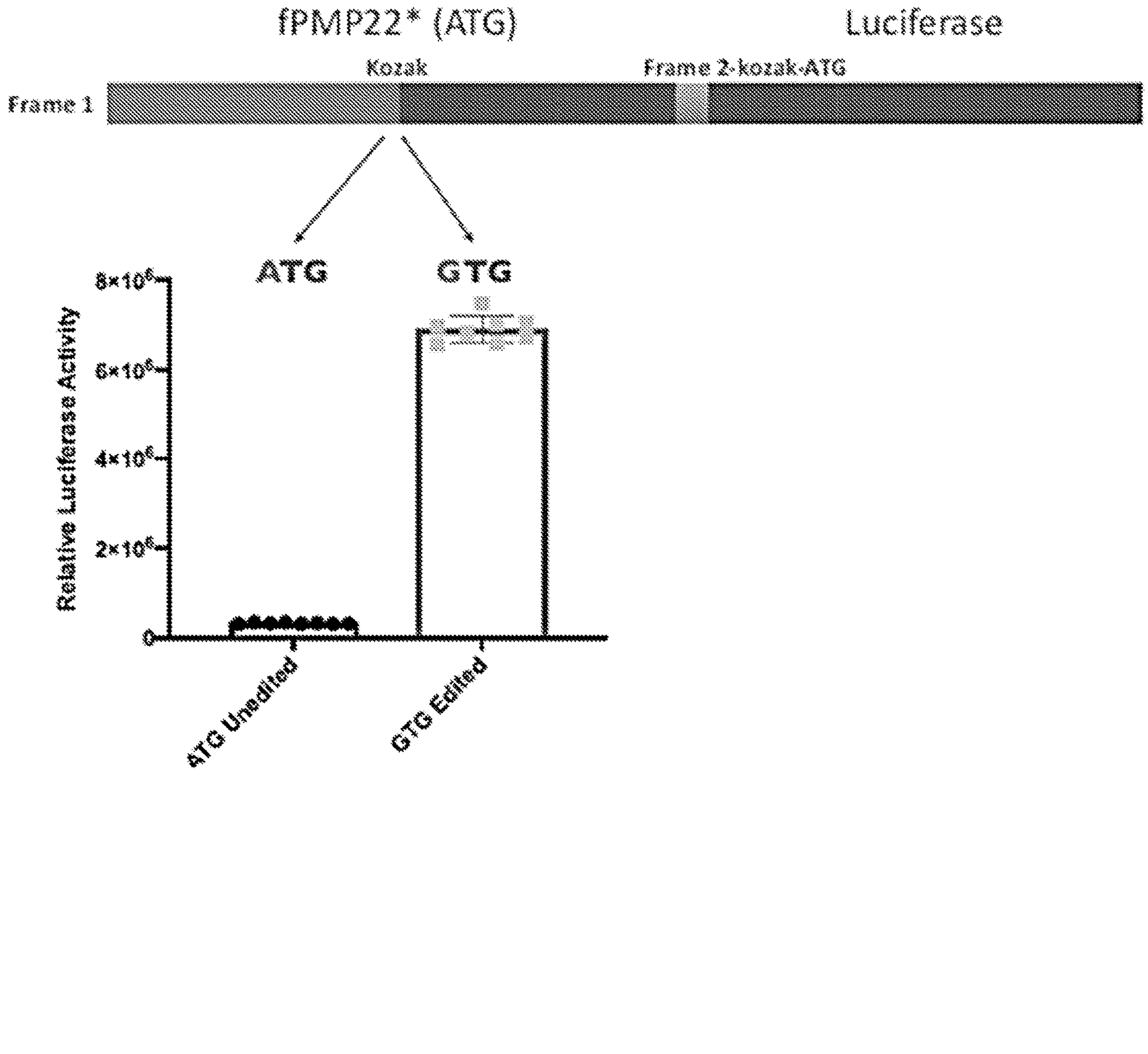
FIG. 17A-FIG. 17C show an exemplary assay to screen for any of the engineered polynucleotides provided herein, including but not limited to SNCA, APP, and Tau.

Provided herein are methods for optimizing engineered polynucleotides in human cells A robust assay for screening guide RNAs This example describes a robust assay for screening engineered polynucleotide in human cells. A luciferase reporter (for example but not limited to, fPMP22) was developed the RNA editing efficiency of the engineered polynucleotide (or guide). As shown in FIG. 17A, the reporter contains two open reading frames, each with one kozak ATG start codons. The first open reading frame contains a target RNA sequence, while the second one contains a luciferase. When the translation starts from the first ATG start codon, the translation of the luciferase is inhibited. When the target adenosine of the first ATG is mutated to a guanine in which no translation can be initiated, the translation of the luciferase increases. By incorporating the target RNA sequence surrounding the first ATG, the RNA editing efficiencies of the guides with different features—such as the length of the guide, the location of the bulge in the guide, or the location of the GLUR2-recruiting domains in the guide can be tested.

Figure 17B:
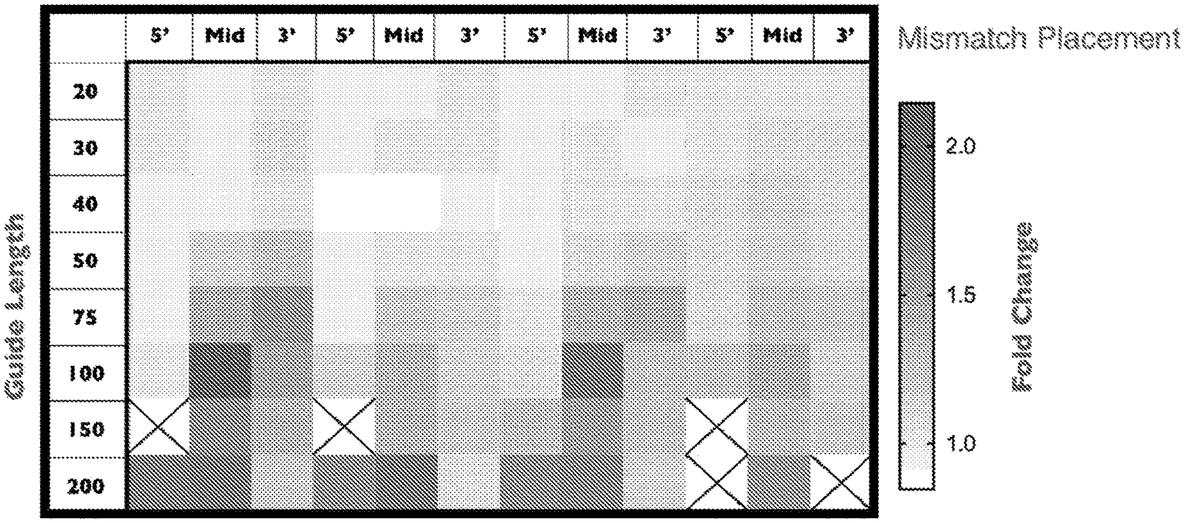
Figure 17C:
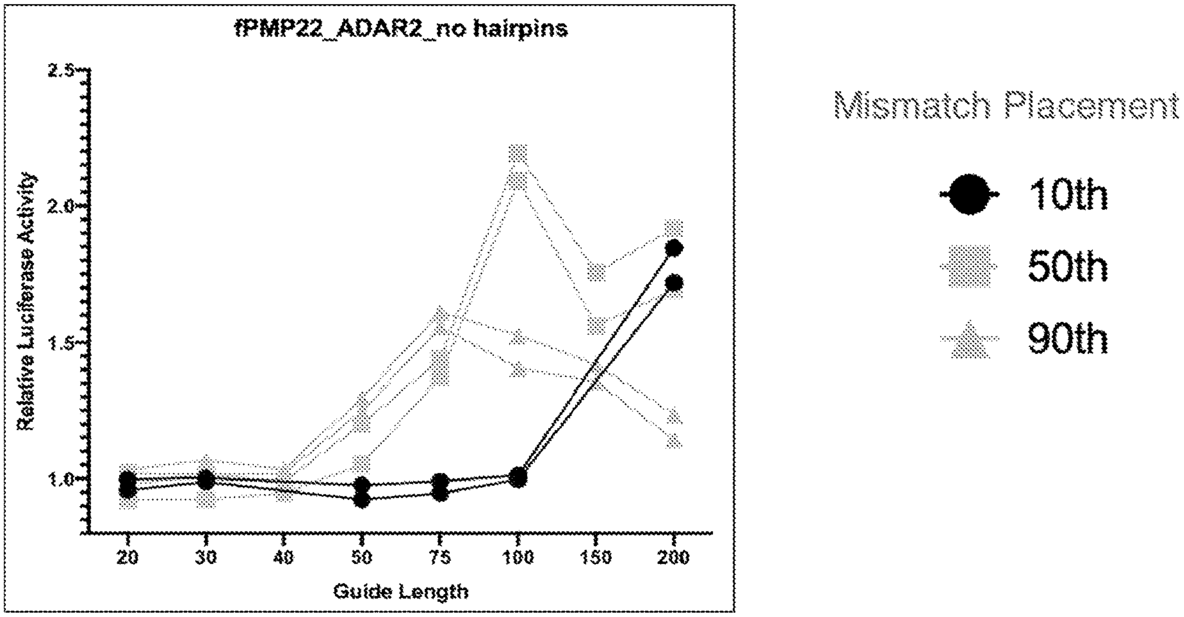

FIG. 17B-FIG. 17C describe the result of a screen using an fPMP22 reporter for use with any one of the compositions or methods provided herein, including but not limited to SNCA, APP, and Tau. FIG. 17B shows a heatmap of the luciferase expression in a fPMP22 reporter. The fPMP22 reporter was generated by inserting the target transcript sequence in Charcot-Marie-Tooth Syndrome 1A into the first open reading frame. The reporter was transposed into HEK293 cells for stable expression. Guides with different lengths (20, 30, 40, 50, 75, 100, 150, and 200 nucleotides); mismatch placement (10th percentile (5' end), 90th percentile (3' end), or 50th percentile (middle)) of the guide as it's transcribed from 5' to 3' from the plasmid were transiently expressed. In some cases, the inclusion/exclusion of specific GLUR2-recruiting domains (0, 1, or 2) and their location (5' end, 3' end, both or neither) can also be tested. The fold-change of the luciferase expression normalized to that of cells transfected with plasmids with non-specific guides and ADAR2 (ST0145). The sequences of these guides are listed in TABLE 19.

TABLE 19

Sequences of the guide RNAs used in the fPMP22 reporter screen.

| SEQ ID NO | Length | Percentile | Sequence |
|---|---|---|---|
| 169 | 20 | 10 | ACTCTGGCGGCAAGTTCTGC |
| 170 | 30 | 10 | CACTCTGGCGGCAAGTTCTGCTCAGCGGAG |
| 171 | 40 | 10 | GCACTCTGGCGGCAAGTTCTGCTCAGCGGAGTTTCTGCCC |
| 172 | 50 | 10 | AGCACTCTGGCGGCAAGTTCTGCTCAGCGGAGTTTCTGCCCGGCCAAACA |
| 173 | 75 | 10 | AGGAGCACTCTGGCGGCAAGTTCTGCTCAGCGGAGTTTCTGCCCGGCCAAACAGCGTAACCCCTTCTTCCAAGCA |
| 174 | 100 | 10 | GGAGGAGCACTCTGGCGGCAAGTTCTGCTCAGCGGAGTTTCTGCCCGGCCAAACAGCGTAACCCCTTCTTCCAAGCAGATTTCTTTGCAGCCAAATGCAA |
| 175 | 150 | 10 | CAACAGGAGGAGCACTCTGGCGGCAAGTTCTGCTCAGCGGAGTTTCTGCCCGGCCAAACAGCGTAACCCCTTCTTCCAAGCAGATTTCTTTGCAGCCAAATGCAAGGGATGTTAAGGCAAGACCCTCCCCACAGGGCAGTCAGAGACCCG |
| 176 | 200 | 10 | CTCAGCAACAGGAGGAGCACTCTGGCGGCAAGTTCTGCTCAGCGGAGTTTCTGCCCGGCCAAACAGCGTAACCCCTTCTTCCAAGCAGATTTCTTTGCAGCCAAATGCAAGGGATGTTAAGGCAAGACCCTCCCCACAGGGCAGTCAGAGACCCGCAGCCGACAGACTAAGCCTGCAGCTTCCAACCAGGCTCCCCGAGA |
| 177 | 20 | 50 | AGGAGGAGCACTCTGGCGGC |
| 178 | 30 | 50 | GCAACAGGAGGAGCACTCTGGCGGCAAGTT |
| 179 | 40 | 50 | ACTCAGCAACAGGAGGAGCACTCTGGCGGCAAGTTCTGCT |
| 180 | 50 | 50 | ATGATACTCAGCAACAGGAGGAGCACTCTGGCGGCAAGTTCTGCTCAGCG |
| 181 | 75 | 50 | ACGTGGAGGACGATGATACTCAGCAACAGGAGGAGCACTCTGGCGGCAAGTTCTGCTCAGCGGAGTTTCTGCCCG |
| 182 | 100 | 50 | CACCAGCACCGCGACGTGGAGGACGATGATACTCAGCAACAGGAGGAGCACTCTGGCGGCAAGTTCTGCTCAGCGGAGTTTCTGCCCGGCCAAACAGCGT |
| 183 | 150 | 50 | TGACGATCGTGGAGACGAACAGCAGCACCAGCACCGCGACGTGGAGGACGATGATACTCAGCAACAGGAGGAGCACTCTGGCGGCAAGTTCTGCTCAGCGGAGTTTCTGCCCGGCCAAACAGCGTAACCCCTTCTTCCAAGCAGATTTCT |
| 184 | 200 | 50 | TGTCCATTGCCCACGATCCATTGGCTGACGATCGTGGAGACGAACAGCAGCACCAGCACCGCGACGTGGAGGACGATGATACTCAGCAACAGGAGGAGCACTCTGGCGGCAAGTTCTGCTCAGCGGAGTTTCTGCCCGGCCAAACAGCGTAACCCCTTCTTCCAAGCAGATTTCTTTGCAGCCAAATGCAAGGGATGTTA |
| 185 | 20 | 90 | TCAGCAACAGGAGGAGCACT |
| 186 | 30 | 90 | CGATGATACTCAGCAACAGGAGGAGCACTC |
| 187 | 40 | 90 | CGTGGAGGACGATGATACTCAGCAACAGGAGGAGCACTCT |
| 188 | 50 | 90 | GCACCGCGACGTGGAGGACGATGATACTCAGCAACAGGAGGAGCACTCTG |
| 189 | 75 | 90 | GTGGAGACGAACAGCAGCACCAGCACCGCGACGTGGAGGACGATGATACTCAGCAACAGGAGGAGCACTCTGGCG |
| 190 | 100 | 90 | CCACGATCCATTGGCTGACGATCGTGGAGACGAACAGCAGCACCAGCACCGCGACGTGGAGGACGATGATACTCAGCAACAGGAGGAGCACTCTGGCGGC |
| 191 | 150 | 90 | AGAGGTGCTACAGTTCTGCCAGAGATCAGTTGCGTGTCCATTGCCCACGATCCATTGGCTGACGATCGTGGAGACGAACAGCAGCACCAGCACCGCGACGTGGAGGACGATGATACTCAGCAACAGGAGGAGCACTCTGGCGGCAAGTTC |

~50,000 HEK293 cells expressing the reporter transcript were transfected with 300 ng of each of the above guide expressing plasmids in biological duplicate. Twenty-four hours post transfection, supernatant was collected and assessed for luciferase activity. Measurements of absorbance after incubation with luciferase substrate were taken on the varioskan lux and normalized against a plasmid expressing a non-specific guide to control for plasmid and/or ADAR expression.

FIG. 17C shows a line graph of the relationship of the guide length (x-axis) and the fold-change of the reporter expression (y-axis) in two biological replicates for each guide. The result of 3 sets of experiments, in which the guide contained a GLUR2-recruiting domain in the β' end of the guide and the location of the bulge was varied, was shown.

Cell Line Development

Different cells lines were engineered to examine RNA editing.

Figure 18A:
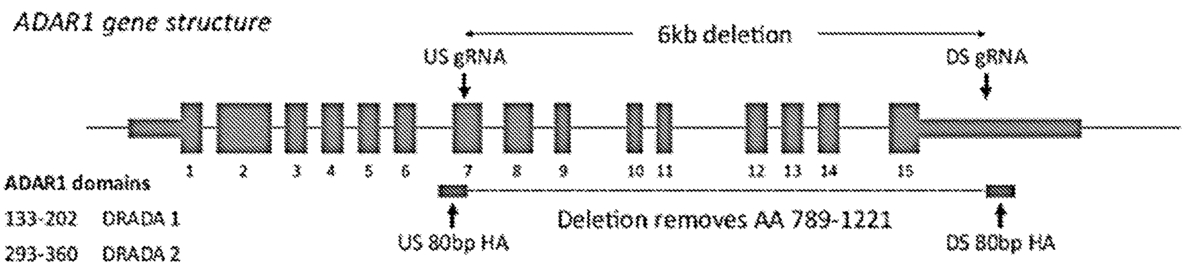
FIG. 18A and FIG. 18B show the generation of ADAR1 knockout cell lines.
Figure 18B:
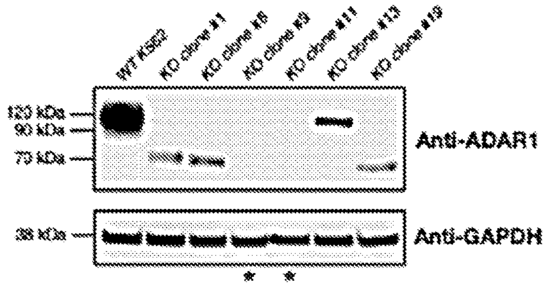

Endogenous ADAR1 was modified to examine its function in RNA editing. FIG. 18A shows the knockout strategy of the ADAR1 locus. Two gRNAs US gRNA and DS gRNA were designed to cover a 6 kb region of the ADAR1 locus, encompassing the deaminase domain ($789^{th}$ to $1221^{st}$ amino acid). A K562 cell line was transfected with the gRNAs and a homology directed repair (HDR) oligo with 80 bp homology arms outside the 6 kb region. The gRNAs nicked the DNA strands. The HDR oligo would create the 6 kb deletion in the ADAR1 locus through the homologous recombination repair pathway, removing the deaminase domain. FIG. 18B shows a western blot of ADAR1 in different clones transfected with US and DS gRNA. GAPDH was used as a control. Two clones #9 and #11 showed no detectable ADAR1 protein expression by the western blot.

Figure 19A:
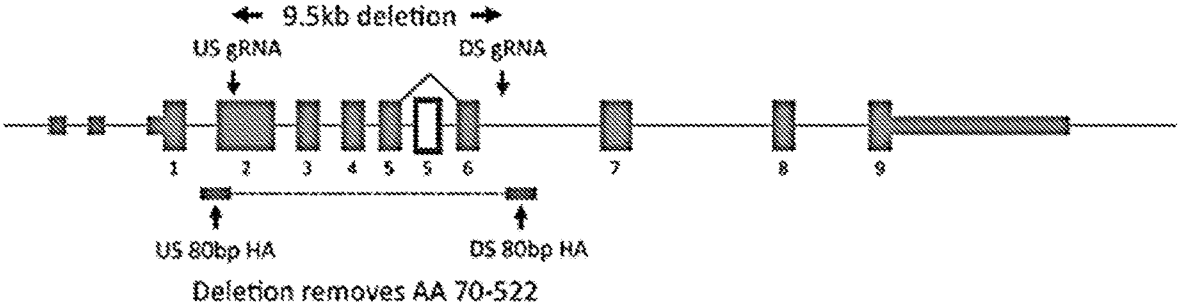
FIG. 19A and FIG. 19B show the generation of ADAR2 knockout cell lines.
Figure 19B:
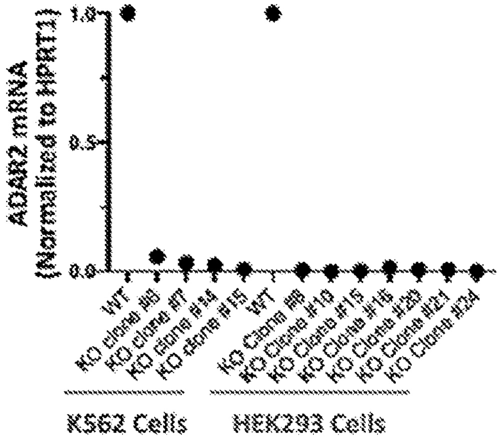

Endogenous ADAR2 was modified to examine its function in RNA editing. FIG. 19A shows the knockout strategy of the ADAR2 locus. Two gRNAs US gRNA and DS gRNA were designed to cover a 9.5 kb region of the ADAR1 locus, encompassing the deaminase domain ($70^{th}$ to $522^{nd}$ amino acid). A K562 cell line was transfected with the gRNAs and a homology directed repair (HDR) oligo with 80 bp homology arms outside the 9.5 kb region. The gRNAs nicked the DNA strands. The HDR oligo would create the 9.5 kb deletion in the ADAR2 locus through the homologous recombination repair pathway, removing the deaminase domain.

Figure 20A:
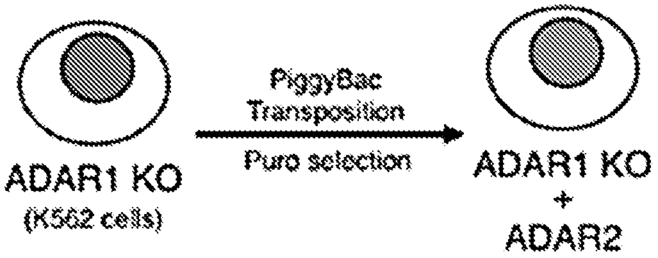
FIG. 20A and FIG. 20B show the generation of ADAR1 knockout cell lines that overexpress (OE) ADAR2.
Figure 20B:
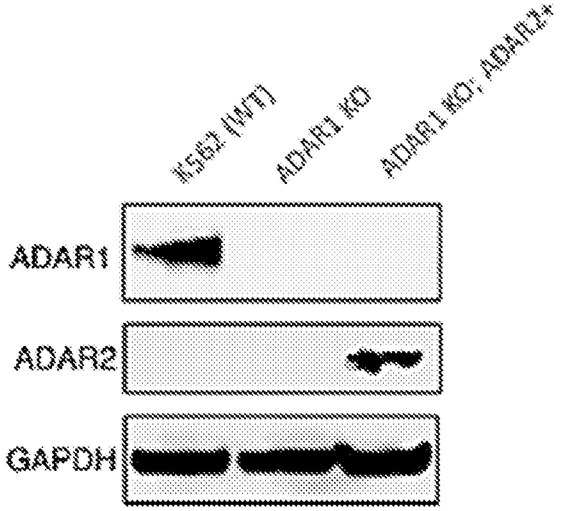

A cell line that expresses ADAR2 but not ADAR1 was generated. FIG. 20A shows the strategy to generate the ADAR1 knockout (KO) cell line that overexpresses ADAR2. An ADAR2 overexpression construct, maintained as a PiggyBac transposon with a puromycin-resistant marker, was transfected and integrated into an ADAR1 KO K562 cell line. The successfully integrated cell was selected by puromycin resistance. FIG. 20B shows a western blot of ADAR1 and ADAR2 protein expression in wildtype, ADAR1 KO, and ADAR1 KO+ADAR2 cell. GAPDH was used as a control. The wildtype or ADAR1 KO cell did not express ADAR2. Only the ADAR1 KO cell successfully integrated with ADAR2 OE construct expressed ADAR2.

An assay to measure RNA editing

An assay utilizing digital droplet PCR and fluorescence quantification to measure RNA editing efficiencies was developed.

Figure 21:
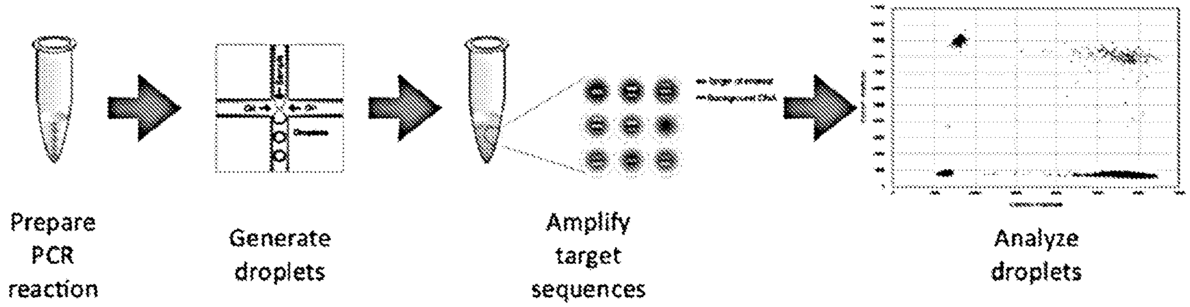
FIG. 21 shows a carton schematic of using a Bio-Rad drop-off digital droplet PCR (ddPCR) assay to measure RNA editing efficiency. PCR samples are prepared and then processed on fluidic chips to generate droplets of PCR reactions in oil suspension. The target and background reference sequences are detected: 1, by PCR amplification with intercalating fluorescent dyes; or 2, by fluorescent TaqMan style probes on the PCR amplified products. The resultant signal is analyzed by a droplet reader. Data is then presented in a two-dimensional dot plot, showing high and low populations of droplets for each fluorescent channel.

FIG. 21 shows the general scheme of a Bio-Rad Drop-off digital droplet PCR (ddPCR) assay to measure RNA editing efficiency. PCR samples prepared and then processed on fluidic chips to generate droplets of PCR reactions in oil suspension. The target and background reference sequences are detected: 1, by PCR amplification with intercalating fluorescent dyes; or 2, by fluorescent TaqMan style probes on the PCR amplified products. The resultant signal is analyzed by a droplet reader. Data is then presented in a two-dimensional dot plot, showing high and low populations of droplets for each fluorescent channel.

Figure 22A:
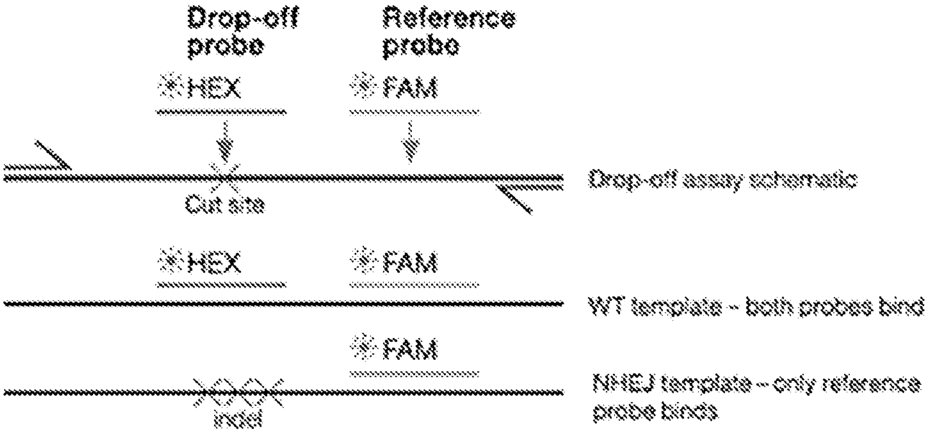
FIG. 22A and FIG. 22B show a carton schematic of using the drop-off ddPCR assay in FIG. 22 to measure RNA editing efficiency in human cells.
Figure 22B:
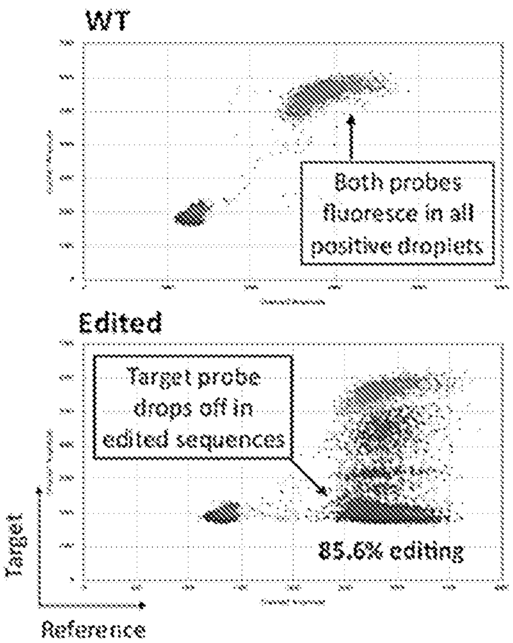

FIG. 22 shows the design of ddPCR Drop-off assay probes. A forward and reverse primer were designed to flank the Rab7 mRNA (A genomic locus can also be targeted in the case of measuring DNA editing). A Drop-off probe and reference TaqMan probe was designed to bind a target site in Rab7 and the region adjacent to the target site, respectively. Both probes could bind the wildtype sequence of the target site and the adjacent site to release signals; the Drop-off probe could not bind an edited or mutated sequence on the target site to release the signal. Each Rab7A mRNA molecule was converted to a cDNA molecule by reverse transcription and PCR amplification and allocated into individual droplet. The percentage of the populations of the edited vs wildtype Rab7 mRNA molecule, measured by the ddPCR, was counted to determine the editing frequency. FIG. 22B shows the result of this experiment: In the wild-type control (WT) sample with no editing, most droplets showed high fluorescent intensity for both probes. In the edited sample, about 85% of the droplets showed decreased fluorescent intensity in the Drop-off probe, suggesting that an equivalent percentage of sequences were edited.

An Assay to Quantify gRNA Level

An assay to quantify gRNA level was developed.

Figure 23:
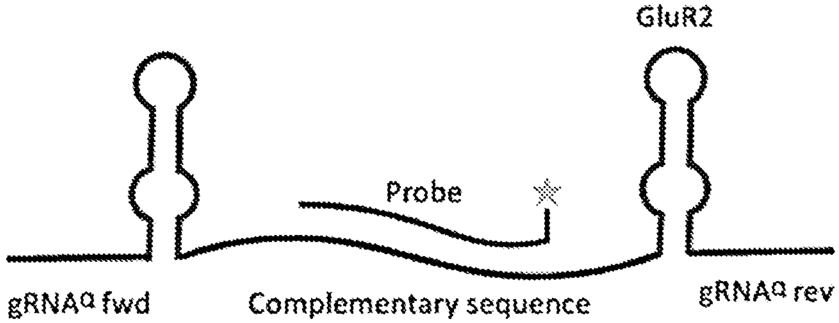
FIG. 23 shows a carton schematic of the design of universal gRNA quantification (gRNA$^{Q}$) tags that are added to the 5' and 3' ends of a guide RNA. These universal sequences allow for detection of any guide RNA inserted between the tags with addition of a guide specific TaqMan probe. In qPCR or ddPCR the primers will bind the gRNA$^{Q}$ tags for amplification. The guide specific TaqMan probe will the produce a fluorescent signal that can be quantified using a standard curve with qPCR or ddPCR.

FIG. 23 shows the design of a pair of universal gRNA quantification (gRNAQ) tags to quantify gRNA abundance. They are added to the 5' and 3' ends of a guide RNA. The universal sequences allow for detection of any guide RNA inserted between the tags with addition of a guide specific TaqMan probe. In qPCR or ddPCR, the primers will bind the gRNAQ tags for amplification. The guide specific TaqMan probe will the produce a fluorescent signal that can be quantified using a standard curve with qPCR or ddPCR to measure gRNA abundance.

Figure 24A:
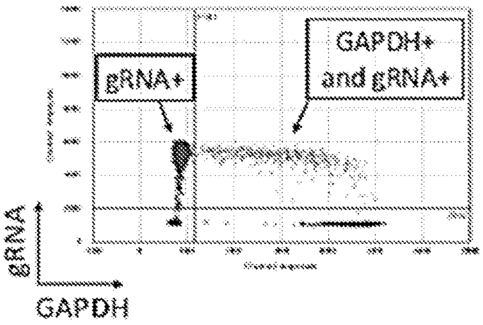
FIG. 24A shows the result of the quantification of Rab7A gRNA with gRNA$^{Q}$ tags and GRAPH mRNA in a ddPCR reaction. The total number of positive droplets for Rab7 gRNA and GAPGH were counted and then analyzed by Poisson distribution to determine the frequency of all events.

FIG. 24A shows the result of the quantification of gRNA targeting Rab7 with $gRNA^{Q}$ tag. GRAPH mRNA was used as a control. The total number of positive droplets for Rab7 gRNA and GAPGH were counted. Assuming a Poisson distribution, the frequency of all events was determined.

Figure 24B:
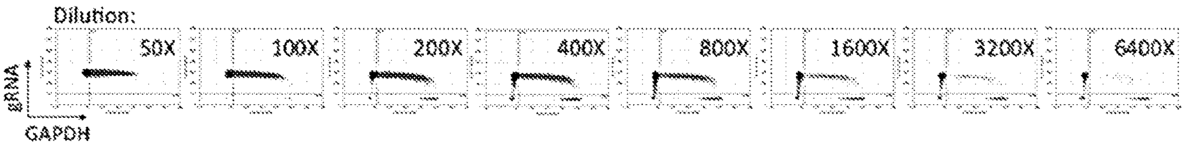
FIG. 24B shows the dot plots demonstrating that multiple serial dilutions of the sample to obtain amplification of GAPDH mRNA and gRNA in the sample. Since a dominant target can use up all the amplification reagents, diluting the sample can ensure that every target, even one with minute amount, is adequately amplified.

Since a highly abundant target could use up all the amplification reagents, the less abundant targets might not be able to be allocated with enough amplification agents; one get-around is to dilute the sample so that every target, even one in a minute amount, is adequately amplified. FIG. 24B shows the dot plots demonstrating that multiple serial dilutions (50×, 100×, 200×, 400×, 800×, 1600×, 3200×, 6400×) of the sample to obtain amplification of GAPDH mRNA and Rab7 gRNA in the sample. As GAPDH mRNA was diluted out with increasing dilution factors, more Rab7 gRNA—positive droplets were identified.

gRNA Structure

Figure 25A:
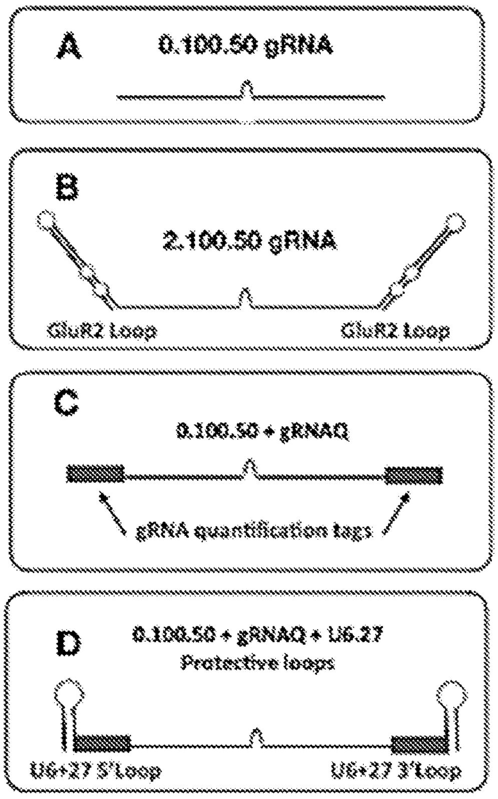
FIG. 25A shows a carton schematic of the RNA structures of different gRNAs against Rab7a. gRNA A 0.100.50 does not comprise any GluR2 loop to recruit ADAR. gRNA B 2.100.50 comprise two GluR2 loop on each end. gRNA C comprises two gRNA quantification tag (gRNA$^{Q}$ tag) of FIGS. 23 and 24. gRNA D comprises one 0.100.50 (gRNA A), and a gRNA$^{Q}$ tag and a U6.27 protective loop on each end.
Figure 25B:
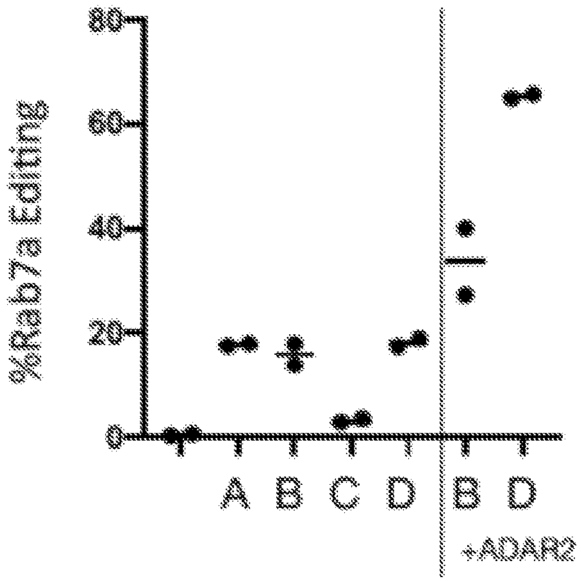
FIG. 25B shows the RNA editing efficiencies of using the gRNAs of FIG. 25A. Co-expressing ADAR2 with gRNA B and D could increase the Rab7a RNA editing efficiency.

As shown in FIG. 25, the gRNA with protective loops at both ends of the gRNA could increase the RNA editing efficiency of the gRNA. Cells were transfected with different gRNAs and vectors expressing ADAR2. Cells transfected with vectors that did not express ADAR2 were used as controls. After at least two days of transfection, cells were lysed, and Rab7a RNA editing efficiency was analyzed by Sanger sequencing, as shown in Example 13, 14, and 18. Two biological replicates were provided.

Optimizing gRNA Expression

The expression of guide RNAs was optimized to enhance RNA editing efficiency.

gRNA targeting Rab7 was driven by CMV enhancers. Two configurations of the CMV enhancer were oriented against the hU6 promoter in several of the constructs and listed in TABLE 20. The constructs were designed to co-express ADAR2 or GFP as well as two GluRD domains on the 5' and 3' ends of the guide targeting Rab7a. The guides used is 100nt long with the A/C mismatch placed at the $50^{th}$ base position. The guide sequence used is listed in SEQ ID NO: 192.

```
SEQ ID NO: 192:
TGATAAAAGGCGTACATAATTCTTGTGTCTACTGTACAGAATACTGCCGC

CAGCTGGATTTCCCAATTCTGAGTAACACTCTGCAATCCAAACAGGGTT

C.
```

Figure 26:
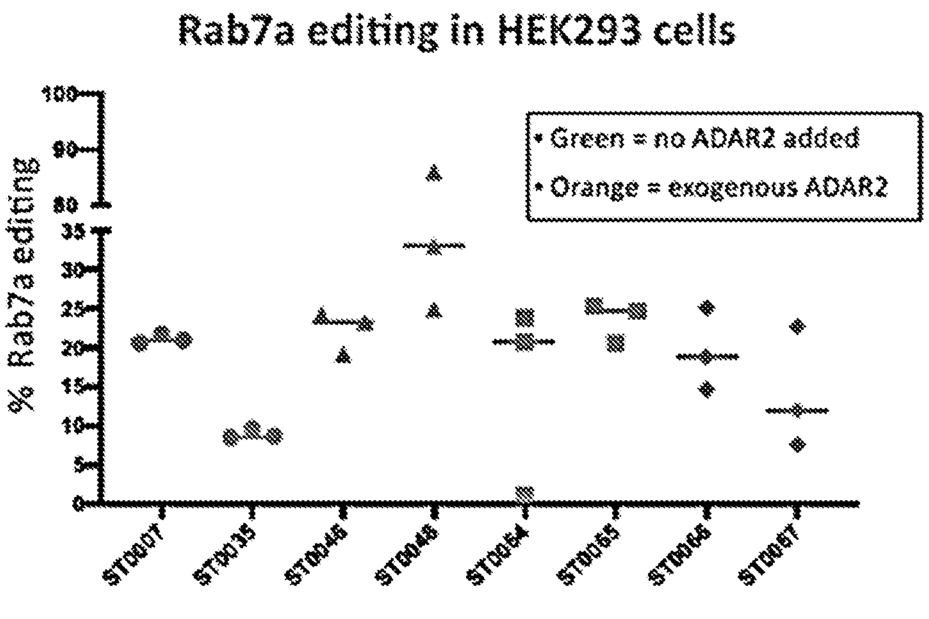
FIG. 26 shows a bar graph of the optimization of mRNA editing with the expression of gRNAs using different enhancer elements. The guide RNA, listed in SEQ ID NO: 124, was designed to target the Rab7a mRNA. It was driven by a hU6 promoter. Two configurations of the CMV enhancer were oriented against the hU6 promoter in several of the constructs and listed in TABLE 17. The constructs were designed to co-express ADAR2 or GFP as well as two GluRD domains on the 5' and 3' ends of the guide targeting Rab7a. 20,000 HEK293 cells were transfected with 1 μg of plasmid expressing SEQ ID NO: 124. Total RNA was collected 48 hours post transfection. Three biological replicates were tested.

~20,000 HEK293 cells were transfected with 1 μg of plasmid expressing SEQ ID NO: 192. Total RNA was collected 48 hours post transfection. Three biological replicates were tested. The editing results are shown in FIG. 26. The features of each experiment are listed in TABLE 20.

TABLE 20

Construct used in FIG. 26.

| Construct # | Construction Description |
| --- | --- |
| ST0007 | hu6_2_100_50_GFP |
| ST0035 | ADAR2 only, no gRNA |

TABLE 20-continued

| Construct used in FIG. 26. | |
|---|---|
| Construct # | Construction Description |
| ST0046 | hu6_2_100_50_2 bulge_GFP |
| ST0048 | hu6_2_100_50_2 bulge_ADAR2 |
| ST0064 | xiaCMVen-hu6_2_100_50_2 bulge_GFP |
| ST0065 | xiaCMVen-hu6_2_100_50_2 bulge_ADAR2 |
| ST0066 | sgCMVen-hu6_2_100_50_2 bulge_GFP |
| ST0067 | sgCMVen-hu6_2_100_50_2 bulge_ADAR2 |

Different promoters, such as human U6 (hu6), xiaCMVen-hu6, and sgCMVen-hu6 promoters were used to drive the expression of gRNA against Rab7a. The gRNA comprises two bulges. When no gRNA was provided (ST0035), RNA editing was at the minimum. Co-expression of ADAR2, when the gRNA is expressed by hu6, boosts the RNA editing efficiency.

Design

Figure 27:
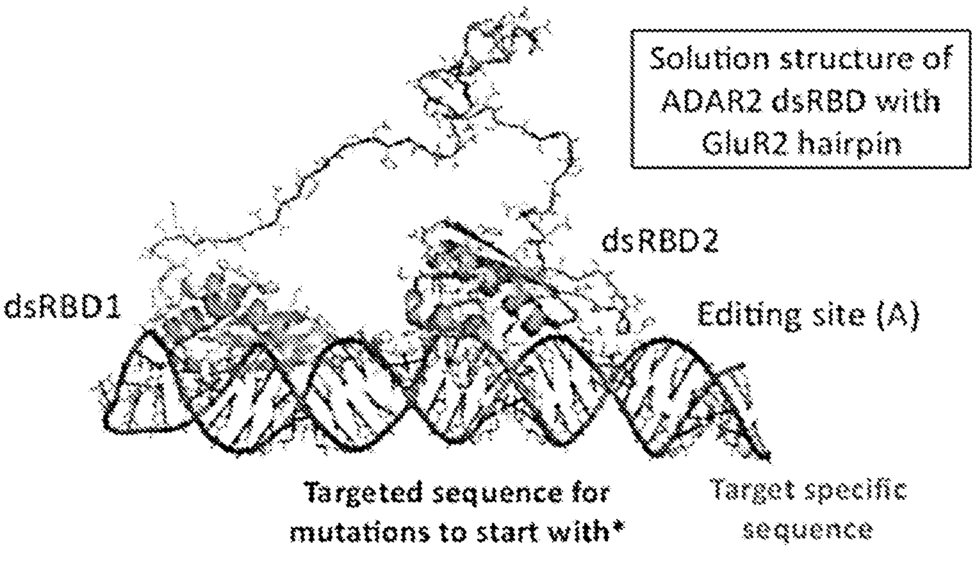
FIG. 27 shows the three-dimensional structure of ADAR2 double-stranded RNA-binding domain (dsRBD) binding to the GluR2 hairpin binding of the gRNA/target RNA complex. The editing adenosine site is shown.

The 3-dimensional solution structure of ADAR2 binding to the gRNA/target RNA complex is shown in FIG. 27. The structure shows the location of the contact of the two dsRBD (dsRBD 1 and 2) binding to the GluR2 hairpin of the gRNA/target RNA complex. The target editing site adenosine is located close to dsRBD2. The structure of gRNA or ADAR2 proteins can be rationally optimized based on the contacts of the solution structure.

Example 18: Platforms for Processing RNA Editing Data

Provided herein are platforms for platforms for processing RNA editing data.

EditR is an algorithm to process and analyze RNA editing data. It is available as an R package or online through Shiny. Sequencing data, either with Sanger or Next-Generation Sequencing, can be analyzed with EditR.

For example, as in the A-to-I mRNA editing in converting a G to an A, three parameters of the sequence are specified in EditR: 1, the sequence, as in the Sanger file format (.ab1), is loaded into the program platform; 2, the region of interest is specified, usually the entire target region of the gRNA used in the experiment; 3, the sequence is specified as the target or reverse complement sequence.

EditR then assess the sequence for potential editing across the specified target region. Using the peak height and area under the curve for each base at each position, it predicts the percentage of each base at each position. The frequency of A and G in the target residue is then determined.

Example 19: RNA Hyper-Editing

Provided herein are methods for RNA hyper-editing.

In some cases, editing more than one nucleotide can be advantageous. This type of editing, as referred herein as hyper-editing, can generate an edited RNA molecule with more than one nucleotide changes. The nucleotides can lead to more than one amino acid substitution in some cases. The nucleotides may not lead to any amino acid substitutions in other cases. Either way, the hyper-edited RNA and the modified polypeptide encoded by it can have advantageous therapeutic potential. For example, multiple nucleotide substitutions in the 5'UTR and coding sequences of an mRNA can create artificial kozak start codons or and eliminate the endogenous one. In this case, the translational frame of an mRNA is disrupted. Multiple nucleotide substitutions in the 3'UTR can disrupt sequences important for RNA stability or transport, such as the poly-A tail of an mRNA, diminishing its ability to be translated. Multiple nucleotide substitutions in the coding sequence can confer multiple amino acid substitutions. These changes can affect the protein function, such as the target sites by processing enzymes. One example is the post-translational processing of secretory or trans-membrane proteins, usually involving multiple enzymes and cleavages (and glycosylation).

Hyper-editing can be achieved by designing a guide RNA with multiple mis-matches to the target region; for example, the gRNA listed in TABLE 16 is used to create hyper-editing of the 3'UTR of the SNCA mRNA. An example of creating multiple amino acid substitution with multiple nucleotide substitutions in the coding sequence of an mRNA is shown in Example 1. SEQ ID NO: 51 is used to create multiple amino acid changes that lead that impact the APP processing by BACE1, according to TABLE 8.

Hyper-editing can also be achieved by the design of the elements of the guide RNA, other than those base-pairing with the target region; for example, a guide RNA can have an RNA editing entity recruiting domain may not release the RNA editing entity once engaged, forcing multiple editing on the target RNA.

Example 20: Additional Assays to Measure Effects of RNA Editing

Provided herein are methods to measure various biological effects of RNA editing. These methods can apply to any target RNA or the polypeptide encoded by the target RNA. Such target RNA can include the APP, SNCA, or Tau mRNA or pre-mRNA.

RNA editing can affect the abundance of the target RNA. It can create nucleotide substitutions that decrease the target mRNA abundance. To measure such effect, using Tau as an illustrative example, a cell is transfected with a gRNA targeting the target mRNA. At least 48 hours after transfection, the mRNA of the cells can be prepared, and the Tau mRNA can be measured by Q-PCR.

RNA editing can affect the abundance of a polypeptide of encoded by the target RNA. To measure such effect, using Tau as an illustrative example, a cell is transfected with a gRNA targeting the target mRNA. At least 48 hours after transfection, the protein lysate of the cells can be prepared, and the Tau polypeptide can be measured by western blot using a Tau-specific antibody. If an antibody is not available, one can co-transfect the cell with a vector that comprises a nucleic acid that expresses a fusion Tau mRNA that encodes a Tau polypeptide with an affinity tag. Such affinity can be FLAG, HIS, HA, MYC, or any other affinity tags known in the art. The abundance of the tagged Tau polypeptide, reflecting the RNA editing efficiency, can be traced and measured using the affinity tag and western blot.

RNA editing can affect the enzymatic processing such as cleavage of a polypeptide of encoded by the target RNA. To measure such effect, using Tau as an illustrative example, a cell is transfected with a gRNA targeting the target mRNA. At least 48 hours after transfection, the protein lysate of the cells can be prepared, and the Tau polypeptide can be measured by western blot using a Tau-specific antibody. If an antibody is not available, one can co-transfect the cell with a vector that comprises a nucleic acid that expresses a fusion Tau mRNA that encodes a Tau polypeptide with an affinity tag. Such affinity can be FLAG, HIS, HA, MYC, or any other affinity tags known in the art. The enzymatic processing such as cleavage of the tagged Tau polypeptide, reflecting the RNA editing efficiency, can be traced and measured using the affinity tag and western blot.

RNA editing can affect the phosphorylation status of a polypeptide of encoded by the target RNA. To measure such effect, using Tau as an illustrative example, a cell is transfected with a gRNA targeting the target mRNA. At least 48 hours after transfection, the protein lysate of the cells can be prepared, and the Tau polypeptide can be measured by western blot using Tau-specific antibody. If an antibody is not available, one can co-transfect the cell with a vector that comprises a nucleic acid that expresses a fusion Tau mRNA that encodes a Tau polypeptide with an affinity tag. Such affinity can be FLAG, HIS, HA, MYC, or any other affinity tags known in the art. The phosphorylation of the tagged Tau polypeptide, reflecting the RNA editing efficiency, can be traced and measured using the affinity tag and western blot. In these cases, the molecular weight of the Tau polypeptide is affected by the phosphorylation status of the polypeptide. Usually a polypeptide with more phosphorylation migrates slower than one with fewer phosphorylation. This phenomenon is also known in the art as gel-shift.

RNA editing can affect the aggregation status of a polypeptide of encoded by the target RNA. To measure such effect, using Tau as an illustrative example, a cell is transfected with a gRNA targeting the target mRNA. At least 48 hours after transfection, the protein lysate of the cells can be prepared, and the Tau polypeptide can be measured by western blot using a Tau-specific antibody. If an antibody is not available, one can co-transfect the cell with a vector that comprises a nucleic acid that expresses a fusion Tau mRNA that encodes a Tau polypeptide with an affinity tag. Such affinity can be FLAG, HIS, HA, MYC, or any other affinity tags known in the art. The aggregation status of the tagged Tau polypeptide, reflecting the RNA editing efficiency, can be traced and measured using the affinity tag and western blot. Aggregated Tau polypeptide is detected with a large gel-shift.

The phosphorylation status of a polypeptide can also be measured by a phosphorylation site specific, phosphorylation fragment specific, or phosphorylation polypeptide specific antibody. In this case, only a phosphorylated Tau polypeptide is detected by the antibody The phosphorylation status of a polypeptide is also measured by mass-spectroscopy. An endogenous or epitope tagged proteins are immunopurified (IP) from cell lysates, purified via gel electrophoresis or precipitation and enzymatically digested into peptides. Samples can be optionally enriched for phosphopeptides using immobilized metal affinity chromatography (IMAC) or titanium dioxide (TiO2) and then analyzed by microcapillary liquid chromatography/tandem mass spectrometry (LC-MS/MS).

The ability of a polypeptide to be phosphorylated is also measured by an in vitro phosphorylation assay. In vitro kinase assays are often performed using radioactive $^{32}$P- or $^{33}$P-labeled ATP. The transfer of the gamma phosphate from ATP (or sometimes GTP) to a substrate, Tau in this example, is measured. A protein is expressed and purified. The purified protein is incubated with a kinase and $^{32}$P- or $^{33}$P-labeled ATP. When a polypeptide is phosphorylated, it is radioactively labelled by the radioactive ATP. When this protein is run in a western blot, an autoradiograph is used to measure the amount of radioactive ATP, representing the amount of phosphorylation on the polypeptide during the in vitro kinase assay.

Embodiments

Embodiment 1 An engineered polynucleotide that comprises a targeting sequence that is at least partially complementary to a region of a target RNA, wherein the region of the target RNA: (a) at least partially encodes for: an amyloid precursor protein (APP) polypeptide, an alpha-synuclein (SNCA) polypeptide, or a Tau polypeptide; (b) comprises a sequence that is proximal to (a); or (c) comprises (a) and (b); wherein the engineered polynucleotide is configured to: facilitate an editing of a base of a nucleotide of a polynucleotide in the region of the target RNA by an RNA editing entity; facilitate a modulation of the expression of the APP polypeptide, the SNCA polypeptide, or the Tau polypeptide; or a combination thereof.

Embodiment 2 The engineered polynucleotide of embodiment 1, wherein by the facilitating the editing of the base of the nucleotide of the polynucleotide in the region of the target RNA by the RNA editing entity, the engineered polynucleotide is configured to facilitate modulation of processing and/or cleavage of the target RNA by a secretase enzyme.

Embodiment 3 The engineered polynucleotide of embodiment 2, wherein the target RNA is the APP polypeptide.

Embodiment 4 The engineered polynucleotide of any one of embodiments 1-3, wherein the region of the target RNA is cleaved by a secretase enzyme.

Embodiment 5 The engineered polynucleotide of embodiment 4, wherein the secretase is: a beta secretase; a γ-secretase; or a beta secretase and a γ-secretase.

Embodiment 6 The engineered polynucleotide of embodiment 5, comprising the beta secretase, and wherein the beta secretase comprises beta-site amyloid precursor protein cleaving enzyme 1, cathepsin B, or Meprin beta.

Embodiment 7 The engineered polynucleotide of any one of embodiments 1-6, comprising (b), wherein the sequence that is proximal to the region of the target RNA at least partially encoding the APP polypeptide, the SNCA polypeptide, or the Tau polypeptide comprises at least a portion of a three prime untranslated region (3' UTR).

Embodiment 8 The engineered polynucleotide of any one of embodiments 1-7, comprising (b), wherein the sequence that is proximal to the region of the target RNA at least partially encoding the APP polypeptide, the SNCA polypeptide, or the Tau polypeptide comprises at least a portion of a five prime untranslated region (5' UTR).

Embodiment 9 The engineered polynucleotide of embodiment 8, wherein the editing of a base of the 5'UTR results in at least partially regulating gene translation of the APP polypeptide, the SNCA polypeptide, or the Tau polypeptide.

Embodiment 10 The engineered polynucleotide of embodiment 8, wherein the editing of the base of the nucleotide of the polynucleotide of the region of the 5'UTR results in facilitating regulating mRNA translation of the APP.

Embodiment 11 The engineered polynucleotide of any one of embodiments 1-10, comprising (b), wherein the sequence that is proximal to the region of the target RNA at least partially encoding the APP polypeptide, the SNCA polypeptide, or the Tau polypeptide comprises at least a portion of: a poly(A) tail, microRNA response element (MRE), AU-rich element (ARE), or any combination thereof.

Embodiment 12 The engineered polynucleotide of any one of embodiments 1-11, wherein the region of the target RNA at least partially encodes for the APP polypeptide.

Embodiment 13 The engineered polynucleotide of any one of embodiments 1-11, wherein the region of the target RNA at least partially encodes for the SNCA polypeptide.

Embodiment 14 The engineered polynucleotide of any one of embodiments 1-11, wherein the region of the target RNA at least partially encodes for the Tau polypeptide.

Embodiment 15 The engineered polynucleotide of embodiment 6, wherein the engineered polynucleotide is configured to facilitate the cleavage of the target RNA by the beta-site amyloid precursor protein cleaving enzyme 1.

Embodiment 16 The engineered polynucleotide of any one of embodiments 1-15, wherein the engineered polynucleotide is configured to facilitate the editing of the base of the nucleotide of the polynucleotide of the region of the target RNA by the RNA editing entity.

Embodiment 17 The engineered polynucleotide of any one of embodiments 1-16, wherein the targeting sequence that is at least partially complementary to the region of the target RNA comprises at least one nucleotide that is not complementary to a nucleotide in the region of the target RNA.

Embodiment 18 The engineered polynucleotide of embodiment 17, wherein the at least one nucleotide that is not complementary is an adenosine (A), and wherein the A is comprised in an A/C mismatch.

Embodiment 19 The engineered polynucleotide of any one of embodiments 1-18, wherein the target RNA is selected from the group comprising: a mRNA, a tRNA, a lncRNA, a lincRNA, a miRNA, a rRNA, a snRNA, a microRNA, a siRNA, a piRNA, a snoRNA, a snRNA, a exRNA, a scaRNA, a YRNA, and a hnRNA.

Embodiment 20 The engineered polynucleotide of embodiment 19, wherein the target RNA is the mRNA.

Embodiment 21 The engineered polynucleotide of any one of embodiments 1-20, wherein the region of the target RNA comprises a mutation as compared to an otherwise comparable region encoding a wildtype APP polypeptide, a wildtype SNCA polypeptide, or a wildtype Tau polypeptide.

Embodiment 22 The engineered polynucleotide of embodiment 21, wherein the mutation comprises a polymorphism.

Embodiment 23 The engineered polynucleotide of any one of embodiments 1-22, wherein the targeting sequence is about: 40, 60, 80, 100, or 120 nucleotides in length.

Embodiment 24 The engineered polynucleotide of embodiment 23, wherein the targeting sequence is about 100 nucleotides in length.

Embodiment 25 The engineered polynucleotide of any one of embodiments 1-24, wherein the engineered polynucleotide further comprises an RNA editing entity recruiting domain that is capable of recruiting the RNA editing entity.

Embodiment 26 The engineered polynucleotide of embodiment 25, wherein the RNA editing entity recruiting domain is at least 1 to about 75 nucleotides in length.

Embodiment 27 The engineered polynucleotide of embodiment 26, wherein the RNA editing entity recruiting domain is at least 30-50 nucleotides in length.

Embodiment 28 The engineered polynucleotide of any one of embodiments 25-27, wherein the RNA editing entity recruiting domain comprises a glutamate ionotropic receptor AMPA type subunit 2 (GluR2) sequence.

Embodiment 29 The engineered polynucleotide of embodiment 28, wherein the GluR2 sequence comprises at least about 80%, 85%, 90%, 95%, or 99% sequence identity to SEQ ID NO: 1.

Embodiment 30 The engineered polynucleotide of embodiment 29, wherein the GluR2 sequences comprises SEQ ID NO: 1.

Embodiment 31 The engineered polynucleotide of any one of embodiments 1-30, wherein the RNA editing entity comprises an adenosine deaminase acting on RNA (ADAR) polypeptide or biologically active fragment thereof or adenosine deaminase acting on tRNA (ADAT) polypeptide or biologically active fragment thereof.

Embodiment 32 The engineered polynucleotide of embodiment 31, comprising the ADAR polypeptide or biologically active fragment thereof, which comprises ADAR1 or ADAR2.

Embodiment 33 The engineered polynucleotide of any one of embodiments 1-24, wherein the engineered polynucleotide lacks a recruiting domain.

Embodiment 34 The engineered polynucleotide of any one of embodiments 1-33, wherein the engineered polynucleotide further comprises a structural feature which at least in part recruits an RNA editing entity.

Embodiment 35 The engineered polynucleotide of embodiment 34, wherein the structural feature comprises: a bulge, a hairpin, an internal loop, a structured motif, and any combination thereof.

Embodiment 36 The engineered polynucleotide of embodiment 35, wherein the structural feature comprises the bulge.

Embodiment 37 The engineered polynucleotide of embodiment 36, wherein the bulge is an asymmetric bulge.

Embodiment 38 The engineered polynucleotide of embodiment 36, wherein the bulge is a symmetric bulge.

Embodiment 39 The engineered polynucleotide of any one of embodiments 36-38, wherein the bulge is from 1-29 nucleotides in length.

Embodiment 40 The engineered polynucleotide of embodiment 35, wherein the structural feature comprises the hairpin.

Embodiment 41 The engineered polynucleotide of embodiment 35, wherein the structural feature comprises the internal loop.

Embodiment 42 The engineered polynucleotide of embodiment 41, wherein the internal loop is an asymmetric loop.

Embodiment 43 The engineered polynucleotide of embodiment 41, wherein the internal loop is a symmetric loop.

Embodiment 44 The engineered polynucleotide of embodiment 35, wherein the structural feature comprises the structured motif.

Embodiment 45 The engineered polynucleotide of embodiment 44, wherein the structured motif comprises at least two of: the bulge, the hairpin, and the internal loop.

Embodiment 46 The engineered polynucleotide of embodiment 45, wherein the structured motif comprises the bulge and the hairpin.

Embodiment 47 The engineered polynucleotide of embodiment 45, wherein the structured motif comprises the bulge and the internal loop.

Embodiment 48 The engineered polynucleotide of any one of embodiments 1-47, wherein the engineered polynucleotide comprises a backbone that comprises a plurality of sugar and phosphate moieties covalently linked together, and wherein the backbone comprises a 5' reducing hydroxyl, a 3' reducing hydroxyl, or both.

Embodiment 49 The engineered polynucleotide of embodiment 48, wherein each of the 5' reducing hydroxyl in the backbone is linked to each of the 3' reducing hydroxyl via a phosphodiester bond.

Embodiment 50 The engineered polynucleotide of any one of embodiments 1-47, wherein the engineered polynucleotide comprises a backbone that comprises a plurality of sugar and phosphate moieties covalently linked together, and wherein the backbone lacks a 5' reducing hydroxyl, a 3' reducing hydroxyl, or both.

Embodiment 51 The engineered polynucleotide of any one of embodiments 1-50, wherein when the engineered polynucleotide associates with the region of the target RNA, the association comprises hybridized polynucleotide strands.

Embodiment 52 The engineered polynucleotide of embodiment 51, wherein the hybridized polynucleotide strands at least in part form a duplex.

Embodiment 53 The engineered polynucleotide of any one of embodiments 1-52, wherein the engineered polynucleotide further comprises a chemical modification.

Embodiment 54 The engineered polynucleotide of any one of embodiments 1-53, wherein the engineered polynucleotide comprises RNA, DNA, or both.

Embodiment 55 The engineered polynucleotide of embodiment 54, wherein the engineered polynucleotide comprises the RNA.

Embodiment 56 An engineered polynucleotide configured to facilitate an editing of a base of a nucleotide of a polynucleotide of a region of a target RNA at least partially encoding an amyloid precursor protein (APP), wherein an RNA editing entity, in association with the engineered polynucleotide and the target RNA, edits the base of the nucleotide of the polynucleotide of the region of the target RNA, wherein the editing results in generation of an edited target RNA at least partially encoding a modified amyloid precursor protein (APP).

Embodiment 57 The engineered polynucleotide of embodiment 56, wherein the RNA editing entity comprises a secretase enzyme.

Embodiment 58 The engineered polynucleotide of embodiment 57, wherein the secretase enzyme is beta secretase; a γ-secretase; or a beta secretase and a γ-secretase.

Embodiment 59 The engineered polynucleotide of embodiment 58, wherein the secretase enzyme is the beta secretase, and wherein the beta secretase is selected from the group consisting of: beta-site amyloid precursor protein cleaving enzyme 1, cathepsin B, and Meprin beta.

Embodiment 60 An engineered polynucleotide configured to facilitate, by an RNA editing entity, an editing of a base of a nucleotide of a polynucleotide of a region of a target RNA at least partially encoding an amyloid precursor protein (APP), wherein the editing results in generation of an edited target RNA that comprises at least one amino acid substitution compared to an otherwise comparable unedited target RNA, wherein the edited target RNA encodes an APP with an altered susceptibility to a beta secretase cleavage compared to the otherwise comparable APP encoded by the otherwise comparable unedited target RNA; and wherein a cell expressing an APP polypeptide generated from the edited target RNA has substantially no decrease in beta secretase activity on an endogenous substrate of beta secretase compared to a corresponding cell expressing an APP polypeptide generated from the unedited target RNA, as determined by an in vitro assay comprising a measurement of a metabolite indicative of cleavage of the endogenous substrate by beta-site amyloid precursor protein cleaving enzyme 1 (BACE1), and wherein the endogenous substrate comprises amyloid-like protein 1 (APLP1), amyloid-like protein 2 (APLP2), Contactin 2, Jagged 1, neural cell adhesion molecule L1 (CHL1), Neurexin 1α, Neurexin 3β, neuregulin 1 (NRG1), seizure related protein 6 (SEZ6), seizure related protein 6 precursor protein (SEZ6L), a 13 (131-4) Auxiliary subunit of the voltage-gated sodium ion channel (VGSC) subtype Nav1, VGSC Accessory Subunits KCNE1 or KCNE2, a functional portion of any of these, or any combination of thereof.

Embodiment 61 The engineered polynucleotide of embodiment 60, wherein the beta secretase comprises BACE1, cathepsin B, or Meprin beta.

Embodiment 62 The engineered polynucleotide of embodiment 60, wherein the endogenous substrate comprises the NRG1, the SEZ6, or the CHL1.

Embodiment 63 An engineered polynucleotide configured to facilitate, by an RNA editing entity, an editing of a base of a nucleotide of a polynucleotide of a region of a target RNA at least partially encoding an amyloid precursor protein (APP), wherein the editing results in generation of a modified APP encoded by an edited target RNA that comprises at least one amino acid substitution compared to an otherwise comparable unmodified APP encoded by an comparable unedited target RNA, and wherein the modified APP polypeptide generated from the edited target RNA: (i) produces a lower amount of Abeta40, Abeta42, or both when expressed in a cell as compared to an APP polypeptide generated from the unedited target RNA as measured by an Abeta40 or Abeta42 enzyme linked immunosorbent assay (ELISA); (ii) produces an increased amount of secreted ectodomain APP alpha (sAPPa) when expressed in a cell as compared to the sAPPa generated from the unedited target RNA as measured by an sAPPa ELISA; or (iii) any combination of (i) and (ii).

Embodiment 64 A vector that comprises: (a) the engineered polynucleotide of any one of embodiments 1-63, (b) a polynucleotide encoding the engineered polynucleotide of any one of embodiments 1-63; or (c) (a) and (b).

Embodiment 65 The vector of embodiment 64, further comprising a second engineered polynucleotide or a second polynucleotide encoding the second engineered polynucleotide.

Embodiment 66 The vector of embodiment 65, wherein the engineered polynucleotide and the second engineered polynucleotide are the same.

Embodiment 67 The vector of embodiment 65, wherein the engineered polynucleotide and the second engineered polynucleotide are different.

Embodiment 68 The vector of any one of embodiments 64-67, wherein the second engineered polynucleotide comprises a second targeting sequence that at least partially hybridizes to a region of a second target RNA.

Embodiment 69 The vector of any one of embodiments 65-68, wherein the second engineered polynucleotide comprises an siRNA, an shRNA, an miRNA, a piRNA, an anti-sense oligonucleotide; or does not comprise at least one of these.

Embodiment 70 The vector of any one of embodiments 65-69, wherein the engineered polynucleotide and the second engineered polynucleotide are contiguous with each other.

Embodiment 71 The vector of any one of embodiments 65-70, wherein the polynucleotide of the vector independently encodes: the engineered polynucleotide and the second engineered polynucleotide, are operatively linked to a same promoter sequence.

Embodiment 72 The vector of any one of embodiments 65-70, wherein the engineered polynucleotide and the second engineered polynucleotide not contiguous with each other.

Embodiment 73 The vector of any one of embodiments 65-72, wherein the engineered polynucleotide comprises a targeting sequence that is at least partially complementary to a region of the APP target RNA, and wherein the second engineered polynucleotide comprises a targeting sequence that is at least partially complementary to a region of the SNCA or the Tau target RNA.

Embodiment 74 The vector of any one of embodiments 65-73, wherein the engineered polynucleotide comprises a targeting sequence that is at least partially complementary to a region of the APP target RNA, and wherein the second engineered polynucleotide comprises the siRNA, the shRNA, the miRNA, the piRNA, or the anti-sense oligonucleotide that targets the SNCA polypeptide or the Tau polypeptide.

Embodiment 75 The vector of any one of embodiments 64-74, wherein the vector is a viral vector.

Embodiment 76 The vector of embodiment 75, wherein the viral vector is an AAV vector, and wherein the AAV vector is of a serotype selected from the group comprising: AAV2, AAV5, AAV6, AAV8, AAV9, a portion thereof, a fusion product thereof, and any combination thereof.

Embodiment 77 The vector of embodiment 76, wherein the AAV vector comprises rep and ITR sequences from AAV2 and a cap sequence from AAV5.

Embodiment 78 The vector of any one of embodiments 76-77, wherein the AAV vector comprises an ITR sequence that is a self-complementary ITR.

Embodiment 79 The vector of any one of embodiments 76-78, wherein the AAV vector that encodes for the engineered polynucleotide is self-complementary.

Embodiment 80 A pharmaceutical composition in unit dose form comprising the engineered polynucleotide of any one of embodiments 1-63 or the vector of any one of embodiments 64-79.

Embodiment 81 The pharmaceutical composition in unit dose form of embodiment 80, further comprising a pharmaceutically acceptable: excipient, carrier, or diluent.

Embodiment 82 A method of making a pharmaceutical composition comprising admixing the engineered polynucleotide of any one of embodiment 1-63 with a pharmaceutically acceptable excipient, diluent, or carrier.

Embodiment 83 An isolated cell comprising the engineered polynucleotide of any one of embodiments 1-63, the vector of any one of embodiments 64-79, or both.

Embodiment 84 A kit comprising the engineered polynucleotide of any one of embodiments 1-63, the vector of any one of embodiments 64-79, or both in a container.

Embodiment 85 A method of making a kit comprising inserting the engineered polynucleotide of any one of embodiments 1-63 into a container.

Embodiment 86 A method of treating or preventing a disease or condition in a subject in need thereof, the method comprising administering to a subject in need thereof: (a) the vector of any one of embodiments 64-79; (b) the pharmaceutical composition of any one of embodiments 80-81; or (c) (a) and (b).

Embodiment 87 A method of treating or preventing a disease or condition comprising administering a therapeutic to a subject in need thereof, wherein the therapeutic facilitates, by an RNA editing entity, an editing of a base of a nucleotide of a polynucleotide of a region of a target RNA that at least partially encodes for an amyloid precursor protein (APP), thereby generating an edited RNA that at least partially encodes for a beta secretase-resistant APP as compared to an otherwise comparable APP encoded by an otherwise comparable RNA lacking the edit as determined by in vitro assay comprising contacting the beta secretase-resistant APP and the otherwise comparable APP with: a) a beta secretase; b) a γ-secretase; c) or a beta secretase and a γ-secretase.

Embodiment 88 The method of embodiment 87, wherein the beta secretase comprises beta-site amyloid precursor protein cleaving enzyme 1, cathepsin B, or Meprin beta.

Embodiment 89 The method of embodiment 88, wherein the therapeutic comprises a vector comprising or encoding an engineered polynucleotide that comprises a targeting sequence that at least partially hybridizes to a region of the target RNA.

Embodiment 90 The method of any one of embodiments 87-89, wherein the engineered polynucleotide further comprises an RNA editing entity recruiting domain that is capable of recruiting the RNA editing entity.

Embodiment 91 The method of embodiment 90, wherein the RNA editing entity recruiting domain is at least 1 to about 75 nucleotides in length.

Embodiment 92 The method of any one of embodiments 90-91, wherein the RNA editing entity recruiting domain comprises a glutamate ionotropic receptor AMPA type subunit 2 (GluR2) sequence.

Embodiment 93 The method of any one of embodiments 87-92, wherein the RNA editing entity comprises an adenosine deaminase acting on RNA (ADAR) polypeptide or biologically active fragment thereof or adenosine deaminase acting on tRNA (ADAT) polypeptide or biologically active fragment thereof.

Embodiment 94 The method of embodiment 93, wherein the RNA editing entity comprises the ADAR polypeptide or biologically active fragment thereof, and wherein the ADAR comprises ADAR1 or ADAR2.

Embodiment 95 The method of any one of embodiments 87-89, wherein the engineered polynucleotide lacks an RNA editing entity recruiting sequence.

Embodiment 96 The method of any one of embodiments 87-95, wherein the engineered polynucleotide further comprises a structural feature.

Embodiment 97 The method of embodiment 96, wherein the structural feature comprises: a bulge, a hairpin, an internal loop, a structured motif, and any combination thereof.

Embodiment 98 The method of embodiment 97, wherein the structural feature comprises the bulge.

Embodiment 99 The method of embodiment 98, wherein the bulge is an asymmetric bulge.

Embodiment 100 The method of embodiment 98, wherein the bulge is a symmetric bulge.

Embodiment 101 The method of any one of embodiments 98-100, wherein the bulge is from 1-29 nucleotides in length.

Embodiment 102 The method of embodiment 97, wherein the structural feature comprises the hairpin.

Embodiment 103 The method of embodiment 97, wherein the structural feature comprises the internal loop.

Embodiment 104 The method of embodiment 103, wherein the internal loop is asymmetric.

Embodiment 105 The method of embodiment 103, wherein the internal loop is asymmetric.

Embodiment 106 The method of embodiment 97, wherein the structural feature comprises the structured motif Embodiment 107 The method of embodiment 97, wherein the structured motif comprises at least two of: the bulge, the hairpin, and the internal loop.

Embodiment 108 The method of embodiment 107, wherein the structured motif comprises the bulge and the hairpin.

Embodiment 109 The method of embodiment 107, wherein the structured motif comprises the bulge and the internal loop.

Embodiment 110 The method of any one of embodiments 87-109, wherein the engineered polynucleotide comprises a backbone that comprises a plurality of sugar and phosphate moieties covalently linked together, and wherein the backbone comprises a 5' reducing hydroxyl, a 3' reducing hydroxyl, or both.

Embodiment 111 The engineered polynucleotide of embodiment 110, wherein each of the 5' reducing hydroxyl in the backbone is linked to each of the 3' reducing hydroxyl via a phosphodiester bond.

Embodiment 112 The engineered polynucleotide of any one of embodiments 87-109, wherein the engineered polynucleotide comprises a backbone that comprises a plurality of sugar and phosphate moieties covalently linked together, and wherein the backbone lacks a 5' reducing hydroxyl, a 3' reducing hydroxyl, or both.

Embodiment 113 The method of any one of embodiments 87-112, wherein the beta secretase-resistant APP has reduced susceptibility to cleavage at a position cleavable by a beta secretase as compared to the otherwise comparable APP produced from the otherwise comparable RNA lacking the edit.

Embodiment 114 The method of embodiment 113, wherein the beta secretase comprises BACE1, cathepsin B, or Meprin beta.

Embodiment 115 The method of any one of embodiments 87-114, wherein the nucleotide is comprised in a codon which encodes an amino acid in proximity to a cleavage site of the APP.

Embodiment 116 The method of embodiment 115, wherein the cleavage site at the APP is selected from the group consisting of: an α-secretase cleavage site, a β-secretase cleavage site, a β'-secretase cleavage site, a γ-secretase cleavage site, and any combination thereof.

Embodiment 117 The method of any one of embodiments 87-116, wherein the amino acid is at position 669, 670, 671, 672, 673, 682, 683, 684, 687, 688, 711, 712, 713, or 714 of the APP of SEQ ID NO: 2.

Embodiment 118 The method of any one of embodiments 87-117, wherein the BACE protease-resistant APP comprises at least one amino acid residue difference as compared to the otherwise comparable APP produced from the otherwise comparable RNA lacking the edit.

Embodiment 119 The method of embodiment 118, wherein the one amino acid residue difference comprises an amino acid substitution that results in a change in charge, hydrophobicity, or polarity of the amino acid, or any combination thereof.

Embodiment 120 The method of any one of embodiments 118-119, wherein the difference in the amino acid comprises a conservative substitution.

Embodiment 121 The method of any one of embodiments 118-119, wherein the difference in the amino acid comprises a charge neutral substitution.

Embodiment 122 The method of any one of embodiments 118-119, wherein the difference in the amino acid residue comprises a K to E change, a K to R change, a K to G change, an M to V change, a D to G change, an E to G change, an H to R change, or any combination thereof.

Embodiment 123 The method of embodiment 122, wherein the difference in the amino acid residue comprises K670E, K670R, K670G, M671V, D672G, E682G, H684R, K687R, K687E, or K687G of the amyloid precursor protein of SEQ ID NO: 2.

Embodiment 124 The method of embodiment 122 or 123, wherein the change in the one amino acid comprises K670G or M671V of the amyloid precursor protein of SEQ ID NO: 2.

Embodiment 125 The method of any one of embodiments 87-124, wherein the target RNA is selected from the group comprising: an mRNA, a tRNA, a lncRNA, a lincRNA, a miRNA, a rRNA, a snRNA, a siRNA, a piRNA, a snoRNA, a exRNA, a scaRNA, a YRNA, an eRNA, and a hnRNA.

Embodiment 126 The method of embodiment 125, wherein the target RNA is the mRNA.

Embodiment 127 The method of any one of embodiments 87-125, wherein the therapeutic directly facilitates the edit.

Embodiment 128 The method of any one of embodiments 87-125, wherein the therapeutic indirectly facilitates the edit.

Embodiment 129 The method of any one of embodiments 87-128, wherein the disease or condition comprises a neurodegenerative disease or condition.

Embodiment 130 The method of embodiment 129, wherein the neurodegenerative condition comprises Alzheimer's disease, Parkinson's disease, dementia, Lewy Body Dementia, progressive supranuclear palsy, frontotemporal lobar degeneration, corticobasal degeneration, or any combination thereof.

Embodiment 131 The method of any one of embodiments 87-128, wherein the condition comprises traumatic brain injury, Down's syndrome, cancer, Fragile X Syndrome, autism, amyotrophic lateral sclerosis, multiple sclerosis, Lesch-Nyhan disease, metabolic disorder, or any combination thereof.

Embodiment 132 The method of any one of embodiments 87-131, wherein the edited RNA or the BACE protease-resistant APP is generated in at least 5%, 8%, 10%, 15%, 20%, 30%, 40%, or 50% of the subjects administered the therapeutic in a clinical trial.

Embodiment 133 The method of any one of embodiments 87-132, further comprising a second administering of an additional therapeutic agent.

Embodiment 134 The method of embodiment 133, wherein the administering and the second administering are consecutive.

Embodiment 135 The method of embodiment 133, wherein the administering and the second administering are concurrent.

Embodiment 136 The method of any one of embodiments 133-135, wherein the administering or the second administering or both are independently repeated at least once a week.

Embodiment 137 The method of any one of embodiments 133-136, wherein the administering or the second administering or both are independently performed by parenteral route of administration.

Embodiment 138 The method of any one of embodiments 133-137, wherein the administering or the second administering or both are independently performed by parenchymal injection, intra-thecal injection, intra-ventricular injection, intra-cisternal injection, intravenous injection, or intranasal administration or any combination thereof

What is claimed is:

1. A composition that comprises: an engineered guide RNA comprising a targeting sequence that has complementarity to a region of a target RNA sufficient for the targeting sequence to hybridize to the region of the target RNA, wherein the region of the target RNA comprises a sequence that encodes an amyloid precursor protein (APP) polypeptide; and wherein the engineered guide RNA is configured to hybridize to the region of the target RNA and to facilitate editing of an adenosine in the target RNA by an RNA editing entity, thereby generating an edited target RNA, wherein the adenosine is comprised in a codon which encodes an amino acid in proximity to a cleavage site of the APP polypeptide, and wherein the amino acid is at position 670 or 671, or both positions of the APP polypeptide comprising the polypeptide sequence of SEQ ID NO: 2, wherein the cleavage site is selected from the group consisting of: an alpha-secretase cleavage site, a beta-secretase cleavage site, a beta'-secretase cleavage site, a gamma-secretase cleavage site, and any combination thereof, wherein the target RNA encodes an unmodified APP polypeptide that comprises at least one amino acid residue difference as compared to a modified APP polypeptide generated from translation of the edited target RNA, and wherein the modified APP polypeptide comprises a K670G substitution, a M671V substitution, or both substitution of the unmodified APP polypeptide comprising the polypeptide sequence of SEQ ID NO: 2 and wherein the modification of the APP polypeptide results in reduced levels of Abeta 40, Abeta 42, or both peptides produced by a cell as compared to the unmodified APP polypeptide.

2. The composition of claim 1, wherein the engineered guide RNA, when hybridized with the target RNA, forms a structural feature.

3. The composition of claim 2, wherein the structural feature comprises a bulge, an internal loop, a hairpin, a mismatch, a wobble base pair, or any combination thereof.

4. The composition of claim 3, wherein the structural feature comprises the bulge.

5. The composition of claim 4, wherein the bulge comprises an asymmetric bulge.

6. The composition of claim 4, wherein the bulge comprises a symmetric bulge.

7. The composition of claim 4, wherein the bulge comprises from about 1 to about 4 nucleotides of the engineered guide RNA and from about 0 to about 4 nucleotides of the target RNA.

8. The composition of claim 4, wherein the bulge comprises from about 0 to about 4 nucleotides of the engineered guide RNA and from about 1 to about 4 nucleotides of the target RNA.

9. The composition of claim 4, wherein the bulge comprises 3 nucleotides of the engineered guide RNA and 3 nucleotides of the target RNA.

10. The composition of claim 4, wherein the bulge comprises 3 nucleotides of the engineered guide RNA and 2 nucleotides of the target RNA.

11. The composition of claim 4, wherein the engineered guide RNA, when associated with the target RNA, forms a second structural feature.

12. The composition of claim 11, wherein the second structural feature is a bulge that comprises 2 nucleotides of the engineered guide RNA and 2 nucleotides of the target RNA.

13. The composition of claim 11, wherein the second structural feature is a G/G mismatch followed by an A/C mismatch.

14. The composition of claim 13, wherein the base of the nucleotide of the target RNA is an adenosine of the A/C mismatch.

15. The composition of claim 11, wherein the structural feature is a bulge that comprises 2 nucleotides of the engineered guide RNA and 2 nucleotides of the target RNA; and wherein the second structural feature is a bulge that comprises 3 nucleotides of the engineered guide RNA and 2 nucleotides of the target RNA.

16. The composition of claim 3, wherein the structural feature comprises the internal loop.

17. The composition of claim 16, wherein the internal loop comprises an asymmetric internal loop.

18. The composition of claim 16, wherein the internal loop comprises a symmetric internal loop.

19. The composition of claim 16, wherein the internal loop is formed by from about 5 to about 10 nucleotides of either the engineered guide RNA or the target RNA.

20. The composition of claim 3, wherein the structural feature comprises the mismatch and wherein the mismatch comprises a base in the targeting sequence of the engineered guide RNA opposite to and unpaired with the base of the nucleotide of the target RNA.

21. The composition of claim 20, wherein the mismatch comprises a base in the targeting sequence of the engineered guide RNA opposite to and unpaired with the base of the nucleotide of the target RNA.

22. The composition of claim 20, wherein the mismatch comprises a guanine-guanine mismatch.

23. The composition of claim 20, wherein the mismatch comprises an adenosine-cytosine mismatch, and wherein the adenosine is in the target RNA and the cytosine is in the targeting sequence of the engineered guide RNA.

24. The composition of claim 23, wherein the adenosine in the adenosine-cytosine mismatch is the adenosine in the target RNA edited by the RNA editing entity.

25. The composition of claim 3, wherein the structural feature comprises the wobble base pair.

26. The composition of claim 25, wherein the wobble base pair comprises a guanine paired with a uracil.

27. The composition of claim 1, wherein the RNA editing entity comprises an adenosine deaminase acting on RNA (ADAR) polypeptide or biologically active fragment thereof, wherein the ADAR polypeptide or the biologically active fragment thereof comprises ADAR1, ADAR2, or a biologically active fragment of any of these.

28. The composition of claim 1, wherein the editing of the adenosine in the target RNA by the RNA editing entity is sufficient to reduce β-amyloid peptide, which comprises preventing or eliminating formation of the β-amyloid peptide.

29. The composition of claim 28, wherein the editing is sufficient to eliminate the β-amyloid peptide formation.

30. The composition of claim 28, wherein the editing is sufficient to increase an amount of secreted ectodomain APP alpha (sAPPa).

31. The composition of claim 1, wherein the engineered guide RNA is configured to facilitate editing of two bases of the target RNA by the RNA editing entity, wherein the two bases are comprised in codons that encode amino acids at position 670 and position 671.

32. The composition of claim 1, wherein the engineered guide RNA is encoded by a polynucleotide sequence comprised in a vector.

33. The composition of claim 32, wherein the vector is an adeno associated viral (AAV) vector.

34. The composition of claim 33, wherein the AAV vector is of a serotype selected from the group comprising: AAV2, AAVS, AAV6, AAV8, AAV9, a fusion product thereof, and any combination thereof.

* * * * *

SEQUENCE LISTING

<160> NUMBER OF SEQ ID NOS: 225

<210> SEQ ID NO 1
<211> LENGTH: 45
<212> TYPE: RNA
<213> ORGANISM: Unknown
<220> FEATURE:
<221> NAME/KEY: source
<223> OTHER INFORMATION: /note="Description of Unknown:
GluR2 sequence"

<400> SEQUENCE: 1
guggaauagu auaacaauau gcuaaauguu guuauaguau cccac 45

<210> SEQ ID NO 2
<211> LENGTH: 770
<212> TYPE: PRT
<213> ORGANISM: Homo sapiens

<400> SEQUENCE: 2

Met Leu Pro Gly Leu Ala Leu Leu Leu Leu Ala Ala Trp Thr Ala Arg
1 5 10 15

Ala Leu Glu Val Pro Thr Asp Gly Asn Ala Gly Leu Leu Ala Glu Pro
20 25 30

Gln Ile Ala Met Phe Cys Gly Arg Leu Asn Met His Met Asn Val Gln
35 40 45

Asn Gly Lys Trp Asp Ser Asp Pro Ser Gly Thr Lys Thr Cys Ile Asp
50 55 60

Thr Lys Glu Gly Ile Leu Gln Tyr Cys Gln Glu Val Tyr Pro Glu Leu
65 70 75 80

Gln Ile Thr Asn Val Val Glu Ala Asn Gln Pro Val Thr Ile Gln Asn
85 90 95

Trp Cys Lys Arg Gly Arg Lys Gln Cys Lys Thr His Pro His Phe Val
100 105 110

Ile Pro Tyr Arg Cys Leu Val Gly Glu Phe Val Ser Asp Ala Leu Leu
115 120 125

Val Pro Asp Lys Cys Lys Phe Leu His Gln Glu Arg Met Asp Val Cys
130 135 140

Glu Thr His Leu His Trp His Thr Val Ala Lys Glu Thr Cys Ser Glu
145 150 155 160

Lys Ser Thr Asn Leu His Asp Tyr Gly Met Leu Leu Pro Cys Gly Ile
165 170 175

Asp Lys Phe Arg Gly Val Glu Phe Val Cys Cys Pro Leu Ala Glu Glu
180 185 190

Ser Asp Asn Val Asp Ser Ala Asp Ala Glu Glu Asp Asp Ser Asp Val
195 200 205

Trp Trp Gly Gly Ala Asp Thr Asp Tyr Ala Asp Gly Ser Glu Asp Lys
210 215 220

Val Val Glu Val Ala Glu Glu Glu Glu Val Ala Glu Val Glu Glu Glu
225 230 235 240

Glu Ala Asp Asp Asp Glu Asp Asp Glu Asp Gly Asp Glu Val Glu Glu
245 250 255

Glu Ala Glu Glu Pro Tyr Glu Glu Ala Thr Glu Arg Thr Thr Ser Ile
260 265 270

Ala Thr Thr Thr Thr Thr Thr Thr Glu Ser Val Glu Glu Val Val Arg
275 280 285

Glu Val Cys Ser Glu Gln Ala Glu Thr Gly Pro Cys Arg Ala Met Ile

-continued

```
    290                 295                 300

Ser Arg Trp Tyr Phe Asp Val Thr Glu Gly Lys Cys Ala Pro Phe Phe
305                 310                 315                 320

Tyr Gly Gly Cys Gly Gly Asn Arg Asn Asn Phe Asp Thr Glu Glu Tyr
                325                 330                 335

Cys Met Ala Val Cys Gly Ser Ala Met Ser Gln Ser Leu Leu Lys Thr
            340                 345                 350

Thr Gln Glu Pro Leu Ala Arg Asp Pro Val Lys Leu Pro Thr Thr Ala
        355                 360                 365

Ala Ser Thr Pro Asp Ala Val Asp Lys Tyr Leu Glu Thr Pro Gly Asp
    370                 375                 380

Glu Asn Glu His Ala His Phe Gln Lys Ala Lys Glu Arg Leu Glu Ala
385                 390                 395                 400

Lys His Arg Glu Arg Met Ser Gln Val Met Arg Glu Trp Glu Glu Ala
                405                 410                 415

Glu Arg Gln Ala Lys Asn Leu Pro Lys Ala Asp Lys Lys Ala Val Ile
            420                 425                 430

Gln His Phe Gln Glu Lys Val Glu Ser Leu Glu Gln Glu Ala Ala Asn
        435                 440                 445

Glu Arg Gln Gln Leu Val Glu Thr His Met Ala Arg Val Glu Ala Met
    450                 455                 460

Leu Asn Asp Arg Arg Arg Leu Ala Leu Glu Asn Tyr Ile Thr Ala Leu
465                 470                 475                 480

Gln Ala Val Pro Pro Arg Pro Arg His Val Phe Asn Met Leu Lys Lys
                485                 490                 495

Tyr Val Arg Ala Glu Gln Lys Asp Arg Gln His Thr Leu Lys His Phe
            500                 505                 510

Glu His Val Arg Met Val Asp Pro Lys Lys Ala Ala Gln Ile Arg Ser
        515                 520                 525

Gln Val Met Thr His Leu Arg Val Ile Tyr Glu Arg Met Asn Gln Ser
    530                 535                 540

Leu Ser Leu Leu Tyr Asn Val Pro Ala Val Ala Glu Glu Ile Gln Asp
545                 550                 555                 560

Glu Val Asp Glu Leu Leu Gln Lys Glu Gln Asn Tyr Ser Asp Asp Val
                565                 570                 575

Leu Ala Asn Met Ile Ser Glu Pro Arg Ile Ser Tyr Gly Asn Asp Ala
            580                 585                 590

Leu Met Pro Ser Leu Thr Glu Thr Lys Thr Thr Val Glu Leu Leu Pro
        595                 600                 605

Val Asn Gly Glu Phe Ser Leu Asp Asp Leu Gln Pro Trp His Ser Phe
    610                 615                 620

Gly Ala Asp Ser Val Pro Ala Asn Thr Glu Asn Glu Val Glu Pro Val
625                 630                 635                 640

Asp Ala Arg Pro Ala Ala Asp Arg Gly Leu Thr Thr Arg Pro Gly Ser
                645                 650                 655

Gly Leu Thr Asn Ile Lys Thr Glu Glu Ile Ser Glu Val Lys Met Asp
            660                 665                 670

Ala Glu Phe Arg His Asp Ser Gly Tyr Glu Val His His Gln Lys Leu
        675                 680                 685

Val Phe Phe Ala Glu Asp Val Gly Ser Asn Lys Gly Ala Ile Ile Gly
    690                 695                 700

Leu Met Val Gly Gly Val Val Ile Ala Thr Val Ile Val Ile Thr Leu
705                 710                 715                 720
```

-continued

```
Val Met Leu Lys Lys Lys Gln Tyr Thr Ser Ile His His Gly Val Val
                725                 730                 735

Glu Val Asp Ala Ala Val Thr Pro Glu Glu Arg His Leu Ser Lys Met
            740                 745                 750

Gln Gln Asn Gly Tyr Glu Asn Pro Thr Tyr Lys Phe Phe Glu Gln Met
        755                 760                 765

Gln Asn
    770


<210> SEQ ID NO 3
<211> LENGTH: 3583
<212> TYPE: RNA
<213> ORGANISM: Homo sapiens

<400> SEQUENCE: 3

gucaguuucc ucggcagcgg uaggcgagag cacgcggagg agcgugcgcg ggggccccgg     60

gagacggcgg cgguggcggc gcgggcagag caaggacgcg gcggauccca cucgcacagc    120

agcgcacucg gugccccgcg cagggucgcg augcugcccg guuuggcacu gcuccugcug    180

gccgccugga cggcucgggc gcuggaggua cccacugaug guaaugcugg ccugcuggcu    240

gaaccccaga uugccauguu cuguggcaga cugaacaugc acaugaaugu ccagaauggg    300

aagugggauu cagauccauc agggaccaaa accugcauug auaccaagga aggcauccug    360

caguauugcc aagaagucua cccugaacug cagaucacca augugguaga agccaaccaa    420

ccagugacca uccagaacug gugcaagcgg ggccgcaagc agugcaagac ccaucccac     480

uuugugauuc ccuaccgcug cuuaguuggu gaguuuguaa gugaugcccu ucucguuccu    540

gacaagugca aauucuuaca ccaggagagg auggauguuu gcgaaacuca ucuucacugg    600

cacaccgucg ccaaagagac augcagugag aagaguacca acuugcauga cuacggcaug    660

uugcugcccu gcggaauuga caaguuccga gggguagagu uuguguguug cccacuggcu    720

gaagaaagug acaaugugga uucugcugau gcggaggagg augacucgga ugucuggugg    780

ggcggagcag acacagacua ugcagauggg agugaagaca aaguaguaga aguagcagag    840

gaggaagaag uggcugaggu ggaagaagaa gaagccgaug augacgagga cgaugaggau    900

ggugaugagg uagaggaaga ggcugaggaa cccuacgaag aagccacaga gagaaccacc    960

agcauugcca ccaccaccac caccaccaca gagucugugg aagagguggu ucgagaggug   1020

ugcucugaac aagccgagac ggggccgugc cgagcaauga ucucccgcug guacuuugau   1080

gugacugaag ggaagugugc cccauucuuu uacggcggau guggcggcaa ccggaacaac   1140

uuugacacag aagaguacug cauggccgug uguggcagcg ccaugucca aaguuuacuc    1200

aagacuaccc aggaaccucu ugcccgagau ccuguuaaac uuccuacaac agcagccagu   1260

accccugaug ccguugacaa guaucucgag acaccugggg augagaauga acaugcccau   1320

uuccagaaag ccaaagagag gcuugaggcc aagcaccgag agagaauguc ccaggucaug   1380

agagaauggg aagaggcaga acgucaagca aagaacuugc cuaaagcuga uaagaaggca   1440

guuauccagc auuuccagga gaaaguggaa ucuuuggaac aggaagcagc caacgagaga   1500

cagcagcugg uggagacaca cauggccaga guggaagcca ugcucaauga ccgccgccgc   1560

cuggcccugg agaacuacau caccgcucug caggcuguuc cuccucggcc ucgucacgug   1620

uucaauaugc uaaagaagua uguccgcgca gaacagaagg acagacagca cacccuaaag   1680

cauuucgagc augugcgcau gguggauccc aagaaagccg cucagauccg gucccagguu   1740
```

-continued augacacacc uccgugugau uuaugagcgc augaaucagu cucucucccu gcucuacaac 1800
gugccugcag uggccgagga gauucaggau gaaguugaug agcugcuuca gaaagagcaa 1860
aacuauucag augacgucuu ggccaacaug auuagugaac caaggaucag uuacggaaac 1920
gaugcucuca ugccaucuuu gaccgaaacg aaaaccaccg uggagcuccu ucccgugaau 1980
ggagaguuca gccuggacga ucuccagccg uggcauucuu uuggggcuga cucugugcca 2040
gccaacacag aaaacgaagu ugagccuguu gaugcccgcc cugcugccga ccgaggacug 2100
accacucgac cagguucugg guugacaaau aucaagacgg aggagaucuc ugaagugaag 2160
auggaugcag aauuccgaca ugacucagga uaugaaguuc aucaucaaaa auuggguguuc 2220 uuugcagaag augugggguuc aaacaaaggu gcaaucauug gacucauggu gggcggugu 2280 gucauagcga cagugaucgu caucaccuug gugaugcuga agaagaaaca guacacaucc 2340
auucaucaug guguggugga gguugacgcc gcugucaccc cagaggagcg ccaccugucc 2400
aagaugcagc agaacggcua cgaaaaucca accuacaagu ucuuugagca gaugcagaac 2460
uagacccccg ccacagcagc cucugaaguu ggacagcaaa accauugcuu cacuacccau 2520 cggugucau uuauagaaua auguggggaag aaacaaaccc guuuuaugau uuacucauua 2580
ucgccuuuug acagcugugc uguaacacaa guagaugccu gaacuugaau uaauccacac 2640
aucaguaaug uauucuaucu cucuuuacau uuuggucucu auacuacauu auuaaugggu 2700
uuuguguacu guaaagaauu uagcuguauc aaacuagugc augaauagau ucucuccuga 2760
uuauuuauca cauagccccu uagccaguug uauauuauuc uugugguuug ugacccaauu 2820
aaguccuacu uuacauaugc uuuaagaauc gaugggggau gcuucaugug aacgugggag 2880
uucagcugcu ucucuugccu aaguauuccu uuccugauca cuaugcauuu uaaaguuaaa 2940
cauuuuuaag uauuucagau gcuuuagaga gauuuuuuuu ccaugacugc auuuuacugu 3000
acagauugcu gcuucugcua uauuugugau auaggaauua agaggauaca cacguuuguu 3060
ucuucgugcc uguuuuaugu gcacacauua ggcauugaga cuucaagcuu uucuuuuuuu 3120
guccacguau cuuugggucu uugauaaaga aaagaauccc uguucauugu aagcacuuuu 3180
acggggcggg uggggagggg ugcucugcug gucuucaauu accaagaauu cuccaaaaca 3240
auuuucugca ggaugauugu acagaaucau ugcuuaugac augaucgcuu ucuacacugu 3300
auuacauaaa uaaauuaaau aaaauaaccc cgggcaagac uuuucuuuga aggaugacua 3360
cagacauuaa auaaucgaag uaauuuuggg uggggagaag aggcagauuc aauuuucuuu 3420
aaccagucug aaguuucauu uaugauacaa aagaagauga aaauggaagu ggcaauauaa 3480
ggggaugagg aaggcaugcc uggacaaacc cuucuuuuaa gaugugucuu caauuuguau 3540
aaaauggugu uuucauguaa auaaauacau ucuuggagga gca 3583

<210> SEQ ID NO 4
<211> LENGTH: 3526
<212> TYPE: RNA
<213> ORGANISM: Homo sapiens

<400> SEQUENCE: 4
gucaguuucc ucggcagcgg uaggcgagag cacgcggagg agcgugcgcg ggggccccgg 60
gagacggcgg cgguggcggc gcgggcagag caaggacgcg gcggauccca cucgcacagc 120
agcgcacucg gugccccgcg cagggucgcg augcugcccg guuuggcacu gcuccugcug 180
gccgccugga cggcucgggc gcuggaggua cccacugaug guaaugcugg ccugcuggcu 240
gaaccccaga uugccauguu cuguggcaga cugaacaugc acaugaaugu ccagaauggg 300

-continued

```
aagugggauu cagauccauc agggaccaaa accugcauug auaccaagga aggcauccug    360
caguauugcc aagaagucua cccugaacug cagaucacca auguggua ga agccaaccaa    420
ccagugacca uccagaacug gugcaagcgg ggccgcaagc agugcaagac ccauccccac    480
uugugauuc ccuaccgcug cuuaguuggu gaguuuguaa gugaugcccu ucucguuccu    540
gacaagugca aauucuuaca ccaggagagg auggauguuu gcgaaacuca ucuucacugg    600
cacaccgucg ccaaagagac augcagugag aagaguacca acuugcauga cuacggcaug    660
uugcugcccu gcggaauuga caaguuccga gggguagagu uugugugu ug cccacuggcu    720
gaagaaagug acaaugugga uucugcugau gcggaggagg augacucgga ugucuggugg    780
ggcggagcag acacagacua ugcagauggg agugaagaca aaguaguaga aguagcagag    840
gaggaagaag uggcugaggu ggaagaagaa gaagccgaug augacgagga cgaugaggau    900
ggugaugagg uagaggaaga ggcugaggaa cccuacgaag aagccacaga gagaaccacc    960
agcauugcca ccaccaccac caccaccaca gagucugugg aagagguggu ucgagaggug   1020
ugcucugaac aagccgagac ggggccgugc cgagcaauga ucucccgcug guacuuugau   1080
gugacugaag ggaagugugc cccauucuuu uacggcggau guggcggcaa ccggaacaac   1140
uuugacacag aagaguacug cauggccgug uguggcagcg ccauuccuac aacagcagcc   1200
aguaccccug augccguuga caaguaucuc gagacaccug gggaugagaa ugaacaugcc   1260
cauuuccaga aagccaaaga gaggcuugag gccaagcacc gagagagaau gucccagguc   1320
augagagaau gggaagaggc agaacgucaa gcaaagaacu ugccuaaagc ugauaagaag   1380
gcaguuaucc agcauuucca ggagaaagug gaaucuuugg aacaggaagc agccaacgag   1440
agacagcagc ugguggagac acacauggcc agaguggaag ccaugcucaa ugaccgccgc   1500
cgccuggccc uggagaacua caucaccgcu cugcaggcug uuccuccucg gccucgucac   1560
guguucaaua ugcuaaagaa guauguccgc gcagaacaga aggacagaca gcacacccua   1620
aagcauuucg agcaugugcg caugguggau cccaagaaag ccgcucagau ccggucccag   1680
guuaugacac accuccgugu gauuuaugag cgcaugaauc agucucucuc ccugcucuac   1740
aacgugccug caguggccga ggagauucag gaugaaguug augagcugcu ucagaaagag   1800
caaaacuauu cagaugacgu cuuggccaac augauuagug aaccaaggau caguuacgga   1860
aacgaugcuc ucaugccauc uuugaccgaa acgaaaacca ccguggagcu ccuucccgug   1920
aauggagagu ucagccugga cgaucuccag ccguggcauu cuuuuggggc ugacucugug   1980
ccagccaaca cagaaaacga aguugagccu guugaugccc gcccugcugc cgaccgagga   2040
cugaccacuc gaccagguuc uggguugaca aauaucaaga cggaggagau cucugaagug   2100
aagauggaug cagaauuccg acaugacuca ggauaugaag uucaucauca aaaauuggug   2160
uucuuugcag aagauguggg uucaaacaaa ggugcaauca uuggacucau ggugggcggu   2220
guugucauag cgacagugau cgucaucacc uuggugaugc ugaagaagaa acaguacaca   2280
uccauucauc augguguggu ggagguugac gccgcuguca ccccagagga gcgccaccug   2340
uccaagaugc agcagaacgg cuacgaaaau ccaaccuaca aguucuuuga gcagaugcag   2400
aacuagaccc ccgccacagc agccucugaa guuggacagc aaaaccauug cuucacuacc   2460
caucggugu c cauuuauaga auaaugu ggg aagaaacaaa cccguuuuau gauuuacuca   2520
uuaucgccuu uugacagcug ugcuguaaca caaguagaug ccugaacuug aauuaaucca   2580
cacaucagua auguauucua ucucucuuua cauuuugguc ucuauacuac auuauuaaug   2640
```

gguuuugugu acuguaaaga auuuagcugu aucaaacuag ugcaugaaua gauucucucc 2700
ugauuauuua ucacauagcc ccuuagccag uuguauauua uucuugugu uugugaccca 2760
auuaaguccu acuuuacaua ugcuuuaaga aucgaugggg gaugcuucau gugaacgugg 2820
gaguucagcu gcuucucuug ccuaaguauu ccuuuccuga ucacuaugca uuuuaaaguu 2880
aaacauuuuu aaguauuuca gaugcuuuag agagauuuuu uuuccaugac ugcauuuuac 2940
uguacagauu gcugcuucug cuauauuugu gauauaggaa uuaagaggau acacacguuu 3000
guuucuucgu gccuguuuua ugugcacaca uuaggcauug agacuucaag cuuuucuuuu 3060
uuuguccacg uaucuuuggg ucuuugauaa agaaaagaau cccuguucau uguaagcacu 3120
uuuacggggc ggguggggag gggugcucug cuggucuuca auuaccaaga auucuccaaa 3180
acaauuuucu gcaggaugau uguacagaau cauugcuuau gacaugaucg cuuucuacac 3240
uguauuacau aaauaaauua aauaaaauaa ccccgggcaa gacuuuucuu ugaaggauga 3300
cuacagacau uaaauaaucg aaguaauuuu gggugggggag aagaggcaga uucaauuuuc 3360
uuuaaccagu cugaaguuuc auuuaugaua caaaagaaga ugaaaaugga aguggcaaua 3420
uaaggggaug aggaaggcau gccuggacaa acccuucuuu uaagaugugu cuucaauuug 3480
uauaaaaugg uguuuucaug uaaauaaaua cauucuugga ggagca 3526

<210> SEQ ID NO 5
<211> LENGTH: 3358
<212> TYPE: RNA
<213> ORGANISM: Homo sapiens

<400> SEQUENCE: 5
gucaguuucc ucggcagcgg uaggcgagag cacgcggagg agcgugcgcg ggggccccgg 60
gagacggcgg cgguggcggc gcgggcagag caaggacgcg gcggauccca cucgcacagc 120
agcgcacucg gugccccgcg cagggucgcg augcugcccg guuuggcacu gcuccugcug 180
gccgccugga cggcucgggc gcuggaggua cccacugaug guaaugcugg ccugcuggcu 240
gaaccccaga uugccauguu cuguggcaga cugaacaugc acaugaaugu ccagaauggg 300
aagugggauu cagauccauc agggaccaaa accugcauug auaccaagga aggcauccug 360
caguauugcc aagaagucua cccugaacug cagaucacca auguggguaga agccaaccaa 420
ccagugacca uccagaacug gugcaagcgg ggccgcaagc agugcaagac ccaucccccac 480
uuugugauuc ccuaccgcug cuuaguuggu gaguuuguaa gugaugcccu ucucguuccu 540
gacaagugca aauucuuaca ccaggagagg auggauguuu gcgaaacuca ucuucacugg 600
cacaccgucg ccaaagagac augcagugag aagaguacca acuugcauga cuacggcaug 660
uugcugcccu gcggaauuga caaguuccga gggguagagu uugugguuug cccacuggcu 720
gaagaaagug acaaugugga uucugcugau gcggaggagg augacucgga ugucuggugg 780
ggcggagcag acacagacua ugcagauggg agugaagaca aaguaguaga aguagcagag 840
gaggaagaag uggcugaggu ggaagaagaa gaagccgaug augacgagga cgaugaggau 900
ggugaugagg uagaggaaga ggcugaggaa cccuacgaag aagccacaga gagaaccacc 960
agcauugcca ccaccaccac caccaccaca gagucugugg aagagguggu ucgaguuccu 1020
acaacagcag ccaguacccc ugaugccguu gacaaguauc ucgagacacc uggggaugag 1080
aaugaacaug cccauuucca gaaagccaaa gagaggcuug aggccaagca ccgagagaga 1140
augucccagg ucaugagaga augggaagag gcagaacguc aagcaaagaa cuugccuaaa 1200
gcugauaaga aggcaguuau ccagcauuuc caggagaaag uggaaucuuu ggaacaggaa 1260
gcagccaacg agagacagca gcugguggag acacacaugg ccagagugga agccaugcuc 1320
aaugaccgcc gccgccuggc ccuggagaac uacaucaccg cucugcaggc uguuccuccu 1380
cggccucguc acguguucaa uaugcuaaag aaguaugucc gcgcagaaca gaaggacaga 1440
cagcacaccc uaaagcauuu cgagcaugug cgcauggugg aucccaagaa agccgcucag 1500
auccgguccc agguuaugac acaccuccgu gugauuuaug agcgcaugaa ucagucucuc 1560
ucccugcucu acaacgugcc ugcaguggcc gaggagauuc aggaugaagu ugaugagcug 1620
cuucagaaag agcaaaacua uucagaugac gucuuggcca acaugauuag ugaaccaagg 1680
aucaguuacg gaaacgaugc ucucaugcca ucuuugaccg aaacgaaaac caccguggag 1740
cuccuucccg ugaauggaga guucagccug gacgaucucc agccguggca uucuuuuggg 1800
gcugacucug ugccagccaa cacagaaaac gaaguugagc cuguugaugc ccgcccugcu 1860
gccgaccgag gacugaccac ucgaccaggu ucuggguuga caaauaucaa gacggaggag 1920
aucucugaag ugaagaugga ugcagaauuc cgacaugacu caggauauga aguucaucau 1980
caaaaauugg uguucuuugc agaagaugug gguucaaaca aaggugcaau cauuggacuc 2040
auggugggcg guguugucau agcgacagug aucgucauca ccuuggugau gcugaagaag 2100
aaacaguaca cauccauuca ucauggugug guggagguug acgccgcugu cacccccagag 2160 gagcgccacc uguccaagau gcagcagaac ggcuacgaaa auccaaccua caaguucuuu 2220
gagcagaugc agaacuagac ccccgccaca gcagccucug aaguuggaca gcaaaaccau 2280
ugcuucacua cccaucggug uccauuuaua gaauaaugug ggaagaaaca aacccguuuu 2340
augauuuacu cauuaucgcc uuuugacagc ugugcuguaa cacaaguaga ugccugaacu 2400
ugaauuaauc cacacaucag uaauguauuc uaucucucuu uacauuuugg ucucuauacu 2460
acauuauuaa uggguuuugu guacuguaaa gaauuuagcu guaucaaacu agugcaugaa 2520
uagauucucu ccugauuauu uaucacauag ccccuuagcc aguuguauau uauucuugug 2580
guuugugacc caauuaaguc cuacuuuaca uaugcuuuaa gaaucgaugg gggaugcuuc 2640
augugaacgu gggaguucag cugcuucucu ugccuaagua uuccuuuccu gaucacuaug 2700
cauuuuaaag uuaaacauuu uuaaguauuu cagaugcuuu agagagauuu uuuuuccaug 2760
acugcauuuu acuguacaga uugcugcuuc ugcuauauuu gugauauagg aauuaagagg 2820
auacacacgu uuguuucuuc gugccuguuu uaugugcaca cauuaggcau ugagacuuca 2880
agcuuuucuu uuuuugucca cguaucuuug ggucuuugau aaagaaaaga aucccuguuc 2940
auuguaagca cuuuuacggg gcgggugggg aggggugcuc ugcuggucuu caauuaccaa 3000
gaauucucca aaacaauuuu cugcaggaug auuguacaga aucauugcuu augacaugau 3060
cgcuuucuac acuguauuac auaaauaaau uaaauaaaau aaccccgggc aagacuuuuc 3120
uuugaaggau gacuacagac auuaaauaau cgaaguaauu uuggguggggg agaagaggca 3180 gauucaauuu ucuuuaacca gucugaaguu ucauuuauga uacaaaagaa gaugaaaaug 3240
gaaguggcaa uauaagggga ugaggaaggc augccuggac aaacccuucu uuuaagaugu 3300
gucuucaauu uguauaaaau gguguuuuca uguaaauaaa uacauucuug gaggagca 3358

<210> SEQ ID NO 6
<211> LENGTH: 3572
<212> TYPE: RNA
<213> ORGANISM: Homo sapiens

<400> SEQUENCE: 6

-continued

```
aaauagcaca gccuugcugu gcgugguaga aguuggguua guguugacau gcuguugacu      60
cacccucccg aggauggaag cucuggccug ggucaaguug uggucacugc aguuaacagu     120
uuguugaucu cagggaguau uccacaguug cugauguaau ugacaaugau uggagccagc     180
ucuuccccag auucaaaugg accaauuaga ggacuuguug guucuguuua ucaacuaugu     240
acccacugau gguaaugcug gccugcuggc ugaaccccag auugccaugu ucuguggcag     300
acugaacaug cacaugaaug uccagaaugg gaagugggau ucagauccau cagggaccaa     360
aaccugcauu gauaccaagg aaggcauccu gcaguauugc caagaagucu acccugaacu     420
gcagaucacc aaugugguag aagccaacca accagugacc auccagaacu ggugcaagcg     480
gggccgcaag cagugcaaga cccaucccca cuuugugauu cccuaccgcu gcuuaguugg     540
ugaguuugua agugaugccc uucucguucc ugacaagugc aaauucuuac accaggagag     600
gauggauguu ugcgaaacuc aucuucacug gcacaccguc gccaaagaga caugcaguga     660
gaagaguacc aacuugcaug acuacggcau guugcugccc ugcggaauug acaaguuccg     720
aggggguagag uuugugguuu gcccacuggc ugaagaaagu gacaaugugg auucugcuga     780
ugcggaggag gaugacucgg augucuggug gggcggagca gacacagacu augcagaugg     840
gagugaagac aaaguaguag aaguagcaga ggaggaagaa guggcugagg uggaagaaga     900
agaagccgau gaugacgagg acgaugagga uggugaugag guagaggaag aggcugagga     960
acccuacgaa gaagccacag agagaaccac cagcauugcc accaccacca ccaccaccac    1020
agagucugug gaagaggugg uucgagaggu gugcucugaa caagccgaga cggggccgug    1080
ccgagcaaug aucucccgcu gguacuuuga ugugacugaa gggaagugug ccccauucuu    1140
uuacggcgga uguggcggca accggaacaa cuuugacaca gaagaguacu gcauggccgu    1200
guguggcagc gccauuccua caacagcagc caguaccccu gaugccguug acaaguaucu    1260
cgagacaccu ggggaugaga augaacaugc ccauuuccag aaagccaaag agaggcuuga    1320
ggccaagcac cgagagagaa ugucccaggu caugagagaa ugggaagagg cagaacguca    1380
agcaaagaac uugccuaaag cugauaagaa ggcaguuauc cagcauuucc aggagaaagu    1440
ggaaucuuug gaacaggaag cagccaacga gagacagcag cugguggaga cacacauggc    1500
cagaguggaa gccaugcuca augaccgccg ccgccuggcc cuggagaacu acaucaccgc    1560
ucugcaggcu guuccuccuc ggccucguca cguguucaau augcuaaaga aguauguccg    1620
cgcagaacag aaggacagac agcacacccu aaagcauuuc gagcaugugc gcauggugga    1680
ucccaagaaa gccgcucaga uccgguccca gguuaugaca caccuccgug ugauuuauga    1740
gcgcaugaau cagucucucu cccugcucua caacgugccu gcaguggccg aggagauuca    1800
ggaugaaguu gaugagcugc uucagaaaga gcaaaacuau ucagaugacg ucuuggccaa    1860
caugauuagu gaaccaagga ucaguuacgg aaacgaugcu cucaugccau cuuugaccga    1920
aacgaaaacc accguggagc uccuucccgu gaauggagag uucagccugg acgaucucca    1980
gccguggcau ucuuuugggg cugacucugu gccagccaac acagaaaacg aaguugagcc    2040
uguugaugcc cgcccugcug ccgaccgagg acugaccacu cgaccagguu cuggguugac    2100
aaauaucaag acggaggaga ucucugaagu gaagauggau gcagaauucc gacaugacuc    2160
aggauaugaa guucaucauc aaaaauuggu guucuuugca gaagaugugg guucaaacaa    2220
aggugcaauc auuggacuca ugguggggcgg uguugucaua gcgacaguga ucgucaucac    2280
cuuggugaug cugaagaaga aacaguacac auccauucau cauggugugg uggagguuga    2340
cgccgcuguc accccagagg agcgccaccu guccaagaug cagcagaacg gcuacgaaaa    2400
```

uccaaccuac aaguucuuug agcagaugca gaacuagacc cccgccacag cagccucuga 2460
aguuggacag caaaaccauu gcuucacuac ccaucggugu ccauuuauag aauaaugugg 2520
gaagaaacaa acccguuuua ugauuuacuc auuaucgccu uuugacagcu gugcuguaac 2580
acaaguagau gccugaacuu gaauuaaucc acacaucagu aauguauucu aucucucuuu 2640
acauuuuggu cucuauacua cauuauuaau ggguuuugug uacuguaaag aauuuagcug 2700
uaucaaacua gugcaugaau agauucucuc cugauuauuu aucacauagc cccuuagcca 2760
guuguauauu auucuugugg uuugugaccc aauuaagucc uacuuuacau augcuuuaag 2820
aaucgauggg ggaugcuuca ugugaacgug ggaguucagc ugcuucucuu gccuaaguau 2880
uccuuuccug aucacuaugc auuuuaaagu uaaacauuuu uaaguauuuc agaugcuuua 2940
gagagauuuu uuuuccauga cugcauuuua cuguacagau ugcugcuucu gcuauauuug 3000
ugauauagga auuaagagga uacacacguu uguuucuucg ugccuguuuu augugcacac 3060
auuaggcauu gagacuucaa gcuuuucuuu uuuuguccac guaucuuugg gucuuugaua 3120
aagaaaagaa ucccuguuca uuguaagcac uuuuacgggg cggguggggga ggggugcucu 3180 gcuggucuuc aauuaccaag aauucuccaa aacaauuuuc ugcaggauga uuguacagaa 3240
ucauugcuua ugacaugauc gcuuucuaca cuguauuaca uaaauaaauu aaauaaaaua 3300
accccgggca agacuuuucu uugaaggaug acuacagaca uuaaauaauc gaaguaauuu 3360 uggguggggga gaagaggcag auucaauuuu cuuuaaccag ucugaaguuu cauuuaugau 3420
acaaaagaag augaaaaugg aaguggcaau auaaggggau gaggaaggca ugccuggaca 3480
aacccuucuu uuaagaugug ucuucaauuu guauaaaaug guguuuucau guaaauaaau 3540
acauucuugg aggagcaaaa aaaaaaaaaa aa 3572

<210> SEQ ID NO 7
<211> LENGTH: 3190
<212> TYPE: RNA
<213> ORGANISM: Homo sapiens

<400> SEQUENCE: 7
gucaguuucc ucggcagcgg uaggcgagag cacgcggagg agcgugcgcg ggggccccgg 60
gagacggcgg cgguggcggc gcgggcagag caaggacgcg gcggauccca cucgcacagc 120
agcgcacucg gugccccgcg cagggucgcg augcugcccg guuuggcacu gcuccugcug 180
gccgccugga cggcucgggc gcuggagguc uacccugaac ugcagaucac caaugugggua 240 gaagccaacc aaccagugac cauccagaac uggugcaagc ggggccgcaa gcagugcaag 300
acccaucccc acuuugugau ucccuaccgc ugcuuaguug gugaguuugu aagugaugcc 360
cuucucguuc cugacaagug caaauucuua caccaggaga ggauggaugu uugcgaaacu 420
caucuucacu ggcacaccgu cgccaaagag acaugcagug agaagaguac caacuugcau 480
gacuacggca uguugcugcc cugcggaauu gacaaguucc gaggggguaga guuuguguguu 540 ugcccacugg cugaagaaag ugacaaugug gauucugcug augcggagga ggaugacucg 600
gaugucuggu ggggcggagc agacacagac uaugcagaug ggagugaaga caaaguagua 660
gaaguagcag aggaggaaga aguggcugag guggaagaag aagaagccga ugaugacgag 720
gacgaugagg augguggauga gguagaggaa gaggcugagg aacccuacga agaagccaca 780
gagagaacca ccagcauugc caccaccacc accaccacca cagagucugu ggaagaggug 840 guucgagguuc cuacaacagc agccaguacc ccugaugccg uugacaagua ucucgagaca 900

-continued

```
ccuggggaug agaaugaaca ugcccauuuc cagaaagcca aagagaggcu ugaggccaag    960
caccgagaga gaauguccca ggucaugaga gaaugggaag aggcagaacg ucaagcaaag   1020
aacuugccua aagcugauaa gaaggcaguu auccagcauu uccaggagaa aguggaaucu   1080
uuggaacagg aagcagccaa cgagagacag cagcuggugg agacacacau ggccagagug   1140
gaagccaugc ucaaugaccg ccgccgccug gcccuggaga acuacaucac cgcucugcag   1200
gcuguuccuc cucggccucg ucacguguuc aauaugcuaa agaaguaugu ccgcgcagaa   1260
cagaaggaca gacagcacac ccuaaagcau uucgagcaug ugcgcauggu ggaucccaag   1320
aaagccgcuc agauccgguc ccagguuaug acacaccucc gugugauuua ugagcgcaug   1380
aaucagucuc ucucccugcu cuacaacgug ccugcagugg ccgaggagau ucaggaugaa   1440
guugaugagc ugcuucagaa agagcaaaac uauucagaug acgucuuggc caacaugauu   1500
agugaaccaa ggaucaguua cggaaacgau gcucucaugc caucuuugac cgaaacgaaa   1560
accaccgugg agcuccuucc cgugaaugga gaguucagcc uggacgaucu ccagccgugg   1620
cauucuuuug ggcugacuc ugugccagcc aacacagaaa acgaaguuga gccuguugau   1680
gcccgcccug cugccgaccg aggacugacc acucgaccag guucuggguu gacaaauauc   1740
aagacggagg agaucucuga agugaagaug gaugcagaau uccgacauga cucaggauau   1800
gaaguucauc aucaaaaauu gguguucuuu gcagaagaug uggguucaaa caaaggugca   1860
aucauuggac ucaugguggg cggugguguc auagcgacag ugaucgucau caccuuggug   1920
augcugaaga agaaacagua cacauccauu caucauggug ugguggaggu ugacgccgcu   1980
gucaccccag aggagcgcca ccuguccaag augcagcaga acggcuacga aaauccaacc   2040
uacaaguucu uugagcagau gcagaacuag accccgcca cagcagccuc ugaaguugga   2100
cagcaaaacc auugcuucac uacccaucgg uguccauuua uagaauaaug ugggaagaaa   2160
caaacccguu uuaugauuua cucauuaucg ccuuuugaca gcugugcugu aacacaagua   2220
gaugccugaa cuugaauuaa uccacacauc aguaauguau ucuaucucuc uuuacauuuu   2280
ggucucuaua cuacauuauu aaugggguuuu guguacugua aagaauuuag cuguaucaaa   2340
cuagugcaug aauagauucu cuccugauua uuuaucacau agccccuuag ccaguuguau   2400
auuauucuug ugguuuguga cccaauuaag uccuacuuua cauaugcuuu aagaaucgau   2460
gggggaugcu ucaugugaac gugggaguuc agcugcuucu cuugccuaag uauuccuuuc   2520
cugaucacua ugcauuuuaa aguuaaacau uuuuaaguau uucagaugcu uuagagagau   2580
uuuuuuucca ugacugcauu uuacuguaca gauugcugcu ucugcuauau uugugauaua   2640
ggaauuaaga ggauacacac guuuguuucu ucgugccugu uuuaugugca cacauuaggc   2700
auugagacuu caagcuuuuc uuuuuuuguc cacguaucuu ugggucuuug auaaagaaaa   2760
gaaucccugu ucauuguaag cacuuuuacg gggcgggugg ggaggggugc ucugcugguc   2820
uucaauuacc aagaauucuc caaaacaauu uucugcagga ugauuguaca gaaucauugc   2880
uuaugacaug aucgcuuucu acacuguauu acauaaauaa auuaaauaaa auaaccccgg   2940
gcaagacuuu ucuuugaagg augacuacag acauuaaaua aucgaaguaa uuuugggugg   3000
ggagaagagg cagauucaau uuucuuuaac cagucugaag uuucauuuau gauacaaaag   3060
aagaugaaaa uggaagugge aauauaaggg gaugaggaag gcaugccugg acaaacccuu   3120
cuuuuaagau gugucuucaa uuuguauaaa auggugguuu cauguaaaua aauacauucu   3180
uggaggagca                                                          3190
```

<210> SEQ ID NO 8
<211> LENGTH: 3415
<212> TYPE: RNA
<213> ORGANISM: Homo sapiens

<400> SEQUENCE: 8

```
gucaguuucc ucggcagcgg uaggcgagag cacgcggagg agcgugcgcg ggggccccgg     60

gagacggcgg cgguggcggc gcgggcagag caaggacgcg gcggauccca cucgcacagc    120

agcgcacucg gugccccgcg cagggucgcg augcugcccg guuuggcacu gcuccugcug    180

gccgccugga cggcucgggc gcuggagguc uacccugaac ugcagaucac caauguggua    240

gaagccaacc aaccagugac cauccagaac uggugcaagc ggggccgcaa gcagugcaag    300

acccaucccc acuuugugau ucccuaccgc ugcuuaguug gugaguuugu aagugaugcc    360

cuucucguuc cugacaagug caaauucuua caccaggaga ggauggaugu uugcgaaacu    420

caucuucacu ggcacaccgu cgccaaagag acaugcagug agaagaguac caacuugcau    480

gacuacggca uguugcugcc cugcggaauu gacaaguucc gaggggguaga guuugugugu    540

ugcccacugg cugaagaaag ugacaaugug gauucugcug augcggagga ggaugacucg    600

gaugucuggu ggggcggagc agacacagac uaugcagaug ggagugaaga caaaguagua    660

gaaguagcag aggaggaaga aguggcugag guggaagaag aagaagccga ugaugacgag    720

gacgaugagg auggugauga gguagaggaa gaggcugagg aacccuacga agaagccaca    780

gagagaacca ccagcauugc caccaccacc accaccacca cagagucugu ggaagaggug    840

guucgagagg ugugcucuga acaagccgag acggggccgu gccgagcaau gaucuccccgc    900

ugguacuuug augugacuga agggaagugu gccccauucu uuuacggcgg auguggcggc    960

aaccggaaca acuuugacac agaagaguac ugcauggccg ugugugggcag cgccaugucc   1020

caaaguuuac ucaagacuac ccaggaaccu cuugcccgag auccuguuaa acuuccuaca   1080

acagcagcca guaccccuga ugccguugac aaguaucucg agacaccugg ggaugagaau   1140

gaacaugccc auuuccagaa agccaaagag aggcuugagg ccaagcaccg agagagaaug   1200

ucccagguca ugagagaaug ggaagaggca gaacgucaag caaagaacuu gccuaaagcu   1260

gauaagaagg caguuaucca gcauuuccag gagaaagugg aaucuuugga acaggaagca   1320

gccaacgaga gacagcagcu gguggagaca cacauggcca gaguggaagc caugcucaau   1380

gaccgccgcc gccuggcccu ggagaacuac aucaccgcuc ugcaggcugu uccuccucgg   1440

ccucgucacg uguucaauau gcuaaagaag uauguccgcg cagaacagaa ggacagacag   1500

cacacccuaa agcauuucga gcaugugcgc augguggauc ccaagaaagc cgcucagauc   1560

cggucccagg uuaugacaca ccuccgugug auuuaugagc gcaugaauca gucucucucc   1620

cugcucuaca acgugccugc aguggccgag gagauucagg augaaguuga ugagcugcuu   1680

cagaaagagc aaaacuauuc agaugacguc uuggccaaca ugauuaguga accaaggauc   1740

aguuacggaa acgaugcucu caugccaucu uugaccgaaa cgaaaaccac cguggagcuc   1800

cuucccguga auggagaguu cagccuggac gaucuccagc cguggcauuc uuuugggggcu   1860

gacucugugc cagccaacac agaaaacgaa guugagccug uugaugcccg cccugcugcc   1920

gaccgaggac ugaccacucg accagguucu ggguugacaa auaucaagac ggaggagauc   1980

ucugaaguga agauggaugc agaauuccga caugacucag gauaugaagu ucaucaucaa   2040

aaauuggugu ucuuugcaga agaugugggu ucaaacaaag gugcaaucau uggacucaug   2100

gugggcggug uugucauagc gacagugauc gucaucaccu uggugaugcu gaagaagaaa   2160
```

caguacacau ccauucauca uggugugug gagguugacg ccgcugucac cccagaggag 2220
cgccaccugu ccaagaugca gcagaacggc uacgaaaauc caaccuacaa guucuuugag 2280
cagaugcaga acuagacccc cgccacagca gccucugaag uuggacagca aaaccauugc 2340
uucacuaccc aucggugucc auuuauagaa uaaugugga agaaacaaac ccguuuuaug 2400
auuuacucau uaucgccuuu ugacagcugu gcuguaacac aaguagaugc cugaacuuga 2460
auuaauccac acaucaguaa uguauucuau cucucuuuac auuuuggucu cuauacuaca 2520
uuauuaaugg guuuugugua cuguaaagaa uuuagcugua ucaaacuagu gcaugaauag 2580
auucucuccu gauuauuuau cacauagccc cuuagccagu uguauauuau ucuuguggu 2640 ugugacccaa uuaaguccua cuuuacauau gcuuuaagaa ucgaugggg augcuucaug 2700 ugaacguggg aguucagcug cuucucuugc cuaaguauuc cuuuccugau cacuaugcau 2760
uuuaaaguua aacauuuuua aguauuucag augcuuuaga gagauuuuuu uuccaugacu 2820
gcauuuuacu guacagauug cugcuucugc uauauuugug auauaggaau uaagaggaua 2880
cacacguuug uuucuucgug ccuguuuuau gugcacacau uaggcauuga gacuucaagc 2940
uuuucuuuuu uuguccacgu aucuuugggu cuuugauaaa gaaaagaauc ccuguucauu 3000
guaagcacuu uuacggggcg ggugggggagg ggugcucugc uggucuucaa uuaccaagaa 3060
uucuccaaaa caauuuucug caggaugauu guacagaauc auugcuuaug acaugaucgc 3120
uuucuacacu guauuacaua aauaaauuaa auaaaauaac cccgggcaag acuuuucuuu 3180
gaaggaugac uacagacauu aaauaaucga aguaauuuug ggugggggaga agaggcagau 3240 ucaauuuucu uuaaccaguc ugaaguuuca uuuaugauac aaaagaagau gaaaauggaa 3300
guggcaauau aaggggauga ggaaggcaug ccuggacaaa cccuucuuuu aagaugugc 3360 uucaauuugu auaaaauggu guuuucaugu aaauaaauac auucuuggag gagca 3415

<210> SEQ ID NO 9
<211> LENGTH: 3295
<212> TYPE: RNA
<213> ORGANISM: Homo sapiens

<400> SEQUENCE: 9
gucggaugau ucaagcucac ggggacgagc aggagcgcuc ucgacuuuuc uagagccuca 60
gcguccuagg acucaccuuu cccugauccu gcaccguccc ucuccuggcc ccagacucuc 120
ccucccacug uucacgaagc ccagguaccc acugauggua augcuggccu gcuggcugaa 180
ccccagauug ccauguucug uggcagacug aacaugcaca ugaaugucca gaaugggaag 240
ugggauucag auccaucagg gaccaaaacc ugcauugaua ccaaggaagg cauccugcag 300
uauugccaag aagucuaccc ugaacugcag aucaccaaug ugguagaagc caaccaacca 360
gugaccaucc agaacuggug caagcggggc cgcaagcagu gcaagaccca uccccacuuu 420
gugauucccu accgcugcuu aguuggugag uuuguaagug augcccuucu cguuccugac 480
aagugcaaau ucuuacacca ggagaggaug gauguuugcg aaacucaucu ucacuggcac 540
accgucgcca aagagacaug cagugagaag aguaccaacu ugcaugacua cggcauguug 600
cugcccugcg gaauugacaa guuccgaggg guagaguuug uguguugccc acuggcugaa 660
gaaagugaca auguggauuc ugcugaugcg gaggaggaug acucggaugu cugguggggc 720
ggagcagaca cagacuaugc agaugggagu gaagacaaag uaguagaagu agcagaggag 780
gaagaagugg cugaggugga agaagaagaa gccgaugaug acgaggacga ugaggauggu 840
gaugagguag aggaagaggc ugaggaaccc uacgaagaag ccacagagag aaccaccagc 900

-continued

```
auugccacca ccaccaccac caccacagag ucuguggaag aggugguucg aguuccuaca    960
acagcagcca guaccccuga ugccguugac aaguaucucg agacaccugg ggaugagaau   1020
gaacaugccc auuuccagaa agccaaagag aggcuugagg ccaagcaccg agagagaaug   1080
ucccagguca ugagagaaug ggaagaggca gaacgucaag caaagaacuu gccuaaagcu   1140
gauaagaagg caguuaucca gcauuuccag gagaaagugg aaucuuugga acaggaagca   1200
gccaacgaga gacagcagcu gguggagaca cacauggcca gaguggaagc caugcucaau   1260
gaccgccgcc gccuggcccu ggagaacuac aucaccgcuc ugcaggcugu uccuccucgg   1320
ccucgucacg uguucaauau gcuaaagaag uauguccgcg cagaacagaa ggacagacag   1380
cacacccuaa agcauuucga gcaugugcgc augguggauc ccaagaaagc cgcucagauc   1440
cggucccagg uuaugacaca ccuccgugug auuuaugagc gcaugaauca gucucucucc   1500
cugcucuaca acgugccugc aguggccgag gagauucagg augaaguuga ugagcugcuu   1560
cagaaagagc aaaacuauuc agaugacguc uuggccaaca ugauuaguga accaaggauc   1620
aguuacggaa acgaugcucu caugccaucu uugaccgaaa cgaaaaccac cguggagcuc   1680
cuucccguga auggagaguu cagccuggac gaucuccagc cguggcauuc uuuuggggcu   1740
gacucugugc cagccaacac agaaaacgaa guugagccug uugaugcccg cccugcugcc   1800
gaccgaggac ugaccacucg accagguucu ggguugacaa auaucaagac ggaggagauc   1860
ucugaaguga agauggaugc agaauuccga caugacucag gauaugaagu ucaucaucaa   1920
aaauuggugu ucuuugcaga agaugugggu ucaaacaaag gugcaaucau uggacucaug   1980
gugggcggug uugucauagc gacagugauc gucaucaccu uggugaugcu gaagaagaaa   2040
caguacacau ccauucauca ugguguggug gagguugacg ccgcugucac cccagaggag   2100
cgccaccugu ccaagaugca gcagaacggc uacgaaaauc caaccuacaa guucuuugag   2160
cagaugcaga acuagacccc cgccacagca gccucugaag uuggacagca aaaccauugc   2220
uucacuaccc aucggugucc auuuauagaa uaauguggga agaaacaaac ccguuuuaug   2280
auuuacucau uaucgccuuu ugacagcugu gcuguaacac aaguagaugc cugaacuuga   2340
auuaauccac acaucaguaa uguauucuau cucucuuuac auuuuggucu cuauacuaca   2400
uuauuaaugg guuuugugua cuguaaagaa uuuagcugua ucaaacuagu gcaugaauag   2460
auucucuccu gauuauuuau cacauagccc cuuagccagu uguauauuau ucuuguggul   2520
ugugacccaa uuaaguccua cuuuacauau gcuuuaagaa ucgauggggg augcuucaug   2580
ugaacguggg aguucagcug cuucucuugc cuaaguauuc cuuuccugau cacuaugcau   2640
uuuaaaguua aacauuuuua aguauuucag augcuuuaga gagauuuuuu uuccaugacu   2700
gcauuuuacu guacagauug cugcuucugc uauauuugug auauaggaau uaagaggaua   2760
cacacguuug uuucuucgug ccuguuuuau gugcacacau uaggcauuga gacuucaagc   2820
uuuucuuuuu uuguccacgu aucuuugggu cuuugauaaa gaaaagaauc ccuguucauu   2880
guaagcacuu uuacggggcg ggugggggagg ggugcucugc uggucuucaa uuaccaagaa   2940
uucuccaaaa caauuuucug caggaugauu guacagaauc auugcuuaug acaugaucgc   3000
uuucuacacu guauuacaua aauaaauuaa auaaaauaac cccgggcaag acuuuucuuu   3060
gaaggaugac uacagacauu aaauaaucga aguaauuuug gguggggaga agaggcagau   3120
ucaauuuucu uuaaccaguc ugaaguuuca uuuaugauac aaaagaagau gaaaauggaa   3180
guggcaauau aaggggauga ggaaggcaug ccuggacaaa cccuucuuuu aagaugugac   3240
```

uucaauuugu auaaaaauggu guuuucaugu aaauaaaauac auucuuggag gagca 3295

<210> SEQ ID NO 10
<211> LENGTH: 3529
<212> TYPE: RNA
<213> ORGANISM: Homo sapiens

<400> SEQUENCE: 10
gucaguuucc ucggcagcgg uaggcgagag cacgcggagg agcgugcgcg ggggccccgg 60
gagacggcgg cgguggcggc gcgggcagag caaggacgcg gcggaucccca cucgcacagc 120 agcgcacucg gugccccgcg cagggucgcg augcugcccg guuuggcacu gcuccugcug 180
gccgccugga cggcucgggc gcuggaggua cccacugaug guaaugcugg ccugcuggcu 240
gaaccccaga uugccauguu cuguggcaga cugaacaugc acaugaaugu ccagaauggg 300
aagugggauu cagauccauc agggaccaaa accugcauug auaccaagga aggcauccug 360
caguauugcc aagaagucua cccugaacug cagaucacca auguggua aga agccaaccaa 420 ccagugacca uccagaacug gugcaagcgg ggccgcaagc agugcaagac ccaucccccac 480 uuugugauuc ccuaccgcug cuuaguuggu gaguuuguaa gugaugcccu ucucguuccu 540
gacaagugca aauucuuaca ccaggagagg auggauguuu gcgaaacuca ucuucacugg 600
cacaccgucg ccaaagagac augcagugag aagaguacca acuugcauga cuacggcaug 660
uugcugcccu gcggaauuga caaguuccga gggguagagu uuguguguug cccacuggcu 720
gaagaaagug acaaugugga uucugcugau gcggaggagg augacucgga ugucuggugg 780
ggcggagcag acacagacua ugcagauggg agugaagaca aaguaguaga aguagcagag 840
gaggaagaag uggcugaggu ggaagaagaa gaagccgaug augacgagga cgaugaggau 900
ggugaugagg uagaggaaga ggcugaggaa cccuacgaag aagccacaga gagaaccacc 960
agcauugcca ccaccaccac caccaccaca gagucugugg aagaggugu ucgagaggug 1020 ugcucugaac aagccgagac ggggccgugc cgagcaauga ucucccgcug guacuuugau 1080
gugacugaag ggaagugugc cccauucuuu uacggcggau guggcggcaa ccggaacaac 1140
uuugacacag aagaguacug cauggccgug uguggcagcg ccauguccca aaguuuacuc 1200
aagacuaccc aggaaccucu ugcccgagau ccuguuaaac uuccuacaac agcagccagu 1260
accccugaug ccguugacaa guaucucgag acaccugggg augagaauga acaugcccau 1320
uuccagaaag ccaaagagag gcuugaggcc aagcaccgag agagaauguc ccaggucaug 1380
agagaauggg aagaggcaga acgucaagca aagaacuugc cuaaagcuga uaagaaggca 1440
guuauccagc auuuccagga gaaaguggaa ucuuuggaac aggaagcagc caacgagaga 1500
cagcagcugg uggagacaca cauggccaga guggaagcca ugcucaauga ccgccgccgc 1560
cuggcccugg agaacuacau caccgcucug caggcuguuc cuccucggcc ucgucacgug 1620
uucaauaugc uaaagaagua uguccgcgca gaacagaagg acagacagca cacccuaaag 1680
cauuucgagc augugcgcau gguggauccc aagaaagccg cucagauccg gucccagguu 1740
augacacacc uccgugugau uuaugagcgc augaaucagu cucucucccu gcucuacaac 1800
gugccugcag uggccgagga gauucaggau gaaguugaug agcugcuuca gaaagagcaa 1860
aacuauucag augacgucuu ggccaacaug auuagugaac caaggaucag uuacggaaac 1920
gaugcucuca ugccaucuuu gaccgaaacg aaaaccaccg uggagcuccu ucccgugaau 1980
ggagaguuca gccuggacga ucuccagccg uggcauucuu uuggggcuga cucugugcca 2040
gccaacacag aaaacgaagg uucuggguug acaaauauca agacggagga gaucucugaa 2100
gugaagaugg augcagaauu ccgacaugac ucaggauaug aaguucauca ucaaaaauug 2160
guguucuuug cagaagaugu ggguucaaac aaaggugcaa ucauuggacu caugguggc 2220 gguguuguca uagcgacagu gaucgucauc accuugguga ugcugaagaa gaaacaguac 2280
acauccauuc aucauggugu gguggagguu gacgccgcug ucaccccaga ggagcgccac 2340
cuguccaaga ugcagcagaa cggcuacgaa aauccaaccu acaaguucuu ugagcagaug 2400
cagaacuaga cccccgccac agcagccucu gaaguuggac agcaaaacca uugcuucacu 2460
acccaucggu guccauuuau agaauaaugu gggaagaaac aaacccguuu uaugauuuac 2520
ucauuaucgc cuuuugacag cugugcugua acacaaguag augccugaac uugaauuaau 2580
ccacacauca guaauguauu cuaucucucu uuacauuuug gucucuauac uacauuauua 2640
augggguuug uguacuguaa agaauuuagc uguaucaaac uagugcauga auagauucuc 2700
uccugauuau uuaucacaua gccccuuagc caguuguaua uuauucuugu gguuugugac 2760
ccaauuaagu ccuacuuuac auaugcuuua agaaucgaug ggggaugcuu caugugaacg 2820
ugggaguuca gcugcuucuc uugccuaagu auuccuuucc ugaucacuau gcauuuuaaa 2880
guuaaacauu uuuaaguauu ucagaugcuu uagagagauu uuuuuuccau gacugcauuu 2940
uacuguacag auugcugcuu cugcuauauu ugugauauag gaauuaagag gauacacacg 3000
uuuguuucuu cgugccuguu uuaugugcac acauuaggca uugagacuuc aagcuuuucu 3060
uuuuuugucc acguaucuuu gggucuuuga uaaagaaaag aaucccuguu cauuguaagc 3120
acuuuuacgg ggcgggugg gaggggugcu cugcuggucu ucaauuacca agaauucucc 3180
aaaacaauuu ucugcaggau gauuguacag aaucauugcu uaugacauga ucgcuuucua 3240
cacuguauua cauaaauaaa uuaaauaaaa uaaccccggg caagacuuuu cuuugaagga 3300
ugacuacaga cauuaaauaa ucgaaguaau uuuggguggg gagaagaggc agauucaauu 3360
uucuuuaacc agucugaagu uucauuuaug auacaaaaga agaugaaaau ggaaguggca 3420
auauaagggg augaggaagg caugccugga caaacccuuc uuuuaagaug ugucuucaau 3480
uuguauaaaa ugguguuuuc auguaaauaa auacauucuu ggaggagca 3529

<210> SEQ ID NO 11
<211> LENGTH: 3472
<212> TYPE: RNA
<213> ORGANISM: Homo sapiens

<400> SEQUENCE: 11
gucaguuucc ucggcagcgg uaggcgagag cacgcggagg agcgugcgcg ggggccccgg 60
gagacggcgg cgguggcggc gcgggcagag caaggacgcg gcggauccca cucgcacagc 120
agcgcacucg gugccccgcg cagggucgcg augcugcccg guuuggcacu gcuccugcug 180
gccgccugga cggcucgggc gcuggaggua cccacugaug guaaugcugg ccugcuggcu 240
gaaccccaga uugccauguu cuguggcaga cugaacaugc acaugaaugu ccagaauggg 300
aagugggauu cagauccauc agggaccaaa accugcauug auaccaagga aggcauccug 360
caguauugcc aagaagucua cccugaacug cagaucacca augugguaga agccaaccaa 420
ccagugacca uccagaacug gugcaagcgg ggccgcaagc agugcaagac ccaucccac 480 uuugugauuc ccuaccgcug cuuaguuggu gaguuuguaa gugaugcccu ucucguuccu 540
gacaagugca aauucuuaca ccaggagagg auggauguuu gcgaaacuca ucuucacugg 600
cacaccgucg ccaaagagac augcagugag aagaguacca acuugcauga cuacggcaug 660

```
uugcugcccu gcggaauuga caaguuccga gggguagagu uuguguguug cccacuggcu    720
gaagaaagug acaaugugga uucugcugau gcggaggagg augacucgga ugucuggugg    780
ggcggagcag acacagacua ugcagauggg agugaagaca aaguaguaga aguagcagag    840
gaggaagaag uggcugaggu ggaagaagaa gaagccgaug augacgagga cgaugaggau    900
ggugaugagg uagaggaaga ggcugaggaa cccuacgaag aagccacaga gagaaccacc    960
agcauugcca ccaccaccac caccaccaca gagucugugg aagaggugga ucgagaggug   1020
ugcucugaac aagccgagac ggggccgugc cgagcaauga ucuccccgcug guacuuugau   1080
gugacugaag ggaagugugc cccauucuuu uacggcggau guggcggcaa ccggaacaac   1140
uuugacacag aagaguacug cauggccgug uguggcagcg ccauuccuac aacagcagcc   1200
aguaccccug augccguuga caaguaucuc gagacaccug gggaugagaa ugaacaugcc   1260
cauuuccaga aagccaaaga gaggcuugag gccaagcacc gagagagaau gucccagguc   1320
augagagaau gggaagaggc agaacgucaa gcaaagaacu ugccuaaagc ugauaagaag   1380
gcaguuaucc agcauuucca ggagaaagug gaaucuuugg aacaggaagc agccaacgag   1440
agacagcagc ugguggagac acacauggcc agaguggaag ccaugcucaa ugaccgccgc   1500
cgccuggccc uggagaacua caucaccgcu cugcaggcug uuccuccucg gccucgucac   1560
guguucaaua ugcuaaagaa guauguccgc gcagaacaga aggacagaca gcacacccua   1620
aagcauuucg agcaugugcg cauggugau cccaagaaag ccgcucagau ccggucccag   1680
guuaugacac accuccgugu gauuuaugag cgcaugaauc agucucucuc ccugcucuac   1740
aacgugccug caguggccga ggagauucag gaugaaguug augagcugcu ucagaaagag   1800
caaaacuauu cagaugacgu cuuggccaac augauuagug aaccaaggau caguuacgga   1860
aacgaugcuc ucaugccauc uuugaccgaa acgaaaacca ccguggagcu ccuucccgug   1920
aauggagagu ucagccugga cgaucuccag ccguggcauu cuuuuggggc ugacucugug   1980
ccagccaaca cagaaaacga agguucuggg uugacaaaua ucaagacgga ggagaucucu   2040
gaagugaaga uggaugcaga auuccgacau gacucaggau augaaguuca ucaucaaaaa   2100
uuggguguucu uugcagaaga uguggguuca aacaaaggug caaucauugg acucauggug   2160
ggcgguguug ucauagcgac agugaucguc aucaccuugg ugaugcugaa gaagaaacag   2220
uacacaucca uucaucaugg ugugguggag guugacgccg cugucacccc agaggagcgc   2280
caccugucca agaugcagca gaacggcuac gaaaauccaa ccuacaaguu cuuugagcag   2340
augcagaacu agacccccgc cacagcagcc ucugaaguug gacagcaaaa ccauugcuuc   2400
acuacccauc gguguccauu uauagaauaa ugugggaaga aacaaacccg uuuuaugauu   2460
uacucauuau cgccuuuuga cagcugugcu guaacacaag uagaugccug aacuugaauu   2520
aauccacaca ucaguaaugu auucuaucuc ucuuuacauu uuggucucua uacuacauua   2580
uuaaugggguu uuguguacug uaaagaauuu agcuguauca aacuagugca ugaauagauu   2640
cucuccugau uauuuaucac auagccccuu agccaguugu auauuauucu uguggguuugu   2700
gacccaauua aguccuacuu uacauaugcu uuaagaaucg augggggaug cuucauguga   2760
acgugggagu ucagcugcuu cucuugccua aguauuccuu uccugaucac uaugcauuuu   2820
aaaguuaaac auuuuuaagu auuucagaug cuuuagagag auuuuuuuuc caugacugca   2880
uuuuacugua cagauugcug cuucugcuau auuugugaua uaggaauuaa gaggauacac   2940
acguuuguuu cuucgugccu guuuuaugug cacacauuag gcauugagac uucaagcuuu   3000
ucuuuuuuug uccacguauc uuugggucuu ugauaaagaa aagaaucccu guucauugua   3060
```

agcacuuuua cggggcgggu ggggaggggu gcucugcugg ucuucaauua ccaagaauuc 3120
uccaaaacaa uuuucugcag gaugauugua cagaaucauu gcuuaugaca ugaucgcuuu 3180
cuacacugua uuacauaaau aaauuaaaua aaauaacccc gggcaagacu uuucuuugaa 3240
ggaugacuac agacauuaaa uaaucgaagu aauuuugggu ggggagaaga ggcagauuca 3300
auuuucuuua accagucuga aguuucauuu augauacaaa agaagaugaa aauggaagug 3360
gcaauauaag gggaugagga aggcaugccu ggacaaaccc uucuuuuaag augugucuuc 3420
aauuuguaua aaauggugu uucauguaaa uaaauacauu cuuggaggag ca 3472

<210> SEQ ID NO 12
<211> LENGTH: 3304
<212> TYPE: RNA
<213> ORGANISM: Homo sapiens

<400> SEQUENCE: 12
gucaguuucc ucggcagcgg uaggcgagag cacgcggagg agcgugcgcg ggggccccgg 60
gagacggcgg cgguggcggc gcgggcagag caaggacgcg gcggauccca cucgcacagc 120
agcgcacucg gugccccgcg cagggucgcg augcugcccg guuuggcacu gcuccugcug 180
gccgccugga cggcucgggc gcuggaggua cccacugaug guaaugcugg ccugcuggcu 240
gaaccccaga uugccauguu cuguggcaga cugaacaugc acaugaaugu ccagaauggg 300
aagugggauu cagauccauc agggaccaaa accugcauug auaccaagga aggcauccug 360
caguauugcc aagaagucua cccugaacug cagaucacca augugguaga agccaaccaa 420
ccagugacca uccagaacug gugcaagcgg ggccgcaagc agugcaagac ccaucccac 480 uuugugauuc ccuaccgcug cuuaguuggu gaguuuguaa gugaugcccu ucucguuccu 540
gacaagugca aauucuuaca ccaggagagg auggauguuu gcgaaacuca ucuucacugg 600
cacaccgucg ccaaagagac augcagugag aagaguacca acuugcauga cuacggcaug 660
uugcugcccu gcggaauuga caaguuccga gggguagagu uuguguguug cccacuggcu 720
gaagaaagug acaaugugga uucugcugau gcggaggagg augacucgga ugucuggugg 780
ggcggagcag acacagacua ugcagauggg agugaagaca aaguaguaga aguagcagag 840
gaggaagaag uggcugaggu ggaagaagaa gaagccgaug augacgagga cgaugaggau 900
ggugaugagg uagaggaaga ggcugaggaa cccuacgaag aagccacaga gagaaccacc 960
agcauugcca ccaccaccac caccaccaca gagucugugg aagaggugu ucgaguuccu 1020 acaacagcag ccaguacccc ugaugccguu gacaaguauc ucgagacacc uggggaugag 1080
aaugaacaug cccauuucca gaaagccaaa gagaggcuug aggccaagca ccgagagaga 1140
augucccagg ucaugagaga augggaagag gcagaacguc aagcaaagaa cuugccuaaa 1200
gcugauaaga aggcaguuau ccagcauuuc caggagaaag uggaaucuuu ggaacaggaa 1260
gcagccaacg agagacagca gcugguggag acacacaugg ccagagugga agccaugcuc 1320
aaugaccgcc gccgccuggc ccuggagaac uacaucaccg cucugcaggc uguuccuccu 1380
cggccucguc acguguucaa uaugcuaaag aaguaugucc gcgcagaaca gaaggacaga 1440
cagcacaccc uaaagcauuu cgagcaugug cgcauggugg aucccaagaa agccgcucag 1500
auccgguccc agguuaugac acaccuccgu gugauuuaug agcgcaugaa ucagucucuc 1560
ucccugcucu acaacgugcc ugcaguggcc gaggagauuc aggaugaagu ugaugagcug 1620
cuucagaaag agcaaaacua uucagaugac gucuuggcca acaugauuag ugaaccaagg 1680
aucaguuacg gaaacgaugc ucucaugcca ucuuugaccg aaacgaaaac caccguggag 1740
cuccuucccg ugaauggaga guucagccug gacgaucucc agccguggca uucuuuuggg 1800
gcugacucug ugccagccaa cacagaaaac gaagguucug gguugacaaa uaucaagacg 1860
gaggagaucu cugaagugaa gauggaugca gaauuccgac augacucagg auaugaaguu 1920
caucaucaaa aauugguguu cuuugcagaa gauguggguu caaacaaagg ugcaaucauu 1980
ggacucaugg ugggcggugu ugucauagcg acagugaucg ucaucaccuu ggugaugcug 2040
aagaagaaac aguacacauc cauucaucau gguguggugg agguugacgc cgcugucacc 2100
ccagaggagc gccaccuguc caagaugcag cagaacggcu acgaaaaucc aaccuacaag 2160
uucuuugagc agaugcagaa cuagaccccc gccacagcag ccucugaagu uggacagcaa 2220
aaccauugcu ucacuaccca ucggugucca uuuauagaau aaugugggaa gaaacaaacc 2280
cguuuuauga uuuacucauu aucgccuuuu gacagcugug cuguaacaca aguagaugcc 2340
ugaacuugaa uuaauccaca ucaguaauu guauucuauc ucucuuuaca uuuuggucuc 2400
uauacuacau uauuaauggg uuuuguguac uguaaagaau uuagcuguau caaacuagug 2460
caugaauaga uucucuccug auuauuuauc acauagcccc uuagccaguu guauauuauu 2520
cuugugguuu gugacccaau uaaguccuac uuuacauaug cuuuaagaau cgauggggga 2580
ugcuucaugu gaacguggga guucagcugc uucucuugcc uaaguauucc uuuccugauc 2640
acuaugcauu uuaaaguuaa acauuuuuaa guauuucaga ugcuuuagag agauuuuuuu 2700
uccaugacug cauuuuacug uacagauugc ugcuucugcu auauuuguga uauaggaauu 2760
aagaggauac acacguuugu uucuucgugc cuguuuuaug ugcacacauu aggcauugag 2820
acuucaagcu uuucuuuuuu uguccacgua ucuuugggucuuugauaaag aaaagaaucc 2880 cuguucauug uaagcacuuu uacggggcgg gugggggagg gugcucugcu ggucuucaau 2940
uaccaagaau ucuccaaaac aauuuucugc aggaugauug uacagaauca uugcuuauga 3000
caugaucgcu uucuacacug uauuacauaa auaaauuaaa uaaaauaacc ccgggcaaga 3060
cuuuucuuug aaggaugacu acagacauua aauaaucgaa guaauuuugg gugggggagaa 3120 gaggcagauu caauuuucuu uaaccagucu gaaguuucau uuaugauaca aaagaagaug 3180
aaaauggaag uggcaauaua aggggaugag gaaggcaugc cuggacaaac ccuucuuuua 3240 agauguguu ucaauuugua uaaaauggug uuuucaugua aauaaauaca uucuuggagg 3300
agca 3304

<210> SEQ ID NO 13
<211> LENGTH: 3415
<212> TYPE: RNA
<213> ORGANISM: Homo sapiens

<400> SEQUENCE: 13
gucaguuucc ucggcagcgg uaggcgagag cacgcggagg agcgugcgcg ggggccccgg 60
gagacggcgg cgguggcggc gcgggcagag caaggacgcg gcggauccca cucgcacagc 120
agcgcacucg gugccccgcg cagggucgcg augcugcccg guuuggcacu gcuccugcug 180
gccgccugga cggcucgggc gcuggaggua cccacugaug guaaugcugg ccugcuggcu 240
gaaccccaga uugccauguu cuguggcaga cugaacaugc acaugaaugu ccagaauggg 300
aagugggauu cagauccauc agggaccaaa accugcauug auaccaagga aggcauccug 360
caguauugcc aagaagucua cccugaacug cagaucacca augugguaga agccaaccaa 420
ccagugacca uccagaacug gugcaagcgg ggccgcaagc agugcaagac ccaucccac 480 uuugugauuc ccuaccgcug cuuaguuggu gaguuuguaa gugaugcccu ucucguuccu 540
gacaagugca aauucuuaca ccaggagagg auggauguuu gcgaaacuca ucuucacugg 600
cacaccgucg ccaaagagac augcagugag aagaguacca acuugcauga cuacggcaug 660
uugcugcccu gcggaauuga caaguuccga gggguagagu uugugugiuug cccacuggcu 720
gaagaaagug acaaugugga uucugcugau gcggaggagg augacucgga ugucuggugg 780
ggcggagcag acacagacua ugcagauggg agugaagaca aaguaguaga aguagcagag 840
gaggaagaag uggcugaggu ggaagaagaa gaagccgaug augacgagga cgaugaggau 900
ggugaugagg uagaggaaga ggcugaggaa cccuacgaag aagccacaga gagaaccacc 960
agcauugcca ccaccaccac caccaccaca gagucugugg aagaggugu ucgagugucc 1020
caaaguuuac ucaagacuac ccaggaaccu cuugcccgag auccuguuaa acuuccuaca 1080
acagcagcca guaccccuga ugccguugac aaguaucucg agacaccugg ggaugagaau 1140
gaacaugccc auuuccagaa agccaaagag aggcuugagg ccaagcaccg agagagaaug 1200
ucccagguca ugagagaaug ggaagaggca gaacgucaag caaagaacuu gccuaaagcu 1260
gauaagaagg caguuaucca gcauuuccag gagaaagugg aaucuuugga acaggaagca 1320
gccaacgaga gacagcagcu gguggagaca cacauggcca gaguggaagc caugcucaau 1380
gaccgccgcc gccuggcccu ggagaacuac aucaccgcuc ugcaggcugu uccuccucgg 1440
ccucgucacg uguucaauau gcuaaagaag uauguccgcg cagaacagaa ggacagacag 1500
cacacccuaa agcauuucga gcaugugcgc auggugg auc ccaagaaagc cgcucagauc 1560
cggucccagg uuaugacaca ccuccgugug auuuaugagc gcaugaauca gucucucucc 1620
cugcucuaca acgugccugc aguggccgag gagauucagg augaaguuga ugagcugcuu 1680
cagaaagagc aaaacuauuc agaugacguc uuggccaaca ugauuaguga accaaggauc 1740
aguuacggaa acgaugcucu caugccaucu uugaccgaaa cgaaaaccac cguggagcuc 1800
cuucccguga auggagaguu cagccuggac gaucuccagc cguggcauuc uuuuggggcu 1860
gacucugugc cagccaacac agaaaacgaa guugagccug uugaugcccg cccugcugcc 1920
gaccgaggac ugaccacucg accagguucu ggguugacaa auaucaagac ggaggagauc 1980
ucugaaguga agauggaugc agaauuccga caugacucag gauaugaagu ucaucaucaa 2040
aaauuggugu ucuuugcaga agaugugggu ucaaacaaag gugcaaucau uggacucaug 2100
guggggcggug uugucauagc gacagugauc gucaucaccu uggugaugcu gaagaagaaa 2160
caguacacau ccauucauca uggugguggug gagguugacg ccgcugucac cccagaggag 2220
cgccaccugu ccaagaugca gcagaacggc uacgaaaauc caaccuacaa guucuuugag 2280
cagaugcaga acuagacccc cgccacagca gccucugaag uuggacagca aaaccauugc 2340
uucacuaccc aucggugucc auuuauagaa uaauguggga agaaacaaac ccguuuuaug 2400
auuuacucau uaucgccuuu ugacagcugu gcuguaacac aaguagaugc cugaacuuga 2460
auuaauccac acaucaguaa uguauucuau cucucuuuac auuuuggucu cuauacuaca 2520
uuauuaaugg guuuugugua cuguaaagaa uuuagcugua ucaaacuagu gcaugaauag 2580
auucucuccu gauuauuuau cacauagccc cuuagccagu uguauauuau ucuugugguu 2640
ugugacccaa uuaaguccua cuuuacauau gcuuuaagaa ucgauggggg augcuucaug 2700
ugaacguggg aguucagcug cuucucuugc cuaaguauuc cuuuccugau cacuaugcau 2760
uuuaaaguua aacauuuuua aguauuucag augcuuuaga gagauuuuuu uuccaugacu 2820
gcauuuuacu guacagauug cugcuucugc uauauuugug auauaggaau uaagaggaua 2880
cacacguuug uuucuucgug ccuguuuuau gugcacacau uaggcauuga gacuucaagc 2940
uuuucuuuuu uuguccacgu aucuuugggu cuuugauaaa gaaaagaauc ccuguucauu 3000
guaagcacuu uuacggggcg ggugggggagg ggugcucugc uggucuucaa uuaccaagaa 3060
uucuccaaaa caauuuucug caggaugauu guacagaauc auugcuuaug acaugaucgc 3120
uuucuacacu guauuacaua aauaaauuaa auaaaauaac cccgggcaag acuuuucuuu 3180
gaaggaugac uacagacauu aaauaaucga aguaauuuug ggugggggaga agaggcagau 3240 ucaauuuucu uuaaccaguc ugaaguuuca uuuaugauac aaaagaagau gaaaauggaa 3300
guggcaauau aaggggauga ggaaggcaug ccuggacaaa cccuucuuuu aagaugugc 3360 uucaauuugu auaaaauggu guuuucaugu aaauaaauac auucuuggag gagca 3415

<210> SEQ ID NO 14
<211> LENGTH: 40
<212> TYPE: PRT
<213> ORGANISM: Homo sapiens

<400> SEQUENCE: 14

Asp Ala Glu Phe Arg His Asp Ser Gly Tyr Glu Val His His Gln Lys
1 5 10 15

Leu Val Phe Phe Ala Glu Asp Val Gly Ser Asn Lys Gly Ala Ile Ile
20 25 30

Gly Leu Met Val Gly Gly Val Val
35 40

<210> SEQ ID NO 15
<211> LENGTH: 42
<212> TYPE: PRT
<213> ORGANISM: Homo sapiens

<400> SEQUENCE: 15

Asp Ala Glu Phe Arg His Asp Ser Gly Tyr Glu Val His His Gln Lys
1 5 10 15

Leu Val Phe Phe Ala Glu Asp Val Gly Ser Asn Lys Gly Ala Ile Ile
20 25 30

Gly Leu Met Val Gly Gly Val Val Ile Ala
35 40

<210> SEQ ID NO 16
<211> LENGTH: 6590
<212> TYPE: RNA
<213> ORGANISM: Homo sapiens

<400> SEQUENCE: 16
gcagucaccg ccacccacca gcuccggcac caacagcagc gccgcugcca ccgcccaccu 60
ucugccgccg ccaccacagc caccuucucc uccuccgcug uccucucccg uccucgccuc 120
ugucgacuau cagguggaacu uugaaccagg auggcugagc cccgccagga guucgaagug 180
auggaagauc acgcugggac guacggguug ggggacagga aagaucaggg gggcuacacc 240
augcaccaag accaagaggg ugacacggac gcuggccuga aagaaucucc ccugcagacc 300
cccacugagg acggaucuga ggaaccgggc ucugaaaccu cugaugcuaa gagcacucca 360
acagcggaag augugacagc acccuuagug gaugagggag cucccggcaa gcaggcugcc 420
gcgcagcccc acacggagau cccagaagga accacagcug aagaagcagg cauuggagac 480
acccccagcc uggaagacga agcugcuggu cacgugaccc aagagccuga aagugguaag 540

```
guggguccagg aaggcuuccu ccgagagcca ggccccccag gucugagcca ccagcucaug    600
uccggcaugc cuggggcucc ccuccugccu gagggcccca gagaggccac acgccaaccu    660
ucggggacag gaccugagga cacagagggc ggccgccacg ccccugagcu gcucaagcac    720
cagcuucuag gagaccugca ccaggagggg ccgccgcuga agggggcagg gggcaaagag    780
aggccgggga gcaaggagga gguggaugaa gaccgcgacg ucgaugaguc cuccccccaa    840
gacuccccuc ccuccaaggc cuccccagcc caagaugggc ggccucccca gacagccgcc    900
agagaagcca ccagcauccc aggcuuccca gcggagggug ccaucccccu cccuguggau    960
uuccucucca aaguuuccac agagauccca gccucagagc ccgacgggcc caguguaggg   1020
cgggccaaag ggcaggaugc cccccuggag uucacguuuc acguggaaau cacacccaac   1080
gugcagaagg agcaggcgca cucggaggag cauuugggaa gggcugcauu uccaggggcc   1140
ccuggagagg ggccagaggc ccggggcccc ucuuugggag aggacacaaa agaggcugac   1200
cuuccagagc ccucugaaaa gcagccugcu gcugcuccgc gggggaagcc cgucagccgg   1260
gucccucaac ucaaagcucg cauggucagu aaaagcaaag acgggacugg aagcgaugac   1320
aaaaaagcca agacauccac acguuccucu gcuaaaaccu ugaaaaauag gccuugccuu   1380
agccccaaac accccacucc ugguagcuca gacccucuga uccaacccuc cagccccugcu   1440
gugugcccag agccaccuuc cucuccuaaa uacgucucuu cugucacuuc ccgaacuggc   1500
aguucuggag caaaggagau gaaacucaag ggggcugaug guaaaacgaa gaucgccaca   1560
ccgcggggag cagccccucc aggccagaag ggccaggcca acgccaccag gauuccagca   1620
aaaaccccgc ccgcuccaaa gacaccaccc agcucuggug aaccuccaaa aucaggggau   1680
cgcagcggcu acagcagccc cggcuccccca ggcacucccg gcagccgcuc ccgcaccccg   1740
ucccuuccaa ccccacccac ccgggagccc aagaaggugg caguggucccg uacuccaccc   1800
aagucgccgu cuuccgccaa gagccgccug cagacagccc ccgugcccau gccagaccug   1860
aagaauguca aguccaagau cggcuccacu gagaaccuga agcaccagcc gggaggcggg   1920
aaggugcaga uaauuaauaa gaagcuggau cuuagcaacg uccaguccaa guguggcuca   1980
aaggauaaua ucaaacacgu cccgggaggc ggcagugugc aaauagucua caaaccaguu   2040
gaccugagca aggugaccuc caaguguggc ucauuaggca acauccauca uaaaccagga   2100
gguggccagg uggaaguaaa aucugagaag cuugacuuca aggacagagu ccagucgaag   2160
auugggaccc uggacaauau cacccacguc ccuggcggag gaaauaaaaa gauugaaacc   2220
cacaagcuga ccuuccgcga gaacgccaaa gccaagacag accacggggc ggagaucgug   2280
uacaagucgc caguggugcuc uggggacacg ucuccacggc aucucagcaa ugucuccucc   2340
accggcagca ucgacauggu agacucgccc cagcucgcca cgcuagcuga cgaggugucu   2400
gccucccugg ccaagcaggg uuugugauca ggccccuggg gcggucaaua auuguggaga   2460
ggagagaaug agagagugug gaaaaaaaaa gaauaaugac ccggccccccg cccucugccc   2520
ccagcugcuc cucgcaguuc gguuaauugg uuaaucacuu aaccugcuuu ugucacucgg   2580
cuuuggcucg ggacuucaaa aucagugaug ggaguaagag caaauuucau cuuuccaaau   2640
ugaugggugg gcuaguaaua aaauauuuaa aaaaaaacau ucaaaaacau ggccacaucc   2700
aacauuuccu caggcaauuc cuuuugauuc uuuuuucuuc ccccuccaug uagaagaggg   2760
agaaggagag gcucugaaag cugcuucugg gggauuucaa gggacugggg gugccaacca   2820
ccucuggccc uguuguggggg gugucacaga ggcaguggca gcaacaaagg auuugaaacu   2880
```

-continued

```
uggugguguuc guggagccac aggcagacga ugucaaccuu gugugagugu gacggggguu   2940
ggggugggggc gggaggccac gggggaggcc gaggcagggg cugggcagag gggagaggaa   3000
gcacaagaag ugggaguggg agaggaagcc acgugcugga gaguagacau cccccuccuu   3060
gccgcuggga gagccaaggc cuaugccacc ugcagcgucu gagcggccgc cuguccuugg   3120
uggccggggg ugggggccug cuguggguca gugugccacc cucugcaggg cagccugugg   3180
gagaagggac agcggguaaa aagagaaggc aagcuggcag gaggguggca cuucguggau   3240
gaccuccuua gaaaagacug accuugaugu cuugagagcg cuggccucuu ccucccuccc   3300
ugcaggguag ggggccugag uugaggggcu ucccucugcu ccacagaaac ccuguuuuau   3360
ugaguucuga agguuggaac ugcugccaug auuuuggcca cuuugcagac cugggacuuu   3420
agggcuaacc aguucucuuu guaaggacuu gugccucuug ggagacgucc acccguuucc   3480
aagccugggc cacuggcauc ucuggagugu gugggggucu gggaggcagg ucccgagccc   3540
ccuguccuuc ccacggccac ugcagucacc ccgucugcgc cgcugugcug uugucugccg   3600
ugagagccca aucacugccu auaccccuca ucacacguca caauguccg aauucccagc   3660
cucaccaccc cuucucagua augacccugg uugguugcag gagguaccua cuccauacug   3720
agggugaaau uaagggaagg caaaguccag gcacaagagu gggaccccag ccucucacuc   3780
ucaguuccac ucauccaacu gggacccuca ccacgaaucu caugaucuga uucgguuccc   3840
ugucuccucc ucccgucaca gaugugagcc agggcacugc ucagcuguga cccuaggugu   3900
uucugccuug uugacaugga gagagcccuu uccccugaga aggccuggcc ccuuccugug   3960
cugagcccac agcagcaggc ugggugucuu gguugucagu gguggcacca ggauggaagg   4020
gcaaggcacc cagggcaggc ccacaguccc gcuguccccc acuugcaccc uagcuuguag   4080
cugccaaccu cccagacagc ccagcccgcu gcucagcucc acaugcauag uaucagcccu   4140
ccacacccga caaaggggaa cacacccccu uggaaauggu ucuuuucccc caguccccagc   4200
uggaagccau gcugucuguu cugcuggagc agcugaacau auacauagau guugcccugc   4260
ccucccccauc ugcacccugu ugaguuguag uuggauuugu cuguuuaugc uuggauucac   4320
cagagugacu augauaguga aaagaaaaaa aaaaaaaaaa aaggacgcau guaucuugaa   4380
augcuuguaa agagguuucu aacccacccu cacgaggugu cucucacccc cacacuggga   4440
cucgugugggc cugugugggug ccacccugcu ggggccuccc aaguuuugaa aggcuuuccu   4500
cagcaccugg gacccaacag agaccagcuu cuagcagcua aggaggccgu ucagcuguga   4560
cgaaggccug aagcacagga uuaggacuga agcgaugaug uccccuuccc uacuucccccu   4620
uggggcuccc ugugucaggg cacagacuag gucuuguggc uggucuggcu ugcggcgcga   4680
ggaugguucu cucuggucau agcccgaagu cucauggcag ucccaaagga ggcuuacaac   4740
uccugcauca caagaaaaag gaagccacug ccagcugggg ggaucugcag cucccagaag   4800
cuccgugagc cucagccacc ccucagacug gguuccucuc caagcucgcc cucuggaggg   4860
gcagcgcagc cucccaccaa gggcccugcg accacagcag ggauugggau gaauugccug   4920
uccuggaucu gcucuagagg cccaagcugc cugccugagg aaggaugacu ugacaaguca   4980
ggagacacug uucccaaagc cuugaccaga gcaccucagc ccgcugaccu ugcacaaacu   5040
ccaucugcug ccaugagaaa agggaagccg ccuuugcaaa acauugcugc cuaaagaaac   5100
ucagcagccu caggcccaau ucugccacuu cugguuuggg uacaguuaaa ggcaacccug   5160
agggacuugg caguagaaau ccagggccuc cccuggggcu ggcagcuucg ugugcagcua   5220
gagcuuuacc ugaaaggaag ucucugggcc cagaacucuc caccaagagc cucccugccg   5280
```

uucgcugagu cccagcaauu cuccuaaguu gaagggaucu gagaaggaga aggaaaugug 5340
ggguagauuu gguggugguu agagauaugc cccccucauu acugccaaca guuucggcug 5400
cauuucuuca cgcaccucgg uuccucuucc ugaaguucuu gugcccugcu cuucagcacc 5460
augggccuuc uuauacggaa ggcucuggga ucuccccuu guggggcagg cucuuggggc 5520
cagccuaaga ucaugguuua gggugaucag ugcuggcaga uaaauugaaa aggcacgcug 5580
gcuugugauc uuaaaugagg acaauccccc cagggcuggg cacuccuccc cuccccucac 5640
uucucccacc ugcagagcca guguccuugg gugggcuaga uaggauauac uguaugccgg 5700
cuccuucaag cugcugacuc acuuuaucaa uaguuccauu uaaauugacu ucagugguga 5760
gacuguaucc uguuugcuau ugcuuguugu gcuauggggg gaggggggag gaauguguaa 5820
gauaguuaac augggcaaag ggagaucuug gggugcagca cuuaaacugc cucguaaccc 5880
uuuucaugau uucaaccaca uuugcuagag ggagggagca gccacggagu uagaggcccu 5940
uggggguucu cuuuuccacu gacaggcuuu cccaggcagc uggcuaguuc auucccuccc 6000
cagccaggug caggcguagg aauauggaca ucugguugcu uuggccugcu gcccucuuuc 6060 aggggguccua agcccacaau caugccuccc uaagaccuug gcauccuucc cucuaagccg 6120
uuggcaccuc ugugccaccu cucacacugg cuccagacac acagccugug cuuuuggagc 6180
ugagaucacu cgcuucaccc uccucaucuu uguucuccaa guaaagccac gaggucgggg 6240
cgagggcaga ggugaucacc ugcguguccc aucuacagac cugcagcuuc auaaaacuuc 6300
ugauuucucu ucagcuuuga aaaggguuac ccugggcacu ggccuagagc cucaccuccu 6360
aauagacuua gccccaugag uuugccaugu ugagcaggac uauuucuggc acuugcaagu 6420
cccaugauuu cuucgguaau ucugagggug gggggaggga caugaaauca ucuuagcuua 6480
gcuuucuguc ugugaauguc uauauagugu auuguguguu uuaacaaaug auuuacacug 6540
acuguugcug uaaaagugaa uuuggaaaua aaguuauuac ucugauuaaa 6590

<210> SEQ ID NO 17
<211> LENGTH: 5639
<212> TYPE: RNA
<213> ORGANISM: Homo sapiens

<400> SEQUENCE: 17
gcagucaccg ccacccacca gcuccggcac caacagcagc gccgcugcca ccgcccaccu 60
ucugccgccg ccaccacagc caccuucucc uccuccgcug uccucucccg uccucgccuc 120
ugucgacuau caggugaacu uugaaccagg auggcugagc cccgccagga guucgaagug 180
auggaagauc acgcugggac guacggguug ggggacagga aagaucaggg gggcuacacc 240
augcaccaag accaagaggg ugacacggac gcuggccuga aagaaucucc ccugcagacc 300
cccacugagg acggaucuga ggaaccgggc ucugaaaccu cugaugcuaa gagcacucca 360
acagcggaag augugacagc acccuuagug gaugagggag cucccggcaa gcaggcugcc 420
gcgcagcccc acacggagau cccagaagga accacagcug aagaagcagg cauuggagac 480
acccccagcc uggaagacga agcugcuggu cacgugaccc aagcucgcau ggucaguaaa 540
agcaaagacg ggacuggaag cgaugacaaa aaagccaagg gggcugaugg uaaaaacgaag 600 aucgccacac cgcggggagc agccccucca ggccagaagg gccaggccaa cgccaccagg 660
auuccagcaa aaaccccgcc cgcuccaaag acaccaccca gcucugguga accuccaaaa 720
ucaggggauc gcagcggcua cagcagcccc ggcuccccag gcacucccgg cagccgcucc 780

-continued cgcaccccgu cccuuccaac cccacccacc cgggagccca agaagguggc aguggaccgu 840
acuccaccca agucgccguc uuccgccaag agccgccugc agacagcccc cgugcccaug 900
ccagaccuga agaaugucaa guccaagauc ggcuccacug agaaccugaa gcaccagccg 960
ggaggcggga aggugcagau aauuaauaag aagcuggauc uuagcaacgu ccaguccaag 1020
uguggcucaa aggauaauau caaacacguc ccgggaggcg gcagugugca aauagucuac 1080
aaaccaguug accugagcaa ggugaccucc aaguguggcu cauuaggcaa cauccaucau 1140
aaaccaggag guggccaggu ggaaguaaaa ucugagaagc uugacuucaa ggacagaguc 1200
cagucgaaga uuggguccu ggacaauauc acccacgucc cuggcggagg aaauaaaaag 1260
auugaaaccc acaagcugac cuuccgcgag aacgccaaag ccaagacaga ccacggggcg 1320
gagaucgugu acaagucgcc aguggugucu ggggacacgu cuccacggca ucucagcaau 1380
gucuccucca ccggcagcau cgacauggua gacucgcccc agcucgccac gcuagcugac 1440
gaggugucug ccucccuggc caagcagggu uugugaucag gccccugggg cggucaauaa 1500
uuguggagag gagagaauga gagaguguggg aaaaaaaaag aauaaugacc cggcccccgc 1560
ccucugcccc cagcugcucc ucgcaguucg guuaauuggu uaaucacuua accugcuuuu 1620
gucacucggc uuuggcucgg gacuucaaaa ucagugaugg gaguaagagc aaauuucauc 1680
uuuccaaauu gauggguggg cuaguaauaa aauauuuaaa aaaaaacauu caaaaacaug 1740
gccacaucca acauuuccuc aggcaauucc uuuugauucu uuuuucuucc cccuccaugu 1800
agaagaggga gaaggagagg cucugaaagc ugcuucuggg ggauuucaag ggacuggggg 1860
ugccaaccac cucuggcccu guugugggggg ugucacagag gcaguggcag caacaaagga 1920
uuugaaacuu ggugugguucg uggagccaca ggcagacgau gucaaccuug ugugagugug 1980
acgggggguug gggugggggcg ggaggccacg ggggaggccg aggcaggggc ugggcagagg 2040
ggagaggaag cacaagaagu gggaguggga gaggaagcca cgugcuggag aguagacauc 2100
ccccuccuug ccgcugggag agccaaggcc uaugccaccu gcagcgucug agcggccgcc 2160
uguccuuggu ggccgggggu gggggccugc ugugggucag ugugccaccc ucugcagggc 2220
agccuguggg agaagggaca gcggguaaaa agagaaggca agcuggcagg agggugggcac 2280
uucguggaug accuccuuag aaaagacuga ccuugauguc uugagagcgc uggccucuuc 2340
cuccccuccu gcaggguagg gggccugagu ugaggggcuu ccccucugcuc cacagaaacc 2400
cuguuuuauu gaguucugaa gguuggaacu gcugccauga uuuuggccac uuugcagacc 2460
ugggacuuua gggcuaacca guucucuuug uaaggacuug ugccucuugg gagacgucca 2520
cccguuucca agccugggcc acuggcaucu cuggagugug ugggggucug ggaggcaggu 2580
cccgagcccc cuguccuucc cacggccacu gcagucaccc cgucugcgcc gcugugcugu 2640
ugucugccgu gagagcccaa ucacugccua uaccccucau cacacgucac aaugucccga 2700
auucccagcc ucaccacccc uucucaguaa ugacccuggu ugguugcagg agguaccuac 2760
uccauacuga gggugaaauu aagggaaggc aaaguccagg cacaagagug ggaccccagc 2820
cucucacucu caguuccacu cauccaacug ggacccucac cacgaaucuc augaucugau 2880
ucgguucccu gucuccuccu cccgucacag augugagcca gggcacugcu cagcugugac 2940
ccuagguguu ucugccuugu ugacauggag agagcccuuu ccccugagaa ggccuggccc 3000
cuuccugugc ugagcccaca gcagcaggcu gggugucuug guugucagug guggcaccag 3060
gauggaaggg caaggcaccc agggcaggcc cacagucccg cugucccccca cuugcacccu 3120
agcuuguagc ugccaaccuc ccagacagcc cagcccgcug cucagcucca caugcauagu 3180

```
aucagcccuc cacacccgac aaaggggaac acaccccccuu ggaaaugguu cuuuuccccc   3240
agucccagcu ggaagccaug cugucuguuc ugcuggagca gcugaacaua uacauagaug   3300
uugcccugcc cuccccaucu gcacccuguu gaguuguagu uggauuuguc uguuuaugcu   3360
uggauucacc agagugacua ugauagugaa aagaaaaaaa aaaaaaaaaa aggacgcaug   3420
uaucuugaaa ugcuuguaaa gagguuucua acccacccuc acgaggugc ucucacccc   3480
acacugggac ucguguggcc uguguggugc cacccugcug gggccuccca aguuuugaaa   3540
ggcuuuccuc agcaccuggg acccaacaga gaccagcuuc uagcagcuaa ggaggccguu   3600
cagcugugac gaaggccuga agcacaggau uaggacugaa gcgaugaugu ccccuucccu   3660
acuuccccuu ggggcucccu gugucagggc acagacuagg ucuuguggcu ggucuggcuu   3720
gcggcgcgag gaugguucuc ucuggucaua gcccgaaguc ucauggcagu cccaaaggag   3780
gcuuacaacu ccugcaucac aagaaaaagg aagccacugc cagcuggggg gaucugcagc   3840
ucccagaagc uccgugagcc ucagccaccc cucagacugg guuccucucc aagcucgccc   3900
ucuggagggg cagcgcagcc ucccaccaag ggcccugcga ccacagcagg gauugggaug   3960
aauugccugu ccuggaucug cucuagaggc ccaagcugcc ugccugagga aggaugacuu   4020
gacaagucag gagacacugu ucccaaagcc uugaccagag caccucagcc cgcugaccuu   4080
gcacaaacuc caucugcugc caugagaaaa gggaagccgc cuuugcaaaa cauugcugcc   4140
uaaagaaacu cagcagccuc aggcccaauu cugccacuuc ugguuugggu acaguuaaag   4200
gcaacccuga gggacuuggc aguagaaauc cagggccucc ccuggggcug gcagcuucgu   4260
gugcagcuag agcuuuaccu gaaaggaagu cucugggccc agaacucucc accaagagcc   4320
ucccugccgu ucgcugaguc ccagcaauuc uccuaaguug aagggaucug agaaggagaa   4380
ggaaaugugg gguagauuug gugguggua gagauaugcc ccccucauua cugccaacag   4440
uuucggcugc auuucuucac gcaccucggu uccucuuccu gaaguucuug ugcccugcuc   4500
uucagcacca ugggccuucu uauacggaag gcucugggau cucccccuug uggggcaggc   4560
ucuuggggcc agccuaagau caugguuuag ggugaucagu gcuggcagau aaauugaaaa   4620
ggcacgcugg cuugugaucu uaaaugagga caaucccccc agggcugggc acuccucccc   4680
uccccucacu ucucccaccu gcagagccag uguccuuggg ugggcuagau aggauauacu   4740
guaugccggc uccuucaagc ugcugacuca cuuuaucaau aguuccauuu aaauugacuu   4800
caguggugag acuguauccu guuugcuauu gcuuguugug cuaugggggg aggggggagg   4860
aauguguaag auaguuaaca ugggcaaagg gagaucuugg ggugcagcac uuaaacugcc   4920
ucguaacccu uuucaugauu ucaaccacau uugcuagagg gagggagcag ccacggaguu   4980
agaggcccuu gggguuucuc uuuuccacug acaggcuuuc ccaggcagcu ggcuaguuca   5040
uucccucccc agccaggugc aggcguagga auauggacau cugguugcuu uggccugcug   5100
cccucuuuca ggggguccuaa gcccacaauc augccucccu aagaccuugg cauccuuccc   5160
ucuaagccgu uggcaccucu gugccaccuc ucacacuggc uccagacaca cagccugugc   5220
uuuuggagcu gagaucacuc gcuucacccu ccucaucuuu guucuccaag uaaagccacg   5280
aggucggggc gagggcagag gugaucaccu gcguguccca ucuacagacc ugcagcuuca   5340
uaaaacuucu gauuucucuu cagcuuugaa aaggguuacc cugggcacug gccuagagcc   5400
ucaccuccua auagacuuag ccccaugagu uugccauguu gagcaggacu auuucuggca   5460
cuugcaaguc ccaugauuuc uucgguaauu cugagggugg ggggagggac augaaaucau   5520
```

cuuagcuuag cuuucugucu gugaaugucu auauagugua uuguguguuu uaacaaauga 5580
uuuacacuga cuguugcugu aaaagugaau uuggaaauaa aguuauuacu cugauuaaa 5639

<210> SEQ ID NO 18
<211> LENGTH: 5465
<212> TYPE: RNA
<213> ORGANISM: Homo sapiens

<400> SEQUENCE: 18
gcagucaccg ccacccacca gcuccggcac caacagcagc gccgcugcca ccgcccaccu 60
ucugccgccg ccaccacagc caccuucucc uccuccgcug uccucucccg uccucgccuc 120
ugucgacuau caggugaacu uugaaccagg auggcugagc ccgccagga guucgaagug 180 auggaagauc acgcugggac guacggguug ggggacagga aagaucaggg gggcuacacc 240
augcaccaag accaagaggg ugacacggac gcuggccuga aagcugaaga agcaggcauu 300
ggagacaccc ccagccugga agacgaagcu gcuggucacg ugacccaagc ucgcaugguc 360
aguaaaagca aagacgggac uggaagcgau gacaaaaaag ccaagggggc ugaugguaaa 420
acgaagaucg ccacaccgcg gggagcagcc ccuccaggcc agaagggcca ggccaacgcc 480
accaggauuc cagcaaaaac cccgcccgcu ccaaagacac cacccagcuc uggugaaccu 540
ccaaaaucag gggaucgcag cggcuacagc agccccggcu ccccaggcac ucccggcagc 600
cgcucccgca ccccgucccu uccaacccca cccacccggg agcccaagaa gguggcagug 660
guccguacuc cacccaaguc gccgucuucc gccaagagcc gccugcagac agcccccgug 720
cccaugccag accugaagaa ugucaagucc aagaucggcu ccacugagaa ccugaagcac 780
cagccgggag gcgggaaggu gcagauaauu aauaagaagc uggaucuuag caacguccag 840
uccaagugug gcucaaagga uaauaucaaa cacgucccgg gaggcggcag ugugcaaaua 900
gucuacaaac caguugaccu gagcaaggug accuccaagu guggcucauu aggcaacauc 960
caucauaaac caggaggugg ccagguggaa guaaaaucug agaagcuuga cuucaaggac 1020
agaguccagu cgaagauugg gucccuggac aauaucaccc acgucccugg cggaggaaau 1080
aaaaagauug aaacccacaa gcugaccuuc cgcgagaacg ccaaagccaa gacagaccac 1140
ggggcggaga ucguguacaa gucgccagug gugucugggg acacgucucc acggcaucuc 1200
agcaaugucu ccuccaccgg cagcaucgac augguagacu cgccccagcu cgccacgcua 1260
gcugacgagg ugucugccuc ccuggccaag cagggguuugu gaucaggccc cuggggcggu 1320
caauaauugu ggagaggaga gaaugagaga guguggaaaa aaaaagaaua augacccggc 1380
ccccgcccuc ugcccccagc ugcuccucgc aguucgguua auugguuaau cacuuaaccu 1440
gcuuuuguca cucggcuuug gcucgggacu ucaaaaucag ugaugggagu aagagcaaau 1500
uucaucuuuc caaauugaug ggugggcuag uaauaaaaua uuuaaaaaaa aacauucaaa 1560
aacauggcca cauccaacau uucccucaggc aauuccuuuu gauucuuuuu ucuucccccu 1620
ccauguagaa gagggagaag gagaggcucu gaaagcugcu ucugggggau uucaagggac 1680
ugggggugcc aaccaccucu ggcccuguug ugggggguguc acagaggcag uggcagcaac 1740
aaaggauuug aaacuuggug uguucgugga gccacaggca gacgauguca accuugugug 1800
agugugacgg ggguuggggu ggggcgggag gccacggggg aggccgaggc aggggcuggg 1860
cagaggggag aggaagcaca agaagugga guggggagagg aagccacgug cuggagagua 1920 gacaucccc uccuugccgc ugggagagcc aaggccuaug ccaccugcag cgucugagcg 1980
gccgccuguc cuugguggcc gggggugggg gccugcugug ggucagugug ccacccucug 2040
cagggcagcc ugugggagaa gggacagcgg guaaaaagag aaggcaagcu ggcaggaggg 2100
uggcacuucg uggaugaccu ccuuagaaaa gacugaccuu gaugucuuga gagcgcuggc 2160
cucuuccucc cucccugcag gguagggggc cugaguugag gggcuucccu cugcuccaca 2220
gaaacccugu uuuauugagu ucugaagguu ggaacugcug ccaugauuuu ggccacuuug 2280
cagaccuggg acuuuagggc uaaccaguuc ucuuuguaag gacuugugcc ucuugggaga 2340
cguccacccg uuuccaagcc ugggccacug gcaucucugg agugugugggg ggucugggag 2400 gcagguccccg agcccccugu ccuucccacg gccacugcag ucaccccguc ugcgccgcug 2460
ugcuguuguc ugccgugaga gcccaaucac ugccuauacc ccucaucaca cgucacaaug 2520
ucccgaauuc ccagccucac caccccuucu caguaaugac ccugguuggu ugcaggaggu 2580
accuacucca uacugagggu gaaauuaagg gaaggcaaag uccaggcaca agagugggac 2640
cccagccucu cacucucagu uccacucauc caacugggac ccucaccacg aaucucauga 2700
ucugauucgg uucccugucu ccuccucccg ucacagaugu gagccagggc acugcucagc 2760
ugugacccua gguguuucug ccuuguugac auggagagag cccuuucccc ugagaaggcc 2820
uggccccuuc cugugcugag cccacagcag caggcugggu gucuugguug ucaguggugg 2880
caccaggaug gaagggcaag gcacccaggg caggcccaca gucccgcugu cccccacuug 2940
cacccuagcu uguagcugcc aaccucccag acagcccagc ccgcugcuca gcuccacaug 3000
cauaguauca gcccuccaca cccgacaaag gggaacacac ccccuuggaa augguucuuu 3060
ucccccaguc ccagcuggaa gccaugcugu cuguucugcu ggagcagcug aacauauaca 3120
uagauguugc ccugcccucc ccaucugcac ccuguugagu uguaguugga uuugucuguu 3180
uaugcuugga uucaccagag ugacuaugau agugaaaaga aaaaaaaaaa aaaaaaagga 3240
cgcauguauc uugaaaugcu uguaaagagg uuucuaaccc acccucacga ggugucucuc 3300
acccccacac ugggacucgu guggccugug uggugccacc cugcuggggc cucccaaguu 3360
uugaaaggcu uuccucagca ccugggaccc aacagagacc agcuucuagc agcuaaggag 3420
gccguucagc ugugacgaag gccugaagca caggauuagg acugaagcga ugaugucccc 3480
uucccuacuu ccccuugggg cucccugugu cagggcacag acuaggucuu guggcugguc 3540
uggcuugcgg cgcgaggaug guucucucug gucauagccc gaagucucau ggcaguccca 3600
aaggaggcuu acaacuccug caucacaaga aaaaggaagc cacugccagc ugggggggauc 3660 ugcagcuccc agaagcuccg ugagccucag ccaccccuca gacuggguuc cucuccaagc 3720
ucgcccucug gaggggcagc gcagccuccc accaagggcc cugcgaccac agcagggauu 3780
gggaugaauu gccuguccug gaucugcucu agaggcccaa gcugccugcc ugaggaagga 3840
ugacuugaca agucaggaga cacuguuccc aaagccuuga ccagagcacc ucagcccgcu 3900
gaccuugcac aaacuccauc ugcugccaug agaaaaggga agccgccuuu gcaaaacauu 3960
gcugccuaaa gaaacucagc agccucaggc ccaauucugc cacuucuggu uuggguacag 4020
uuaaaggcaa cccugaggga cuuggcagua gaaauccagg gccuccccug gggcuggcag 4080
cuucgugugc agcuagagcu uuaccugaaa ggaagucucu gggcccagaa cucuccacca 4140
agagccuccc ugccguucgc ugagucccag caauucuccu aaguugaagg gaucugagaa 4200
ggagaaggaa auguggggua gauuuggugg ugguuagaga uaugcccccc ucauuacugc 4260
caacaguuuc ggcugcauuu cuucacgcac cucgguuccu cuuccugaag uucuugugcc 4320
cugcucuuca gcaccauggg ccuucuuaua cggaaggcuc ugggaucucc cccuugugggg 4380 gcaggcucuu ggggccagcc uaagaucaug guuuagggug aucagugcug gcagauaaau 4440
ugaaaaggca cgcuggcuug ugaucuuaaa ugaggacaau ccccccaggg cugggcacuc 4500
cuccccuccc cucacuucuc ccaccugcag agccagugcu cuugggguggg cuagauagga 4560 uauacuguau gccggcuccu ucaagcugcu gacucacuuu aucaauaguu ccauuuaaau 4620
ugacuucagu ggugagacug uauccuguuu gcuauugcuu guugugcuau gggggggaggg 4680 gggaggaaug uguaagauag uuaacauggg caaagggaga ucuuggggug cagcacuuaa 4740
acugccucgu aacccuuuuc augauuucaa ccacauuugc uagagggagg gagcagccac 4800
ggaguuagag gcccuugggg uuucucuuuu ccacugacag gcuuucccag gcagcuggcu 4860
aguucauucc cuccccagcc aggugcaggc guaggaauau ggacaucugg uugcuuuggc 4920
cugcugcccu cuuucagggg uccuaagccc acaaucaugc cucccuaaga ccuuggcauc 4980
cuucccucua agccguuggc accucugugc caccucucac acuggcucca gacacacagc 5040
cugugcuuuu ggagcugaga ucacucgcuu cacccuccuc aucuuuguuc uccaaguaaa 5100
gccacgaggu cggggcgagg gcagagguga ucaccugcgu gucccaucua cagaccugca 5160
gcuucauaaa acuucugauu ucucuucagc uuugaaaagg guuacccugg gcacuggccu 5220
agagccucac cuccuaauag acuuagcccc augaguuugc cauguugagc aggacuauuu 5280
cuggcacuug caagucccau gauuucuucg guaauucuga gggugggggg agggacauga 5340
aaucaucuua gcuuagcuuu cugucuguga augucuauau aguguauugu guguuuuaac 5400
aaaugauuua cacugacugu ugcuguaaaa gugaauuugg aaauaaaguu auuacucuga 5460
uuaaa 5465

<210> SEQ ID NO 19
<211> LENGTH: 5372
<212> TYPE: RNA
<213> ORGANISM: Homo sapiens

<400> SEQUENCE: 19
gcagucaccg ccacccacca gcuccggcac caacagcagc gccgcugcca ccgcccaccu 60
ucugccgccg ccaccacagc caccuucucc uccuccgcug uccucucccg uccucgccuc 120
ugucgacuau caggugaacu uugaaccagg auggcugagc cccgccagga guucgaagug 180
auggaagauc acgcugggac guacggguug ggggacagga aagaucaggg gggcuacacc 240
augcaccaag accaagaggg ugacacggac gcuggccuga aagcugaaga agcaggcauu 300
ggagacaccc ccagccugga agacgaagcu gcugguca cg ugacccaagc ucgcaugguc 360
aguaaaagca aagacgggac uggaagcgau gacaaaaaag ccaagggggc ugaugguaaa 420
acgaagaucg ccacaccgcg gggagcagcc ccuccaggcc agaagggcca ggccaacgcc 480
accaggauuc cagcaaaaac cccgcccgcu ccaaagacac cacccagcuc uggugaaccu 540
ccaaaaucag gggaucgcag cggcuacagc agccccggcu ccccaggcac ucccggcagc 600
cgcucccgca ccccgucccu uccaaccccca cccacccggg agcccaagaa gguggcagug 660
guccguacuc cacccaaguc gccgucuucc gccaagagcc gccugcagac agcccccgug 720
cccaugccag accugaagaa ugucaagucc aagaucggcu ccacugagaa ccugaagcac 780
cagccgggag gcgggaaggu gcaaauaguc uacaaaccag uugaccugag caaggugacc 840
uccaagugug gcucauuagg caacauccau cauaaaccag gagguggcca gguggaagua 900
aaaucugaga agcuugacuu caaggacaga guccagucga agauuggguc ccuggacaau 960
aucacccacg ucccuggcgg aggaaauaaa aagauugaaa cccacaagcu gaccuuccgc 1020

-continued

```
gagaacgcca aagccaagac agaccacggg gcggagaucg uguacaaguc gccaguggug   1080
ucuggggaca cgucuccacg gcaucucagc aaugucuccu ccaccggcag caucgacaug   1140
guagacucgc cccagcucgc cacgcuagcu gacgaggugu cugccucccu ggccaagcag   1200
gguuugugau caggccccug gggcggucaa uaauugugga gaggagagaa ugagagagug   1260
uggaaaaaaa aagaauaaug acccggcccc cgcccucugc ccccagcugc uccucgcagu   1320
ucgguuaauu gguuaaucac uuaaccugcu uuugucacuc ggcuuuggcu cgggacuuca   1380
aaaucaguga ugggaguaag agcaaauuuc aucuuuccaa auugaugggu gggcuaguaa   1440
uaaaauauuu aaaaaaaaac auucaaaaac auggccacau ccaacauuuc cucaggcaau   1500
uccuuuugau ucuuuuuucu ucccccucca uguagaagag ggagaaggag aggcucugaa   1560
agcugcuucu gggggauuuc aagggacugg gggugccaac caccucuggc ccuguugugg   1620
gggugucaca gaggcagugg cagcaacaaa ggauuugaaa cuuggugugu ucguggagcc   1680
acaggcagac gaugucaacc uugugugagu gugacggggg uuggggu ggg gcgggaggcc   1740
acgggggagg ccgaggcagg ggcugggcag aggggagagg aagcacaaga agugggagug   1800
ggagaggaag ccacgugcug gagaguagac aucccccucc uugccgcugg gagagccaag   1860
gccuaugcca ccugcagcgu cugagcggcc gccuguccuu gguggccggg ggugggggcc   1920
ugcugugggu cagugugcca cccucugcag ggcagccugu gggagaaggg acagcgggua   1980
aaaagagaag gcaagcuggc aggagggugg cacuucgugg augaccuccu uagaaaagac   2040
ugaccuugau gucuugagag cgcuggccuc uuccucccuc ccugcagggu agggggccug   2100
aguugagggg cuucccucug cuccacagaa acccuguuuu auugaguucu gaagguugga   2160
acugcugcca ugauuuuggc cacuuugcag accugggacu uuagggcuaa ccaguucucu   2220
uuguaaggac uugugccucu ugggagacgu ccacccguuu ccaagccugg gccacuggca   2280
ucucuggagu gugugggggu cugggaggca ggucccgagc cccuguccu ucccacggcc   2340
acugcaguca ccccgucugc gccgcugugc uguugucugc cgugagagcc caaucacugc   2400
cuauaccccu caucacacgu cacaaugucc cgaauuccca gccucaccac cccuucucag   2460
uaaugacccu gguugguugc aggagguacc uacuccauac ugagggugaa auuaagggaa   2520
ggcaaagucc aggcacaaga gugggacccc agccucucac ucucaguucc acucauccaa   2580
cugggacccu caccacgaau cucaugaucu gauucgguuc ccugucuccu ccucccguca   2640
cagaugugag ccagggcacu gcucagcugu gacccuaggu guuucugccu uguugacaug   2700
gagagagccc uuuccccuga gaaggccugg ccccuuccug ugcugagccc acagcagcag   2760
gcugggugic uugguuguca gugguggcac caggauggaa gggcaaggca cccagggcag   2820
gcccacaguc ccgcuguccc ccacuugcac ccuagcuugu agcugccaac cucccagaca   2880
gcccagcccg cugcucagcu ccacaugcau aguaucagcc cuccacaccc gacaaagggg   2940
aacacacccc cuuggaaaug guucuuuucc cccaguccca gcuggaagcc augcugucug   3000
uucugcugga gcagcugaac auauacauag auguugcccu gcccucccca ucugcacccu   3060
guugaguugu aguuggauuu gucuguuuau gcuuggauuc accagaguga cuaugauagu   3120
gaaaagaaaa aaaaaaaaaa aaaaggacgc auguaucuug aaaugcuugu aaagagguuu   3180
cuaacccacc cucacgaggu gucucucacc ccacacugg gacucgugug gccugugugg   3240
ugccacccug cuggggccuc ccaaguuuug aaaggcuuuc cucagcaccu gggacccaac   3300
agagaccagc uucuagcagc uaaggaggcc guucagcugu gacgaaggcc ugaagcacag   3360
```

gauuaggacu gaagcgauga uguccccuuc ccuacuuccc cuuggggcuc ccugugucag 3420
ggcacagacu aggucuugug gcuggucugg cuugcggcgc gaggaugguu cucucugguc 3480
auagcccgaa gucucauggc agucccaaag gaggcuuaca acuccugcau cacaagaaaa 3540
aggaagccac ugccagcugg ggggaucugc agcucccaga agcuccguga gccucagcca 3600
ccccucagac ugggguuccuc uccaagcucg cccucuggag gggcagcgca gccucccacc 3660
aagggcccug cgaccacagc agggauuggg augaauugcc uguccuggau cugcucuaga 3720
ggcccaagcu gccugccuga ggaaggauga cuugacaagu caggagacac uguucccaaa 3780
gccuugacca gagcaccuca gcccgcugac cuugcacaaa cuccaucugc ugccaugaga 3840
aaagggaagc cgccuuugca aaacauugcu gccuaaagaa acucagcagc cucaggccca 3900
auucugccac uucugguuug gguacaguua aaggcaaccc ugagggacuu ggcaguagaa 3960
auccagggcc uccccugggg cuggcagcuu cgugugcagc uagagcuuua ccugaaagga 4020
agucucuggg cccagaacuc uccaccaaga gccuccccugc cguucgcuga gucccagcaa 4080
uucuccuaag uugaagggau cugagaagga gaaggaaaug uggggguagau uugguggugg 4140 uuagagauau gccccccuca uuacugccaa caguuucggc ugcauuucuu cacgcaccuc 4200
gguuccucuu ccugaaguuc uugugcccug cucuucagca ccaugggccu ucuuauacgg 4260
aaggcucugg gaucuccccc uuguggggca ggcucuuggg gccagccuaa gaucaugguu 4320
uagggugauc agugcuggca gauaaauuga aaaggcacgc uggcuuguga ucuuaaauga 4380
ggacaauccc cccagggcug ggcacuccuc ccccuccccuc acuucuccca ccugcagagc 4440
caguguccuu gggugggcua gauaggauau acuguaugcc ggcuccuuca agcugcugac 4500
ucacuuuauc aauaguucca uuuaaauuga cuucagugu gagacuguau ccuguuugcu 4560
auugcuuguu gugcuauggg gggagggggg aggaaugugu aagauaguua acaugggcaa 4620
agggagaucu uggggugcag cacuuaaacu gccucguaac ccuuuucaug auuucaacca 4680
cauuugcuag agggagggag cagccacgga guuagaggcc cuuggggguuu cucuuuucca 4740 cugacaggcu uucccaggca gcuggcuagu ucauucccuc cccagccagg ugcaggcgua 4800
ggaauaugga caucugguug cuuuggccug cugcccucuu ucaggggucc uaagcccaca 4860
aucaugccuc ccuaagaccu uggcauccuu ccccucuaagc cguuggcacc ucugugccac 4920
cucucacacu ggcuccagac acacagccug ugcuuuugga gcugagauca cucgcuucac 4980
ccuccucauc uuuguucucc aaguaaagcc acgaggucgg ggcgagggca gaggugauca 5040
ccugcguguc ccaucuacag accugcagcu ucauaaaacu ucugauuucu cuucagcuuu 5100
gaaaaggguu acccugggca cuggccuaga gccucaccuc cuaauagacu uagccccaug 5160
aguuugccau guugagcagg acuauuucug gcacuugcaa gucccaugau uucuucggua 5220
auucugaggg ugggggagg gacaugaaau caucuuagcu uagcuuucug ucugugaaug 5280
ucuauauagu guauugugug uuuuaacaaa ugauuuacac ugacuguugc uguaaaagug 5340
aauuuggaaa uaaaguuauu acucugauua aa 5372

<210> SEQ ID NO 20
<211> LENGTH: 5552
<212> TYPE: RNA
<213> ORGANISM: Homo sapiens

<400> SEQUENCE: 20
gcagucaccg ccacccacca gcuccggcac caacagcagc gccgcugcca ccgcccaccu 60
ucugccgccg ccaccacagc caccuucucc uccuccgcug uccucucccg uccucgccuc 120

```
ugucgacuau caggugaacu uugaaccagg auggcugagc cccgccagga guucgaagug    180
auggaagauc acgcugggac guacggguug ggggacagga aagaucaggg gggcuacacc    240
augcaccaag accaagaggg ugacacggac gcuggccuga aagaaucucc ccugcagacc    300
cccacugagg acggaucuga ggaaccgggc ucugaaaccu cugaugcuaa gagcacucca    360
acagcggaag cugaagaagc aggcauugga gacaccccca gccuggaaga cgaagcugcu    420
ggucacguga cccaagcucg cauggucagu aaaagcaaag acgggacugg aagcgaugac    480
aaaaaagcca agggggcuga ugguaaaacg aagaucgcca caccgcgggg agcagccccu    540
ccaggccaga agggccaggc caacgccacc aggauuccag caaaaacccc gcccgcucca    600
aagacaccac ccagcucugg ugaaccucca aaaucagggg aucgcagcgg cuacagcagc    660
cccggcuccc caggcacucc cggcagccgc ucccgcaccc cguccciuucc aaccccaccc    720
acccgggagc ccaagaaggu ggcagugguc cguacuccac ccaagucgcc gucuuccgcc    780
aagagccgcc ugcagacagc cccgugccc augccagacc ugaagaaugu caaguccaag    840
aucggcucca cugagaaccu gaagcaccag ccgggaggcg ggaaggugca gauaauuaau    900
aagaagcugg aucuuagcaa cguccagucc aagugugcu caaaggauaa uaucaaacac    960
gucccgggag gcggcagugu gcaaauaguc uacaaaccag uugaccugag caaggugacc   1020
uccaagugug gcucauuagg caacauccau cauaaaccag gagguggcca gguggaagua   1080
aaaucugaga agcuugacuu caaggacaga guccagucga agauugggguc ccuggacaau   1140
aucacccacg ucccuggcgg aggaaauaaa aagauugaaa cccacaagcu gaccuuccgc   1200
gagaacgcca aagccaagac agaccacggg gcggagaucg uguacaaguc gccagugug   1260
ucuggggaca cgucuccacg gcaucucagc aaugucuccu ccaccggcag caucgacaug   1320
guagacucgc cccagcucgc cacgcuagcu gacgaggugu cugccucccu ggccaagcag   1380
gguuugugau caggccccug gggcggucaa uaauugugga gaggagagaa ugagagagug   1440
uggaaaaaaa aagaauaaug acccggcccc cgcccucugc cccagcugc uccucgcagu   1500
ucgguuaauu gguuaaucac uuaaccugcu uuugucacuc ggcuuuggcu cgggacuuca   1560
aaaucaguga ugggaguaag agcaaauuuc aucuuuccaa auugaugggu gggcuaguaa   1620
uaaaauauuu aaaaaaaaac auucaaaaac auggccacau ccaacauuuc cucaggcaau   1680
uccuuuugau ucuuuuuucu ucccccucca uguagaagag ggagaaggag aggcucugaa   1740
agcugcuucu gggggauuuc aagggacugg gggugccaac caccucuggc ccuguugugg   1800
gggugucaca gaggcagugg cagcaacaaa ggauuugaaa cuuggugugu ucguggagcc   1860
acaggcagac gaugucaacc uugugugagu gugacggggg uuggggugg gcgggaggcc   1920
acgggggagg ccgaggcagg ggcugggcag aggggagagg aagcacaaga agugggagug   1980
ggagaggaag ccacgugcug gagaguagac aucccccucc uugccgcugg gagagccaag   2040
gccuaugcca ccugcagcgu cugagcggcc gccuguccuu gguggccggg gguggggcc    2100
ugcugugggu cagugugcca cccucugcag ggcagccugu gggagaaggg acagcgggua   2160
aaaagagaag gcaagcuggc aggagggugg cacuucgugg augaccuccu uagaaaagac   2220
ugaccuugau gucuugagag cgcuggccuc uuccucccuc ccugcagggu agggggccug   2280
aguugagggg cuucccucug cuccacagaa acccuguuuu auugaguucu gaagguugga   2340
acugcugcca ugauuuuggc cacuuugcag accugggacu uuagggcuaa ccaguucucu   2400
uuguaaggac uugugccucu ugggagacgu ccacccguuu ccaagccugg gccacuggca   2460
```

-continued

```
ucucuggagu gugugggggu cugggaggca ggucccgagc ccccuguccu ucccacggcc   2520
acugcaguca ccccgucugc gccgcugugc uguugucugc cgugagagcc caaucacugc   2580
cuauaccccu caucacacgu cacaaugucc cgaauuccca gccucaccac cccuucucag   2640
uaaugacccu gguugguugc aggagguacc uacuccauac ugagggugaa auuaagggaa   2700
ggcaaagucc aggcacaaga gugggacccc agccucucac ucucaguucc acucauccaa   2760
cugggacccu caccacgaau cucaugaucu gauucgguuc ccugucuccu ccucccguca   2820
cagaugugag ccagggcacu gcucagcugu gacccuaggu guuucugccu uguugacaug   2880
gagagagccc uuuccccuga gaaggccugg ccccuuccug ugcugagccc acagcagcag   2940
gcugggugue uugguuguca gugguggcac caggauggaa gggcaaggca cccagggcag   3000
gcccacaguc ccgcuguccc ccacuugcac ccuagcuugu agcugccaac cucccagaca   3060
gcccagcccg cugcucagcu ccacaugcau aguaucagcc cuccacaccc gacaaagggg   3120
aacacacccc cuuggaaaug guucuuuucc cccaguccca gcuggaagcc augcugucug   3180
uucugcugga gcagcugaac auauacauag auguugcccu gcccucccca ucugcacccu   3240
guugaguugu aguuggauuu gucuguuuau gcuuggauuc accagaguga cuaugauagu   3300
gaaaagaaaa aaaaaaaaaa aaaaggacgc auguaucuug aaaugcuugu aaagagguuu   3360
cuaacccacc cucacgaggu gucucucacc cccacacugg gacucgugug gccugugugg   3420
ugccacccug cuggggccuc ccaaguuuug aaaggcuuuc cucagcaccu gggacccaac   3480
agagaccagc uucuagcagc uaaggaggcc guucagcugu gacgaaggcc ugaagcacag   3540
gauuaggacu gaagcgauga uguccccuuc ccuacuuccc cuuggggcuc ccugugucag   3600
ggcacagacu aggucuugug gcuggucugg cuugcggcgc gaggaugguu cucucugguc   3660
auagcccgaa gucucauggc agucccaaag gaggcuuaca acuccugcau cacaagaaaa   3720
aggaagccac ugccagcugg ggggaucugc agcucccaga agcuccguga gccucagcca   3780
ccccucagac uggguuccuc uccaagcucg cccucuggag gggcagcgca gccucccacc   3840
aagggcccug cgaccacagc agggauuggg augaauugcc uguccuggau cugcucuaga   3900
ggcccaagcu gccugccuga ggaaggauga cuugacaagu caggagacac uguucccaaa   3960
gccuugacca gagcaccuca gcccgcugac cuugcacaaa cuccaucugc ugccaugaga   4020
aaagggaagc cgccuuugca aaacauugcu gccuaaagaa acucagcagc cucaggccca   4080
auucugccac uucugguuug gguacaguua aaggcaaccc ugagggacuu ggcaguagaa   4140
auccagggcc uccccugggg cuggcagcuu cgugugcagc uagagcuuua ccugaaagga   4200
agucucuggg cccagaacuc uccaccaaga gccucccugc cguucgcuga gucccagcaa   4260
uucuccuaag uugaagggau cugagaagga gaaggaaaug ugggguagau uuggugguggg   4320
uuagagauau gcccccuca uuacugccaa caguuucggc ugcauuucuu cacgcaccuc   4380
gguuccucuu ccugaaguuc uugugcccug cucuucagca ccaugggccu ucuuauacgg   4440
aaggcucugg gaucuccccc uuguggggca ggcucuuggg gccagccuaa gaucaugguu   4500
uagggugauc agugcuggca gauaaauuga aaaggcacgc uggcuuguga ucuuaaauga   4560
ggacaauccc cccagggcug ggcacuccuc cccuccccuc acuucuccca ccugcagagc   4620
caguguccuu gggugggcua gauaggauau acuguaugcc ggcuccuuca agcugcugac   4680
ucacuuuauc aauaguucca uuuaaauuga cuucaguggu gagacuguau ccuguuugcu   4740
auugcuuguu gugcuauggg gggagggggg aggaaugugu aagauaguua acaugggcaa   4800
agggagaucu uggggugcag cacuuaaacu gccucguaac ccuuuucaug auuucaacca   4860
```

cauuugcuag agggagggag cagccacgga guuagaggcc cuuggggguuu cucuuuucca 4920 cugacaggcu uucccaggca gcuggcuagu ucauucccuc cccagccagg ugcaggcgua 4980
ggaauaugga caucugguug cuuuggccug cugcccucuu ucaggggucc uaagcccaca 5040
aucaugccuc ccuaagaccu uggcauccuu cccucuaagc cguuggcacc ucugugccac 5100
cucucacacu ggcuccagac acacagccug ugcuuuugga gcugagauca cucgcuucac 5160
ccuccucauc uuuguucucc aaguaaagcc acgaggucgg ggcgagggca gaggugauca 5220
ccugcguguc ccaucuacag accugcagcu ucauaaaacu ucugauuucu cuucagcuuu 5280
gaaaaggguu acccugggca cuggccuaga gccucaccuc cuaauagacu uagccccaug 5340
aguuugccau guugagcagg acuauuucug gcacuugcaa gucccaugau uucuucggua 5400
auucugaggg ugggggggagg gacaugaaau caucuuagcu uagcuuucug ucugugaaug 5460
ucuauauagu guauugugug uuuuaacaaa ugauuuacac ugacuguugc uguaaaagug 5520
aauuuggaaa uaaaguuauu acucugauua aa 5552

<210> SEQ ID NO 21
<211> LENGTH: 6644
<212> TYPE: RNA
<213> ORGANISM: Homo sapiens

<400> SEQUENCE: 21
gcagucaccg ccacccacca gcuccggcac caacagcagc gccgcugcca ccgcccaccu 60
ucugccgccg ccaccacagc caccuucucc uccuccgcug uccucucccg uccucgccuc 120
ugucgacuau caggugaacu uugaaccagg auggcugagc ccgccagga guucgaagug 180 auggaagauc acgcugggac guacggguug ggggacagga aagaucaggg gggcuacacc 240
augcaccaag accaagaggg ugacacggac gcuggccuga aagaaucucc ccugcagacc 300
cccacugagg acggaucuga ggaaccgggc ucugaaaccu cugaugcuaa gagcacucca 360
acagcggaag augugacagc acccuuagug gaugagggag cucccggcaa gcaggcugcc 420
gcgcagcccc acacggagau cccagaagga accacagcug aagaagcagg cauuggagac 480
acccccagcc uggaagacga agcugcuggu cacgugaccc aagagccuga aagugguaag 540
gugguccagg aaggcuuccu ccgagagcca ggcccccag gucugagcca ccagcucaug 600
uccggcaugc cuggggcucc ccuccugccu gagggcccca gagaggccac acgccaaccu 660
ucggggacag gaccugagga cacagagggc ggccgccacg ccccugagcu gcucaagcac 720
cagcuucuag gagaccugca ccaggagggg ccgccgcuga agggggcagg gggcaaagag 780
aggccgggga gcaaggagga gguggaugaa gaccgcgacg ucgaugaguc cucccccaa 840 gacuccccuc ccuccaaggc cuccccagcc caagaugggc ggccuccccca gacagccgcc 900 agagaagcca ccagcauccc aggcuuccca gcggagggug ccaucccccu cccuguggau 960
uuccucucca aaguuuccac agagauccca gccucagagc ccgacgggcc caguguaggg 1020
cgggccaaag ggcaggaugc cccccuggag uucacguuuc acguggaaau cacacccaac 1080
gugcagaagg agcaggcgca cucggaggag cauuugggaa gggcugcauu uccaggggcc 1140
ccuggagagg ggccagaggc ccggggcccc ucuuugggag aggacacaaa agaggcugac 1200
cuuccagagc ccucugaaaa gcagccugcu gcugcuccgc gggggaagcc cgucagccgg 1260
gucccucaac ucaaagcucg cauggucagu aaaagcaaag acgggacugg aagcgaugac 1320
aaaaaagcca agacauccac acguuccucu gcuaaaaccu ugaaaaauag gccuugccuu 1380

```
agccccaaac accccacucc ugguagcuca gacccucuga uccaacccuc cagcccugcu   1440
gugugcccag agccaccuuc cucuccuaaa uacgucucuu cugucacuuc ccgaacuggc   1500
aguucuggag caaaggagau gaaacucaag ggggcugaug guaaaacgaa gaucgccaca   1560
ccgcggggag cagccccucc aggccagaag ggccaggcca acgccaccag gauuccagca   1620
aaaaccccgc ccgcuccaaa gacaccaccc agcucugcga cuaagcaagu ccagagaaga   1680
ccacccccug cagggcccag aucugagaga ggugaaccuc caaaaucagg ggaucgcagc   1740
ggcuacagca gccccggcuc ccaggcacu cccggcagcc gcucccgcac cccgucccuu   1800
ccaaccccac ccacccggga gcccaagaag guggcagugg uccguacucc acccaagucg   1860
ccgucuuccg ccaagagccg ccugcagaca gcccccgugc ccaugccaga ccugaagaau   1920
gucaagucca agaucggcuc cacugagaac cugaagcacc agccgggagg cgggaaggug   1980
cagauaauua auaagaagcu ggaucuuagc aacguccagu ccaagugugg cucaaaggau   2040
aauaucaaac acgucccggg aggcggcagu gugcaaauag ucuacaaacc aguugaccug   2100
agcaagguga ccuccaagug uggcucauua ggcaacaucc aucauaaacc aggagguggc   2160
cagguggaag uaaaaucuga gaagcuugac uucaaggaca gaguccaguc gaagauuggg   2220
ucccuggaca auaucaccca cgucccuggc ggaggaaaua aaaagauuga aacccacaag   2280
cugaccuucc gcgagaacgc caaagccaag acagaccacg gggcggagau cguguacaag   2340
ucgccagugg ugucugggga cacgucucca cggcaucuca gcaaugucuc cuccaccggc   2400
agcaucgaca ugguagacuc gccccagcuc gccacgcuag cugacgaggu gucugccucc   2460
cuggccaagc aggguuugug aucaggcccc uggggcgguc aauaauugug gagaggagag   2520
aaugagagag uguggaaaaa aaaagaauaa ugacccggcc cccgcccucu gcccccagcu   2580
gcuccucgca guucgguuaa uugguuaauc acuuaaccug cuuuugucac ucggcuuugg   2640
cucgggacuu caaaaucagu gaugggagua agagcaaauu ucaucuuucc aaauugaugg   2700
gugggcuagu aauaaaauau uuaaaaaaaa acauucaaaa acauggccac auccaacauu   2760
uccucaggca auuccuuuug auucuuuuuu cuucccccuc cauguagaag agggagaagg   2820
agaggcucug aaagcugcuu cugggggauu ucaagggacu gggggugcca accaccucug   2880
gcccuguugu ggggguguca cagaggcagu ggcagcaaca aaggauuuga aacuuggugu   2940
guucguggag ccacaggcag acgaugucaa ccuuguguga gugugacggg gguuggggug   3000
gggcgggagg ccacgggga ggccgaggca ggggcugggc agaggggaga ggaagcacaa   3060
gaagugggag ugggagagga agccacgugc uggagaguag acauccccu ccuugccgcu   3120
gggagagcca aggccuaugc caccugcagc gucugagcgg ccgccugucc uugguggccg   3180
gggguggggg ccugcugugg gucagugugc cacccucugc agggcagccu gugggagaag   3240
ggacagcggg uaaaaagaga aggcaagcug gcaggagggu ggcacuucgu ggaugaccuc   3300
cuuagaaaag acugaccuug augucuugag agcgcuggcc ucuucccucc ucccugcagg   3360
guaggggcc ugaguugagg ggcuucccuc ugcuccacag aaacccuguu uuauugaguu   3420
cugaagguug gaacugcugc caugauuuug gccacuuugc agaccuggga cuuuagggcu   3480
aaccaguucu cuuuguaagg acuugugccu cuugggagac guccacccgu uuccaagccu   3540
gggccacugg caucucugga gugugugggg gucugggagg caggucccga gcccccuguc   3600
cuucccacgg ccacugcagu caccccgucu gcgccgcugu gcuguugucu gccgugagag   3660
cccaaucacu gccuauaccc cucaucacac gucacaaugu cccgaauucc cagccucacc   3720
accccuucuc aguaaugacc cugguugguu gcaggaggua ccuacuccau acugagggug   3780
```

```
aaauuaaggg aaggcaaagu ccaggcacaa gagugggacc ccagccucuc acucucaguu   3840
ccacucaucc aacugggacc cucaccacga aucucaugau cugauucggu ucccugucuc   3900
cuccucccgu cacagaugug agccagggca cugcucagcu gugacccuag guguuucugc   3960
cuuguugaca uggagagagc ccuuuccccu gagaaggccu ggccccuucc ugugcugagc   4020
ccacagcagc aggcugggug ucuugguugu caguggugge accaggaugg aagggcaagg   4080
cacccagggc aggcccacag ucccgcuguc ccccacuugc acccuagcuu guagcugcca   4140
accucccaga cagcccagcc cgcugcucag cuccacaugc auaguaucag cccuccacac   4200
ccgacaaagg ggaacacacc cccuuggaaa ugguucuuuu cccccagucc cagcuggaag   4260
ccaugcuguc uguucugcug gagcagcuga acauauacau agauguugcc cugccucccc   4320
caucugcacc cuguugaguu guaguuggau uugucuguuu augcuuggau ucaccagagu   4380
gacuaugaua gugaaaagaa aaaaaaaaaa aaaaaaggac gcauguaucu ugaaaugcuu   4440
guaaagaggu uucuaaccca cccucacgag gugucucuca cccccacacu gggacucgug   4500
uggccugugu ggugccaccc ugcuggggcc ucccaaguuu ugaaaggcuu uccucagcac   4560
cugggaccca acagagacca gcuucuagca gcuaaggagg ccguucagcu gugacgaagg   4620
ccugaagcac aggauuagga cugaagcgau gauguccccu ucccuacuuc cccuuggggc   4680
ucccuguguc agggcacaga cuaggucuug uggcuggucu ggcuugcggc gcgaggaugg   4740
uucucucugg ucauagcccg aagucucaug gcagucccaa aggaggcuua caacuccugc   4800
aucacaagaa aaaggaagcc acugccagcu ggggggaucu gcagcuccca gaagcuccgu   4860
gagccucagc caccccucag acuggguucc ucuccaagcu cgcccucugg aggggcagcg   4920
cagccuccca ccaagggccc ugcgaccaca gcagggauug ggaugaauug ccuguccugg   4980
aucugcucua gaggcccaag cugccugccu gaggaaggau gacuugacaa gucaggagac   5040
acuguuccca aagccuugac cagagcaccu cagcccgcug accuugcaca aacuccaucu   5100
gcugccauga gaaaagggaa gccgccuuug caaaacauug cugccuaaag aaacucagca   5160
gccucaggcc caauucugcc acuucugguu uggguacagu uaaaggcaac ccugagggac   5220
uuggcaguag aaauccaggg ccuccccugg ggcuggcagc uucgugugca gcuagagcuu   5280
uaccugaaag gaagucucug ggcccagaac ucuccaccaa gagccucccu gccguucgcu   5340
gagucccagc aauucuccua aguugaaggg aucugagaag gagaaggaaa uguggggguag   5400
auuuggugggu gguuagagau augccccccu cauuacugcc aacaguuucg gcugcauuuc   5460
uucacgcacc ucgguuccuc uuccugaagu ucuugugccc ugcucuucag caccaugggc   5520
cuucuuauac ggaaggcucu gggaucuccc ccuugugggg caggcucuug gggccagccu   5580
aagaucaugg uuuaggguga ucagugcugg cagauaaauu gaaaaggcac gcuggcuugu   5640
gaucuuaaau gaggacaauc cccccagggc ugggcacucc ucccccuccc ucacuucucc   5700
caccugcaga gccagugucc uuggguggge uagauaggau auacuguaug ccggcuccuu   5760
caagcugcug acucacuuua ucaauaguuc cauuuaaauu gacuucagug gugagacugu   5820
auccuguuug cuauugcuug uugugcuaug gggggagggg ggaggaaugu guaagauagu   5880
uaacaugggc aaagggagau cuugggggugc agcacuuaaa cugccucgua acccuuuuca   5940
ugauuucaac cacauuugcu agagggaggg agcagccacg gaguuagagg cccuuggggu   6000
uucucuuuuc cacugacagg cuuucccagg cagcuggcua guucauuccc uccccagcca   6060
ggugcaggcg uaggaauaug gacaucuggu ugcuuuggcc ugcugcccuc uuucaggggu   6120
```

ccuaagccca caaucaugcc ucccuaagac cuuggcaucc uucccucuaa gccguuggca 6180
ccucugugcc accucucaca cuggcuccag acacacagcc ugugcuuuug gagcugagau 6240
cacucgcuuc acccuccuca ucuuuguucu ccaaguaaag ccacgagguc ggggcgaggg 6300
cagaggugau caccugcgug ucccaucuac agaccugcag cuucauaaaa cuucugauuu 6360
cucuucagcu uugaaaaggg uuacccuggg cacuggccua gagccucacc uccuaauaga 6420
cuuagcccca ugaguuugcc auguugagca ggacuauuuc uggcacuugc aagucccaug 6480
auuucuucgg uaauucugag ggugggggga gggacaugaa aucaucuuag cuuagcuuuc 6540
ugucugugaa ugucuauaua guguauugug uguuuuaaca aaugauuuac acugacuguu 6600
gcuguaaaag ugaauuugga aauaaaguua uuacucugau uaaa 6644

<210> SEQ ID NO 22
<211> LENGTH: 5459
<212> TYPE: RNA
<213> ORGANISM: Homo sapiens

<400> SEQUENCE: 22
gcagucaccg ccacccacca gcuccggcac caacagcagc gccgcugcca ccgcccaccu 60
ucugccgccg ccaccacagc caccuucucc ucccuccgcug uccucucccg uccucgccuc 120
ugucgacuau caggugaacu uugaaccagg auggcugagc cccgccagga guucgaagug 180
auggaagauc acgcugggac guacggguug ggggacagga aagaucaggg gggcuacacc 240
augcaccaag accaagaggg ugacacggac gcuggccuga aagaaucucc ccugcagacc 300
cccacugagg acggaucuga ggaaccgggc ucugaaaccu cugaugcuaa gagcacucca 360
acagcggaag cugaagaagc aggcauugga gacacccccca gccuggaaga cgaagcugcu 420
ggucacguga cccaagcucg cauggucagu aaaagcaaag acgggacugg aagcgaugac 480
aaaaaagcca agggggcuga ugguaaaacg aagaucgcca caccgcgggg agcagccccu 540
ccaggccaga agggccaggc caacgccacc aggauuccag caaaaacccc gcccgcucca 600
aagacaccac ccagcucugg ugaaccucca aaaucagggg aucgcagcgg cuacagcagc 660
cccggcuccc caggcacucc cggcagccgc ucccgcaccc cgucccuucc aaccccaccc 720
acccgggagc ccaagaaggu ggcagugguc cguacuccac ccaagucgcc gucuuccgcc 780
aagagccgcc ugcagacagc ccccgugccc augccagacc ugaagaaugu caaguccaag 840
aucggcucca cugagaaccu gaagcaccag ccgggaggcg ggaaggugca aauagucuac 900
aaaccaguug accugagcaa ggugaccucc aaguguggcu cauuaggcaa cauccaucau 960
aaaccaggag guggccaggu ggaaguaaaa ucugagaagc uugacuucaa ggacagaguc 1020
cagucgaaga uugggucccu ggacaauauc acccacgucc cuggcggagg aaauaaaaag 1080
auugaaaccc acaagcugac cuuccgcgag aacgccaaag ccaagacaga ccacggggcg 1140
gagaucgugu acaagucgcc aguggugucu ggggacacgu cuccacggca ucucagcaau 1200
gucuccucca ccggcagcau cgacauggua gacucgcccc agcucgccac gcuagcugac 1260
gaggugucug ccucccuggc caagcagggu uugugaucag gccccugggg cggucaauaa 1320
uuguggagag gagagaauga gagagugugg aaaaaaaaag aauaaugacc cggcccccgc 1380
ccucugcccc cagcugcucc ucgcaguucg guuaauuggu uaaucacuua accugcuuuu 1440
gucacucggc uuuggcucgg gacuucaaaa ucagugaugg gaguaagagc aaauuucauc 1500
uuuccaaauu gaugggaggg cuaguaauaa aauauuuaaa aaaaaacauu caaaaacaug 1560
gccacaucca acauuuccuc aggcaauucc uuuugauucu uuuucuuccc cccuccaugu 1620

-continued

```
agaagaggga gaaggagagg cucugaaagc ugcuucuggg ggauuucaag ggacuggggg   1680
ugccaaccac cucuggcccu guuguggggg ugucacagag gcaguggcag caacaaagga   1740
uuugaaacuu ggugugu ucg uggagccaca ggcagacgau gucaaccuug ugugagugug   1800
acgggggguug gggugggcg ggaggccacg ggggaggccg aggcaggggc ugggcagagg   1860
ggagaggaag cacaagaagu gggaguggga gaggaagcca cgugcuggag aguagacauc   1920
ccccuccuug ccgcugggag agccaaggcc uaugccaccu gcagcgucug agcggccgcc   1980
uguccuuggu ggccgggggu gggggccugc ugugggucag ugugccaccc ucugcagggc   2040
agccuguggg agaagggaca gcggguaaaa agagaaggca agcuggcagg agggugcac   2100
uucguggaug accuccuuag aaaagacuga ccuugauguc uugagagcgc uggccucuuc   2160
cucccucccu gcaggguagg gggccugagu ugaggggcuu cccucugcuc cacagaaacc   2220
cuguuuuauu gaguucugaa gguuggaacu gcugccauga uuuuggccac uuugcagacc   2280
ugggacuuua gggcuaacca guucucuuug uaaggacuug ugccucuugg gagacgucca   2340
cccguuucca agccugggcc acuggcaucu cuggagugug ugggggucug ggaggcaggu   2400
cccgagcccc cuguccuucc cacggccacu gcagucaccc cgucugcgcc gcugugcugu   2460
ugucugccgu gagagcccaa ucacugccua uaccccucau cacacgucac aaugucccga   2520
auucccagcc ucaccacccc uucucaguaa ugacccuggu ugguugcagg agguaccuac   2580
uccauacuga gggugaaauu aagggaaggc aaaguccagg cacaagagug ggaccccagc   2640
cucucacucu caguuccacu cauccaacug ggacccucac cacgaaucuc augaucugau   2700
ucgguucccu gucuccuccu cccgucacag augugagcca gggcacugcu cagcugugac   2760
ccuagguguu ucugccuugu ugacauggag agagcccuuu ccccugagaa ggccuggccc   2820
cuuccugugc ugagcccaca gcagcaggcu gggugucuug guugucagug guggcaccag   2880
gauggaaggg caaggcaccc agggcaggcc cacagucccg cugucccccca cuugcacccu   2940
agcuuguagc ugccaaccuc ccagacagcc cagcccgcug cucagcucca caugcauagu   3000
aucagcccuc cacacccgac aaaggggaac acacccccuu ggaaaugguu cuuuucccc   3060
agucccagcu ggaagccaug cugucuguuc ugcuggagca gcugaacaua uacauagaug   3120
uugcccugcc cuccccaucu gcacccuguu gaguuguagu uggauuuguc uguuuaugcu   3180
uggauucacc agagugacua ugauagugaa aagaaaaaaa aaaaaaaaaa aggacgcaug   3240
uaucuugaaa ugcuuguaaa gagguuucua acccacccuc acgaggugc ucucaccccc   3300
acacugggac ucguguggcc uguguggugc cacccugcug gggccuccca aguuuugaaa   3360
ggcuuuccuc agcaccuggg acccaacaga gaccagcuuc uagcagcuaa ggaggccguu   3420
cagcugugac gaaggccuga agcacaggau uaggacugaa gcgaugaugu ccccuucccu   3480
acuuccccuu ggggcucccu gugucagggc acagacuagg ucuuguggcu ggucuggcuu   3540
gcggcgcgag gaugguucuc ucuggucaua gcccgaaguc ucauggcagu cccaaaggag   3600
gcuuacaacu ccugcaucac aagaaaaagg aagccacugc cagcuggggg gaucugcagc   3660
ucccagaagc uccgugagcc ucagccaccc cucagacugg guuccucucc aagcucgccc   3720
ucuggagggg cagcgcagcc ucccaccaag ggcccugcga ccacagcagg gauugggaug   3780
aauugccugu ccuggaucug cucuagaggc ccaagcugcc ugccugagga aggaugacuu   3840
gacaagucag gagacacugu ucccaaagcc uugaccagag caccucagcc cgcugaccuu   3900
gcacaaacuc caucugcugc caugagaaaa gggaagccgc cuuugcaaaa cauugcugcc   3960
```

uaaagaaacu cagcagccuc aggcccaauu cugccacuuc ugguuugggu acaguuaaag 4020
gcaacccuga gggacuuggc aguagaaauc cagggccucc ccuggggcug gcagcuucgu 4080
gugcagcuag agcuuuaccu gaaaggaagu cucugggccc agaacucucc accaagagcc 4140
ucccugccgu ucgcugaguc ccagcaauuc uccuaaguug aagggaucug agaaggagaa 4200
ggaaaugugg gguagauuug guggugguua gagauaugcc ccccucauua cugccaacag 4260
uuucggcugc auuucuucac gcaccucggu ucccucuuccu gaaguucuug ugcccugcuc 4320
uucagcacca ugggccuucu uauacggaag gcucugggau cucccccuug uggggcaggc 4380
ucuuggggcc agccuaagau caugguuuag ggugaucagu gcuggcagau aaauugaaaa 4440
ggcacgcugg cuugugaucu uaaaugagga caaucccccc agggcugggc acuccucccc 4500
uccccucacu ucucccaccu gcagagccag uguccuuggg ugggcuagau aggauauacu 4560
guaugccggc uccuucaagc ugcugacuca cuuuaucaau aguuccauuu aaauugacuu 4620
caguggugag acuguauccu guuugcuauu gcuuguugug cuaugggggg aggggggagg 4680
aauguguaag auaguuaaca ugggcaaagg gagaucuugg ggugcagcac uuaaacugcc 4740
ucguaacccu uuucaugauu ucaaccacau uugcuagagg gagggagcag ccacggaguu 4800
agaggcccuu gggguuucuc uuuuccacug acaggcuuuc ccaggcagcu ggcuaguuca 4860
uucccucccc agccaggugc aggcguagga auauggacau cugguugcuu uggccugcug 4920
cccucuuuca ggggucc uaa gcccacaauc augccucccu aagaccuugg cauccuuccc 4980
ucuaagccgu uggcaccucu gugccaccuc ucacacuggc uccagacaca cagccugugc 5040
uuuuggagcu gagaucacuc gcuucacccu ccucaucuuu guucuccaag uaaagccacg 5100
aggucggggc gagggcagag gugaucaccu gcguguccca ucuacagacc ugcagcuuca 5160
uaaaacuucu gauuucucuu cagcuuugaa aaggguuacc cugggcacug gccuagagcc 5220
ucaccuccua auagacuuag ccccaugagu uugccauguu gagcaggacu auuucuggca 5280
cuugcaaguc ccaugauuuc uucgguaauu cugagggugg ggggagggac augaaaucau 5340
cuuagcuuag cuuucugucu gugaaugucu auauagugua uuguguguuu uaacaaauga 5400
uuuacacuga cuguugcugu aaaagugaau uuggaaauaa aguuauuacu cugauuaaa 5459

<210> SEQ ID NO 23
<211> LENGTH: 5546
<212> TYPE: RNA
<213> ORGANISM: Homo sapiens

<400> SEQUENCE: 23
gcagucaccg ccacccacca gcuccggcac caacagcagc gccgcugcca ccgcccaccu 60
ucugccgccg ccaccacagc caccuucucc uccuccgcug uccucucccg uccucgccuc 120
ugucgacuau cagguguaacu uugaaccagg auggcugagc cccgccagga guucgaagug 180
auggaagauc acgcugggac guacggguug ggggacagga aagaucaggg gggcuacacc 240
augcaccaag accaagaggg ugacacggac gcuggccuga aagaaucucc ccugcagacc 300
cccacugagg acggaucuga ggaaccgggc ucugaaaccu cugaugcuaa gagcacucca 360
acagcggaag augugacagc acccuuagug gaugagggag cucccggcaa gcaggcugcc 420
gcgcagcccc acacggagau cccagaagga accacagcug aagaagcagg cauuggagac 480 accccccagcc uggaagacga agcugcuggu cacgugaccc aagcucgcau ggucaguaaa 540
agcaaagacg ggacuggaag cgaugacaaa aaagccaagg gggcugaugg uaaaacgaag 600
aucgccacac cgcggggagc agccccucca ggccagaagg gccaggccaa cgccaccagg 660

-continued

```
auuccagcaa aaaccccgcc cgcuccaaag acaccaccca gcucugguga accuccaaaa    720
ucaggggauc gcagcggcua cagcagcccc ggcuccccag gcacuccegg cagccgcucc    780
cgcaccccgu cccuuccaac cccacccacc cgggagccca agaaggugge aguggucegu    840
acuccaccca agucgccguc uuccgccaag agccgccugc agacagcccc cgugcccaug    900
ccagaccuga agaaugucaa guccaagauc ggcuccacug agaaccugaa gcaccagccg    960
ggaggcggga aggugcaaau agucuacaaa ccaguugacc ugagcaaggu gaccuccaag   1020
uguggcucau uaggcaacau ccaucauaaa ccaggaggug gccaggugga aguaaaaucu   1080
gagaagcuug acuucaagga cagaguccag ucgaagauug ggucccugga caauaucacc   1140
cacgucccug gcggaggaaa uaaaaagauu gaaacccaca agcugaccuu ccgcgagaac   1200
gccaaagcca agacagacca cggggcggag aucguguaca agucgccagu ggugucuggg   1260
gacacgucuc cacggcaucu cagcaauguc uccuccaccg gcagcaucga caugguagac   1320
ucgccccagc ucgccacgcu agcugacgag gugucugccu cccuggccaa gcaggguuug   1380
ugaucaggcc ccuggggcgg ucaauaauug uggagaggag agaaugagag aguguggaaa   1440
aaaaaagaau aaugacccgg cccccgcccu cugcccccag cugcuccucg caguucgguu   1500
aauugguuaa ucacuuaacc ugcuuuuguc acucggcuuu ggcucgggac uucaaaauca   1560
gugaugggag uaagagcaaa uuucaucuuu ccaaauugau gggugggcua guaauaaaau   1620
auuuaaaaaa aaacauucaa aaacauggcc acauccaaca uuuccucagg caauuccuuu   1680
ugauucuuuu uucuuccccc uccauguaga agagggagaa ggagaggcuc ugaaagcugc   1740
uucuggggga uuucaaggga cugggggugc caaccaccuc uggcccuguu gugggggugu   1800
cacagaggca guggcagcaa caaaggauuu gaaacuuggu guguucgugg agccacaggc   1860
agacgauguc aaccuugugu gagugugacg gggguugggg uggggcggga ggccacgggg   1920
gaggccgagg caggggcugg gcagagggga gaggaagcac aagaaguggg agugggagag   1980
gaagccacgu gcuggagagu agacaucccc cuccuugccg cugggagagc caaggccuau   2040
gccaccugca gcgucugagc ggccgccugu ccuuggugge cgggggugggg ggccugcugu   2100
gggucagugu gccacccucu gcagggcagc cugugggaga agggacagcg gguaaaaaga   2160
gaaggcaagc uggcaggagg guggcacuuc guggaugacc uccuuagaaa agacugaccu   2220
ugaugucuug agagcgcugg ccucuuccuc ccucccugca ggguaggggg ccugaguuga   2280
ggggcuuccc ucugcuccac agaaacccug uuuuauugag uucugaaggu uggaacugcu   2340
gccaugauuu uggccacuuu gcagaccugg gacuuuaggg cuaaccaguu cucuuuguaa   2400
ggacuugugc cucuugggag acguccaccc guuuccaagc cugggccacu ggcaucucug   2460
gagugugugg gggucuggga ggcagguccc gagcccccug uccuucccac ggccacugca   2520
gucaccccgu cugcgccgcu gugcuguugu cugccgugag agcccaauca cugccuauac   2580
cccucaucac acgucacaau gucccgaauu cccagccuca ccaccccuuc ucaguaauga   2640
cccugguugg uugcaggagg uaccuacucc auacugaggg ugaaauuaag ggaaggcaaa   2700
guccaggcac aagaguggga ccccagccuc ucacucucag uuccacucau ccaacuggga   2760
cccucaccac gaaucucaug aucugauucg guucccuguc uccuccuccc gucacagaug   2820
ugagccaggg cacugcucag cugugacccu agguguuucu gccuuguuga cauggagaga   2880
gcccuuuccc cugagaaggc cuggccccuu ccugugcuga gcccacagca gcaggcuggg   2940
ugucuugguu gucagugug gcaccaggau ggaagggcaa ggcacccagg gcaggcccac   3000
```

-continued

```
agucccgcug ucccccacuu gcacccuagc uuguagcugc caaccuccca gacagcccag   3060
cccgcugcuc agcuccacau gcauaguauc agcccuccac acccgacaaa ggggaacaca   3120
cccccuugga aaugguucuu uucccccagu cccagcugga agccaugcug ucuguucugc   3180
uggagcagcu gaacauauac auagauguug cccugcccuc cccaucugca cccuguugag   3240
uuguaguugg auuugucugu uuaugcuugg auucaccaga gugacuauga uagugaaaag   3300
aaaaaaaaaa aaaaaaaagg acgcauguau cuugaaaugc uuguaaagag guuucuaacc   3360
cacccucacg aggugucucu cacccccaca cugggacucg uguggccugu guggugccac   3420
ccugcugggg ccucccaagu uuugaaaggc uuuccucagc accugggacc caacagagac   3480
cagcuucuag cagcuaagga ggccguucag cugugacgaa ggccugaagc acaggauuag   3540
gacugaagcg augauguccc cuucccuacu uccccuuggg gcucccugug ucagggcaca   3600
gacuaggucu uguggcuggu cuggcuugcg gcgcgaggau gguucucucu ggucauagcc   3660
cgaagucuca uggcaguccc aaaggaggcu uacaacuccu gcaucacaag aaaaaggaag   3720
ccacugccag cugggggau cugcagcucc cagaagcucc gugagccuca gccaccccuc    3780
agacuggguu ccucuccaag cucgcccucu ggaggggcag cgcagccucc caccaagggc   3840
ccugcgacca cagcagggau uggaugaau ugccuguccu ggaucugcuc uagaggccca    3900
agcugccugc cugaggaagg augacuugac aagucaggag acacuguucc caaagccuug   3960
accagagcac cucagcccgc ugaccuugca caaacuccau cugcugccau gagaaaaggg   4020
aagccgccuu ugcaaaacau ugcugccuaa agaaacucag cagccucagg cccaauucug   4080
ccacuucugg uuuggguaca guuaaaggca acccugaggg acuuggcagu agaaauccag   4140
ggccuccccu ggggcuggca gcuucgugug cagcuagagc uuuaccugaa aggaagucuc   4200
ugggcccaga acucuccacc aagagccucc cugccguucg cugaguccca gcaauucucc   4260
uaaguugaag ggaucugaga aggagaagga aauguggggu agauuuggug gugguuagag   4320
auaugccccc cucauuacug ccaacaguuu cggcugcauu ucuucacgca ccucgguucc   4380
ucuuccugaa guucuugugc ccugcucuuc agcaccaugg gccuucuuau acggaaggcu   4440
cugggaucuc ccccuugugg ggcaggcucu uggggccagc cuaagaucau gguuuagggu   4500
gaucagugcu ggcagauaaa uugaaaaggc acgcuggcuu gugaucuuaa augaggacaa   4560
uccccccagg gcugggcacu ccucccccucc ccucacuucu cccaccugca gagccagugu  4620
ccuuggguggg gcuagauagg auauacugua ugccggcucc uucaagcugc ugacucacuu  4680
uaucaauagu uccauuuaaa uugacuucag uggugagacu guauccuguu ugcuauugcu   4740
uguugugcua ugggggggagg ggggaggaau guguaagaua guuaacaugg gcaaagggag  4800
aucuuggggu gcagcacuua aacugccucg uaacccuuuu caugauuuca accacauuug   4860
cuagagggag ggagcagcca cggaguuaga ggcccuuggg guuucucuuu uccacugaca   4920
ggcuuuccca ggcagcuggc uaguucauuc ccucccccagc caggugcagg cguaggaaua  4980
uggacaucug guugcuuugg ccugcugccc ucuuucaggg guccuaagcc cacaaucaug   5040
ccucccuaag accuuggcau ccuucccucu aagccguugg caccucugug ccaccucuca   5100
cacuggcucc agacacacag ccugugcuuu uggagcugag aucacucgcu ucacccuccu   5160
caucuuuguu cuccaaguaa agccacgagg ucggggcgag ggcagaggug aucaccugcg   5220
ugucccaucu acagaccugc agcuucauaa aacuucugau uucucuucag cuuugaaaag   5280
gguuacccug ggcacuggcc uagagccuca ccuccuaaua gacuuagccc caugaguuug   5340
ccauguugag caggacuauu ucuggcacuu gcaagucccca ugauuucuuc gguaauucug  5400
```

agggugggggg gagggacaug aaaucaucuu agcuuagcuu ucugucugug aaugucuaua 5460
uaguguauug uguguuuuaa caaaugauuu acacugacug uugcuguaaa agugaauuug 5520
gaaauaaagu uauuacucug auuaaa 5546

<210> SEQ ID NO 24
<211> LENGTH: 6815
<212> TYPE: RNA
<213> ORGANISM: Homo sapiens

<400> SEQUENCE: 24
gcagucaccg ccacccacca gcuccggcac caacagcagc gccgcugcca ccgcccaccu 60
ucugccgccg ccaccacagc caccuucucc uccuccgcug ucccucuccg uccucgccuc 120
ugucgacuau caggugaacu uugaaccagg auggcugagc ccgccagga guucgaagug 180 auggaagauc acgcugggac guacggguug ggggacagga aagaucaggg gggcuacacc 240
augcaccaag accaagaggg ugacacggac gcuggccuga aagaaucucc ccugcagacc 300
cccacugagg acggaucuga ggaaccgggc ucugaaaccu cugaugcuaa gagcacucca 360
acagcggaag cugaagaagc aggcauugga gacaccccca gccuggaaga cgaagcugcu 420
ggucacguga cccaagagga guugagaguu ccgggccggc agaggaaggc gccugaaagg 480
ccccuggcca augagauuag cgcccacguc cagccuggac ccugcggaga ggccucuggg 540
gucucugggc cgugccucgg ggagaaagag ccagaagcuc ccgucccgcu gaccgcgagc 600
cuuccucagc accgucccgu uugcccagcg ccuccuccaa caggaggccc ucaggagccc 660
ucccuggagu ggggacaaaa aggcggggac ugggccgaga aggguccggc cuuuccgaag 720
cccgccacca cugcguaucu ccacacagag ccugaaagug guaaggugguccaggaaggc 780 uuccuccgag agccaggccc cccaggucug agccaccagc ucauguccgg caugccuggg 840
gcuccccucc ugccugaggg ccccagagag gccacacgcc aaccuucggg gacaggaccu 900
gaggacacag agggcggccg ccacgccccu gagcugcuca agcaccagcu ucuaggagac 960
cugcaccagg aggggccgcc gcugaagggg gcagggggca aagagaggcc ggggagcaag 1020
gaggaggugg augaagaccg cgacgucgau gaguccuccc cccaagacuc cccucccucc 1080
aaggccuccc cagcccaaga ugggcggccu ccccagacag ccgccagaga agccaccagc 1140
aucccaggcu ucccagcgga gggugccauc cccucccug uggauuuccu cuccaaaguu 1200
uccacagaga ucccagccuc agagcccgac gggcccagug uagggcgggc caaagggcag 1260 gaugccccccc uggaguucac guuucacgug gaaaucacac ccaacgugca gaaggagcag 1320
gcgcacucgg aggagcauuu gggaagggcu gcauuuccag gggccccugg agaggggcca 1380
gaggcccggg gccccucuuu gggagaggac acaaaagagg cugaccuucc agagcccucu 1440
gaaaagcagc cugcugcugc uccgcggggg aagcccguca gccggguccc ucaacucaaa 1500
gcucgcaugg ucaguaaaag caaagacggg acuggaagcg augacaaaaa agccaagaca 1560
uccacacguu ccucugcuaa aaccuugaaa aauaggccuu gccuuagccc caaacacccc 1620
acuccuggua gcucagaccc ucugauccaa cccuccagcc cugcugugug cccagagcca 1680
ccuuccucuc cuaaauacgu cucuucuguc acuucccgaa cuggcaguuc uggagcaaag 1740
gagaugaaac ucaagggggc ugaugguaaa acgaagaucg ccacaccgcg gggagcagcc 1800
ccuccaggcc agaagggcca ggccaacgcc accaggauuc cagcaaaaac cccgcccgcu 1860
ccaaagacac cacccagcuc uggugaaccu ccaaaaucag gggaucgcag cggcuacagc 1920

-continued agccccggcu ccccaggcac ucccggcagc cgcucccgca ccccgucccu uccaacccca 1980
cccacccggg agcccaagaa gguggcagug guccguacuc cacccaaguc gccgucuucc 2040
gccaagagcc gccugcagac agcccccgug cccaugccag accugaagaa ugucaagucc 2100
aagaucggcu ccacugagaa ccugaagcac cagccgggag gcgggaaggu gcagauaauu 2160
aauaagaagc uggaucuuag caacguccag uccaagugug gcucaaagga uaauaucaaa 2220
cacgucccgg gaggcggcag ugugcaaaua gucuacaaac caguugaccu gagcaaggug 2280
accuccaagu guggcucauu aggcaacauc caucauaaac caggaggugg ccagguggaa 2340
guaaaaucug agaagcuuga cuucaaggac agaguccagu cgaagauugg gucccuggac 2400
aauaucaccc acgucccugg cggaggaaau aaaaagauug aaacccacaa gcugaccuuc 2460
cgcgagaacg ccaaagccaa gacagaccac ggggcggaga ucguguacaa gucgccagug 2520
gugucugggg acacgucucc acggcaucuc agcaaugucu ccuccaccgg cagcaucgac 2580
augguagacu cgccccagcu cgccacgcua gcugacgagg ugucugccuc ccuggccaag 2640
cagggguugu gaucaggccc cuggggcggu caauaauugu ggagaggaga gaaugagaga 2700
guguggaaaa aaaaagaaua augacccggc ccccgcccuc ugcccccagc ugcuccucgc 2760
aguucgguua auugguuaau cacuuaaccu gcuuuuguca cucggcuuug gcucgggacu 2820
ucaaaaucag ugaugggagu aagagcaaau uucaucuuuc caaauugaug ggugggcuag 2880
uaauaaaaua uuuaaaaaaa aacauucaaa aacauggcca cauccaacau uuccucaggc 2940
aauuccuuuu gauucuuuuu ucuucccccu ccauguagaa gagggagaag gagaggcucu 3000
gaaagcugcu ucugggggau uucaagggac ugggggugcc aaccaccucu ggcccuguug 3060
ugggggugucacagaggcag uggcagcaac aaaggauuug aaacuuggug uguucgugga 3120
gccacaggca gacgauguca accuugugug agugugacgg ggguuggggu ggggcgggag 3180
gccacggggg aggccgaggc aggggcuggg cagaggggag aggaagcaca agaaguggga 3240
gugggagagg aagccacgug cuggagagua gacauccccc uccuugccgc ugggagagcc 3300
aaggccuaug ccaccugcag cgucugagcg gccgccuguc cuugguggcc gggggugggg 3360
gccugcugug ggucagugug ccacccucug cagggcagcc ugugggagaa gggacagcgg 3420
guaaaaagag aaggcaagcu ggcaggaggg uggcacuucg uggaugaccu ccuuagaaaa 3480
gacugaccuu gaugucuuga gagcgcuggc cucuuccucc cucccugcag gguagggggc 3540
cugaguugag ggcuucccu cugcuccaca gaaacccugu uuuauugagu ucugaagguu 3600
ggaacugcug ccaugauuuu ggccacuuug cagaccuggg acuuuagggc uaaccaguuc 3660
ucuuuguaag gacuugugcc ucuugggaga cguccacccg uuuccaagcc ugggccacug 3720
gcaucucugg agugugugg ggucugggag gcaggucccg agcccccugu ccuucccacg 3780
gccacugcag ucaccccguc ugcgccgcug ugcuguugucugccgugaga gcccaaucac 3840
ugccuauacc ccucaucaca cgucacaaug ucccgaauuc ccagccucac caccccuucu 3900
caguaaugac ccugguuggu ugcaggaggu accuacucca uacugagggu gaaauuaagg 3960
gaaggcaaag uccaggcaca agagugggac cccagccucu cacucucagu uccacucauc 4020
caacugggac ccucaccacg aaucucauga ucugauucgg uucccugucu ccuccucccg 4080
ucacagaugu gagccagggc acugcucagc ugugacccua gguguuucug ccuuguugac 4140
auggagagag cccuuucccc ugagaaggcc uggccccuuc cugugcugag cccacagcag 4200
caggcugggu gucuugguug ucaguggugg caccaggaug gaagggcaag gcacccaggg 4260
caggcccaca gucccgcugu cccccacuug cacccuagcu uguagcugcc aaccucccag 4320

```
acagcccagc ccgcugcuca gcuccacaug cauaguauca gcccuccaca cccgacaaag   4380
gggaacacac ccccuuggaa augguucuuu ucccccaguc ccagcuggaa gccaugcugu   4440
cuguucugcu ggagcagcug aacauauaca uagauguugc ccugcccucc ccaucugcac   4500
ccuguugagu uguaguugga uuugucuguu uaugcuugga uucaccagag ugacuaugau   4560
agugaaaaga aaaaaaaaaa aaaaaaagga cgcauguauc uugaaaugcu uguaaagagg   4620
uuucuaaccc acccucacga ggugucucuc acccccacac ugggacucgu guggccugug   4680
uggugccacc cugcuggggc cucccaaguu uugaaaggcu uuccucagca ccugggaccc   4740
aacagagacc agcuucuagc agcuaaggag gccguucagc ugugacgaag gccugaagca   4800
caggauuagg acugaagcga ugaugucccc uucccuacuu ccccuugggg cucccugugu   4860
cagggcacag acuaggucuu guggcugguc uggcuugcgg cgcgaggaug guucucucug   4920
gucauagccc gaagucucau ggcaguccca aaggaggcuu acaacuccug caucacaaga   4980
aaaaggaagc cacugccagc ugggggggauc ugcagcuccc agaagcuccg ugagccucag   5040
ccaccccuca gacuggguuc cucuccaagc ucgcccucug gaggggcagc gcagccuccc   5100
accaagggcc cugcgaccac agcagggauu gggaugaauu gccuguccug gaucugcucu   5160
agaggcccaa gcugccugcc ugaggaagga ugacuugaca agucaggaga cacuguuccc   5220
aaagccuuga ccagagcacc ucagcccgcu gaccuugcac aaacuccauc ugcugccaug   5280
agaaaaggga agccgccuuu gcaaaacauu gcugccuaaa gaaacucagc agccucaggc   5340
ccaauucugc cacuucuggu uuggguacag uuaaaggcaa cccugaggga cuuggcagua   5400
gaaauccagg gccuccccug gggcuggcag cuucgugugc agcuagagcu uuaccugaaa   5460
ggaagucucu gggcccagaa cucuccacca agagccuccc ugccguucgc ugagucccag   5520
caauucuccu aaguugaagg gaucugagaa ggagaaggaa augugggua gauuuggugg   5580
ugguuagaga uaugcccccc ucauuacugc caacaguuuc ggcugcauuu cuucacgcac   5640
cucgguuccu cuuccugaag uucuugugcc cugcucuuca gcaccauggg ccuucuuaua   5700
cggaaggcuc ugggaucucc ccuuguggg gcaggcucuu ggggccagcc uaagaucaug   5760
guuuagggug aucagugcug gcagauaaau ugaaaaggca cgcuggcuug ugaucuuaaa   5820
ugaggacaau ccccccaggg cugggcacuc cucccccuccc cucacuucuc ccaccugcag   5880
agccaguguc cuuggguggg cuagauagga uauacuguau gccggcuccu ucaagcugcu   5940
gacucacuuu aucaauaguu ccauuuaaau ugacuucagu ggugagacug uauccuguuu   6000
gcuauugcuu guugugcuau gggggggaggg gggaggaaug uguaagauag uuaacauggg   6060
caaagggaga ucuuggggug cagcacuuaa acugccucgu aacccuuuuc augauuucaa   6120
ccacauuugc uagagggagg gagcagccac ggaguuagag gcccuugggg uuucucuuuu   6180
ccacugacag gcuuucccag gcagcuggcu aguucauucc cuccccagcc aggugcaggc   6240
guaggaauau ggacaucugg uugcuuuggc cugcugcccu cuuucagggg uccuaagccc   6300
acaaucaugc cucccuaaga ccuuggcauc cuucccucua agccguuggc accucugugc   6360
caccucucac acuggcucca gacacacagc cugugcuuuu ggagcugaga ucacucgcuu   6420
cacccuccuc aucuuuguuc uccaaguaaa gccacgaggu cggggcgagg gcagagguga   6480
ucaccugcgu gucccaucua cagaccugca gcuucauaaa acuucugauu ucucuucagc   6540
uuugaaaagg guuacccugg gcacuggccu agagccucac cuccuaauag acuuagcccc   6600
augaguuugc cauguugagc aggacuauuu cuggcacuug caagucccau gauuucuucg   6660
```

gtaauucuga gggugggggg agggacauga aaucaucuua gcuuagcuuu cugucuguga 6720
augucuauau aguguauugu guguuuuaac aaaugauuua cacugacugu ugcuguaaaa 6780
gugaauuugg aaauaaaguu auuacucuga uuaaa 6815

<210> SEQ ID NO 25
<211> LENGTH: 6524
<212> TYPE: RNA
<213> ORGANISM: Homo sapiens

<400> SEQUENCE: 25
gcagucaccg ccacccacca gcuccggcac caacagcagc gccgcugcca ccgcccaccu 60
ucugccgccg ccaccacagc caccuucucc uccuccgcug uccucucccg uccucgccuc 120
ugucgacuau caggugaacu uugaaccagg auggcugagc cccgccagga guucgaagug 180
auggaagauc acgcugggac guacggguug ggggacagga aagaucaggg gggcuacacc 240
augcaccaag accaagaggg ugacacggac gcuggccuga aagaaucucc ccugcagacc 300
cccacugagg acggaucuga ggaaccgggc ucugaaaccu cugaugcuaa gagcacucca 360
acagcggaag cugaagaagc aggcauugga gacaccccca gccuggaaga cgaagcugcu 420
ggucacguga cccaagagga guugagaguu ccgggccggc agaggaaggc gccugaaagg 480
ccccuggcca augagauuag cgcccacguc cagccuggac ccugcggaga ggccucuggg 540
gucucugggc cgugccucgg ggagaaagag ccagaagcuc ccgucccgcu gaccgcgagc 600
cuuccucagc accgucccgu uugcccagcg ccuccuccaa caggaggccc ucaggagccc 660
ucccuggagu ggggacaaaa aggcggggac ugggccgaga agggguccggc cuuuccgaag 720 cccgccacca cugcguaucu ccacacagag ccugaaagug guaaggugu ccaggaaggc 780 uuccuccgag agccaggccc cccaggucug agccaccagc ucauguccgg caugccuggg 840 gcucccccucc ugccugaggg ccccagagag gccacacgcc aaccuucggg gacaggaccu 900
gaggacacag agggcggccg ccacgccccu gagcugcuca agcaccagcu ucuaggagac 960
cugcaccagg aggggccgcc gcugaagggg gcagggggca aagagaggcc ggggagcaag 1020
gaggaggugg augaagaccg cgacgucgau gaguccuccc cccaagacuc cccucccucc 1080
aaggccuccc cagcccaaga ugggcggccu ccccagacag ccgccagaga agccaccagc 1140
aucccaggcu ucccagcgga gggugccauc ccccucccug uggauuuccu cuccaaaguu 1200
uccacagaga ucccagccuc agagcccgac gggcccagug uagggcgggc caaagggcag 1260
gaugcccccc uggaguucac guuucacgug gaaaucacac ccaacgugca gaaggagcag 1320
gcgcacucgg aggagcauuu gggaagggcu gcauuuccag gggccccugg agaggggcca 1380
gaggcccggg gccccucuuu gggagaggac acaaaagagg cugaccuucc agagcccucu 1440
gaaaagcagc cugcugcugc uccgcggggg aagcccguca gccggguccc ucaacucaaa 1500
gcucgcaugg ucaguaaaag caaagacggg acuggaagcg augacaaaaa agccaagggg 1560
gcugauggua aaacgaagau cgccacaccg cggggagcag ccccuccagg ccagaagggc 1620
caggccaacg ccaccaggau uccagcaaaa accccgcccg cuccaaagac accacccagc 1680
ucuggugaac cuccaaaauc aggggaucgc agcggcuaca gcagccccgg cuccccaggc 1740
acucccggca gccgcucccg caccccgucc cuuccaaccc cacccacccg ggagcccaag 1800
aagguggcag ugguccguac uccacccaag ucgccgucuu ccgccaagag ccgccugcag 1860
acagcccccg ugcccaugcc agaccugaag aaugucaagu ccaagaucgg cuccacugag 1920
aaccugaagc accagccggg aggcgggaag gugcaaauag ucuacaaacc aguugaccug 1980

-continued agcaaggugua ccuccaagug uggcucauua ggcaacaucc aucauaaacc aggagguggc 2040
cagguggaag uaaaaucuga gaagcuugac uucaaggaca gaguccaguc gaagauuggg 2100
ucccuggaca auaucaccca cgucccuggc ggaggaaaua aaaagauuga aacccacaag 2160
cugaccuucc gcgagaacgc caaagccaag acagaccacg gggcggagau cguguacaag 2220
ucgccagugg ugucugggga cacgucucca cggcaucuca gcaaugucuc cuccaccggc 2280
agcaucgaca ugguagacuc gccccagcuc gccacgcuag cugacgaggu gucugccucc 2340
cuggccaagc aggguuugug aucaggcccc uggggcgguc aauaauugug gagaggagag 2400
aaugagagag uguggaaaaa aaaagaauaa ugacccggcc cccgcccucu gcccccagcu 2460
gcuccucgca guucgguuaa uugguuaauc acuuaaccug cuuuugucac ucggcuuugg 2520
cucgggacuu caaaaucagu gaugggagua agagcaaauu ucaucuuucc aaauugaugg 2580
gugggcuagu aauaaaauau uuaaaaaaaa acauucaaaa acauggccac auccaacauu 2640
uccucaggca auuccuuuug auucuuuuuu cuuccccccuc cauguagaag agggagaagg 2700
agaggcucug aaagcugcuu cugggggauu ucaagggacu gggggugcca accaccucug 2760
gcccuguugu gggggguguca cagaggcagu ggcagcaaca aaggauuuga aacuuggugu 2820
guucguggag ccacaggcag acgaugucaa ccuuguguga gugugacggg gguuggggug 2880
gggcgggagg ccacgggga ggccgaggca ggggcugggc agaggggaga ggaagcacaa 2940
gaagugggag ugggagagga agccacgugc uggagaguag acaucccccu ccuugccgcu 3000
gggagagcca aggccuaugc caccugcagc gucugagcgg ccgccugucc uugguggccg 3060
gggguggggg ccugcugugg gucagugugc cacccucugc agggcagccu gugggagaag 3120
ggacagcggg uaaaaagaga aggcaagcug gcaggagggu ggcacuucgu ggaugaccuc 3180
cuuagaaaag acugaccuug augucuugag agcgcuggcc ucuuccuccc ucccugcagg 3240
guagggggcc ugaguugagg ggcuucccuc ugcuccacag aaacccuguu uuauugaguu 3300
cugaagguug gaacugcugc caugauuuug gccacuuugc agaccuggga cuuuagggcu 3360
aaccaguucu cuuuguaagg acuugugccu cuugggagac guccacccgu uuccaagccu 3420
gggccacugg caucucugga gugugugggg gucugggagg caggucccga gcccccuguc 3480
cuucccacgg ccacugcagu caccccgucu gcgccgcugu gcuguugucu gccgugagag 3540
cccaaucacu gccuauaccc cucaucacac gucacaaugu cccgaauucc cagccucacc 3600
accccuucuc aguaaugacc cugguugguu gcaggaggua ccuacuccau acugagggug 3660
aaauuaaggg aaggcaaagu ccaggcacaa gagugggacc ccagccucuc acucucaguu 3720
ccacucaucc aacugggacc cucaccacga aucucaugau cugauucggu ucccugucuc 3780
cucccucccgu cacagaugug agccagggca cugcucagcu gugacccuag guguuucugc 3840
cuuguugaca uggagagagc ccuuuccccu gagaaggccu ggccccuucc ugugcugagc 3900
ccacagcagc aggcugggug ucuugguugu caguggugc accaggaugg aagggcaagg 3960
cacccagggc aggcccacag ucccgcuguc ccccacuugc acccuagcuu guagcugcca 4020
accucccaga cagcccagcc cgcugcucag cuccacaugc auaguaucag cccuccacac 4080
ccgacaaagg ggaacacacc cccuuggaaa ugguucuuuu cccccagucc cagcuggaag 4140
ccaugcuguc uguucugcug gagcagcuga acauauacau agauguugcc cugcccuccc 4200
caucugcacc cuguugaguu guaguuggau uugucuguuu augcuuggau ucaccagagu 4260
gacuaugaua gugaaaagaa aaaaaaaaaa aaaaaaggac gcauguaucu ugaaaugcuu 4320

-continued

```
guaaagaggu uucuaaccca cccucacgag gugucucuca cccccacacu gggacucgug   4380
uggccugugu ggugccaccc ugcuggggcc ucccaaguuu ugaaaggcuu ucccucagcac   4440
cugggaccca acagagacca gcuucuagca gcuaaggagg ccguucagcu gugacgaagg   4500
ccugaagcac aggauuagga cugaagcgau gaugucccccu ucccuacuuc cccuuggggc   4560
ucccugugúc agggcacaga cuaggucuug uggcuggucu ggcuugcggc gcgaggaugg   4620
uucucucugg ucauagcccg aagucucaug gcagucccaa aggaggcuua caacuccugc   4680
aucacaagaa aaaggaagcc acugccagcu gggggggaucu gcagcuccca gaagcuccgu   4740
gagccucagc caccccucag acuggguucc ucuccaagcu cgcccucugg aggggcagcg   4800
cagccuccca ccaagggccc ugcgaccaca gcagggauug ggaugaauug ccuguccugg   4860
aucugcucua gaggcccaag cugccugccu gaggaaggau gacuugacaa gucaggagac   4920
acuguuccca aagccuugac cagagcaccu cagcccgcug accuugcaca aacuccaucu   4980
gcugccauga gaaaagggaa gccgccuuug caaaacauug cugccuaaag aaacucagca   5040
gccucaggcc caauucugcc acuucugguu uggguacagu uaaaggcaac ccugagggac   5100
uuggcaguag aaauccaggg ccuccccugg ggcuggcagc uucgugugca gcuagagcuu   5160
uaccugaaag gaagucucug ggcccagaac ucuccaccaa gagccucccu gccguucgcu   5220
gagucccagc aauucuccua aguugaaggg aucugagaag gagaaggaaa ugugggguag   5280
auuugguggu gguuagagau augccccccu cauuacugcc aacaguuucg gcugcauuuc   5340
uucacgcacc ucgguuccuc uuccugaagu ucuugugccc ugcucuucag caccaugggc   5400
cuucuuauac ggaaggcucu gggaucuccc ccuuguggggg caggcucuug gggccagccu   5460
aagaucaugg uuuagggguga ucagugcugg cagauaaauu gaaaaggcac gcuggcuugu   5520
gaucuuaaau gaggacaauc cccccagggc ugggcacucc ucccucccc ucacuucucc   5580
caccugcaga gccagugucc uuggguggge uagauaggau auacuguaug ccggcuccuu   5640
caagcugcug acucacuuua ucaauaguuc cauuuaaauu gacuucagug gugagacugu   5700
auccuguuug cuauugcuug uugugcuaug gggggagggg ggaggaaugu guaagauagu   5760
uaacaugggc aaagggagau cuuggggugc agcacuuaaa cugccucgua acccuuuuca   5820
ugauuucaac cacauuugcu agagggaggg agcagccacg gaguuagagg cccuuggggu   5880
uucucuuuuc cacugacagg cuuucccagg cagcuggcua guucauuccc uccccagcca   5940
ggugcaggcg uaggaauaug gacaucuggu ugcuuuggcc ugcugcccuc uuucaggggu   6000
ccuaagccca caaucaugcc ucccuaagac cuuggcaucc uucccucuaa gccguuggca   6060
ccucugugcc accucucaca cuggcuccag acacacagcc ugugcuuuug gagcugagau   6120
cacucgcuuc acccuccuca ucuuuguucu ccaaguaaag ccacgagguc ggggcgaggg   6180
cagaggugau caccugcgug ucccaucuac agaccugcag cuucauaaaa cuucugauuu   6240
cucuucagcu uugaaaaggg uuacccuggg cacuggccua gagccucacc uccuaauaga   6300
cuuagcccca ugaguuugcc auguugagca ggacuauuuc uggcacuugc aagucccaug   6360
auuucuucgg uaauucugag ggugggggga gggacaugaa aucaucuuag cuuagcuuuc   6420
ugucugugaa ugucuauaua guguauugug uguuuuaaca aaugauuuac acugacuguu   6480
gcuguaaaag ugaauuugga aauaaaguua uuacucugau uaaa                    6524
```

<210> SEQ ID NO 26
<211> LENGTH: 4139
<212> TYPE: RNA
<213> ORGANISM: Homo sapiens

<400> SEQUENCE: 26
gcagucaccg ccacccacca gcuccggcac caacagcagc gccgcugcca ccgcccaccu 60
ucugccgccg ccaccacagc caccuucucc uccucccgcug uccucucccg uccucgccuc 120
ugucgacuau caggugaacu uugaaccagg auggcugagc cccgccagga guucgaagug 180
auggaagauc acgcugggac guacggguug ggggacagga aagaucaggg gggcuacacc 240
augcaccaag accaagaggg ugacacggac gcuggccuga aagaaucucc ccugcagacc 300
cccacugagg acggaucuga ggaaccgggc ucugaaaccu cugaugcuaa gagcacucca 360
acagcggaag cugaagaagc aggcauugga gacaccccca gccuggaaga cgaagcugcu 420
ggucacguga cccaagcucg cauggucagu aaaagcaaag acgggacugg aagcgaugac 480
aaaaaagcca agggggcuga ugguaaaacg aagaucgcca caccgcgggg agcagccccu 540
ccaggccaga agggccaggc caacgccacc aggauuccag caaaaacccc gcccgcucca 600
aagacaccac ccagcucugg ugaaccucca aaaucagggg aucgcagcgg cuacagcagc 660
cccggcuccc caggcacucc cggcagccgc ucccgcaccc cgucccuucc aaccccaccc 720
acccgggagc ccaagaaggu ggcaguggu cguacuccac ccaagucgcc gucuuccgcc 780
aagagccgcc ugcagacagc cccccgugccc augccagacc ugaagaaugu caaguccaag 840
aucggcucca cugagaaccu gaagcaccag ccgggaggcg ggaaggugca aauagucuac 900
aaaccaguug accugagcaa gguuggaacu gcugccauga uuuuggccac uuugcagacc 960
ugggacuuua gggcuaacca guucucuuug uaaggacuug ugccucuugg gagacgucca 1020
cccguuucca agccugggcc acuggcaucu cuggagugug uggggggucug ggaggcaggu 1080
cccgagcccc cuguccuucc cacggccacu gcagucaccc cgucugcgcc gcugugcugu 1140
ugucugccgu gagagcccaa ucacugccua uaccccucau cacacgucac aaugucccga 1200
auucccagcc ucaccacccc uucucaguaa ugacccuggu ugguugcagg agguaccuac 1260
uccauacuga gggugaaauu aagggaaggc aaaguccagg cacaagagug ggaccccagc 1320
cucucacucu caguuccacu cauccaacug ggacccucac cacgaaucuc augaucugau 1380
ucgguucccu gucuccuccu cccgucacag augugagcca gggcacugcu cagcugugac 1440
ccuaggugu ucugccuugu ugacauggag agagcccuuu ccccugagaa ggccuggccc 1500
cuuccugugc ugagcccaca gcagcaggcu gggugucuug guugucagug guggcaccag 1560
gauggaaggg caaggcaccc agggcaggcc cacagucccg cuguccccca cuugcacccu 1620
agcuuguagc ugccaaccuc ccagacagcc cagcccgcug cucagcucca caugcauagu 1680
aucagcccuc cacacccgac aaaggggaac acacccccuu ggaaaugguu cuuuuccccc 1740
agucccagcu ggaagccaug cugucuguuc ugcuggagca gcugaacaua uacauagaug 1800
uugcccugcc cuccccaucu gcacccuguu gaguuguagu uggauuuguc uguuuaugcu 1860
uggauucacc agagugacua ugauagugaa aagaaaaaaa aaaaaaaaaa aggacgcaug 1920
uaucuugaaa ugcuuguaaa gagguuucua acccacccuc acgaggugucc ucucacccccc 1980
acacugggac ucguguggcc ugugugguggc cacccugcug gggccuccca aguuuugaaa 2040
ggcuuuccuc agcaccuggg acccaacaga gaccagcuuc uagcagcuaa ggaggccguu 2100
cagcugugac gaaggccuga agcacaggau uaggacugaa gcgaugaugu ccccuucccu 2160
acuuccccuu ggggcucccu gugucagggc acagacuagg ucuuguggcu ggucuggcuu 2220
gcggcgcgag gaugguucuc ucuggucaua gcccgaaguc ucauggcagu cccaaaggag 2280
gcuuacaacu ccugcaucac aagaaaaagg aagccacugc cagcuggggg gaucugcagc 2340
ucccagaagc uccgugagcc ucagccaccc cucagacugg guuccucucc aagcucgccc 2400
ucuggagggg cagcgcagcc ucccaccaag ggcccugcga ccacagcagg gauugggaug 2460
aauugccugu ccuggaucug cucuagaggc ccaagcugcc ugccugagga aggaugacuu 2520
gacaagucag gagacacugu ucccaaagcc uugaccagag caccucagcc cgcugaccuu 2580
gcacaaacuc caucugcugc caugagaaaa gggaagccgc cuuugcaaaa cauugcugcc 2640
uaaagaaacu cagcagccuc aggcccaauu cugccacuuc ugguuugggu acaguuaaag 2700
gcaacccuga gggacuuggc aguagaaauc cagggccucc ccuggggcug gcagcuucgu 2760
gugcagcuag agcuuuaccu gaaaggaagu cucugggccc agaacucucc accaagagcc 2820
ucccugccgu ucgcugaguc ccagcaauuc uccuaaguug aagggaucug agaaggagaa 2880
ggaaaugugg gguagauuug gugguggguua gagauaugcc ccccucauua cugccaacag 2940
uuucggcugc auuucuucac gcaccucggu uccucuuccu gaaguucuug ugcccugcuc 3000
uucagcacca ugggccuucu uauacggaag gcucugggau cucccccuug uggggcaggc 3060
ucuuggggcc agccuaagau caugguuuag ggugaucagu gcuggcagau aaauugaaaa 3120
ggcacgcugg cuugugaucu uaaaugagga caaucccccc agggcugggc acuccucccc 3180
uccccucacu ucucccaccu gcagagccag uguccuuggg ugggcuagau aggauauacu 3240
guaugccggc uccuucaagc ugcugacuca cuuuaucaau aguuccauuu aaauugacuu 3300
caguggugag acuguauccu guuugcuauu gcuuguugug cuaugggggg aggggggagg 3360
aauguguaag auaguuaaca ugggcaaagg gagaucuugg ggugcagcac uuaaacugcc 3420
ucguaacccu uuucaugauu ucaaccacau uugcuagagg gagggagcag ccacggaguu 3480
agaggcccuu gggguuucuc uuuuccacug acaggcuuuc ccaggcagcu ggcuaguuca 3540
uucccucccc agccaggugc aggcguagga auauggacau cugguugcuu uggccugcug 3600
cccucuuuca ggggguccuaa gcccacaauc augccucccu aagaccuugg cauccuuccc 3660
ucuaagccgu uggcaccucu gugccaccuc ucacacuggc uccagacaca cagccugugc 3720
uuuuggagcu gagaucacuc gcuucacccu ccucaucuuu guucuccaag uaaagccacg 3780
aggucggggc gagggcagag gugaucaccu gcguguccca ucuacagacc ugcagcuuca 3840
uaaaacuucu gauuucucuu cagcuuugaa aaggguuacc cugggcacug gccuagagcc 3900
ucaccuccua auagacuuag ccccaugagu uugccauguu gagcaggacu auuucuggca 3960
cuugcaaguc ccaugauuuc uucgguaauu cugagggugg ggggagggac augaaaucau 4020
cuuagcuuag cuuucugucu gugaaugucu auauagugua uuguguguuu uaacaaauga 4080
uuuacacuga cuguugcugu aaaagugaau uuggaaauaa aguuauuacu cugauuaaa 4139

<210> SEQ ID NO 27
<211> LENGTH: 5525
<212> TYPE: RNA
<213> ORGANISM: Homo sapiens

<400> SEQUENCE: 27
gcagucaccg ccacccacca gcuccggcac caacagcagc gccgcugcca ccgcccaccu 60
ucugccgccg ccaccacagc caccuucucc uccuccgcug uccucucccg uccucgccuc 120
ugucgacuau cagacaggcu cugcugaugc uguccccucuc cuguucaguc gugcccucac 180
cguuaaagag aaagagcaaa cugcugggca gcagcauuga uuuuuuuaau gaaguggaaa 240
gagagcuggg aauaacaagu cgggcccacc ucaccugccu caccugguga acuuugaacc 300

```
aggauggcug agccccgcca ggaguucgaa gugauggaag aucacgcugg gacguacggg    360
uugggggaca ggaaagauca ggggggcuac accaugcacc aagaccaaga gggugacacg    420
gacgcuggcc ugaaagcuga agaagcaggc auuggagaca cccccagccu ggaagacgaa    480
gcugcugguc acgugaccca agcucgcaug gucaguaaaa gcaaagacgg gacuggaagc    540
gaugacaaaa aagccaaggg ggcugauggu aaaacgaaga ucgccacacc gcggggagca    600
gccccuccag gccagaaggg ccaggccaac gccaccagga uuccagcaaa aaccccgccc    660
gcuccaaaga caccacccag cucuggugaa ccuccaaaau caggggaucg cagcggcuac    720
agcagccccg gcuccccagg cacucccggc agccgcuccc gcaccccguc ccuuccaacc    780
ccacccaccc gggagcccaa gaagguggca gugguccgua cuccacccaa gucgccgucu    840
uccgccaaga gccgccugca gacagccccc gugcccaugc cagaccugaa gaaugucaag    900
uccaagaucg gcuccacuga gaaccugaag caccagccgg gaggcgggaa ggugcaaaua    960
gucuacaaac caguugaccu gagcaaggug accuccaagu guggcucauu aggcaacauc   1020
caucauaaac caggaggugg ccagguggaa guaaaaucug agaagcuuga cuucaaggac   1080
agaguccagu cgaagauugg gucccuggac aauaucaccc acgucccugg cggaggaaau   1140
aaaaagauug aaacccacaa gcugaccuuc cgcgagaacg ccaaagccaa gacagaccac   1200
ggggcggaga ucguguacaa gucgccagug gugucugggg acacgucucc acggcaucuc   1260
agcaaugucu ccuccaccgg cagcaucgac augguagacu cgccccagcu cgccacgcua   1320
gcugacgagg ugucugccuc ccuggccaag cagggguugu gaucaggccc cuggggcggu   1380
caauaauugu ggagaggaga gaaugagaga guguggaaaa aaaaagaaua augacccggc   1440
ccccgcccuc ugcccccagc ugcuccucgc aguucgguua auugguuaau cacuuaaccu   1500
gcuuuuguca cucggcuuug gcucgggacu ucaaaaucag ugaugggagu aagagcaaau   1560
uucaucuuuc caaauugaug ggugggcuag uaauaaaaua uuuaaaaaaa aacauucaaa   1620
aacauggcca cauccaacau uuccucaggc aauuccuuuu gauucuuuuu ucuucccccu   1680
ccauguagaa gagggagaag gagaggcucu gaaagcugcu ucugggggau uucaagggac   1740
ugggggugcc aaccaccucu ggcccuguug ugggggguguc acagaggcag uggcagcaac   1800
aaaggauuug aaacuuggug uguucgugga gccacaggca gacgauguca accuugugug   1860
agugugacgg ggguuggggu ggggcgggag gccacggggg aggccgaggc aggggcuggg   1920
cagaggggag aggaagcaca agaaguggga gugggagagg aagccacgug cuggagagua   1980
gacauccccc uccuugccgc ugggagagcc aaggccuaug ccaccugcag cgucugagcg   2040
gccgccuguc cuugguggcc gggggugggg gccugcugug ggucagugug ccacccucug   2100
cagggcagcc ugugggagaa gggacagcgg guaaaaagag aaggcaagcu ggcaggaggg   2160
uggcacuucg uggaugaccu ccuuagaaaa gacugaccuu gaugucuuga gagcgcuggc   2220
cucuuccucc cucccugcag gguagggggc cugaguugag ggcuucccu cugcuccaca   2280
gaaacccugu uuuauugagu ucugaagguu ggaacugcug ccaugauuuu ggccacuuug   2340
cagaccuggg acuuuagggc uaaccaguuc ucuuuguaag gacuugugcc ucuugggaga   2400
cguccacccg uuuccaagcc ugggccacug gcaucucugg agugugugg ggucugggag   2460
gcaggucccg agcccccugu ccuucccacg gccacugcag ucaccccguc ugcgccgcug   2520
ugcuguuguc ugccgugaga gcccaaucac ugccuauacc ccucaucaca cgucacaaug   2580
ucccgaauuc ccagccucac caccccuucu caguaaugac ccugguuggu ugcaggaggu   2640
```

-continued

```
accuacucca uacugagggu gaaauuaagg gaaggcaaag uccaggcaca agagugggac   2700
cccagccucu cacucucagu uccacucauc caacugggac ccucaccacg aaucucauga   2760
ucugauucgg uucccugucu ccucccucccg ucacagaugu gagccagggc acugcucagc   2820
ugugacccua gguguuucug ccuuguugac auggagagag cccuuucccc ugagaaggcc   2880
uggccccuuc cugugcugag cccacagcag caggcugggu gucuugguug ucagugugg   2940
caccaggaug gaagggcaag gcacccaggg caggcccaca gucccgcugu cccccacuug   3000
cacccuagcu uguagcugcc aaccucccag acagcccagc ccgcugcuca gcuccacaug   3060
cauaguauca gcccuccaca cccgacaaag gggaacacac ccccuuggaa augguucuuu   3120
ucccccaguc ccagcuggaa gccaugcugu cuguucugcu ggagcagcug aacauauaca   3180
uagauguugc ccugcccucc ccaucugcac ccuguugagu uguaguugga uuugucuguu   3240
uaugcuugga uucaccagag ugacuaugau agugaaaaga aaaaaaaaaa aaaaaaagga   3300
cgcauguauc uugaaaugcu uguaaagagg uuucuaaccc acccucacga ggugucucuc   3360
acccccacac ugggacucgu guggccugug uggugccacc cugcuggggc cucccaaguu   3420
uugaaaggcu uuccucagca ccugggaccc aacagagacc agcuucuagc agcuaaggag   3480
gccguucagc ugugacgaag gccugaagca caggauuagg acugaagcga ugaugucccc   3540
uucccuacuu ccccuugggg cucccugugu cagggcacag acuaggucuu guggcugguc   3600
uggcuugcgg cgcgaggaug guucucucug gucauagccc gaagucucau ggcaguccca   3660
aaggaggcuu acaacuccug caucacaaga aaaaggaagc cacugccagc ugggggggauc   3720
ugcagcuccc agaagcuccg ugagccucag ccaccccuca gacuggguuc cucuccaagc   3780
ucgcccucug gaggggcagc gcagccuccc accaagggcc cugcgaccac agcagggauu   3840
gggaugaauu gccuguccug gaucugcucu agaggcccaa gcugccugcc ugaggaagga   3900
ugacuugaca agucaggaga cacuguuccc aaagccuuga ccagagcacc ucagcccgcu   3960
gaccuugcac aaacuccauc ugcugccaug agaaaaggga agccgccuuu gcaaaacauu   4020
gcugccuaaa gaaacucagc agccucaggc ccaauucugc cacuucuggu uuggguacag   4080
uuaaaggcaa cccugaggga cuuggcagua gaaauccagg gccuccccug gggcuggcag   4140
cuucgugugc agcuagagcu uuaccugaaa ggaagucucu gggcccagaa cucuccacca   4200
agagccuccc ugccguucgc ugagucccag caauucuccu aaguugaagg gaucugagaa   4260
ggagaaggaa auguggggua gauuuggugg ugguuagaga uaugcccccc ucauuacugc   4320
caacaguuuc ggcugcauuu cuucacgcac cucgguuccu cuuccugaag uucuugugcc   4380
cugcucuuca gcaccauggg ccuucuuaua cggaaggcuc ugggaucucc cccuuguggg   4440
gcaggcucuu ggggccagcc uaagaucaug guuuagggug aucagugcug gcagauaaau   4500
ugaaaaggca cgcuggcuug ugaucuuaaa ugaggacaau ccccccaggg cugggcacuc   4560
cuccccuccc cucacuucuc ccaccugcag agccaguguc cuugggguggg cuagauagga   4620
uauacuguau gccggcuccu ucaagcugcu gacucacuuu aucaauaguu ccauuuaaau   4680
ugacuucagu ggugagacug uauccuguuu gcuauugcuu guugugcuau gggggggaggg   4740
gggaggaaug uguaagauag uuaacauggg caaagggaga ucuuggggug cagcacuuaa   4800
acugccucgu aacccuuuuc augauuucaa ccacauuugc uagagggagg gagcagccac   4860
ggaguuagag gcccuugggg uuucucuuuu ccacugacag gcuuucccag gcagcuggcu   4920
aguucauucc cuccccagcc aggugcaggc guaggaauau ggacaucugg uugcuuuggc   4980
cugcugcccu cuuucagggg uccuaagccc acaaucaugc cucccuaaga ccuuggcauc   5040
```

```
cuucccucua agccguuggc accucugugc caccucucac acuggcucca gacacacagc   5100

cugugcuuuu ggagcugaga ucacucgcuu cacccucccuc aucuuuguuc uccaaguaaa   5160

gccacgaggu cggggcgagg gcagagguga ucaccugcgu gucccaucua cagaccugca   5220

gcuucauaaa acuucugauu ucucuucagc uuugaaaagg guuacccugg gcacuggccu   5280

agagccucac cuccuaauag acuuagcccc augaguuugc cauguugagc aggacuauuu   5340

cuggcacuug caagucccau gauuucuucg guaauucuga gggugggggg agggacauga   5400

aaucaucuua gcuuagcuuu cugucuguga augucuauau aguguauugu guguuuuaac   5460

aaaugauuua cacugacugu ugcuguaaaa gugaauuugg aaauaaaguu auuacucuga   5520

uuaaa                                                               5525
```

<210> SEQ ID NO 28
<211> LENGTH: 862
<212> TYPE: PRT
<213> ORGANISM: Homo sapiens

<400> SEQUENCE: 28

```
Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Glu Glu Leu Arg
        115                 120                 125

Val Pro Gly Arg Gln Arg Lys Ala Pro Glu Arg Pro Leu Ala Asn Glu
    130                 135                 140

Ile Ser Ala His Val Gln Pro Gly Pro Cys Gly Glu Ala Ser Gly Val
145                 150                 155                 160

Ser Gly Pro Cys Leu Gly Glu Lys Glu Pro Glu Ala Pro Val Pro Leu
                165                 170                 175

Thr Ala Ser Leu Pro Gln His Arg Pro Val Cys Pro Ala Pro Pro Pro
            180                 185                 190

Thr Gly Gly Pro Gln Glu Pro Ser Leu Glu Trp Gly Gln Lys Gly Gly
        195                 200                 205

Asp Trp Ala Glu Lys Gly Pro Ala Phe Pro Lys Pro Ala Thr Thr Ala
    210                 215                 220

Tyr Leu His Thr Glu Pro Glu Ser Gly Lys Val Val Gln Glu Gly Phe
225                 230                 235                 240

Leu Arg Glu Pro Gly Pro Pro Gly Leu Ser His Gln Leu Met Ser Gly
                245                 250                 255

Met Pro Gly Ala Pro Leu Leu Pro Glu Gly Pro Arg Glu Ala Thr Arg
            260                 265                 270

Gln Pro Ser Gly Thr Gly Pro Glu Asp Thr Glu Gly Gly Arg His Ala
```

-continued

```
        275                 280                 285

Pro Glu Leu Leu Lys His Gln Leu Leu Gly Asp Leu His Gln Glu Gly
    290                 295                 300

Pro Pro Leu Lys Gly Ala Gly Gly Lys Glu Arg Pro Gly Ser Lys Glu
305                 310                 315                 320

Glu Val Asp Glu Asp Arg Asp Val Asp Glu Ser Ser Pro Gln Asp Ser
                325                 330                 335

Pro Pro Ser Lys Ala Ser Pro Ala Gln Asp Gly Arg Pro Pro Gln Thr
            340                 345                 350

Ala Ala Arg Glu Ala Thr Ser Ile Pro Gly Phe Pro Ala Glu Gly Ala
        355                 360                 365

Ile Pro Leu Pro Val Asp Phe Leu Ser Lys Val Ser Thr Glu Ile Pro
    370                 375                 380

Ala Ser Glu Pro Asp Gly Pro Ser Val Gly Arg Ala Lys Gly Gln Asp
385                 390                 395                 400

Ala Pro Leu Glu Phe Thr Phe His Val Glu Ile Thr Pro Asn Val Gln
                405                 410                 415

Lys Glu Gln Ala His Ser Glu Glu His Leu Gly Arg Ala Ala Phe Pro
            420                 425                 430

Gly Ala Pro Gly Glu Gly Pro Glu Ala Arg Gly Pro Ser Leu Gly Glu
        435                 440                 445

Asp Thr Lys Glu Ala Asp Leu Pro Glu Pro Ser Glu Lys Gln Pro Ala
    450                 455                 460

Ala Ala Pro Arg Gly Lys Pro Val Ser Arg Val Pro Gln Leu Lys Ala
465                 470                 475                 480

Arg Met Val Ser Lys Ser Lys Asp Gly Thr Gly Ser Asp Asp Lys Lys
                485                 490                 495

Ala Lys Thr Ser Thr Arg Ser Ser Ala Lys Thr Leu Lys Asn Arg Pro
            500                 505                 510

Cys Leu Ser Pro Lys His Pro Thr Pro Gly Ser Ser Asp Pro Leu Ile
        515                 520                 525

Gln Pro Ser Ser Pro Ala Val Cys Pro Glu Pro Pro Ser Ser Pro Lys
    530                 535                 540

Tyr Val Ser Ser Val Thr Ser Arg Thr Gly Ser Ser Gly Ala Lys Glu
545                 550                 555                 560

Met Lys Leu Lys Gly Ala Asp Gly Lys Thr Lys Ile Ala Thr Pro Arg
                565                 570                 575

Gly Ala Ala Pro Pro Gly Gln Lys Gly Gln Ala Asn Ala Thr Arg Ile
            580                 585                 590

Pro Ala Lys Thr Pro Pro Ala Pro Lys Thr Pro Pro Ser Ser Gly Glu
        595                 600                 605

Pro Pro Lys Ser Gly Asp Arg Ser Gly Tyr Ser Ser Pro Gly Ser Pro
    610                 615                 620

Gly Thr Pro Gly Ser Arg Ser Arg Thr Pro Ser Leu Pro Thr Pro Pro
625                 630                 635                 640

Thr Arg Glu Pro Lys Lys Val Ala Val Val Arg Thr Pro Pro Lys Ser
                645                 650                 655

Pro Ser Ser Ala Lys Ser Arg Leu Gln Thr Ala Pro Val Pro Met Pro
            660                 665                 670

Asp Leu Lys Asn Val Lys Ser Lys Ile Gly Ser Thr Glu Asn Leu Lys
        675                 680                 685

His Gln Pro Gly Gly Gly Lys Val Gln Ile Ile Asn Lys Lys Leu Asp
    690                 695                 700
```

-continued

Leu Ser Asn Val Gln Ser Lys Cys Gly Ser Lys Asp Asn Ile Lys His
705 710 715 720

Val Pro Gly Gly Gly Ser Val Gln Ile Val Tyr Lys Pro Val Asp Leu
725 730 735

Ser Lys Val Thr Ser Lys Cys Gly Ser Leu Gly Asn Ile His His Lys
740 745 750

Pro Gly Gly Gly Gln Val Glu Val Lys Ser Glu Lys Leu Asp Phe Lys
755 760 765

Asp Arg Val Gln Ser Lys Ile Gly Ser Leu Asp Asn Ile Thr His Val
770 775 780

Pro Gly Gly Gly Asn Lys Lys Ile Glu Thr His Lys Leu Thr Phe Arg
785 790 795 800

Glu Asn Ala Lys Ala Lys Thr Asp His Gly Ala Glu Ile Val Tyr Lys
805 810 815

Ser Pro Val Val Ser Gly Asp Thr Ser Pro Arg His Leu Ser Asn Val
820 825 830

Ser Ser Thr Gly Ser Ile Asp Met Val Asp Ser Pro Gln Leu Ala Thr
835 840 845

Leu Ala Asp Glu Val Ser Ala Ser Leu Ala Lys Gln Gly Leu
850 855 860

<210> SEQ ID NO 29
<211> LENGTH: 831
<212> TYPE: PRT
<213> ORGANISM: Homo sapiens

<400> SEQUENCE: 29

Met Ala Glu Pro Arg Gln Glu Phe Glu Val Met Glu Asp His Ala Gly
1 5 10 15

Thr Tyr Gly Leu Gly Asp Arg Lys Asp Gln Gly Gly Tyr Thr Met His
20 25 30

Gln Asp Gln Glu Gly Asp Thr Asp Ala Gly Leu Lys Glu Ser Pro Leu
35 40 45

Gln Thr Pro Thr Glu Asp Gly Ser Glu Glu Pro Gly Ser Glu Thr Ser
50 55 60

Asp Ala Lys Ser Thr Pro Thr Ala Glu Asp Val Thr Ala Pro Leu Val
65 70 75 80

Asp Glu Gly Ala Pro Gly Lys Gln Ala Ala Ala Gln Pro His Thr Glu
85 90 95

Ile Pro Glu Gly Thr Thr Ala Glu Glu Ala Gly Ile Gly Asp Thr Pro
100 105 110

Ser Leu Glu Asp Glu Ala Ala Gly His Val Thr Gln Glu Glu Leu Arg
115 120 125

Val Pro Gly Arg Gln Arg Lys Ala Pro Glu Arg Pro Leu Ala Asn Glu
130 135 140

Ile Ser Ala His Val Gln Pro Gly Pro Cys Gly Glu Ala Ser Gly Val
145 150 155 160

Ser Gly Pro Cys Leu Gly Glu Lys Glu Pro Glu Ala Pro Val Pro Leu
165 170 175

Thr Ala Ser Leu Pro Gln His Arg Pro Val Cys Pro Ala Pro Pro Pro
180 185 190

Thr Gly Gly Pro Gln Glu Pro Ser Leu Glu Trp Gly Gln Lys Gly Gly
195 200 205

Asp Trp Ala Glu Lys Gly Pro Ala Phe Pro Lys Pro Ala Thr Thr Ala

-continued

```
    210                 215                 220

Tyr Leu His Thr Glu Pro Glu Ser Gly Lys Val Val Gln Glu Gly Phe
225                 230                 235                 240

Leu Arg Glu Pro Gly Pro Pro Gly Leu Ser His Gln Leu Met Ser Gly
                245                 250                 255

Met Pro Gly Ala Pro Leu Leu Pro Glu Gly Pro Arg Glu Ala Thr Arg
            260                 265                 270

Gln Pro Ser Gly Thr Gly Pro Glu Asp Thr Glu Gly Gly Arg His Ala
        275                 280                 285

Pro Glu Leu Leu Lys His Gln Leu Leu Gly Asp Leu His Gln Glu Gly
    290                 295                 300

Pro Pro Leu Lys Gly Ala Gly Gly Lys Glu Arg Pro Gly Ser Lys Glu
305                 310                 315                 320

Glu Val Asp Glu Asp Arg Asp Val Asp Glu Ser Ser Pro Gln Asp Ser
                325                 330                 335

Pro Pro Ser Lys Ala Ser Pro Ala Gln Asp Gly Arg Pro Pro Gln Thr
            340                 345                 350

Ala Ala Arg Glu Ala Thr Ser Ile Pro Gly Phe Pro Ala Glu Gly Ala
        355                 360                 365

Ile Pro Leu Pro Val Asp Phe Leu Ser Lys Val Ser Thr Glu Ile Pro
    370                 375                 380

Ala Ser Glu Pro Asp Gly Pro Ser Val Gly Arg Ala Lys Gly Gln Asp
385                 390                 395                 400

Ala Pro Leu Glu Phe Thr Phe His Val Glu Ile Thr Pro Asn Val Gln
                405                 410                 415

Lys Glu Gln Ala His Ser Glu Glu His Leu Gly Arg Ala Ala Phe Pro
            420                 425                 430

Gly Ala Pro Gly Glu Gly Pro Glu Ala Arg Gly Pro Ser Leu Gly Glu
        435                 440                 445

Asp Thr Lys Glu Ala Asp Leu Pro Glu Pro Ser Glu Lys Gln Pro Ala
    450                 455                 460

Ala Ala Pro Arg Gly Lys Pro Val Ser Arg Val Pro Gln Leu Lys Ala
465                 470                 475                 480

Arg Met Val Ser Lys Ser Lys Asp Gly Thr Gly Ser Asp Asp Lys Lys
                485                 490                 495

Ala Lys Thr Ser Thr Arg Ser Ser Ala Lys Thr Leu Lys Asn Arg Pro
            500                 505                 510

Cys Leu Ser Pro Lys His Pro Thr Pro Gly Ser Ser Asp Pro Leu Ile
        515                 520                 525

Gln Pro Ser Ser Pro Ala Val Cys Pro Glu Pro Pro Ser Ser Pro Lys
    530                 535                 540

Tyr Val Ser Ser Val Thr Ser Arg Thr Gly Ser Ser Gly Ala Lys Glu
545                 550                 555                 560

Met Lys Leu Lys Gly Ala Asp Gly Lys Thr Lys Ile Ala Thr Pro Arg
                565                 570                 575

Gly Ala Ala Pro Pro Gly Gln Lys Gly Gln Ala Asn Ala Thr Arg Ile
            580                 585                 590

Pro Ala Lys Thr Pro Pro Ala Pro Lys Thr Pro Pro Ser Ser Gly Glu
        595                 600                 605

Pro Pro Lys Ser Gly Asp Arg Ser Gly Tyr Ser Ser Pro Gly Ser Pro
    610                 615                 620

Gly Thr Pro Gly Ser Arg Ser Arg Thr Pro Ser Leu Pro Thr Pro Pro
625                 630                 635                 640
```

Thr Arg Glu Pro Lys Lys Val Ala Val Val Arg Thr Pro Pro Lys Ser
645 650 655

Pro Ser Ser Ala Lys Ser Arg Leu Gln Thr Ala Pro Val Pro Met Pro
660 665 670

Asp Leu Lys Asn Val Lys Ser Lys Ile Gly Ser Thr Glu Asn Leu Lys
675 680 685

His Gln Pro Gly Gly Gly Lys Val Gln Ile Val Tyr Lys Pro Val Asp
690 695 700

Leu Ser Lys Val Thr Ser Lys Cys Gly Ser Leu Gly Asn Ile His His
705 710 715 720

Lys Pro Gly Gly Gly Gln Val Glu Val Lys Ser Glu Lys Leu Asp Phe
725 730 735

Lys Asp Arg Val Gln Ser Lys Ile Gly Ser Leu Asp Asn Ile Thr His
740 745 750

Val Pro Gly Gly Gly Asn Lys Lys Ile Glu Thr His Lys Leu Thr Phe
755 760 765

Arg Glu Asn Ala Lys Ala Lys Thr Asp His Gly Ala Glu Ile Val Tyr
770 775 780

Lys Ser Pro Val Val Ser Gly Asp Thr Ser Pro Arg His Leu Ser Asn
785 790 795 800

Val Ser Ser Thr Gly Ser Ile Asp Met Val Asp Ser Pro Gln Leu Ala
805 810 815

Thr Leu Ala Asp Glu Val Ser Ala Ser Leu Ala Lys Gln Gly Leu
820 825 830

<210> SEQ ID NO 30
<211> LENGTH: 804
<212> TYPE: PRT
<213> ORGANISM: Homo sapiens

<400> SEQUENCE: 30

Met Ala Glu Pro Arg Gln Glu Phe Glu Val Met Glu Asp His Ala Gly
1 5 10 15

Thr Tyr Gly Leu Gly Asp Arg Lys Asp Gln Gly Gly Tyr Thr Met His
20 25 30

Gln Asp Gln Glu Gly Asp Thr Asp Ala Gly Leu Lys Ala Glu Glu Ala
35 40 45

Gly Ile Gly Asp Thr Pro Ser Leu Glu Asp Glu Ala Ala Gly His Val
50 55 60

Thr Gln Glu Glu Leu Arg Val Pro Gly Arg Gln Arg Lys Ala Pro Glu
65 70 75 80

Arg Pro Leu Ala Asn Glu Ile Ser Ala His Val Gln Pro Gly Pro Cys
85 90 95

Gly Glu Ala Ser Gly Val Ser Gly Pro Cys Leu Gly Glu Lys Glu Pro
100 105 110

Glu Ala Pro Val Pro Leu Thr Ala Ser Leu Pro Gln His Arg Pro Val
115 120 125

Cys Pro Ala Pro Pro Pro Thr Gly Gly Pro Gln Glu Pro Ser Leu Glu
130 135 140

Trp Gly Gln Lys Gly Gly Asp Trp Ala Glu Lys Gly Pro Ala Phe Pro
145 150 155 160

Lys Pro Ala Thr Thr Ala Tyr Leu His Thr Glu Pro Glu Ser Gly Lys
165 170 175

Val Val Gln Glu Gly Phe Leu Arg Glu Pro Gly Pro Pro Gly Leu Ser

-continued

```
            180                 185                 190

His Gln Leu Met Ser Gly Met Pro Gly Ala Pro Leu Leu Pro Glu Gly
        195                 200                 205

Pro Arg Glu Ala Thr Arg Gln Pro Ser Gly Thr Gly Pro Glu Asp Thr
    210                 215                 220

Glu Gly Gly Arg His Ala Pro Glu Leu Leu Lys His Gln Leu Leu Gly
225                 230                 235                 240

Asp Leu His Gln Glu Gly Pro Pro Leu Lys Gly Ala Gly Gly Lys Glu
                245                 250                 255

Arg Pro Gly Ser Lys Glu Glu Val Asp Glu Asp Arg Asp Val Asp Glu
            260                 265                 270

Ser Ser Pro Gln Asp Ser Pro Pro Ser Lys Ala Ser Pro Ala Gln Asp
        275                 280                 285

Gly Arg Pro Pro Gln Thr Ala Ala Arg Glu Ala Thr Ser Ile Pro Gly
    290                 295                 300

Phe Pro Ala Glu Gly Ala Ile Pro Leu Pro Val Asp Phe Leu Ser Lys
305                 310                 315                 320

Val Ser Thr Glu Ile Pro Ala Ser Glu Pro Asp Gly Pro Ser Val Gly
                325                 330                 335

Arg Ala Lys Gly Gln Asp Ala Pro Leu Glu Phe Thr Phe His Val Glu
            340                 345                 350

Ile Thr Pro Asn Val Gln Lys Glu Gln Ala His Ser Glu Glu His Leu
        355                 360                 365

Gly Arg Ala Ala Phe Pro Gly Ala Pro Gly Glu Gly Pro Glu Ala Arg
    370                 375                 380

Gly Pro Ser Leu Gly Glu Asp Thr Lys Glu Ala Asp Leu Pro Glu Pro
385                 390                 395                 400

Ser Glu Lys Gln Pro Ala Ala Ala Pro Arg Gly Lys Pro Val Ser Arg
                405                 410                 415

Val Pro Gln Leu Lys Ala Arg Met Val Ser Lys Ser Lys Asp Gly Thr
            420                 425                 430

Gly Ser Asp Asp Lys Lys Ala Lys Thr Ser Thr Arg Ser Ser Ala Lys
        435                 440                 445

Thr Leu Lys Asn Arg Pro Cys Leu Ser Pro Lys His Pro Thr Pro Gly
    450                 455                 460

Ser Ser Asp Pro Leu Ile Gln Pro Ser Ser Pro Ala Val Cys Pro Glu
465                 470                 475                 480

Pro Pro Ser Ser Pro Lys Tyr Val Ser Ser Val Thr Ser Arg Thr Gly
                485                 490                 495

Ser Ser Gly Ala Lys Glu Met Lys Leu Lys Gly Ala Asp Gly Lys Thr
            500                 505                 510

Lys Ile Ala Thr Pro Arg Gly Ala Ala Pro Pro Gly Gln Lys Gly Gln
        515                 520                 525

Ala Asn Ala Thr Arg Ile Pro Ala Lys Thr Pro Pro Ala Pro Lys Thr
    530                 535                 540

Pro Pro Ser Ser Gly Glu Pro Pro Lys Ser Gly Asp Arg Ser Gly Tyr
545                 550                 555                 560

Ser Ser Pro Gly Ser Pro Gly Thr Pro Gly Ser Arg Ser Arg Thr Pro
                565                 570                 575

Ser Leu Pro Thr Pro Pro Thr Arg Glu Pro Lys Lys Val Ala Val Val
            580                 585                 590

Arg Thr Pro Pro Lys Ser Pro Ser Ser Ala Lys Ser Arg Leu Gln Thr
        595                 600                 605
```

Ala Pro Val Pro Met Pro Asp Leu Lys Asn Val Lys Ser Lys Ile Gly
610 615 620

Ser Thr Glu Asn Leu Lys His Gln Pro Gly Gly Gly Lys Val Gln Ile
625 630 635 640

Ile Asn Lys Lys Leu Asp Leu Ser Asn Val Gln Ser Lys Cys Gly Ser
645 650 655

Lys Asp Asn Ile Lys His Val Pro Gly Gly Gly Ser Val Gln Ile Val
660 665 670

Tyr Lys Pro Val Asp Leu Ser Lys Val Thr Ser Lys Cys Gly Ser Leu
675 680 685

Gly Asn Ile His His Lys Pro Gly Gly Gly Gln Val Glu Val Lys Ser
690 695 700

Glu Lys Leu Asp Phe Lys Asp Arg Val Gln Ser Lys Ile Gly Ser Leu
705 710 715 720

Asp Asn Ile Thr His Val Pro Gly Gly Gly Asn Lys Lys Ile Glu Thr
725 730 735

His Lys Leu Thr Phe Arg Glu Asn Ala Lys Ala Lys Thr Asp His Gly
740 745 750

Ala Glu Ile Val Tyr Lys Ser Pro Val Val Ser Gly Asp Thr Ser Pro
755 760 765

Arg His Leu Ser Asn Val Ser Ser Thr Gly Ser Ile Asp Met Val Asp
770 775 780

Ser Pro Gln Leu Ala Thr Leu Ala Asp Glu Val Ser Ala Ser Leu Ala
785 790 795 800

Lys Gln Gly Leu

<210> SEQ ID NO 31
<211> LENGTH: 796
<212> TYPE: PRT
<213> ORGANISM: Homo sapiens

<400> SEQUENCE: 31

Met Ala Glu Pro Arg Gln Glu Phe Glu Val Met Glu Asp His Ala Gly
1 5 10 15

Thr Tyr Gly Leu Gly Asp Arg Lys Asp Gln Gly Gly Tyr Thr Met His
20 25 30

Gln Asp Gln Glu Gly Asp Thr Asp Ala Gly Leu Lys Glu Ser Pro Leu
35 40 45

Gln Thr Pro Thr Glu Asp Gly Ser Glu Glu Pro Gly Ser Glu Thr Ser
50 55 60

Asp Ala Lys Ser Thr Pro Thr Ala Glu Asp Val Thr Ala Pro Leu Val
65 70 75 80

Asp Glu Gly Ala Pro Gly Lys Gln Ala Ala Ala Gln Pro His Thr Glu
85 90 95

Ile Pro Glu Gly Thr Thr Ala Glu Glu Ala Gly Ile Gly Asp Thr Pro
100 105 110

Ser Leu Glu Asp Glu Ala Ala Gly His Val Thr Gln Glu Glu Leu Arg
115 120 125

Val Pro Gly Arg Gln Arg Lys Ala Pro Glu Arg Pro Leu Ala Asn Glu
130 135 140

Ile Ser Ala His Val Gln Pro Gly Pro Cys Gly Glu Ala Ser Gly Val
145 150 155 160

Ser Gly Pro Cys Leu Gly Glu Lys Glu Pro Glu Ala Pro Val Pro Leu
165 170 175

```
Thr Ala Ser Leu Pro Gln His Arg Pro Val Cys Pro Ala Pro Pro Pro
            180                 185                 190

Thr Gly Gly Pro Gln Glu Pro Ser Leu Glu Trp Gly Gln Lys Gly Gly
        195                 200                 205

Asp Trp Ala Glu Lys Gly Pro Ala Phe Pro Lys Pro Ala Thr Thr Ala
    210                 215                 220

Tyr Leu His Thr Glu Pro Glu Ser Gly Lys Val Val Gln Glu Gly Phe
225                 230                 235                 240

Leu Arg Glu Pro Gly Pro Pro Gly Leu Ser His Gln Leu Met Ser Gly
                245                 250                 255

Met Pro Gly Ala Pro Leu Leu Pro Glu Gly Pro Arg Glu Ala Thr Arg
            260                 265                 270

Gln Pro Ser Gly Thr Gly Pro Glu Asp Thr Glu Gly Gly Arg His Ala
        275                 280                 285

Pro Glu Leu Leu Lys His Gln Leu Leu Gly Asp Leu His Gln Glu Gly
    290                 295                 300

Pro Pro Leu Lys Gly Ala Gly Gly Lys Glu Arg Pro Gly Ser Lys Glu
305                 310                 315                 320

Glu Val Asp Glu Asp Arg Asp Val Asp Glu Ser Ser Pro Gln Asp Ser
                325                 330                 335

Pro Pro Ser Lys Ala Ser Pro Ala Gln Asp Gly Arg Pro Pro Gln Thr
            340                 345                 350

Ala Ala Arg Glu Ala Thr Ser Ile Pro Gly Phe Pro Ala Glu Gly Ala
        355                 360                 365

Ile Pro Leu Pro Val Asp Phe Leu Ser Lys Val Ser Thr Glu Ile Pro
    370                 375                 380

Ala Ser Glu Pro Asp Gly Pro Ser Val Gly Arg Ala Lys Gly Gln Asp
385                 390                 395                 400

Ala Pro Leu Glu Phe Thr Phe His Val Glu Ile Thr Pro Asn Val Gln
                405                 410                 415

Lys Glu Gln Ala His Ser Glu Glu His Leu Gly Arg Ala Ala Phe Pro
            420                 425                 430

Gly Ala Pro Gly Glu Gly Pro Glu Ala Arg Gly Pro Ser Leu Gly Glu
        435                 440                 445

Asp Thr Lys Glu Ala Asp Leu Pro Glu Pro Ser Glu Lys Gln Pro Ala
    450                 455                 460

Ala Ala Pro Arg Gly Lys Pro Val Ser Arg Val Pro Gln Leu Lys Ala
465                 470                 475                 480

Arg Met Val Ser Lys Ser Lys Asp Gly Thr Gly Ser Asp Asp Lys Lys
                485                 490                 495

Ala Lys Gly Ala Asp Gly Lys Thr Lys Ile Ala Thr Pro Arg Gly Ala
            500                 505                 510

Ala Pro Pro Gly Gln Lys Gly Gln Ala Asn Ala Thr Arg Ile Pro Ala
        515                 520                 525

Lys Thr Pro Pro Ala Pro Lys Thr Pro Pro Ser Ser Gly Glu Pro Pro
    530                 535                 540

Lys Ser Gly Asp Arg Ser Gly Tyr Ser Ser Pro Gly Ser Pro Gly Thr
545                 550                 555                 560

Pro Gly Ser Arg Ser Arg Thr Pro Ser Leu Pro Thr Pro Pro Thr Arg
                565                 570                 575

Glu Pro Lys Lys Val Ala Val Val Arg Thr Pro Pro Lys Ser Pro Ser
            580                 585                 590
```

```
Ser Ala Lys Ser Arg Leu Gln Thr Ala Pro Val Pro Met Pro Asp Leu
        595                 600                 605

Lys Asn Val Lys Ser Lys Ile Gly Ser Thr Glu Asn Leu Lys His Gln
    610                 615                 620

Pro Gly Gly Gly Lys Val Gln Ile Ile Asn Lys Lys Leu Asp Leu Ser
625                 630                 635                 640

Asn Val Gln Ser Lys Cys Gly Ser Lys Asp Asn Ile Lys His Val Pro
                645                 650                 655

Gly Gly Gly Ser Val Gln Ile Val Tyr Lys Pro Val Asp Leu Ser Lys
            660                 665                 670

Val Thr Ser Lys Cys Gly Ser Leu Gly Asn Ile His His Lys Pro Gly
        675                 680                 685

Gly Gly Gln Val Glu Val Lys Ser Glu Lys Leu Asp Phe Lys Asp Arg
    690                 695                 700

Val Gln Ser Lys Ile Gly Ser Leu Asp Asn Ile Thr His Val Pro Gly
705                 710                 715                 720

Gly Gly Asn Lys Lys Ile Glu Thr His Lys Leu Thr Phe Arg Glu Asn
                725                 730                 735

Ala Lys Ala Lys Thr Asp His Gly Ala Glu Ile Val Tyr Lys Ser Pro
            740                 745                 750

Val Val Ser Gly Asp Thr Ser Pro Arg His Leu Ser Asn Val Ser Ser
        755                 760                 765

Thr Gly Ser Ile Asp Met Val Asp Ser Pro Gln Leu Ala Thr Leu Ala
    770                 775                 780

Asp Glu Val Ser Ala Ser Leu Ala Lys Gln Gly Leu
785                 790                 795


<210> SEQ ID NO 32
<211> LENGTH: 765
<212> TYPE: PRT
<213> ORGANISM: Homo sapiens

<400> SEQUENCE: 32

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Glu Glu Leu Arg
        115                 120                 125

Val Pro Gly Arg Gln Arg Lys Ala Pro Glu Arg Pro Leu Ala Asn Glu
    130                 135                 140

Ile Ser Ala His Val Gln Pro Gly Pro Cys Gly Glu Ala Ser Gly Val
145                 150                 155                 160

Ser Gly Pro Cys Leu Gly Glu Lys Glu Pro Glu Ala Pro Val Pro Leu
                165                 170                 175
```

Thr Ala Ser Leu Pro Gln His Arg Pro Val Cys Pro Ala Pro Pro Pro
180 185 190

Thr Gly Gly Pro Gln Glu Pro Ser Leu Glu Trp Gly Gln Lys Gly Gly
195 200 205

Asp Trp Ala Glu Lys Gly Pro Ala Phe Pro Lys Pro Ala Thr Thr Ala
210 215 220

Tyr Leu His Thr Glu Pro Glu Ser Gly Lys Val Val Gln Glu Gly Phe
225 230 235 240

Leu Arg Glu Pro Gly Pro Pro Gly Leu Ser His Gln Leu Met Ser Gly
245 250 255

Met Pro Gly Ala Pro Leu Leu Pro Glu Gly Pro Arg Glu Ala Thr Arg
260 265 270

Gln Pro Ser Gly Thr Gly Pro Glu Asp Thr Glu Gly Gly Arg His Ala
275 280 285

Pro Glu Leu Leu Lys His Gln Leu Leu Gly Asp Leu His Gln Glu Gly
290 295 300

Pro Pro Leu Lys Gly Ala Gly Gly Lys Glu Arg Pro Gly Ser Lys Glu
305 310 315 320

Glu Val Asp Glu Asp Arg Asp Val Asp Glu Ser Ser Pro Gln Asp Ser
325 330 335

Pro Pro Ser Lys Ala Ser Pro Ala Gln Asp Gly Arg Pro Pro Gln Thr
340 345 350

Ala Ala Arg Glu Ala Thr Ser Ile Pro Gly Phe Pro Ala Glu Gly Ala
355 360 365

Ile Pro Leu Pro Val Asp Phe Leu Ser Lys Val Ser Thr Glu Ile Pro
370 375 380

Ala Ser Glu Pro Asp Gly Pro Ser Val Gly Arg Ala Lys Gly Gln Asp
385 390 395 400

Ala Pro Leu Glu Phe Thr Phe His Val Glu Ile Thr Pro Asn Val Gln
405 410 415

Lys Glu Gln Ala His Ser Glu Glu His Leu Gly Arg Ala Ala Phe Pro
420 425 430

Gly Ala Pro Gly Glu Gly Pro Glu Ala Arg Gly Pro Ser Leu Gly Glu
435 440 445

Asp Thr Lys Glu Ala Asp Leu Pro Glu Pro Ser Glu Lys Gln Pro Ala
450 455 460

Ala Ala Pro Arg Gly Lys Pro Val Ser Arg Val Pro Gln Leu Lys Ala
465 470 475 480

Arg Met Val Ser Lys Ser Lys Asp Gly Thr Gly Ser Asp Asp Lys Lys
485 490 495

Ala Lys Gly Ala Asp Gly Lys Thr Lys Ile Ala Thr Pro Arg Gly Ala
500 505 510

Ala Pro Pro Gly Gln Lys Gly Gln Ala Asn Ala Thr Arg Ile Pro Ala
515 520 525

Lys Thr Pro Pro Ala Pro Lys Thr Pro Pro Ser Ser Gly Glu Pro Pro
530 535 540

Lys Ser Gly Asp Arg Ser Gly Tyr Ser Ser Pro Gly Ser Pro Gly Thr
545 550 555 560

Pro Gly Ser Arg Ser Arg Thr Pro Ser Leu Pro Thr Pro Pro Thr Arg
565 570 575

Glu Pro Lys Lys Val Ala Val Val Arg Thr Pro Pro Lys Ser Pro Ser
580 585 590

Ser Ala Lys Ser Arg Leu Gln Thr Ala Pro Val Pro Met Pro Asp Leu
595 600 605

Lys Asn Val Lys Ser Lys Ile Gly Ser Thr Glu Asn Leu Lys His Gln
610 615 620

Pro Gly Gly Gly Lys Val Gln Ile Val Tyr Lys Pro Val Asp Leu Ser
625 630 635 640

Lys Val Thr Ser Lys Cys Gly Ser Leu Gly Asn Ile His His Lys Pro
645 650 655

Gly Gly Gly Gln Val Glu Val Lys Ser Glu Lys Leu Asp Phe Lys Asp
660 665 670

Arg Val Gln Ser Lys Ile Gly Ser Leu Asp Asn Ile Thr His Val Pro
675 680 685

Gly Gly Gly Asn Lys Lys Ile Glu Thr His Lys Leu Thr Phe Arg Glu
690 695 700

Asn Ala Lys Ala Lys Thr Asp His Gly Ala Glu Ile Val Tyr Lys Ser
705 710 715 720

Pro Val Val Ser Gly Asp Thr Ser Pro Arg His Leu Ser Asn Val Ser
725 730 735

Ser Thr Gly Ser Ile Asp Met Val Asp Ser Pro Gln Leu Ala Thr Leu
740 745 750

Ala Asp Glu Val Ser Ala Ser Leu Ala Lys Gln Gly Leu
755 760 765

<210> SEQ ID NO 33
<211> LENGTH: 507
<212> TYPE: PRT
<213> ORGANISM: Homo sapiens

<400> SEQUENCE: 33

Met Ala Glu Pro Arg Gln Glu Phe Glu Val Met Glu Asp His Ala Gly
1 5 10 15

Thr Tyr Gly Leu Gly Asp Arg Lys Asp Gln Gly Gly Tyr Thr Met His
20 25 30

Gln Asp Gln Glu Gly Asp Thr Asp Ala Gly Leu Lys Glu Ser Pro Leu
35 40 45

Gln Thr Pro Thr Glu Asp Gly Ser Glu Glu Pro Gly Ser Glu Thr Ser
50 55 60

Asp Ala Lys Ser Thr Pro Thr Ala Glu Asp Val Thr Ala Pro Leu Val
65 70 75 80

Asp Glu Gly Ala Pro Gly Lys Gln Ala Ala Ala Gln Pro His Thr Glu
85 90 95

Ile Pro Glu Gly Thr Thr Ala Glu Glu Ala Gly Ile Gly Asp Thr Pro
100 105 110

Ser Leu Glu Asp Glu Ala Ala Gly His Val Thr Gln Ala Arg Met Val
115 120 125

Ser Lys Ser Lys Asp Gly Thr Gly Ser Asp Asp Lys Lys Ala Lys Thr
130 135 140

Ser Thr Arg Ser Ser Ala Lys Thr Leu Lys Asn Arg Pro Cys Leu Ser
145 150 155 160

Pro Lys His Pro Thr Pro Gly Ser Ser Asp Pro Leu Ile Gln Pro Ser
165 170 175

Ser Pro Ala Val Cys Pro Glu Pro Pro Ser Ser Pro Lys Tyr Val Ser
180 185 190

Ser Val Thr Ser Arg Thr Gly Ser Ser Gly Ala Lys Glu Met Lys Leu
195 200 205

Lys Gly Ala Asp Gly Lys Thr Lys Ile Ala Thr Pro Arg Gly Ala Ala
210 215 220

Pro Pro Gly Gln Lys Gly Gln Ala Asn Ala Thr Arg Ile Pro Ala Lys
225 230 235 240

Thr Pro Pro Ala Pro Lys Thr Pro Pro Ser Ser Gly Glu Pro Pro Lys
245 250 255

Ser Gly Asp Arg Ser Gly Tyr Ser Ser Pro Gly Ser Pro Gly Thr Pro
260 265 270

Gly Ser Arg Ser Arg Thr Pro Ser Leu Pro Thr Pro Pro Thr Arg Glu
275 280 285

Pro Lys Lys Val Ala Val Val Arg Thr Pro Pro Lys Ser Pro Ser Ser
290 295 300

Ala Lys Ser Arg Leu Gln Thr Ala Pro Val Pro Met Pro Asp Leu Lys
305 310 315 320

Asn Val Lys Ser Lys Ile Gly Ser Thr Glu Asn Leu Lys His Gln Pro
325 330 335

Gly Gly Gly Lys Val Gln Ile Ile Asn Lys Lys Leu Asp Leu Ser Asn
340 345 350

Val Gln Ser Lys Cys Gly Ser Lys Asp Asn Ile Lys His Val Pro Gly
355 360 365

Gly Gly Ser Val Gln Ile Val Tyr Lys Pro Val Asp Leu Ser Lys Val
370 375 380

Thr Ser Lys Cys Gly Ser Leu Gly Asn Ile His His Lys Pro Gly Gly
385 390 395 400

Gly Gln Val Glu Val Lys Ser Glu Lys Leu Asp Phe Lys Asp Arg Val
405 410 415

Gln Ser Lys Ile Gly Ser Leu Asp Asn Ile Thr His Val Pro Gly Gly
420 425 430

Gly Asn Lys Lys Ile Glu Thr His Lys Leu Thr Phe Arg Glu Asn Ala
435 440 445

Lys Ala Lys Thr Asp His Gly Ala Glu Ile Val Tyr Lys Ser Pro Val
450 455 460

Val Ser Gly Asp Thr Ser Pro Arg His Leu Ser Asn Val Ser Ser Thr
465 470 475 480

Gly Ser Ile Asp Met Val Asp Ser Pro Gln Leu Ala Thr Leu Ala Asp
485 490 495

Glu Val Ser Ala Ser Leu Ala Lys Gln Gly Leu
500 505

<210> SEQ ID NO 34
<211> LENGTH: 478
<212> TYPE: PRT
<213> ORGANISM: Homo sapiens

<400> SEQUENCE: 34

Met Ala Glu Pro Arg Gln Glu Phe Glu Val Met Glu Asp His Ala Gly
1 5 10 15

Thr Tyr Gly Leu Gly Asp Arg Lys Asp Gln Gly Gly Tyr Thr Met His
20 25 30

Gln Asp Gln Glu Gly Asp Thr Asp Ala Gly Leu Lys Glu Ser Pro Leu
35 40 45

Gln Thr Pro Thr Glu Asp Gly Ser Glu Glu Pro Gly Ser Glu Thr Ser
50 55 60

Asp Ala Lys Ser Thr Pro Thr Ala Glu Ala Glu Glu Ala Gly Ile Gly

```
65                  70                  75                  80

Asp Thr Pro Ser Leu Glu Asp Glu Ala Ala Gly His Val Thr Gln Ala
                85                  90                  95

Arg Met Val Ser Lys Ser Lys Asp Gly Thr Gly Ser Asp Asp Lys Lys
            100                 105                 110

Ala Lys Thr Ser Thr Arg Ser Ser Ala Lys Thr Leu Lys Asn Arg Pro
        115                 120                 125

Cys Leu Ser Pro Lys His Pro Thr Pro Gly Ser Ser Asp Pro Leu Ile
    130                 135                 140

Gln Pro Ser Ser Pro Ala Val Cys Pro Glu Pro Pro Ser Ser Pro Lys
145                 150                 155                 160

Tyr Val Ser Ser Val Thr Ser Arg Thr Gly Ser Ser Gly Ala Lys Glu
                165                 170                 175

Met Lys Leu Lys Gly Ala Asp Gly Lys Thr Lys Ile Ala Thr Pro Arg
            180                 185                 190

Gly Ala Ala Pro Pro Gly Gln Lys Gly Gln Ala Asn Ala Thr Arg Ile
        195                 200                 205

Pro Ala Lys Thr Pro Pro Ala Pro Lys Thr Pro Pro Ser Ser Gly Glu
    210                 215                 220

Pro Pro Lys Ser Gly Asp Arg Ser Gly Tyr Ser Ser Pro Gly Ser Pro
225                 230                 235                 240

Gly Thr Pro Gly Ser Arg Ser Arg Thr Pro Ser Leu Pro Thr Pro Pro
                245                 250                 255

Thr Arg Glu Pro Lys Lys Val Ala Val Val Arg Thr Pro Pro Lys Ser
            260                 265                 270

Pro Ser Ser Ala Lys Ser Arg Leu Gln Thr Ala Pro Val Pro Met Pro
        275                 280                 285

Asp Leu Lys Asn Val Lys Ser Lys Ile Gly Ser Thr Glu Asn Leu Lys
    290                 295                 300

His Gln Pro Gly Gly Gly Lys Val Gln Ile Ile Asn Lys Lys Leu Asp
305                 310                 315                 320

Leu Ser Asn Val Gln Ser Lys Cys Gly Ser Lys Asp Asn Ile Lys His
                325                 330                 335

Val Pro Gly Gly Gly Ser Val Gln Ile Val Tyr Lys Pro Val Asp Leu
            340                 345                 350

Ser Lys Val Thr Ser Lys Cys Gly Ser Leu Gly Asn Ile His His Lys
        355                 360                 365

Pro Gly Gly Gly Gln Val Glu Val Lys Ser Glu Lys Leu Asp Phe Lys
    370                 375                 380

Asp Arg Val Gln Ser Lys Ile Gly Ser Leu Asp Asn Ile Thr His Val
385                 390                 395                 400

Pro Gly Gly Gly Asn Lys Lys Ile Glu Thr His Lys Leu Thr Phe Arg
                405                 410                 415

Glu Asn Ala Lys Ala Lys Thr Asp His Gly Ala Glu Ile Val Tyr Lys
            420                 425                 430

Ser Pro Val Val Ser Gly Asp Thr Ser Pro Arg His Leu Ser Asn Val
        435                 440                 445

Ser Ser Thr Gly Ser Ile Asp Met Val Asp Ser Pro Gln Leu Ala Thr
    450                 455                 460

Leu Ala Asp Glu Val Ser Ala Ser Leu Ala Lys Gln Gly Leu
465                 470                 475

<210> SEQ ID NO 35
```

<211> LENGTH: 449
<212> TYPE: PRT
<213> ORGANISM: Homo sapiens

<400> SEQUENCE: 35

```
Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Ala Glu Glu Ala
        35                  40                  45

Gly Ile Gly Asp Thr Pro Ser Leu Glu Asp Glu Ala Ala Gly His Val
    50                  55                  60

Thr Gln Ala Arg Met Val Ser Lys Ser Lys Asp Gly Thr Gly Ser Asp
65                  70                  75                  80

Asp Lys Lys Ala Lys Thr Ser Thr Arg Ser Ser Ala Lys Thr Leu Lys
                85                  90                  95

Asn Arg Pro Cys Leu Ser Pro Lys His Pro Thr Pro Gly Ser Ser Asp
            100                 105                 110

Pro Leu Ile Gln Pro Ser Ser Pro Ala Val Cys Pro Glu Pro Pro Ser
        115                 120                 125

Ser Pro Lys Tyr Val Ser Ser Val Thr Ser Arg Thr Gly Ser Ser Gly
    130                 135                 140

Ala Lys Glu Met Lys Leu Lys Gly Ala Asp Gly Lys Thr Lys Ile Ala
145                 150                 155                 160

Thr Pro Arg Gly Ala Ala Pro Pro Gly Gln Lys Gly Gln Ala Asn Ala
                165                 170                 175

Thr Arg Ile Pro Ala Lys Thr Pro Pro Ala Pro Lys Thr Pro Pro Ser
            180                 185                 190

Ser Gly Glu Pro Pro Lys Ser Gly Asp Arg Ser Gly Tyr Ser Ser Pro
        195                 200                 205

Gly Ser Pro Gly Thr Pro Gly Ser Arg Ser Arg Thr Pro Ser Leu Pro
    210                 215                 220

Thr Pro Pro Thr Arg Glu Pro Lys Lys Val Ala Val Val Arg Thr Pro
225                 230                 235                 240

Pro Lys Ser Pro Ser Ser Ala Lys Ser Arg Leu Gln Thr Ala Pro Val
                245                 250                 255

Pro Met Pro Asp Leu Lys Asn Val Lys Ser Lys Ile Gly Ser Thr Glu
            260                 265                 270

Asn Leu Lys His Gln Pro Gly Gly Gly Lys Val Gln Ile Ile Asn Lys
        275                 280                 285

Lys Leu Asp Leu Ser Asn Val Gln Ser Lys Cys Gly Ser Lys Asp Asn
    290                 295                 300

Ile Lys His Val Pro Gly Gly Gly Ser Val Gln Ile Val Tyr Lys Pro
305                 310                 315                 320

Val Asp Leu Ser Lys Val Thr Ser Lys Cys Gly Ser Leu Gly Asn Ile
                325                 330                 335

His His Lys Pro Gly Gly Gly Gln Val Glu Val Lys Ser Glu Lys Leu
            340                 345                 350

Asp Phe Lys Asp Arg Val Gln Ser Lys Ile Gly Ser Leu Asp Asn Ile
        355                 360                 365

Thr His Val Pro Gly Gly Gly Asn Lys Lys Ile Glu Thr His Lys Leu
    370                 375                 380

Thr Phe Arg Glu Asn Ala Lys Ala Lys Thr Asp His Gly Ala Glu Ile
```

```
385                 390                 395                 400

Val Tyr Lys Ser Pro Val Val Ser Gly Asp Thr Ser Pro Arg His Leu
                405                 410                 415

Ser Asn Val Ser Ser Thr Gly Ser Ile Asp Met Val Asp Ser Pro Gln
            420                 425                 430

Leu Ala Thr Leu Ala Asp Glu Val Ser Ala Ser Leu Ala Lys Gln Gly
        435                 440                 445

Leu


<210> SEQ ID NO 36
<211> LENGTH: 3177
<212> TYPE: RNA
<213> ORGANISM: Homo sapiens

<400> SEQUENCE: 36

ggcgacgacc agaaggggcc caagagaggg ggcgagcgac cgagcgccgc gacgcggaag     60

ugaggugcgu gcgggcugca gcgcagaccc cggcccggcc ccuccgagag cguccugggc    120

gcucccucac gccuugccuu caagccuucu gccuuuccac ccucgugagc ggagaacugg    180

gaguggccau ucgacgacag uguggguguaa aggaauucau uagccaugga uguauucaug    240

aaaggacuuu caaaggccaa ggagggaguu guggcugcug cugagaaaac caaacagggu    300

guggcagaag cagcaggaaa gacaaaagag gguguucucu auguaggcuc caaaaccaag    360

gagggagugg ugcauggugu ggcaacagug gcugagaaga ccaaagagca agugacaaau    420

guuggaggag caguggugac gggugugaca gcaguagccc agaagacagu ggagggagca    480

gggagcauug cagcagccac uggcuuuguc aaaaaggacc aguugggcaa gaaugaagaa    540

ggagccccac aggaaggaau ucuggaagau augccugugg auccugacaa ugaggcuuau    600

gaaaugccuu cugaggaagg guaucaagac uacgaaccug aagccuaaga aauaucuuug    660

cucccaguuu cuugagaucu gcugacagau guuccauccu guacaagugc ucaguuccaa    720

ugugcccagu caugacauuu cucaaaguuu uuacagugua ucucgaaguc uuccaucagc    780

agugauugaa guaucuguac cugcccccac ucagcauuuc ggugcuuccc uuucacugaa    840

gugaauacau gguagcaggg ucuuugugug cuguggauuu uguggcuuca aucuacgaug    900

uuaaaacaaa uuaaaaacac cuaagugacu accacuuauu ucuaaauccu cacuauuuuu    960

uuguugcugu uguucagaag uuguuaguga uuugcuauca uauauuauaa gauuuuuagg   1020

ugucuuuuaa ugauacuguc uaagaauaau gacguauugu gaaauuuguu aauauauaua   1080

auacuuaaaa auaugugagc augaaacuau gcaccuauaa auacuaaaua ugaaauuuua   1140

ccauuuugcg auguguuuua uucacuugug uuuguauaua aauggugaga auuaaaauaa   1200

aacguuaucu cauugcaaaa auauuuuauu uuuaucccau cucacuuuaa uaauaaaaau   1260

caugcuuaua agcaacauga auuaagaacu gacacaaagg acaaaaauau aaaguuauua   1320

auagccauuu gaagaaggag gaauuuuaga agagguagag aaaauggaac auuaacccua   1380

cacucggaau ucccugaagc aacacugcca gaagugugu uugguaugca cugguuccuu   1440

aaguggcugu gauuaauuau ugaaaguggg guguugaaga ccccaacuac uauuguagag   1500

uggucuauuu cucccuucaa uccugucaau guuugcuuua cguauuuugg ggaacuguug   1560

uuugaugugu auguguuuau aauuguuaua cauuuuuaau ugagccuuuu auuaacauau   1620

auuguuauuu uugucucgaa auaauuuuuu aguuaaaauc uauuuugucu gauauuggug   1680

ugaaugcugu accuuucuga caauaaauaa uauucgacca ugaauaaaaa aaaaaaaaaa   1740
```

gugggguuccc gggaacuaag caguguagaa gaugauuuug acuacacccu ccuuagagag 1800
ccauaagaca cauuagcaca uauuagcaca uucaaggcuc ugagagaaug ugguuaacuu 1860
uguuuaacuc agcauuccuc acuuuuuuuu uuuaaucauc agaaauucuc ucucucucuc 1920
ucucuuuuuc ucucgcucuc uuuuuuuuuu uuuuuuuaca ggaaaugccu uuaaacaucg 1980
uuggaacuac cagagucacc uuaaaggaga ucaauucucu agacugauaa aaauuucaug 2040
gccuccuuua aauguugcca aauauaugaa uucuaggauu uuuccuuagg aaagguuuuu 2100
cucuuucagg gaagaucuau uaacucccca ugggugcuga aaauaaacuu gauggugaaa 2160
aacucuguau aaauuaauuu aaaaauuauu ugguuucucu uuuuaauuau ucuggggcau 2220
agucauuucu aaaagucacu aguagaaagu auaauuucaa gacagaauau ucuagacaug 2280
cuagcaguuu auauguauuc augaguaaug ugauauauau ugggcgcugg ugaggaagga 2340
aggaggaaug agugacuaua aggaugguua ccauagaaac uuccuuuuuu accuaauuga 2400
agagagacua cuacagagug cuaagcugca ugugucaucu uacacuagag agaaauggua 2460
aguuucuugu uuuauuuaag uuauguuuaa gcaaggaaag gauuuguuau ugaacaguau 2520
auuucaggaa gguuagaaag uggcgguuag gauauauuuu aaaucuaccu aaagcagcau 2580
auuuuaaaaa uuuaaaagua uugguauuaa auuaagaaau agaggacaga acuagacuga 2640
uagcagugac cuagaacaau uugagauuag gaaaguugug accaugaauu uaaggauuua 2700
uguggauaca aauucuccuu uaaaguguuu cuucccuuaa uauuuaucug acgguaauuu 2760
uugagcagug aauuacuuua uauaucuuaa uaguuuauuu gggaccaaac acuuaaacaa 2820
aaaguucuuu aagucauaua agccuuuuca ggaagcuugu cucauauuca cucccgagac 2880
auucaccugc caaguggccu gaggaucaau ccaguccuag guuuauuuug cagacuuaca 2940
uucucccaag uuauucagcc ucauaugacu ccacggucgg cuuuaccaaa acaguucaga 3000
gugcacuuug gcacacaauu gggaacagaa caaucuaaug ugugguuugg uauuccaagu 3060
ggggucuuuu ucagaaucuc ugcacuagug ugagaugcaa acauguuucc ucaucuuucu 3120
ggcuuaucca guauguagcu auuugugaca uaauaaauau auacauauau gaaaaua 3177

<210> SEQ ID NO 37
<211> LENGTH: 3396
<212> TYPE: RNA
<213> ORGANISM: Homo sapiens

<400> SEQUENCE: 37
ggcgacgacc agaaggggcc caagagaggg ggcgagcgac cgagcgccgc gacgcggaag 60
ugaggugcgu gcgggcugca gcgcagaccc cggcccggcc ccuccgagag cguccugggc 120
gcucccucac gccuugccuu caagccuucu gccuuuccac ccucgugagc ggagaacugg 180
gaguggccau ucgacgacag guuagcgggu uugccuccca cucccccagc cucgcgucgc 240
cggcucacag cggccuccuc uggggacagu cccccccggg ugccgccucc gcccuuccug 300
ugcgcuccuu uuccuucuuc uuuccuauua aauauuauuu gggaauuguu uaaauuuuuu 360
uuuuaaaaaa agagagaggc ggggaggagu cggaguugug gagaagcaga gggacucagu 420
gugguguaaa ggaauucauu agccauggau guauucauga aaggacuuuc aaaggccaag 480
gagggaguug uggcugcugc ugagaaaacc aaacagggug uggcagaagc agcaggaaag 540
acaaaagagg guguucucua uguaggcucc aaaaccaagg agggaguggu gcauggugug 600
gcaacagugg cugagaagac caaagagcaa gugacaaaug uuggaggagc agugguagacg 660 ggugugacag caguagccca gaagacagug gagggagcag ggagcauugc agcagccacu 720
ggcuuuguca aaaaggacca guugggcaag aaugaagaag gagccccaca ggaaggaauu 780
cuggaagaua ugccugugga uccugacaau gaggcuuaug aaaugccuuc ugaggaaggg 840
uaucaagacu acgaaccuga agccuaagaa auaucuuugc ucccaguuuc uugagaucug 900
cugacagaug uuccauccug uacaagugcu caguuccaau gugcccaguc augacauuuc 960
ucaaaguuuu uacaguguau cucgaagucu ucccaucagca gugauugaag uaucuguacc 1020
ugcccccacu cagcauuucg gugcuucccu uucacugaag ugaauacaug guagcagggu 1080
cuuugugugc uguggauuuu guggcuucaa ucuacgaugu uaaaacaaau uaaaaacacc 1140
uaagugacua ccacuuauuu cuaaauccuc acuauuuuuu uguugcuguu guucagaagu 1200
uguuagugau uugcuaucau auauuauaag auuuuuaggu gucuuuuaau gauacugucu 1260
aagaauaaug acguauugug aaauuuguua auauauauaa uacuuaaaaa uaugugagca 1320
ugaaacuaug caccuauaaa uacuaaauau gaaauuuuac cauuuugcga uguguuuuau 1380
ucacuugugu uuguauauaa auggugagaa uuaaaauaaa acguuaucuc auugcaaaaa 1440
uauuuuauuu uuaucccauc ucacuuuaau aauaaaaauc augcuuauaa gcaacaugaa 1500
uuaagaacug acacaaagga caaaaauaua aaguuauuaa uagccauuug aagaaggagg 1560
aauuuuagaa gagguagaga aaauggaaca uuaacccuac acucggaauu cccugaagca 1620
acacugccag aagugguguuu ugguaugcac ugguuccuua aguggcugug auuaauuauu 1680
gaaagugggg uguugaagac cccaacuacu auuguagagu ggucuauuuc ucccuucaau 1740
ccugucaaug uuugcuuuac guauuuuggg gaacuguugu uugaugugua uguguuuaua 1800
auuguuauac auuuuuaauu gagccuuuua uuaacauaua uuguuauuuu ugucucgaaa 1860
uaauuuuuua guuaaaaucu auuuugucug auauuggugu gaaugcugua ccuuucugac 1920
aauaaauaau auucgaccau gaauaaaaaa aaaaaaaaag ugggguucccg ggaacuaagc 1980
aguguagaag augauuuuga cuacacccuc cuuagagagc cauaagacac auuagcacau 2040
auuagcacau ucaaggcucu gagagaaugu gguuaacuuu guuuaacuca gcauuccuca 2100
cuuuuuuuuu uuaaucauca gaaauucucu cucucucucu cucuuuuucu cucgcucucu 2160
uuuuuuuuuu uuuuuuacag gaaaugccuu uaaacaucgu uggaacuacc agagucaccu 2220
uaaaggagau caauucucua gacugauaaa aauuucaugg ccuccuuuaa auguugccaa 2280
auauaugaau ucuaggauuu uuccuuagga aagguuuuuc ucuuucaggg aagaucuauu 2340
aacuccccau gggugcugaa aauaaacuug auggugaaaa acucuguaua aauuaauuua 2400
aaaauuauuu gguuucucuu uuuaauuauu cuggggcaua gucauuucua aaagucacua 2460
guagaaagua uaauuucaag acagaauauu cuagacaugc uagcaguuua uauguauuca 2520
ugaguaaugu gauauauauu gggcgcuggu gaggaaggaa ggaggaauga gugacuauaa 2580
ggaugguuac cauagaaacu uccuuuuuua ccuaauugaa gagagacuac uacagagugc 2640
uaagcugcau gugucaucuu acacuagaga gaaaugguaa guuucuuguu uuauuuaagu 2700
uauguuuaag caaggaaagg auuuguuauu gaacaguaua uuucaggaag guuagaaagu 2760
ggcgguuagg auauauuuua aaucuaccua aagcagcaua uuuuaaaaau uuaaaaguau 2820
ugguauuaaa uuaagaaaua gaggacagaa cuagacugau agcagugacc uagaacaauu 2880
ugagauuagg aaaguuguga ccaugaauuu aaggauuuau guggauacaa auucuccuuu 2940
aaaguguuuc uucccuuaau auuuaucuga cgguaauuuu ugagcaguga auuacuuuau 3000
auaucuuaau aguuuauuug ggaccaaaca cuuaaacaaa aaguucuuua agucauauaa 3060

-continued gccuuuucag gaagcuuguc ucauauucac ucccgagaca uucaccugcc aaguggccug 3120
aggaucaauc caguccuagg uuuauuuugc agacuuacau ucucccaagu uauucagccu 3180
cauaugacuc cacggucggc uuuaccaaaa caguucagag ugcacuuugg cacacaauug 3240
ggaacagaac aaucuaaugu gugguuuggu auuccaagug gggucuuuuu cagaaucucu 3300
gcacuagugu gagaugcaaa cauguuuccu caucuuucug gcuuauccag uauguagcua 3360
uuugugacau aauaaauaua uacauauaug aaaaua 3396

<210> SEQ ID NO 38
<211> LENGTH: 3030
<212> TYPE: RNA
<213> ORGANISM: Homo sapiens

<400> SEQUENCE: 38
gcuucuccau ucuggugaga uccaggaaca gcugucuucc agcucugaaa gagugugguc 60
uaaaggaauu cauuagccau ggauguauuc augaaaggac uuucaaaggc caaggaggga 120
guuguggcug cugcugagaa aaccaaacag gguguggcag aagcagcagg aaagacaaaa 180
gagggguguc ucuauguagg cuccaaaacc aaggagggag uggugcaugg uguggcaaca 240
guggcugaga agaccaaaga gcaagugaca aauguuggag gagcaguggu gacgggugug 300
acagcaguag cccagaagac aguggaggga gcagggagca uugcagcagc cacuggcuuu 360
gucaaaaagg accaguuggg caagaaugaa gaaggagccc cacaggaagg aauucuggaa 420
gauaugccug uggauccuga caaugaggcu uaugaaaugc cuucugagga aggguaucaa 480
gacuacgaac cugaagccua agaaauaucu uugcucccag uuucuugaga ucugcugaca 540
gauguuccau ccuguacaag ugcucaguuc caaugugccc agucaugaca uuucucaaag 600
uuuuuacagu guaucucgaa gucuuccauc agcagugauu gaaguaucug uaccugcccc 660
cacucagcau uucggugcuu cccuuucacu gaagugaaua caugguagca gggucuuugu 720
gugcugugga uuuuguggcu ucaaucuacg auguuaaaac aaauuaaaaa caccuaagug 780
acuaccacuu auuucuaaau ccucacuauu uuuuuguugc uguuguucag aaguuguuag 840
ugauuugcua ucauauauua uaagauuuuu aggugucuuu uaaugauacu gucuaagaau 900
aaugacguau ugugaaauuu guuaauauau auaauacuua aaaauaugug agcaugaaac 960
uaugcaccua uaaauacuaa auaugaaauu uuaccauuuu gcgauguguu uuauucacuu 1020
guguuuguau auaaauggug agaauuaaaa uaaaacguua ucucauugca aaaauauuuu 1080
auuuuuaucc caucucacuu uaauaauaaa aaucaugcuu auaagcaaca ugaauuaaga 1140
acugacacaa aggacaaaaa uauaaaguua uuaauagcca uuugaagaag gaggaauuuu 1200
agaagaggua gagaaaaugg aacauuaacc cuacacucgg aauucccuga agcaacacug 1260
ccagaagugu guuuugguau gcacugguuc cuuaaguggc ugugauuaau uauugaaagu 1320
gggguguuga agaccccaac uacuauugua gaguggucua uuucucccuu caauccuguc 1380
aauguuugcu uuacguauuu uggggaacug uuguuugaug uguaugugu uauaauuguu 1440 auacauuuuu aauugagccu uuuauuaaca uauauuguua uuuuugucuc gaaauaauuu 1500
uuuaguuaaa aucuauuuug ucugauauug gugugaaugc uguaccuuuc ugacaauaaa 1560
uaauauucga ccaugaauaa aaaaaaaaaa aaagugggu cccgggaacu aagcagugua 1620
gaagaugauu uugacuacac ccuccuuaga gagccauaag acacauuagc acauauuagc 1680
acauucaagg cucugagaga augugguuaa cuuuguuuaa cucagcauuc cucacuuuuu 1740
uuuuuuaauc aucagaaauu cucucucucu cucucucuuu uucucucgcu cucuuuuuuu 1800
uuuuuuuuuu acaggaaaug ccuuuaaaca ucguuggaac uaccagaguc accuuaaagg 1860
agaucaauuc ucuagacuga uaaaaauuuc auggccuccu uuaaauguug ccaaauauau 1920
gaauucuagg auuuuuccuu aggaaagguu uuucucuuuc agggaagauc uauuaacucc 1980
ccaugggugc ugaaaauaaa cuugauggug aaaaacucug uauaaauuaa uuuaaaaauu 2040
auuugguuuc ucuuuuuaau uauucugggg cauagucauu ucuaaaaguc acuaguagaa 2100
aguauaauuu caagacagaa uauucuagac augcuagcag uuuauaugua uucaugagua 2160
augugauaua uauugggcgc uggugaggaa ggaaggagga augagugacu auaaggaugg 2220
uuaccauaga aacuuccuuu uuuaccuaau ugaagagaga cuacuacaga gugcuaagcu 2280
gcauguguca ucuuacacua gagagaaaug guaaguuucu uguuuuauuu aaguuauguu 2340
uaagcaagga aaggauuugu uauugaacag uauauuucag gaagguuaga aaguggcggu 2400
uaggauauau uuuaaaucua ccuaaagcag cauauuuuaa aaauuuaaaa guauugguau 2460
uaaauuaaga aauagaggac agaacuagac ugauagcagu gaccuagaac aauuugagau 2520
uaggaaaguu gugaccauga auuuaaggau uuauguggau acaaauucuc cuuuaaagug 2580
uuucuucccu uaauauuuau cugacgguaa uuuuugagca gugaauuacu uuauauaucu 2640
uaauaguuua uuugggacca aacacuuaaa caaaaaguuc uuuaagucau auaagccuuu 2700
ucaggaagcu ugucucauau ucacuccga gacauucacc ugccaagugg ccugaggauc 2760
aauccagucc uagguuuauu uugcagacuu acauucuccc aaguuauuca gccucauaug 2820
acuccacggu cggcuuuacc aaaacaguuc agagugcacu uuggcacaca auugggaaca 2880
gaacaaucua augugugguu ugguauucca agugggucu uuuucagaau cucugcacua 2940
gugugagaug caaacauguu uccucaucuu ucuggcuuau ccaguaugua gcuauuugug 3000
acauaauaaa uauauacaua uaugaaaaua 3030

<210> SEQ ID NO 39
<211> LENGTH: 3312
<212> TYPE: RNA
<213> ORGANISM: Homo sapiens

<400> SEQUENCE: 39
ggcgacgacc agaaggggcc caagagaggg ggcgagcgac cgagcgccgc gacgcggaag 60
ugaggugcgu gcgggcugca gcgcagaccc cggcccggcc ccuccgagag cguccugggc 120
gcucccucac gccuugccuu caagccuucu gccuuuccac ccucgugagc ggagaacugg 180
gaguggccau ucgacgacag guuagcgggu uugccuccca cucccccagc cucgcgucgc 240
cggcucacag cggccuccuc uggggacagu ccccccggg ugccgccucc gcccuuccug 300
ugcgcuccuu uuccuucuuc uuuccuauua aauauuauuu gggaauuguu uaaauuuuuu 360
uuuuaaaaaa agagagaggc ggggaggagu cggaguugug gagaagcaga gggacucagu 420
gugguguaaa ggaauucauu agccauggau guauucauga aaggacuuuc aaaggccaag 480
gagggaguug uggcugcugc ugagaaaacc aaacagggug uggcagaagc agcaggaaag 540
acaaaagagg guguucucua uguaggcucc aaaaccaagg agggaguggu gcauggugug 600
gcaacagugg cugagaagac caaagagcaa gugacaaaug uuggaggagc agugguggacg 660 ggugugacag caguagccca gaagacagug gagggagcag ggagcauugc agcagccacu 720
ggcuuuguca aaaaggacca guugggcaag gaaggguauc aagacuacga accugaagcc 780
uaagaaauau cuuugcuccc aguuucuuga gaucugcuga cagauguucc auccuguaca 840
agugcucagu uccaaugugc ccagucauga cauuucucaa aguuuuuaca guguaucucg 900
aagucuucca ucagcaguga uugaaguauc uguaccugcc cccacucagc auuucggugc 960
uucccuuuca cugaagugaa uacaugguag cagggucuuu gugugcugug gauuuugugg 1020
cuucaaucua cgauguuaaa acaaauuaaa aacaccuaag ugacuaccac uuauuucuaa 1080
auccucacua uuuuuuuguu gcuguuguuc agaaguuguu agugauuugc uaucauauau 1140
uauaagauuu uuaggugucu uuuaaugaua cugucuaaga auaaugacgu auugugaaau 1200
uuguuaauau auauaauacu uaaaaauaug ugagcaugaa acuaugcacc uauaaaauacu 1260
aaauaugaaa uuuuaccauu uugcgaugug uuuuauucac uuguguuugu auauaaaugg 1320
ugagaauuaa aauaaaacgu uaucucauug caaaaauauu uuauuuuuau cccaucucac 1380
uuuaauaaua aaaaucaugc uuauaagcaa caugaauuaa gaacugacac aaaggacaaa 1440
aauauaaagu uauuaauagc cauuugaaga aggaggaauu uuagaagagg uagagaaaau 1500
ggaacauuaa cccuacacuc ggaauucccu gaagcaacac ugccagaagu guguuuuggu 1560
augcacuggu uccuuaagug gcugugauua auuauugaaa guggggguuu gaagacccca 1620
acuacuauug uagagugguc uauuucuccc uucaauccug ucaauguuug cuuuacguau 1680
uuuggggaac uguuguuuga uguguaugug uuuuauaauug uuauacauuu uuaauugagc 1740
cuuuuauuaa cauauauugu uauuuuuguc ucgaaauaau uuuuuaguua aaaucuauuu 1800
ugucugauau uggugugaau gcuguaccuu ucugacaaua aauaauauuc gaccaugaau 1860
aaaaaaaaaa aaaaaguggg uucccgggaa cuaagcagug uagaagauga uuuugacuac 1920
acccuccuua gagagccaua agacacauua gcacauauua gcacauucaa ggcucugaga 1980
gaauguguguu aacuuuguuu aacucagcau ucccucacuuu uuuuuuuuaa ucaucagaaa 2040
uucucucucu cucucucucu uuuucucucg cucucuuuuu uuuuuuuuuu uuacaggaaa 2100
ugccuuuaaa caucguugga acuaccagag ucaccuuaaa ggagaucaau ucucuagacu 2160
gauaaaaauu ucauggccuc cuuuaaaugu ugccaaauau augaauucua ggauuuuucc 2220
uuaggaaagg uuuuucucuu ucagggaaga ucuauuaacu ccccaugggu gcugaaaaua 2280
aacuugaugg ugaaaaacuc uguauaaauu aauuuaaaaa uuauuugguu ucucuuuuua 2340
auuauucugg ggcauaguca uuucuaaaag ucacuaguag aaaguauaau uucaagacag 2400
aauauucuag acaugcuagc aguuuauaug uauucaugag uaaugugaua uauauugggc 2460
gcuggugagg aaggaaggag gaaugaguga cuauaaggau gguuaccaua gaaacuuccu 2520
uuuuuaccua auugaagaga gacuacuaca gagugcuaag cugcaugugu caucuuacac 2580
uagagagaaa ugguaaguuu cuuguuuuau uuaaguuaug uuuaagcaag gaaaggauuu 2640
guuauugaac aguauauuuc aggaagguua gaaaguggcg guuaggauau auuuuaaauc 2700
uaccuaaagc agcauauuuu aaaaauuuaa aaguauuggu auuaaauuaa gaaauagagg 2760
acagaacuag acugauagca gugaccuaga acaauuugag auuaggaaag uugugaccau 2820
gaauuuaagg auuuaugugg auacaaauuc uccuuuaaag uguuucuucc cuuaauauuu 2880
aucugacggu aauuuuugag cagugaauua cuuuauauau cuuaauaguu uauuugggac 2940
caaacacuua aacaaaaagu ucuuuaaguc auauaagccu uuucaggaag cuugucucau 3000
auucacuccc gagacauuca ccugccaagu ggccugagga ucaauccagu ccuagguuua 3060
uuuugcagac uuacauucuc ccaaguuauu cagccucaua ugacuccacg gucggcuuua 3120
ccaaaacagu ucagagugca cuuuggcaca caauugggaa cagaacaauc uaaugugugg 3180
uuugguauuc caaguggggu cuuuuucaga aucucugcac uagugugaga ugcaaacaug 3240
uuuccucauc uuucuggcuu auccaguaug uagcuauuug ugacauaaua aauauauaca 3300
uauaugaaaa ua 3312

<210> SEQ ID NO 40
<211> LENGTH: 3099
<212> TYPE: RNA
<213> ORGANISM: Homo sapiens

<400> SEQUENCE: 40
gcuucuccau ucugguguga uccaggaaca gcugucuucc agcucugaaa gagggcugag 60
agauuaggcu gcuucuccgg gauccgcuuu uccccgggaa acgcgaggau gcuccaugga 120
gcuguggugu aaaggaauuc auuagccaug gauguauuca ugaaaggacu uucaaaggcc 180
aaggagggag uuguggcugc ugcugagaaa accaaacagg guguggcaga agcagcagga 240
aagacaaaag agggguguucu cuauguaggc uccaaaacca aggagggagu ggugcauggu 300
guggcaacag uggcugagaa gaccaaagag caagugacaa auguuggagg agcagguggug 360 acgggguguga cagcaguagc ccagaagaca guggagggag cagggagcau ugcagcagcc 420
acuggcuuug ucaaaaagga ccaguugggc aagaaugaag aaggagcccc acaggaagga 480
auucuggaag auaugccugu ggauccugac aaugaggcuu augaaaugcc uucugaggaa 540
ggguaucaag acuacgaacc ugaagccuaa gaaauaucuu ugcucccagu uucuugagau 600
cugcugacag auguuccauc cuguacaagu gcucaguucc aaugugccca gucaugacau 660
uucucaaagu uuuuacagug uaucucgaag ucuuccauca gcagugauug aaguaucugu 720
accugccccc acucagcauu ucggugcuuc ccuuucacug aagugaauac augguagcag 780
ggucuuugug ugcuguggau uuuguggcuu caaucuacga uguuaaaaca aauuaaaaac 840
accuaaguga cuaccacuua uuucuaaauc cucacuauuu uuuuguugcu guuguucaga 900
aguuguuagu gauuugcuau cauauauuau aagauuuuua ggugucuuuu aaugauacug 960
ucuaagaaua augacguauu gugaaauuug uuaauauaua uaauacuuaa aaauauguga 1020
gcaugaaacu augcaccuau aaauacuaaa uaugaaauuu uaccauuuug cgauguguuu 1080
uauucacuug uguuuguaua uaaaugguga gaauuaaaau aaaacguuau cucauugcaa 1140
aaauauuuua uuuuuauccc aucucacuuu aauaauaaaa aucaugcuua uaagcaacau 1200
gaauuaagaa cugacacaaa ggacaaaaau auaaaguuau uaauagccau uugaagaagg 1260
aggaauuuua gaagagguag agaaaaugga acauuaaccc uacacucgga auucccugaa 1320
gcaacacugc cagaagugug uuuugguaug cacugguucc uuaaguggcu gugauuaauu 1380
auugaaagug gggguguugaa gaccccaacu acuauuguag aguggucuau uucucccuuc 1440
aauccuguca auguuugcuu uacguauuuu ggggaacugu uguuugaugu guauguguuu 1500
auaauuguua uacauuuuua auugagccuu uuauuaacau auauuguuau uuuugucucg 1560
aaauaauuuu uuaguuaaaa ucuauuuugu cugauauugg ugugaaugcu guaccuuucu 1620
gacaauaaau aauauucgac caugaauaaa aaaaaaaaaa aagugggguuc ccgggaacua 1680 agcaguguag aagaugauuu ugacuacacc cuccuuagag agccauaaga cacauuagca 1740
cauauuagca cauucaaggc ucugagagaa ugugguuaac uuuguuuaac ucagcauucc 1800
ucacuuuuuu uuuuuaauca ucagaaauuc ucucucucuc ucucucuuuu ucucucgcuc 1860
ucuuuuuuuu uuuuuuuuua caggaaaugc cuuuaaacau cguuggaacu accagaguca 1920
ccuuaaagga gaucaauucu cuagacugau aaaaauuuca uggccuccuu uaaauguugc 1980

-continued caaauauaug aauucuagga uuuuuccuua ggaaagguuu uucucuuuca gggaagaucu 2040
auuaacuccc caugggugcu gaaaauaaac uugauggug a aaaacucugu auaaauuaau 2100
uuaaaaauua uuugguuucu cuuuuuaauu auucuggggc auagucauuu cuaaaaguca 2160
cuaguagaaa guauaauuuc aagacagaau auucuagaca ugcuagcagu uuauauguau 2220
ucaugaguaa ugugauauau auugggcgcu ggugaggaag gaaggaggaa ugagugacua 2280
uaaggauggu uaccauagaa acuuccuuuu uuaccuaauu gaagagagac uacuacagag 2340
ugcuaagcug caugugucau cuuacacuag agagaaaugg uaaguuucuu guuuuauuua 2400
aguuauguuu aagcaaggaa aggauuuguu auugaacagu auauuucagg aagguuagaa 2460
aguggcgguu aggauauauu uuaaaucuac cuaaagcagc auauuuuaaa aauuuaaaag 2520
uauugguauu aaauuaagaa auagaggaca gaacuagacu gauagcagug accuagaaca 2580
auuugagauu aggaaaguug ugaccaugaa uuuaaggauu uauguggaua caaauucucc 2640
uuuaaagugu uucuucccuu aauauuuauc ugacgguaau uuuugagcag ugaauuacuu 2700
uauauaucuu aauaguuuau uugggaccaa acacuuaaac aaaaaguucu uuaagucaua 2760
uaagccuuuu caggaagcuu gucucauauu cacucccgag acauucaccu gccaaguggc 2820
cugaggauca auccaguccu agguuuauuu ugcagacuua cauucuccca aguuauucag 2880
ccucauauga cuccacgguc ggcuuuacca aaacaguuca gagugcacuu uggcacacaa 2940
uugggaacag aacaaucuaa ugugugguuu gguauuccaa guggggucuu uuucagaauc 3000
ucugcacuag ugugagaugc aaacauguuu ccucaucuuu cuggcuuauc caguauguag 3060
cuauuuguga cauaauaaau auauacauau augaaaaua 3099

<210> SEQ ID NO 41
<211> LENGTH: 3041
<212> TYPE: RNA
<213> ORGANISM: Homo sapiens

<400> SEQUENCE: 41
ggcgacgacc agaaggggcc caagagaggg ggcgagcgac cgagcgccgc gacgcggaag 60 ugagugguggu guaaaggaau ucauuagcca uggauguauu caugaaagga cuuucaaagg 120
ccaaggaggg aguuguggcu gcugcugaga aaaccaaaca gggugugggca gaagcagcag 180 gaaagacaaa agaggguguu cucuauguag gcuccaaaac caaggaggga guggugcaug 240
guguggcaac aguggcugag aagaccaaag agcaagugac aaauguugga ggagcagugg 300
ugacgggugu gacagcagua gcccagaaga caguggaggg agcagggagc auugcagcag 360
ccacuggcuu ugucaaaaag gaccaguugg gcaagaauga agaaggagcc ccacaggaag 420
gaauucugga agauaugccu guggauccug acaaugaggc uuaugaaaug ccuucugagg 480
aaggguauca agacuacgaa ccugaagccu aagaaauauc uuugcuccca guuucuugag 540
aucugcugac agauguucca uccuguacaa gugcucaguu ccaaugugcc cagucaugac 600
auuucucaaa guuuuuacag uguaucucga agucuuccau cagcagugau ugaaguaucu 660
guaccugccc ccacucagca uuucggugcu ucccuuucac ugaagugaau acaugguagc 720
agggucuuug ugugcugugg auuuuguggc uucaaucuac gauguuaaaa caaauuaaaa 780
acaccuaagu gacuaccacu uauuucuaaa uccucacuau uuuuuuguug cuguuguuca 840
gaaguuguua gugauuugcu aucauauauu auaagauuuu uagguguucuu uuaaugauac 900 ugucuaagaa uaaugacgua uugugaaauu uguuaauaua uauaauacuu aaaaauaugu 960
gagcaugaaa cuaugcaccu auaaaauacua aauaugaaau uuuaccauuu ugcgaugugu 1020

```
uuuauucacu uguguuugua uauaaauggu gagaauuaaa auaaaacguu aucucauugc   1080
aaaaauauuu uauuuuuauc ccaucucacu uuaauaauaa aaaucaugcu uauaagcaac   1140
augaauuaag aacugacaca aaggacaaaa auauaaaguu auuaauagcc auuugaagaa   1200
ggaggaauuu uagaagaggu agagaaaaug gaacauuaac ccuacacucg gaauucccug   1260
aagcaacacu gccagaagug uguuuuggua ugcacugguu ccuuaagugg cugugauuaa   1320
uuauugaaag uggggguguug aagaccccaa cuacuauugu agaguggucu auuucucccu   1380
ucaauccugu caauguuugc uuuacguauu uuggggaacu guuguuugau guguaugugu   1440
uuauaauugu uauacauuuu uaauugagcc uuuuauuaac auauauuguu auuuuugucu   1500
cgaaauaauu uuuuaguuaa aaucuauuuu gucugauauu ggugugaaug cuguaccuuu   1560
cugacaauaa auaauauucg accaugaaua aaaaaaaaaa aaaagugggu ucccgggaac   1620
uaagcagugu agaagaugau uuugacuaca cccuccuuag agagccauaa gacacauuag   1680
cacauauuag cacauucaag gcucugagag aauguggutua acuuuguuua acucagcauu   1740
ccucacuuuu uuuuuuuaau caucagaaau ucucucucuc ucucucucuu uuucucucgc   1800
ucucuuuuuu uuuuuuuuuu uacaggaaau gccuuuaaac aucguuggaa cuaccagagu   1860
caccuuaaag gagaucaauu cucuagacug auaaaaauuu cauggccucc uuuaaauguu   1920
gccaaauaua ugaauucuag gauuuuuccu uaggaaaggu uuuucucuuu cagggaagau   1980
cuauuaacuc cccaugggug cugaaaauaa acuugauggu gaaaaacucu guauaaauua   2040
auuuaaaaau uauuugguuu cucuuuuuaa uuauucuggg gcauagucau uucuaaaagu   2100
cacuaguaga aaguauaauu ucaagacaga auauucuaga caugcuagca guuuauaugu   2160
auucaugagu aaugugauau auauugggcg cuggugagga aggaaggagg aaugagugac   2220
uauaaggaug guuaccauag aaacuuccuu uuuuaccuaa uugaagagag acuacuacag   2280
agugcuaagc ugcaugugucu aucuuacacu agagagaaau gguaaguuuc uuguuuuauu   2340
uaaguuaugu uuaagcaagg aaaggauuug uuauugaaca guauauuuca ggaagguuag   2400
aaaguggcgg uuaggauaua uuuuaaaucu accuaaagca gcauauuuua aaaauuuaaa   2460
aguauuggua uuaaaauuaag aaauagagga cagaacuaga cugauagcag ugaccuagaa   2520
caauuugaga uuaggaaagu ugugaccaug aauuuaagga uuuaugugga uacaaauucu   2580
ccuuuaaagu guuucuuccc uuaauauuua ucugacggua auuuuugagc agugaauuac   2640
uuuauauauc uuaauaguuu auuugggacc aaacacuuaa acaaaaaguu cuuuaaguca   2700
uauaagccuu uucaggaagc uugucucaua uucacucccg agacauucac cugccaagug   2760
gccugaggau caauccaguc cuagguuuau uuugcagacu uacauucucc caaguuauuc   2820
agccucauau gacuccacgg ucggcuuuac caaaacaguu cagagugcac uuuggcacac   2880
aauugggaac agaacaaucu aaugugugu uugguauucc aagugggguc uuuuucagaa   2940
ucucugcacu agugugagau gcaaacaugu uuccucaucu uucuggcuua uccaguaugu   3000
agcuauuugu gacauaauaa auauauacau auaugaaaau a                       3041
```

<210> SEQ ID NO 42
<211> LENGTH: 3465
<212> TYPE: RNA
<213> ORGANISM: Homo sapiens

<400> SEQUENCE: 42

```
ggcgacgacc agaaggggcc caagagaggg ggcgagcgac cgagcgccgc gacgcggaag     60
```

-continued

```
ugaggugcgu gcgggcugca gcgcagaccc cggcccggcc ccuccgagag cguccugggc    120
gcucccucac gccuugccuu caagccuucu gccuuuccac ccucgugagc ggagaacugg    180
gaguggccau ucgacgacag guuagcgggu uugccuccca cucccccagc cucgcgucgc    240
cggcucacag cggccuccuc uggggacagu cccccccggg ugccgccucc gcccuuccug    300
ugcgcuccuu uuccuucuuc uuuccuauua aauauuauuu gggaauuguu uaaauuuuuu    360
uuuuaaaaaa agagagaggc ggggaggagu cggaguugug gagaagcaga gggacucagg    420
gcugagagau uaggcugcuu cuccgggauc cgcuuuuccc cgggaaacgc gaggaugcuc    480
cauggagcug ugguguaaag gaauucauua gccauggaug uauucaugaa aggacuuuca    540
aaggccaagg agggaguugu ggcugcugcu gagaaaacca aacagggugu ggcagaagca    600
gcaggaaaga caaaagaggg uguucucuau guaggcucca aaaccaagga gggaguggug    660
cauggugugg caacaguggc ugagaagacc aaagagcaag ugacaaaugu uggaggagca    720
guggugacgg gugugacagc aguagcccag aagacagugg agggagcagg gagcauugca    780
gcagccacug gcuuugucaa aaaggaccag uugggcaaga augaagaagg agccccacag    840
gaaggaauuc uggaagauau gccuguggau ccugacaaug aggcuuauga aaugccuucu    900
gaggaagggu aucaagacua cgaaccugaa gccuaagaaa uaucuuugcu cccaguuucu    960
ugagaucugc ugacagaugu uccauccugu acaagugcuc aguuccaaug ugcccaguca   1020
ugacauuucu caaaguuuuu acagugugauc ucgaagucuu ccaucagcag ugauugaagu   1080
aucuguaccu gcccccacuc agcauuucgg ugcuucccuu ucacugaagu gaauacaugg   1140
uagcaggguc uuugugugcu guggauuuug uggcuucaau cuacgauguu aaaacaaauu   1200
aaaaacaccu aagugacuac cacuuauuuc uaaauccuca cuauuuuuuu guugcuguug   1260
uucagaaguu guuagugauu ugcuaucaua uauuauaaga uuuuuaggug ucuuuuaaug   1320
auacugucua agaauaauga cguauuguga aauuuguuaa uauauauaau acuuaaaaau   1380
augugagcau gaaacuaugc accuauaaau acuaaauaug aaauuuuacc auuuugcgau   1440
guguuuuauu cacuuguguu uguauauaaa uggugagaau uaaaauaaaa cguuaucuca   1500
uugcaaaaau auuuuauuuu uaucccaucu cacuuuaaua auaaaaauca ugcuuauaag   1560
caacaugaau uaagaacuga cacaaaggac aaaaauauaa aguuauuaau agccauuuga   1620
agaaggagga auuuuagaag agguagagaa aauggaacau uaacccuaca cucggaauuc   1680
ccugaagcaa cacugccaga aguguguuuu gguaugcacu gguuccuuaa guggcuguga   1740
uuaauuauug aaaguggggu guugaagacc ccaacuacua uuguagagug gucuauuucu   1800
cccuucaauc cugucaaugu uugcuuuacg uauuuugggg aacuguuguu ugauguguau   1860
guguuuauaa uuguuauaca uuuuuaauug agccuuuuau uaacauauau uguuauuuuu   1920
gucucgaaau aauuuuuuag uuaaaaucua uuuugucuga uauuggugug aaugcuguac   1980
cuuucugaca auaaaauaaua uucgaccaug aauaaaaaaa aaaaaaaagu ggguucccgg   2040
gaacuaagca guguagaaga ugauuuugac uacacccucc uuagagagcc auaagacaca   2100
uuagcacaua uuagcacauu caaggcucug agagaaugug guuaacuuug uuuaacucag   2160
cauuccucac uuuuuuuuuu uaaucaucag aaauucucuc ucucucucuc ucuuuuucuc   2220
ucgcucucuu uuuuuuuuuu uuuuuacagg aaaugccuuu aaacaucguu ggaacuacca   2280
gagucaccuu aaaggagauc aauucucuag acugauaaaa auuucauggc cuccuuuaaa   2340
uguugccaaa uauaugaauu cuaggauuuu uccuuaggaa agguuuuucu cuuucaggga   2400
agaucuauua acuccccaug ggugcugaaa auaaacuuga uggugaaaaa cucuguauaa   2460
```

auuaauuuaa aaauuauuug guuucucuuu uuaauuauuc uggggcauag ucauuucuaa 2520
aagucacuag uagaaaguau aauuucaaga cagaauauuc uagacaugcu agcaguuuau 2580
auguauucau gaguaaugug auauauauug ggcgcuggug aggaaggaag gaggaaugag 2640
ugacuauaag gaugguuacc auagaaacuu ccuuuuuuac cuaauugaag agagacuacu 2700
acagagugcu aagcugcaug ugucaucuua cacuagagag aaaugguaag uuucuuguuu 2760
uauuuaaguu auguuuaagc aaggaaagga uuuguuauug aacaguauau uucaggaagg 2820
uuagaaagug gcgguuagga uauauuuuaa aucuaccuaa agcagcauau uuuaaaaauu 2880
uaaaaguauu gguauuaaau uaagaaauag aggacagaac uagacugaua gcagugaccu 2940
agaacaauuu gagauuagga aaguugugac caugaauuua aggauuuaug uggauacaaa 3000
uucuccuuua aaguguuucu ucccuuaaua uuuaucugac gguaauuuuu gagcagugaa 3060
uuacuuuaua uaucuuaaua guuuauuugg gaccaaacac uuaaacaaaa aguucuuuaa 3120
gucauauaag ccuuuucagg aagcuugucu cauauucacu cccgagacau ucaccugcca 3180
aguggccuga ggaucaaucc aguccuaggu uuauuuugca gacuuacauu cucccaaguu 3240
auucagccuc auaugacucc acggucggcu uuaccaaaac aguucagagu gcacuuuggc 3300
acacaauugg gaacagaaca aucuaaugug ugguuuggua uuccaagugg ggucuuuuuc 3360
agaaucucug cacuagugug agaugcaaac auguuuccuc aucuuucugg cuuauccagu 3420
auguagcuau uugugacaua auaaauauau acauauauga aaaua 3465

<210> SEQ ID NO 43
<211> LENGTH: 3091
<212> TYPE: RNA
<213> ORGANISM: Homo sapiens

<400> SEQUENCE: 43
gagugugagc ggcgccugcu cagggguagau agcugagggc gggggguggau guuggaugga 60 uuagaaccau cacacuuggg ccugcuguuu gccugaguuu gaaccacacc ccgauguggu 120
guaaaggaau ucauuagcca uggauguauu caugaaagga cuuucaaagg ccaaggaggg 180
aguuguggcu gcugcugaga aaaccaaaca gggugugggca gaagcagcag gaaagacaaa 240
agaggguguu cucuauguag gcuccaaaac caaggaggga guggugcaug guguggcaac 300
aguggcugag aagaccaaag agcaagugac aaauguugga ggagcagugg ugacgggugu 360
gacagcagua gcccagaaga caguggaggg agcagggagc auugcagcag ccacuggcuu 420
ugucaaaaag gaccaguugg gcaagaauga agaaggagcc ccacaggaag gaauucugga 480
agauaugccu guggauccug acaaugaggc uuaugaaaug ccuucugagg aagguauca 540 agacuacgaa ccugaagccu aagaaauauc uuugcuccca guuucuugag aucugcugac 600
agauguucca uccuguacaa gugcucaguu ccaaugugcc cagucaugac auuucucaaa 660
guuuuuacag uguaucucga agucuuccau cagcagugau ugaaguaucu guaccugccc 720
ccacucagca uuucggugcu ucccuuucac ugaagugaau acaugguagc agggucuuug 780
ugugcugugg auuuuguggc uucaaucuac gauguuaaaa caaauuaaaa acaccuaagu 840
gacuaccacu uauuucuaaa uccucacuau uuuuuuguug cuguuguuca gaaguuguua 900
gugauuugcu aucauauauu auaagauuuu uaggugucuu uuaaugauac ugucuaagaa 960
uaaugacgua uugugaaauu uguuaauaua uauaauacuu aaaaauaugu gagcaugaaa 1020
cuaugcaccu auaaauacua aauaugaaau uuuaccauuu ugcgaugugu uuuauucacu 1080
uguguuugua uauaaaauggu gagaauuaaa auaaaacguu aucucauugc aaaaauauuu 1140
uauuuuuauc ccaucucacu uuaauaauaa aaaucaugcu uauaagcaac augaauuaag 1200
aacugacaca aaggacaaaa auauaaaguu auuaauagcc auuugaagaa ggaggaauuu 1260
uagaagaggu agagaaaaug gaacauuaac ccuacacucg gaauucccug aagcaacacu 1320
gccagaagug uguuuuggua ugcacugguu ccuuaagugg cugugauuaa uuauugaaag 1380 uggggguguug aagaccccaa cuacuauugu agaguggucu auuucucccu ucaauccugu 1440
caauguuugc uuuacguauu uuggggaacu guuguuugau guguaugugu uuauaauugu 1500
uauacauuuu uaauugagcc uuuuauuaac auauauuguu auuuuugucu cgaaauaauu 1560
uuuuaguuaa aaucuauuuu gucugauauu ggugugaaug cuguaccuuu cugacaauaa 1620
auaauauucg accaugaaua aaaaaaaaaa aaaaguggguu ucccgggaac uaagcagugu 1680
agaagaugau uuugacuaca cccuccuuag agagccauaa gacacauuag cacauauuag 1740
cacauucaag gcucugagag aauguggua acuuuguuua acucagcauu ccucacuuuu 1800
uuuuuuuaau caucagaaau ucucucucuc ucucucucuu uuucucucgc ucucuuuuuu 1860
uuuuuuuuuu uacaggaaau gccuuuaaac aucguuggaa cuaccagagu caccuuaaag 1920
gagaucaauu cucuagacug auaaaaauuu cauggccucc uuuaaauguu gccaaauaua 1980
ugaauucuag gauuuuuccu uaggaaaggu uuuucucuuu cagggaagau cuauuaacuc 2040
cccaugggug cugaaaauaa acuugauggu gaaaaacucu guauaaauua auuuaaaaau 2100
uauuugguuu cucuuuuuaa uuauucuggg gcauagucau uucuaaaagu cacuaguaga 2160
aaguauaauu ucaagacaga auauucuaga caugcuagca guuuauaugu auucaugagu 2220
aaugugauau auauugggcg cuggugagga aggaaggagg aaugagugac uauaaggaug 2280
guuaccauag aaacuuccuu uuuuaccuaa uugaagagag acuacuacag agugcuaagc 2340 ugcaugugc aucuuacacu agagagaaau gguaaguuuc uuguuuuauu uaaguuaugu 2400
uuaagcaagg aaaggauuug uuauugaaca guauauuuca ggaagguuag aaaguggcgg 2460
uuaggauaua uuuuaaaucu accuaaagca gcauauuuua aaaauuuaaa aguauuggua 2520
uuaaauuaag aaauagagga cagaacuaga cugauagcag ugaccuagaa caauuugaga 2580
uuaggaaagu ugugaccaug aauuuaagga uuuaugugga uacaaauucu ccuuuaaagu 2640
guuucuuccc uuaauauuua ucugacggua auuuuugagc agugaauuac uuuauauauc 2700
uuaauaguuu auuugggacc aaacacuuaa acaaaaaguu cuuuaaguca uauaagccuu 2760
uucaggaagc uugucucaua uucacucccg agacauucac cugccaagug gccugaggau 2820
caauccaguc cuagguuuau uuugcagacu uacauucucc caaguuauuc agccucauau 2880
gacuccacgg ucggcuuuac caaaacaguu cagagugcac uuuggcacac aauugggaac 2940
agaacaaucu aaugugugggu uugguauucc aaguggggguc uuuuucagaa ucucugcacu 3000
agugugagau gcaaacaugu uuccucaucu uucuggcuua uccaguaugu agcuauuugu 3060
gacauaauaa auauauacau auaugaaaau a 3091

<210> SEQ ID NO 44
<211> LENGTH: 2984
<212> TYPE: RNA
<213> ORGANISM: Homo sapiens

<400> SEQUENCE: 44
gcucuaauuc ucugcaccuu cucaagcauu gugcagauug guuucugga uuaucagccu 60 gaaggacaaa acgaagaaac agccauuagc uccugucucc cauugucuga gagcugccac 120

-continued

```
uaggauauua acuuccugaa auucugcaga aaucuccucu uacuuuggca cuggagaugc    180
ccauacgcag aaagcaaaaa ggcacagcau auuuaaggaa gcucauaaga aacagugcau    240
ccagaagugg cgagaauugg aggaauggac augagacucu aagaaccagc gccuuugaug    300
uuccuuuuga ucuguuaugu agcucuucuu guacacagaa ugaagaagga gccccacagg    360
aaggaauucu ggaagauaug ccuguggauc cugacaauga ggcuuaugaa augccuucug    420
aggaagggua ucaagacuac gaaccugaag ccuaagaaau aucuuugcuc ccaguuucuu    480
gagaucugcu gacagauguu ccauccugua caagugcuca guuccaaugu gcccagucau    540
gacauuucuc aaaguuuuua caguguaucu cgaagucuuc caucagcagu gauugaagua    600
ucuguaccug cccccacuca gcauuucggu gcuucccuuu cacugaagug aauacauggu    660
agcagggucu uugugugcug uggauuuugu ggcuucaauc uacgauguua aaacaaauua    720
aaaacaccua agugacuacc acuuauuucu aaauccucac uauuuuuuug uugcuguugu    780
ucagaaguug uuagugauuu gcuaucauau auuauaagau uuuuaggugu cuuuuaauga    840
uacugucuaa gaauaaugac guauugugaa auuuguuaau auauauaaua cuuaaaaaua    900
ugugagcaug aaacuaugca ccuauaaaua cuaaauauga aauuuuacca uuuugcgaug    960
uguuuuauuc acuuguguuu guauauaaau ggugagaauu aaaauaaaac guuaucucau   1020
ugcaaaaaua uuuuauuuuu aucccaucuc acuuuaauaa uaaaaaucau gcuuauaagc   1080
aacaugaauu aagaacugac acaaaggaca aaaauauaaa guuauuaaua gccauuugaa   1140
gaaggaggaa uuuuagaaga gguagagaaa auggaacauu aacccuacac ucggaauucc   1200
cugaagcaac acugccagaa guguguuuug guaugcacug guuccuuaag uggcugugau   1260
uaauuauuga aaguggggug uugaagaccc caacuacuau uguagagugg ucuauuucuc   1320
ccuucaaucc ugucaauguu ugcuuuacgu auuuugggga acuguuguuu gauguguaug   1380
uguuuauaau uguuauacau uuuuaauuga gccuuuuauu aacauauauu guuauuuuug   1440
ucucgaaaua auuuuuuagu uaaaaucuau uuugucugau auuggaguga augcuguacc   1500
uuucugacaa uaaauaauau ucgaccauga auaaaaaaaa aaaaaaagug gguucccggg   1560
aacuaagcag uguagaagau gauuuugacu acacccuccu uagagagcca uaagacacau   1620
uagcacauau uagcacauuc aaggcucuga gagaaugugg uuaacuuugu uuaacucagc   1680
auuccucacu uuuuuuuuuu aaucaucaga aauucucucu cucucucucu cuuuuucucu   1740
cgcucucuuu uuuuuuuuuu uuuuacagga aaugccuuua aacaucguug gaacuaccag   1800
agucaccuua aaggagauca auucucuaga cugauaaaaa uuucauggcc uccuuuaaau   1860
guugccaaau auaugaauuc uaggauuuuu ccuuaggaaa gguuuuucuc uuucagggaa   1920
gaucuauuaa cuccccaugg gugcugaaaa uaaacuugau ggugaaaaac ucuguauaaa   1980
uuaauuuaaa aauuauuugg uuucucuuuu uaauuauucu ggggcauagu cauuucuaaa   2040
agucacuagu agaaaguaua auuucaagac agaauauucu agacaugcua gcaguuuaua   2100
uguauucaug aguaauguga uauauauugg gcgcugguga ggaaggaagg aggaaugagu   2160
gacuauaagg augguuacca uagaaacuuc cuuuuuuacc uaauugaaga gagacuacua   2220
cagagugcua agcugcaugu gucaucuuac acuagagaga aaugguaagu uucuuguuuu   2280
auuuaaguua uguuuaagca aggaaaggau uuguuauuga acaguauauu ucaggaaggu   2340
uagaaagugg cgguuaggau auauuuuaaa ucuaccuaaa gcagcauauu uuaaaaauuu   2400
aaaaguauug guauuaaauu aagaaauaga ggacagaacu agacugauag cagugaccua   2460
```

```
gaacaauuug agauuaggaa aguugugacc augaauuuaa ggauuuaugu ggauacaaau   2520

ucuccuuuaa aguguuucuu cccuuaauau uuaucugacg guaauuuuug agcagugaau   2580

uacuuuauau aucuuaauag uuuauuuggg accaaacacu uaaacaaaaa guucuuuaag   2640

ucauauaagc cuuuucagga agcuugucuc auauucacuc ccgagacauu caccugccaa   2700

guggccugag gaucaaucca guccuagguu uauuuugcag acuuacauuc ucccaaguua   2760

uucagccuca uaugacucca cggucggcuu uaccaaaaca guucagagug cacuuuggca   2820

cacaauuggg aacagaacaa ucuaaugugu gguuugguau uccaaguggg gucuuuuuca   2880

gaaucucugc acuaguguga gaugcaaaca uguuuccuca ucuuucuggc uuauccagua   2940

uguagcuauu ugugacauaa uaaauauaua cauauaugaa aaua                    2984
```

<210> SEQ ID NO 45
<211> LENGTH: 140
<212> TYPE: PRT
<213> ORGANISM: Homo sapiens

<400> SEQUENCE: 45

```
Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
            20                  25                  30

Thr Lys Glu Gly Val Leu Tyr Val Gly Ser Lys Thr Lys Glu Gly Val
        35                  40                  45

Val His Gly Val Ala Thr Val Ala Glu Lys Thr Lys Glu Gln Val Thr
    50                  55                  60

Asn Val Gly Gly Ala Val Val Thr Gly Val Thr Ala Val Ala Gln Lys
65                  70                  75                  80

Thr Val Glu Gly Ala Gly Ser Ile Ala Ala Ala Thr Gly Phe Val Lys
                85                  90                  95

Lys Asp Gln Leu Gly Lys Asn Glu Glu Gly Ala Pro Gln Glu Gly Ile
            100                 105                 110

Leu Glu Asp Met Pro Val Asp Pro Asp Asn Glu Ala Tyr Glu Met Pro
        115                 120                 125

Ser Glu Glu Gly Tyr Gln Asp Tyr Glu Pro Glu Ala
    130                 135                 140
```

<210> SEQ ID NO 46
<211> LENGTH: 112
<212> TYPE: PRT
<213> ORGANISM: Homo sapiens

<400> SEQUENCE: 46

```
Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
            20                  25                  30

Thr Lys Glu Gly Val Leu Tyr Val Gly Ser Lys Thr Lys Glu Gly Val
        35                  40                  45

Val His Gly Val Ala Thr Val Ala Glu Lys Thr Lys Glu Gln Val Thr
    50                  55                  60

Asn Val Gly Gly Ala Val Val Thr Gly Val Thr Ala Val Ala Gln Lys
65                  70                  75                  80

Thr Val Glu Gly Ala Gly Ser Ile Ala Ala Ala Thr Gly Phe Val Lys
                85                  90                  95
```

```
Lys Asp Gln Leu Gly Lys Glu Gly Tyr Gln Asp Tyr Glu Pro Glu Ala
            100                 105                 110


<210> SEQ ID NO 47
<211> LENGTH: 92
<212> TYPE: PRT
<213> ORGANISM: Homo sapiens

<400> SEQUENCE: 47

Met Pro Ile Arg Arg Lys Gln Lys Gly Thr Ala Tyr Leu Arg Lys Leu
1               5                   10                  15

Ile Arg Asn Ser Ala Ser Arg Ser Gly Glu Asn Trp Arg Asn Gly His
            20                  25                  30

Glu Thr Leu Arg Thr Ser Ala Phe Asp Val Pro Phe Asp Leu Leu Cys
        35                  40                  45

Ser Ser Ser Cys Thr Gln Asn Glu Glu Gly Ala Pro Gln Glu Gly Ile
    50                  55                  60

Leu Glu Asp Met Pro Val Asp Pro Asp Asn Glu Ala Tyr Glu Met Pro
65                  70                  75                  80

Ser Glu Glu Gly Tyr Gln Asp Tyr Glu Pro Glu Ala
                85                  90


<210> SEQ ID NO 48
<211> LENGTH: 90
<212> TYPE: DNA
<213> ORGANISM: Unknown
<220> FEATURE:
<221> NAME/KEY: source
<223> OTHER INFORMATION: /note="Description of Unknown:
      APP target sequence"

<400> SEQUENCE: 48

tatcaagacg gaggagatct ctgaagtgaa gatggatgca gaattccgac atgactcagg     60

atatgaagtt catcatcaaa aattggtgtt                                       90


<210> SEQ ID NO 49
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 49

tctgcaccca tcttcacttc                                                  20


<210> SEQ ID NO 50
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 50

tcatatcctg agtcatgtcg gaattctgca cccatcttca cttcagagat ctcctccgtc     60


<210> SEQ ID NO 51
<211> LENGTH: 60
<212> TYPE: DNA
<213> ORGANISM: Artificial Sequence
<220> FEATURE:
```

<221> NAME/KEY: source
<223> OTHER INFORMATION: /note="Description of Artificial Sequence:
      Synthetic oligonucleotide"

<400> SEQUENCE: 51
tcatatcctg agtcatgccg gaattctgca cccatcttca cttcagagac ctcctccgtc     60

<210> SEQ ID NO 52
<211> LENGTH: 105
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: misc_feature
<222> LOCATION: (46)..(105)
<223> OTHER INFORMATION: /note="This region may encompass one of the
      following sequences: 'tctgcacccatcttcacttc' or
      'tcatatcctgagtcatgtcggaattctgc acccatcttcacttcagagatctcctccgtc'
      or 'tcatatcctgagtcatgc
      cggaattctgcacccatcttcacttcagagacctcctccgtc'"

<400> SEQUENCE: 52
gtggaatagt ataacaatat gctaaatgtt gttatagtat cccacnnnnn nnnnnnnnnn     60
nnnnnnnnnn nnnnnnnnnn nnnnnnnnnn nnnnnnnnnn nnnnn                    105

<210> SEQ ID NO 53
<211> LENGTH: 150
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: misc_feature
<222> LOCATION: (46)..(105)
<223> OTHER INFORMATION: /note="This region may encompass one of the
      following sequences: 'tctgcacccatcttcacttc' or
      'tcatatcctgagtcatgtcggaattctgc acccatcttcacttcagagatctcctccgtc'
      or 'tcatatcctgagtcatgc
      cggaattctgcacccatcttcacttcagagacctcctccgtc'"

<400> SEQUENCE: 53
gtggaatagt ataacaatat gctaaatgtt gttatagtat cccacnnnnn nnnnnnnnnn     60
nnnnnnnnnn nnnnnnnnnn nnnnnnnnnn nnnnnnnnnn nnnnngtgga atagtataac    120
aatatgctaa atgttgttat agtatcccac                                      150

<210> SEQ ID NO 54
<211> LENGTH: 323
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: misc_feature
<222> LOCATION: (117)..(176)
<223> OTHER INFORMATION: /note="This region may encompass one of the
      following sequences: 'tctgcacccatcttcacttc' or
      'tcatatcctgagtcatgtcggaattctgc acccatcttcacttcagagatctcctccgtc'
      or 'tcatatcctgagtcatgc
      cggaattctgcacccatcttcacttcagagacctcctccgtc'"

<400> SEQUENCE: 54
ggccgggcgc ggtggctcac gcctgtaatc ccagcacttt gggaggccga ggcggggaga     60
ttgcttgagc ccaggagttc gagaccagcc tgggcaacat agcgagaccc cgtctcnnnn 120
nnnnnnnnnn nnnnnnnnnn nnnnnnnnnn nnnnnnnnnn nnnnnnnnnn nnnnnnagcc 180
gggcgtggtg gcgcgcgcct gtagtcccag ctactcggga ggctgaggca ggaggatcgc 240
ttgagcccag gagttcgagg ctgcagtgag ctatgatcgc gccactgcac tccagcctgg 300
gcgacagagc gagaccctgt ctc 323

<210> SEQ ID NO 55
<211> LENGTH: 5905
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 55
ctcgagtagt tattaatagt aatcaattac ggggtcatta gttcatagcc catatatgga 60
gttccgcgtt acataactta cggtaaatgg cccgcctggc tgaccgccca acgacccccg 120
cccattgacg tcaataatga cgtatgttcc catagtaacg ccaataggga ctttccattg 180
acgtcaatgg gtggagtatt tacggtaaac tgcccacttg gcagtacatc aagtgtatca 240
tatgccaagt acgcccccta ttgacgtcaa tgacggtaaa tggcccgcct ggcattatgc 300
ccagtacatg accttatggg actttcctac ttggcagtac atctacgtat tagtcatcgc 360
tattaccatg gtgatgcggt tttggcagta catcaatggg cgtggatagc ggtttgactc 420
acggggattt ccaagtctcc accccattga cgtcaatggg agtttgtttt ggcaccaaaa 480
tcaacgggac tttccaaaat gtcgtaacaa ctccgcccca ttgacgcaaa tgggcggtag 540
gcgtgtacgg tgggaggtct atataagcag agctggttta gtgaaccgtc agatccgcta 600
gggatcctct agtcagctga cgcgtgctag cgcggccgca tcgataatgc tccctggact 660
tgctttgctg cttttggcag cctggactgc tcgagcactc gaggtcccaa cggatggaaa 720
cgcgggtctt ttggcagagc ctcaaatagc aatgttttgc ggaagactca acatgcatat 780
gaacgttcag aatgggaaat gggactccga ccccagtggt acgaagacat gtattgacac 840
aaaggaggga atactccagt actgccagga agtgtacccg gagcttcaga ttacgaatgt 900
ggtagaggct aatcaacccg taactatcca aaattggtgt aagagaggca ggaagcaatg 960
caagactcat cctcatttcg taattccgta tcgatgtttg gtgggagaat ttgtctctga 1020
cgcattgctt gttcctgaca agtgtaagtt tcttcaccag gaacgcatgg acgtgtgcga 1080
gacacacttg cactggcata ccgttgcgaa ggagacgtgt tccgaaaaga gtacaaatct 1140
ccatgactac ggcatgttgc tcccgtgcgg aatagataag ttccgaggcg tggagtttgt 1200
atgctgtccg ctggcagagg agagcgataa tgtcgattcc gcagatgccg aagaggacga 1260
cagcgacgtc tggtggggag gagcggacac tgattacgct gatggtagtg aggacaaagt 1320
agtcgaggtg gcagaagaag aagaagtggc ggaggttgaa gaagaagagg cagacgatga 1380
cgaagacgat gaggacggtg atgaggtaga agaagaagcg gaagaaccgt acgaagaagc 1440
tacggaacgc actacaagta ttgctaccac tacaaccact acaaccgaat cagttgagga 1500
agtggtgcga gtccccacta cggctgccag tacaccggat gccgtcgaca aatacctgga 1560
gactcctggc gacgaaaacg aacatgctca tttccagaag gcgaaggaac gcctcgaagc 1620
aaagcacaga gagagaatgt cacaggtaat gagggaatgg gaggaggcgg aacgccaagc 1680

-continued

```
aaagaacctg cctaaagcgg acaagaaggc agttatccaa catttccaag agaaagtgga   1740
gagtctcgaa caggaggcag cgaacgagag gcaacaattg gtagaaacgc acatggcgag   1800
ggtggaagct atgctcaatg accgaagacg acttgccttg gaaaattaca ttactgccct   1860
tcaagccgtc ccaccgcgcc cacgccatgt ctttaacatg cttaagaagt atgttcgagc   1920
tgaacagaag gatcggcaac acaccctgaa acacttcgaa catgtcagaa tggttgaccc   1980
gaagaaggct gcacagattc gaagtcaagt tatgacccat ttgagggtaa tatatgagag   2040
aatgaaccaa agtctgagcc ttctctacaa tgtccccgct gtggccgagg aaattcagga   2100
cgaagtcgat gagctcctgc aaaaggagca gaactactct gacgatgtac ttgctaatat   2160
gatttcagag ccaaggatca gttatggaaa cgacgccctg atgcctagtc ttaccgaaac   2220
caagactacg gtagaactcc ttcccgttaa cggagagttc agcttggacg accttcagcc   2280
ttggcactca ttcggagctg attccgtacc agccaatacg gagaatgaag tagagcccgt   2340
agacgcaaga cctgcagcgg acagagggct gacgacgaga cccggtagcg gtttgacaaa   2400
tatcaagacg gaggagatct ctgaagtgaa gatggatgca gaattccgac atgactcagg   2460
atatgaagtt catcatcaaa aattggtgtt ctttgcagaa gatgtcggtt ctaacaaggg   2520
tgctatcata ggccttatgg tgggtggcgt cgtgattgcg accgtgatag ttattacgct   2580
tgtcatgctg aagaagaaac agtatacgtc catccatcac ggtgtggtag aggtagatgc   2640
ggccgtaact cccgaagagc gccatctttc taagatgcag cagaatggat acgagaaccc   2700
cacgtacaaa ttctttgagc aaatgcaaaa ctgatgtcga cgatatctcc agaggatcat   2760
aatcagccat accacatttg tagaggtttt acttgcttta aaaaacctcc cacacctccc   2820
cctgaacctg aaacataaaa tgaatgcaat tgttgttgtt aacttgttta ttgcagctta   2880
taatggttac aaataaagca atagcatcac aaatttcaca aataaagcat ttttttcact   2940
gccccgagct tcctcgctca ctgactcgct gcgctcggtc gttcggctgc ggcgagcggt   3000
atcagctcac tcaaaggcgg taatacggtt atccacagaa tcaggggata acgcaggaaa   3060
gaacatgtga gcaaaaggcc agcaaaaggc caggaaccgt aaaaaggccg cgttgctggc   3120
gtttttccat aggctccgcc cccctgacga gcatcacaaa aatcgacgct caagtcagag   3180
gtggcgaaac ccgacaggac tataaagata ccaggcgttt ccccctggaa gctccctcgt   3240
gcgctctcct gttccgaccc tgccgcttac cggatacctg tccgcctttc tcccttcggg   3300
aagcgtggcg ctttctcata gctcacgctg taggtatctc agttcggtgt aggtcgttcg   3360
ctccaagctg ggctgtgtgc acgaaccccc cgttcagccc gaccgctgcg ccttatccgg   3420
taactatcgt cttgagtcca acccggtaag acacgactta tcgccactgg cagcagccac   3480
tggtaacagg attagcagag cgaggtatgt aggcggtgct acagagttct tgaagtggtg   3540
gcctaactac ggctacacta gaagaacagt atttggtatc tgcgctctgc tgaagccagt   3600
taccttcgga aaaagagttg gtagctcttg atccggcaaa caaaccaccg ctggtagcgg   3660
tggttttttt gtttgcaagc agcagattac gcgcagaaaa aaaggatctc aagaagatcc   3720
tttgatcttt tctacggggt ctgacgctca gtggaacgaa aactcacgtt aagggatttt   3780
ggtcatgaga ttatcaaaaa ggatcttcac ctagatcctt ttaaattaaa aatgaagttt   3840
taaatcaatc taaagtatat atgagtaaac ttggtctgac agttaccaat gcttaatcag   3900
tgaggcacct atctcagcga tctgtctatt tcgttcatcc atagttgcct gactccccgt   3960
cgtgtagata actacgatac gggagggctt accatctggc cccagtgctg caatgatacc   4020
gcgagaccca cgctcaccgg ctccagattt atcagcaata aaccagccag ccggaagggc   4080
```

cgagcgcaga agtggtcctg caactttatc cgcctccatc cagtctatta attgttgccg 4140
ggaagctaga gtaagtagtt cgccagttaa tagtttgcgc aacgttgttg ccattgctac 4200
aggcatcgtg gtgtcacgct cgtcgtttgg tatggcttca ttcagctccg gttcccaacg 4260
atcaaggcga gttacatgat cccccatgtt gtgcaaaaaa gcggttagct ccttcggtcc 4320
tccgatcgtt gtcagaagta agttggccgc agtgttatca ctcatggtta tggcagcact 4380
gcataattct cttactgtca tgccatccgt aagatgcttt tctgtgactg gtgagtactc 4440
aaccaagtca ttctgagaat agtgtatgcg gcgaccgagt tgctcttgcc cggcgtcaac 4500
acgggataat accgcgccac atagcagaac tttaaaagtg ctcatcattg gaaaacgttc 4560
ttcggggcga aaactctcaa ggatcttacc gctgttgaga tccagttcga tgtaacccac 4620
tcgtgcaccc aactgatctt cagcatcttt tactttcacc agcgtttctg ggtgagcaaa 4680
aacaggaagg caaaatgccg caaaaaaggg aataagggcg acacggaaat gttgaatact 4740
catactcttc ctttttcaat attattgaag catttatcag ggttattgtc tcatgagcgg 4800
atacatattt gaatgtattt agaaaaataa acaaataggg gttccgcgca catttccccg 4860
aaaagtgcca cctgacgtcg gcagtgaaaa aaatgcttta tttgtgaaat ttgtgatgct 4920
attgctttat ttgtaaccat tataagctgc aataaacaag ttaacaacaa caattgcatt 4980
cattttatgt ttcaggttca gggggaggtg tgggaggttt tttaaagcaa gtaaaacctc 5040
tacaaatgtg gtatggctga ttatgatcct ctagactgca gcctcaggag atctgggccc 5100
ccgcggcata tgaccggtgc tacttgtaca gctcgtccat gccgccggtg gagtgtctac 5160
cctcggcgcg ttcgtactgt tccacgatgg tgtagtcctc gttgtgggag gtgatgtcca 5220
acttgatgtt gacgttgtag gcgccgggca gctgcacggg cttcttggcc ttgtaggtgg 5280
tcttgacctc agcgtcgtag tggccgccgt ccttcagctt cagcctctgc ttgatctcgc 5340
ccttcagggc gccgtcctcg gggtacatcc gctcggagga ggcctcccag cccatggtct 5400
tcttctgcat tacggggccg tcggagggga agttggtgcc gcgcagcttc accttgtaga 5460
tgaactcgcc gtcttgcagg gaggagtcct gggtcacggt caccacgccg ccgtcctcga 5520
agttcatcac gcgctcccac ttgaagccct cggggaagga cagcttcaag tagtcgggga 5580
tgtcggcggg gtgcttcacg taggccttgg agccgtacat gaattgaggg gacaggatgt 5640
cccaggcgaa gggcaggggg ccacccttgg tcaccttcag cttggcggtc tgggtgccct 5700
cgtaggggcg accttcaccc tcgccctcga tctcgaactc gtggccgttc acggagccct 5760
ccatgtgcac cttgaagcgc atgaactcct tgatgatggc catgttatcc tcctcgccct 5820
tagaaaccat ctccaggcga tctgacggtt cactaaacga gctctgctta tataggcctc 5880
ccaccgtaca cgccacctcg acata 5905

<210> SEQ ID NO 56
<211> LENGTH: 2088
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 56
augcucccug gacuugcuuu gcugcuuuug gcagccugga cugcucgagc acucgagguc 60
ccaacggaug gaaacgcggg ucuuuuggca gagccucaaa uagcaauguu uugcggaaga 120
cucaacaugc auaugaacgu ucagaauggg aaaugggacu ccgaccccag ugguacgaag 180
acauguauug acacaaagga gggaauacuc caguacugcc aggaagugua cccggagcuu 240
cagauuacga augugguaga ggcuaaucaa cccguaacua uccaaaauug guguaagaga 300
ggcaggaagc aaugcaagac ucauccucau uucguaauuc cguaucgaug uuuggugga 360 gaauuugucu cugacgcauu gcuuguuccu gacaagugua aguuucuuca ccaggaacgc 420
auggacgugu gcgagacaca cuugcacugg cauaccguug cgaaggagac guguuccgaa 480
aagaguacaa aucuccauga cuacggcaug uugcuccegu gcggaauaga uaaguuccga 540
ggcguggagu uuguaugcug uccgcuggca gaggagagcg auaaugucga uuccgcagau 600
gccgaagagg acgacagcga cgucuggugg ggaggagcgg acacugauua cgcugauggu 660
agugaggaca aaguagucga gguggcagaa gaagaagaag uggcggaggu ugaagaagaa 720
gaggcagacg augacgaaga cgaugaggac ggugaugagg uagaagaaga agcggaagaa 780
ccguacgaag aagcuacgga acgcacuaca aguauugcua ccacuacaac cacuacaacc 840
gaaucaguug aggaagugu gcgagucccc acuacggcug ccaguacacc ggaugccguc 900
gacaaauacc uggagacucc uggcgacgaa aacgaacaug cucauuucca gaaggcgaag 960
gaacgccucg aagcaaagca cagagagaga augucacagg uaaugaggga augggaggag 1020
gcggaacgcc aagcaaagaa ccugccuaaa gcggacaaga aggcaguuau ccaacauuuc 1080
caagagaaag uggagagucu cgaacaggag gcagcgaacg agaggcaaca auugguagaa 1140
acgcacaugg cgagggugga agcuaugcuc aaugaccgaa gacgacuugc cuuggaaaau 1200
uacauuacug cccuucaagc cgucccaccg cgcccacgcc augucuuuaa caugcuuaag 1260
aaguauguuc gagcugaaca gaaggaucgg caacacaccc ugaaacacuu cgaacauguc 1320
agaaugguug acccgaagaa ggcugcacag auucgaaguc aaguuaugac ccauuugagg 1380
guaauauaug agagaaugaa ccaaagucug agccuucucu acaaugucce cgcuguggcc 1440 gaggaaauuc aggacgaagu cgaugagcuc cugcaaaagg agcagaacua cucugacgau 1500
guacuugcua auaugauuuc agagccaagg aucaguuaug gaaacgacgc ccugaugccu 1560
agucuuaccg aaaccaagac uacgguagaa cuccuucccg uuaacggaga guucagcuug 1620
gacgaccuuc agccuuggca cucauucgga gcugauuccg uaccagccaa uacggagaau 1680
gaaguagagc ccguagacgc aagaccugca gcggacagag ggcugacgac gagacccggu 1740
agcgguuuga caaauaucaa gacggaggag aucucugaag ugaggaugga ugcagaauuc 1800
cgacaugacu caggauauga aguucaucau caaaaaauugg uguucuuugc agaagauguc 1860
gguucuaaca agggugcuau cauaggccuu augguggggug gcgucgugau ugcgaccgug 1920
auaguuauua cgcuugucau gcugaagaag aaacaguaua cguccaucca ucacggugug 1980
guagagguag augcggccgu aacucccgaa gagcgccauc uuucuaagau gcagcagaau 2040
ggauacgaga accccacgua caaauucuuu gagcaaaugc aaaacuga 2088

<210> SEQ ID NO 57
<211> LENGTH: 2088
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 57
augcucccug gacuugcuuu gcugcuuuug gcagccugga cugcucgagc acucgagguc 60

```
ccaacggaug gaaacgcggg ucuuuuggca gagccucaaa uagcaauguu uugcggaaga    120

cucaacaugc auaugaacgu ucagaauggg aaaugggacu ccgaccccag ugguacgaag    180

acauguauug acacaaagga gggaauacuc caguacugcc aggaagugua cccggagcuu    240

cagauuacga augugguaga ggcuaaucaa cccguaacua uccaaaauug guguaagaga    300

ggcaggaagc aaugcaagac ucauccucau uucguaauuc cguaucgaug uuugguggga    360

gaauuugucu cugacgcauu gcuuguuccu gacaagugua aguuucuuca ccaggaacgc    420

auggacgugu gcgagacaca cuugcacugg cauaccguug cgaaggagac guguuccgaa    480

aagaguacaa aucuccauga cuacggcaug uugcucccgu gcggaauaga uaaguuccga    540

ggcguggagu uuguaugcug uccgcuggca gaggagagcg auaaugucga uuccgcagau    600

gccgaagagg acgacagcga cgucuggugg ggaggagcgg acacugauua cgcugauggu    660

agugaggaca aaguagucga ggugcagaa gaagaagaag uggcggaggu ugaagaagaa    720

gaggcagacg augacgaaga cgaugaggac ggugaugagg uagaagaaga agcggaagaa    780

ccguacgaag aagcuacgga acgcacuaca aguauugcua ccacuacaac cacuacaacc    840

gaaucaguug aggaaguggu gcgagucccc acuacggcug ccaguacacc ggaugccguc    900

gacaaauacc uggagacucc uggcgacgaa aacgaacaug cucauuucca gaaggcgaag    960

gaacgccucg aagcaaagca cagagagaga augucacagg uaaugaggga augggaggag   1020

gcggaacgcc aagcaaagaa ccugccuaaa gcggacaaga aggcaguuau ccaacauuuc   1080

caagagaaag uggagagucu cgaacaggag gcagcgaacg agaggcaaca auugguagaa   1140

acgcacaugg cgagggugga agcuaugcuc aaugaccgaa gacgacuugc cuuggaaaau   1200

uacauuacug cccuucaagc cgucccaccg cgcccacgcc augucuuuaa caugcuuaag   1260

aaguauguuc gagcugaaca gaaggaucgg caacacaccc ugaaacacuu cgaacauguc   1320

agaaugguug acccgaagaa ggcugcacag auucgaaguc aaguuaugac ccauuugagg   1380

guaauauaug agagaaugaa ccaaagucug agccuucucu acaaaugucc cgcuguggcc   1440

gaggaaauuc aggacgaagu cgaugagcuc cugcaaaagg agcagaacua cucugacgau   1500

guacuugcua auaugauuuc agagccaagg aucaguuaug gaaacgacgc ccugaugccu   1560

agucuuaccg aaaccaagac uacgguagaa cuccuucccg uuaacggaga guucagcuug   1620

gacgaccuuc agccuuggca cucauucgga gcugauuccg uaccagccaa uacggagaau   1680

gaaguagagc ccguagacgc aagaccugca gcggacagag ggcugacgac gagacccggu   1740

agcgguuuga caaauaucaa gacggaggag aucucugaag uggagaugga ugcagaauuc   1800

cgacaugacu caggauauga aguucaucau caaaaauugg uguucuuugc agaagauguc   1860

gguucuaaca agggugcuau cauaggccuu augguggug gcgucgugau ugcgaccgug   1920

auaguuauua cgcuugucau gcugaagaag aaacaguaua cguccaucca ucacggugug   1980

guagagguag augcggccgu aacucccgaa gagcgccauc uuucuaagau gcagcagaau   2040

ggauacgaga accccacgua caaauucuuu gagcaaaugc aaaacuga               2088
```

<210> SEQ ID NO 58
<211> LENGTH: 2088
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

-continued

<400> SEQUENCE: 58

```
augcucccug gacuugcuuu gcugcuuuug gcagccugga cugcucgagc acucgagguc     60
ccaacggaug gaaacgcggg ucuuuuggca gagccucaaa uagcaauguu uugcggaaga    120
cucaacaugc auaugaacgu ucagaauggg aaaugggacu ccgaccccag ugguacgaag    180
acauguauug acacaaagga gggaauacuc caguacugcc aggaagugua cccggagcuu    240
cagauuacga augugguaga ggcuaaucaa cccguaacua uccaaaauug guguaagaga    300
ggcaggaagc aaugcaagac ucauccucau uucguaauuc cguaucgaug uuuggugga     360
gaauuugucu cugacgcauu gcuuguuccu gacaagugua aguuucuuca ccaggaacgc    420
auggacgugu gcgagacaca cuugcacugg cauaccguug cgaaggagac guguuccgaa    480
aagaguacaa aucuccauga cuacggcaug uugcuccccgu gcggaauaga uaaguuccga   540
ggcguggagu uuguaugcug uccgcuggca gaggagagcg auaaugucga uuccgcagau    600
gccgaagagg acgacagcga cgucuggugg ggaggagcgg acacugauua cgcugauggu    660
agugaggaca aaguagucga gguggcagaa gaagaagaag uggcggaggu ugaagaagaa    720
gaggcagacg augacgaaga cgaugaggac ggugaugagg uagaagaaga agcggaagaa    780
ccguacgaag aagcuacgga acgcacuaca aguauugcua ccacuacaac cacuacaacc    840
gaaucaguug aggaaguggu gcgagucccc acuacggcug ccaguacacc ggaugccguc    900
gacaaauacc uggagacucc uggcgacgaa aacgaacaug cucauuucca gaaggcgaag    960
gaacgccucg aagcaaagca cagagagaga augucacagg uaaugaggga augggaggag   1020
gcggaacgcc aagcaaagaa ccugccuaaa gcggacaaga aggcaguuau ccaacauuuc   1080
caagagaaag uggagagucu cgaacaggag gcagcgaacg agaggcaaca auugguagaa   1140
acgcacaugg cgagggugga agcuaugcuc aaugaccgaa gacgacuugc cuuggaaaau   1200
uacauuacug cccuucaagc cgucccaccg cgcccacgcc augucuuuaa caugcuuaag   1260
aaguauguuc gagcugaaca gaaggaucgg caacacaccc ugaaacacuu cgaacauguc   1320
agaaugguug acccgaagaa ggcugcacag auucgaaguc aaguuaugac ccauuugagg   1380
guaauauaug agagaaugaa ccaaagucug agccuucucu acaaugucccc cgcuguggcc   1440
gaggaaauuc aggacgaagu cgaugagcuc cugcaaaagg agcagaacua cucugacgau   1500
guacuugcua auaugauuuc agagccaagg aucaguuaug gaaacgacgc ccugaugccu   1560
agucuuaccg aaaccaagac uacgguagaa cuccuucccg uuaacggaga guucagcuug   1620
gacgaccuuc agccuuggca cucauucgga gcugauuccg uaccagccaa uacggagaau   1680
gaaguagagc ccguagacgc aagaccugca gcggacagag ggcugacgac gagacccggu   1740
agcgguuuga caaauaucaa gacggaggag aucucugaag uggggaugga ugcagaauuc   1800
cgacaugacu caggauauga aguucaucau caaaaaauugg uguucuuugc agaagauguc  1860
gguucuaaca agggugcuau cauaggccuu augguggug gcgucgugau ugcgaccgug    1920
auaguuauua cgcuugucau gcugaagaag aaacaguaua cguccaucca ucacggugug   1980
guagagguag augcggccgu aacucccgaa gagcgccauc uuucuaagau gcagcagaau   2040
ggauacgaga accccacgua caaauucuuu gagcaaaugc aaaacuga                2088
```

<210> SEQ ID NO 59
<211> LENGTH: 2088
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 59
augcucccug gacuugcuuu gcugcuuuug gcagccugga cugcucgagc acucgagguc 60
ccaacggaug gaaacgcggg ucuuuuggca gagccucaaa uagcaauguu uugcggaaga 120
cucaacaugc auaugaacgu ucagaauggg aaaugggacu ccgaccccag ugguacgaag 180
acauguauug acacaaagga gggaauacuc caguacugcc aggaagugua cccggagcuu 240
cagauuacga augugguaga ggcuaaucaa cccguaacua uccaaaauug guguaagaga 300
ggcaggaagc aaugcaagac ucauccucau uucguaauuc cguaucgaug uuugguggga 360
gaauuugucu cugacgcauu gcuuguuccu gacaagugua aguuucuuca ccaggaacgc 420
auggacgugu gcgagacaca cuugcacugg cauaccguug cgaaggagac guguuccgaa 480
aagaguacaa aucuccauga cuacggcaug uugcuccccgu gcggaauaga uaaguuccga 540
ggcguggagu uuguaugcug uccgcuggca gaggagagcg auaaugucga uuccgcagau 600
gccgaagagg acgacagcga cgucuggugg ggaggagcgg acacugauua cgcugauggu 660
agugaggaca aaguagucga gguggcagaa gaagaagaag uggcggaggu ugaagaagaa 720
gaggcagacg augacgaaga cgaugaggac ggugaugagg uagaagaaga agcggaagaa 780
ccguacgaag aagcuacgga acgcacuaca aguauugcua ccacuacaac cacuacaacc 840
gaaucaguug aggaagugu gcgagucccc acuacggcug ccaguacacc ggaugccguc 900
gacaaauacc uggagacucc uggcgacgaa aacgaacaug cucauuucca gaaggcgaag 960
gaacgccucg aagcaaagca cagagagaga augucacagg uaaugaggga augggaggag 1020
gcggaacgcc aagcaaagaa ccugccuaaa gcggacaaga aggcaguuau ccaacauuuc 1080
caagagaaag uggagagucu cgaacaggag gcagcgaacg agaggcaaca auugguagaa 1140
acgcacaugg cgagggugga agcuaugcuc aaugaccgaa gacgacuugc cuuggaaaau 1200
uacauuacug cccuucaagc cgucccaccg cgcccacgcc augucuuuaa caugcuuaag 1260
aaguauguuc gagcugaaca gaaggaucgg caacacaccc ugaaacacuu cgaacauguc 1320
agaaugguug acccgaagaa ggcugcacag auucgaaguc aaguuaugac ccauuugagg 1380
guaauauaug agagaaugaa ccaaagucug agccuucucu acaaugaccc cgcuguggcc 1440
gaggaaauuc aggacgaagu cgaugagcuc cugcaaaagg agcagaacua cucugacgau 1500
guacuugcua auaugauuuc agagccaagg aucaguuaug gaaacgacgc ccugaugccu 1560
agucuuaccg aaaccaagac uacgguagaa cuccuucccg uuaacggaga guucagcuug 1620
gacgaccuuc agccuuggca cucauucgga gcugauuccg uaccagccaa uacggagaau 1680
gaaguagagc ccguagacgc aagaccugca gcggacagag ggcugacgac gagacccggu 1740
agcgguuuga caaauaucaa gacggaggag aucucugaag ugagggugga ugcagaauuc 1800
cgacaugacu caggauauga aguucaucau caaaaauugg uguucuuugc agaagauguc 1860
gguucuaaca agggugcuau cauaggccuu augguggug gcgucgugau ugcgaccgug 1920
auaguuauua cgcuugucau gcugaagaag aaacaguaua cguccaucca ucacggugug 1980
guagagguag augcggccgu aacucccgaa gagcgccauc uuucuaagau gcagcagaau 2040
ggauacgaga accccacgua caaauucuuu gagcaaaugc aaaacuga 2088

<210> SEQ ID NO 60
<211> LENGTH: 2088
<212> TYPE: RNA

<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 60

```
augcucccug gacuugcuuu gcugcuuuug gcagccugga cugcucgagc acucgagguc      60
ccaacggaug gaaacgcggg ucuuuuggca gagccucaaa uagcaauguu uugcggaaga     120
cucaacaugc auaugaacgu ucagaauggg aaaugggacu ccgaccccag ugguacgaag     180
acauguauug acacaaagga gggaauacuc caguacugcc aggaagugua cccggagcuu     240
cagauuacga augugguaga ggcuaaucaa cccguaacua uccaaaauug guguaagaga     300
ggcaggaagc aaugcaagac ucauccucau uucguaauuc cguaucgaug uuugguggga     360
gaauuugucu cugacgcauu gcuuguuccu gacaagugua aguuucuuca ccaggaacgc     420
auggacgugu gcgagacaca cuugcacugg cauaccguug cgaaggagac guguuccgaa     480
aagaguacaa aucuccauga cuacggcaug uugcuccccgu gcggaauaga uaaguuccga     540
ggcguggagu uuguaugcug uccgcuggca gaggagagcg auaaugucga uuccgcagau     600
gccgaagagg acgacagcga cgucuggugg ggaggagcgg acacugauua cgcugauggu     660
agugaggaca aaguagucga gguggcagaa gaagaagaag uggcggaggu ugaagaagaa     720
gaggcagacg augacgaaga cgaugaggac ggugaugagg uagaagaaga agcggaagaa     780
ccguacgaag aagcuacgga acgcacuaca aguauugcua ccacuacaac cacuacaacc     840
gaaucaguug aggaaguggu gcgaguccc c acuacggcug ccaguacacc ggaugccguc     900
gacaaauacc uggagacucc uggcgacgaa aacgaacaug cucauuucca gaaggcgaag     960
gaacgccucg aagcaaagca cagagagaga augucacagg uaaugaggga augggaggag    1020
gcggaacgcc aagcaaagaa ccugccuaaa gcggacaaga aggcaguuau ccaacauuuc    1080
caagagaaag uggagagucu cgaacaggag gcagcgaacg agaggcaaca auugguagaa    1140
acgcacaugg cgagggugga agcuaugcuc aaugaccgaa gacgacuugc cuuggaaaau    1200
uacauuacug cccuucaagc cgucccaccg cgcccacgcc augucuuuaa caugcuuaag    1260
aaguauguuc gagcugaaca gaaggaucgg caacacaccc ugaaacacuu cgaacauguc    1320
agaaugguug acccgaagaa ggcugcacag auucgaaguc aaguuaugac ccauuugagg    1380
guaaauauaug agagaaugaa ccaaagucug agccuucucu acaaugucc c cgcuguggcc    1440
gaggaaauuc aggacgaagu cgaugagcuc cugcaaaagg agcagaacua cucugacgau    1500
guacuugcua auaugauuuc agagccaagg aucaguuaug gaaacgacgc ccugaugccu    1560
agucuuaccg aaaccaagac uacgguagaa cuccuucccg uuaacggaga guucagcuug    1620
gacgaccuuc agccuuggca cucauucgga gcugauuccg uaccagccaa uacggagaau    1680
gaaguagagc ccguagacgc aagaccugca gcggacagag ggcugacgac gagacccggu    1740
agcgguuuga caaauaucaa gacggaggag aucucugaag uggaggugga ugcagaauuc    1800
cgacaugacu caggauauga aguucaucau caaaaauugg uguucuuugc agaagauguc    1860
gguucuaaca agggugcuau cauaggccuu augguggggug gcgucgugau ugcgaccgug    1920
auaguuauua cgcuugucau gcugaagaag aaacaguaua cguccaucca ucacggugug    1980
guagagguag augcggccgu aacucccgaa gagcgccauc uuucuaagau gcagcagaau    2040
ggauacgaga accccacgua caaauucuuu gagcaaaugc aaaacuga                 2088
```

```
<210> SEQ ID NO 61
<211> LENGTH: 2088
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 61

augcucccug gacuugcuuu gcugcuuuug gcagccugga cugcucgagc acucgagguc     60

ccaacggaug gaaacgcggg ucuuuuggca gagccucaaa uagcaauguu uugcggaaga    120

cucaacaugc auaugaacgu ucagaauggg aaaugggacu ccgaccccag ugguacgaag    180

acauguauug acacaaagga gggaauacuc caguacugcc aggaagugua cccggagcuu    240

cagauuacga augugguaga ggcuaaucaa cccguaacua uccaaaauug guguaagaga    300

ggcaggaagc aaugcaagac ucauccucau uucguaauuc cguaucgaug uuuggugga    360

gaauuugucu cugacgcauu gcuuguuccu gacaagugua aguuucuuca ccaggaacgc    420

auggacgugu gcgagacaca cuugcacugg cauaccguug cgaaggagac guguuccgaa    480

aagaguacaa aucuccauga cuacggcaug uugcuccccgu gcggaauaga uaaguuccga    540

ggcguggagu uuguaugcug uccgcuggca gaggagagcg auaaugucga uuccgcagau    600

gccgaagagg acgacagcga cgucuggugg ggaggagcgg acacugauua cgcugauggu    660

agugaggaca aaguagucga gguggcagaa gaagaagaag uggcggaggu ugaagaagaa    720

gaggcagacg augacgaaga cgaugaggac ggugaugagg uagaagaaga agcggaagaa    780

ccguacgaag aagcuacgga acgcacuaca aguauugcua ccacuacaac cacuacaacc    840

gaaucaguug aggaaguggu gcgaguccc acuacggcug ccaguacacc ggaugccguc    900

gacaaauacc uggagacucc uggcgacgaa aacgaacaug cucauuucca gaaggcgaag    960

gaacgccucg aagcaaagca cagagagaga augucacagg uaaugaggga augggaggag   1020

gcggaacgcc aagcaaagaa ccugccuaaa gcggacaaga aggcaguuau ccaacauuuc   1080

caagagaaag uggagagucu cgaacaggag gcagcgaacg agaggcaaca auugguagaa   1140

acgcacaugg cgagggugga agcuaugcuc aaugaccgaa gacgacuugc cuuggaaaau   1200

uacauuacug cccuucaagc cgucccaccg cgcccacgcc augucuuuaa caugcuuaag   1260

aaguauguuc gagcugaaca gaaggaucgg caacacaccc ugaaacacuu cgaacauguc   1320

agaaugguug acccgaagaa ggcugcacag auucgaaguc aaguuaugac ccauuugagg   1380

guaauauaug agagaaugaa ccaaagucug agccuucucu acaaugucccc cgcuguggcc   1440

gaggaaauuc aggacgaagu cgaugagcuc cugcaaaagg agcagaacua cucugacgau   1500

guacuugcua auaugauuuc agagccaagg aucaguuaug gaaacgacgc ccugaugccu   1560

agucuuaccg aaaccaagac uacgguagaa cuccuucccg uuaacggaga guucagcuug   1620

gacgaccuuc agccuuggca cucauucgga gcugauuccg uaccagccaa uacggagaau   1680

gaaguagagc ccguagacgc aagaccugca gcggacagag ggcugacgac gagacccggu   1740

agcgguuuga caaauaucaa gacggaggag aucucugaag uggggguggaa ugcagaauuc   1800

cgacaugacu caggauauga aguucaucau caaaaauugg uguucuuugc agaagauguc   1860

gguucuaaca agggugcuau cauaggccuu auggugggug gcgucgugau ugcgaccgug   1920

auaguuauua cgcuuugucau gcugaagaag aaacaguaua cguccaucca ucacggugug   1980

guagagguag augcggccgu aacucccgaa gagcgccauc uuucuaagau gcagcagaau   2040
```

ggauacgaga accccacgua caaauucuuu gagcaaaugc aaaacuga 2088

<210> SEQ ID NO 62
<211> LENGTH: 2088
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 62
augcucccug gacuugcuuu gcugcuuuug gcagccugga cugcucgagc acucgagguc 60
ccaacggaug gaaacgcggg ucuuuuggca gagccucaaa uagcaauguu uugcggaaga 120
cucaacaugc auaugaacgu ucagaauggg aaaugggacu ccgaccccag ugguacgaag 180
acauguauug acacaaagga gggaauacuc caguacugcc aggaagugua cccggagcuu 240
cagauuacga augugguaga ggcuaaucaa cccguaacua uccaaaauug guguaagaga 300
ggcaggaagc aaugcaagac ucauccucau uucguaauuc cguaucgaug uuugguggga 360
gaauuugucu cugacgcauu gcuuguuccu gacaagugua aguucuuca ccaggaacgc 420 auggacgugu gcgagacaca cuugcacugg cauaccguug cgaaggagac guguuccgaa 480
aagaguacaa aucuccauga cuacggcaug uugcucccgu gcggaauaga uaaguuccga 540
ggcguggagu uuguaugcug uccgcuggca gaggagagcg auaaugucga uuccgcagau 600
gccgaagagg acgacagcga cgucuggugg ggaggagcgg acacugauua cgcugauggu 660
agugaggaca aaguagucga gguggcagaa gaagaagaag uggcggaggu ugaagaagaa 720
gaggcagacg augacgaaga cgaugaggac ggugaugagg uagaagaaga agcggaagaa 780
ccguacgaag aagcuacgga acgcacuaca aguauugcua ccacuacaac cacuacaacc 840
gaaucaguug aggaagugu gcgagucccc acuacggcug ccaguacacc ggaugccguc 900
gacaaauacc uggagacucc uggcgacgaa aacgaacaug cucauuucca gaaggcgaag 960
gaacgccucg aagcaaagca cagagagaga augucacagg uaaugaggga augggaggag 1020
gcggaacgcc aagcaaagaa ccugccuaaa gcggacaaga aggcaguuau ccaacauuuc 1080
caagagaaag uggagagucu cgaacaggag gcagcgaacg agaggcaaca auugguagaa 1140
acgcacaugg cgagggugga agcuaugcuc aaugaccgaa gacgacuugc cuuggaaaau 1200
uacauuacug cccuucaagc cgucccaccg cgcccacgcc augucuuuaa caugcuuaag 1260
aaguauguuc gagcugaaca gaaggaucgg caacacaccc ugaaacacuu cgaacauguc 1320
agaaugguug acccgaagaa ggcugcacag auucgaaguc aaguuaugac ccauuugagg 1380
guaauauaug agagaaugaa ccaaagucug agccuucucu acaaugucccc cgcuguggcc 1440 gaggaaauuc aggacgaagu cgaugagcuc cugcaaaagg agcagaacua cucugacgau 1500
guacuugcua auaugauuuc agagccaagg aucaguuaug gaaacgacgc ccugaugccu 1560
agucuuaccg aaaccaagac uacgguagaa cuccuucccg uuaacggaga guucagcuug 1620
gacgaccuuc agccuuggca cucauucgga gcugauuccg uaccagccaa uacggagaau 1680
gaaguagagc ccguagacgc aagaccugca gcggacagag ggcugacgac gagacccggu 1740
agcgguuuga caaauaucaa gacggaggag aucucugaag ugaaggugga ugcagaauuc 1800
cgacaugacu caggauauga aguucaucau caaaaauugg uguucuuugc agaagauguc 1860
gguucuaaca agggugcuau cauaggccuu augguggug gcgucgugau ugcgaccgug 1920
auaguuauua cgcuugucau gcugaagaag aaacaguaua cguccaucca ucacggugug 1980
guagagguag augcggccgu aacuccccgaa gagcgccauc uuucuaagau gcagcagaau 2040
ggauacgaga accccacgua caaauucuuu gagcaaaugc aaaacuga 2088

<210> SEQ ID NO 63
<211> LENGTH: 2088
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 63
augcucccug gacuugcuuu gcugcuuuug gcagccugga cugcucgagc acucgagguc 60
ccaacggaug gaaacgcggg ucuuuuggca gagccucaaa uagcaauguu uugcggaaga 120
cucaacaugc auaugaacgu ucagaauggg aaaugggacu ccgaccccag ugguacgaag 180
acauguauug acacaaagga gggaauacuc caguacugcc aggaagugua cccggagcuu 240
cagauuacga auguggguaga ggcuaaucaa cccguaacua uccaaaauug guguaagaga 300
ggcaggaagc aaugcaagac ucauccucau uucguaauuc cguaucgaug uuugguggga 360
gaauuugucu cugacgcauu gcuuguuccu gacaagugua aguuucuuca ccaggaacgc 420
auggacgugu gcgagacaca cuugcacugg cauaccguug cgaaggagac guguuccgaa 480
aagaguacaa aucuccauga cuacggcaug uugcuccccgu gcggaauaga uaaguuccga 540
ggcguggagu uuguaugcug uccgcuggca gaggagagcg auaaugucga uuccgcagau 600
gccgaagagg acgacagcga cgucuggugg ggaggagcgg acacugauua cgcugauggu 660
agugaggaca aaguagucga gguggcagaa gaagaagaag uggcggaggu ugaagaagaa 720
gaggcagacg augacgaaga cgaugaggac ggugaugagg uagaagaaga agcggaagaa 780
ccguacgaag aagcuacgga acgcacuaca aguauugcua ccacuacaac cacuacaacc 840
gaaucaguug aggaaguggu gcgagucccc acuacggcug ccaguacacc ggaugccguc 900
gacaaauacc uggagacucc uggcgacgaa aacgaacaug cucauuucca gaaggcgaag 960
gaacgccucg aagcaaagca cagagagaga augucacagg uaaugaggga augggaggag 1020
gcggaacgcc aagcaaagaa ccugccuaaa gcggacaaga aggcaguuau ccaacauuuc 1080
caagagaaag uggagagucu cgaacaggag gcagcgaacg agaggcaaca auugguagaa 1140
acgcacaugg cgagggugga agcuaugcuc aaugaccgaa gacgacuugc cuuggaaaau 1200
uacauuacug cccuucaagc cgucccaccg cgcccacgcc augucuuuaa caugcuuaag 1260
aaguauguuc gagcugaaca gaaggaucgg caacacaccc ugaaacacuu cgaacauguc 1320
agaaugguug acccgaagaa ggcugcacag auucgaaguc aaguuaugac ccauuugagg 1380
guaauauaug agagaaugaa ccaaagucug agccuucucu acaaugucccc cgcuguggcc 1440 gaggaaauuc aggacgaagu cgaugagcuc cugcaaaagg agcagaacua cucugacgau 1500
guacuugcua auaugauuuc agagccaagg aucaguuaug gaaacgacgc ccugaugccu 1560
agucuuaccg aaaccaagac uacgguagaa cuccuucccg uuaacggaga guucagcuug 1620
gacgaccuuc agccuuggca cucauucgga gcugauuccg uaccagccaa uacggagaau 1680
gaaguagagc ccguagacgc aagaccugca gcggacagag ggcugacgac gagacccggu 1740
agcgguuuga caaauaucaa gacggaggag aucucugaag ugaagauggg ugcagaauuc 1800
cgacaugacu caggauauga aguucaucau caaaaauugg uguucuuugc agaagauguc 1860

-continued

| | |
|---|---|
| gguucuaaca agggugcuau cauaggccuu augguggug gcgucgugau ugcgaccgug | 1920 |
| auaguuauua cgcuugucau gcugaagaag aaacaguaua cguccaucca ucacggugug | 1980 |
| guagagguag augcggccgu aacucccgaa gagcgccauc uuucuaagau gcagcagaau | 2040 |
| ggauacgaga accccacgua caaauucuuu gagcaaaugc aaaacuga | 2088 |

<210> SEQ ID NO 64
<211> LENGTH: 2088
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 64

| | |
|---|---|
| augcucccug acuugcuuu gcugcuuuug gcagccugga cugcucgagc acucgagguc | 60 |
| ccaacggaug gaaacgcggg ucuuuuggca gagcccucaaa uagcaauguu uugcggaaga | 120 |
| cucaacaugc auaugaacgu ucagaauggg aaauggacu ccgaccccag gguacgaag | 180 |
| acauguauug acacaaagga gggaauacuc caguacugcc aggaagugua cccggagcuu | 240 |
| cagauuacga auggguaga ggcuaaucaa cccguaacua uccaaaauug guguaagaga | 300 |
| ggcaggaagc aaugcaagac ucauccucau uucguaauuc cguaucgaug uuuggguggga | 360 |
| gaauuugucu cugacgcauu gcuuguuccu gacaaguguaa aguucuuca ccaggaacgc | 420 |
| auggacgugu gcgagacaca cuugcacugg cauaccguug cgaaggagac guguuccgaa | 480 |
| aagaguacaa aucccauga cuacggcaug uugcucccgu gcggaauaga uaaguuccga | 540 |
| ggcguggagu uuguaugcug uccgcuggca gaggagagcg auaaugucga uccgcagau | 600 |
| gccgaagagg acgacagcga cgucggggugg ggaggagcgg acacgauua cgcugauggu | 660 |
| agugaggaca aguagucga ggugcagaa aagaagaag uggcggaggu ugaagaagaa | 720 |
| gaggcagacg augacgaaga cgaugaggac ggugaugagg uagaagaaga agcggaagaa | 780 |
| ccguacgaag aagcuacgga acgcacuaca aguauugcua ccacuacaac cacuacaacc | 840 |
| gaaucgauug aggaaguggu gcgaguccccc acuacggcug ccaguacacc ggaugccguc | 900 |
| gacaaauacc uggagacucc uggcgacgaa acgaacaug cucauuucca gaaggcgaag | 960 |
| gaacgccucg aagcaaagca cagagagaga augucacagg uaaugaggga augggaggag | 1020 |
| gcggaacgcc aagcaaagaa ccugccuaaa gcggacaaga aggcaguuau ccaacauuuc | 1080 |
| caagagaaag uggagagucu cgaacaggag gcagcgaacg agaggcaaca auugguagaa | 1140 |
| acgcacaugg cgagggugga agcuaugcuc aaugaccgaa gacgacuugc cuuggaaaau | 1200 |
| uacauuacug cccuucaagc cguccaccg cgcccacgcc augucuuuaa caugcuuaag | 1260 |
| aaguauguuc gagcugaaca gaaggaucgg caacacaccc ugaaacacuu cgaacaugc | 1320 |
| agaaugguu acccgaagaa ggcugcacag auucgaaguc aaguuaugac ccauuugagg | 1380 |
| guaauauaug agagaaugaa ccaaagucug agccuucucu acaauguccc cgcugggcc | 1440 |
| gaggaaauuc aggacgaagu cgaugagcuc cugcaaaagg agcagaacua cucugacgau | 1500 |
| guacuugcua auaugauuuc agagccaagg aucaguuaug aaacgacgc ccugaugccu | 1560 |
| agucuuaccg aaaccaagac uacgguagaa cuccuucccg uuaacggaga guucagcuug | 1620 |
| gacgaccuuc agccuuggca cucauucgga gcugauuccg uaccagccaa uacggagaau | 1680 |
| gaaguagagc ccguagacgc aagaccugca gcggacagag gcugacgac gagacccggu | 1740 |
| agcgguuuga caaauaucaa gacggaggag aucucugaag ugaagaugga gugggaauuc | 1800 |

cgacaugacu caggauauga aguucaucau caaaaaauugg uguucuuugc agaagauguc 1860
gguucuaaca agggugcuau cauaggccuu auggugggug gcgucgugau ugcgaccgug 1920
auaguuauua cgcuugucau gcugaagaag aaacaguaua cguccaucca ucacggugug 1980
guagagguag augcggccgu aacucccgaa gagcgccauc uuucuaagau gcagcagaau 2040
ggauacgaga accccacgua caaauucuuu gagcaaaugc aaaacuga 2088

<210> SEQ ID NO 65
<211> LENGTH: 2088
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 65
augcucccug gacuugcuuu gcugcuuuug gcagccugga cugcucgagc acucgagguc 60
ccaacggaug gaaacgcggg ucuuuuggca gagccucaaa uagcaauguu uugcggaaga 120
cucaacaugc auaugaacgu ucagaauggg aaaugggacu ccgaccccag ugguacgaag 180
acauguauug acacaaagga gggaauacuc caguacugcc aggaagugua cccggagcuu 240
cagauuacga auguugguaga ggcuaaucaa cccguaacua uccaaaauug guguaagaga 300
ggcaggaagc aaugcaagac ucauccucau uucguaauuc cguaucgaug uuugguggga 360
gaauuugucu cugacgcauu gcuuguuccu gacaagugua aguuucuuca ccaggaacgc 420
auggacgugu gcgagacaca cuugcacugg cauaccguug cgaaggagac guguuccgaa 480
aagaguacaa aucuccauga cuacggcaug uugcucccgu gcggaauaga uaaguuccga 540
ggcguggagu uuguaugcug uccgcuggca gaggagagcg auaaugucga uuccgcagau 600
gccgaagagg acgacagcga cgucuggugg ggaggagcgg acacugauua cgcugauggu 660
agugaggaca aaguagucga gguggcagaa gaagaagaag uggcggaggu ugaagaagaa 720
gaggcagacg augacgaaga cgaugaggac ggugaugagg uagaagaaga agcggaagaa 780
ccguacgaag aagcuacgga acgcacuaca aguauugcua ccacuacaac cacuacaacc 840
gaaucaguug aggaaguggu gcgagucccc acuacggcug ccaguacacc ggaugccguc 900
gacaaauacc uggagacucc uggcgacgaa aacgaacaug cucauuucca gaaggcgaag 960
gaacgccucg aagcaaagca cagagagaga augucacagg uaaugaggga augggaggag 1020
gcggaacgcc aagcaaagaa ccugccuaaa gcggacaaga aggcaguuau ccaacauuuc 1080
caagagaaag uggagagucu cgaacaggag gcagcgaacg agaggcaaca auugguagaa 1140
acgcacaugg cgagggugga agcuaugcuc aaugaccgaa gacgacuugc cuuggaaaau 1200
uacauuacug cccuucaagc cgucccaccg cgcccacgcc augucuuuaa caugcuuaag 1260
aaguauguuc gagcugaaca gaaggaucgg caacacaccc ugaaacacuu cgaacauguc 1320
agaaugguug acccgaagaa ggcugcacag auucgaaguc aaguuaugac ccauuugagg 1380
guaauauaug agagaaugaa ccaaagucug agccuucucu acaaugaccc cgcuguggcc 1440
gaggaaauuc aggacgaagu cgaugagcuc cugcaaaagg agcagaacua cucugacgau 1500
guacuugcua auaugauuuc agagccaagg aucaguuaug gaaacgacgc ccugaugccu 1560
agucuuaccg aaaccaagac uacgguagaa cuccuucccg uuaacggaga guucagcuug 1620
gacgaccuuc agccuuggca cucauucgga gcugauuccg uaccagccaa uacggagaau 1680
gaaguagagc ccguagacgc aagaccugca gcggacagag ggcugacgac gagacccggu 1740
agcgguuuga caaauaucaa gacggaggag aucucugaag ugaagaugga uacagaauuc 1800
cgacaugacu caggauauga aguucaucau caaaaauugg uguucuuugc agaagauguc 1860
gguucuaaca agggugcuau cauaggccuu augguggug gcgucgugau ugcgaccgug 1920
auaguuauua cgcuugucau gcugaagaag aaacaguaua cguccaucca ucacggugug 1980
guagagguag augcggccgu aacucccgaa gagcgccauc uuucuaagau gcagcagaau 2040
ggauacgaga accccacgua caaauucuuu gagcaaaugc aaaacuga 2088

<210> SEQ ID NO 66
<211> LENGTH: 2088
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 66
augcucccug gacuugcuuu gcugcuuuug gcagccugga cugcucgagc acucgagguc 60
ccaacggaug gaaacgcggg ucuuuuggca gagccucaaa uagcaauguu uugcggaaga 120
cucaacaugc auaugaacgu ucagaauggg aaaugggacu ccgaccccag ugguacgaag 180
acauguauug acacaaagga gggaauacuc caguacugcc aggaagugua cccggagcuu 240
cagauuacga augugguaga ggcuaaucaa cccguaacua uccaaaauug guguaagaga 300
ggcaggaagc aaugcaagac ucauccucau uucguaauuc cguaucgaug uuuggugga 360 gaauuugucu cugacgcauu gcuuguuccu gacaagugua aguuucuuca ccaggaacgc 420
auggacgugu gcgagacaca cuugcacugg cauaccguug cgaaggagac guguuccgaa 480
aagaguacaa aucuccauga cuacggcaug uugcuccgu gcggaauaga uaaguuccga 540
ggcguggagu uuguaugcug uccgcuggca gaggagagcg auaaugucga uuccgcagau 600
gccgaagagg acgacagcga cgucuggugg ggaggagcgg acacugauua cgcugauggu 660
agugaggaca aaguagucga gguggcagaa gaagaagaag uggcggaggu ugaagaagaa 720
gaggcagacg augacgaaga cgaugaggac ggugaugagg uagaagaaga agcggaagaa 780
ccguacgaag aagcuacgga acgcacuaca aguauugcua ccacuacaac cacuacaacc 840
gaaucaguug aggaaguggu gcgaguccc acuacggcug ccaguacacc ggaugccguc 900
gacaaauacc uggagacucc uggcgacgaa aacgaacaug cucauuucca gaaggcgaag 960
gaacgccucg aagcaaagca cagagagaga augucacagg uaaugaggga augggaggag 1020
gcggaacgcc aagcaaagaa ccugccuaaa gcggacaaga aggcaguuau ccaacauuuc 1080
caagagaaag uggagagucu cgaacaggag gcagcgaacg agaggcaaca auugguagaa 1140
acgcacaugg cgagggugga agcuaugcuc aaugaccgaa gacgacuugc cuuggaaaau 1200
uacauuacug cccuucaagc cgucccaccg cgcccacgcc augucuuuaa caugcuuaag 1260
aaguauguuc gagcugaaca gaaggaucgg caacacaccc ugaaacacuu cgaacauguc 1320
agaaugguug acccgaagaa ggcugcacag auucgaaguc aaguuaugac ccauuugagg 1380
guaauauaug agagaaugaa ccaaagucug agccuucucu acaaugcccc cgcuguggcc 1440
gaggaaauuc aggacgaagu cgaugagcuc cugcaaaagg agcagaacua cucugacgau 1500
guacuugcua auaugauuuc agagccaagg aucaguuaug gaaacgacgc ccugaugccu 1560
agucuuaccg aaaccaagac uacgguagaa cuccuucccg uuaacggaga guucagcuug 1620
gacgaccuuc agccuuggca cucauucgga gcugauuccg uaccagccaa uacggagaau 1680
gaaguagagc ccguagacgc aagaccugca gcggacagag ggcugacgac gagacccggu 1740
agcgguuuga caaauaucaa gacggaggag aucucugaag ugaagaugga ugcagaauuc 1800
cgacaugacu caggauauga aguucaucau caaagauugg uguucuuugc agaagauguc 1860
gguucuaaca agggugcuau cauaggccuu augguggug gcgucgugau ugcgaccgug 1920
auaguuauua cgcuugucau gcugaagaag aaacaguaua cguccaucca ucacggugug 1980
guagagguag augcggccgu aacucccgaa gagcgccauc uuucuaagau gcagcagaau 2040
ggauacgaga accccacgua caaauucuuu gagcaaaugc aaaacuga 2088

<210> SEQ ID NO 67
<211> LENGTH: 2088
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 67
augcucccug gacuugcuuu gcugcuuuug gcagccugga cugcucgagc acucgagguc 60
ccaacggaug gaaacgcggg ucuuuuggca gagccucaaa uagcaauguu uugcggaaga 120
cucaacaugc auaugaacgu ucagaauggg aaaugggacu ccgaccccag ugguacgaag 180
acauguauug acacaaagga gggaauacuc caguacugcc aggaagugua cccggagcuu 240
cagauuacga augugguaga ggcuaaucaa cccguaacua uccaaaauug guguaagaga 300
ggcaggaagc aaugcaagac ucauccucau uucguaauuc cguaucgaug uuugguggga 360
gaauuugucu cugacgcauu gcuuguuccu gacaagugua aguuucuuca ccaggaacgc 420
auggacgugu gcgagacaca cuugcacugg cauaccguug cgaaggagac guguuccgaa 480
aagaguacaa aucuccauga cuacggcaug uugcucccgu gcggaauaga uaaguuccga 540
ggcguggagu uuguaugcug uccgcuggca gaggagagcg auaaugucga uuccgcagau 600
gccgaagagg acgacagcga cgucuggugg ggaggagcgg acacugauua cgcugauggu 660
agugaggaca aaguagucga gguggcagaa gaagaagaag uggcggaggu ugaagaagaa 720
gaggcagacg augacgaaga cgaugaggac ggugaugagg uagaagaaga agcggaagaa 780
ccguacgaag aagcuacgga acgcacuaca aguauugcua ccacuacaac cacuacaacc 840
gaaucaguug aggaaguggu gcgagucccc acuacggcug ccaguacacc ggaugccguc 900
gacaaauacc uggagacucc uggcgacgaa aacgaacaug cucauuucca gaaggcgaag 960
gaacgccucg aagcaaagca cagagagaga augucacagg uaaugaggga augggaggag 1020
gcggaacgcc aagcaaagaa ccugccuaaa gcggacaaga aggcaguuau ccaacauuuc 1080
caagagaaag uggagagucu cgaacaggag gcagcgaacg agaggcaaca auugguagaa 1140
acgcacaugg cgagggugga agcuaugcuc aaugaccgaa gacgacuugc cuuggaaaau 1200
uacauuacug cccuucaagc cgucccaccg cgcccacgcc augucuuuaa caugcuuaag 1260
aaguauguuc gagcugaaca gaaggaucgg caacacaccc ugaaacacuu cgaacauguc 1320
agaaugguug acccgaagaa ggcugcacag auucgaaguc aaguuaugac ccauuugagg 1380
guaauauaug agagaaugaa ccaaagucug agccuucucu acaauguccc cgcuguggcc 1440
gaggaaauuc aggacgaagu cgaugagcuc cugcaaaagg agcagaacua cucugacgau 1500
guacuugcua auaugauuuc agagccaagg aucaguuaug gaaacgacgc ccugaugccu 1560
agucuuaccg aaaccaagac uacgguagaa cuccuucccg uuaacggaga guucagcuug 1620
gacgaccuuc agccuuggca cucauucgga gcugauuccg uaccagccaa uacggagaau 1680
gaaguagagc ccguagacgc aagaccugca gcggacagag ggcugacgac gagacccggu 1740
agcgguuuga caaauaucaa gacggaggag aucucugaag ugaagaugga ugcagaauuc 1800
cgacaugacu caggauauga aguucaucau caagaauugg uguucuuugc agaagauguc 1860
gguucuaaca agggugcuau cauaggccuu augguggggug gcgucgugau ugcgaccgug 1920
auaguuauua cgcuugucau gcugaagaag aaacaguaua cguccaucca ucacggugug 1980
guagagguag augcggccgu aacucccgaa gagcgccauc uuucuaagau gcagcagaau 2040
ggauacgaga accccacgua caaauucuuu gagcaaaugc aaaacuga 2088

<210> SEQ ID NO 68
<211> LENGTH: 2088
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 68
augcucccug gacuugcuuu gcugcuuuug gcagccugga cugcucgagc acucgagguc 60
ccaacggaug gaaacgcggg ucuuuuggca gagccucaaa uagcaauguu uugcggaaga 120
cucaacaugc auaugaacgu ucagaauggg aaaugggacu ccgaccccag ugguacgaag 180
acauguauug acacaaagga gggaauacuc caguacugcc aggaagugua cccggagcuu 240
cagauuacga augugguaga ggcuaaucaa cccguaacua uccaaaauug guguaagaga 300
ggcaggaagc aaugcaagac ucauccucau uucguaauuc cguaucgaug uuugguggga 360
gaauuugucu cugacgcauu gcuuguuccu gacaagugua aguuucuuca ccaggaacgc 420
auggacgugu gcgagacaca cuugcacugg cauaccguug cgaaggagac guguuccgaa 480
aagaguacaa aucuccauga cuacggcaug uugcuccccgu gcggaauaga uaaguuccga 540
ggcguggagu uuguaugcug uccgcuggca gaggagagcg auaaugucga uuccgcagau 600
gccgaagagg acgacagcga cgucuggugg ggaggagcgg acacugauua cgcugauggu 660
agugaggaca aaguagucga ggugggcagaa gaagaagaag uggcggaggu ugaagaagaa 720
gaggcagacg augacgaaga cgaugaggac ggugaugagg uagaagaaga agcggaagaa 780
ccguacgaag aagcuacgga acgcacuaca aguauugcua ccacuacaac cacuacaacc 840
gaaucaguug aggaagugggu gcgagucccc acuacggcug ccaguacacc ggaugccguc 900
gacaaauacc uggagacucc uggcgacgaa aacgaacaug cucauuucca gaaggcgaag 960
gaacgccucg aagcaaagca cagagagaga augucacagg uaaugaggga augggaggag 1020
gcggaacgcc aagcaaagaa ccugccuaaa gcggacaaga aggcaguuau ccaacauuuc 1080
caagagaaag uggagagucu cgaacaggag gcagcgaacg agaggcaaca auugguagaa 1140
acgcacaugg cgagggugga agcuaugcuc aaugaccgaa gacgacuugc cuuggaaaau 1200
uacauuacug cccuucaagc cgucccaccg cgcccacgcc augucuuuaa caugcuuaag 1260
aaguauguuc gagcugaaca gaaggaucgg caacacaccc ugaaacacuu cgaacauguc 1320
agaaugguug acccgaagaa ggcugcacag auucgaaguc aaguuaugac ccauuugagg 1380
guaauauaug agagaaugaa ccaaagucug agccuucucu acaaaugccc cgcuguggcc 1440

```
gaggaaauuc aggacgaagu cgaugagcuc cugcaaaagg agcagaacua cucugacgau   1500

guacuugcua auaugauuuc agagccaagg aucaguuaug gaaacgacgc ccugaugccu   1560

agucuuaccg aaaccaagac uacgguagaa cuccuucccg uuaacggaga guucagcuug   1620

gacgaccuuc agccuuggca cucauucgga gcugauuccg uaccagccaa uacggagaau   1680

gaaguagagc ccguagacgc aagaccugca gcggacagag ggcugacgac gagacccggu   1740

agcgguuuga caaauaucaa gacggaggag aucucugaag ugaagaugga ugcagaauuc   1800

cgacaugacu caggauauga aguucaucau caaggauugg uguucuuugc agaagauguc   1860

gguucuaaca agggugcuau cauaggccuu augguggug gcgucgugau ugcgaccgug    1920

auaguuauua cgcuugucau gcugaagaag aaacaguaua cguccaucca ucacggugug   1980

guagagguag augcggccgu aacucccgaa gagcgccauc uuucuaagau gcagcagaau   2040

ggauacgaga accccacgua caaauucuuu gagcaaaugc aaaacuga                2088
```

<210> SEQ ID NO 69
<211> LENGTH: 2088
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 69

```
augcucccug gacuugcuuu gcugcuuuug gcagccugga cugcucgagc acucgagguc     60

ccaacggaug gaaacgcggg ucuuuuggca gagccucaaa uagcaauguu uugcggaaga    120

cucaacaugc auaugaacgu ucagaauggg aaaugggacu ccgaccccag ugguacgaag    180

acauguauug acacaaagga gggaauacuc caguacugcc aggaagugua cccggagcuu    240

cagauuacga augugguaga ggcuaaucaa cccguaacua uccaaaauug guguaagaga    300

ggcaggaagc aaugcaagac ucauccucau uucguaauuc cguaucgaug uuuggugga     360

gaauuugucu cugacgcauu gcuuguuccu gacaagugua aguuucuuca ccaggaacgc    420

auggacgugu gcgagacaca cuugcacugg cauaccguug cgaaggagac guguuccgaa    480

aagaguacaa aucuccauga cuacggcaug uugcucccgu gcggaauaga uaaguuccga    540

ggcguggagu uuguaugcug uccgcuggca gaggagagcg auaaugucga uuccgcagau    600

gccgaagagg acgacagcga cgucuggugg ggaggagcgg acacugauua cgcugauggu    660

agugaggaca aaguagucga gguggcagaa gaagaagaag uggcggaggu ugaagaagaa    720

gaggcagacg augacgaaga cgaugaggac ggugaugagg uagaagaaga agcggaagaa    780

ccguacgaag aagcuacgga acgcacuaca aguauugcua ccacuacaac cacuacaacc    840

gaaucaguug aggaaguggu gcgagucccc acuacggcug ccaguacacc ggaugccguc    900

gacaaauacc uggagacucc uggcgacgaa aacgaacaug cucauuucca gaaggcgaag    960

gaacgccucg aagcaaagca cagagagaga augucacagg uaaugaggga augggaggag   1020

gcggaacgcc aagcaaagaa ccugccuaaa gcggacaaga aggcaguuau ccaacauuuc   1080

caagagaaag uggagagucu cgaacaggag gcagcgaacg agaggcaaca auugguagaa   1140

acgcacaugg cgagggugga agcuaugcuc aaugaccgaa gacgacuugc cuuggaaaau   1200

uacauuacug cccuucaagc cgucccaccg cgcccacgcc augucuuuaa caugcuuaag   1260

aaguauguuc gagcugaaca gaaggaucgg caacacaccc ugaaacacuu cgaacauguc   1320
```

agaaugguug acccgaagaa ggcugcacag auucgaaguc aaguuaugac ccauuugagg 1380
guaauauaug agagaaugaa ccaaagucug agccuucucu acaaugucccc cgcuguggcc 1440 gaggaaauuc aggacgaagu cgaugagcuc cugcaaaagg agcagaacua cucugacgau 1500
guacuugcua auaugauuuc agagccaagg aucaguuaug gaaacgacgc ccugaugccu 1560
agucuuaccg aaaccaagac uacgguagaa cuccuucccg uuaacggaga guucagcuug 1620
gacgaccuuc agccuuggca cucauucgga gcugauuccg uaccagccaa uacggagaau 1680
gaaguagagc ccguagacgc aagaccugca gcggacagag ggcugacgac gagacccggu 1740
agcgguuuga caaauaucaa gacggaggag aucucugaag ugaagaugga ugcagaauuc 1800
cgacaugacu caggauauga aguucgucau caaaaaauugg uguucuuugc agaagauguc 1860
gguucuaaca agggugcuau cauaggccuu auggugggug gcgucgugau ugcgaccgug 1920
auaguuauua cgcuugucau gcugaagaag aaacaguaua cguccaucca ucacggugug 1980
guagagguag augcggccgu aacucccgaa gagcgccauc uuucuaagau gcagcagaau 2040
ggauacgaga accccacgua caaauucuuu gagcaaaugc aaaacuga 2088

<210> SEQ ID NO 70
<211> LENGTH: 2088
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 70
augcucccug gacuugcuuu gcugcuuuug gcagccugga cugcucgagc acucgagguc 60
ccaacggaug gaaacgcggg ucuuuuggca gagccucaaa uagcaauguu uugcggaaga 120
cucaacaugc auaugaacgu ucagaauggg aaaugggacu ccgaccccag ugguacgaag 180
acauguauug acacaaagga gggaauacuc caguacugcc aggaagugua cccggagcuu 240
cagauuacga augugguaga ggcuaaucaa cccguaacua uccaaaauug guguaagaga 300
ggcaggaagc aaugcaagac ucauccucau uucguaauuc cguaucgaug uuuggugggga 360 gaauuugucu cugacgcauu gcuuguuccu gacaagugua aguuucuuca ccaggaacgc 420
auggacgugu gcgagacaca cuugcacugg cauaccguug cgaaggagac guguuccgaa 480
aagaguacaa aucuccauga cuacggcaug uugcuccccgu gcggaauaga uaaguuccga 540
ggcguggagu uuguaugcug uccgcuggca gaggagagcg auaaugucga uuccgcagau 600
gccgaagagg acgacagcga cgucuggugg ggaggagcgg acacugauua cgcugauggu 660
agugaggaca aaguagucga gguggcagaa gaagaagaag uggcggaggu ugaagaagaa 720
gaggcagacg augacgaaga cgaugaggac ggugaugagg uagaagaaga agcggaagaa 780
ccguacgaag aagcuacgga acgcacuaca aguauugcua ccacuacaac cacuacaacc 840
gaaucaguug aggaaguggu gcgagucccc acuacggcug ccaguacacc ggaugccguc 900
gacaaauacc uggagacucc uggcgacgaa aacgaacaug cucauuucca gaaggcgaag 960
gaacgccucg aagcaaagca cagagagaga augucacagg uaaugaggga augggaggag 1020
gcggaacgcc aagcaaagaa ccugccuaaa gcggacaaga aggcaguuau ccaacauuuc 1080
caagagaaag uggagagucu cgaacaggag gcagcgaacg agaggcaaca auugguagaa 1140
acgcacaugg cgagggugga agcuaugcuc aaugaccgaa gacgacuugc cuuggaaaau 1200
uacauuacug cccuucaagc cgucccaccg cgcccacgcc augucuuuaa caugcuuaag 1260
aaguauguuc gagcugaaca gaaggaucgg caacacaccc ugaaacacuu cgaacauguc 1320
agaaugguug acccgaagaa ggcugcacag auucgaaguc aaguuaugac ccauuugagg 1380
guaauauaug agagaaugaa ccaaagucug agccuucucu acaaugucccc cgcuguggcc 1440 gaggaaauuc aggacgaagu cgaugagcuc cugcaaaagg agcagaacua cucugacgau 1500
guacuugcua auaugauuuc agagccaagg aucaguuaug gaaacgacgc ccugaugccu 1560
agucuuaccg aaaccaagac uacgguagaa cuccuucccg uuaacggaga guucagcuug 1620
gacgaccuuc agccuuggca cucauucgga gcugauuccg uaccagccaa uacggagaau 1680
gaaguagagc ccguagacgc aagaccugca gcggacagag ggcugacgac gagacccggu 1740
agcgguuuga caaauaucaa gacggaggag aucucugaag ugaagaugga ugcagaauuc 1800
cgacaugacu caggauaugg aguucaucau caaaaaauugg uguucuuugc agaagauguc 1860
gguucuaaca agggugcuau cauaggccuu augguggug gcgucgugau ugcgaccgug 1920
auaguuauua cgcuugucau gcugaagaag aaacaguaua cguccaucca ucacggugug 1980
guagagguag augcggccgu aacucccgaa gagcgccauc uuucuaagau gcagcagaau 2040
ggauacgaga accccacgua caaauucuuu gagcaaaugc aaaacuga 2088

<210> SEQ ID NO 71
<211> LENGTH: 289
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 71
ggugcucgcu ucggcagcac auauacuuug ugaaagaagg acgggucacc uugucuuucc 60
ugcugcuucu gccacacccu guuuggucuu cucagcagca gccacaacuc ccuccuuggc 120
cuuugaaagu ccuuucacga auacauccac ggcuaaugaa uuccuuuaca ccacacuguc 180
gucgaauggc cacucccagu ucuccgcuca cgagggugga aaggcagaag gcuugaaggc 240
aaggcgugag uggccuguga cuaacugugc caagcggacu ucgguccgc 289

<210> SEQ ID NO 72
<211> LENGTH: 147
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 72
gaacaucgua gauugaagcc acaaaaucca cagcacacaa agacccugcc accauguauu 60
cacuucagug aaagggaagc accgaaaugc ugagugggggg cguggaauuu uuggagcagg 120
uuuucugacu ucggucggaa aaccccu 147

<210> SEQ ID NO 73
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 73
aggagaagga gaaggaggag gacugggagg aggaggacgg cgacgaccag aaggggccca 60

<210> SEQ ID NO 74
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 74
cgacgaccag aaggggccca agagaggggg cgggcgaccg agcgccgcga cgcggaagug 60

<210> SEQ ID NO 75
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 75
agcgccgcga cgcggaagug aggugcgugc gggcugcggc gcagaccccg gcccggcccc 60

<210> SEQ ID NO 76
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 76
gcagaccccg gcccggcccc uccgagggcg uccugggcgc ucccucacgc cuugccuuca 60

<210> SEQ ID NO 77
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 77
ucccucacgc cuugccuuca agccuucugc cuuuccgccc ucgugagcgg agaacuggga 60

<210> SEQ ID NO 78
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 78
ucgugagcgg agaacuggga guggccauuc gacgacggug ugguguaaag gaauucauua 60

<210> SEQ ID NO 79
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 79 uggguaaag gaauucauua gccguggaug uauucaugaa aggacuuuca aaggccgagg 60

<210> SEQ ID NO 80
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 80
aggacuuuca aaggccgagg agggaguugu ggcugcugcu gagaaaucca aacagggugu 60

<210> SEQ ID NO 81
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 81
gagaaaucca aacagggugu ggcagaagca gcaggaaaga caaaugaggg uguucucuau 60

<210> SEQ ID NO 82
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 82
caaaugaggg uguucucuau guaggcuccg aaaccaagga gggaguggug cauggugugg 60

<210> SEQ ID NO 83
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 83
gggaguggug cauggugugg caacgguggc ugagaagacc aaagagcaag ugacaaaugu 60

<210> SEQ ID NO 84
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 84
aaagagcaag ugacaaaugu uggaggagcg guggugacgg gugugacagc aguagcccag 60

<210> SEQ ID NO 85
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 85
gugugacagc aguagcccag aagacggugg agggagcagg gagcauugca gcagccacug 60

<210> SEQ ID NO 86
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 86
gagcauugca gcagccacug gcuuugucaa gaaggaccag uugggcaaga augaagaagg 60

<210> SEQ ID NO 87
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 87
uugggcaaga augaagaagg agccccacgg gaaggaauuc uggaagauau gccuguggau 60

<210> SEQ ID NO 88
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 88
uggaagauau gccuguggau ccugacgaug aggcuuauga aaugccuucu gaggaagggu 60

<210> SEQ ID NO 89
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 89
aaugccuucu gaggaagggu aucaagacug cgaaccugaa gccuaagaaa uaucuuugcu 60

<210> SEQ ID NO 90
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 90
gccuaagaaa uaucuuugcu cccgguuucu ugagaucugc ugacagaugu uccauccugu    60

<210> SEQ ID NO 91
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 91
ugacagaugu uccauccugu acaagugcuc gguuccaaug ugcccaguca ugacauuucu    60

<210> SEQ ID NO 92
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 92
ugcccaguca ugacauuucu caaaguuuuu gcaguguauc ucgaagucuu ccaucagcag    60

<210> SEQ ID NO 93
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 93
ucgaagucuu ccaucagcag ugauugaagu gucuguaccu gcccccacuc agcauuucgg    60

<210> SEQ ID NO 94
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 94
gcccccacuc agcauuucgg ugcuucccuu ucgcugaagu gaauacaugg uagcaggguc    60

<210> SEQ ID NO 95
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 95
gaauacaugg uagcaggguc uuugugugcu guggguuuug uggcuucaau cuacgauguu    60

<210> SEQ ID NO 96
<211> LENGTH: 60
<212> TYPE: RNA

<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 96
uggcuucaau cuacgauguu aagacaaauu aagaacaccu aagugacuac cacuuauuuc 60

<210> SEQ ID NO 97
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 97
aagugacuac cacuuauuuc uaaauccucg cuauuuuuuu guugcuguug uucagaaguu 60

<210> SEQ ID NO 98
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 98
guugcuguug uucagaaguu guuggugauu ugcuaucaua uauuauaaga uuuuuaggug 60

<210> SEQ ID NO 99
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 99
uauuauaaga uuuuuaggug ucuuuuaaug augcugucua agaauaauga cguauuguga 60

<210> SEQ ID NO 100
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 100
agaauaauga cguauuguga aauuuguuga uauauauaau acuuaauaau augugagcau 60

<210> SEQ ID NO 101
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 101
acuuaauaau augugagcau gaaacuaugc gccuauaaau acuaaauaug aaauuuuacc 60

<210> SEQ ID NO 102
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 102
acuaaauaug aaauuuuacc guuuugcgau guguuuuauu cacuuguguu uguauauaaa 60

<210> SEQ ID NO 103
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 103
cacuuguguu uguauauaaa uggugagaau uagaauaaua cguuaucuca uugcauaaau 60

<210> SEQ ID NO 104
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 104
cguuaucuca uugcauaaau auuuuauuuu uaucccgucu cacuuuaaua auaauaauca 60

<210> SEQ ID NO 105
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 105
tgggcccctt ctggtcgtcg ccgtcctcct cctcccagtc ctcctccttc tccttctcct 60

<210> SEQ ID NO 106
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 106
cacttccgcg tcgcggcgct cggtcgcccg ccccctctct tgggcccctt ctggtcgtcg 60

<210> SEQ ID NO 107
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 107
acctcacttc cgcgtcgcgg cgctcggtcg ctcgcccccct ctcttgggcc ccttctggtc 60

<210> SEQ ID NO 108
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 108
ggggccgggc cggggtctgc gccgcagccc gcacgcacct cacttccgcg tcgcggcgct 60

<210> SEQ ID NO 109
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 109
ggacgctctc ggaggggccg ggccggggtc tgcgccgcag cccgcacgca cctcacttcc 60

<210> SEQ ID NO 110
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 110
tgaaggcaag gcgtgaggga gcgcccagga cgccctcgga ggggccgggc cggggtctgc 60

<210> SEQ ID NO 111
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 111
tcccagttct ccgctcacga gggcggaaag gcagaaggct tgaaggcaag gcgtgaggga 60

<210> SEQ ID NO 112
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 112
taatgaattc ctttacacca caccgtcgtc gaatggccac tcccagttct ccgctcacga 60

<210> SEQ ID NO 113
<211> LENGTH: 60

<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 113
cctcggcctt tgaaagtcct ttcatgaata catccacggc taatgaattc ctttacacca 60

<210> SEQ ID NO 114
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 114
acaccctgtt tggatttctc agcagcagcc acaactccct cctcggcctt tgaaagtcct 60

<210> SEQ ID NO 115
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 115
atagagaaca ccctcatttg tctttcctgc tgcttctgcc acaccctgtt tggatttctc 60

<210> SEQ ID NO 116
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 116
ccacaccatg caccactccc tccttggttt cggagcctac atagagaaca ccctcatttg 60

<210> SEQ ID NO 117
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 117
acatttgtca cttgctcttt ggtcttctca gccaccgttg ccacaccatg caccactccc 60

<210> SEQ ID NO 118
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 118
ctgggctact gctgtcacac ccgtcaccac cgctcctcca acatttgtca cttgctcttt 60

<210> SEQ ID NO 119
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 119
cagtggctgc tgcaatgctc cctgctccct ccaccgtctt ctgggctact gctgtcacac 60

<210> SEQ ID NO 120
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 120
ccttcttcat tcttgcccaa ctggtccttc ttgacaaagc cagtggctgc tgcaatgctc 60

<210> SEQ ID NO 121
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 121
atccacaggc atatcttcca gaattccttc ccgtggggct ccttcttcat tcttgcccaa 60

<210> SEQ ID NO 122
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 122
acccttcctc agaaggcatt tcataagcct catcgtcagg atccacaggc atatcttcca 60

<210> SEQ ID NO 123
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 123
agcaaagata tttcttaggc ttcaggttcg cagtcttgat acccttcctc agaaggcatt 60

<210> SEQ ID NO 124
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 124
acaggatgga acatctgtca gcagatctca agaaaccggg agcaaagata tttcttaggc 60

<210> SEQ ID NO 125
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 125
agaaatgtca tgactgggca cattggaacc gagcacttgt acaggatgga acatctgtca 60

<210> SEQ ID NO 126
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 126
ctgctgatgg aagacttcga gatacactgc aaaaactttg agaaatgtca tgactgggca 60

<210> SEQ ID NO 127
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 127
ccgaaatgct gagtgggggc aggtacagac acttcaatca ctgctgatgg aagacttcga 60

<210> SEQ ID NO 128
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 128
gaccctgcta ccatgtattc acttcagcga aagggaagca ccgaaatgct gagtgggggc 60

<210> SEQ ID NO 129
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 129
aacatcgtag attgaagcca caaaacccac agcacacaaa gaccctgcta ccatgtattc 60

<210> SEQ ID NO 130

<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 130
gaaataagtg gtagtcactt aggtgttctt aatttgtctt aacatcgtag attgaagcca 60

<210> SEQ ID NO 131
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 131
aacttctgaa caacagcaac aaaaaaatag cgaggattta gaaataagtg gtagtcactt 60

<210> SEQ ID NO 132
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 132
cacctaaaaa tcttataata tatgatagca aatcaccaac aacttctgaa caacagcaac 60

<210> SEQ ID NO 133
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 133
tcacaatacg tcattattct tagacagcat cattaaaaga cacctaaaaa tcttataata 60

<210> SEQ ID NO 134
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 134
atgctcacat attattaagt attatatata tcaacaaatt tcacaatacg tcattattct 60

<210> SEQ ID NO 135
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 135
ggtaaaattt catatttagt atttataggc gcatagtttc atgctcacat attattaagt 60

<210> SEQ ID NO 136
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 136
tttatataca aacacaagtg aataaaacac atcgcaaaac ggtaaaattt catatttagt 60

<210> SEQ ID NO 137
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 137
atttatgcaa tgagataacg tattattcta attctcacca tttatataca aacacaagtg 60

<210> SEQ ID NO 138
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 138
tgattattat tattaaagtg agacgggata aaaataaaat atttatgcaa tgagataacg 60

<210> SEQ ID NO 139
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 139
gctgggggag tgggaggcaa acccgctaac ccgtcgtcga atggccactc ccagttctcc 60

<210> SEQ ID NO 140
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 140
gcaccaaact gacatttggg gtttacctac ccacatagag aacaccctct tgtgtctttc 60

<210> SEQ ID NO 141
<211> LENGTH: 60
<212> TYPE: DNA
<213> ORGANISM: Artificial Sequence
<220> FEATURE:

<221> NAME/KEY: source
<223> OTHER INFORMATION: /note="Description of Artificial Sequence:
Synthetic oligonucleotide"

<400> SEQUENCE: 141
atctttggat ataagcacaa tggagcttac ccgttgccac accatgcacc actccctcct 60

<210> SEQ ID NO 142
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 142
aaatgtaaca caaaacgtac acagccatac cttgcccaac tggtccttgt tgacaaagcc 60

<210> SEQ ID NO 143
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 143
ttgttagaaa gattcagctt ggactcctac cccagaaggc atttcataag cctcattgtc 60

<210> SEQ ID NO 144
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 144
atccatggct aatgaattcc tttacaccac accggaaaac ataaaataca ctttgaatga 60

<210> SEQ ID NO 145
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 145
tgcaccactc cctccttggt tttggagccc acaaaaacaa attcaagaca taagtctcaa 60

<210> SEQ ID NO 146
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 146
ttgtcacttg ctctttggtc ttctcagcca ctggtacaaa taaagagcaa caacagatta 60

<210> SEQ ID NO 147
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 147
attccttcct gtggggctcc ttcttcattc caatatttaa agtaagaagc acaaaaagaa 60

<210> SEQ ID NO 148
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 148
cttcaggttc gtagtcttga tacccttccc aatattagaa aaatcaaaaa gacagcacac 60

<210> SEQ ID NO 149
<211> LENGTH: 5632
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 149
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accatatgcg gtgtgaaata ccgcacagat gcgtaaggag aaaataccgc atcaggcgcc 240
attcgccatt caggctgcgc aactgttggg aagggcgatc ggtgcgggcc tcttcgctat 300
tacgccagct ggcgaaaggg ggatgtgctg caaggcgatt aagttgggta acgccagggt 360
tttcccagtc acgacgttgt aaaacgacgg ccagtgaatt gacgcgccat tgggatgttg 420
taaaacgacg gccagtgaac ctgcaggcag ctgcgcgctc gctcgctcac tgaggccgcc 480
cgggcaaagc ccgggcgtcg ggcgaccttt ggtcgcccgg cctcagtgag cgagcgagcg 540
cgcagagagg gagtggccaa ctccatcact aggggttcct gcggccgcac gcgtggagta 600
aggaccagct tctttgggag agaacagacg caggggcggg agggaaaaag ggagaggcag 660
acgtcacttc ctcttggcga ctctggcagc agattggtcg gttgagtggc agaaaggcag 720
acggggactg ggcaaggcac tgtcggtgac atcacggaca gggcgacttc tatgtagatg 780
aggcagcgca gaggctgctg cttcgccact tgctgcttcg ccacgaaggg agttcccgtg 840
ccctgggagc gggttcagga ccgctgatcg gaagtgagaa tcccagctgt gtgtcagggc 900
tggaaagggc tcgggagtgc gcggggcaag tgaccgtgtg tgtaaagagt gaggcgtatg 960
aggctgtgtc ggggcagagc ccgaagatct caccgaacat cgtagatcga agccacaaaa 1020
cccacagcac acaaagaccc tgccaccatg cattcacttc agcgaaaggg aagcaccgaa 1080
atgccgagtg gggcgtgga atttttggag caggttttct gacttcggtc ggaaaacccc 1140
tcccaatttc actggtctac aatgaaagca aaacagttct cttccccgct ccccggtgtg 1200

-continued

```
tgagaggggc tttgatcctt ctctggtttc ctaggaaacg cgtatgtgct agcgtactga   1260
gtcgcccagt ctcagataga tccgacgccg ccatctctag gcccgcgccg gccccctcgc   1320
acagacttgt gggagaagct cggctactcc cctgccccgg ttaatttgca tataatattt   1380
cctagtaact atagaggctt aatgtgcgat aaaagacaga taatctgttc tttttaatac   1440
tagctacatt ttacatgata ggcttggatt tctataagag atacaaatac taaattatta   1500
ttttaaaaaa cagcacaaag gaaactcacc ctaactgtaa agtaattgtg tgttttgaga   1560
ctataaatat cccttggaga aaagccttgt ttggaattca tacgcgttga cattgattat   1620
tgactagtta ttaatagtaa tcaattacgg ggtcattagt tcatagccca tatatggagt   1680
tccgcgttac ataacttacg gtaaatggcc cgcctggctg accgcccaac gacccccgcc   1740
cattgacgtc aataatgacg tatgttccca tagtaacgcc aatagggact ttccattgac   1800
gtcaatgggt ggagtattta cggtaaactg cccacttggc agtacatcaa gtgtatcata   1860
tgccaagtac gccccctatt gacgtcaatg acggtaaatg gcccgcctgg cattatgccc   1920
agtacatgac cttatgggac tttcctactt ggcagtacat ctacgtatta gtcatcgcta   1980
ttaccatggt gatgcggttt tggcagtaca tcaatgggcg tggatagcgg tttgactcac   2040
ggggatttcc aagtctccac cccattgacg tcaatgggag tttgttttgg caccaaaatc   2100
aacgggactt tccaaaatgt cgtaacaact ccgccccatt gacgcaaatg ggcggtaggc   2160
gtgtacggtg ggaggtctat ataagcagag ctcgtttagt gaaccgtcag atcgcctgga   2220
gacgccatcc acgctgtttt gacctccata gaagacaccg ggaccgatcc agcctccgga   2280
ctctagagga tcgaaccctt aagccgccac catggtgagc aagggcgagg agctgttcac   2340
cggggtggtg cccatcctgg tcgagctgga cggcgacgta aacggccaca agttcagcgt   2400
gtccggcgag ggcgagggcg atgccaccta cggcaagctg accctgaagt tcatctgcac   2460
caccggcaag ctgcccgtgc cctggcccac cctcgtgacc accctgacct acggcgtgca   2520
gtgcttcagc cgctaccccg accacatgaa gcagcacgac ttcttcaagt ccgccatgcc   2580
cgaaggctac gtccaggagc gcaccatctt cttcaaggac gacggcaact acaagacccg   2640
cgccgaggtg aagttcgagg gcgacaccct ggtgaaccgc atcgagctga agggcatcga   2700
cttcaaggag gacggcaaca tcctggggca caagctggag tacaactaca acagccacaa   2760
cgtctatatc atggccgaca agcagaagaa cggcatcaag gtgaacttca agatccgcca   2820
caacatcgag gacggcagcg tgcagctcgc cgaccactac cagcagaaca cccccatcgg   2880
cgacggcccc gtgctgctgc ccgacaacca ctacctgagc acccagtccg ccctgagcaa   2940
agaccccaac gagaagcgcg atcacatggt cctgctggag ttcgtgaccg ccgccgggat   3000
cactctcggc atggacgagc tgtacaagta ctcagatctc gagctcaagt gaaccggtca   3060
gacatgataa gatacattga tgagtttgga caaaccacaa ctagaatgca gtgaaaaaaa   3120
tgctttattt gtgaaatttg tgatgctatt gctttatttg taaccattat aagctgcaat   3180
aaacaagtta acaacaacaa ttgcattcat tttatgtttc aggttcaggg ggaggtgtgg   3240
gaggtttttt aaacacgtgc ggaccgagcg gccgcaggaa cccctagtga tggagttggc   3300
cactccctct ctgcgcgctc gctcgctcac tgaggccggg cgaccaaagg tcgcccgacg   3360
cccgggcttt gcccgggcgg cctcagtgag cgagcgagcg cgcagctgcc tgcaggcttg   3420
gatcccaatg gcgcgccgag cttggctcga gcatggtcat agctgtttcc tgtgtgaaat   3480
tgttatccgc tcacaattcc acacaacata cgagccggaa gcataaagtg taaagcctgg   3540
ggtgcctaat gagtgagcta actcacatta attgcgttgc gctcactgcc cgctttccag   3600
```

tcgggaaacc tgtcgtgcca gctgcattaa tgaatcggcc aacgcgcggg gagaggcggt 3660
ttgcgtattg ggcgctcttc cgcttcctcg ctcactgact cgctgcgctc ggtcgttcgg 3720
ctgcggcgag cggtatcagc tcactcaaag gcggtaatac ggttatccac agaatcaggg 3780
gataacgcag gaaagaacat gtgagcaaaa ggccagcaaa aggccaggaa ccgtaaaaag 3840
gccgcgttgc tggcgttttt ccataggctc cgcccccctg acgagcatca caaaaatcga 3900
cgctcaagtc agaggtggcg aaacccgaca ggactataaa gataccaggc gtttccccct 3960
ggaagctccc tcgtgcgctc tcctgttccg accctgccgc ttaccggata cctgtccgcc 4020
tttctccctt cgggaagcgt ggcgctttct catagctcac gctgtaggta tctcagttcg 4080
gtgtaggtcg ttcgctccaa gctgggctgt gtgcacgaac cccccgttca gcccgaccgc 4140
tgcgccttat ccggtaacta tcgtcttgag tccaacccgg taagacacga cttatcgcca 4200
ctggcagcag ccactggtaa caggattagc agagcgaggt atgtaggcgg tgctacagag 4260
ttcttgaagt ggtggcctaa ctacggctac actagaagaa cagtatttgg tatctgcgct 4320
ctgctgaagc cagttacctt cggaaaaaga gttggtagct cttgatccgg caaacaaacc 4380
accgctggta gcggtggttt ttttgtttgc aagcagcaga ttacgcgcag aaaaaaagga 4440
tctcaagaag atcctttgat cttttctacg gggtctgacg ctcagtggaa cgaaaactca 4500
cgttaaggga ttttggtcat gagattatca aaaaggatct tcacctagat ccttttaaat 4560
taaaaatgaa gttttaaatc aatctaaagt atatatgagt aaacttggtc tgacagttag 4620
aaaaactcat cgagcatcaa atgaaactgc aatttattca tatcaggatt atcaatacca 4680
tatttttgaa aaagccgttt ctgtaatgaa ggagaaaact caccgaggca gttccatagg 4740
atggcaagat cctggtatcg gtctgcgatt ccgactcgtc caacatcaat acaacctatt 4800
aatttcccct cgtcaaaaat aaggttatca agtgagaaat caccatgagt gacgactgaa 4860
tccggtgaga atggcaaaag tttatgcatt tctttccaga cttgttcaac aggccagcca 4920
ttacgctcgt catcaaaatc actcgcatca accaaaccgt tattcattcg tgattgcgcc 4980
tgagcgagac gaaatacgcg atcgctgtta aaaggacaat tacaaacagg aatcgaatgc 5040
aaccggcgca ggaacactgc cagcgcatca acaatatttt cacctgaatc aggatattct 5100
tctaatacct ggaatgctgt tttcccaggg atcgcagtgg tgagtaacca tgcatcatca 5160
ggagtacgga taaaatgctt gatggtcgga agaggcataa attccgtcag ccagtttagt 5220
ctgaccatct catctgtaac atcattggca acgctacctt tgccatgttt cagaaacaac 5280
tctggcgcat cgggcttccc atacaatcga tagattgtcg cacctgattg cccgacatta 5340
tcgcgagccc atttataccc atataaatca gcatccatgt tggaatttaa tcgcggccta 5400
gagcaagacg tttcccgttg aatatggctc atactcttcc tttttcaata ttattgaagc 5460
atttatcagg gttattgtct catgagcgga tacatatttg aatgtattta gaaaaataaa 5520
caaatagggg ttccgcgcac atttccccga aaagtgccac ctgacgtcta agaaaccatt 5580
attatcatga cattaaccta taaaaatagg cgtatcacga ggccctttcg tc 5632

<210> SEQ ID NO 150
<211> LENGTH: 100
<212> TYPE: RNA
<213> ORGANISM: Unknown
<220> FEATURE:
<221> NAME/KEY: source
<223> OTHER INFORMATION: /note="Description of Unknown:
APP target sequence"

<400> SEQUENCE: 150
accagguucu ggguugacaa auaucaagac ggaggagauc ucugaaguga agauggaugc 60
agaauuccga caugacucag gauaugaagu ucaucaucaa 100

<210> SEQ ID NO 151
<211> LENGTH: 100
<212> TYPE: RNA
<213> ORGANISM: Unknown
<220> FEATURE:
<221> NAME/KEY: source
<223> OTHER INFORMATION: /note="Description of Unknown:
APP target sequence"

<400> SEQUENCE: 151
uacagguucu ggguugacaa auaucaagac ggaggagauc ucugaaguga agauggaugc 60
agaauuccga caugacucag gauaugaagu ucaucaucaa 100

<210> SEQ ID NO 152
<211> LENGTH: 90
<212> TYPE: RNA
<213> ORGANISM: Unknown
<220> FEATURE:
<221> NAME/KEY: source
<223> OTHER INFORMATION: /note="Description of Unknown:
APP target sequence"

<400> SEQUENCE: 152 guucugggguu gacaaauauc aagacggagg agaucucuga agugaagaug gaugcagaau 60
uccgacauga cucaggauau gaaguucauc 90

<210> SEQ ID NO 153
<211> LENGTH: 90
<212> TYPE: DNA
<213> ORGANISM: Unknown
<220> FEATURE:
<221> NAME/KEY: source
<223> OTHER INFORMATION: /note="Description of Unknown:
APP target sequence"

<400> SEQUENCE: 153
tctgggttga caaatatcaa gacggaggag atctctgaag tgaagatgga tgcagaattc 60
cgacatgact caggatatga agttcatcat 90

<210> SEQ ID NO 154
<211> LENGTH: 90
<212> TYPE: DNA
<213> ORGANISM: Unknown
<220> FEATURE:
<221> NAME/KEY: source
<223> OTHER INFORMATION: /note="Description of Unknown:
APP target sequence"

<400> SEQUENCE: 154
aggagatctc tgaagtgaag atggatgcag aattccgaca tgactcagga tatgaagttc 60
atcatcaaaa attggtgttc tttgcagaag 90

<210> SEQ ID NO 155
<211> LENGTH: 90
<212> TYPE: DNA
<213> ORGANISM: Unknown
<220> FEATURE:
<221> NAME/KEY: source
<223> OTHER INFORMATION: /note="Description of Unknown:
APP target sequence"

<400> SEQUENCE: 155
tctgggttga caaatatcaa gacggaggag atctggaagt gaacatggat gaagaattcc 60
gacatgactc aggatatgaa gttcatcatc 90

<210> SEQ ID NO 156
<211> LENGTH: 90
<212> TYPE: DNA
<213> ORGANISM: Unknown
<220> FEATURE:
<221> NAME/KEY: source
<223> OTHER INFORMATION: /note="Description of Unknown: APP target sequence"

<400> SEQUENCE: 156
aggagatctg gaagtgaaca tggatgaaga attccgacat gactcaggat atgaagttca 60
tcatcaaaaa ttggtgttct ttgcagaaga 90

<210> SEQ ID NO 157
<211> LENGTH: 60
<212> TYPE: DNA
<213> ORGANISM: Unknown
<220> FEATURE:
<221> NAME/KEY: source
<223> OTHER INFORMATION: /note="Description of Unknown: APP target sequence"

<400> SEQUENCE: 157
atcaagacgg aggagatctg gaagtgaaca tggatgaaga attccgacat gactcaggat 60

<210> SEQ ID NO 158
<211> LENGTH: 60
<212> TYPE: DNA
<213> ORGANISM: Unknown
<220> FEATURE:
<221> NAME/KEY: source
<223> OTHER INFORMATION: /note="Description of Unknown: APP target sequence"

<400> SEQUENCE: 158
aggagatctg gaagtgaaca tggatgaaga attccgacat gactcaggat atgaagttca 60

<210> SEQ ID NO 159
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 159
uugaugauga acuucauauc cugagucaug ucggaauucu gcauccaucc ucacuucaga 60
gaucuccucc gucuugauau uugucaaccc agaaccuggu 100

<210> SEQ ID NO 160
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 160

-continued

```
uugaugauga acuucauauc cugagucaug ucggaauucu gcauccaucc ucacuucaga     60

gaucuccucc gucuugauau uugucaaccc agaaccugua                          100


<210> SEQ ID NO 161
<211> LENGTH: 90
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 161

gaugaacuuc auauccugag ucaugucgga auucugcauc cauccucacu ucagagaucu     60

ccuccgucuu gauauuuguc aacccagaac                                      90


<210> SEQ ID NO 162
<211> LENGTH: 90
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 162

atgatgaact tcatatcctg agtcatgtcg gaattctgca tccaccttca cttcagagat     60

ctcctccgtc ttgatatttg tcaacccaga                                      90


<210> SEQ ID NO 163
<211> LENGTH: 90
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 163

cttctgcaaa gaacaccaat ttttgatgat gaacttcata tcctgagtca tgtcggaatt     60

ctgcatccac cttcacttca gagatctcct                                      90


<210> SEQ ID NO 164
<211> LENGTH: 90
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 164

gatgatgaac ttcatatcct gagtcatgtc ggaattcttc atccacgttc acttccagat     60

ctcctccgtc ttgatatttg tcaacccaga                                      90


<210> SEQ ID NO 165
<211> LENGTH: 90
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 165
```

tcttctgcaa agaacaccaa tttttgatga tgaacttcat atcctgagtc atgtcggaat 60
tcttcatcca cgttcacttc cagatctcct 90

<210> SEQ ID NO 166
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 166
atcctgagtc atgtcggaat tcttcatcca cgttcacttc cagatctcct ccgtcttgat 60

<210> SEQ ID NO 167
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 167
tgaacttcat atcctgagtc atgtcggaat tcttcatcca cgttcacttc cagatctcct 60

<210> SEQ ID NO 168
<211> LENGTH: 5288
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 168
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accatatgcg gtgtgaaata ccgcacagat gcgtaaggag aaaataccgc atcaggcgcc 240
attcgccatt caggctgcgc aactgttggg aagggcgatc ggtgcgggcc tcttcgctat 300
tacgccagct ggcgaaaggg ggatgtgctg caaggcgatt aagttgggta acgccagggt 360
tttcccagtc acgacgttgt aaaacgacgg ccagtgaatt gacgcgccat tgggatgttg 420
taaaacgacg gccagtgaac ctgcaggcag ctgcgcgctc gctcgctcac tgaggccgcc 480
cgggcaaagc ccgggcgtcg ggcgaccttt ggtcgcccgg cctcagtgag cgagcgagcg 540
cgcagagagg gagtggccaa ctccatcact aggggttcct gcggccgcac gcgtggagga 600
gggcctattt cccatgattc cttcatattt gcatatacga tacaaggctg ttagagagat 660
aattagaatt aatttgactg taaacacaaa gatattagta caaaatacgt gacgtagaaa 720
gtaataattt cttgggtagt ttgcagtttt aaaattatgt tttaaaatgg actatcatat 780
gcttaccgta acttgaaagt atttcgattt cttggcttta tatatcttgt ggaaaggacg 840
aaacaccgag agaccagctg gatggtctct ttttttcgt actgagtcgc ccagtctcag 900
atagatccga cgccgccatc tctaggcccg cgccggcccc ctcgcacaga cttgtgggag 960
aagctcggct actcccctgc cccggttaat ttgcatataa tatttcctag taactataga 1020

```
ggcttaatgt gcgataaaag acagataatc tgttcttttt aatactagct acattttaca   1080
tgataggctt ggatttctat aagagataca aatactaaat tattatttta aaaaacagca   1140
caaaaggaaa ctcaccctaa ctgtaaagta attgtgtgtt ttgagactat aaatatccct   1200
tggagaaaag ccttgtttgg atgtcttcac aggaagacgc tttttttgcg gccgcatacg   1260
cgttgacatt gattattgac tagttattaa tagtaatcaa ttacggggtc attagttcat   1320
agcccatata tggagttccg cgttacataa cttacggtaa atggcccgcc tggctgaccg   1380
cccaacgacc cccgcccatt gacgtcaata atgacgtatg ttcccatagt aacgccaata   1440
gggactttcc attgacgtca atgggtggag tatttacggt aaactgccca cttggcagta   1500
catcaagtgt atcatatgcc aagtacgccc cctattgacg tcaatgacgg taaatggccc   1560
gcctggcatt atgcccagta catgacctta tgggactttc ctacttggca gtacatctac   1620
gtattagtca tcgctattac catggtgatg cggttttggc agtacatcaa tgggcgtgga   1680
tagcggtttg actcacgggg atttccaagt ctccacccca ttgacgtcaa tgggagtttg   1740
ttttggcacc aaaatcaacg ggactttcca aaatgtcgta acaactccgc cccattgacg   1800
caaatgggcg gtaggcgtgt acggtgggag gtctatataa gcagagctcg tttagtgaac   1860
cgtcagatcg cctggagacg ccatccacgc tgttttgacc tccatagtag acaccgggac   1920
cgatccagcc tccggactct agaggatcga acccttaagc cgccaccatg gtgagcaagg   1980
gcgaggagct gttcaccggg gtggtgccca tcctggtcga gctggacggc gacgtaaacg   2040
gccacaagtt cagcgtgtcc ggcgagggcg agggcgatgc cacctacggc aagctgaccc   2100
tgaagttcat ctgcaccacc ggcaagctgc ccgtgccctg gcccaccctc gtgaccaccc   2160
tgacctacgg cgtgcagtgc ttcagccgct accccgacca catgaagcag cacgacttct   2220
tcaagtccgc catgcccgaa ggctacgtcc aggagcgcac catcttcttc aaggacgacg   2280
gcaactacaa gacccgcgcc gaggtgaagt tcgagggcga caccctggtg aaccgcatcg   2340
agctgaaggg catcgacttc aaggaggacg gcaacatcct ggggcacaag ctggagtaca   2400
actacaacag ccacaacgtc tatatcatgg ccgacaagca gaagaacggc atcaaggtga   2460
acttcaagat ccgccacaac atcgaggacg gcagcgtgca gctcgccgac cactaccagc   2520
agaacacccc catcggcgac ggccccgtgc tgctgcccga caaccactac ctgagcaccc   2580
agtccgccct gagcaaagac cccaacgaga agcgcgatca catggtcctg ctggagttcg   2640
tgaccgccgc cgggatcact ctcggcatgg acgagctgta caagtactca gatctcgagc   2700
tcaagtgaac cggtcagaca tgataagata cattgatgag tttggacaaa ccacaactag   2760
aatgcagtga aaaaaatgct ttatttgtga aatttgtgat gctattgctt tatttgtaac   2820
cattataagc tgcaataaac aagttaacaa caacaattgc attcatttta tgtttcaggt   2880
tcagggggag gtgtgggagg ttttttaaac acgtgcggac cgagcggccg caggaacccc   2940
tagtgatgga gttggccact ccctctctgc gcgctcgctc gctcactgag gccgggcgac   3000
caaaggtcgc ccgacgcccg ggctttgccc gggcggcctc agtgagcgag cgagcgcgca   3060
gctgcctgca ggcttggatc ccaatggcgc gccgagcttg gctcgagcat ggtcatagct   3120
gtttcctgtg tgaaattgtt atccgctcac aattccacac aacatacgag ccggaagcat   3180
aaagtgtaaa gcctggggtg cctaatgagt gagctaactc acattaattg cgttgcgctc   3240
actgcccgct ttccagtcgg gaaacctgtc gtgccagctg cattaatgaa tcggccaacg   3300
cgcggggaga ggcggtttgc gtattgggcg ctcttccgct tcctcgctca ctgactcgct   3360
gcgctcggtc gttcggctgc ggcgagcggt atcagctcac tcaaaggcgg taatacggtt   3420
```

```
atccacagaa tcaggggata acgcaggaaa gaacatgtga gcaaaaggcc agcaaaaggc   3480
caggaaccgt aaaaaggccg cgttgctggc gtttttccat aggctccgcc cccctgacga   3540
gcatcacaaa aatcgacgct caagtcagag gtggcgaaac ccgacaggac tataaagata   3600
ccaggcgttt ccccctggaa gctccctcgt gcgctctcct gttccgaccc tgccgcttac   3660
cggatacctg tccgcctttc tcccttcggg aagcgtggcg ctttctcata gctcacgctg   3720
taggtatctc agttcggtgt aggtcgttcg ctccaagctg ggctgtgtgc acgaaccccc   3780
cgttcagccc gaccgctgcg ccttatccgg taactatcgt cttgagtcca acccggtaag   3840
acacgactta tcgccactgg cagcagccac tggtaacagg attagcagag cgaggtatgt   3900
aggcggtgct acagagttct tgaagtggtg gcctaactac ggctacacta gaagaacagt   3960
atttggtatc tgcgctctgc tgaagccagt taccttcgga aaaagagttg gtagctcttg   4020
atccggcaaa caaaccaccg ctggtagcgg tggttttttt gtttgcaagc agcagattac   4080
gcgcagaaaa aaaggatctc aagaagatcc tttgatcttt tctacggggt ctgacgctca   4140
gtggaacgaa aactcacgtt aagggatttt ggtcatgaga ttatcaaaaa ggatcttcac   4200
ctagatcctt ttaaattaaa aatgaagttt taaatcaatc taaagtatat atgagtaaac   4260
ttggtctgac agttagaaaa actcatcgag catcaaatga aactgcaatt tattcatatc   4320
aggattatca ataccatatt tttgaaaaag ccgtttctgt aatgaaggag aaaactcacc   4380
gaggcagttc cataggatgg caagatcctg gtatcggtct gcgattccga ctcgtccaac   4440
atcaatacaa cctattaatt tcccctcgtc aaaaataagg ttatcaagtg agaaatcacc   4500
atgagtgacg actgaatccg gtgagaatgg caaaagttta tgcatttctt tccagacttg   4560
ttcaacaggc cagccattac gctcgtcatc aaaatcactc gcatcaacca aaccgttatt   4620
cattcgtgat tgcgcctgag cgagacgaaa tacgcgatcg ctgttaaaag gacaattaca   4680
aacaggaatc gaatgcaacc ggcgcaggaa cactgccagc gcatcaacaa tattttcacc   4740
tgaatcagga tattcttcta atacctggaa tgctgttttc ccagggatcg cagtggtgag   4800
taaccatgca tcatcaggag tacggataaa atgcttgatg gtcggaagag gcataaattc   4860
cgtcagccag tttagtctga ccatctcatc tgtaacatca ttggcaacgc tacctttgcc   4920
atgtttcaga aacaactctg gcgcatcggg cttcccatac aatcgataga ttgtcgcacc   4980
tgattgcccg acattatcgc gagcccattt atacccatat aaatcagcat ccatgttgga   5040
atttaatcgc ggcctagagc aagacgtttc ccgttgaata tggctcatac tcttcctttt   5100
tcaatattat tgaagcattt atcagggtta ttgtctcatg agcggataca tatttgaatg   5160
tatttagaaa aataaacaaa taggggttcc gcgcacattt ccccgaaaag tgccacctga   5220
cgtctaagaa accattatta tcatgacatt aacctataaa aataggcgta tcacgaggcc   5280
ctttcgtc                                                            5288
```

<210> SEQ ID NO 169
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 169

```
actctggcgg caagttctgc                                                 20
```

<210> SEQ ID NO 170
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 170
cactctggcg gcaagttctg ctcagcggag 30

<210> SEQ ID NO 171
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 171
gcactctggc ggcaagttct gctcagcgga gtttctgccc 40

<210> SEQ ID NO 172
<211> LENGTH: 50
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 172
agcactctgg cggcaagttc tgctcagcgg agtttctgcc cggccaaaca 50

<210> SEQ ID NO 173
<211> LENGTH: 75
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 173
aggagcactc tggcggcaag ttctgctcag cggagtttct gcccggccaa acagcgtaac 60
cccttcttcc aagca 75

<210> SEQ ID NO 174
<211> LENGTH: 100
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 174
ggaggagcac tctggcggca agttctgctc agcggagttt ctgcccggcc aaacagcgta 60 acccccttctt ccaagcagat ttctttgcag ccaaatgcaa 100

<210> SEQ ID NO 175
<211> LENGTH: 150
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 175
caacaggagg agcactctgg cggcaagttc tgctcagcgg agtttctgcc cggccaaaca 60
gcgtaacccc ttcttccaag cagatttctt tgcagccaaa tgcaagggat gttaaggcaa 120
gaccctcccc acagggcagt cagagacccg 150

<210> SEQ ID NO 176
<211> LENGTH: 200
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 176
ctcagcaaca ggaggagcac tctggcggca agttctgctc agcggagttt ctgcccggcc 60
aaacagcgta accccttctt ccaagcagat ttctttgcag ccaaatgcaa gggatgttaa 120
ggcaagaccc tccccacagg gcagtcagag acccgcagcc gacagactaa gcctgcagct 180
tccaaccagg ctccccgaga 200

<210> SEQ ID NO 177
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 177
aggaggagca ctctggcggc 20

<210> SEQ ID NO 178
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 178
gcaacaggag gagcactctg gcggcaagtt 30

<210> SEQ ID NO 179
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 179
actcagcaac aggaggagca ctctggcggc aagttctgct 40

<210> SEQ ID NO 180
<211> LENGTH: 50
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 180

atgatactca gcaacaggag gagcactctg gcggcaagtt ctgctcagcg            50

<210> SEQ ID NO 181
<211> LENGTH: 75
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 181

acgtggagga cgatgatact cagcaacagg aggagcactc tggcggcaag ttctgctcag  60

cggagtttct gcccg                                                  75

<210> SEQ ID NO 182
<211> LENGTH: 100
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 182

caccagcacc gcgacgtgga ggacgatgat actcagcaac aggaggagca ctctggcggc  60

aagttctgct cagcggagtt tctgcccggc caaacagcgt                       100

<210> SEQ ID NO 183
<211> LENGTH: 150
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 183

tgacgatcgt ggagacgaac agcagcacca gcaccgcgac gtggaggacg atgatactca  60

gcaacaggag gagcactctg gcggcaagtt ctgctcagcg gagtttctgc ccggccaaac  120

agcgtaaccc cttcttccaa gcagatttct                                  150

<210> SEQ ID NO 184
<211> LENGTH: 200
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 184

tgtccattgc ccacgatcca ttggctgacg atcgtggaga cgaacagcag caccagcacc  60

gcgacgtgga ggacgatgat actcagcaac aggaggagca ctctggcggc aagttctgct  120

cagcggagtt tctgcccggc caaacagcgt aaccccttct tccaagcaga tttctttgca  180

gccaaatgca agggatgtta                                             200
```

```
<210> SEQ ID NO 185
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 185

tcagcaacag gaggagcact                                                20


<210> SEQ ID NO 186
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 186

cgatgatact cagcaacagg aggagcactc                                     30


<210> SEQ ID NO 187
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 187

cgtggaggac gatgatactc agcaacagga ggagcactct                          40


<210> SEQ ID NO 188
<211> LENGTH: 50
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 188

gcaccgcgac gtggaggacg atgatactca gcaacaggag gagcactctg                50


<210> SEQ ID NO 189
<211> LENGTH: 75
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 189

gtggagacga acagcagcac cagcaccgcg acgtggagga cgatgatact cagcaacagg    60

aggagcactc tggcg                                                     75


<210> SEQ ID NO 190
<211> LENGTH: 100
<212> TYPE: DNA
<213> ORGANISM: Artificial Sequence
<220> FEATURE:
```

<221> NAME/KEY: source
<223> OTHER INFORMATION: /note="Description of Artificial Sequence: Synthetic polynucleotide"

<400> SEQUENCE: 190
ccacgatcca ttggctgacg atcgtggaga cgaacagcag caccagcacc gcgacgtgga 60
ggacgatgat actcagcaac aggaggagca ctctggcggc 100

<210> SEQ ID NO 191
<211> LENGTH: 150
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 191
agaggtgcta cagttctgcc agagatcagt tgcgtgtcca ttgcccacga tccattggct 60
gacgatcgtg gagacgaaca gcagcaccag caccgcgacg tggaggacga tgatactcag 120
caacaggagg agcactctgg cggcaagttc 150

<210> SEQ ID NO 192
<211> LENGTH: 100
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 192
tgataaaagg cgtacataat tcttgtgtct actgtacaga atactgccgc cagctggatt 60
tcccaattct gagtaacact ctgcaatcca aacagggttc 100

<210> SEQ ID NO 193
<211> LENGTH: 6
<212> TYPE: PRT
<213> ORGANISM: Homo sapiens

<400> SEQUENCE: 193

Tyr Glu Asn Pro Thr Tyr
1               5

<210> SEQ ID NO 194
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: MOD_RES
<222> LOCATION: (2)..(2)
<223> OTHER INFORMATION: Any amino acid

<400> SEQUENCE: 194

Lys Xaa Lys Glu Gly Val
1               5

<210> SEQ ID NO 195
<211> LENGTH: 9
<212> TYPE: PRT
<213> ORGANISM: Artificial Sequence

```
<220> FEATURE:
<221> NAME/KEY: source
<223> OTHER INFORMATION: /note="Description of Artificial Sequence:
      Synthetic peptide"

<400> SEQUENCE: 195

Val Gly Gly Ala Val Val Thr Gly Val
1               5


<210> SEQ ID NO 196
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 196

Asp Pro Asp Asn Glu Ala
1               5


<210> SEQ ID NO 197
<211> LENGTH: 65
<212> TYPE: PRT
<213> ORGANISM: Homo sapiens

<400> SEQUENCE: 197

Lys Thr Glu Glu Ile Ser Glu Val Lys Met Asp Ala Glu Phe Arg His
1               5                   10                  15

Asp Ser Gly Tyr Glu Val His His Gln Lys Leu Val Phe Phe Ala Glu
            20                  25                  30

Asp Val Gly Ser Asn Lys Gly Ala Ile Ile Gly Leu Met Val Gly Gly
        35                  40                  45

Val Val Ile Ala Thr Val Ile Val Ile Thr Leu Val Met Leu Lys Lys
    50                  55                  60

Lys
65


<210> SEQ ID NO 198
<211> LENGTH: 12
<212> TYPE: PRT
<213> ORGANISM: Homo sapiens

<400> SEQUENCE: 198

Lys Thr Glu Glu Ile Ser Glu Val Lys Met Asp Ala
1               5                   10


<210> SEQ ID NO 199
<211> LENGTH: 59
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 199

Glu Val Lys Met Asp Ala Glu Phe Arg His Asp Ser Gly Tyr Glu Val
1               5                   10                  15

His His Gln Lys Leu Val Phe Phe Ala Glu Asp Val Gly Ser Asn Lys
            20                  25                  30

Gly Ala Ile Ile Gly Leu Met Val Gly Gly Val Val Ile Ala Thr Val
        35                  40                  45
```

Ile Val Ile Thr Leu Val Met Leu Lys Lys Gln
    50                  55

<210> SEQ ID NO 200
<211> LENGTH: 66
<212> TYPE: PRT
<213> ORGANISM: Homo sapiens

<400> SEQUENCE: 200

Glu Ile Ser Glu Val Lys Met Asp Ala Glu Phe Arg His Asp Ser Gly
1               5                   10                  15

Tyr Glu Val His His Gln Lys Leu Val Phe Phe Ala Glu Asp Val Gly
            20                  25                  30

Ser Asn Lys Gly Ala Ile Ile Gly Leu Met Val Gly Gly Val Val Ile
        35                  40                  45

Ala Thr Val Ile Val Ile Thr Leu Val Met Leu Lys Lys Lys Gln Tyr
    50                  55                  60

Thr Ser
65

<210> SEQ ID NO 201
<211> LENGTH: 52
<212> TYPE: PRT
<213> ORGANISM: Unknown
<220> FEATURE:
<221> NAME/KEY: source
<223> OTHER INFORMATION: /note="Description of Unknown:
      APP sequence"
<220> FEATURE:
<221> NAME/KEY: VARIANT
<222> LOCATION: (6)..(6)
<223> OTHER INFORMATION: /replace="Thr"
<220> FEATURE:
<221> NAME/KEY: VARIANT
<222> LOCATION: (15)..(15)
<223> OTHER INFORMATION: /replace="Lys"
<220> FEATURE:
<221> NAME/KEY: SITE
<222> LOCATION: (1)..(52)
<223> OTHER INFORMATION: /note="Variant residues given in the sequence
      have no preference with respect to those in the annotations
      for variant positions"
<220> FEATURE:
<221> NAME/KEY: source
<223> OTHER INFORMATION: /note="See specification as filed for detailed
      description of substitutions and preferred embodiments"

<400> SEQUENCE: 201

Glu Val Lys Met Asp Ala Glu Phe Arg His Asp Ser Gly Tyr Glu Val
1               5                   10                  15

His His Gln Lys Leu Val Phe Phe Ala Glu Asp Val Gly Ser Asn Lys
            20                  25                  30

Gly Ala Ile Ile Gly Leu Met Val Gly Gly Val Val Ile Ala Thr Val
        35                  40                  45

Ile Val Ile Thr
    50

<210> SEQ ID NO 202
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 202
attagccatg gatgtattca tga 23

<210> SEQ ID NO 203
<211> LENGTH: 52
<212> TYPE: PRT
<213> ORGANISM: Unknown
<220> FEATURE:
<221> NAME/KEY: source
<223> OTHER INFORMATION: /note="Description of Unknown:
APP sequence"
<220> FEATURE:
<221> NAME/KEY: VARIANT
<222> LOCATION: (3)..(3)
<223> OTHER INFORMATION: /replace="Glu" or "Gly" or "Arg"
<220> FEATURE:
<221> NAME/KEY: VARIANT
<222> LOCATION: (4)..(4)
<223> OTHER INFORMATION: /replace="Val"
<220> FEATURE:
<221> NAME/KEY: VARIANT
<222> LOCATION: (5)..(5)
<223> OTHER INFORMATION: /replace="Gly"
<220> FEATURE:
<221> NAME/KEY: VARIANT
<222> LOCATION: (15)..(15)
<223> OTHER INFORMATION: /replace="Gly"
<220> FEATURE:
<221> NAME/KEY: VARIANT
<222> LOCATION: (20)..(20)
<223> OTHER INFORMATION: /replace="Glu" or "Gly" or "Arg"
<220> FEATURE:
<221> NAME/KEY: SITE
<222> LOCATION: (1)..(52)
<223> OTHER INFORMATION: /note="Variant residues given in the sequence
have no preference with respect to those in the annotations
for variant positions"
<220> FEATURE:
<221> NAME/KEY: source
<223> OTHER INFORMATION: /note="See specification as filed for detailed
description of substitutions and preferred embodiments"

<400> SEQUENCE: 203

```
Glu Val Lys Met Asp Ala Glu Phe Gly His Asp Ser Gly Phe Glu Val
1               5                   10                  15

Arg His Gln Lys Leu Val Phe Phe Ala Glu Asp Val Gly Ser Asn Lys
            20                  25                  30

Gly Ala Ile Ile Gly Leu Met Val Gly Gly Val Val Ile Ala Thr Val
        35                  40                  45

Ile Val Ile Thr
    50
```

<210> SEQ ID NO 204
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 204
tacatggtag caggg 15

<210> SEQ ID NO 205
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 205
tacatggtgg caggg                                                          15

<210> SEQ ID NO 206
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 206
gaagtgaata catggtagca gg                                                  22

<210> SEQ ID NO 207
<211> LENGTH: 70
<212> TYPE: DNA
<213> ORGANISM: Homo sapiens

<400> SEQUENCE: 207
tctgaagtga agatggatgc agaattccga catgactcag gatatgaagt tcatcatcaa     60
aaattggtgt                                                                70

<210> SEQ ID NO 208
<211> LENGTH: 23
<212> TYPE: PRT
<213> ORGANISM: Homo sapiens

<400> SEQUENCE: 208

Ser Glu Val Lys Met Asp Ala Glu Phe Arg His Asp Ser Gly Tyr Glu
1               5                   10                  15

Val His His Gln Lys Leu Val
            20

<210> SEQ ID NO 209
<211> LENGTH: 70
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 209
tctgaagtga ggatggatgc agaattccga catgactcag gatatgaagt tcatcatcaa     60
aaattggtgt                                                                70

<210> SEQ ID NO 210
<211> LENGTH: 70
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 210
tctgaagtgg agatggatgc agaattccga catgactcag gatatgaagt tcatcatcaa     60
aaattggtgt                                                                70

<210> SEQ ID NO 211
<211> LENGTH: 70
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 211
tctgaagtgg ggatggatgc agaattccga catgactcag gatatgaagt tcatcatcaa 60
aaattggtgt 70

<210> SEQ ID NO 212
<211> LENGTH: 70
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 212
tctgaagtga gggtggatgc agaattccga catgactcag gatatgaagt tcatcatcaa 60
aaattggtgt 70

<210> SEQ ID NO 213
<211> LENGTH: 70
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 213
tctgaagtgg aggtggatgc agaattccga catgactcag gatatgaagt tcatcatcaa 60
aaattggtgt 70

<210> SEQ ID NO 214
<211> LENGTH: 70
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 214
tctgaagtgg gggtggatgc agaattccga catgactcag gatatgaagt tcatcatcaa 60
aaattggtgt 70

<210> SEQ ID NO 215
<211> LENGTH: 70
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 215
tctgaagtga aggtggatgc agaattccga catgactcag gatatgaagt tcatcatcaa 60
aaattggtgt 70

<210> SEQ ID NO 216
<211> LENGTH: 70
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 216
tctgaagtga agatgggtgc agaattccga catgactcag gatatgaagt tcatcatcaa 60
aaattggtgt 70

<210> SEQ ID NO 217
<211> LENGTH: 70
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 217
tctgaagtga agatggatgt ggaattccga catgactcag gatatgaagt tcatcatcaa 60
aaattggtgt 70

<210> SEQ ID NO 218
<211> LENGTH: 70
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 218
tctgaagtga agatggatac agaattccga catgactcag gatatgaagt tcatcatcaa 60
aaattggtgt 70

<210> SEQ ID NO 219
<211> LENGTH: 82
<212> TYPE: DNA
<213> ORGANISM: Homo sapiens

<400> SEQUENCE: 219
ctctgaagtg aagatggatg cagaattccg acatgactca ggatatgaag ttcatcatca 60
aaaattggtg ttctttgcag aa 82

<210> SEQ ID NO 220
<211> LENGTH: 27
<212> TYPE: PRT
<213> ORGANISM: Homo sapiens

<400> SEQUENCE: 220

Ser Glu Val Lys Met Asp Ala Glu Phe Arg His Asp Ser Gly Tyr Glu
1 5 10 15

Val His His Gln Lys Leu Val Phe Phe Ala Glu
20 25

<210> SEQ ID NO 221
<211> LENGTH: 82
<212> TYPE: DNA

<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 221
ctctgaagtg aagatggatg cagaattccg acatgactca ggatatgaag ttcatcatca 60
aagattggtg ttctttgcag aa 82

<210> SEQ ID NO 222
<211> LENGTH: 82
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 222
ctctgaagtg aagatggatg cagaattccg acatgactca ggatatgaag ttcatcatca 60
agaattggtg ttctttgcag aa 82

<210> SEQ ID NO 223
<211> LENGTH: 82
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 223
ctctgaagtg aagatggatg cagaattccg acatgactca ggatatgaag ttcatcatca 60
aggattggtg ttctttgcag aa 82

<210> SEQ ID NO 224
<211> LENGTH: 82
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 224
ctctgaagtg aagatggatg cagaattccg acatgactca ggatatgaag ttcgtcatca 60
aaaattggtg ttctttgcag aa 82

<210> SEQ ID NO 225
<211> LENGTH: 82
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 225
ctctgaagtg aagatggatg cagaattccg acatgactca ggatatggag ttcatcatca 60
aaaattggtg ttctttgcag aa 82